US007153678B2

(12) United States Patent
Jackson et al.

(10) Patent No.: US 7,153,678 B2
(45) Date of Patent: Dec. 26, 2006

(54) POLYNUCLEOTIDES ENCODING THE NOVEL HUMAN PHOSPHATASE, RET31, AND VARIANTS THEREOF

(75) Inventors: Donald G. Jackson, Lawrenceville, NJ (US); Chandra S. Ramanathan, Wallingford, CT (US); John N. Feder, Belle Mead, NJ (US); Liana Lee, San Francisco, CA (US); Thomas C. Nelson, Lawrenceville, NJ (US); Nathan Siemers, Pennington, NJ (US); Suzanne J. Suchard, Wilmington, DE (US); Joshua Finger, Spring City, PA (US); C. Gordon Todderud, Newtown, PA (US); Dana Banas, Hamilton, NJ (US)

(73) Assignee: Bristol-Myers Squibb, Princeton, NJ (US)

(*) Notice: Subject to any disclaimer, the term of this patent is extended or adjusted under 35 U.S.C. 154(b) by 734 days.

(21) Appl. No.: 10/029,345

(22) Filed: Dec. 20, 2001

(65) Prior Publication Data
US 2005/0130286 A1    Jun. 16, 2005

Related U.S. Application Data

(60) Provisional application No. 60/300,465, filed on Jun. 25, 2001, provisional application No. 60/295,848, filed on Jun. 5, 2001, provisional application No. 60/287,735, filed on May 1, 2001, provisional application No. 60/280,186, filed on Mar. 30, 2001, provisional application No. 60/256,868, filed on Dec. 20, 2000.

(51) Int. Cl.
C12N 9/18      (2006.01)
C12N 1/20      (2006.01)
C12N 15/00     (2006.01)
C07H 21/04     (2006.01)

(52) U.S. Cl. ............... 435/196; 435/320.1; 435/252.3; 435/252.33; 435/348; 435/419; 435/254.1; 435/254.2; 435/325; 536/23.2

(58) Field of Classification Search ............... 435/196, 435/19, 320.1, 252.3, 252.33, 348, 419, 254.1, 435/254.2, 325; 536/23.2
See application file for complete search history.

(56) References Cited

U.S. PATENT DOCUMENTS

| 5,849,902 | A | 12/1998 | Arrow et al. |
| 6,664,089 | B1 | 12/2003 | Meyers |
| 2002/0034807 | A1 | 3/2002 | Meyers |
| 2004/0009501 | A1 | 1/2004 | Curtis et al. |

FOREIGN PATENT DOCUMENTS

| EP | 1 293 569 | 3/2003 |
| WO | WO9201050 | 1/1992 |
| WO | WO9706245 | 2/1997 |
| WO | WO0039751 | 7/2000 |
| WO | WO0105983 | 1/2001 |
| WO | WO0109316 | 2/2001 |
| WO | WO0109345 | 2/2001 |
| WO | WO0112819 | 2/2001 |
| WO | WO0120004 | 3/2001 |
| WO | WO0146394 | 6/2001 |
| WO | WO 01/53455 | 7/2001 |
| WO | WO0173059 | 10/2001 |
| WO | WO0175067 | 10/2001 |
| WO | WO0177340 | 10/2001 |
| WO | WO0200677 | 1/2002 |
| WO | WO0210363 | 2/2002 |
| WO | WO0220747 | 3/2002 |
| WO | WO0222660 | 3/2002 |
| WO | WO 02/31111 | 4/2002 |
| WO | WO0226997 | 4/2002 |
| WO | WO 02/057460 | 7/2002 |
| WO | WO0252005 | 7/2002 |
| WO | WO 02/068649 | 9/2002 |
| WO | WO 03/000844 | 1/2003 |
| WO | WO 03/010327 | 2/2003 |
| WO | WO 03/018812 | 3/2003 |
| WO | WO 03/072035 | 9/2003 |

OTHER PUBLICATIONS

Genbank Data Base Acc#AB051487/gi: 12697944. Nagase et al Feb. 7, 2001.*
Issued Patents Data Base US6,664,089 Seq ID No. 3. Meyers et al Dec. 16, 2003; priority date Feb. 24, 2000.*
SPTREMBL_25 Database Masuda et al Accession No. Q920R2 Dec. 1, 2001 from J. Biol Chem 275; 39002-39011 (2001). Alignment with SEQ ID No: 109.*
Johnson et al Regulation of dual-specificity phosphatases M3/6 and hVH5 by phorbol esters. Analysis of a delta-like domain J Biol Chem. Oct.13, 2000;275(41):31755-62.*
Duesterhoeft et al., "*Homo sapiens* mRNA, cDNA DKFZp434C035 (from clone DKFZp434C035)", Database Accession No. AL137633 XP002211554, retrieved from EBI, Accession No. HSM802399, Jan. 27, 2000.

(Continued)

Primary Examiner—Rebecca E. Prouty
(74) Attorney, Agent, or Firm—Stephen C. D'Amico

(57) ABSTRACT

The present invention provides novel polynucleotides encoding human phosphatase polypeptides, fragments and homologues thereof. Also provided are vectors, host cells, antibodies, and recombinant and synthetic methods for producing said polypeptides. The invention further relates to diagnostic and therapeutic methods for applying these novel human phosphatase polypeptides to the diagnosis, treatment, and/or prevention of various diseases and/or disorders related to these polypeptides, particularly cardiovascular diseases and/or disorders. The invention further relates to screening methods for identifying agonists and antagonists of the polynucleotides and polypeptides of the present invention.

28 Claims, 67 Drawing Sheets

OTHER PUBLICATIONS

Figure 11:
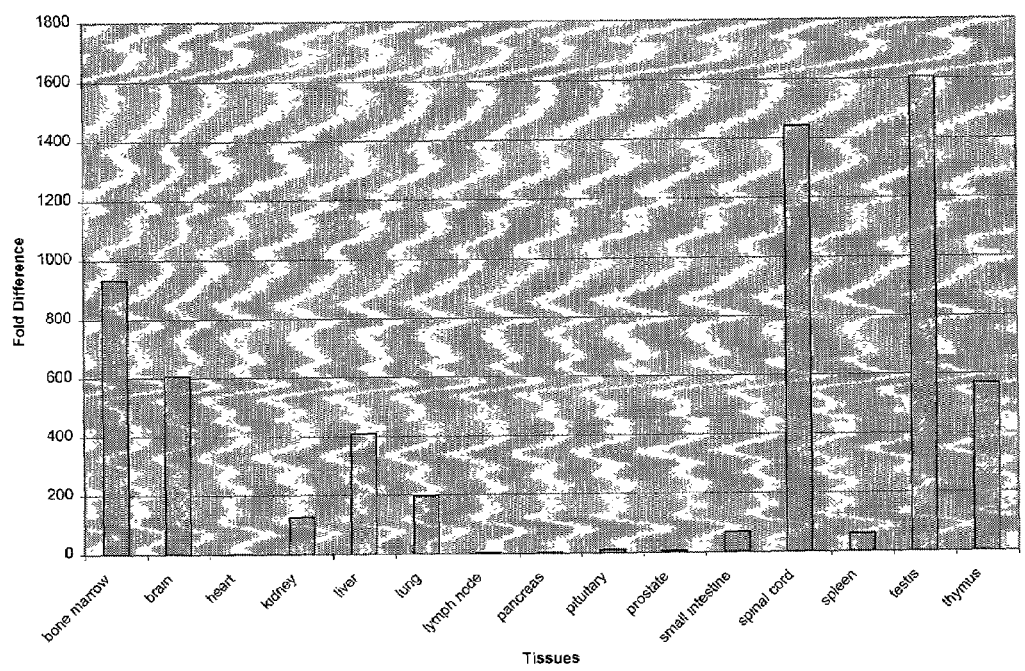

ENSEMBL:ENSP00000204051.

Isogai et al., "*Homo sapiens* cDNA FLJ12041 fis, clone HEMBB1001945", Database accession No. AK022103 XP002211553, retrieved from EBI, Sep. 29, 2000.

JBC Manuscript M104600200, MKP-7, a novel MAP Kinase Phosphatase, functions as a shuttle protein, Masuda et al., Aug. 6, 2001.

Martell, K.J. et al., "hVH-5: A Protein Tyrosine Phosphatase Abundant in Brain that Inactivates Mitogen-Activated Protein Kinase", Journal of Neurochemistry, vol. 65, No. 4, 1995, pp. 1823-1833, XP000196676.

Nagase et al. (2000) DNA Research, 7:347-355.

NCBI Entrez Accession No. gi|12654609, Strausberg, R., Jul. 12, 2001.

NCBI Entrez Accession No. gi|12697945, Nagase, T. et al., Feb. 7, 2001.

NCBI Entrez Accession No. gi|13990989, Masuda, K. et al., Oct. 18, 2001.

NCBI Entrez Accession NO gi|14728095, NCBI Annotation Project, National Center for Biotechnology, Jul. 16, 2001.

NCBI Entrez Accession NO gi|14756395, NCBI Annotation Project, National Center for Biotechnology, Aug. 1, 2002.

NCBI Entrez Accession No. gi|17402248, Johnson, C., Dec. 5, 2001.

NCBI Entrez Accession NO gi|20137933, Masuda, K. et al., Jun. 15, 2002.

NCBI Entrez Accession NO gi|21594973, Strausberg, R., Jun. 26, 2002.

NCBI Entrez Accession No. gi|22748893, Ninomiya, K. et al., Sep. 6, 2002.

NCBI Entrez Accession NO gi|8923413, Watanabe, K. et al., Feb. 10, 2002.

NCBI Entrez Accession NO gi|9280136, Hashimoto, K. et al., Oct. 11, 2001.

NCBI Entrez Accession No. gi|AK000449, Watanabe, K. et al., Feb. 22, 2000.

NCBI Entrez Accession No. gi|AK055973, Tashiro, H. et al., Aug. 1, 2002.

NCBI Entrez Accession No. gi|AL360020, Johnson, C., Dec. 5, 2001.

NCBI Entrez Accession No. gi|BAB40814, Masuda, K. et al., Oct. 18, 2001.

NCBI Entrez Accession No. gi|BAB71060, Tashiro, H. et al., Aug. 1, 2002.

NCBI Entrez Accession No. gi|BC001140, Strausberg, R., Jul. 12, 2001.

Shafer et al., "Human Immunodeficiency Virus Reverse Transcriptase and Protease Sequence Database", Nucleic Acids Research, vol. 28, No. 1, Jan. 1, 2000, pp. 346-348, XP002202302.

Swiss-Prot Accession No: Q8WX19, Release 20, Mar. 2002.

Swiss-Prot Accession No: Q920R2, Release 19, Dec. 2001.

Swiss-Prot Accession No: Q96N49, Release, 19, Dec. 2001.

Swiss-Prot Accession No: Q9BVJ7, Release, Jun. 17, 2001.

Swiss-Prot Accession No: Q9BY84, Release 41, Jun. 2002.

Swiss-Prot Accession No: Q9N091, Release 15, Oct. 2000.

Swiss-Prot Accession No: Q9NX48, Release 15, Oct. 2000.

Swiss-Prot Accession No: Q9C0G3 (J. Biol. Chem. 276:39002-39011 (2001).

NCBI Entrez Accession No. gi|AX260340, Meyers, R.A., Oct. 26, 2001.

NCBI Entrez Accession No. gi|NP_085143, Hoornaert, I. et al., Jan. 26, 2004.

NCBI Entrez Accession No. gi|XP_059988, NCBI Annotation Project, Aug. 1, 2002.

NCBI Entrez Accession No. gi|7020545, Watanabe, K. et al., Sep. 13, 2003.

NCBI Entrez Accession No. gi|16165772, NCBI Annotation Project, May 8. 2002.

NCBI Entrez Accession. No. gi|20834581, NCBI Annotation Project, May 16, 2002.

NCBI Entrez Accession No. gi|25050344, NCBI Annotation Project, Nov. 17, 2002.

NCBI Entrez Accession No. gi|27469789, Stausberg, R.L. et al., Oct. 7, 2003.

NCBI Entrez Accession No. gi|27497737, Guo, J.H. et al., Jan. 4, 2003.

NCBI Entrez Accession No. gi|27764880, Guo, J.H. et al., Apr. 7, 2003.

NCBI Entrez Accession No. gi|30089950, Ota, T. et al., May 6, 2004.

NCBI Entrez Accession No. gi|30089952, Ota, T. et al., May 6, 2004.

NCBI Entrez Accession No. gi|34880952, Oct. 23, 2002.

NCBI Entrez Accession No. gi|45501280, Strausberg, R.L. et al., May 10, 2004.

Hoornaert, I. et al., "MAPK phosphatase DUSP 16/MKP-7, a candidate tumor suppressor for chromosome region 12p12-13, reduces BCR-ABL-induced transformation", Oncogene, vol. 22, pp. 7728-7736 (2003).

Mammalian Gene Collection (MGC) Program Team, "Generation and initial analysis of more than 15,000 full-length human and mouse cDNA sequences", Proc. Natl. Acad Sci. USA, vol. 99, No. 26, pp. 16899-16903 (2002).

Ota, T. et al., "Complete sequencing and characterization of 21,243 full-length human cDNAs", Nature Genetics, vol. 36, No. 1, pp. 40-45 (2004).

Saha, S. et al., "A Phosphatase Associated with Metastasis of Colorectal Cancer", Science, vol. 294, pp. 1343-1346 (2001).

Altschul, et al., "Gapped BLAST and PSI-BLAST: a new generation of protein database search programs", Nucleic Acids Res., vol. 25(17), pp. 3389-3402 (1997).

Altschul, et al., "Basic Local Alignment Search Tool", J. Mol. Biol., vol. 215, pp. 403-410 (1990).

Arlin, et al., "Eukaryotic methionyl aminopeptidases: Two classes of cobalt-dependent enzymes", PNAS, vol. 92, pp. 7714-7718 (1995).

Bateman, et al., "The Pfam Protein Families Database", Nucleic Acids Res., vol. 28(1), pp. 263-266 (2000).

Bazan, et al., "Sequence and structure comparison suggest that methionine aminopeptidase prolidase, aminopeptidase P, and creatinase share a common fold", PNAS, vol. 91, pp. 2473-2477 (1994).

Bernstein, et al., "The Protein Data Bank: A computer-based Archival File for Macromolecular Structures", J. Mol. Biol., vol. 112, pp. 535-542 (1977).

Böhm, HJ., "The computer program LUDI: A new method for the de novo design of enzyme inhibitors", J. Computer Aided Mol. Design, vol. 6, pp. 61-78 (1992).

Bradshaw, et al., "N-Terminal processing: the methionine aminopeptidase and $N^{\alpha}$-acetyl transferase families", TIBS, vol. 23, pp. 263-267 (1998).

Burge, et al., "Prediction of Complete Gene Structures in Human Genomic DNA", JMB, vol. 268, pp. 78-94 (1997).

Cantley, et al., "Oncogenes and Signal Transduction", Cell, vol. 64, pp. 281-302 (1991).

Cardozo, et al., "Homology Modeling by the ICM Method", Proteins, vol. 23, pp. 403-414 (1995).

Chang, et al., "Mammalian MAP kinase signaling cascades", Nature, vol. 410, pp. 37-40 (2001).

Chang, et al., "Molecular Cloning, Sequencing, Deletion, and Overexpression of a Methionine Aminopeptidase Gene from *Saccharomyces cerevisiae*", JBC., vol. 267(12), pp. 8007-8011 (1992).

Charbonneau, et al., "The Leukocyte common antigen (CD45): A putative receptor-linked protein tyrosine phosphatase", PNAS, vol. 85, pp. 7182-7186 (1988).

Charbonneau, et al., "Human placenta protein-tyrosine-phosphatase: Amino acid sequence and relationship to a family or receptor-like protins", PNAS, vol. 86, pp. 5252-5256 (1989).

Chernoff, et al., "Cloning of a cDNA for a major human protein-tyrosine phosphatase", PNAS, vol. 87, pp. 2735-2739 (1990).

Cool, et al., "cDNA isolated from a human T-cell library encodes a member of the protein-tyrosine-phosphatase family", PNAS, vol. 86, pp. 5257-5261 (1989).

Datta, Bansidhar, "MAPs and POEP of the roads from prokaryotic to eukaryotic kingdoms", Biochimie, vol. 82, pp. 95-107 (2000).
D'Amico, et al., "The Integrin-linked Kinase Regulates the Cyclin D1 Gene through Glycogen Synthase Kinase 3β and cAMP-responsive Element-binding Protein-dependent Pathways", JBC., vol. 275(42), pp. 32649-32657 (2000).
Diatchenko, et al., "Suppression subtractive hybridization: A method for generating differentially regulated or tissue-specific cDNA probes and libraries", PNAS, vo. 93, pp. 6025-6030 (1996).
Edwards, et al., "Oligodeoxyribonucleotide ligation to single-stranded cDNAs: a new tool for cloning 5' ends to mRNAs and for constructing cDNA libraries by in vitro amplification", Nucleic Acids Res., vol. 19(19), pp. 5227-5232 (1991).
Fauman, et al., "Structure and function of the protein tyrosine phosphatases", TIBS, vol. 21, pp. 413-417 (1996).
Frearson, et al., "The role of phosphotyrosine phosphatases in haematopoietic cell signal trasnduction", BioEssays, vol. 19(5), pp.417-427 (1997).
Fromont-Racine, et al., "A highly sensitive method for mapping the 5 'termini of mRNAs", Nucleic Acids Res., vol. 21(7), pp. 1683-1684 (1993).
Frohman, et al., "Rapid production of full-length cDNAs from rare transcripts: Amplification using a single gene-specific oligonucleotide primer", PNAS, vol. 85, pp. 8998-9002 (1988).
Gerner, et al., "The Fas-induced Apoptosis Analyzed by High Throughput Proteome Analysis", JBC, vol. 275(5), pp. 39018-39026 (2000).
Gloria-Bottini, et al., "Phosphotyrosine-Protein-Phosphatases And Human Reproduction: An Association Between Low Molecular Weight Acid Phosphatase (ACP1) And Spontaneous Abortion", Disease Markers, vol. 12, pp. 261-269 (1996).
Greer, Jonathan, "Comparative Modeling of Homologous Proteins", Methods in Enzymology, vol. 202, pp. 239-253 (1991).
Goodford, P.J., "A Computational Procedure for Determining Energetically Favorable Binding Sites on Biologically Important Macromolecules", J. Med. Chem., vol. 28, pp. 849-857 (1985).
Goodsell, et al., "Automated Docking of Substrates to Proteins by Simulated Annealing", Proteins, vol. 8, pp. 195-202 (1990).
Gu, et al., "Identification, cloning, and expression of a cytosolic megakaryocyte protein-tyrosine-phosphatase with sequence homology to cytoskeletal protein 4.1", PNAS, vol. 88, pp. 5867-5871 (1991).
Hanks, et al., "The Protein Kinase Family: Conserved Features and Deduced Phylogeny of the Catalytic Domains", Science, vol. 241, pp. 42-52 (1988).
Hariharan, et al., "Cloning and characterization of a receptor-class phosphotyrosine phosphatase gene expressed on central nervous system axons in Drosophila melanogaster", PNAS, vol. 88, pp. 11266-11270 (1991).
Hendlich, et al., "Identification of Native Protein Folds Amongst a Large Number of Incorrect Models", J. Mol. Biol., vol. 216, pp. 167-180 (1990).
Henikoff, et al., "Amino acid substitution matrices from protein blocks", PNAS, vol. 89, pp. 10915-10919 (1992).
Herlaar, et al., "p38 MAPK signaling cascades in inflammatory disease", Molec. Med. Today, vol. 5, pp. 439-447 (1999).
Hunter, Tony, "Protein-Tyrosine Phosphatases: The Other Side of the Coin", Cell, vol. 58, pp. 1013-1016 1989.
Hunter, Tony, "A Tail of Two srs's: Mutatis Mutandis", Cell, vol 49, pp. 1-4 (1987)
Hunter, et al., "Protein-Tyrosine Kinases", Ann. Rev. Biochem., vol. 54, pp. 897-930 (1985).
Jia, et al., "Structural Basis for Phosphotyrosine Peptide Recognition by Protein Thyrosine Phosphatase 1B", Science, vol. 268, pp. 1754-1758 (1995).
Jirik, et al., "Cloning and chromosomal assignment of a widely expressed human receptor-like protein-tyrosine phosphatase", FEBS Letters, vol. 273(1,2), pp. 239-242 (1990).
Kaplan, et al., "Cloning of three human tyrosine phosphatases reveals a multigene family of receptor-linked protein-tyrosine-phosphatases expressed in brain", PNAS, vol. 87, pp. 7000-7004 (1990).

Katz, et al., "The SJL/J T Cell Response To Both Spontaneous And Transplantable Syngeneic Reticulum Cell Sarcoma Is Mediated Predominantly By The Vβ17a+ T Cell Clonotype", J. Exp. Med., vol. 168, pp. 1553-1562 (1988).
Keeling, et al., "Methionine aminopeptidase-1:the MAP for the mitochondrion?", TIBS, pp. 285-286 (1996).
Kendall, et al., "Isolation and Characterization of the Methionine Aminopeptidase from Porcine Liver Responsible for the Co-translational Processing of Proteins", JBC, vol. 267(29), pp. 20667-20673 (1992).
Krejsa, et al., "Role of Oxidative Stress in the Action of Vanadium Phosphotyrosine Phosphatase Inhibitors", JBC, vol. 272(17), pp. 11541-11549 (1997).
Krueger, et al., "Structural diversity and evolution of human receptor-like protein tyrosine phosphatases", EMBO J., vol. 9(10), pp. 3241-3252 (1990).
Kruger, et al., "TNP-470: an angiogenesis inhibitor in clinical development for cancer", Exp. Opin. Invest. Drugs, vol. 9(6), pp. 1383-1396 (2000).
Kuntz, et al., "A Geometric Approach to Macromolecule-Ligand Interactions", J. Mol. Biol., vol. 161, pp. 269-288 (1982).
Kunkel, Thomas A., "Rapid and efficient site-specific mutagenesis without phenotypic selection", PNAS, vol. 82, pp. 488-492 (1985).
Kusaka, et al., Cytostatic Inhibition of endothelial cell growth by the antiogenesis inhibitor TNP-470 (AGM-1470), Br. J. Cancer, vol. 69, pp. 212-216 (1994).
Lee, et al., Paclitaxel (Taxol)-induced Gene Expression and Cell Death Are Both Mediated by the Activation of c-Jun $NH_2$-terminal Kinase (JNK/SAPK), JBC, vol. 273(43), pp. 28253-28260 (1998).
Lesk, et al., "Homology modeling: inferences from tables of aligned sequences", Curr. Opin. Struc. Biol., vol. 2, pp. 242-247 (1992).
Levitt, Michael, "Accurate Modeling of Protein Conformation by Automatic Segment Matching", J. Mol. Biol., vol. 226, pp. 507-533 (1992).
Li, et al., "Amino-terminal protein processing in Saccharomycess cerevisiae is an essential function that requires two distinct methionine aminopeptidases", PNAS, vol. 92, pp. 12357-12361 (1995).
Lin, et al., "β-Catenin, a novel prognostic marker for breast cancer: Its roles in cyclin D1 expression and cancer progression", PNAS, vol 97(8), pp. 4262-4266 (2000).
Lombroso, et al., "Molecular characterization of a protein-tyrosine-phosphatase enriched in striatum", PNAS, vol. 88, pp. 7242-7246 (1991
Lowther, et al., "Structure and function of the methionine aminopeptidases", Bioch. Biophy. Acta, vol. 1477, pp. 157-167 (2000).
Matthews, et al., "Identification of an additional member of the protein-tyrosine-phosphatase family: Evidence for alternative splicing in the tyrosine phosphatase domain", PNAS vol. 87, pp. 4444-4448 (1990).
Michaelson, et al., "β-catenin is a downstream effector of Wnt-mediated tumorigenesis in the mammary gland", Oncogene, vol. 20, pp. 5093-5099 (2001).
Martin, Yvonne C., "3D Database Searching in Drug Design", J. Med. Chem., vol. 35(12), pp. 2145-2154 (1992).
Masuda, et al., "MKP-7, a Novel Mitogen-activated Protein Kinase Phosphatase, Functions as a Shuttle Protein", JBC, vol. 276(42), pp. 39002-39011 (2001.
Morla, et al., "Dephosphorylation Accompanies Activation during Entry into Mitosis", Cell, vol. 58, pp. 193-203 (1989).
Musgrove, et al., "Cyclins and Breast Cancer", J. Mammary Gland Biology Neoplasia, vol. 1(2), pp. 153-162 (1996).
Mustelin, et al., "Rapid activation of the T-cell tyrosine protein kinase pp. 56[lck] by the CD45 phosphotyrosine phosphatase", PNAS, vol. 86, pp. 6302-6306 (1989).
Nagase, et al., "Prediciton of the Coding Sequences of Unidentified Human Genes. III. The Coding Sequences of 40 New Genes (KIAA0081-KIAA0120) Deduced by Analysis of cDNA Clones from Human Cell Line KG-1", DNA Res., vol. 2, pp. 37-43 (1995).

Nagase, et al., "Prediciton of the Coding Sequences of Unidentified Human Genes. XIX. The complete Sequences of 100 New cDNA Clones from Brain Which Code for large Proteins *in vitro*", DNA Res., vol. 7, pp. 347-355 (2000).

Nguyen, et al., "Prostatic Acid Phosphatase in Serum of Patients with Prostatic Cancer is a Specific Phosphotyrosine Acid Phosphatase", Clin. Chem., vol. 36(8), pp. 1450-1455 (1990).

Novotny, et al., "Criteria That Discriminate Between Native Proteins and Incorrectly Folded Models", Proteins, vol. 4, pp. 19-30 (1988).

Nurse, Paul, "Universal control mechanism regulating onset of M-phase", Nature, vol. 344, pp. 503-508 (1990).

Ohagi, et al., Sequence of a cDNA encoding human LRP (leukocyte common antigen-related peptide), Nucleic Acids Res., vol. 18(23), pp. 7159 (1990).

Ostergaard, et al., "Expression of CD45 alters phosphorylation of the *lck*-encoded tyrosine protein kinase in murine lymphoma T-cell lines", PNAS, vol. 86, pp. 8959-8963 (1989).

Pearson, William R., "Rapid and Sensitive Sequence Comparison with FASTP and FASTA", Methods in Enzymol., vol. 183, pp. 63-98 (1990).

Ralph, et al., "Structural variants of human T200 glycoprotein (leukocyte-common antigen)", EMBO J., vol. 6(5), 1251-1257 (1987).

Sap, et al., "Cloning and expression of a widely expressed receptor tyrosine phosphatase", PNAS, vol. 87, pp. 6112-6116 (1990).

Schaefer, Brian C., "Revolutions in Rapid Amplification of cDNA Ends: New Strategies for Polymerase Chain Reaction Cloning of Full-Length cDNA Ends", Anal. Biochem., vol. 227, pp. 255-273 (1995).

Seidman, et al., "The Role of ERK 1/2 and p38 MAP-Kinase Pathways in Taxol-Induced Apoptosis in Human Ovarian Carcinoma Cells", Experimental Cell Res., vol. 268, pp. 84-92 (2001).

Shimohama, et al., "Reduction of Low-Molecular-Weight Acid Phosphatase Activity in Alzheimer Brains", Ann. Neurol., vol. 33, pp. 616-621 (1993).

Sin, et al., "The anti-angiogenic agent fumagillin covalently binds and inhibits the methionine aminopeptidase, MetAP-2", PNAS, vol. 04, pp. 6099-6103 (1997).

Sonnhammer, et al., "Pfam: A Comprehensive Database of Protein Domain Families Based on Seed Alignments", Proteins, vol. 28, pp. 405-420 (1997).

Stewart, et al., "Crystal structure of the MAPK phosphatase Pyst 1 catalytic domain and implications for regulated activation", Nature Struc. Biol., vol. 6(2), pp. 174-181 (1999).

Streuli, et al., "A family of receptor-linked protein tyrosine phosphatases in humans and *Drosophila*", PNAS, vol. 86, pp. 8698-8702 (1989).

Streuli, et al., "Distinct functional roles of the two intracellular phosphatase like domains of the receptor-linked protein tyrosine phosphatases LCA and LAR", EMBO J., vol. 9(8), pp. 2399-2407 (1990).

Sugimoto, et al., "A Simple and Efficient Method for the Oligonucleotide-Directed Mutagenesis Using Plasmid DNA Template and Phosphorothioate-Modified Nucleotide", Analytical Biochem., vol. 179, pp. 309-311 (1989).

Tanoue, et al., "A Novel MAPK Phosphatase MKP-7 Acts Preferentially on JNK/SAPK and p38α and β MAPKs", JBC, vol. 276(28), pp. 26629-26639 (2001).

Taylor, et al., "The rapid generation of oligonucleotide-directed mutations at high frequency using phosphorothioate-modified DNA", Nucleic Acids Res., vol. 13(24), pp. 8765-8785 (1985).

Thomas, Matthew L., "The Leukocyte Common Antigen Family", Ann. Rev. Immunol., vol. 7, pp. 339-369 (1989).

Tsai, et al., "Isolation and Characterization of Temperature-sensitive and Thermostable Mutants of the Human Receptor-like Protein Tyrosine Phosphatase LAR", JBC, vol. 266(16), pp. 10534-10543 (1991).

Ullrich, et al., "Signal Transduction by Receptors with Tyrosine Kinase Activity", Cell, vol. 61, pp. 203-212 (1990).

Vandeyar, et al., "A simple and rapid method for the selection of oligodeoxynucleotide-directed mutants", Gene, vol. 65, pp. 129-133 (1988).

Weaver, et al., "CDB+, T-Cell Clones Deficient in the Expression of the CD45 Protein Tyrosine Phosphatase Have Impaired Responses to T-Cell Receptor Stimuli", Molec. Cell. Biol., vol. 11(9), pp. 4415-4422 (1991).

Weiss, Arthur, "Molecular and Genetic Insights Into T Cell Antigen Receptor Structure And Function", Annu. Rev. Genet., vol. 25, pp. 487-510 (1991).

Yi, et al., "Protein Tyrosine Phosphatase Containing SH2 Domains: Characterization, Preferential Expression in Hematopoietic Cells, and Localization to Human Chromosome 12p12-p13", Molec. Cell. Biol., vol. 12(2), pp. 836-846 (1992).

Yoon, et al., "Protein Tyrosine Kinase Inhibitors Block the Stimulatory Actions of Phosphotyrosine Phosphatase Inhibitors to Increase Cell Proliferation, Alkaline Phosphatase Activity, and Collagen Synthesis in Normal Human Bone Cells", Am. J. Nephrol., vol. 20, pp. 153-162 (2000).

Yuvaniyama, et al., "Crystal Structure of the Dual Specificity Protein Phosphatase VHR", Science, vol. 272, pp. 1328-1331 (1996).

NCBI Entrez Accession No. A55148 (gi:1083770), Mauro, et al., Sep. 10, 1999.

NCBI Entrez Accession No. AAB40597 (gi:1777755), Crowell, et al., Jul. 30, 1999.

NCBI Entrez Accession No. AAB40598 (gi:1777757), Crowell, et al., Jul. 30, 1999.

NCBI Entrez Accession No. AAF53506 (gi:22946607), Adams, et al., Nov. 12, 2004.

NCBI Entrez Accession No. AAG28768 (gi:11066925), Morrison, et al., Nov. 17, 2000.

NCBI Entrez Accession No. AAH01140 (gi:12654609), Strausberg, et al., Jun. 29, 2004.

NCBI Entrez Accession No. AB013382 (gi:3869139), Furukawa, T., Mar. 27, 1999.

NCBI Entrez Accession No. AB026436 (gi:5138994), Tanoue, T., Jul. 22, 1999.

NCBI Entrez Accession No. AL354751 (gi:9187237), Clark, G., Jan. 4, 2005.

NCBI Entrez Accession No. AL360020 (gi:13872351), Johnson, C., Jan. 6, 2005.

NCBI Entrez Accession No. BAB40814 (gi:13548677), Masuda, et al., Oct. 18, 2001.

NCBI Entrez Accession No. BAB71060 (gi:16550836), Ota, et al., Jan. 30, 2004.

NCBI Entrez Accession No. CAD13382 (gi:17402248), Johnson, C., Jan. 6, 2005.

NCBI Entrez Accession No. JC5981 (gi:7513774), Zeng, et al., Mar. 17, 1999.

NCBI Entrez Accession No. NP_002839 (gi:4506323), Aguiar, et al., Oct. 26, 2004.

NCBI Entrez Accession No. NP_003662 (gi:4502699), Li, et al., Oct. 26, 2004.

NCBI Entrez Accession No. NP_003663 (gi:15451929), Kaiser, et al., Oct. 26, 2004.

NCBI Entrez Accession No. NP_004411 (gi:4758212), Hink, et al., Oct. 26, 2004.

NCBI Entrez Accession No. NP_032774 (gi:6679156), Strausberg, et al., Oct. 28, 2004.

NCBI Entrez Accession No. NP_035346 (gi:47059069), Beltran, et al., Oct. 28, 2004.

NCBI Entrez Accession No. NP_060293 (gi:56786144), Takagaki, et al., Dec. 22, 2004.

NCBI Entrez Accession No. P32587 (gi:417568), Millar, et al., Jan. 25, 2005.

NCBI Entrez Accession No. XP_049675 (gi:16165772), NCBI's Annotation Process, May 8, 2002.

NCBI Entrez Accession No. 1AAX (gi:2981942), Barford, et al., Jan. 16, 1997.

NCBI Entrez Accession No. 1MKP (gi:5822131), Stewart, et al., Jul. 11, 1998.

NCBI Entrez Accession No. 1VHRA (gi:1633321), Ishibashi, et al., Feb. 20, 1996.

NCBI Entrez Accession No. U27193 (gi:1109781), Martell, et al., Dec. 8, 1995.

* cited by examiner

Figure 1

BMY_HPP1_A

```
  1 CTAGTTTACT TCTACAATTT CGGATGGAAG GATTATGGTG TAGCGTCTCT TACTACTATC 60
  1 L   V   Y   F   Y   N   F   G   W   K   D   Y   G   V   A   S   L   T   T   I   20

61 CTAGATATGG TGAAGGTGAT GACATTTGCC TTACAGGAAG GAAAAGTAGC TATCCATTGT 120
 21 L   D   M   V   K   V   M   T   F   A   L   Q   E   G   K   V   A   I   H   C   40

121 CATGCAGGGC TTGGTCGAAC AGGT 144
 41 H   A   G   L   G   R   T   G   48
```

BMY_HPP1_B

```
  1 GATGTCTTCT GGGCCCTCCT GTGGAACACA GTT 33
  1 D   V   F   W   A   L   L   W   N   T   V   11
```

Figure 2

```
  1  GTGGCCCGGGAGGCGCCGAGGCCAGGTAGGTGCGATGGGCGTGCAGCCCCCAACTTCTC    60
  1   W  P  G  R  R  R  G  Q  V  G  A  M  G  V  Q  P  P  N  F  S   20

61  CTGGGTGCTTCCGGGCCGGCTGGCGGGACTGGCGCTGCCGCGGCTCCCCGCCCACTACCA   120
 21   W  V  L  P  G  R  L  A  G  L  A  L  P  R  L  P  A  H  Y  Q   40

121  GTTCCTGTTGGACCTGGGCGTGCGGCACCTGGTGTCCCTGACGGAGCGCGGGCCCCCTCA   180
 41   F  L  L  D  L  G  V  R  H  L  V  S  L  T  E  R  G  P  P  H   60

181  CAGCGACAGCTGCCCCGGCCTCACCCTGCACCGCCTGCGCATCCCCGACTTCTGCCCGCC   240
 61   S  D  S  C  P  G  L  T  L  H  R  L  R  I  P  D  F  C  P  P   80

241  GGCCCCCGACCAGATCGACCGCTTCGTGCAGATCGTGGACGAGGCCAACGCACGGGGAGA   300
 81   A  P  D  Q  I  D  R  F  V  Q  I  V  D  E  A  N  A  R  G  E  100

301  GGCTGTGGGAGTGCACTGTGCTCTGGGCTTTGGCCGCACTGGCACCATGCTGGCCTGTTA   360
101   A  V  G  V  H  C  A  L  G  F  G  R  T  G  T  M  L  A  C  Y  120

361  CCTGGTGAAGGAGCGGGGCTTGGCTGCAGGAGATGCCATTGCTGAAATCCGACGACTACG   420
121   L  V  K  E  R  G  L  A  A  G  D  A  I  A  E  I  R  R  L  R  140

421  ACCCGGCCCCATCGAGACCTATGAGCAGGAGAAAGCAGTCTTCCAGTTCTACCAGCGAAC   480
141   P  G  P  I  E  T  Y  E  Q  E  K  A  V  F  Q  F  Y  Q  R  T  160

481  GAAATAAGGGCCTTAGTACCCTTCTACCAGGCCCTCACTCCCCTTCCCCATGTTGTCGA   540
161   K  *  G  A  L  V  P  F  Y  Q  A  L  T  P  L  P  H  V  V  D  180

541  TGGGGCCAGAGATGAAGGGAAGTGGACTAAAGTATTAAACCCTCTAGCTCCCATTGGCTG   600
181   G  A  R  D  E  G  K  W  T  K  V  L  N  P  L  A  P  I  G  *  200

601  AAGACACTGAAGTAGCCCACCCCTGCAGGCAGGTCCTGATTGAAGGGGAGGCTTGTACTG   660
201   R  H  *  S  S  P  P  L  Q  A  G  P  D  *  R  G  G  L  Y  C  220

661  CTTTGTTGAATAAATGAGTTTTACGAACCAGGGAAAAAAAAAAAAAAAAAAAAGAAAAAA   720
221   F  V  E  *  M  S  F  T  N  Q  G  K  K  K  K  K  R  K  K      240

721  AAAAAAAAAAAAAAAAAAAAAGAA    746
241   K  K  K  K  K  K  R        248
```

Figure 3

```
  1 ATGGCTAGAA TGAACCTCCC TGCTTCTGTG GACATTGCAT ACAAAAATGT GAGATTTCTT  60
  1 M  A  R  M  N  L  P  A  S  V  D  I  A  Y  K  N  V  R  F  L      20

61 ATTACACACA ACCCAACCAA TACCTACTTT AATAGATTCT TACAGGAACT TAAGCAGGAT 120
 21 I  T  H  N  P  T  N  T  Y  F  N  R  F  L  Q  E  L  K  Q  D      40

121 GGAGTTACCA CCATAGTAAG AGTATGAAAA GCAACTTACA ACATTGCTCT TTTAGAGAAG 180
 41 G  V  T  T  I  V  R  V  *  K  A  T  Y  N  I  A  L  L  E  K      60

181 GGAAGCATCC AGGTTCCGGA CTGGCCTTTT GATGATGGTA CAGCACCATC CAGCCAGATA 240
 61 G  S  I  Q  V  P  D  W  P  F  D  D  G  T  A  P  S  Q  I         80

241 ATTGATAACT GGTTAAAACT TATGAAAAAT AAATTTCATG AAGATCCTGG TTGTTGTATT 300
 81 I  D  N  W  L  K  L  M  K  N  K  F  H  E  D  P  G  C  C  I     100

301 GCAATTCACT GTGTTGTAGG TTTTGGGTGA GCTCCAGTTG CTAGTTGCCC TAGCTTTAAT 360
101 A  I  H  C  V  V  G  F  G  *  A  P  V  A  S  C  P  S  F  N     120

361 TGAAGGTGGA ATGAAATATG AAAATGTAGT ACAGTTCATC AGATAAAAGT GACATGGAAC 420
121 *  R  W  N  E  I  *  K  C  S  T  V  H  Q  I  K  V  T  W  N     140

421 TTTTAACAGC AAACAACTTT TGTATTTGGA GAAATATTGT CTTAAAATAT GCTTGCACCT 480
141 F  *  Q  Q  T  T  F  V  F  G  E  I  L  S  *  N  M  L  A  P     160

481 CAGAAATCCC AGAAATAACT GTTTCCTTCA G 511
161 Q  K  S  Q  K  *  L  F  P  S        171
```

Figure 4A

```
   1 CTCAGGCAGA ACTATGAGGC CAAGAGTGCT CATGCGCACC AGGCTTTCTT TTTGAAATTC  60
   1 L  R  Q  N   Y  E  A   K  S  A    H  A  H  Q   A  F  F    L  K  F    20

61 GAGGAGCTGA AGGAGGTGAG CAAGGAGCAG CCCAGACTGG AGGCTGAGTA CCCTGCCAAC 120
  21 E  E  L  K   E  V  S   K  E  Q    P  R  L  E   A  E  Y    P  A  N    40

121 ACCACCAAGA ACTGTTAACC ACATGTGCTA CCCTATGACC ACTCCAGGGT CAGGCTGACC 180
  41 T  T  K  N   C  *  P   H  V  L    P  Y  D  H   S  R  V    R  L  T    60

181 CAGCTGGAGG GAGAGCCTCA TTCTGACTAC ATCAATGCCA ACTTGGTCCC AGGCTACACC 240
  61 Q  L  E  G   E  P  H   S  D  Y    I  N  A  N   L  V  P    G  Y  T    80

241 CGCCCACAGG AGTTCATTGC CTCTCAGGGG CCTCTCAAGA AAACACTGGA GAACTTCTGG 300
  81 R  P  Q  E   F  I  A   S  Q  G    P  L  K  K   T  L  E    N  F  W   100

301 CGGCTGGTGC GGGAGCAGCA GGTCCGCATC ATCATCATGC CGACCATCAG CATGGAGAAC 360
 101 R  L  V  R   E  Q  Q   V  R  I    I  I  M  P   T  I  S    M  E  N   120

361 GGGAGGGTGC TGTGTGAGCA TTACTGGCTG ACCGACTCTA CCCCGGACAC CCATGGTCAC 420
 121 G  R  V  L   C  E  H   Y  W  L    T  D  S  T   P  D  T    H  G  H   140

421 ATCACCATCC ACCTCCTAGC TGAGGAGCCT GAGGATGAGT GGACCAAGCG GGAATTCCAG 480
 141 I  T  I  H   L  L  A   E  E  P    E  D  E  W   T  K  R    E  F  Q   160

481 CTGCAGCACG TTGTCCAGCA ACATCAACGG AGGGTGGAGC AACTGCAGTT CACCACCTGA 540
 161 L  Q  H  V   V  Q  Q   H  Q  R    R  V  E  Q   L  Q  F    T  T  *   180

541 TCCGACCACA GCATCCTTGA GGCTCCCAGC TCCCTGCTCG CCTTTATGGA GCTGGTACAG 600
 181 S  D  H  S   I  L  E   A  P  S    S  L  L  A   F  M  E    L  V  Q   200

601 TAGCAGGCAA GGGCCACCCA GGGCGTGGGA CCCATCCTGG TGCACTGCAG GGGCTGTCCC 660
 201 *  Q  A  R   A  T  Q   G  V  G    P  I  L  V   H  C  R    G  C  P   220

661 TGCGGTGTGG GCATGGGCCG GACAGGCACC TTCGTGGCCC TGTCGAGGCT GCTGCAGCAG 720
 221 C  G  V  G   M  G  R   T  G  T    F  V  A  L   S  R  L    L  Q  Q   240

721 CTGGAGGAGG AGCAGATGGT AGACGTGTTC CATGCTGTGT ATGCACTCCG GATGCACCAG 780
 241 L  E  E  E   Q  M  V   D  V  F    H  A  V  Y   A  L  R    M  H  Q   260

781 CCCCTCATGA TCCAGACCCT GAGCCAGTAC GTCTTCCTGC ACAGCTGCCT ACTGAACAAG 840
 261 P  L  M  I   Q  T  L   S  Q  Y    V  F  L  H   S  C  L    L  N  K   280

841 ATTCTGGAAG GACCCTTCAA CATCTCTGAG TCTTGGCCCA TCTCTGTGAC GGACCTCCCG 900
 281 I  L  E  G   P  F  N   I  S  E    S  W  P  I   S  V  T    D  L  P   300

901 CAGGCGTGTG CCAAGAGGGC AGCCAGTGCC AATGCTGGCT TCTTGAAGGA GTACGAGGCC 960
 301 Q  A  C  A   K  R  A   A  S  A    N  A  G  F   L  K  E    Y  E  A   320

961 ATCAAGGACG AGGCTGGCTT TTCCGCACCC CCGCCTGGCT ATGAGCAGGA CAGCCCCGTC 1020
 321 I  K  D  E   A  G  F   S  A  P    P  P  G  Y   E  Q  D    S  P  V   340

1021 TCCTATGACC GTTCTCAGGG GCAGTTTTCT CCGGTGGAGG AGAGCCCCCC TGACGACATG 1080
 341 S  Y  D  R   S  Q  G   Q  F  S    P  V  E  E   S  P  P    D  D  M   360

1081 CCTCTCTGGA AGCCAATGAT CTGTGCTCTG CAGGGTGGGC CCTCTGGCCG TGATCATACG 1140
 361 P  L  W  K   P  M  I   C  A  L    Q  G  G  P   S  G  R    D  H  T   380
```

Figure 4B

```
1141 GTGCTGACTG GCCCCGCAGG GCCAAAGGAG CTCTGGGAGC TGGTGTGGCA GCACAGGGCT 1200
 381 V  L  T  G   P  A  G    P  K  E    L  W  E  L    V  W  Q    H  R  A   400

1201 CATGTGCTTG TCTCTCTTTG CCCACCCAAT GTCATGGAGA AGGAATTCTG GCCAACGGAG 1260
 401 H  V  L    S  L  C     P  P  N    V  M  E    E  F  W      P  T  E    420

1261 ATGCAGCCCG TAGTCACAGA CATGGTGACG GTGCACTGGG TGGCTGAGAG CAGCACAGCA 1320
 421 M  Q  P  V   V  T  D   M  V  T    V  H  W  V   A  E  S    S  T  A    440

1321 GGCTGGTTCT GTACCCTCCT CAGGGTCACA CATGGGGAGA GCAGGAAGGA AAGGGAGGTG 1380
 441 G  W  F  C   T  L  L   R  V  T    H  G  E  S   R  K  E    R  E  V    460

1381 CAGAGACTGC AATTTCCATA CCTGGAGCCT GGGCATGAGC TGCCCGCCAC CACCCTGCTG 1440
 461 Q  R  L  Q   F  P  Y   L  E  P    G  H  E  L   P  A  T    T  L  L    480

1441 CCCTTCCTGG CTGCTGTGGG CCAGTGCTGC TCTCGGGGCA ACAACAAGAA GCCGGGCACA 1500
 481 P  F  L  A   V  G      Q  C  C    S  R  G  N   N  K  K    P  G  T    500

1501 CTGCTCAGCC ACTCCAACAA GGGTGCAACC CAGCTGGGCA CCTTCCTGGC CATGGAGCAG 1560
 501 L  L  S  H   S  N  K   G  A  T    Q  L  G  T   F  L  A    M  E  Q    520

1561 CTGCTGCAGC AGGCAGGGTC TGAGTGCACC GTGGATATCT TTAACGTGGC CCTGCAGCAG 1620
 521 L  L  Q  Q   A  G  S   E  C  T    V  D  I  F   N  V  A    L  Q  Q    540

1621 TCTCAGGCCT GTGGCCTTAT GACCCCAACA CTGAAGCAGT ATGTCTACCT CTACAACTGT 1680
 541 S  Q  A  C   G  L  M   T  P  T    L  K  Q  Y   V  Y  L    Y  N  C    560

1681 CTGAACAGCG CGCTGGCAGA CGGGCTGCCC 1710
 561 L  N  S  A   L  A  D   G  L  P   570
```

Figure 5A

```
  1  ATGTTCATTTTAAAAAACTTCAGGATGGGCACAAACACACAGAAGTGGGAAATGAATAAA    60

61  AGAGTATTGATAAATTTTGAAAATTGTTGAAGCTGAGTAATGGGCTTTCAGTCCAGTGT   120

121  AAAGCTGTTGGAGCGCGGGAGCAAAGGTAAAGAATGATGTAATGCGCTGGCTGCTCCAAA  180

181  GCATCTTTTGTTGTGGAATGGTTATTCCAGTCATCTCTTTATGAATCAAATGTGAGGGGC  240

241  TGCTTTGTGGACGGAGTCCTTTGCAAGAGCACATCAACGGGAAAGAGAAAGAGACATTCA  300

301  CTTGGAGGGCTCTTGCTGAAAATGGGTTTAACTCTCCTTTTGCCAGTCACCACCAGCCTG  360

361  ACCTCATACACTTTTAGTACAATGGAGTGGCTGAGCCTTTGAGCACACCACCATTACATC  420

421  ATCGTGGCAAATTAAAGAAGGAGGTGGGAAAAGAGGACTTATTGTTGTCATGGCCCATGA  480
  1                                                        M  A  H  E     4

481  GATGATTGGAACTCAAATTGTTACTGAGAGGTTGGTGGCTCTGCTGGAAAGTGGAACGGA  540
  5   M  I  G  T  Q  I  V  T  E  R  L  V  A  L  L  E  S  G  T  E    24

541  AAAAGTGCTGCTAATTGATAGCCGGCCATTTGTGGAATACAATACATCCCACATTTTGGA  600
 25   K  V  L  L  I  D  S  R  P  F  V  E  Y  N  T  S  H  I  L  E    44

601  AGCCATTAATATCAACTGCTCCAAGCTTATGAAGCGAAGGTTGCAACAGGACAAAGTGTT  660
 45   A  I  N  I  N  C  S  K  L  M  K  R  R  L  Q  Q  D  K  V  L    64

661  AATTACAGAGCTCATCCAGCATTCAGCGAAACATAAGGTTGACATTGATTGCAGTCAGAA  720
 65   I  T  E  L  I  Q  H  S  A  K  H  K  V  D  I  D  C  S  Q  K    84

721  GGTTGTAGTTTACGATCAAAGCTCCCAAGATGTTGCCTCTCTCTTCAGACTGTTTTCT    780
 85   V  V  V  Y  D  Q  S  S  Q  D  V  A  S  L  S  S  D  C  F  L   104

781  CACTGTACTTCTGGGTAAACTGGAGAAGAGCTTCAACTCTGTTCACCTGCTTGCAGGTGG  840
105   T  V  L  L  G  K  L  E  K  S  F  N  S  V  H  L  L  A  G  G   124

841  GTTTGCTGAGTTCTCTCGTTGTTTCCCTGGCCTCTGTGAAGGAAAATCCACTCTAGTCCC  900
125   F  A  E  F  S  R  C  F  P  G  L  C  E  G  K  S  T  L  V  P   144

901  TACCTGCATTTCTCAGCCTTGCTTACCTGTTGCCAACATTGGGCCAACCCGAATTCTTCC  960
145   T  C  I  S  Q  P  C  L  P  V  A  N  I  G  P  T  R  I  L  P   164
```

Figure 5B

```
 961  CAATCTTTATCTTGGCTGCCAGCGAGATGTCCTCAACAAGGAGCTGATGCAGCAGAATGG  1020
 165   N  L  Y  L  G  C  Q  R  D  V  L  N  K  E  L  M  Q  Q  N  G     184

1021  GATTGGTTATGTGTTAAATGCCAGCAATACCTGTCCAAAGCCTGACTTTATCCCCGAGTC  1080
 185   I  G  Y  V  L  N  A  S  N  T  C  P  K  P  D  F  I  P  E  S     204

1081  TCATTTCCTGCGTGTGCCTGTGAATGACAGCTTTTGTGAGAAAATTTTGCCGTGGTTGGA  1140
 205   H  F  L  R  V  P  V  N  D  S  F  C  E  K  I  L  P  W  L  D     224

1141  CAAATCAGTAGATTTCATTGAGAAAGCAAAAGCCTCCAATGGATGTGTTCTAGTGCACTG  1200
 225   K  S  V  D  F  I  E  K  A  K  A  S  N  G  C  V  L  V  H  C     244

1201  TTTAGCTGGGATCTCCCGCTCCGCCACCATCGCTATCGCCTACATCATGAAGAGGATGGA  1260
 245   L  A  G  I  S  R  S  A  T  I  A  I  A  Y  I  M  K  R  M  D     264

1261  CATGTCTTTAGATGAAGCTTACAGATTTGTGAAAGAAAAAAGACCTACTATATCTCCAAA  1320
 265   M  S  L  D  E  A  Y  R  F  V  K  E  K  R  P  T  I  S  P  N     284

1321  CTTCAATTTTCTGGGCCAACTCCTGGCCTATGAGAAGAAGATTAAGAACCAGACTGGAGC  1380
 285   F  N  F  L  G  Q  L  L  A  Y  E  K  K  I  K  N  Q  T  G  A     304

1381  ATCAGGGCCAAAGAGCAAACTCAAGCTGCTGCCCCTGGAGAAGCCAAATGAACCTGTCCC  1440
 305   S  G  P  K  S  K  L  K  L  L  P  L  E  K  P  N  E  P  V  P     324

1441  TGCTGTCTCAGAGGGTGGACAGAAAAGCGAGACGCCCCTCAGTCCACCCTGTGCCGACTC  1500
 325   A  V  S  E  G  G  Q  K  S  E  T  P  L  S  P  P  C  A  D  S     344

1501  TGCTACCTCAGAGGCAGCAGGACAAAGGCCCGTGCATCCCGCCAGCGTGCCCAGCGTGCC  1560
 345   A  T  S  E  A  A  G  Q  R  P  V  H  P  A  S  V  P  S  V  P     364

1561  CAGCGTGCAGCCGTCGCTGTTAGAGGACAGCCCGCTGGTACAGGCGCTCAGTGGGCTGCA  1620
 365   S  V  Q  P  S  L  L  E  D  S  P  L  V  Q  A  L  S  G  L  H     384

1621  CCTGTCCGCAGACAGGCTGGAAGACAGCAATAAGCTCAAGCGTTCCTTCTCTCTGGATAT  1680
 385   L  S  A  D  R  L  E  D  S  N  K  L  K  R  S  F  S  L  D  I     404

1681  CAAATCAGTTTCATATTCAGCCAGCATGGCAGCATCCTTACATGGCTTCTCCTCATCAGA  1740
 405   K  S  V  S  Y  S  A  S  M  A  A  S  L  H  G  F  S  S  S  E     424

1741  AGATGCTTTGGAATACTACAAACCTTCCACTACTCTGGATGGGACCAACAAGCTATGCCA  1800
 425   D  A  L  E  Y  Y  K  P  S  T  T  L  D  G  T  N  K  L  C  Q     444

1801  GTTCTCCCCTGTTCAGGAACTATCGGAGCAGACTCCCGAAACCAGTCCTGATAAGGAGGA  1860
 445   F  S  P  V  Q  E  L  S  E  Q  T  P  E  T  S  P  D  K  E  E     464
```

Figure 5C

```
1861 AGCCAGCATCCCCAAGAAGCTGCAGACCGCCAGGCCTTCAGACAGCCAGAGCAAGCGATT 1920
 465   A   S   I   P   K   K   L   Q   T   A   R   P   S   D   S   Q   S   K   R   L   484

1921 GCATTCGGTCAGAACCAGCAGCAGTGGCACCGCCCAGAGGTCCCTTTTATCTCCACTGCA 1980
 485   H   S   V   R   T   S   S   S   G   T   A   Q   R   S   L   L   S   P   L   H   504

1981 TCGAAGTGGGAGCGTGGAGGACAATTACCACACCAGCTTCCTTTTCGGCCTTTCCACCAG 2040
 505   R   S   G   S   V   E   D   N   Y   H   T   S   F   L   F   G   L   S   T   S   524

2041 CCAGCAGCACCTCACGAAGTCTGCTGGCCTGGGCCTTAAGGGCTGGCACTCCGATATCTT 2100
 525   Q   Q   H   L   T   K   S   A   G   L   G   L   K   G   W   H   S   D   I   L   544

2101 GGCCCCCCAGACCTCTACCCCTTCCCTCACCAGCAGCTGGTATTTTGCCACAGAGTCCTC 2160
 545   A   P   Q   T   S   T   P   S   L   T   S   S   W   Y   F   A   T   E   S   S   564

2161 ACACTTCTACTCTGCCTCAGCCATCTACGGAGGCAGTGCCAGTTACTCTGCCTACAGCTG 2220
 565   H   F   Y   S   A   S   A   I   Y   G   G   S   A   S   Y   S   A   Y   S   C   584

2221 CAGCCAGCTGCCCACTTGCGGAGACCAAGTCTATTCTGTGCGCAGGCGGCAGAAGCCAAG 2280
 585   S   Q   L   P   T   C   G   D   Q   V   Y   S   V   R   R   R   Q   K   P   S   604

2281 TGACAGAGCTGACTCGCGGCGGAGCTGGCATGAAGAGAGCCCCTTTGAAAAGCAGTTTAA 2340
 605   D   R   A   D   S   R   R   S   W   H   E   E   S   P   F   E   K   Q   F   K   624

2341 ACGCAGAAGCTGCCAAATGGAATTTGGAGAGAGCATCATGTCAGAGAACAGGTCACGGGA 2400
 625   R   R   S   C   Q   M   E   F   G   E   S   I   M   S   E   N   R   S   R   E   644

2401 AGAGCTGGGGAAAGTGGGCAGTCAGTCTAGCTTTTCGGGCAGCATGGAAATCATTGAGGT 2460
 645   E   L   G   K   V   G   S   Q   S   S   F   S   G   S   M   E   I   I   E   V   664

2461 CTCCTGAGAAGAAAGACACTTGTGACTTCTATAGACAATTTTTTTTTCTTGTTCACAAAA 2520
 665   S                                                                                665

2521 AAATTCCCTGGGAATCTGAAATATGTATGTGGGCATACATATATATTTTTGGAAAATGGA 2580

2581 GCTATGGTGTAAAAGCAACAGGTGGATCAACCCAGTTGTTACTCTCTTAACATCTGCATT 2640

2641 TCAGAGATCAGCTAATACTTGCTCTCAACAAAAATGGAAGGGCAGATGCTAGAATCCCCC 2700

2701 CTAGACGGAGGAAAACCATTTTATTCAGTGAATTACACATCCTCTTGTTCTTAAAAAGC 2760

2761 AAGTGTCTTTGGTGTTGGAGGACAAAATCCCCTACCATTTTCACGTTGTGCTACTAAGAG 2820
```

Figure 5D

```
2821  ATCTCAAATATTAGTCTTTGTCCGGACCCTTCCATAGTACACCTTAGCGCTGAGACTGAG  2880

2881  CCAGCTTGGGGGTCAGGTAGGTAGACCCTGTTAGGGACAGAGCCTAGTGGTAAATCCAAG  2940

2941  AGAAATGATCCTATCCAAAGCTGATTCACAAACCCACGCTCACCTGACAGCCGAGGGACA  3000

3001  CGAGCATCACTCTGCTGGACGGACCATTAGGGGCCTTGCCAAGGTCTACCTTAGAGCAAA  3060

3061  CCCAGTACCTCAGACAGGAAAGTCGGGGCTTTGACCACTACCATATCTGGTAGCCCATTT  3120

3121  TCTAGGCATTGTGAATAGGTAGGTAGCTAGTCACACTTTTCAGACCAATTCAAACTGTCT  3180

3181  ATGCACAAAATTCCCGTGGGCCTAGATGGAGATAATTTTTTTTCTTCTCAGCTTTATGA  3240

3241  AGAGAAGGGAAACTGTCTAGGATTCAGCTGAACCACCAGGAACCTGGCAACATCACGATT  3300

3301  TAAGCTAAGGTTGGGAGGCTAACGAGTCTACCTCCCTCTTTGTAAATCAAAGAATTGTTT  3360

3361  AAAATGGGATTGTCAATCCTTTAAATAAAGATGAACTTGGTTTCAAGCCAAATGTGAATT  3420

3421  TATTTGGGTTGGTAGCAGAGCAGCAGCACCTTCAAATTCTCAGCCAAAGCAGATGTTTTT  3480

3481  GCCCTTTCTGCTTCACTGCATGGATACAGTTGGTAAAATGTAATAATATGGCAGAATTTT  3540

3541  ATAGGAAACTTCCTAGGGAGGTAAATTATGGGAAGATTAAGAAAGGTACAAATTGCTGAG  3600

3601  GAGAAGCAGGAAACCTGTTTCCTTAGTGGCTTTTATCCCCTCGGCATGCGATGGGCTGA  3660

3661  TGTTTCTATAATTGCCTCAGACTTTCACATTTACTAGTAGGGCTGAGAGAGGCTTTAGTG  3720

3721  AGGAAAGAATATTCAGAATAAAACGGTTGAGAAAGCTGAGAAGACCATTGAGTTTTGATC  3780

3781  AGTTGTGAATAGAGTGCAAAGCCATGGCCAAGCTGTTTTTGGAAACGCTGGCCGGCGTGT  3840

3841  CTTCAGTGGAAAAAGCAAATCAAAATGGAGCGAGAGCAAAGGGGCGTCCTCAGTCCTCAA  3900

3901  CCTACAATCACTGTATGGAATCGGTCCTGGCAGCTGAACATAGGAGGTCACTGGAACAAG  3960

3961  TGATAGTGCAGATTGGCTTTCAAACATCCTCCTGGCTTGAGTTTTATCAGCTACAATGTG  4020
```

Figure 5E

```
4021  GGTCCTCTTTTGAAGCCTTAATTCACAACAGCAGCTTTTTGGGGGTGGGGCTGGGCGGGT  4080

4081  GTTGTCATTGTTCTTTCCCTTCCTGTAAGTGTCGCTAGTTGCTGCCTCGTATCTCAGGTT  4140

4141  TTTCTCTGTTTTTGAGAAATGGACAGTTTTTTGACCAGGATGTGACTTCATGTTTCCTAT  4200

4201  GGTGACTTCTAAAACCAGCACAGAATGATATGACTCAACACAGACCGACTTGGTTATGGG  4260

4261  GATGATGAGCCGCACAGACCTCACTAGTTGTGCACAAATAATGTGCTATGATGGGGTGTA  4320

4321  AAGTGAAGGCAGAAGAGGGTCAGCCGCATTGTTATGATACTGGGAAAGTGCCGGTCAACG  4380

4381  ATTTGAGTTAGTTTTTAGATATACATTGAAATCTTTAATCAGACATTCTCAAGTTTCACA  4440

4441  CAGTAGTTTTTGATGTTATGTACACACACACCAAATGTGTAACAGTTCACCACTTCCAGA  4500

4501  GTGTGGTCATGCCCAAAACATGTTTAAGAAAGGAAAGCAGTAGCTCCTTGCTAACGATGT  4560

4561  TTCAGGAGGTTTGGGGCACTTGGTTTTAATGAGCTTCTGTCATTTAGGGCTTCTCTTGGC  4620

4621  CATGGTCCCCTTCCTTCTGGAACTGTGATGTAGTCACATCCTACAGCCTTTAGTGCTGGT  4680

4681  TCACTAGTGTCAGATAATCAGTTCTTGGAATCGAGACTGCCGTGGCGAAGGGGTGGCCTC  4740

4741  GGAGGCAGGCTCTGGAGCTGCTTGGATGTCTTTAGGTGGGGTGGTGGCTGGCTCTCTTCA  4800

4801  GCATGTAATTGGGGAAACCCTCGCGTCTACTAGGGGTGATACAGATGGTGATTTTAAAGA  4860

4861  GCAAAACTAGACTTCTATGTGAGAAGTGCTGGAAAATGATTTAGGACGTGTAAAGTTAGA  4920

4921  TGGAAAGACTGTAAATGTTTAATATGAATATAGTGTTCTTTTGAAGTAAGGCCAGCTGTT  4980

4981  GAACGGTTAAACTGTGCATTTCTCATTTTGATGTGTCATGTATGTTAATGTATGAAATGA  5040

5041  TTAAATAAAATCAAAACTGGTACCTGTTTATCCATAAAAAAAAAAAAAAAAAAAAAAAA  5100

5101  AAAAAAAAAG  5111
```

Figure 6A

```
                        1                                               50
BMY_HPP1_FL     (1)   --------------------------------------------------
BMY_HPP1_A      (1)   --------------------------------------------------
BMY_HPP1_B      (1)   --------------------------------------------------
HS_RPTPO        (1)   MGHLPTGIHGARRLLPLLWLFVLFKNATAFHVTVQDDNNIVVSLEASDVI
MM_RPTPO        (1)   --------------------------------------------------
PYP3_SP         (1)   --------------------------------------------------

51                                              100
BMY_HPP1_FL     (1)   --------------------------------------------------
BMY_HPP1_A      (1)   --------------------------------------------------
BMY_HPP1_B      (1)   --------------------------------------------------
HS_RPTPO       (51)   SPASVYVVKITGESKNYFFEFEEFNSTLPPPVIFKASYHGLYYIITLVVV
MM_RPTPO        (1)   --------------------------------------------------
PYP3_SP         (1)   --------------------------------------------------

101                                             150
BMY_HPP1_FL     (1)   --------------------------------------------------
BMY_HPP1_A      (1)   --------------------------------------------------
BMY_HPP1_B      (1)   --------------------------------------------------
HS_RPTPO      (101)   NGNVVTKPSRSITVLTKPLPVTSVSIYDYKPSPETGVLFEIHYPEKYNVF
MM_RPTPO        (1)   --------------------------------------------------
PYP3_SP         (1)   --------------------------------------------------

151                                             200
BMY_HPP1_FL     (1)   --------------------------------------------------
BMY_HPP1_A      (1)   --------------------------------------------------
BMY_HPP1_B      (1)   --------------------------------------------------
HS_RPTPO      (151)   TRVNISYWEGKDFRTMLYKDFFKGKTVFNHWLPGMCYSNITFQLVSEATF
MM_RPTPO        (1)   --------------------------------------------------
PYP3_SP         (1)   --------------------------------------------------

201                                             250
BMY_HPP1_FL     (1)   --------------------------------------------------
BMY_HPP1_A      (1)   --------------------------------------------------
BMY_HPP1_B      (1)   --------------------------------------------------
HS_RPTPO      (201)   NKSTLVEYSGVSHEPKQHRTAPYPPQNISVRIVNLNKNNWEEQSGNFPEE
MM_RPTPO        (1)   --------------------------------------------------
PYP3_SP         (1)   --------------------------------------------------

251                                             300
BMY_HPP1_FL     (1)   --------------------------------------------------
BMY_HPP1_A      (1)   --------------------------------------------------
BMY_HPP1_B      (1)   --------------------------------------------------
HS_RPTPO      (251)   SFMRSQDTIGKEKLFHFTEETPEIPSGNISSGWPDFNSSDYETTSQPYWW
MM_RPTPO        (1)   --------------------------------------------------
PYP3_SP         (1)   --------------------------------------------------

301                                             350
BMY_HPP1_FL     (1)   --------------------------------------------------
BMY_HPP1_A      (1)   --------------------------------------------------
BMY_HPP1_B      (1)   --------------------------------------------------
HS_RPTPO      (301)   DSASAAPESEDEFVSVLPMEYENNSTLSETEKSTSGSFSFFPVQMILTWL
MM_RPTPO        (1)   --------------------------------------------------
PYP3_SP         (1)   --------------------------------------------------

351                                             400
BMY_HPP1_FL     (1)   --------------------------------------------------
BMY_HPP1_A      (1)   --------------------------------------------------
BMY_HPP1_B      (1)   --------------------------------------------------
HS_RPTPO      (351)   PPKPPTAFDGFHIHIEREENFTEYLMVDEEAHEFVAELKEPGKYKLSVTT
MM_RPTPO        (1)   --------------------------------------------------
PYP3_SP         (1)   --------------------------------------------------
```

FIGURE 6B

```
                        401                                               450
BMY_HPP1_FL     (1)   --------------------------------------------------
BMY_HPP1_A      (1)   --------------------------------------------------
BMY_HPP1_B      (1)   --------------------------------------------------
HS_RPTPO      (401)   FSSSGSCETRKSQSAKSLSFYISPSGEWIEELTEKPQHVSVHVLSSTTAL
MM_RPTPO        (1)   --------------------------------------------------
PYP3_SP         (1)   --------------------------------------------------

451                                               500
BMY_HPP1_FL     (1)   --------------------------------------------------
BMY_HPP1_A      (1)   --------------------------------------------------
BMY_HPP1_B      (1)   --------------------------------------------------
HS_RPTPO      (451)   MSWTSSQENYNSTIVSVVSLTCQKQKESQRLEKQYCTQVNSSKPIIENLV
MM_RPTPO        (1)   --------------------------------------------------
PYP3_SP         (1)   --------------------------------------------------

501                                               550
BMY_HPP1_FL     (1)   --------------------------------------------------
BMY_HPP1_A      (1)   --------------------------------------------------
BMY_HPP1_B      (1)   --------------------------------------------------
HS_RPTPO      (501)   PGAQYQVVIYLRKGPLIGPPSDPVTFAIVPTGIKDLMLYPLGPTAVVLSW
MM_RPTPO        (1)   --------------------------------------------------
PYP3_SP         (1)   --------------------------------------------------

551                                               600
BMY_HPP1_FL     (1)   --------------------------------------------------
BMY_HPP1_A      (1)   --------------------------------------------------
BMY_HPP1_B      (1)   --------------------------------------------------
HS_RPTPO      (551)   TRPYLGVFRKYVVEMFYFNPATMTSEWTTYYEIAATVSLTASVRIANLLP
MM_RPTPO        (1)   --------------------------------------------------
PYP3_SP         (1)   --------------------------------------------------

601                                               650
BMY_HPP1_FL     (1)   --------------------------------------------------
BMY_HPP1_A      (1)   --------------------------------------------------
BMY_HPP1_B      (1)   --------------------------------------------------
HS_RPTPO      (601)   AWYYNFRVTMVTWGDPELSCCDSSTISFITAPVAPEITSVEYFNSLLYIS
MM_RPTPO        (1)   --------------------------------------------------
PYP3_SP         (1)   --------------------------------------------------

651                                               700
BMY_HPP1_FL     (1)   -----------MEAGIRFNFGWKDYGVASLTI-IDMVKVMTFALQEG-K
BMY_HPP1_A      (1)   --------------LVYHYNFGWKDYGVASLTTILDMVKVMTFALQEGKV
BMY_HPP1_B      (1)   --------------------------------------------------
HS_RPTPO      (651)   WTYGDDTTDLSHSRMLHNMVVREGKKKIKKSVERNVMTAILGLPPGDIYN
MM_RPTPO        (1)   --------------------------------------------------
PYP3_SP         (1)   --------------------------------------------------

701                                               750
BMY_HPP1_FL    (37)   VIHCHAGLGRRGVLIAYLVFATRMTADQAIIVRAKRPNSIQTRGQLCVRE
BMY_HPP1_A     (37)   AIHCHAGLGRRG--------------------------------------
BMY_HPP1_B      (1)   --------------------------------------------------
HS_RPTPO      (701)   LSVTACTERGSNTSMLRLVKLEPAPPKSLFAVNKTQTSVTLLWVEEGVAD
MM_RPTPO        (1)   --------------------------------------------------
PYP3_SP         (1)   --------------------------------------------------

751                                               800
BMY_HPP1_FL    (87)   FTQFLTPLRNISCCDPKAHAVTLPQYIRQRHLLHGYEARLLHVPKIIHLV
BMY_HPP1_A     (49)   --------------------------------------------------
BMY_HPP1_B      (1)   --------------------------------------------------
HS_RPTPO      (751)   FFEVFCQQVGSSQKTKLQEPVAVSSHVVTISSLLPATAYNCSVTSFSHDS
MM_RPTPO        (1)   --------------------------------------------------
PYP3_SP         (1)   --------------------------------------------------
```

FIGURE 6C

```
                     801                                              850
BMY_HPP1_FL   (137)  CKLLLDAENRPVMMKDVSEGPLSAEIEKTMSELVTMLDKELLRHDSDVSM
BMY_HPP1_A    (49)   --------------------------------------------------
BMY_HPP1_B    (1)    --------------------------------------------------
HS_RPTPO      (801)  PSVPTFIAVSTIVTEMNPNVVYISVIAILSPLIEGIILVTIMILRKKHLE
MM_RPTPO      (1)    ----------MVTEVNPNVVVISVIAILSTLIIGIILVTIMILRKKHLQ
PYP3_SP       (1)    --------------------------------------------------

851                                              900
BMY_HPP1_FL   (187)  PNPTAVAADEDNRGMISNEQQFDPLWKRRN----VCLQPLTHLKRRLSYS
BMY_HPP1_A    (49)   --------------------------------------------------
BMY_HPP1_B    (1)    --------------------------------------------------
HS_RPTPO      (851)  MARECGASTFVNPASPERIGKLPYNWS-----------------------
MM_RPTPO      (40)   MARECGASTFVNFASLERFGKLPYSWRRSVFALLTLLPSCLWTDYLLAFY
PYP3_SP       (1)    --------------------------------------------------

901                                              950
BMY_HPP1_FL   (233)  SDLKRAENLLEQGETQTVPAQILVGHKPRQKLISHCYIPQSPEPDHKEAL
BMY_HPP1_A    (49)   --------------------------------------------------
BMY_HPP1_B    (1)    --------------------------------------------------
HS_RPTPO      (878)  -----KNGYKKRKLCNPVQLDPFDAYIKDMAKDSDYKFSLQFEELKLIGL
MM_RPTPO      (90)   INPWSKNGYKKRKLINPVQLDDFDSYIKDMAKDSDYKFSLQFEELKLIGL
PYP3_SP       (1)    -----------MSFKEVSTENGVLTPLITIKEKAYMIEGLNEEEIEL 951                                              1000
BMY_HPP1_FL   (283)  VRSTLSFWSQKFGGLEGLKDNGSPIHGRIIPKEAQQSGAFADVVSSHSPG
BMY_HPP1_A    (49)   --------------------------------------------------
BMY_HPP1_B    (1)    --------------------------------------------------
HS_RPTPO      (923)  DIPHFAADLPLNRCKNRYENILPYDFSRVRLVSMNEEEGADYINANYIPG
MM_RPTPO      (140)  DIPHFAADLPLNRCKNRYENILPYDFSRVRLVSMNEEEGADYINANYIPG
PYP3_SP       (38)   LNTRLEKLSKKALASNRYSNIVPYENTRVRIDPWWK-EACDYINASIVKI 1001                                             1050
BMY_HPP1_FL   (333)  EPVSPFANVHKDENPAHQQVICQCKTHGVGSPGSVQNSRTPRSPLDCGSS
BMY_HPP1_A    (49)   --------------------------------------------------
BMY_HPP1_B    (1)    ------------------DVFMAKLWHTV---------------------
HS_RPTPO      (973)  YNSPQEVIATQGPLPETRNDFWKMVLQQK--SQIIVMLTQCNERRVKCD
MM_RPTPO      (190)  YNSPQEVIATQGPLPETRNDFWKMVLQQK--SHIIVMLTQCNERRVKCD
PYP3_SP       (87)   P-SGKTFIATQGPTSNCIDVFWKMVWQSVPXSGIIVMLTKLREPHRLKCD 1051                                             1100
BMY_HPP1_FL   (383)  KAQFLVEHETQDSKDSEAASHSALQSELSAARRILAAKALANLNEVKKEE
BMY_HPP1_A    (49)   --------------------------------------------------
BMY_HPP1_B    (12)   --------------------------------------------------
HS_RPTPO      (1021) HYWPFTEEPIAYGDITVEMLSEE---------------EQD-DWACRHGR
MM_RPTPO      (238)  HYWPFTEEPIAYGDITVEMVSEE---------------EEE-DWASRHGR
PYP3_SP       (136)  IYWPVELFETINIGDLSVILVKVYT-------------LTSLNEVQVRELE 1101                                             1150
BMY_HPP1_FL   (433)  LKRKVDMWQKLNSRDGAWERICGERPFILCSLMWSWVEXLEPVITKEDVD
BMY_HPP1_A    (49)   --------------------------------------------------
BMY_HPP1_B    (12)   --------------------------------------------------
HS_RPTPO      (1055) INYADEMQDVIHFNYTAWPDHGVPTANAAESILQFVHMVRQQATKSKGEM
MM_RPTPO      (272)  INYADEAQDVIHFNYTGWPDHGVPPANAAESILQFVFTVRQQAAKSKCEV
PYP3_SP       (174)  INKDGVKKKLHFYYNGWPLFCAPHTFLLSLTRYNKSLSYSPDFETAPL 1151                                             1200
BMY_HPP1_FL   (483)  LVDRADAEEALFIEEKGQHTILCVLHCIVNLQTFVCVEEAFLAPALAF
BMY_HPP1_A    (49)   --------------------------------------------------
BMY_HPP1_B    (12)   --------------------------------------------------
HS_RPTPO      (1105) TIHCSAGVGRTGTFIALDRILQHIRDHEFVDILGLVSEMRSYRMSMVQTE
MM_RPTPO      (322)  TIHCSAGVGRCGTFIALDRILQHIRDHEFVDILGLVSEMRSYRMSMVQTE
PYP3_SP       (224)  TYHCSAGCGRTGTFFALFELLSQTDDSTSTSKFELDNIANIVSSLRSCRM
```

FIGURE 6D

```
                    1201                                 1237
BMY_HPP1_FL  (533)  KVNFDSENGPTVYNTKKIFKHTEEKRKMTDGPKPGL
BMY_HPP1_A   (49)   ------------------------------------
BMY_HPP1_B   (12)   ------------------------------------
HS_RPTPO    (1155)  EQYIFIHQCVQLMWMKKKQQFCISDVIYENVSKS---
MM_RPTPO     (372)  EQYIFIHQCVQLMWRKKQQFCISDVIYENVSKS---
PYP3_SP      (274)  QSVQSVDQLVFLYTVSQELLQGKEFILPQL-------
```

Figure 7A

FIGURE 7B

```
                    451                                           500
BMY_HPP2_FL    (151) ----------------------------------------------
BMY_HPP2.partial (234) KKKKRKKKKKKKKKR-------------------------------
HS_CDC14A      (384) KLRALKSQSQPRTSPSCAFRSDDTKGHPRAVSQPFRLSSLQGSAVTLKT
HS_CDC14B      (430) RLRALKSRQ-------SK-----------TNAIPLLSISRDKTVLR-
SC_CDC14       (401) ALSPRNSSP----------------------STANNGSNSFKSSAVPQTS 501                                           550
BMY_HPP2_FL    (151) ----------------------------------------------
BMY_HPP2.partial (249) ----------------------------------------------
HS_CDC14A      (434) SKMALSPSATAKRINRTSLSSGATVRSFSINSRLASSLGNLNAATDDPEN
HS_CDC14B      (460) ----------------------------------------------
SC_CDC14       (430) -------------------PGQPRKGQNGSNTIEDINNNRNPTSHANR 551                                           600
BMY_HPP2_FL    (151) ----------------------------------------------
BMY_HPP2.partial (249) ----------------------------------------------
HS_CDC14A      (484) KKTSSSSKAGFTASPFTNLLNGSSQPTTRNYPELNNNQYNRSSNSNGGNL
HS_CDC14B      (460) ----------------------------------------------
SC_CDC14       (459) KVVIESNNSDDESMQDTNGTSNHYPKVSRKKNDISSASSSRMEDNEPSAT 601                                        647
BMY_HPP2_FL    (151) -------------------------------------------
BMY_HPP2.partial (249) -------------------------------------------
HS_CDC14A      (534) NSPPGPHSAKTEEHTTILRPSYTGLSSSSARFLSRSIPSLQSEYVHY
HS_CDC14B      (460) -------------------------------------------
SC_CDC14       (509) NINNAADDTILRQLLPKNRRVTSGRRTTSAAGGIRKISGSIKK----
```

Figure 8

```
                          1                                                  50
BMY_HPP3      (1)  -----MARMNLPASVDIAYKNVRFLITHNPTNTYFNRFLQELKQDGVTTI
DM_PRL1       (1)  MSITMRQKDLRPAPALIEYKGMRFLITDRPSDITINHYIMELKKNNVNTV
HS_PTPCAAX1   (1)  -----MARMNRPAPVEVIYKNMRFLITHNPTNATLNKFIEELKKYGVTTI
HS_PTPCAAX2   (1)  --------MNRPAPVEISYENMRFLITHNPTNATLNKFIEELKKYGVTTI
MM_PTPCAAX    (1)  --------MNRPAPVEISYENMRFLITHNPTNATLNKFIEELKKYGVTTI
CONSENSUS     (1)         RMNRPAPVEISYKNMRFLITHNPTNATLNKFIEELKKYGVTTI 51                                                 100
BMY_HPP3     (46)  VRVKKATYNIALIEKGSTQVPDWPFDDGTAPSSQIIDNWEKLMKNKEHED
DM_PRL1      (51)  VRVCEPSYNTDELETQCITVKDLAFEDGTFPPQQVIDEWFEFFVVLYRYQ
HS_PTPCAAX1  (46)  VRVCEATYDTTLVEKEGIHVLDWFFDGAPFSNQIVDDWISLVKIKFREE
HS_PTPCAAX2  (43)  VRVCDATYDKAPVEKEGIHVLDWPFDDGAPPPNQIDDWLNLLKTKFREE
MM_PTPCAAX   (43)  VRVCDATYDKAPVEKEGIIVLDWPFDDGAPPPNQIDDWLNLEKTLFREE
CONSENSUS    (51)  VRVCDATYD A VEKEGIHVLDWPFDDGAPPPNQIVDDWL LLK KFREE 101                                                150
BMY_HPP3     (96)  --PGCCIAIHCVVGFGKLQLLVALALIEGGMKYENVVQFIRXKXHGTTNS
DM_PRL1     (101)  QNPEACVAVHCVAGLGRAPVLVALALIELGLKYEAIVEMIRDKRRGAINA
HS_PTPCAAX1  (96)  --PGCCIAVHCVAGLGRAPVLVALALIEGGMKYEDAVQFIRQKRRGAFNS
HS_PTPCAAX2  (93)  --PGCCVAVHCVAGLGRAPVLVALALIECGMKYEDAVQFIRQKRRGAFNS
MM_PTPCAAX   (93)  --PGCCVAVHCVAGLGRAPVLVALALIECGMKYEDAVQFIRQKRRGAFNS
CONSENSUS   (101)    PGCCVAVHCVAGLGRAPVLVALALIE GMKYEDAVQFIRQKRRGAFNS 151                    180
BMY_HPP3    (144)  KQLLYLEKYCLKICIHLRNPRNN---CFDQ
DM_PRL1     (151)  KQLSFLEKYKEKARLKHKNGHKN--SCSVQ
HS_PTPCAAX1 (144)  KQLLYLEKYRKMRLRFKDSNGHRNNCCIQ
HS_PTPCAAX2 (141)  KQLLYLEKYRPKMRLRFRDTNGH---CCVQ
MM_PTPCAAX  (141)  KQLLYLEKYRPKMRLRFRDTNGH---CCVQ
CONSENSUS   (151)  KQLLYLEKYRPKMRLRFRDTNGH   CCVQ
```

Figure 9A

Figure 9B

```
                    1651                                              1700
BMY_HPP4     (502)  TQLGTFLAMEQLLQQAGSECTVDFFNVALQQSQACGLMTPTI-QYVYLYN
MM_OST-PTP  (1641)  NQLSTFLAMEQLLQQAGERTVDVFSVALKQIQACGLKTPILQYIYLYN
RN_PTP-OST  (1642)  NQLGTFLAMEQLLQQAGTERTVDFFNVALKQSQACGLMTPTLQYIYLYN
CONSENSUS   (1651)  NQLGTFLAMEQLLQQAGTERTVDVFNVALKQSQACGLMTPTLEQYIYLYN 1701         1720
BMY_HPP4     (551)  CLNSALADGLP---------
MM_OST-PTP  (1691)  CLNSARNRLPRARK-----
RN_PTP-OST  (1692)  CLNSALNGLPRAGKWPAPC
CONSENSUS   (1701)  CLNSAL NGLPRA K
```

Figure 10A

```
                     1                                                   50
BMY_HPP5      (1)   -MAHEKIGTQEVTEPLVALLESGTEKVLIDSRPFVEYNSEELEATNIN
HS_DSPP8      (1)   MAGDRLPRKVMDAKKLASLLRGGPGGPLVIDSRSFVEYNSEVLSSVNIC
MM_NPP1       (1)   MAGDRLPRKVMDAKKLASLLRGSPGGPLVIDSREFVEYNSEVLSSVNIC
CONSENSUS     (1)   MAGDRLPRKVMDAKKLASLLRGGPGGPLVIDSRSFVEYNS HVLSSVNIC 51                                                  100
BMY_HPP5     (50)   CSKLVKRRLQQDKVLITELIQHSAKHKVIIDCSQKVVVYDQSSQDVASLS
HS_DSPP8     (51)   CSKLVKRRLQQCKVTIAELIQPAARSQVDATEPQDVVVYDQSTRDASVIA
MM_NPP1      (51)   CSKLVKRRLQQCKVTIAELICPATESQVDATEPQDVVVYDQSTRDASVLA
CONSENSUS    (51)   CSKLVKRRLQQGKVTIAELIQPAARSQVDATEPQDVVVYDQSTRDASVIA 101                                                  150
BMY_HPP5    (100)   SDCFLTVLLGKLEKSENSVHLLAGGFAEFSRCFPGLCEGK-STLVFTCTS
HS_DSPP8    (101)   ADSFLSILLSKLDGCFDSVAILTGGFATFSSCFPGLCEGKPATLLPMSLS
MM_NPP1     (101)   ADSFLSILISKLDGCFDSVAILTGGFATFSSCFPGLCEGKPATLPSMSLS
CONSENSUS   (101)   ADSFLSILLSKLDGCFDSVAILTGGFATFSSCFPGLCEGKPATL PMSLS 151                                                  200
BMY_HPP5    (149)   QPCLPVANEGFTRILPNLYLGCQRDVLNKELMQQNGIEYVLNASNTCPKP
HS_DSPP8    (151)   QPCLPVPSVGLTRILPHLYLGSQKDVLNKDLMTQNGISYVLNASNSCPKP
MM_NPP1     (151)   QPCLPVPSVGLTRILPHLYLGSQKDVLNKDLMTQNGISYVLNASNSCPKP
CONSENSUS   (151)   QPCLPVPSVGLTRILPHLYLGSQKDVLNKDLMTQNGISYVLNASNSCPKP 201                                                  250
BMY_HPP5    (199)   DFIPESHFLRVPANDSECEKLLPWLDKSVEFIEKAKASNGCVIVHCLAGI
HS_DSPP8    (201)   DFICESRFARVPINDNYCEKLLPWLDKSIEFIDKAKLSSCQVIVHCLAGI
MM_NPP1     (201)   DFICESRFMRVPINDNYCEKLLPWLDKSIEFIDKAKISSCQVIVHCLAGI
CONSENSUS   (201)   DFICESRFMRVPINDNYCEKLLPWLDKSIEFIDKAKLSSCQVIVHCLAGI 251                                                  300
BMY_HPP5    (249)   SRSATIAIAYIMKRMDSLLEAYRFVKEKRETISPNFNFLGQLIAYEKKT
HS_DSPP8    (251)   SRSATIAIAYIMKEMGMSSDDAYRFVKDRRPSISPNFNFLGQLLEYERTL
MM_NPP1     (251)   SRSATIAIAYIMKTMGMSSDDAYRFVKSRPSISPNFNFLGQLLEYERSL
CONSENSUS   (251)   SRSATIAIAYIMKTMGMSSDDAYRFVKDRRPSISPNFNFLGQLLEYER L 301                                                  350
BMY_HPP5    (299)   KNQTQASGPKSKLKLEPLEKPNEEVEAVGEGGQKSETPLSEPCADSATSE
HS_DSPP8    (301)   KLLAALSGDPG---TPSGTP--EPPSPYAGAPLP--RLPPPTSESAAEG
MM_NPP1     (301)   KLLAALCTEGP---HEGTP---EPLMGPAAGIPLP--RLPESTSESAATS
CONSENSUS   (301)   KLLAALQGD     L       EP P PAAG PLP  RLPPPTSESAATG 351                                                  400
BMY_HPP5    (349)   AAGQRP--VHPASVPSVESVQESLLEDSPLVQALSGLHLSADRIEDSNKL
HS_DSPP8    (344)   NAAAR---EGGLSAGEEPPAPPLPPATSALQQGLRGLHLSSDRLQDTNRL
MM_NPP1     (343)   SEAATAAREGSPSAGGDALIPSTAPAISALQQGLRGLHLSSDRLQDTNRL
CONSENSUS   (351)    AAAR   EG  SAGG PP PPT PATSALQQGLRGLHLSSDRLQDTNRL 401                                                  450
BMY_HPP5    (397)   KRSFSLDIKSVSYSASMAASLHGFSSSEDALEYYKPSTTLDGTNKLCQFS
HS_DSPP8    (391)   KRSFSLDIKSAYAESSRRPDGPGPP-----------DPGEAPKLCKLD
MM_NPP1     (393)   KRSFSLDIKSAYAPSRRPDFPGPP-----------DPGEAPKLCKLD
CONSENSUS   (401)   KRSFSLDIKSAYAPSRRPD PGPP           DPGEAPKLCKLD 451                                                  500
BMY_HPP5    (447)   PVQELSECTPETSPEKEEASIPKKLQTAEPSDSQSKRLHSVRTSSSGTAQ
HS_DSPP8    (427)   SPSEAAEGLSSPSPDPPTAAEEAAKRPEREPRP--P-----------AG
MM_NPP1     (429)   SESGGTEGLEESPDEPDSVPECKEEPRERPE------------AS
CONSENSUS   (451)   SPSG  LGLPSPSPDSPDA PE RPRPRRR  P              A 501                                                  550
BMY_HPP5    (497)   RSLLSELHRSGS-VEDNYHTSFLFGLSTSQQHLTKSAGLGLKGWHSDILA
HS_DSPP8    (463)   SPARSPAHSLGLNFGDAARQTPRHGLSALSAPGLPGFGQPAGGAVAPFL
MM_NPP1     (464)   SPARSPAHLGLGLNFGDTANQTPRHGLSALAAPGLPGFGQPAGGGVVPFL
CONSENSUS   (501)   SPARSPAH LGLNFGD ARQTPRHGLSALSAPGLPGFGQPAGEG W PFL
```

Figure 10B

```
              551                                                      600
BMY_HPP5  (546) PQTSTPSLTSSWYFATESSHFYSASAIYGGSASYSAYSCSQLPTCG----
HS_DSPP8  (513) DSEGTPSPDGPWCFSPEG-------AQGAGGVLEAPEGRAGAPGPG----
MM_NPP1   (514) DSPGTPSPDGPWCFSPEG-------AQGPGAVFSAFGRVSAGAPGPGNS
CONSENSUS (551) DSPGTPSPDGPWCFSPEG       A  GGGA FSAFGR  AP PG 601                                                      650
BMY_HPP5  (592) --------------------DQVYSVRRRQKPS---------------DRA
HS_DSPP8  (552) --------------------GGSDLRRREAARA---------------EPR
MM_NPP1   (556) SSSGGGGGGGGGGGGGGGGGGGSSSNSSSSSSSSSSSSSSSSSSSSDLRRR
CONSENSUS (601)                     GGS S RR     S                  RR 651                                                      700
BMY_HPP5  (608) DSRRSWHEESPFEKQFKRRSCQMEFGESIMSENRSREELGKVGSQSSFSG
HS_DSPP8  (568) DARTGWPEEPAPETQFKRRSCQMEFEEGMVEGRARGEELAALGKQASFSG
MM_NPP1   (606) DVRIGWPEEPAADAQFKRRSCQMEFEEGMVEGRARGEELAALGKQTSFSG
CONSENSUS (651) D RTGWPEEPA E QFKRRSCQMEFEEGMVEGRARGEELAALGKQ SFSG

701
BMY_HPP5  (658) SMEIEVS
HS_DSPP8  (618) SVEVIEVS
MM_NPP1   (656) SVEVIEVS
CONSENSUS (701) SVEVIEVS
```

Figure 12.

BMY_HPP5

| Protein | Genbank ID | Identities | Similarities |
|---|---|---|---|
| human dual specificity phosphatase 8 | gi| NP_004411 | 46% | 58% |
| mouse neuronal tyrosine/threonine phosphatase 1 | gi| NP_032774 | 43% | 56% |

RET31

| Protein | Genbank ID | Identities | Similarities |
|---|---|---|---|
| human protein-tyrosine phosphatase DUS8 protein | gi| U27193 | 50.3% | 56.8% |
| the human dual specificity MAP kinase DUSP6 protein | gi| AB013382 | 36.5% | 48.3% |
| human map kinase phosphatase MKP-5 protein | gi| AB026436 | 34.3% | 47.2% |
| mouse RET31 protein | N/A | 90% | 92% | mRET31

| Protein | Genbank ID | Identities | Similarities |
|---|---|---|---|
| human protein-tyrosine phosphatase DUS8 protein | gi| U27193 | 48.5% | 55.7% |
| the human dual specificity MAP kinase DUSP6 protein | gi| AB013382 | 37.4% | 49.7% |
| human map kinase phosphatase MKP-5 protein | gi| AB026436 | 35.2% | 46.9% |
| human RET31 protein | N/A | 90% | 92% |

Figure 13A

```
  1 GAAAAGAAGACGAGGAGGAGAGCGACGGGACGGGACGCGAGCGGGAGCGCAGCCGCCCTC   60

61 TCGGCTCCGCGGCGGCGCCTCGCAAGTCCGGGAGGCGAGGGGGCCCGACGGCAGACGCC   120

121 GTGACAACTTTCGTTTCCCTCTGAGGGAATTGGGAGGTCGGCGGCCCCAAAAGCTTTCAG   180

181 TCCAGTGTAAAGCTGTTGGAGCGCGGGAGCAAAGGTAAAGAATGATGTAATGCGCTGGCT   240

241 GCTCCAAAGCATCTTTTGTTGTGGAATGGTTATTCCAGTCATCTCTTTATGAATCAAATG   300

301 TGAGGGGCTGCTTTGTGGACGGAGTCCTTTGCAAGAGCACATCAACGGGAAAGAGAAAGA   360

361 GACATTCACTTGGAGGGCTCTTGCTGAAAATGGGTTTAACTCTCCTTTTGCCAGTCACCA   420

421 CCAGCCTGACCTCATACACTTTTAGTACAATGGAGTGGCTGAGCCTTTGAGCACACCACC   480

481 ATTACATCATCGTGGCAAATTAAAGAAGGAGGTGGGAAAAGAGGACTTATTGTTGTCATG   540
  1                                                            M    1

541 GCCCATGAGATGATTGGAACTCAAATTGTTACTGAGAGGTTGGTGGCTCTGCTGGAAAGT   600
  2  A  H  E  M  I  G  T  Q  I  V  T  E  R  L  V  A  L  L  E  S    21

601 GGAACGGAAAAAGTGCTGCTAATTGATAGCCGGCCATTTGTGGAATACAATACATCCCAC   660
 22  G  T  E  K  V  L  L  I  D  S  R  P  F  V  E  Y  N  T  S  H    41

661 ATTTTGGAAGCCATTAATATCAACTGCTCCAAGCTTATGAAGCGAAGGTTGCAACAGGAC   720
 42  I  L  E  A  I  N  I  N  C  S  K  L  M  K  R  R  L  Q  Q  D    61

721 AAAGTGTTAATTACAGAGCTCATCCAGCATTCAGCGAAACATAAGGTTGACATTGATTGC   780
 62  K  V  L  I  T  E  L  I  Q  H  S  A  K  H  K  V  D  I  D  C    81

781 AGTCAGAAGGTTGTAGTTTACGATCAAAGCTCCCAAGATGTTGCCTCTCTCTCTTCAGAC   840
 82  S  Q  K  V  V  V  Y  D  Q  S  S  Q  D  V  A  S  L  S  S  D   101

841 TGTTTTCTCACTGTACTTCTGGGTAAACTGGAGAAGAGCTTCAACTCTGTTCACCTGCTT   900
102  C  F  L  T  V  L  L  G  K  L  E  K  S  F  N  S  V  H  L  L   121

901 GCAGGTGGGTTTGCTGAGTTCTCTCGTTGTTTCCCTGGCCTCTGTGAAGGAAAATCCACT   960
122  A  G  G  F  A  E  F  S  R  C  F  P  G  L  C  E  G  K  S  T   141
```

Figure 13B

```
 961  CTAGTCCCTACCTGCATTTCTCAGCCTTGCTTACCTGTTGCCAACATTGGGCCAACCCGA  1020
 142   L  V  P  T  C  I  S  Q  P  C  L  P  V  A  N  I  G  P  T  R    161

1021  ATTCTTCCCAATCTTTATCTTGGCTGCCAGCGAGATGTCCTCAACAAGGAGCTGATACAG  1080
 162   I  L  P  N  L  Y  L  G  C  Q  R  D  V  L  N  K  E  L  I  Q    181

1081  CAGAATGGGATTGGTTATGTGTTAAATGCCAGCTATACCTGTCCAAAGCCTGACTTTATC  1140
 182   Q  N  G  I  G  Y  V  L  N  A  S  Y  T  C  P  K  P  D  F  I    201

1141  CCCGAGTCTCATTTCCTGCGTGTGCCTGTGAATGACAGCTTTTGTGAGAAAATTTTGCCG  1200
 202   P  E  S  H  F  L  R  V  P  V  N  D  S  F  C  E  K  I  L  P    221

1201  TGGTTGGACAAATCAGTAGATTTCATTGAGAAAGCAAAAGCCTCCAATGGATGTGTTCTA  1260
 222   W  L  D  K  S  V  D  F  I  E  K  A  K  A  S  N  G  C  V  L    241

1261  GTGCACTGTTTAGCTGGGATCTCCCGCTCCGCCACCATCGCTATCGCCTACATCATGAAG  1320
 242   V  H  C  L  A  G  I  S  R  S  A  T  I  A  I  A  Y  I  M  K    261

1321  AGGATGGACATGTCTTTAGATGAAGCTTACAGATTTGTGAAAGAAAAAGACCTACTATA   1380
 262   R  M  D  M  S  L  D  E  A  Y  R  F  V  K  E  K  R  P  T  I    281

1381  TCTCCAAACTTCAATTTTCTGGGCCAACTCCTGGACTATGAGAAGAAGATTAAGAACCAG  1440
 282   S  P  N  F  N  F  L  G  Q  L  L  D  Y  E  K  K  I  K  N  Q    301

1441  ACTGGAGCATCAGGGCCAAAGAGCAAACTCAAGCTGCTGCACCTGGAGAAGCCAAATGAA  1500
 302   T  G  A  S  G  P  K  S  K  L  K  L  L  H  L  E  K  P  N  E    321

1501  CCTGTCCCTGCTGTCTCAGAGGGTGCACAGAAAAGCGAGACGCCCCTCAGTCCACCCTGT  1560
 322   P  V  P  A  V  S  E  G  G  Q  K  S  E  T  P  L  S  P  P  C    341

1561  GCCGACTCTGCTACCTCAGAGGCAGCAGGACAAAGGCCCGTGCATCCCGCCAGCGTGCCC  1620
 342   A  D  S  A  T  S  E  A  A  G  Q  R  P  V  H  P  A  S  V  P    361

1621  AGCGTGCCCAGCGTGCAGCCGTCGCTGTTAGAGGACAGCCCGCTGGTACAGGCGCTCAGT  1680
 362   S  V  P  S  V  Q  P  S  L  L  E  D  S  P  L  V  Q  A  L  S    381

1681  GGGCTGCACCTCTCCGCAGACAGGCTGGAAGACAGCAATAAGCTCAAGCGTTCCTTCTCT  1740
 382   G  L  H  L  S  A  D  R  L  E  D  S  N  K  L  K  R  S  F  S    401

1741  CTGGATATCAAATCAGTTTCATATTCAGCCAGCATGGCAGCATCCTTACATGGCTTCTCC  1800
 402   L  D  I  K  S  V  S  Y  S  A  S  M  A  A  S  L  H  G  F  S    421

1801  TCATCAGAAGATGCCTTGGAATACTACAAACCTTCCACTACTCTGGATGGGACCAACAAG  1860
 422   S  S  E  D  A  L  E  Y  Y  K  P  S  T  T  L  D  G  T  N  K    441
```

Figure 13C

```
1861  CTATGCCAGTTCTCCCCTGTTCAGGAACTATCGGAGCAGACTCCCGAAACCAGTCCTGAT  1920
 442   L  C  Q  F  S  P  V  Q  E  L  S  E  Q  T  P  E  T  S  P  D    461

1921  AAGGAGGAAGCCAGCATCCCCAAGAAGCTGCAGACCGCCAGGCCTTCAGACAGCCAGAGC  1980
 462   K  E  E  A  S  I  P  K  K  L  Q  T  A  R  P  S  D  S  Q  S    481

1981  AAGCGATTGCATTCGGTCAGAACCAGCAGCAGTGGCACCGCCCAGAGGTCCCTTTTATCT  2040
 482   K  R  L  H  S  V  R  T  S  S  S  G  T  A  Q  R  S  L  L  S    501

2041  CCACTGCATCGAAGTGGGAGCGTGGAGGACAATTACCACACCAGCTTCCTTTTCGGCCTT  2100
 502   P  L  H  R  S  G  S  V  E  D  N  Y  H  T  S  F  L  F  G  L    521

2101  TCCACCAGCCAGCAGCACCTCACGAAGTCTGCTGGCCTGGGCCTTAAGGGCTGGCACTCG  2160
 522   S  T  S  Q  Q  H  L  T  K  S  A  G  L  G  L  K  G  W  H  S    541

2161  GATATCTTGGCCCCCCAGACCTCTACCCCTTCCCTGACCAGCAGCTGGTATTTTGCCACA  2220
 542   D  I  L  A  P  Q  T  S  T  P  S  L  T  S  S  W  Y  F  A  T    561

2221  GAGTCCTCACACTTCTACTCTGCCTCAGCCATCTACGGAGGCAGTGCCAGTTACTCTGCC  2280
 562   E  S  S  H  F  Y  S  A  S  A  I  Y  G  G  S  A  S  Y  S  A    581

2281  TACAGCTGCAGCCAGCTGCCCACTTGCGGAGACCAAGTCTATTCTGTGCGCAGGCGGCAG  2340
 582   Y  S  C  S  Q  L  P  T  C  G  D  Q  V  Y  S  V  R  R  R  Q    601

2341  AAGCCAAGTGACAGAGCTGACTCGCGGCGGAGCTGGCATGAAGAGAGCCCCTTTGAAAAG  2400
 602   K  P  S  D  R  A  D  S  R  R  S  W  H  E  S  P  F  E  K      621

2401  CAGTTTAAACGCAGAAGCTGCCAAATGGAATTTGGAGAGAGCATCATGTCAGAGAACAGG  2460
 622   Q  F  K  R  R  S  C  Q  M  E  F  G  E  S  I  M  S  E  N  R    641

2461  TCACGGGAAGAGCTGGGGAAAGTGGGCAGTCAGTCTAGCTTTTCGGGCAGCATGGAAATC  2520
 642   S  R  E  E  L  G  K  V  G  S  Q  S  S  F  S  G  S  M  E  I    661

2521  ATTGAGGTCTCCTGAGAAGAAAGACACTTGTGACTTCTATAGACAATTTTTTTTTCTTG  2580
 662   I  E  V  S                                                    665

2581  TTCACAAAAAAATTCCCTGTAAATCTGAAATATATATATGTACATACATATATATTTTTG  2640

2641  GAAAATGGAGCTATGGTGTAAAAGCAACAGGTGGATCAACCCAGTTGTTACTCTCTTAAC  2700

2701  ATCTGCATTTGAGAGATCAGCTAATACTTCTCTCAACAAAAATGGAAGGGCAGATGCTAG  2760

2761  AATCCCCCCTAGACGGAGGAAAACCATTTTATTCAGTGAATTACACATCCTCTTGTTCTT  2820
```

Figure 13D

```
2821  AAAAAAGCAAGTGTCTTTGGTGTTGGAGGACAAAATCCCCTACCATTTTCACGTTGTGCT  2880

2881  ACTAAGAGATCTCAAATATTAGTCTTTGTCCGGACCCTTCCATAGTACACCTTAGCGCTG  2940

2941  AGACTGAGCCAGCTTGGGGGTCAGGTAGGTAGACCCTGTTAGGGACAGAGCCTAGTGGTA  3000

3001  AATCCAAGAGAAATGATCCTATCCAAAGCTGATTCACAAACCCACGCTCACCTGACAGCC  3060

3061  GAGGGACACGAGCATCACTCTGCTGGACGGACCATTAGGGGCCTTGCCAAGGTCTACCTT  3120

3121  AGAGCAAACCCAGTACCTCAGACAGGAAAGTCGGGGCTTTCACCACTACCATATCTGGTA  3180

3181  GCCCATTTTCTAGGCATTGTGAATAGGTAGGTAGCTAGTCACACTTTTCAGACCAATTCA  3240

3241  AACTGTCTATGCACAAAATTCCCGTGGGCCTAGATGGAGATAATTTTTTTTTCTTCTCAG  3300

3301  CTTTATGAAGAGAAGGGAAACTGTCTAGGATTCAGCTGAACCACCAGGAACCTGGCAACA  3360

3361  TCACGATTTAAGCTAAGGTTGGGAGGCTAACGAGTCTACCTCCCTCTTTGTAAATCAAAG  3420

3421  AATTGTTTAAAATGGGATTGTCAATCCTTTAAATAAAGATGAACTTGGTTTCAAGCCAAA  3480

3481  TGTGAATTTATTTGGGTTGGTAGCAGAGCAGCAGCACCTTCAAATTCTCAGCCAAAGCAG  3540

3541  ATGTTTTTGCCCTTTCTGCTTCACTGCATGGATACAGTTGGTAAAATGTAATAATATGGC  3600

3601  AGAATTTTATAGGAAACTTCCTAGGGAGGTAAATTATGGGAAGATTAAGAAAGGTACAAA  3660

3661  TTGCTGAGGAGAAGCAGGAAACCTGTTTCCTTAGTGGCTTTTATCCCCTCGGCATGCGAT  3720

3721  GGGGCTGATGTTTCTATGATTGCCTCAGACTTTCACATTTACTAGTAGGGCTGAGAGAGG  3780

3781  CTTTAGTGAGGAAGGAATATTCAGAATAAAACGGTTGAGAAAGCTGAGAAGACCATTGAG  3840

3841  TTTTGATCAGTTGTGAATAGAGTGCAAAGCCATGGCCAAGCTGTTTTTGGAAACGCTGGC  3900

3901  CGGCGTGTCTTCAGTGGAAAAAGCAAATCAAAATGGAGCGAGAGCAAAGGGGCGTCCTCA  3960
```

Figure 13E

```
3961  GTCCTCAACCTACAATCACTGTATGGAATCGGTCCTGGCAGCTGAACATAGGAGGTCACT  4020

4021  GGAACAAGTGATAGTGCAGATTGGCTTTCAAACATCCTCCTGGCTTGAGTTTTATCAGCT  4080

4081  ACAATGTGGGTCCTCTTTTGAAGCCTTAATTCACAACAGCAGCTTTTTGGGGGTGGGGCT  4140

4141  GGGCGGGTGTTGTCATTGTTCTTTCCCTTCCTGTAAGTGTCGCTAGTTGCTGCCTCGTAT  4200

4201  CTCAGGTTTTTCTCTGTTTTTGAGAAATGGACAGTTTTTTGACCAGGATGTGACTTCATG  4260

4261  TTTCCTATGGTGACTTCTAAAACCAGCACAGAATGATATGACTCAACACAGACCGACTTG  4320

4321  GTTATGGGGATGATGAGCCGCACAGACCTCACTAGTTGTGCACAAATAATGTGCTATGAT  4380

4381  GGGGTGTAAAGTGAAGGCAGAAGAGGGTCAGCCGCATTGTTATGATACTGGGAAAGTGCT  4440

4441  GGTCAACGATTTGAGTTAGTTTTTAGATATACATTGAAATCTTTAATCAGACATTCTCAA  4500

4501  GTTTCACACAGTAGTTTTTGATGTTATGTACACACACACCAAATGTGTAACAGTTCACCA  4560

4561  CTTCCAGAGTGTGGTCATGCCCAAAACATGTTTAAGAAAGGAAAGCAGTAGCTCCTTGCT  4620

4621  AACGATGTTTCACGAGGTTTGGGGCACTTGGTTTTAATGAGCTTCTGTCATTTAGGGCTT  4680

4681  CTCTTGGCCATGGTCCCCTTCCTTCTGGAACTGTGATGTAGTCACATCCTACAGCCTTTA  4740

4741  GTGCTGGTTCACTAGTGTCAGATAATCAGTTCTTGGAATCGAGACTGCCGTGGCGAAGGG  4800

4801  GTGGCCTCGGAGGCAGGCTCTGGAGCTGCTTGGATGTCTTTAGGTGGGGTGGTGGCTGGC  4860

4861  TCTCTTCAGCATGTAATTGGGGAAACCCTCGCGTCTACTAGGGGTGATACAGATGGTGAT  4920

4921  TTTAAAGAGCAAAACTAGACTTCTATGTGAGAAGTGCTGGAAAATGATTTAGGACATGTG  4980

4981  TAAAGTTAGATGGAAAGACTGTAAATGTTTAATATGAATATAGTGTTCTTTTGAAGTAAG  5040

5041  GCCAGCTGTTGAACGGTTAAACTGTGCATTTCTCATTTTGATGTGTCATGTATGTTAATG  5100

5101  TATGAAATGATTAAATAAAATCAAAACTGGTACCTGTTTATACATAAATACGAGAAAACA  5160
```

Figure 13F

```
5161  CCTATCTTTGCAGCCATAAACTCGGTGGGAACACCACCACTCAAGTTGCCAAAGGAGGCA  5220

5221  GTGGTGAAACCTGTCCTGTTCTCACTTAAATGAGGATTTAGCTCAAAATAAAGTGGTGGT  5280

5281  GTCATCAGGTTTATTCCGTGTTCTGTCATTCACATGGAACACCGGATGATTAGCTAACAG  5340

5341  TTTAGTGCCAGCCTTCATTCTTTACTGTGTACGTTAAATGCACACTACAGTGAAAAGCC   5400

5401  TAAGACACTTGGTAAATATTTTCTAGCTGACTGATTCCAGAACACACAAG  5450
```

Figure 14A

Figure 14B

```
              401                                                 450
RET31  (212)  NDSFCEKLLPWLDKSVDFIEKAKASNGCVLVHCLAGISRSATIAIAYIMK
mRET31 (212)  NDSFCEKLLPWLDKSVDFIEKAKASNGCVLTHCLAGISRSATIAIAYIMK
DUS6   (261)  SDHNSONLSQFFPEALSFIDEARGNCGVLVHCLAGISRSVTVIAYLMQ
DUS8   (214)  NDNYCEKLLPWLDKSLFIDKAKLSSCVVHCLAGISRSATIAIAYIMK
MKP-5  (376)  TDSNKQNLRQYFDDAFLFIEDAHQGKGLLTHCAGVSRSATIMIAYVMK 451                                                 500
RET31  (262)  RMDMSLDEAYRFVKTKRPTESPNFNFLGQLLDYEKKTKNQTGASGPKSKL
mRET31 (262)  RMDMSLDEAYRFVKEKRPTESPNFNFMGQLLDYETNNQTGMSGPKSKL
DUS6   (311)  KLNLSMDAYDLVKMKSSTSPNFNMGQLLDLETLGLSSPCDNRVPAQ
DUS8   (264)  TMGMSSDDAYRFVKRRPFISPNFNFLGQLLPYETLKLLAALQGDPG--
MKP-5  (426)  HTRMWTDAYKFVKCKRPITSPNFNFMGQLLEFEDLNNGVTPRILTPKL 501                                                 550
RET31  (312)  KLPHLEKPNEPVFAVSETGQKSETPLSPPCADSATSEAAGQRP--VHPAS
mRET31 (312)  KLLHLDKPSEPVEAASEGGWKSALSLSPPCAN-GTEASGQRL--VHPAS
DUS6   (361)  QLYFTTPSNQNVYQVPSLQST-----------------------------
DUS8   (312)  -TPSG----TPEEPPSPAAGAPLPRLPPETSESAATGNAAAREGGLSAGG
MKP-5  (476)  MGVETVV-------------------------------------------

551                                                 600
RET31  (360)  VESVPSVQPSLLEDSPLVQALSGLHLSPPRLEDSNKLKRSFSLDIKSVSY
mRET31 (359)  VP---RLQPSLLEDSPLVQALSGLQLSSERLEDSTKLKRSFSLDIKSVSY
DUS6   (382)  --------------------------------------------------
DUS8   (357)  EP---PAPETPPATSALQQGPRGLHLSSDRLQENRLKRSFSLDIKSA-Y
MKP-5  (483)  --------------------------------------------------

601                                                 650
RET31  (410)  SASMAASLHCFSSSELALEYYKPSTTLDGTNKLCQFSPVQEFSEQFETS
mRET31 (406)  SASMAASLHCFSS-ELALDYCKPSATLDGTNKLCQFSPVQEVSEQSETS
DUS6   (382)  --------------------------------------------------
DUS8   (403)  APSRRPDGPGPPDPCEAPKLCKLDSPSG---------AALGPSSPSP-DS
MKP-5  (483)  --------------------------------------------------

651                                                 700
RET31  (460)  PDKEEASIPKKLQTARPSDSQSKRLHSVRTSSSGTAQRSLLSFLERSCS-
mRET31 (455)  PDKEEAHIPKQPQPPRPSESQVTRLHSVRTGSSGSTQRPFFSFLRSCS-
DUS6   (382)  --------------------------------------------------
DUS8   (443)  PDAAPEARPKPRRRPREP------------------AGSPARSPAHSLGLN
MKP-5  (483)  --------------------------------------------------

701                                                 750
RET31  (509)  VEDNYHTSFLFGLSTSQQHLTKSAG--LGLKGNHSDILAPQTSTPSLTSS
mRET31 (504)  VEDNYHTNFLFGLSTSQQHLTKSAG--LGLKGWHSDILAPQSSAPSLTSS
DUS6   (382)  --------------------------------------------------
DUS8   (476)  FGDAARQTPRHGLSALSAPGLPGPGQPAGPGAWAPPLDSP--GTPSPDGP
MKP-5  (483)  --------------------------------------------------

751                                                 800
RET31  (557)  WYFATESSHFYSASAIYGGSASYSASCSQLETCGDQVYSVRRRQKPSDR
mRET31 (552)  WYFATEPSHLYSASAIYGGNSSYSASCSGQLETCSDQIYSVRRRQKPTCR
DUS6   (382)  --------------------------------------------------
DUS8   (524)  WCFSPE-------GAQGAGGVLIAPIGRAGAPGPGGGSDLRREAARAEP
MKP-5  (483)  --------------------------------------------------
```

Figure 14C

```
              801                                                850
RET31  (607)  ADSRRSWHEESPFEKQFKRRSCQMEFGESTMSENRSREELGKVGSQSSFS
mRET31 (602)  ADSRRSWHEESPFEKQFKRRSCQMEFGESTMSENRSREELGKVGSQSSFS
DUS6   (382)  --------------------------------------------------
DUS8   (567)  RDARTGWPEEPAPETQFKRRSCQMEFEEGMVEGRARGEELAALGKQASFS
MKP-5  (483)  --------------------------------------------------

851
RET31  (657)  GSVEIIEVS
mRET31 (652)  GSVEIIEVS
DUS6   (382)  ---------
DUS8   (617)  GSVEVIEVS
MKP-5  (483)  ---------
```

Figure 16A

```
  1 GACTGAGGTTGTCAGCCCAGTGTAAAGCTGTTGGAGTGAGGGCAGAAAGGTAAAGGATGA    60

61 TGTAATGCCTGGCTGCCCTAGAGCATCTTTTGTTGTGGGATGGGTATTCCCATCATCTCT   120

121 ATGAATCTAGTGTGAGGGGCTGCTTTGTGGAAGGAATCCTTTGCAAGAGCATATCAACAG   180

181 GAAAGAGAAAGAGACATTCAGTTGGAGGGCTCTTGCTGAAATGGATTTAACTCTCCTCTT   240

241 GCCAGTCACCACTAGCCTGACCTCATACATTTTAGTACAATGGAGTGGCTGAGCCTTTG    300

301 AGCACAGCACCATTACATCATCGTGGCAAATTAAAGAACGAGGTGGGGAAAGAGGACTTA   360

361 TTGTTGTCATGGCCCATGAGATGATTGGAACTCAAATTGTTACTGAGAGCTTGGTGGCTC   420
  1         M  A  H  E  M  I  G  T  Q  I  V  T  E  S  L  V  A  L    18

421 TGCTGGAAAGTGGAACGGAAAAAGTGCTGCTAATTGATAGCCGACCATTTGTGGAATACA   480
 19  L  E  S  G  T  E  K  V  L  L  I  D  S  R  P  F  V  E  Y  N    38

481 ATACGTCTCACATTTTGGAAGCCATTAATATCAACTGCTCCAAACTGATGAAGCGAAGGT   540
 39  T  S  H  I  L  E  A  I  N  I  N  C  S  K  L  M  K  R  R  L    58

541 TGCAACAGGACAAAGTATTAATTACAGAACTAATCCACCAATCTACAAAGCATAAGGTTG   600
 59  Q  Q  D  K  V  L  I  T  E  L  I  H  Q  S  T  K  H  K  V  D    78

601 ACATTGACTGCAATCAAAGAGTGGTAGTTTATGATCACAGTTCACAAGATGTTGGTTCTC   660
 79  I  D  C  N  Q  R  V  V  V  Y  D  H  S  S  Q  D  V  G  S  L    98

661 TGTCGTCAGACTGCTTTCTCACTGTACTTCTGGGTAAGCTGGAGAGAAGCTTCAACTCTG   720
 99  S  S  D  C  F  L  T  V  L  L  G  K  L  E  R  S  F  N  S  V   118

721 TCCACCTGCTTGCAGGTGGCTTTGCTGAGTTCTCTCGTTGTTTCCCTGGCCTCTGTGAAG   780
119  H  L  L  A  G  G  F  A  E  F  S  R  C  F  P  G  L  C  E  G   138

781 GAAAGTCCACTCTAGTCCCTACCTGCATATCTCAGCCTTGCTTACCTGTTGCGAACATTG   840
139  K  S  T  L  V  P  T  C  I  S  Q  P  C  L  P  V  A  N  I  G   158

841 GGCCAACTCGAATTCTTCCCAATCTCTATCTTGGCTGCCAGCGAGATGTCCTCAACAAGG   900
159  P  T  R  I  L  P  N  L  Y  L  G  C  Q  R  D  V  L  N  K  D   178

901 ACCTGATGCAACAGAATGGGATTGGCTATGTGTTAAATGCCAGCAATACCTGTCCAAAGC   960
179  L  M  Q  Q  N  G  I  G  Y  V  L  N  A  S  N  T  C  P  K  P   198
```

Figure 16B

```
 961  CTGACTTCATACCTGAATCTCACTTCCTGCGAGTGCCTGTGAATGACAGCTTTTGTGAGA  1020
 199   D  F  I  P  E  S  H  F  L  R  V  P  V  N  D  S  F  C  E  K   218

1021  AAATCCTACCATGGTTGGACAAGTCTGTGGATTTCATTGAGAAAGCAAAAGCCTCCAATG  1080
 219   I  L  P  W  L  D  K  S  V  D  F  I  E  K  A  K  A  S  N  G   238

1081  GCTGTGTGCTTATCCACTGCTTAGCTGGGATCTCTCGCTCCGCCACTATTGCTATTGCCT  1140
 239   C  V  L  I  H  C  L  A  G  I  S  R  S  A  T  I  A  I  A  Y   258

1141  ACATCATGAAGAGGATGGACATGTCTCTAGATGAGGCTTACAGATTTGTGAAAGAAAAAA  1200
 259   I  M  K  R  M  D  M  S  L  D  E  A  Y  R  F  V  K  E  K  R   278

1201  GACCTACTATATCTCCGAATTTTAATTTTATGGGCCAACTCATGGACTATGAGAAGACGA  1260
 279   P  T  I  S  P  N  F  N  F  M  G  Q  L  M  D  Y  E  K  T  I   298

1261  TTAATAACCAGACTGGAATGTCAGGGCCAAAGAGCAAACTGAAGCTGCTGCACCTAGACA  1320
 299   N  N  Q  T  G  M  S  G  P  K  S  K  L  K  L  L  H  L  D  K   318

1321  AACCCAGTGAGCCCGTGCCTGCAGCCTCAGAGGGCGGATGGAAGAGTGCACTGTCTCTCA  1380
 319   P  S  E  P  V  P  A  A  S  E  G  G  W  K  S  A  L  S  L  S   338

1381  GTCCACCCTGTGCCAACTCGACCTCGGAGGCATCAGGGCAAAGGCTTGTGCATCCTGCAA  1440
 339   P  P  C  A  N  S  T  S  E  A  S  G  Q  R  L  V  H  P  A  S   358

1441  GTGTGCCCCGCTTACAGCCGTCACTCTTAGAGGACAGTCCGCTGGTACAGGCGCTCAGTG  1500
 359   V  P  R  L  Q  P  S  L  L  E  D  S  P  L  V  Q  A  L  S  G   378

1501  GGCTCCAGCTGTCCTCAGAGAAGCTGGAAGACAGCACTAAGCTCAAGCGTTCCTTCTCTC  1560
 379   L  Q  L  S  S  E  K  L  E  D  S  T  K  L  K  R  S  F  S  L   398

1561  TCGATATCAAATCTGTTTCATATTCAGCCAGTATGGCCGCGTCCCTACACGGCTTCTCGT  1620
 399   D  I  K  S  V  S  Y  S  A  S  M  A  A  S  L  H  G  F  S  S   418

1621  CAGAGGAGGCTTTAGACTACTGCAAACCTTCTGCCACACTGGATGGGACCAACAAGCTCT  1680
 419   E  E  A  L  D  Y  C  K  P  S  A  T  L  D  G  T  N  K  L  C   438

1681  GCCAGTTCTCCCCCGTTCAGGAGGTATCAGAACAGAGTCCAGAGACCAGCCCGGATAAGG  1740
 439   Q  F  S  P  V  Q  E  V  S  E  Q  S  P  E  T  S  P  D  K  E   458

1741  AGGAGGCCCACATCCCCAAGCAGCCCCAACCTCCCAGGCCTTCTGAGAGCCAGGTCACAC  1800
 459   E  A  H  I  P  K  Q  P  Q  P  P  R  P  S  E  S  Q  V  T  R   478

1801  GCTTGCACTCAGTGAGAACCGGCAGTAGTGGGTCCACCCAGAGGCCCTTCTTCTCGCCAC  1860
 479   L  H  S  V  R  T  G  S  S  G  S  T  Q  R  P  F  F  S  P  L   498
```

Figure 16C

```
1861 TGCATCGGAGCGGGAGTGTAGAGGACAATTACCATACCAACTTCCTTTTTGGCCTTTCCA 1920
 499  H   R   S   G   S   V   E   D   N   Y   H   T   N   F   L   F   G   L   S   T   518

1921 CCAGCCAGCAACACCTCACCAAGTCTGCAGGGCTTGGCCTCAAGGGCTGGCACTCAGATA 1980
 519  S   Q   Q   H   L   T   K   S   A   G   L   G   L   K   G   W   H   S   D   I   538

1981 TTCTGGCTCCCCAGTCCTCTGCCCCCTCCCTGACCAGCAGTTGGTATTTTGCTACGGAGC 2040
 539  L   A   P   Q   S   S   A   P   S   L   T   S   S   W   Y   F   A   T   E   P   558

2041 CTTCACACTTGTACTCTGCTTCAGCCATCTATGGAGGCAACAGCAGTTACTCTGCCTACA 2100
 559  S   H   L   Y   S   A   S   A   I   Y   G   G   N   S   S   Y   S   A   Y   S   578

2101 GCTGTGGCCAGCTGCCCACTTGCAGTGACCAAATCTATTCTGTTCGTAGGCGGCAGAAGC 2160
 579  C   G   Q   L   P   T   C   S   D   Q   I   Y   S   V   R   R   R   Q   K   P   598

2161 CTACTGACAGAGCTGACTCGAGGCGGAGCTGGCATGAAGAGAGCCCCTTTGAAAAGCAGT 2220
 599  T   D   R   A   D   S   R   R   S   W   H   E   E   S   P   F   E   K   Q   F   618

2221 TTAAACGCAGAAGCTGCCAAATGGAATTTGGAGAGAGCATTATGTCGGAGAACAGGTCCA 2280
 619  K   R   R   S   C   Q   M   E   F   G   E   S   I   M   S   E   N   R   S   R   638

2281 GGGAGGAGCTGGGCAAGGTGGGCAGCCAGTCCAGCTTCTCCGGCAGCATGGAGATCATCG 2340
 639  E   E   L   G   K   V   G   S   Q   S   S   F   S   G   S   M   E   I   I   E   658

2341 AGGTCTCTTGAGAAGACCTCGTCGCTTCTGTTGACAGTTTTGTTTCCTGTTCACAAAAAA 2400
 659  V   S                                                                           660

2401 TAGTCCCTGTAAATCTGAAATATGTATATGTACATACATATATATTTTTGGAATATAGAG 2460

2461 CTACGGTATAAAAGCAACAGATGGATCAACACAGTTGTTCTCTCAGCACCTGCACTGAGA 2520

2521 ATAGCTAACTCTCAGAAAAGATTGGAAGGGTAGATGTTAGAATTCTCCCAGCCAGGAGAA 2580

2581 GAGATTTGGTTCAGTGAATTGCACATCTTCTTGTTCCTACAAAAGCAAGGGTTTTGTTTG 2640

2641 TTTGTATGTTGTTTGTTTTTAATGTTAGAGGGCAAAATCCCTCCCATTTTCACGTGCAAC 2700

2701 AGAGGTCTCAGAACTCATCTCTGTCCAGGCCCTTCCCTAGTGCACCTTAGCGCTAA 2756
```

Figure 17.

Figure 19A

```
  1 GAAAAGAAGACGAGGAGGAGAGCGACGGGACGGGACGCGAGCGGGAGCGCAGCCGCCCTC   60

61 TCGGCTCCGCGGCGGCGCCTCGCAAGTCCGGGAGGCGAGGGGGGCCCGAGGGGAGACGCC  120

121 GTGACAACTTTCGTTTCCCTCTGAGGGAATTGGGAGGTCGGCGGCCCCAAAAGCTTTCAG  180

181 TCCAGTGTAAAGCTGTTGGAGCGCGGGAGCAAAGGTAAAGAATGATGTAATGCGCTGGCT  240

241 GCTCCAAAGCATCTTTTGTTGTGGAATGGTTATTCCAGTCATCTCTTTATGAATCAAATG  300

301 TGAGGGGCTGCTTTGTGGACGGAGTCCTTTGCAAGAGCACATCAACGGGAAAGAGAAAGA  360

361 GACATTCACTTGGAGGGCTCTTGCTGAAAATGGGTTTAACTCTCCTTTTGCCAGTCACCA  420

421 CCAGCCTGACCTCATACACTTTTAGTACAATGGAGTGGCTGAGCCTTTGAGCACACCACC  480

481 ATTACATCATCGTGGCAAATTAAAGAAGGAGGTGGGAAAAGAGGACTTATTGTTGTCATG  540
  1                                                            M    1

541 GCCCATGAGATGATTGGAACTCAAATTGTTACTGAGAGGTTGGTGGCTCTGCTGGAAAGT  600
  2  A   H   E   M   I   G   T   Q   I   V   T   E   R   L   V   A   L   L   E   S   21

601 GGAACGGAAAAAGTGCTGCTAATTGATAGCCGGCCATTTGTGGAATACAATACATCCCAC  660
 22  G   T   E   K   V   L   L   I   D   S   R   P   F   V   E   Y   N   T   S   H   41

661 ATTTTGGAAGCCATTAATATCAACTGCTCCAAGCTTATGAAGCGAAGGTTGCAACAGGAC  720
 42  I   L   E   A   I   N   I   N   C   S   K   L   M   K   R   R   L   Q   Q   D   61

721 AAAGTGTTAATTACAGAGCTCATCCAGCATTCAGCGAAACATAAGGTTGACATTGATTGC  780
 62  K   V   L   I   T   E   L   I   Q   H   S   A   K   H   K   V   D   I   D   C   81

781 AGTCAGAAGGTTGTAGTTTACGATCAAAGCTCCCAAGATGTTGCCTCTCTCTCTTCAGAC  840
 82  S   Q   K   V   V   V   Y   D   Q   S   S   Q   D   V   A   S   L   S   S   D  101

841 TGTTTTCTCACTGTACTTCTGGGTAAACTGGAGAAGAGCTTCAACTCTGTTCACCTGCTT  900
102  C   F   L   T   V   L   L   G   K   L   E   K   S   F   N   S   V   H   L   L  121

901 GCAGGTGGGTTTGCTGAGTTCTCTCGTTGTTTCCCTGGCCTCTGTGAAGGAAAATCCACT  960
122  A   G   G   F   A   E   F   S   R   C   F   P   G   L   C   E   G   K   S   T  141
```

Figure 19B

```
 961  CTAGTCCCTACCTGCATTTCTCAGCCTTGCTTACCTGTTGCCAACATTGGGCCAACCCGA  1020
 142   L  V  P  T  C  I  S  Q  P  C  L  P  V  A  N  I  G  P  T  R   161

1021  ATTCTTCCCAATCTTTATCTTGGCTGCCAGCGAGATGTCCTCAACAAGGAGCTGATACAG  1080
 162   I  L  P  N  L  Y  L  G  C  Q  R  D  V  L  N  K  E  L  I  Q   181

1081  CAGAATGGGATTGGTTATGTGTTAAATGCCAGCTATACCTGTCCAAAGCCTGACTTTATC  1140
 182   Q  N  G  I  G  Y  V  L  N  A  S  Y  T  C  P  K  P  D  F  I   201

1141  CCCGAGTCTCATTTCCTGCGTGTGCCTGTGAATGACAGCTTTTGTGAGAAAATTTTGCCG  1200
 202   P  E  S  H  F  L  R  V  P  V  N  D  S  F  C  E  K  I  L  P   221

1201  TGGTTGGACAAATCAGTAGATTTCATTGAGAAAGCAAAAGCCTCCAATGGATGTGTTCTA  1260
 222   W  L  D  K  S  V  D  F  I  E  K  A  K  A  S  N  G  C  V  L   241

1261  GTGCACTGTTTAGCTGGGATCTCCCGCTCCGCCACCATCGCTATCGCCTACATCATGAAG  1320
 242   V  H  C  L  A  G  I  S  R  S  A  T  I  A  I  A  Y  I  M  K   261

1321  AGGATGGACATGTCTTTAGATGAAGCTTACAGATTTGTGAAAGAAAAAAGACCTACTATA  1380
 262   R  M  D  M  S  L  D  E  A  Y  R  F  V  K  E  K  R  P  T  I   281

1381  TCTCCAAACTTCAATTTTCTGGGCCAACTCCTGGACTATGAGAAGAAGATTAAGAACCAG  1440
 282   S  P  N  F  N  F  L  G  Q  L  L  D  Y  E  K  K  I  K  N  Q   301

1441  ACTGGAGCATCAGGGCCAAAGAGCAAACTCAAGCTGCTGCACCTGGAGAAGCCAAATGAA  1500
 302   T  G  A  S  G  P  K  S  K  L  K  L  L  H  L  E  K  P  N  E   321

1501  CCTGTCCCTGCTGTCTCAGAGGGTGGACAGAAAAGCGAGACGCCCCTCAGTCCACCCTGT  1560
 322   P  V  P  A  V  S  E  G  G  Q  K  S  E  T  P  L  S  P  P  C   341

1561  GCCGACTCTGCTACCTCAGAGGCAGCAGGACAAAGGCCCGTGCATCCCGCCAGCGTGCCC  1620
 342   A  D  S  A  T  S  E  A  A  G  Q  R  P  V  H  P  A  S  V  P   361

1621  AGCGTGCCCAGCGTGCAGCCGTCGCTGTTAGAGGACAGCCCGCTGGTACAGGCGCTCAGT  1680
 362   S  V  P  S  V  Q  P  S  L  L  E  D  S  P  L  V  Q  A  L  S   381

1681  GGGCTGCACCTGTCCGCAGACAGGCTGGAAGACAGCAATAAGCTCAAGCGTTCCTTCTCT  1740
 382   G  L  H  L  S  A  D  R  L  E  D  S  N  K  L  K  R  S  F  S   401

1741  CTGGATATCAAATCAGTTTCATATTCAGCCAGCATGGCAGCATCCTTACATGGCTTCTCC  1800
 402   L  D  I  K  S  V  S  Y  S  A  S  M  A  A  S  L  H  G  F  S   421

1801  TCATCAGAAGATGCTTTGGAATACTACAAACCTTCCACTACTCTGGATGGGACCAACAAG  1860
 422   S  S  E  D  A  L  E  Y  Y  K  P  S  T  T  L  D  G  T  N  K   441
```

Figure 19C

```
1861 CTATGCCAGTTCTCCCCTGTTCAGGAACTATCGGAGCAGACTCCCGAAACCAGTCCTGAT 1920
 442  L   C   Q   F   S   P   V   Q   E   L   S   E   Q   T   P   E   T   S   P   D    461

1921 AAGGAGGAAGCCAGCATCCCCAAGAAGCTGCAGACCGCCAGGCCTTCAGACAGCCAGAGC 1980
 462  K   E   E   A   S   I   P   K   K   L   Q   T   A   R   P   S   D   S   Q   S    481

1981 AAGCGATTGCATTCGGTCAGAACCAGCAGCAGTGGCACCGCCCAGAGGTCCCTTTTATCT 2040
 482  K   R   L   H   S   V   R   T   S   S   S   G   T   A   Q   R   S   L   L   S    501

2041 CCACTGCATCGAAGTGGGAGCGTGGAGGACAATTACCACACCAGCTTCCTTTTCGGCCTT 2100
 502  P   L   H   R   S   G   S   V   E   D   N   Y   H   T   S   F   L   F   G   L    521

2101 TCCACCAGCCAGCAGCACCTCACGAAGTCTGCTGGCCTGGGCCTTAAGGGCTGGCACTCG 2160
 522  S   T   S   Q   Q   H   L   T   K   S   A   G   L   G   L   K   G   W   H   S    541

2161 GATATCTTGGCCCCCCAGACCTCTACCCCTTCCTGACCAGCAGCTGGTATTTTGCCACA 2220
 542  D   I   L   A   P   Q   T   S   T   P   S   L   T   S   S   W   Y   F   A   T    561

2221 GAGTCCTCACACTTCTACTCTGCCTCAGCCATCTACGGAGGCAGTGCCAGTTACTCTGCC 2280
 562  E   S   S   H   F   Y   S   A   S   A   I   Y   G   G   S   A   S   Y   S   A    581

2281 TACAGCTGCAGCCAGCTGCCCACTTGCGGAGACCAAGTCTATTCTGTGCGCAGGCGGCAG 2340
 582  Y   S   C   S   Q   L   P   T   C   G   D   Q   V   Y   S   V   R   R   R   Q    601

2341 AAGCCAAGTGACAGAGCTGACTCGCGGCGGAGCTGGCATGAAGAGAGCCCCTTTGAAAAG 2400
 602  K   P   S   D   R   A   D   S   R   R   S   W   H   E   E   S   P   F   E   K    621

2401 CAGTTTAAACGCAGAAGCTGCCAAATGGAATTTGGAGAGAGCATCATGTCAGAGAACAGG 2460
 622  Q   F   K   R   R   S   C   Q   M   E   F   G   E   S   I   M   S   E   N   R    641

2461 TCACGGGAAGAGCTGGGGAAAGTGGGCAGTCAGTCTAGCTTTTCGGGCAGCATGGAAATC 2520
 642  S   R   E   E   L   G   K   V   G   S   Q   S   S   F   S   G   S   M   E   I    661

2521 ATTGAGGTCTCCTGAGAAGAAAGACACTTGTGACTTCTATAGACAATTTTTTTTTTCTTG 2580
 662  I   E   V   S                                                                    665

2581 TTCACAAAAAAATTCCCTGTAAATCTGAAATATATATATGTACATACATATATATTTTTG 2640

2641 GAAAATGGAGCTATGGTGTAAAAGCAACAGGTGGATCAACCCAGTTGTTACTCTCTTAAC 2700

2701 ATCTGCATTTGAGAGATCAGCTAATACTTCTCTCAACAAAAATGGAAGGGCAGATGCTAG 2760

2761 AATCCCCCCTAGACGGAGGAAAACCATTTTATTCAGTGAATTACACATCCTCTTGTTCTT 2820
```

Figure 19D

```
2821  AAAAAAGCAAGTGTCTTTGGTGTTGGAGGACAAAATCCCCTACCATTTTCACGTTGTGCT  2880

2881  ACTAAGAGATCTCAAATATTAGTCTTTGTCCGGACCCTTCCATAGTACACCTTAGCGCTG  2940

2941  AGACTGAGCCAGCTTGGGGGTCAGGTAGGTAGACCCTGTTAGGGACAGAGCCTAGTGGTA  3000

3001  AATCCAAGAGAAATGATCCTATCCAAAGCTGATTCACAAACCCACGCTCACCTGACAGCC  3060

3061  GAGGGACACGAGCATCACTCTGCTGGACGGACCATTAGGGGCCTTGCCAAGGTCTACCTT  3120

3121  AGAGCAAACCCAGTACCTCAGACAGGAAAGTCGGGCTTTGACCACTACCATATCTGGTA  3180

3181  GCCCATTTTCTAGGCATTGTGAATAGGTAGGTAGCTAGTCACACTTTTCAGACCAATTCA  3240

3241  AACTGTCTATGCACAAAATTCCCGTGGGCCTAGATGGAGATAATTTTTTTTCTTCTCAG  3300

3301  CTTTATGAAGAGAAGGGAAACTGTCTAGGATTCAGCTGAACCACCAGGAACCTGGCAACA  3360

3361  TCACGATTTAAGCTAAGGTTGGGAGGCTAACGAGTCTACCTCCCTCTTTGTAAATCAAAG  3420

3421  AATTGTTTAAAATGGGATTGTCAATCCTTTAAATAAAGATGAACTTGGTTTCAAGCCAAA  3480

3481  TGTGAATTTATTTGGGTTGGTAGCAGAGCAGCAGCACCTTCAAATTCTCAGCCAAAGCAG  3540

3541  ATGTTTTTGCCCTTTCTGCTTCACTGCATGGATACAGTTGGTAAAATGTAATAATATGGC  3600

3601  AGAATTTTATAGGAAACTTCCTAGGGAGGTAAATTATGGGAAGATTAAGAAAGGTACAAA  3660

3661  TTGCTGAGGAGAAGCAGGAAACCTGTTTCCTTAGTGGCTTTTATCCCCTCGGCATGCGAT  3720

3721  GGGGCTGATGTTTCTATGATTGCCTCAGACTTTCACATTTACTAGTAGGGCTGAGAGAGG  3780

3781  CTTTAGTGAGGAAGGAATATTCAGAATAAAACGGTTGAGAAAGCTGAGAAGACCATTGAG  3840

3841  TTTTGATCAGTTGTGAATAGAGTGCAAAGCCATGGCCAAGCTGTTTTTGGAAACGCTGGC  3900

3901  CGGCGTGTCTTCAGTGGAAAAAGCAAATCAAAATGCAGCGAGAGCAAAGGGGCGTCCTCA  3960

3961  GTCCTCAACCTACAATCACTGTATGGAATCGGTCCTGGCAGCTGAACATAGGAGGTCACT  4020
```

Figure 19E

```
4021  GGAACAAGTGATAGTGCAGATTGGCTTTCAAACATCCTCCTGGCTTGAGTTTTATCAGCT  4080

4081  ACAATGTGGGTCCTCTTTTGAAGCCTTAATTCACAACAGCAGCTTTTTGGGGGTGGGGCT  4140

4141  GGGCGGGTGTTGTCATTGTTCTTTCCCTTCCTGTAAGTGTCGCTAGTTGCTGCCTCGTAT  4200

4201  CTCAGGTTTTTCTCTGTTTTTGAGAAATGGACAGTTTTTTGACCAGGATGTGACTTCATG  4260

4261  TTTCCTATGGTGACTTCTAAAACCAGCACAGAATGATATGACTCAACACAGACCGACTTG  4320

4321  GTTATGGGGATGATGAGCCGCACAGACCTCACTAGTTGTGCACAAATAATGTGCTATGAT  4380

4381  GGGGTGTAAAGTGAAGGCAGAAGAGGGTCAGCCGCATTGTTATGATACTGGGAAAGTGCT  4440

4441  GGTCAACGATTTGAGTTAGTTTTTAGATATACATTGAAATCTTTAATCAGACATTCTCAA  4500

4501  GTTTCACACAGTAGTTTTTGATGTTATGTACACACACACCAAATGTGTAACAGTTCACCA  4560

4561  CTTCCAGAGTGTGGTCATGCCCAAAACATGTTTAAGAAAGGAAAGCAGTAGCTCCTTGCT  4620

4621  AACGATGTTTCAGGAGGTTTGGGGCACTTGGTTTTAATCAGCTTCTGTCATTTAGGGCTT  4680

4681  CTCTTGGCCATGGTCCCCTTCCTTCTGGAACTGTGATGTAGTCACATCCTACAGCCTTTA  4740

4741  GTGCTGGTTCACTAGTGTCAGATAATCAGTTCTTGGAATCGAGACTGCCGTGGCGAAGGG  4800

4801  GTGGCCTCGGAGGCAGGCTCTGGAGCTGCTTGGATGTCTTTAGGTGGGGTGGTGGCTGGC  4860

4861  TCTCTTCAGCATGTAATTGGGGAAACCCTCGCGTCTACTAGGGGTGATACAGATGGTGAT  4920

4921  TTTAAAGAGCAAAACTAGACTTCTATGTGAGAAGTGCTGGAAAATGATTTAGGACATGTG  4980

4981  TAAAGTTAGATGGAAAGACTGTAAATGTTTAATATGAATATAGTGTTCTTTTGAAGTAAG  5040

5041  GCCAGCTGTTGAACGGTTAAACTGTGCATTTCTCATTTTGATGTGTCATGTATGTTAATG  5100

5101  TATGAAATGATTAAATAAAATCAAAACTGGTACCTGTTTATACATAAATACGAGAAAAGA  5160
```

Figure 19F

```
5161  CCTATCTTTGCAGCCATAAACTCGGTGGGAACACCACCACTCAAGTTGCCAAAGGAGGCA  5220

5221  GTGGTGAAACCTGTCCTGTTCTCACTTAAATGAGGATTTAGCTCAAAATAAAGTGGTGGT  5280

5281  GTCATCAGGTTTATTCCGTGTTCTGTCATTCACATGGAACACCGGATGATTAGCTAACAG  5340

5341  TTTAGTGCCAGCCTTCATTCTTTACTGTGTACGTTAAATGCACACTACAGTGAAAAAGCC  5400

5401  TAAGACACTTGGTAAATATTTTCTAGCTGACTGATTCCAGAACACACAAG  5450
```

Figures 20A

```
   1 CCACGCGTCCGGCTCTTGCCTCCCAGTGCCATGCAGGTGCAGGATGCAACCAGGCGGCCC  60

61 TCAGCCGTGCGCTTCCTCAGCTCCTTTCTCCAGGGCCGCCGGCACTCCACCTCAGACCCA 120

121 GTACTGCGGCTGCAGCAGGCCCGGCGGGGCTCTGGCTTGGGCTCCGGCTCTGCCACGAAG 180

181 CTGCTGTCCTCGTCCTCTCTCCAGGTGATGGTGGCTGTTTCCTCAGTCAGCCATGCAGAG 240

241 GGAAACCCAACTTTCCCCGAAAGAAAAAGAAATTTAGAACGTCCAACACCAAAGTACACA 300

301 AAAGTAGGGGAGCGTTTACGGCATGTCATTCCTGGACACATGGCATGTTCCATGGCGTGT 360

361 GGCGGTAGAGCTTGCAAGTATGAGAACCCAGCCCGCTGGAGTGAGCAGGAGCAAGCCATT 420

421 AAGGGGGTTTACTCATCCTGGGTCACTGATAATATACTGGCCATGCCCGCCCATCCTCT  480

481 GAGCTCCTGGAGAAGTACCACATCATTGATCAGTTCCTCAGCCATGGCATAAAAACAATA 540

541 ATCAACCTCCAGCGCCCTGGTGAGCATGCTAGCTGTGGGAACCCTCTGGAACAAGAAAGT 600

601 GGCTTCACATACCTTCCTGAGGCTTTCATGGAGGCTGGCATTTACTTCTACAATTTCGGA 660
   1                                 M  E  A  G  I  Y  F  Y  N  F  G   11

661 TGGAAGCATTATGGTGTAGCGTCTCTTACTACTATCCTAGATATGGTGAAGGTGATGACA 720
  12  W  K  D  Y  G  V  A  S  L  T  T  I  L  D  M  V  K  V  M  T   31

721 TTTGCCTTACAGGAAGGAAAAGTAGCTATCCATTGTCATGCAGGGCTTGGTCGAACAGGT 780
  32  F  A  L  Q  E  G  K  V  A  I  H  C  H  A  G  L  G  R  T  G   51

781 GTTTTAATAGCCTGTTACTTAGTTTTTGCAACGAGAATGACTGCTGACCAAGCAATTATA 840
  52  V  L  I  A  C  Y  L  V  F  A  T  R  M  T  A  D  Q  A  I  I   71

841 TTTGTGCGGGCAAAGCGACCCAATTCCATACAAACCAGAGGACAGCTCCTCTGTGTAAGG 900
  72  F  V  R  A  K  R  P  N  S  I  Q  T  R  G  Q  L  L  C  V  R   91

901 GAATTTACTCAGTTTCTAACTCCTCTCCGCAATATATTCTCTTGCTGTGATCCCAAAGCA 960
  92  E  F  T  Q  F  L  T  P  L  R  N  I  F  S  C  C  D  P  K  A  111

961 CATGCTGTCACCTTACCTCAATATCTAATTCGCCAGCGTCATCTGCTTCATGGTTATGAG 1020
 112  H  A  V  T  L  P  Q  Y  L  I  R  Q  R  H  L  L  H  G  Y  E  131

1021 GCACGACTTCTGAAACACGTGCCAAAAATTATCCACCTAGTTTGCAAATTGCTGCTGGAC 1080
 132  A  R  L  L  K  H  V  P  K  I  I  H  L  V  C  K  L  L  D  151

1081 TTAGCGGAGAACAGGCCAGTGATGATGAAGGATGTGTCCGAAGGACCTGGTCTCTCTGCT 1140
 152  L  A  E  N  R  P  V  M  M  K  D  V  S  E  G  P  G  L  S  A  171
```

Figures 20B

```
1141 GAAATAGAAAAGACAATGTCTGAGATGGTCACCATGCAGCTGGATAAAGAGTTACTGAGG 1200
 172 E  I  E  K  T  M  S  E  M  V  T  M  Q  L  D  K  E  L  L  R   191

1201 CATGACAGTGATGTGTCCAACCCGCCTAACCCCACTGCAGTGGCAGCAGATTTTGACAAT 1260
 192 H  D  S  D  V  S  N  P  P  N  P  T  A  V  A  A  D  F  D  N   211

1261 CGAGGCATGATTTTCTCCAATGAGCAACAGTTTGACCCTCTTTGGAAAAGGCGGAATGTT 1320
 212 R  G  M  I  F  S  N  E  Q  Q  F  D  P  L  W  K  R  R  N  V   231

1321 GAGTGCCTTCAACCCCTGACTCATCTGAAAAGGCGGCTCAGCTACAGTGACTCAGATTTA 1380
 232 E  C  L  Q  P  L  T  H  L  K  R  R  L  S  Y  S  D  S  D  L   251

1381 AAGAGGGCCGAGAACCTCCTGGAGCAAGGGGAGACTCCACAGACAGTGCCTGCCCAGATC 1440
 252 K  R  A  E  N  L  L  E  Q  G  E  T  P  Q  T  V  P  A  Q  I   271

1441 TTGGTTGGCCACAAGCCCAGGCAGCAGAAGCTCATAAGCCATTGTTACATCCCACAGTCT 1500
 272 L  V  G  H  K  P  R  Q  Q  K  L  I  S  H  C  Y  I  P  Q  S   291

1501 CCAGAACCAGACTTACACAAGGAAGCCTTGGTTCGCAGCACACTTTCTTTCTGGAGTCAG 1560
 292 P  E  P  D  L  H  K  E  A  L  V  R  S  T  L  S  F  W  S  Q   311

1561 TCAAAGTTTGGAGGCCTGGAAGGACTCAAAGATAATGGGTCACCAATTTTCCATGGAAGG 1620
 312 S  K  F  G  G  L  E  G  L  K  D  N  G  S  P  I  F  H  G  R   331

1621 ATCATTCCAAAGGAAGCACAGCAGAGTGGAGCTTTCTCTGCAGATGTTTCAGGCTCACAC 1680
 332 I  I  P  K  E  A  Q  Q  S  G  A  F  S  A  D  V  S  G  S  H   351

1681 AGCCCTGGGGAGCCAGTTTCACCCAGCTTTGCAAATGTCCATAAGGATCCAAACCCTGCT 1740
 352 S  P  G  E  P  V  S  P  S  F  A  N  V  H  K  D  P  N  P  A   371

1741 CACCAGCAAGTGTCTCACTGTCAGTGTAAAACTCATGGTGTTGGGAGCCCTGGCTCTGTC 1800
 372 H  Q  Q  V  S  H  C  Q  C  K  T  H  G  V  G  S  P  G  S  V   391

1801 AGGCAGAACAGCAGGACACCCCGAAGCCCTCTGGACTGTGGCTCCAGTCCCAAAGCACAG 1860
 392 R  Q  N  S  R  T  P  R  S  P  L  D  C  G  S  S  P  K  A  Q   411

1861 TTCTTGGTTGAACATGAAACCCAGGACAGTAAAGATCTGTCTGAAGCAGCTTCACACTCT 1920
 412 F  L  V  E  H  E  T  Q  D  S  K  D  L  S  E  A  A  S  H  S   431

1921 GCATTACAGTCTGAATTGAGTGCTGAGGCAAGAAGAATACTGGCGGCCAAAGCCCTAGCA 1980
 432 A  L  Q  S  E  L  S  A  E  A  R  R  I  L  A  A  K  A  L      451

1981 AATTTAAATGAATCTGTAGAAAAGGAGGAACTAAAAAGGAAGGTAGAAATGTGGCAGAAA 2040
 452 N  L  N  E  S  V  E  K  E  E  L  K  R  K  V  E  M  W  Q  K   471

2041 GAGCTTAATTCCCGAGATGGAGCTTGGGAAAGAATATGTGGCGAGAGGGACCCTTTCATC 2100
 472 E  L  N  S  R  D  G  A  W  E  R  I  C  G  E  R  D  P  F  I   491
```

Figures 20C

```
2101 CTATGCAGCTTGATGTGGTCTTGGGTGGAGCAACTGAAGGAGCCTGTAATCACCAAAGAG 2160
 492  L  C  S  L  M  W  S  W  V  E  Q  L  K  E  P  V  I  T  K  E   511

2161 GATGTGGACATGTTGGTTGACAGGCGAGCAGATGCCGCAGAAGCACTTTTTTTATTAGAG 2220
 512  D  V  D  M  L  V  D  R  R  A  D  A  A  E  A  L  F  L  L  E   531

2221 AAGGGACAGCACCAGACTATTCTCTGCGTGTTGCACTGCATAGTGAACCTGCAGACAATT 2280
 532  K  G  Q  H  Q  T  I  L  C  V  L  H  C  I  V  N  L  Q  T  I   551

2281 CCCGTGGATGTGGAGGAAGCTTTCCTTGCCCATGCCATTAAGGCATTCACTAAGGTTAAT 2340
 552  P  V  D  V  E  E  A  F  L  A  H  A  I  K  A  F  T  K  V  N   571

2341 TTTGATTCTGAAAATGGACCAACAGTTTACAACACCCTGAAGAAAATATTTAAGCACACG 2400
 572  F  D  S  E  N  G  P  T  V  Y  N  T  L  K  K  I  F  K  H  T   591

2401 CTGGAAGAAAAAGAAAAATGACAAAAGATGGCCCTAAGCCTGGCCTCTAGCTTTCACTC 2460
 592  L  E  E  K  R  K  M  T  K  D  G  P  K  P  G  L  *            607

2461 ATGGTGAATATTTCAGACCTAAAGATCCAGATAGTATCTCTGTTCATATGTGAATAAGTT 2520

2521 GAAGATTGTGGGGCTACTTTTTCTCATAGCACTTTATTTTGAATGTTGTTAGTTTGTGCT 2580

2581 GAGAATGGTCGTCCGTATTTGAACCAATTATTTATTTTAAAATATATTTAAGCTACATTT 2640

2641 TTGTTTTGAAAAATTGCCATAAATTTGGTGCCACTTTCTTTTATTTATTTGACTGAGTTA 2700

2701 ATATTATTGTATTAACATTTTAAGTATATGGTGTTTACATTCTTATTTCTTTTGACATTT 2760

2761 TGGAAATAATCATAACTTGTCTTTCCAAAATAACCATTTTCTTGATGGAACTCTTCCTAG 2820

2821 AGTTTTTACCAAATAGCTAACTTTAGTAGTAAAACCTCATTGTGTATCCATTCCCCCACA 2880

2881 GATGAACTAAGAAAGTCACCAAGTGTCTTAAGCTGTTTATATTTGTTACGAAGAAGGCT 2940

2941 ATTGCTACAATATTTTAAAGGTTTCTTTTTTAACTTTGAAATTTTTTGTTTTTCCTTTT 3000

3001 CTTTTTATAAATGTAACAGAGCGGTTTCAAAGCATATTATTTTCAGAGAGATTTAGTTTT 3060

3061 ACTTTAATGGAGTGACTGTGAAGTGGTTGGGATTTTTTGCTTGTAGAAAGTAGACTTGCT 3120

3121 CTTTGTCAGATTTCCAAACAACCTTGCCAGCCTTGGCTGTCAAAAGGAGGCAGGAGCAGT 3180

3181 TCTCAACACACCAAGCCTTATTCCCACTCCCTTGGGTTGCTGCTGAGCCAAATAGCATCT 3240

3241 TTACAGAGGAAGTGGGATCAGAGGCAGGAAGTGTGGAAAGTTGCTAAGAAGCAGGGCTTG 3300
```

Figures 20D

```
3301 CCTCTGTCCTCCCGGGGACTCCACAGGGATATTCGTGCAGGGCAGGGGCTCTGTGCCAGC 3360

3361 CCTGCTCTCTCAGATGCCACAGCCACTCTGCAGAGGTGACTCTTGGAGCTGGAGGAAGTC 3420

3421 AAAACTGGGCCACTGTTTGTACTGATGGTGTATTAGCATGAGCAGCGTGGCCCTGGCCCC 3480

3481 ACACTCCCAAATCTGCCACTCCATAGACCCACTTGCCTCAAGGCTTTATATTTGGCTGCT 3540

3541 TTCTTACAATGAGAATTAAGATTTTTAAACTGAAGTTGACCATACAGGTTGCATTAGCCC 3600

3601 TAACTGGCTTCATGTAAGAAGGGTGACTGCCTAAACTAGTTCCTTGTAAGCTGAACCATC 3660

3661 AATTATCAGTTGAAGCCATACTTTTATTTAAATTAATATACGTAGATACCAGAGGCCAAG 3720

3721 CCACAGAGAGGATAATAGTTCTTCCCAATAAAGGTGATATTAATCAGACTAATTTCGAAC 3780

3781 TAAAGAAGTTACTGCTTAAAGACGGAATTTCAGGGGAAGCAAGACTCATTTAGAACAAAT 3840

3841 GAAATTTCTCCAGTCCTACATTTCTGAATTGACTTCTAGCACATCAAAAATATTTCAGTC 3900

3901 ATTATCAGTCTCATTAACTGAAATGCCAAATGCTAAATGCAGTGTTCTTTCACACTGTTT 3960

3961 TAATTTTCTTGGGAAATTGAGTCCAGTGGATGTTAATGGAGTGGGTTGCCCATCCCTGAA 4020

4021 ATGTCTTATTTTCAAGTGCCTGGCCTGGGAAAGAAGGGGAAGAAACAATTGCATTATATC 4080

4081 CAAAGATACACTATAAAAATAGAGTTTTTACCAAAAAAAGATGTTTGTTCTCATCTCAGT 4140

4141 AGGCCTCATTTGGGCAAGTGACCCACAGGTCTTTTGGCGAGTTTGCTATTTGCCTGTTGA 4200

4201 AATACTTGTTTCAACTTAGAGAACAGTTATGATGTGACCATAGCATGGCACAACTAAAAA 4260

4261 TCTAAGCCTGAAACCTGAAAAAGAGATATGACAAGGGAAATTAATCAGGCTATACATAA 4320

4321 GTATTGTATTTATTTGAATAAAAATAAAAAGAGCAACCCATAAAAAAAAAAAAAAAAAAA 4380

4381 AAAAAAAAAAAG 4393
```

Figures 21

```
  1 CCACGCGTCCGGCGAGGGGACGCGTGGGCGGAGCGGGGCTGGCCAGCCTCGGCCCCCATG  60

61 ACCCGCTGTCCTGTGCCCTTTCCCAGCGATGGGCGTGCAGCCCCCAACTTCTCCTGGGT 120
  1                                 M  G  V  Q  P  P  N  F  S  W  V   11

121 GCTTCCGGGCCGGCTGGCGGGACTGGCGCTGCCGCGGCTCCCCGCCCACTACCAGTTCCT 180
 11  L  P  G  R  L  A  G  L  A  L  P  R  L  P  A  H  Y  Q  F  L   31

181 GTTGGACCTGGGCGTGCGGCACCTGGTGTCCCTGACGGAGCGCGGGCCCCCTCACAGCGA 240
 31  L  D  L  G  V  R  H  L  V  S  L  T  E  R  G  P  P  H  S  D   51

241 CAGCTGCCCCGGCCTCACCCTGCACCGCCTGCGCATCCCCGACTTCTGCCCGCCGGCCCC 300
 51  S  C  P  G  L  T  L  H  R  L  R  I  P  D  F  C  P  P  A  P   71

301 CGACCAGATCGACCGCTTCGTGCAGATCGTGGACGAGGCCAACGCACGGGAGAGGCTGT 360
 71  D  Q  I  D  R  F  V  Q  I  V  D  E  A  N  A  R  E  A  V   91

361 GGGAGTGCACTGTGCTCTGGGCTTTGGCCGCACTGGCACCATGCTGGCCTGTTACCTGGT 420
 91  G  V  H  C  A  L  G  F  G  R  T  G  T  M  L  A  C  Y  L  V  111

421 GAAGGAGCGGGGCTTGGCTGCAGGAGATGCCATTGCTGAAATCCGACGACTACGACCCGG 480
111  K  E  R  G  L  A  A  G  D  A  I  A  E  I  R  R  L  R  P  G  131

481 CTCCATCGAGACCTATGAGCAGGAGAAAGCAGTCTTCCAGTTCTACCAGCGAACGAAATA 540
131  S  I  E  T  Y  E  Q  E  K  A  V  F  Q  F  Y  Q  R  T  K  *  150

541 AGGGGCCTTAGTACCCTTCTACCAGGCCCTCACTCCCCTTCCCCATGTTGTCGATGGGGC 600

601 CAGAGATGAAGGGAAGTGGACTAAAGTATTAAACCCTCTAGCTCCCATTGGCTGAAGACA 660

661 CTGAAGTAGCCCACCCCTGCAGGCAGGTCCTGATTGAAGGGGAGGCTTGTACTGCTTTGT 720

721 TGAATAAATGAGTTTTACGAACCAGGAAAAAAAAAAAAAAAAAAAAAAAAAAAAAAAAA 780

781 AAAAAAAAAAAAAAAAAAAAAAAAAAAAAAAAAAAAAAAAAAAAAAAAAAAAAAAAAAAA 840

841 AAAAAAAAAAAAAAAAAAAAAAAAAAAAAAAAAAAAGGGC 878
```

Figure 24.

BMY_HPP1

| Protein | Genbank ID | Identities | Similarities |
|---|---|---|---|
| human protein tyrosine phosphatase | gi\| P32587 | 27% | 39.6% |
| mouse protein tyrosine phosphatase | gi\| NP_035346 | 27.9% | 40.5% |
| Schizosacchromyces Pombe protein tyrosine phosphatase PYP3 protein | gi\| NP_002839 | 27.5% | 36.7% |

BMY_HPP2

| Protein | Genbank ID | Identities | Similarities |
|---|---|---|---|
| human S. cerevisiaeCDC14 homolog A | gi\| NP_003663 | 33.1% | 44.1% |
| human S. cerevisiae CDC14 homolog B | gi\| NP_003662 | 33.1% | 45.8% |
| yeast soluble tyrosine-specific protein phosphatase Cdc14p protein | gi\| NP_002839 | 33.1% | 45.8% |

Figure 25.

RET31

| Protein | Genbank ID | Identities | Similarities |
|---|---|---|---|
| human protein-tyrosine phosphatase DUS8 protein | gi| U27193 | 50.3% | 56.8% |
| the human dual specificity MAP kinase DUSP6 protein | gi| AB013382 | 36.5% | 48.3% |
| human map kinase phosphatase MKP-5 protein | gi| AB026436 | 34.3% | 47.2% |
| mouse RET31 protein | N/A | 90% | 92% |

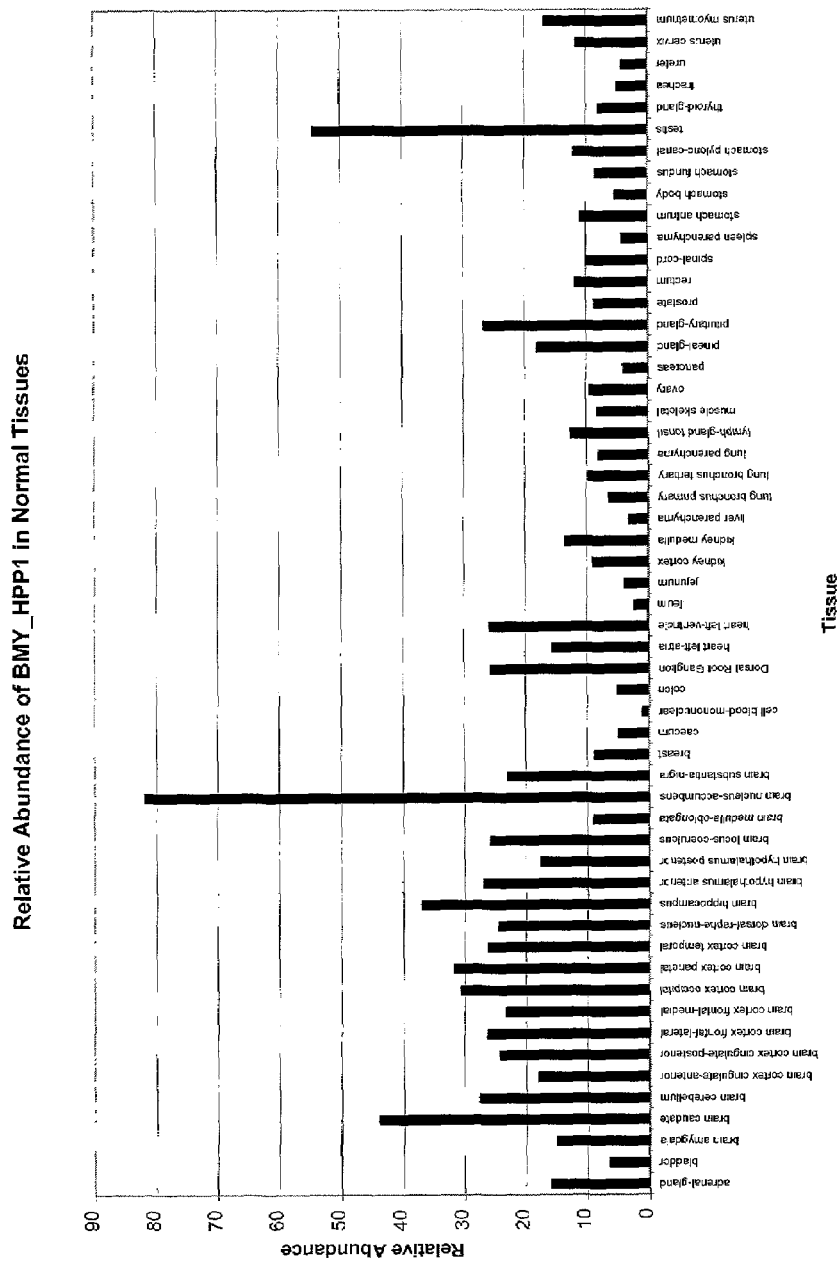

Figure 27

```
HPP1      .......... MAAGVLPQNE QPYSTLVNNS EC.VANMKGN LERPTPKYTK  39
pdb1aax   MEMEKEFEQI DKSGSWAAIY QDIRHEASDF PCRVAKLPKN KNRNRYRDVS  50

HPP1      VGERLRHVIP GHMACSMACG GRACKYENPA RWSEQEQAIK GVYSSWVTDN  89
pdb1aax   PFDH..SRIK LHQEDNDYIN ASLIKME... .....EAQRS YILTQGPLPN  90

HPP1      ILAMARPSSE LLEKYHIIDQ FLSHGIKTII NLQRPGE..H ASCGNPLEQE 137
pdb1aax   .......... ..TCGHFWEM VWEQKSRGVV MLNRVMEKGS LKCAQYWPQK 128

HPP1      S......... .....GFTYL PEAFMEAG.. .......... ...IYFYNFG 158
pdb1aax   EEKEMIFEDT NLKLTLISED IKSYYTVRQL ELENLTTQET REILHFHYTT 178
                     **                         **    *     *
HPP1      WKDYGVA.SL TTILDMVKVM ....TFALQE GKVAIHCHAG LGRTGVLIAC 203
pdb1aax   WPDFGVPESP ASFLNFLFKV RESGSLSPEH GPVVVHSSAG IGRSGTFCLA 228

HPP1      YLVFATR... .....MTADQ AIIFVRAKRP NSI....QTR GQLLCVREFT 241
pdb1aax   DTCLLLMDKR KDPSSVDIKK VLLEMRKFRM GLIQTADQLR FSYLAVIEGA 278

HPP1      QFLTPLRNIF SCCDPKAHAV TLPQYLIRQR HLLHGYEARL LKHVPKIIHL 291
pdb1aax   KFIM...... .......... GDSSVQDQWK ELSHEDLEPP PGHIPPPPRP 312

HPP1      VCKLLLDLAE NRPVMMKDVS EGPGLSAEIE KTMSEMVTMQ LDKELLRHDS 301
pdb1aax   PKRILEPHN. .......... .......... .......... ..........  321
```

HPP1 Homology Model

Figure 31

```
            20         30         40         50         60         70
pdb1vhrA  GCYSLPSQPCNEVTPRIYVGNASVAQDIPKLQKLGITHVLNAAEGRSFMHVNTNANFYKD
                       :  ::.  :...  .:  :.    :  ..
BMY_HPP2  MGVQPPNFSWVLPGRLAGLALPRLPAHYQFLLDLGVRHLVSLIE-RGPPHSDSCP-----
            10         20         30         40         50

80         90        100        110        120        130
pdb1vhrA  SGITYLGIKANDTQEFNLSA--YFERAADFIDQALAQKNGRVLVHCREGYSRSPTLVIAY
           :.:    ..  :    :      ..:  ....:.:  :.  ..  :  :::   :...:.  ..  :
BMY_HPP2  -GLTLHRLRIPD---FCPPAPDQIDRFVQIVDEANARGEA-VGVHCALGFGRTGTMLACY
             60         70         80         90        100

140        150        160        170        180
pdb1vhrA  LMMRQKMPVKSALSIVRQNREIGPNDGFLAQLCQLNDRLAKEGKLKP
           :.  ..   .   . .:..   .:.   :
BMY_HPP2  LVKERGLAAGDAIAEIRRLRPGSIETYEQEKAVFQFYQRTK
            110        120        130        140        150
```

Figure 37

```
                                       10        20        30
pdb1mkp                        ASFPVEILPFLYLGCAKDSTNLDVLEEFGIKYI
                               :..::: :::::: .:  :  ..... :: :.
BMY_HPP5 SRCFPGLCEGKSTLVPTCISQPCLPVANIGPTRILPNLYLGCQRDVLNKELMQQNGIGYV
         130       140       150       160       170       180

40        50        60        70        80        90
pdb1mkp  LNVTPNLPNLFENAGEFKYKQIPISDHWSQNLSQFFPEAISFIDEARGKNCGVLVHSLAG
         :::.. :.  .    : .. ..:..:  ..   .. ....:..:...:  :::: :::
BMY_HPP5 LNASNTCPKP-DFIPESHFLRVPVNDSFCEKILPWLDKSVDFIEKAKASNGCVLVHCLAG
         190       200       210       220       230       240

100       110       120       130       140
pdb1mkp  ISRSVTVTVAYLMQKLNLSMNDAYDIVKMKKSNISPNFNFMGQLLDFERTL
         :::::...::::::::.::  .:: :. .:::::::::.:::: .:. .
BMY_HPP5 ISRSATIAIAYIMKRMDMSLDEAYRFVKEKRPTISPNFNFLGQLLAYEKKIKNQTGASGP
         250       260       270       280       290       300

BMY_HPP5 KSKLKLLPLEKPNEPVPAVSEGGQKSETPLSPPCADSATSEAAGQRPVHPASVPSVPSVQ
         310       320       330       340       350       360
```

POLYNUCLEOTIDES ENCODING THE NOVEL HUMAN PHOSPHATASE, RET31, AND VARIANTS THEREOF

This application claims benefit to provisional application U.S. Ser. No. 60/256,868, filed Dec. 20, 2000; to provisional application U.S. Ser. No. 60/280,186, filed Mar. 30, 2001; to provisional application U.S. Ser. No. 60/287,735, filed May 1, 2001, to provisional application U.S. Ser. No. 60/295,848, filed Jun. 5, 2001, and to provisional application U.S. Ser. No. 60/300,465, filed Jun. 25, 2001.

FIELD OF THE INVENTION

The present invention provides novel polynucleotides encoding human phosphatase polypeptides, fragments and homologues thereof. Also provided are vectors, host cells, antibodies, and recombinant and synthetic methods for producing said polypeptides. The invention further relates to diagnostic and therapeutic methods for applying these novel human phosphatase polypeptides to the diagnosis, treatment, and/or prevention of various diseases and/or disorders related to these polypeptides, particularly cardiovascular diseases and/or disorders. The invention further relates to screening methods for identifying agonists and antagonists of the polynucleotides and polypeptides of the present invention.

BACKGROUND OF THE INVENTION

Phosphorylation of proteins is a fundamental mechanism for regulating diverse cellular processes. While the majority of protein phosphorylation occurs at serine and threonine residues, phosphorylation at tyrosine residues is attracting a great deal of interest since the discovery that many oncogene products and growth factor receptors possess intrinsic protein tyrosine kinase activity. The importance of protein tyrosine phosphorylation in growth factor signal transduction, cell cycle progression and neoplastic transformation is now well established (Hunter et al., Ann. Rev. Biochem. 54:987–930 (1985), Ullrich et al., Cell 61:203–212 (1990), Nurse, Nature 344:503–508 (1990), Cantley et al, Cell 64:281–302 (1991)).

Biochemical studies have shown that phosphorylation on tyrosine residues of a variety of cellular proteins is a dynamic process involving competing phosphorylation and dephosphorylation reactions. The regulation of protein tyrosine phosphorylation is mediated by the reciprocal actions of protein tyrosine kinases (PTKases) and protein tyrosine phosphatases (PTPases). The tyrosine phosphorylation reactions are catalyzed by PTKases. Tyrosine phosphorylated proteins can be specifically dephosphorylated through the action of PTPases. The level of protein tyrosine phosphorylation of intracellular substances is determined by the balance of PTKase and PTPase activities. (Hunter, T., Cell 58:1013–1016 (1989)).

The protein tyrosine kinases (PTKases) are a large family of proteins that includes many growth factor receptors and potential oncogenes. (Hanks et al., Science 241:42–52 (1988)). Many PTKases have been linked to initial signals required for induction of the cell cycle (Weaver et al., Mol. Cell. Biol. 11, 9:4415–4422 (1991)). PTKases comprise a discrete family of enzymes having common ancestry with, but major differences from, serine/threonine-specific protein kinases (Hanks et al., supra). The mechanisms leading to changes in activity of PTKases are best understood in the case of receptor-type PTKases having a transmembrane topology (Ullrich et al. (1990) supra). The binding of specific ligands to the extracellular domain of members of receptor-type PTKases is thought to induce their oligomerization leading to an increase in tyrosine kinase activity and activation of the signal transduction pathways (Ullrich et al., (1990) supra). Deregulation of kinase activity through mutation or overexpression is a well established mechanism for cell transformation (Hunter et al., (1985) supra; Ullrich et al., (1990) supra).

The protein phosphatases are composed of at least two separate and distinct families (Hunter, T. (1989) supra) the protein serine/threonine phosphatases and the protein tyrosine phosphatases (PTPases).

The protein tyrosine phosphatases (PTPases) are a family of proteins that have been classified into two subgroups. The first subgroup is made up of the low molecular weight, intracellular enzymes that contain a single conserved catalytic phosphatase domain. All known intracellular type PTPases contain a single conserved catalytic phosphatase domain. Examples of the first group of PTPases include (1) placental PTPase 1B (Charbonneau et al., Proc. Natl. Acad. Sci. USA 86:5252–5256 (1989); Chernoff et al., Proc. Natl. Acad. Sci. USA 87:2735–2789 (1989)), (2) T-cell PTPase (Cool et al., Proc. Natl. Acad. Sci. USA 86:5257–5261 (1989)), (3) rat brain PTPase (Guan et al., Proc. Natl. Acad. Sci. USA 87:1501–1502 (1990)), (4) neuronal phosphatase (STEP) (Lombroso et al., Proc. Natl. Acad. Sci. USA 88:7242–7246 (1991)), and (5) cytoplasmic phosphatases that contain a region of homology to cytoskeletal proteins (Gu et al., Proc. Natl. Acad. Sci. USA 88:5867–57871 (1991); Yang et al., Proc. Natl. Acad. Sci. USA 88:5949–5953 (1991)).

Enzymes of this class are characterized by an active site motif of $CX_5R$. Within the motif the Cysteine sulfur acts as a nucleophile which cleaves the P—O bond and releases the phosphate; the Arginine interacts with the phosphate and facilitates nucleophilic attack. In many cases the Cysteine is preceded by a Histidine and the Arginine is followed by a Serine or Threonine. In addition, an Aspartate residue located 20 or more amino acids N terminal to the Cysteine acts as a general acid during cleavage [Fauman, 1996].

The second subgroup of protein tyrosine phosphatases is made up of the high molecular weight, receptor-linked PTPases, termed R-PTPases. R-PTPases consist of a) an intracellular catalytic region, b) a single transmembrane segment, and c) a putative ligand-binding extracellular domain (Gebbink et al., supra).

The structures and sizes of the c) putative ligand-binding extracellular "receptor" domains of R-PTPases are quite divergent. In contrast, the a) intracellular catalytic regions of R-PTPases are highly homologous. All RPTPases have two tandemly duplicated catalytic phosphatase homology domains, with the prominent exception of an R-PTPase termed HPTP.beta., which has "only one catalytic phosphatase domain. (Tsai et al., J. Biol. Chem. 266(16):10534–10543 (1991)).

One example of R-PTPases are the leukocyte common antigens (LCA) (Ralph, S. J., EMBO J. 6:1251–1257 (1987)). LCA is a family of high molecular weight glycoproteins expressed on the surface of all leukocytes and their hemopoietic progenitors (Thomas, Ann. Rev. Immunol. 7:339–369 (1989)). A remarkable degree of similarity is detected with the sequence of LCA from several species (Charbonneau et al., Proc. Natl. Acad. Sci. USA 85:7182–7186 (1988)). LCA is referred to in the literature by different names, including T200 (Trowbridge et al., Eur. J. Immunol. 6:557–562 (1962)), B220 for the B cell form (Coffman et al., Nature 289:681–683 (1981)), the mouse allotypic marker Ly-5 (Komuro et al., Immunogenetics 1:452–456 (1975)), and more recently CD45 (Cobbold et al., Leucocyte Typing III, ed. A. J. McMichael et al., pp. 788–803 (1987)).

Several studies suggest that CD45 plays a critical role in T cell activation. These studies are reviewed in Weiss A., Ann. Rev. Genet. 25:487–510 (1991). In one study, T-cell clones that were mutagenized by NSG and selected for their failure to express CD45 had impaired responses to T-cell receptor stimuli (Weaver et al., (1991) supra). These T-cell clones were functionally defective in their responses to signals transmitted through the T cell antigen receptor, including cytolysis of appropriate targets, proliferation, and lymphokine production (Weaver et al., (1991) supra).

Other studies indicate that the PTPase activity of CD45 plays a role in the activation of pp56.sup.lck, a lymphocyte-specific PTKase (Mustelin et al., Proc. Natl. Acad. Sci. USA 86:6302–6306 (1989); Ostergaard et al., Proc. Natl. Acad. Sci. USA 86:8959–8963 (1989)). These authors hypothesized that the phosphatase activity of CD45 activates pp56.sup.lck by dephosphorylation of a C-terminal tyrosine residue, which may, in turn, be related to T-cell activation.

Another example of R-PTPases is the leukocyte common antigen related molecule (LAR) (Streuli et al., J. Exp. Med. 168:1523–1530 (1988)). LAR was initially identified as a homologue of LCA (Streuli et al., supra). Although the a) intracellular catalytic region of the LAR molecule contains two catalytic phosphatase homology domains (domain I and domain II), mutational analyses suggest that only domain I has catalytic phosphatase activity, whereas domain II is enzymatically inactive (Streuli et al., EMBO J. 9(8):2399–2407 (1990)). Chemically induced LAR mutants having tyrosine at amino acid position 1379 changed to a phenylalanine are temperature-sensitive (Tsai et al., J. Biol. Chem. 266(16):10534–10543 (1991)).

A new mouse R-PTP, designated mRPTP.mu., has been cloned which has a) an extracellular domain that shares some structural motifs with LAR. (Gebbink et al., (1991) supra). In addition, these authors have cloned the human homologue of RPTP.mu. and localized the gene on human chromosome 18.

Two *Drosophila* PTPases, termed DLAR and DPTP, have been predicted based on the sequences of cDNA clones (Streuli et al., Proc. Natl. Acad. Sci. USA 35 86:8698–8702 (1989)). cDNAs coding for another *Drosophila* R-PTPase, termed DPTP 99A, have been cloned and characterized (Hariharan et al., Proc. Natl. Acad. Sci. USA 88:11266–11270(1991)).

Other examples of R-PTPases include R-PTPase-.alpha., .beta., .gamma., and .zeta. (Krueger et al., EMBO J. 9:3241–3252 (1990), Sap et al., Proc. Natl. Acad. Sci. USA 87:6112–6116 (1990), Kaplan et al., Proc. Natl. Acad. Sci. USA 87:7000–7004 (1990), Jirik et al., FEBS Lett. 273:239–242 (1990); Mathews et al., Proc. Natl. Acad. Sci. USA 87:4444–4448 (1990), Ohagi et al., Nucl. Acids Res. 18:7159 (1990)). Published application WO92/01050 discloses human R-PTPase-.alpha., .beta. and .gamma., and reports on the nature of the structural homologies found among the conserved domains of these three R-PTPases and other members of this protein family. The murine R-PTPase-. alpha. has 794 amino acids, whereas the human R-PTPase-. alpha. has 802 amino acids. R-PTPase-.alpha. has an intracellular domain homologous to the catalytic domains of other tyrosine phosphatases. The 142 amino acid extracellular domain (including signal peptide of RPTPase-.alpha.) has a high serine and threonine content (32%) and 8 poten-tial N-glycosylation sites. cDNA clones have been produced that code for the R-PTPase-.alpha., and R-PTPase-.alpha. has been expressed from eukaryotic hosts. Northern analysis has been used to identify the natural expression of R-PTPase-.alpha. in various cells and tissues. A polyclonal antibody to R-PTPase-.alpha. has been produced by immunization with a synthetic peptide of R-PTPase-.alpha., which identifies a 130 kDa protein in cells transfected with a cDNA clone encoding a portion of R-PTPase-.alpha.

Another example of R-PTPases is HePTP. (Jirik et al, FASEB J. 4:82082 (1990) Abstract 2253). Jirik et al. screened a cDNA library derived from a hepatoblastoma cell line, HepG2, with a probe encoding the two PTPase domains of LCA, and discovered a cDNA clone encoding a new RPTPase, named HePTP. The HePTP gene appeared to be expressed in a variety of human and murine cell lines and tissues.

Since the initial purification, sequencing, and cloning of a PTPase, additional potential PTPases have been identified at a rapid pace. The number of different PTPases that have been identified is increasing steadily, leading to speculations that this family may be as large as the PTKase family (Hunter (1989) supra).

Conserved amino acid sequences in the catalytic domains of known PTPases have been identified and defined (Krueger et al., EMBO J. 9:3241–3252 (1990) and Yi et al., Mol. Cell. Biol. 12:836–846 (1992), which are incorporated herein by reference.) These amino acid sequences are designated "consensus sequences" herein.

Yi et al. aligned the catalytic phosphatase domain sequences of the following PTPases: LCA, PTP1B, TCPTP, LAR, DLAR, and HPTP.alpha., HPTP.beta., and HPTP.gamma. This alignment includes the following "consensus sequences" (Yi et al., supra, FIG. 2(A), lines 1 and 2): DYINAS/N (SEQ ID NO:77), CXXYWP (SEQ ID NO:78), and I/VVMXXXXE (SEQ ID NO:79).

Krueger et al., aligned the catalytic phosphatase domain sequences of PTP1B, TCPTP, LAR, LCA, HPTP.alpha., .beta., .gamma., .GAMMA., .delta., .epsilon. and .zeta. and DLAR and DPTP. This alignment includes the following "consensus sequences: (Krueger et al., supra, FIG. 7, lines 1 and 2): D/NYINAS/N (SEQ ID NO:80), CXXYWP (SEQ ID NO:81), and I/VVMXXXXE (SEQ ID NO:82).

It is becoming clear that dephosphorylation of tyrosine residues can by itself function as an important regulatory mechanism. Dephosphorylation of a C-terminal tyrosine residue has been shown to activate tyrosine kinase activity in the case of the src family of tyrosine kinases (Hunter, T. Cell 49:1–4 (1987)). Tyrosine dephosphorylation has been suggested to be an obligatory step in the mitotic activation of the maturation-promoting factor (MPF) kinase (Morla et al., Cell 58:193–203 (1989)). These observations point out the need in the art for understanding the mechanisms that regulate tyrosine phosphatase activity.

Modulators (inhibitors or activators) of human phosphatase expression or activity could be used to treat a subject with a disorder characterized by aberrant phosphatase expression or activity or by decreased phosphorylation of a phosphatase substrate protein. Examples of such disorders include but are not limited to: an immune, anti-proliferative, proliferative (e.g. cancer), metabolic (e.g. diabetes or obesity), bone (e.g., osteoporosis), neural, and/or cardiovascular diseases and/or disorders, in addition to, viral pathogenesis.

It is clear that further analysis of structure-function relationships among PTPases are needed to gain important understanding of the mechanisms of signal transduction, cell cycle progression and cell growth, and neoplastic transformation.

The present invention also relates to recombinant vectors, which include the isolated nucleic acid molecules of the present invention, and to host cells containing the recombinant vectors, as well as to methods of making such vectors and host cells, in addition to their use in the production of human phosphatase polypeptides or peptides using recombinant techniques. Synthetic methods for producing the polypeptides and polynucleotides of the present invention are provided. Also provided are diagnostic methods for detecting diseases, disorders, and/or conditions related to the human phosphatase polypeptides and polynucleotides, and therapeutic methods for treating such diseases, disorders, and/or conditions. The invention further relates to screening methods for identifying binding partners of the polypeptides.

BRIEF SUMMARY OF THE INVENTION

The present invention provides isolated nucleic acid molecules, that comprise, or alternatively consist of, a polynucleotide encoding the human BMY_HPP1 phosphatase protein having the amino acid sequence shown as SEQ ID NO:150, or the amino acid sequence encoded by the cDNA clone, BMY_HPP1, deposited as ATCC Deposit Number PTA-3949 on Dec. 22, 2001.

The present invention provides isolated nucleic acid molecules, that comprise, or alternatively consist of, a polynucleotide encoding the human BMY_HPP2 phosphatase protein having the amino acid sequence shown as SEQ ID NO:152, or the amino acid sequence encoded by the cDNA clone, BMY_HPP2, deposited as ATCC Deposit Number PTA-3949 on Dec. 22, 2001.

The present invention provides isolated nucleic acid molecules, that comprise, or alternatively consist of, a polynucleotide encoding the human BMY_HPP5 phosphatase protein having the amino acid sequence shown as SEQ ID NO:42, or the amino acid sequence encoded by the cDNA clone, BMY_HPP5 (also referred to as 7IC-5-E2), deposited as ATCC Deposit Number PTA-2966 on Jan. 24$^{th}$, 2001.

The present invention provides isolated nucleic acid molecules, that comprise, or alternatively consist of, a polynucleotide encoding the human RET31 phosphatase protein having the amino acid sequence shown as SEQ ID NO:109, or the amino acid sequence encoded by the cDNA clone, RET31 (also referred to as 1 hrTNF031, and/or Clone 31), deposited as ATCC Deposit Number PTA-3434 on Jun. 7, 2001.

The present invention provides isolated nucleic acid molecules, that comprise, or alternatively consist of, a polynucleotide encoding the mouse RET31 phosphatase protein having the amino acid sequence shown as SEQ ID NO:114.

The present invention also relates to recombinant vectors, which include the isolated nucleic acid molecules of the present invention, and to host cells containing the recombinant vectors, as well as to methods of making such vectors and host cells, in addition to their use in the production of human phosphatase polypeptides or peptides using recombinant techniques. Synthetic methods for producing the polypeptides and polynucleotides of the present invention are provided. Also provided are diagnostic methods for detecting diseases, disorders, and/or conditions related to the human phosphatase polypeptides and polynucleotides, and therapeutic methods for treating such diseases, disorders, and/or conditions. The invention further relates to screening methods for identifying binding partners of the polypeptides.

The invention further provides an isolated BMY_HPP1 human phosphatase polypeptide having an amino acid sequence encoded by a polynucleotide described herein.

The invention further provides an isolated BMY_HPP2 human phosphatase polypeptide having an amino acid sequence encoded by a polynucleotide described herein.

The invention further provides an isolated BMY_HPP5 human phosphatase polypeptide having an amino acid sequence encoded by a polynucleotide described herein.

The invention further provides an isolated RET31 human phosphatase polypeptide having an amino acid sequence encoded by a polynucleotide described herein.

The invention further provides an isolated RET31 mouse phosphatase polypeptide having an amino acid sequence encoded by a polynucleotide described herein.

The invention further relates to a polynucleotide encoding a polypeptide fragment of SEQ ID NO:150, 152, 8, 10, 42, or 109, or a polypeptide fragment encoded by the cDNA sequence included in the deposited clone, which is hybridizable to SEQ ID NO:149, 151, 7, 9, 41, or 108.

The invention further relates to a polynucleotide encoding a polypeptide domain of SEQ ID NO:150, 152, 8, 10, 42, or 109 or a polypeptide domain encoded by the cDNA sequence included in the deposited clone, which is hybridizable to SEQ ID NO:149, 151, 7, 9, 41, or 108.

The invention further relates to a polynucleotide encoding a polypeptide epitope of SEQ ID NO:150, 152, 8, 10, 42, or 109 or a polypeptide epitope encoded by the cDNA sequence included in the deposited clone, which is hybridizable to SEQ ID NO:149, 151, 7, 9, 41, or 108.

The invention further relates to a polynucleotide encoding a polypeptide of SEQ ID NO:150, 152, 8, 10, 42, or 109 or the cDNA sequence included in the deposited clone, which is hybridizable to SEQ ID NO:149, 151, 7, 9, 41, or 108, having biological activity.

The invention further relates to a polynucleotide which is a variant of SEQ ID NO:149, 151, 7, 9, 41, or 108.

The invention further relates to a polynucleotide which is an allelic variant of SEQ ID NO:149, 151, 7, 9, 41, or 108.

The invention further relates to a polynucleotide which encodes a species homologue of the SEQ ID NO:150, 152, 8, 10, 42, or 109.

The invention further relates to a polynucleotide which represents the complimentary sequence (antisense) of SEQ ID NO:149, 151, 7, 9, 41, or 108.

The invention further relates to a polynucleotide capable of hybridizing under stringent conditions to any one of the polynucleotides specified herein, wherein said polynucleotide does not hybridize under stringent conditions to a nucleic acid molecule having a nucleotide sequence of only A residues or of only T residues.

The invention further relates to an isolated nucleic acid molecule of SEQ ID NO:150, 152, 8, 10, 42, or 109, wherein the polynucleotide fragment comprises a nucleotide sequence encoding a human phosphatase protein.

The invention further relates to an isolated nucleic acid molecule of SEQ ID NO: 149, 151, 7, 9, 41, or 108 wherein the polynucleotide fragment comprises a nucleotide sequence encoding the sequence identified as SEQ ID NO:150, 152, 8, 10, 42, or 109 or the polypeptide encoded by the cDNA sequence included in the deposited clone, which is hybridizable to SEQ ID NO:149, 151, 7, 9, 41, or 108.

The invention further relates to an isolated nucleic acid molecule of SEQ ID NO: 149, 151, 7, 9, 41, or 108, wherein the polynucleotide fragment comprises the entire nucleotide sequence of SEQ ID NO:149, 151, 7, 9, 41, or 108 or the cDNA sequence included in the deposited clone, which is hybridizable to SEQ ID NO:149, 151, 7, 9, 41, or 108.

The invention further relates to an isolated nucleic acid molecule of SEQ ID NO:1, wherein the nucleotide sequence comprises sequential nucleotide deletions from either the C-terminus or the N-terminus.

The invention further relates to an isolated polypeptide comprising an amino acid sequence that comprises a polypeptide fragment of SEQ ID NO:150, 152, 8, 10, 42, or 109 or the encoded sequence included in the deposited clone.

The invention further relates to a polypeptide fragment of SEQ ID NO:150, 152, 8, 10, 42, or 109 or the encoded sequence included in the deposited clone, having biological activity.

The invention further relates to a polypeptide domain of SEQ ID NO:150, 152, 8, 10, 42, or 109 or the encoded sequence included in the deposited clone.

The invention further relates to a polypeptide epitope of SEQ ID NO:150, 152, 8, 10, 42, or 109 or the encoded sequence included in the deposited clone.

The invention further relates to a full length protein of SEQ ID NO:150, 152, 8, 10, 42, or 109 or the encoded sequence included in the deposited clone.

The invention further relates to a variant of SEQ ID NO:150, 152, 8, 10, 42, or 109.

The invention further relates to an allelic variant of SEQ ID NO:150, 152, 8, 10, 42, or 109. The invention further relates to a species homologue of SEQ ID NO:150, 152, 8, 10, 42, or 109.

The invention further relates to the isolated polypeptide of SEQ ID NO:150, 152, 8, 10, 42, or 109, wherein the full length protein comprises sequential amino acid deletions from either the C-terminus or the N-terminus.

The invention further relates to an isolated antibody that binds specifically to the isolated polypeptide of SEQ ID NO:150, 152, 8, 10, 42, or 109.

The invention further relates to a method for preventing, treating, or ameliorating a medical condition, comprising administering to a mammalian subject a therapeutically effective amount of the polypeptide of SEQ ID NO:150, 152, 8, 10, 42, or 109 or the polynucleotide of SEQ ID NO:149, 151, 7, 9, 41, or 108.

The invention further relates to a method of diagnosing a pathological condition or a susceptibility to a pathological condition in a subject comprising the steps of (a) determining the presence or absence of a mutation in the polynucleotide of SEQ ID NO:149, 151, 7, 9, 41, or 108; and (b) diagnosing a pathological condition or a susceptibility to a pathological condition based on the presence or absence of said mutation.

The invention further relates to a method of diagnosing a pathological condition or a susceptibility to a pathological condition in a subject comprising the steps of (a) determining the presence or amount of expression of the polypeptide of SEQ ID NO:150, 152, 8, 10, 42, or 109 in a biological sample; and diagnosing a pathological condition or a susceptibility to a pathological condition based on the presence or amount of expression of the polypeptide.

The invention further relates to a method for identifying a binding partner to the polypeptide of SEQ ID NO:150, 152, 8, 10, 42, or 109 comprising the steps of (a) contacting the polypeptide of SEQ ID NO:150, 152, 8, 10, 42, or 109 with a binding partner; and (b) determining whether the binding partner effects an activity of the polypeptide.

The invention further relates to a gene corresponding to the cDNA sequence of SEQ ID NO:149, 151, 7, 9, 41, or 108.

The invention further relates to a method of identifying an activity in a biological assay, wherein the method comprises the steps of expressing SEQ ID NO:149, 151, 7, 9, 41, or 108 in a cell, (b) isolating the supernatant; (c) detecting an activity in a biological assay; and (d) identifying the protein in the supernatant having the activity.

The invention further relates to a process for making polynucleotide sequences encoding gene products having altered activity selected from the group consisting of SEQ ID NO:150, 152, 8, 10, 42, or 109 activity comprising the steps of (a) shuffling a nucleotide sequence of SEQ ID NO:149, 151, 7, 9, 41, or 108, (b) expressing the resulting shuffled nucleotide sequences and, (c) selecting for altered activity selected from the group consisting of SEQ ID NO:150, 152, 8, 10, 42, or 109 activity as compared to the activity selected from the group consisting of SEQ ID NO:150, 152, 8, 10, 42, or 109 activity of the gene product of said unmodified nucleotide sequence.

The invention further relates to a shuffled polynucleotide sequence produced by a shuffling process, wherein said shuffled DNA molecule encodes a gene product having enhanced tolerance to an inhibitor of any one of the activities selected from the group consisting of SEQ ID NO:150, 152, 8, 10, 42, or 109 activity.

The invention further relates to a method for preventing, treating, or ameliorating a medical condition with the polypeptide provided as SEQ ID NO:150, 152, 8, 10, 42, or 109, in addition to, its encoding nucleic acid, wherein the medical condition is a condition related to aberrant phosphatase activity.

The invention further relates to a method of identifying a compound that modulates the biological activity of a phosphatase, comprising the steps of, (a) combining a candidate modulator compound with a phosphatase having the sequence set forth in one or more of SEQ ID NO:150, 152, 8, 10, 42, or 109; and measuring an effect of the candidate modulator compound on the activity of a phosphatase.

The invention further relates to a method of identifying a compound that modulates the biological activity of a phosphatase, comprising the steps of, (a) combining a candidate modulator compound with a host cell expressing a phosphatase having the sequence as set forth in SEQ ID NO:150, 152, 8, 10, 42, or 109; and, (b) measuring an effect of the candidate modulator compound on the activity of the expressed a phosphatase.

The invention further relates to a method of identifying a compound that modulates the biological activity of a phosphatase, comprising the steps of, (a) combining a candidate modulator compound with a host cell containing a vector described herein, wherein a phosphatase is expressed by the cell; and, (b) measuring an effect of the candidate modulator compound on the activity of the expressed a phosphatase.

The invention further relates to a method of screening for a compound that is capable of modulating the biological activity of a phosphatase, comprising the steps of: (a) providing a host cell described herein; (b) determining the biological activity of a phosphatase in the absence of a modulator compound; (c) contacting the cell with the modulator compound; and (d) determining the biological activity of a phosphatase in the presence of the modulator compound; wherein a difference between the activity of a phosphatase in the presence of the modulator compound and in the absence of the modulator compound indicates a modulating effect of the compound.

The invention further relates to a compound that modulates the biological activity of human a phosphatase as identified by the methods described herein.

Figure 28:
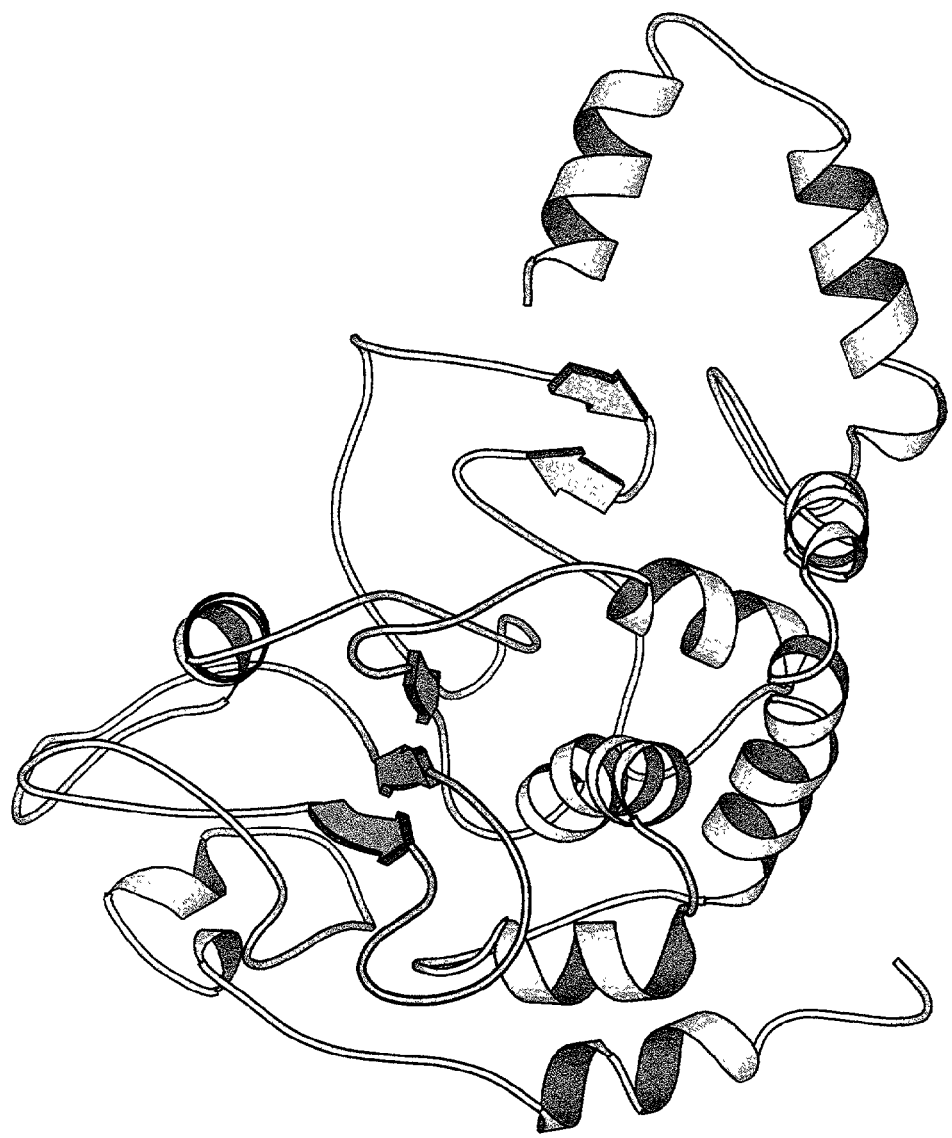

The invention also relates to in silico screening methods including in silico docking and methods of structure based drug design which utilize the three dimensional coordinates of BMY_HPP1 (FIG. 28, Table VIII). Also provided are methods of identifying modulators of BMY_HPP1 that include modulator building or searching utilizing computer programs and algorithms. In an embodiment of the invention a method is provided for designing potential modulators of BMY_HPP1 comprising any combination of steps which utilize said three dimensional structure to design or select potential modulators.

The present invention also provides structure coordinates of the homology model of BMY_HPP1. The complete coordinates are listed in Table VIII and visualized in FIG. 28. The model present in this invention further provides a basis for designing stimulators and inhibitors or antagonists of one or more of the biological functions of BMY_HPP1, or of mutants with altered specificity.

Figure 32:
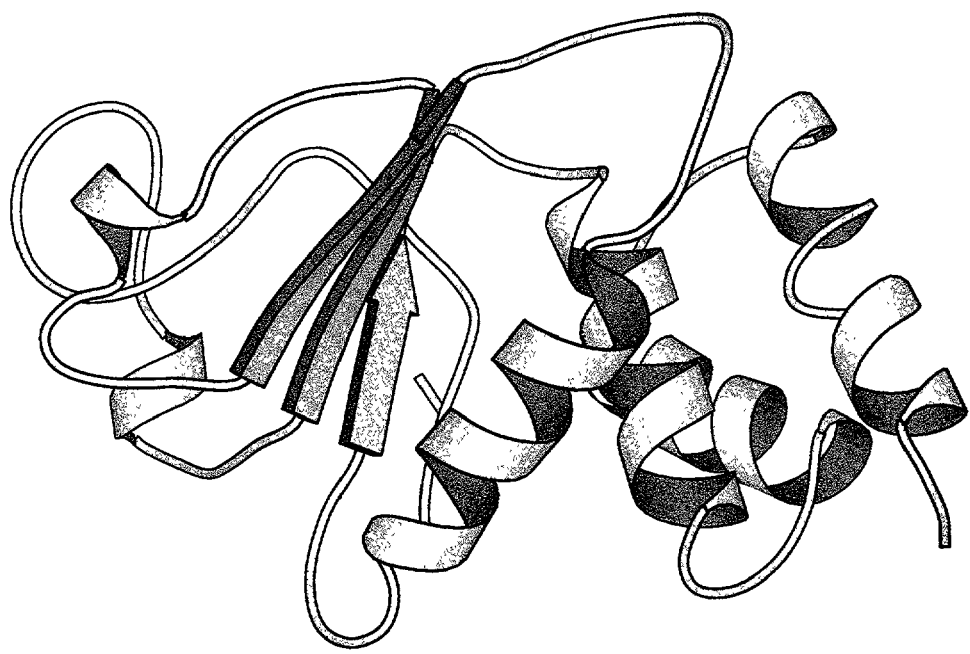

The invention also relates to in silico screening methods including in silico docking and methods of structure based drug design which utilize the three dimensional coordinates of BMY_HPP2 (FIG. 32, Table IX). Also provided are methods of identifying modulators of BMY_HPP2 that include modulator building or searching utilizing computer programs and algorithms. In an embodiment of the invention a method is provided for designing potential modulators of BMY_HPP2 comprising any combination of steps which utilize said three dimensional structure to design or select potential modulators.

The present invention also provides structure coordinates of the homology model of BMY_HPP2. The complete coordinates are listed in Table IX and visualized in FIG. 32. The model present in this invention further provides a basis for designing stimulators and inhibitors or antagonists of one or more of the biological functions of BMY_HPP2, or of mutants with altered specificity.

Figure 38:
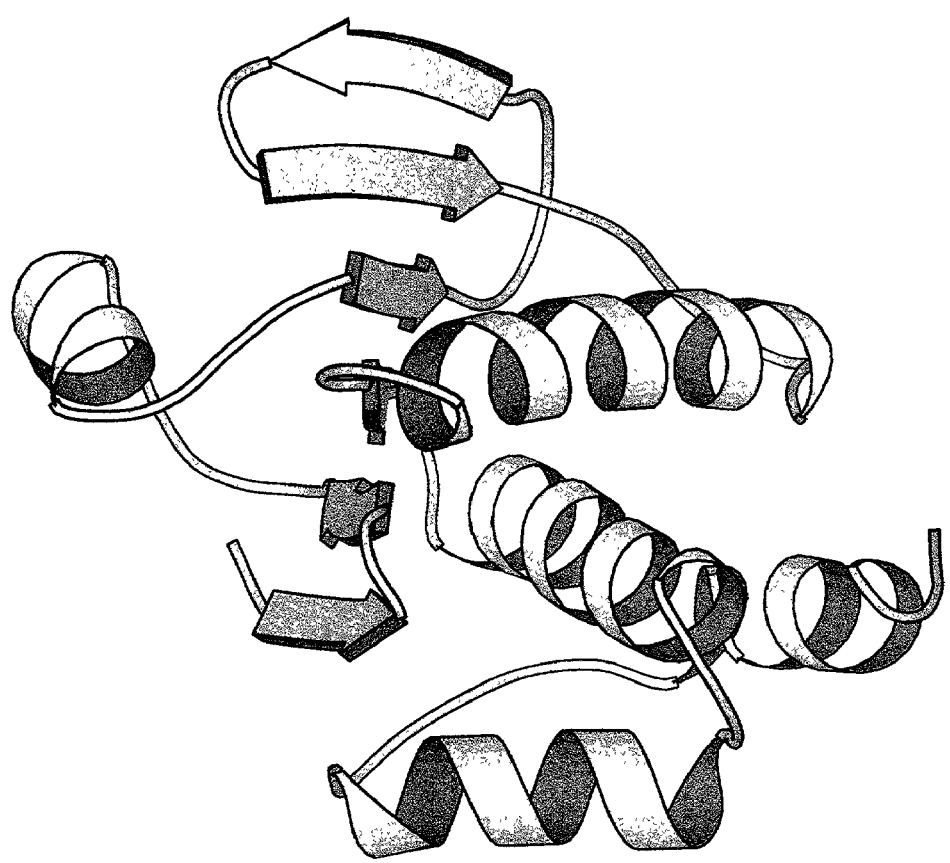

The invention also relates to in silico screening methods including in silico docking and methods of structure based drug design which utilize the three dimensional coordinates of BMY_HPP5 (FIG. 38, Table X). Also provided are methods of identifying modulators of BMY_HPP5 that include modulator building or searching utilizing computer programs and algorithms. In an embodiment of the invention a method is provided for designing potential modulators of BMY_HPP5 comprising any combination of steps which utilize said three dimensional structure to design or select potential modulators.

The present invention also provides structure coordinates of the homology model of BMY_HPP5. The complete coordinates are listed in Table X and visualized in FIG. 38. The model present in this invention further provides a basis for designing stimulators and inhibitors or antagonists of one or more of the biological functions of BMY_HPP5, or of mutants with altered specificity.

The invention also provides a machine readable storage medium which comprises the structure coordinates of BMY_ HPP1, including all or any parts conserved active site regions. Such storage medium encoded with these data are capable of displaying on a computer screen or similar viewing device, a three-dimensional graphical representation of a molecule or molecular complex which comprises said regions or similarly shaped homologous regions.

The invention also provides methods for designing, evaluating and identifying compounds which bind to all or parts of the aforementioned regions. The methods include three dimensional model building (homology modeling) and methods of computer assisted-drug design which can be used to identify compounds which bind or modulate the forementioned regions of the BMY_HPP1 polypeptide. Such compounds are potential inhibitors of BMY_HPP1 or its homologues.

The invention also provides a machine readable storage medium which comprises the structure coordinates of BMY_ HPP2, including all or any parts conserved active site regions. Such storage medium encoded with these data are capable of displaying on a computer screen or similar viewing device, a three-dimensional graphical representation of a molecule or molecular complex which comprises said regions or similarly shaped homologous regions.

The invention also provides methods for designing, evaluating and identifying compounds which bind to all or parts of the aforementioned regions. The methods include three dimensional model building (homology modeling) and methods of computer assisted-drug design which can be used to identify compounds which bind or modulate the forementioned regions of the BMY_HPP2 polypeptide. Such compounds are potential inhibitors of BMY_HPP2 or its homologues.

The invention also provides a machine readable storage medium which comprises the structure coordinates of BMY_ HPP5, including all or any parts conserved active site regions. Such storage medium encoded with these data are capable of displaying on a computer screen or similar viewing device, a three-dimensional graphical representation of a molecule or molecular complex which comprises said regions or similarly shaped homologous regions.

The invention also provides methods for designing, evaluating and identifying compounds which bind to all or parts of the aforementioned regions. The methods include three dimensional model building (homology modeling) and methods of computer assisted-drug design which can be used to identify compounds which bind or modulate the forementioned regions of the BMY_HPP5 polypeptide. Such compounds are potential inhibitors of BMY_HPP5 or its homologues.

The invention also provides a computer for producing a three-dimensional representation of a molecule or molecular complex, wherein said molecule or molecular complex comprises the structural coordinates of the model BMY_ HPP1 in accordance with Table VIII, or a three-dimensional representation of a homologue of said molecule or molecular complex, wherein said homologue comprises backbone atoms that have a root mean square deviation from the backbone atoms of not more than 3.5 angstroms. wherein said computer comprises:

The invention also provides a machine-readable data storage medium, comprising a data storage material encoded with machine readable data, wherein the data is defined by the set of structure coordinates of the model BMY_HPP1 according to Table VIII, or a homologue of said model, wherein said homologue comprises backbone atoms that have a root mean square deviation from the backbone atoms of not more than 3.5 Å; a working memory for storing instructions for processing said machine-readable data; a central-processing unit coupled to said working memory and to said machine-readable data storage medium for processing said machine readable data into said three-dimensional representation; and a display coupled to said central-processing unit for displaying said three-dimensional representation. The invention also provides said computer wherein the machine-readable data storage medium is defined by the set of structure coordinates of the model for BMY_HPP1 according to Table VIII, or a homologue of said molecule, said homologue having a root mean square deviation from the backbone atoms of not more than 3.0 Å.

The invention also provides a model comprising all or any part of the model defined by structure coordinates of BMY_HPP1 according to Table VIII, or a mutant or homologue of said molecule or molecular complex.

The invention also provides a method for identifying a mutant of BMY_HPP1 with altered biological properties, function, or reactivity, the method comprising the step selected from the group consisting of: Using the BMY_HPP1 model or a homologue of said model according to Table VIII, for the design of protein mutants with altered biological function or properties.

The invention also provides a method for identifying structural and chemical features of BMY_HPP1 using the structural coordinates set forth in Table VIII, comprising any steps or combination of steps consisting of: employing identified structural or chemical features to design or select compounds as potential BMY_HPP1 modulators; employing the three-dimensional structural model to design or select compounds as potential BMY_HPP1 modulators; synthesizing the potential BMY_HPP1 modulators; and screening the potential BMY_HPP1 modulators in an assay characterized by binding of a protein to the BMY_HPP1. The invention further provides said method wherein the potential BMY_HPP1 modulator is selected from a database. The invention further provides said method wherein the potential BMY_HPP1 modulator is designed de novo. The invention further provides said method wherein the potential BMY_HPP1 modulator is designed from a known modulator of activity.

The invention also provides a method for identifying a compound that modulates BMY_HPP1 activity, the method comprising any combination of steps of: Modeling test compounds that fit spatially into or near the active site region defined by residues D161-Y162 and H189-C190-G193-R196 of BMY_HPP1 as defined by structure coordinates according to Table VIII, or modeling test compounds that fit spatially into a three-dimensional structural model of the catalytic domain of BMY_HPP1, mutant homologue or portion thereof; using said structure coordinates or said active site region as set forth in prior claims to identify structural and chemical features; employing identified structural or chemical features to design or select compounds as potential BMY_HPP1 modulators including substrates, antagonists and agonists; employing the three-dimensional structural model or the catalytic domain of BMY_HPP1 to design or select compounds as potential BMY_HPP1 inhibitors; screening the potential BMY_HPP1 inhibitors in an assay characterized by binding of a test compound to BMY_HPP1; and/or modifying or replacing one or more amino acids from BMY_HPP1 including but not limited to the residues corresponding to the active site region as set forth in prior claims of BMY_HPP1 according to Table VIII.

The invention also provides a computer for producing a three-dimensional representation of a molecule or molecular complex, wherein said molecule or molecular complex comprises the structural coordinates of the model BMY_HPP2 in accordance with Table IX, or a three-dimensional representation of a homologue of said molecule or molecular complex, wherein said homologue comprises backbone atoms that have a root mean square deviation from the backbone atoms of not more than 3.5 angstroms. wherein said computer comprises:

The invention also provides a machine-readable data storage medium, comprising a data storage material encoded with machine readable data, wherein the data is defined by the set of structure coordinates of the model BMY_HPP2 according to Table IX, or a homologue of said model, wherein said homologue comprises backbone atoms that have a root mean square deviation from the backbone atoms of not more than 3.5 Å; a working memory for storing instructions for processing said machine-readable data; a central-processing unit coupled to said working memory and to said machine-readable data storage medium for processing said machine readable data into said three-dimensional representation; and a display coupled to said central-processing unit for displaying said three-dimensional representation. The invention also provides said computer wherein the machine-readable data storage medium is defined by the set of structure coordinates of the model for BMY_HPP2 according to Table IX, or a homologue of said molecule, said homologue having a root mean square deviation from the backbone atoms of not more than 3.0 Å.

The invention also provides a model comprising all or any part of the model defined by structure coordinates of BMY_HPP2 according to Table IX, or a mutant or homologue of said molecule or molecular complex.

The invention also provides a method for identifying a mutant of BMY_HPP2 with altered biological properties, function, or reactivity, the method comprising the step selected from the group consisting of: Using the BMY_HPP2 model or a homologue of said model according to Table IX, for the design of protein mutants with altered biological function or properties.

The invention also provides a method for identifying structural and chemical features of BMY_HPP2 using the structural coordinates set forth in Table IX, comprising any steps or combination of steps consisting of: employing identified structural or chemical features to design or select compounds as potential BMY_HPP2 modulators; employing the three-dimensional structural model to design or select compounds as potential BMY_HPP2 modulators; synthesizing the potential BMY_HPP2 modulators; and screening the potential BMY_HPP2 modulators in an assay characterized by binding of a protein to the BMY_HPP2. The invention further provides said method wherein the potential BMY_HPP2 modulator is selected from a database. The invention further provides said method wherein the potential BMY_HPP2 modulator is designed de novo. The invention further provides said method wherein the potential BMY_HPP2 modulator is designed from a known modulator of activity.

The invention also provides a method for identifying a compound that modulates BMY_HPP2 activity, the method comprising any combination of steps of: Modeling test compounds that fit spatially into or near the active site region defined by residues D65, H94-C95, G98, and R101 of BMY_HPP2 as defined by structure coordinates according to Table IX, or modeling test compounds that fit spatially into a three-dimensional structural model of the catalytic domain of BMY_HPP2, mutant homologue or portion thereof; using said structure coordinates or said active site region as set forth in prior claims to identify structural and chemical features; employing identified structural or chemical features to design or select compounds as potential BMY_HPP2 modulators including substrates, antagonists and agonists; employing the three-dimensional structural model or the catalytic domain of BMY_HPP2 to design or select compounds as potential BMY_HPP2 inhibitors; screening the potential BMY_HPP2 inhibitors in an assay characterized by binding of a test compound to BMY_HPP2; and/or modifying or replacing one or more amino acids from BMY_HPP2 including but not limited to the residues corresponding to the active site region as set forth in prior claims of BMY_HPP2 according to Table IX.

The invention also provides a computer for producing a three-dimensional representation of a molecule or molecular complex, wherein said molecule or molecular complex comprises the structural coordinates of the model BMY_HPP5 in accordance with Table X, or a three-dimensional representation of a homologue of said molecule or molecular complex, wherein said homologue comprises backbone atoms that have a root mean square deviation from the backbone atoms of not more than 3.5 angstroms. wherein said computer comprises:

The invention also provides a machine-readable data storage medium, comprising a data storage material encoded with machine readable data, wherein the data is defined by the set of structure coordinates of the model BMY_HPP5 according to Table X, or a homologue of said model, wherein said homologue comprises backbone atoms that have a root mean square deviation from the backbone atoms of not more than 3.5 Å; a working memory for storing instructions for processing said machine-readable data; a central-processing unit coupled to said working memory and to said machine-readable data storage medium for processing said machine readable data into said three-dimensional representation; and a display coupled to said central-processing unit for displaying said three-dimensional representation. The invention also provides said computer wherein the machine-readable data storage medium is defined by the set of structure coordinates of the model for BMY_HPP5 according to Table X, or a homologue of said molecule, said homologue having a root mean square deviation from the backbone atoms of not more than 3.0 Å.

The invention also provides a model comprising all or any part of the model defined by structure coordinates of BMY_HPP5 according to Table X, or a mutant or homologue of said molecule or molecular complex.

The invention also provides a method for identifying a mutant of BMY_HPP5 with altered biological properties, function, or reactivity, the method comprising the step selected from the group consisting of: Using the BMY_HPP5 model or a homologue of said model according to Table X, for the design of protein mutants with altered biological function or properties.

The invention also provides a method for identifying structural and chemical features of BMY_HPP5 using the structural coordinates set forth in Table X, comprising any steps or combination of steps consisting of: employing identified structural or chemical features to design or select compounds as potential BMY_HPP5 modulators; employing the three-dimensional structural model to design or select compounds as potential BMY_HPP5 modulators; synthesizing the potential BMY_HPP5 modulators; and screening the potential BMY_HPP5 modulators in an assay characterized by binding of a protein to the BMY_HPP5. The invention further provides said method wherein the potential BMY_HPP5 modulator is selected from a database. The invention further provides said method wherein the potential BMY_HPP5 modulator is designed de novo. The invention further provides said method wherein the potential BMY_HPP5 modulator is designed from a known modulator of activity.

The invention also provides a method for identifying a compound that modulates BMY_HPP5 activity, the method comprising any combination of steps of: Modeling test compounds that fit spatially into or near the active site region defined by residues D213, H243, C244, and R250 of BMY_HPP5 as defined by structure coordinates according to Table X, or modeling test compounds that fit spatially into a three-dimensional structural model of the catalytic domain of BMY_HPP5, mutant homologue or portion thereof; using said structure coordinates or said active site region as set forth in prior claims to identify structural and chemical features; employing identified structural or chemical features to design or select compounds as potential BMY_HPP5 modulators including substrates, antagonists and agonists; employing the three-dimensional structural model or the catalytic domain of BMY_HPP5 to design or select compounds as potential BMY_HPP5 inhibitors; screening the potential BMY_HPP5 inhibitors in an assay characterized by binding of a test compound to BMY_HPP5; and/or modifying or replacing one or more amino acids from BMY_HPP5 including but not limited to the residues corresponding to the active site region as set forth in prior claims of BMY_HPP5 according to Table X.

The invention further relates to a method for preventing, treating, or ameliorating a medical condition, wherein the medical condition is a renal condition.

The invention further relates to a method for preventing, treating, or ameliorating a medical condition, wherein the medical condition is an inflammatory disease.

The invention further relates to a method for preventing, treating, or ameliorating a medical condition, wherein the medical condition is an inflammatory disease where dual-specificity phosphatases, either directly or indirectly, are involved in disease progression.

The invention further relates to a method for preventing, treating, or ameliorating a medical condition, wherein the medical condition is a cancer.

The invention further relates to a method for preventing, treating, or ameliorating a medical condition, wherein the medical condition is a neural disorder.

The invention further relates to a method for preventing, treating, or ameliorating a medical condition, wherein the medical condition is a reproductive disorder.

The invention further relates to a method for preventing, treating, or ameliorating a medical condition, wherein the medical condition is an immunological disorder.

The invention further relates to a method for preventing, treating, or ameliorating a medical condition, wherein the medical condition is a musculo-degenerative disorder.

The invention further relates to a method for preventing, treating, or ameliorating a medical condition, wherein the medical condition is a muscle disorder.

The invention further relates to a method for preventing, treating, or ameliorating a medical condition, wherein the medical condition is a hepatic disorder.

The invention further relates to a method for preventing, treating, or ameliorating a medical condition, wherein the medical condition is an endocrine disorder.

The invention further relates to a method for preventing, treating, or ameliorating a medical condition, wherein the medical condition is a pulmonary disorder.

The invention further relates to a method for preventing, treating, or ameliorating a medical condition, wherein the medical condition is a disorder associated, either directly or indirectly, with TNF-alpha.

The invention further relates to a method for preventing, treating, or ameliorating a medical condition, wherein the medical condition is a disorder associated, either directly or indirectly, with IL-1.

BRIEF DESCRIPTION OF THE FIGURES/DRAWINGS

FIG. 1 shows the polynucleotide sequences (SEQ ID NO:1 and 3) and deduced amino acid sequence (SEQ ID NO:2 and 4) of gene fragments A and B, respectfully, of the novel human phosphatase, BMY_HPP1, of the present invention. The standard one-letter abbreviation for amino acids is used to illustrate the deduced amino acid sequence. The polynucleotide sequence of fragment A contains a sequence of 144 nucleotides (SEQ ID NO:1), encoding a polypeptide of 48 amino acids (SEQ ID NO:2), while the polynucleotide sequence of fragment B contains a sequence of 33 nucleotides (SEQ ID NO:3), encoding a polypeptide of 11 amino acids (SEQ ID NO:4).

FIG. 2 shows the polynucleotide sequence (SEQ ID NO: 5) and deduced amino acid sequence (SEQ ID NO:6) of a gene fragment of the novel human phosphatase, BMY_HPP2, of the present invention. The standard one-letter abbreviation for amino acids is used to illustrate the deduced amino acid sequence. The polynucleotide sequence of this fragment contains a sequence of 746 nucleotides (SEQ ID NO:5), encoding 248 amino acids (SEQ ID NO:6) of the full-length BMY_HPP2 polypeptide, and/or translated portions of the 5' and/or 3' UTR of clone BMY_HPP2. The asterisks ("*") may represent any amino acid.

FIG. 3 shows the polynucleotide sequence (SEQ ID NO: 7) and deduced amino acid sequence (SEQ ID NO:8) of a gene fragment of the novel human phosphatase, BMY_HPP3, of the present invention. The standard one-letter abbreviation for amino acids is used to illustrate the deduced amino acid sequence. The polynucleotide sequence of this fragment contains a sequence of 511 nucleotides (SEQ ID NO:5), encoding 170 amino acids (SEQ ID NO:8) of the full-length BMY_HPP3 polypeptide, and/or translated portions of the 5' and/or 3' UTR of clone BMY_HPP3. The asterisks ("*") may represent any amino acid.

FIGS. 4A–B show the polynucleotide sequence (SEQ ID NO: 9) and deduced amino acid sequence (SEQ ID NO:10) of a gene fragment of the novel human phosphatase, BMY_HPP4, of the present invention. The standard one-letter abbreviation for amino acids is used to illustrate the deduced amino acid sequence. The polynucleotide sequence of this fragment contains a sequence of 1710 nucleotides (SEQ ID NO:9), encoding 570 amino acids (SEQ ID NO:10) of the full-length BMY_HPP3 polypeptide, and/or translated portions of the 5' and/or 3' UTR of clone BMY_HPP4. The asterisks ("*") may represent any amino acid.

FIGS. 5A–E show the polynucleotide sequence (SEQ ID NO: 41) and deduced amino acid sequence (SEQ ID NO:42) of the novel full-length human phosphatase, BMY_HPP5, of the present invention. The standard one-letter abbreviation for amino acids is used to illustrate the deduced amino acid sequence. The polynucleotide sequence of this protein contains a sequence of 5111 nucleotides (SEQ ID NO:41), encoding 665 amino acids (SEQ ID NO:42) of the full-length BMY_HPP5 polypeptide.

FIGS. 6A–D show the regions of identity between the encoded full-length human phosphatase protein BMY_HPP1 (BMY_HPP1_FL; SEQ ID NO:150), and fragments A and B of BMY_HPP1 (BMY_HPP1_A and BMY_HPP1_B; SEQ ID NO:2 and 4, respectfully), to other phosphatase proteins, specifically, the *Schizosacchromyces* Pombe protein tyrosine phosphatase PYP3 protein (PYP3_SP; Genbank Accession No:gil P32587; SEQ ID NO:29); the mouse protein tyrosine phosphatase, receptor type, O, protein (MM_RPTPO; Genbank Accession No:gil NP_035346; SEQ ID NO:28); and the human protein tyrosine phosphatase, receptor type, O, protein (HS_RPTPO; Genbank Accession No:gil NP_002839; SEQ ID NO:27). The alignment was performed using the CLUSTALW algorithm. The darkly shaded amino acids represent regions of matching identity. The lightly shaded amino acids represent regions of matching similarity. Dots ("•") between residues indicate gapped regions of non-identity for the aligned polypeptides. Catalytic residues are indicated in bold.

FIGS. 7A–B show the regions of identity between the encoded full-length human phosphatase protein BMY_HPP2 (BMY_HPP2.FL; SEQ ID NO:152), and the fragment of BMY_HPP2 (BMY_HPP2.partial; SEQ ID NO:6) to other phosphatase proteins, specifically, the human CDC14 (also known as the cell division cycle 14, *S. cerevisiae* Gene A protein) homologue A (HS_CDC14A; Genbank Accession No:gil NP_003663; SEQ ID NO:30); the human *S. cerevisiae* CDC14 homolog, gene B (HS_CDC14B; Genbank Accession No:gil NP_003662; SEQ ID NO:31); and the yeast soluble tyrosine-specific protein phosphatase Cdc14p protein (SC_CDC14; Genbank Accession No:gil NP_002839; SEQ ID NO:32). The alignment was performed using the CLUSTALW algorithm. The darkly shaded amino acids represent regions of matching identity. The lightly shaded amino acids represent regions of matching similarity. Dots ("•") between residues indicate gapped regions of non-identity for the aligned polypeptides. Catalytic residues are indicated in bold.

FIG. 8 shows the regions of identity between the encoded human phosphatase protein fragment of BMY_HPP3 (SEQ ID NO:8) to other phosphatase proteins, specifically, the human protein tyrosine phosphatase PTPCAAX1 PROTEIN (HS_PTPCAAX1; Genbank Accession No:gil AAB40597; SEQ ID NO:33); the human protein tyrosine phosphatase PTPCAAX2 (HS_PTPCAAX2; Genbank Accession No:gil AAB40598; SEQ ID NO:34); the mouse prenylated protein tyrosine phosphatase (MM_PTPCAAX; Genbank Accession No:gil JC5981; SEQ ID NO:35); and the *Drosophila* PRL-1 protein (DM_PRL1; Genbank Accession No:gil AAF53506; SEQ ID NO:36). The alignment was performed using the CLUSTALW algorithm. The darkly shaded amino acids represent regions of matching identity. The lightly shaded amino acids represent regions of matching similarity. Dots ("•") between residues indicate gapped regions of non-identity for the aligned polypeptides. Catalytic residues are indicated in bold.

Figure 9A:
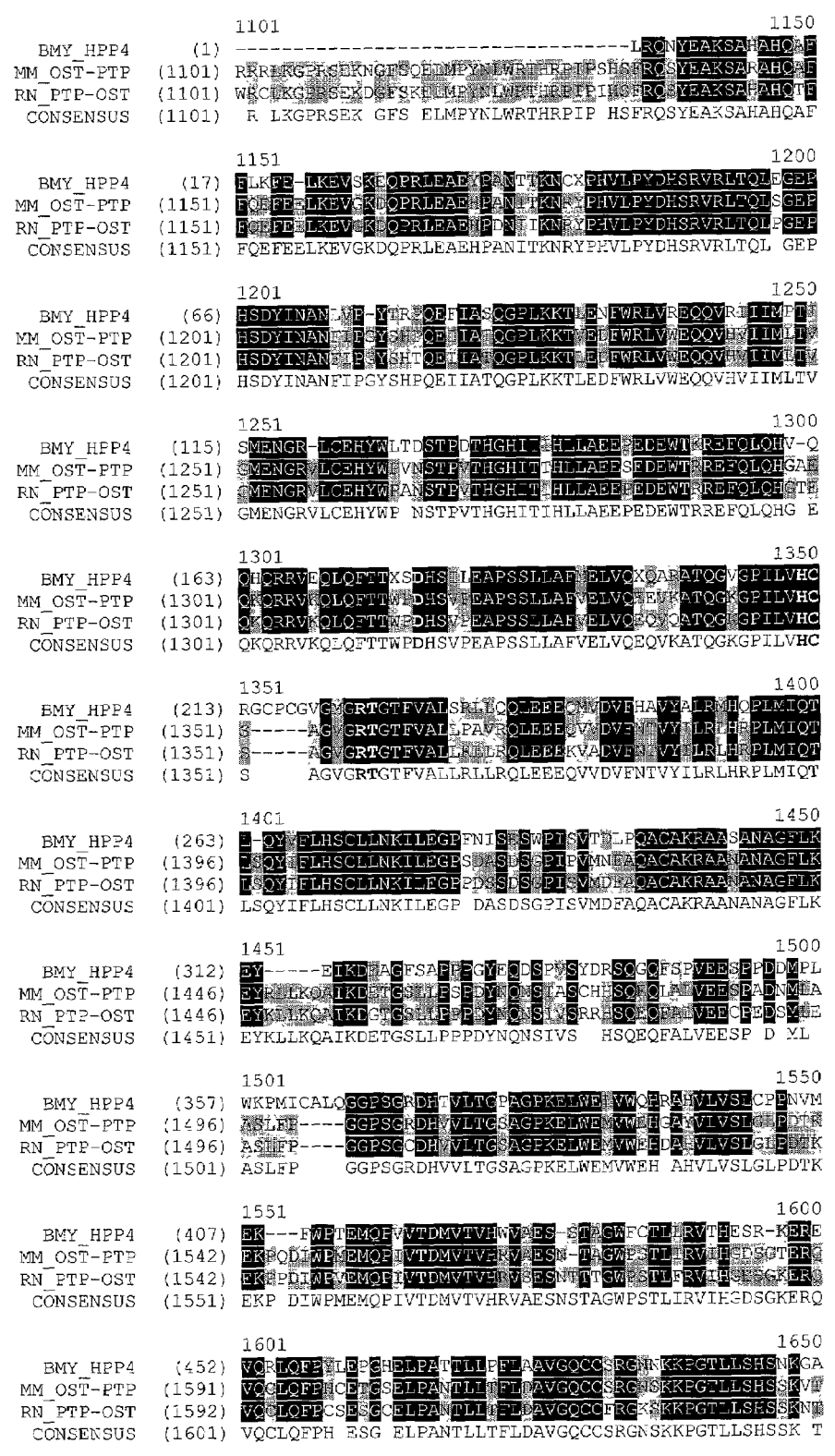

FIGS. 9A–B show the regions of identity between the encoded human phosphatase protein fragment of BMY_HPP4 (SEQ ID NO:10) to other phosphatase proteins, specifically, the mouse osteotesticular protein tyrosine phosphatase (MM_OST-PTP; Genbank Accession No:gil AAG28768; SEQ ID NO:37); and the rat protein-tyrosine-phosphatase (RN_PTP-OST; Genbank Accession No:gil A55148; SEQ ID NO:38). The alignment was performed using the CLUSTALW algorithm. The darkly shaded amino acids represent regions of matching identity. The lightly shaded amino acids represent regions of matching similarity. Dots ("•") between residues indicate gapped regions of non-identity for the aligned polypeptides. Catalytic residues are indicated in bold.

FIGS. 10A–B shows the regions of identity between the encoded human phosphatase protein fragment of BMY_

HPP5 (SEQ ID NO:42) to other phosphatase proteins, specifically, the human dual specificity phosphatase 8 (hs_dspp8; Genbank Accession No:gi| NP_004411; SEQ ID NO:39); and the mouse neuronal tyrosine/threonine phosphatase 1 (r mm_npp1; Genbank Accession No:gi| NP_032774; SEQ ID NO:40). The alignment was performed using the CLUSTALW algorithm. The darkly shaded amino acids represent regions of matching identity. The lightly shaded amino acids represent regions of matching similarity. Dots ("•") between residues indicate gapped regions of non-identity for the aligned polypeptides. Catalytic residues are indicated in bold.

FIG. 11 shows an expression profile of the novel human phosphatase protein BMY_HPP5. The figure illustrates the relative expression level of BMY_HPP5 amongst various mRNA tissue sources. As shown, the BMY_HPP5 polypeptide was expressed to a significant extent, in the testis and spinal cord, and to a lesser extent, in bone marrow, brain, liver, and thymus. Expression data was obtained by measuring the steady state BMY_HPP5 mRNA levels by quantitative PCR using the PCR primer pair provided as SEQ ID NO:67 and 68 as described herein.

FIG. 12 shows a table illustrating the percent identity and percent similarity between the BMY_HPP5 (SEQ ID NO:42), the human RET31 (SEQ ID NO:109), and the mouse RET31 (SEQ ID NO:114) polypeptides of the present invention with other phosphatase proteins. The percent identity and percent similarity values were determined based upon the GAP algorithm (GCG suite of programs; and Henikoff, S. and Henikoff, J. G., Proc. Natl. Acad. Sci. USA 89: 10915–10919(1992)) using the following parameters: gap weight=8, and length weight=2.

FIGS. 13A–F show the polynucleotide sequence (SEQ ID NO: 108) and deduced amino acid sequence (SEQ ID NO:109) of the novel full-length human phosphatase, RET31, of the present invention. The standard one-letter abbreviation for amino acids is used to illustrate the deduced amino acid sequence. The polynucleotide sequence of this protein contains a sequence of 5450 nucleotides (SEQ ID NO:108), encoding 665 amino acids (SEQ ID NO:109) of the full-length RET31 polypeptide. An analysis of the RET31 polypeptide determined that it comprised the following features: a dual specificity phosphatase catalytic domain located from about amino acid 158 to about amino acid 297 (SEQ ID NO:134) of SEQ ID NO:109 represented by double underlining; and a catalytic cysteine amino acid residue located at amino acid 244 of SEQ ID NO:109 represented by shading.

Figure 14A:
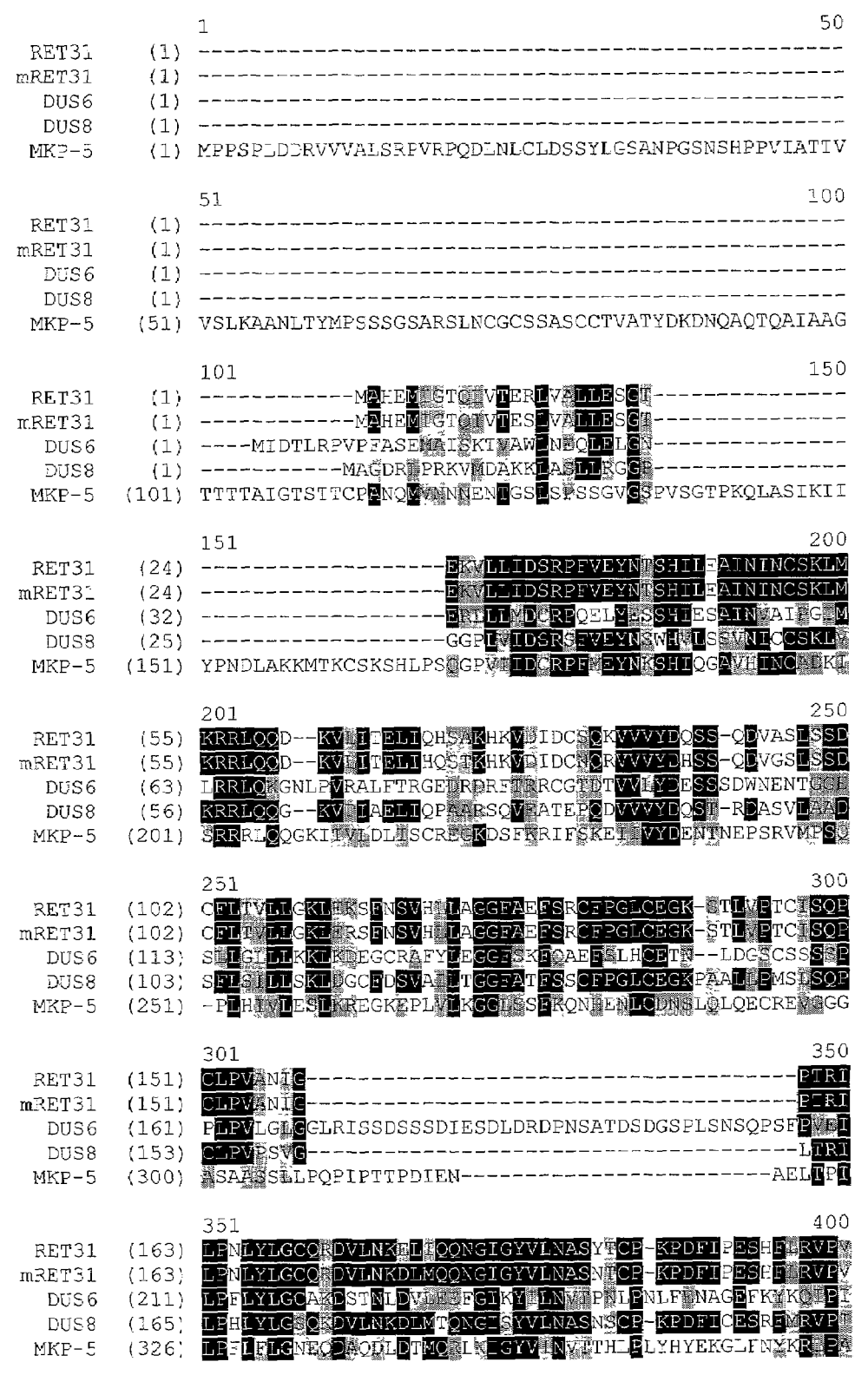

FIGS. 14A–C show the regions of identity between the encoded human phosphatase protein of RET31 (SEQ ID NO:109) to other phosphatase proteins, specifically, the human protein-tyrosine phosphatase DUS8 protein, also referred to as hVH-5 (DUS8; Genbank Accession No:gi|U27193; SEQ ID NO:110); the human dual specificity MAP kinase DUSP6 protein (DUSP6; Genbank Accession No:gi|AB013382; SEQ ID NO:111); the human map kinase phosphatase MKP-5 protein (MKP-5; Genbank Accession No:gi|AB026436; SEQ ID NO:112); and the mouse RET31 protein of the present invention (mRET31; SEQ ID NO:114). The alignment was performed using the CLUSTALW algorithm. The darkly shaded amino acids represent regions of matching identity. The lightly shaded amino acids represent regions of matching similarity. Dots ("•") between residues indicate gapped regions of non-identity for the aligned polypeptides.

Figure 15:
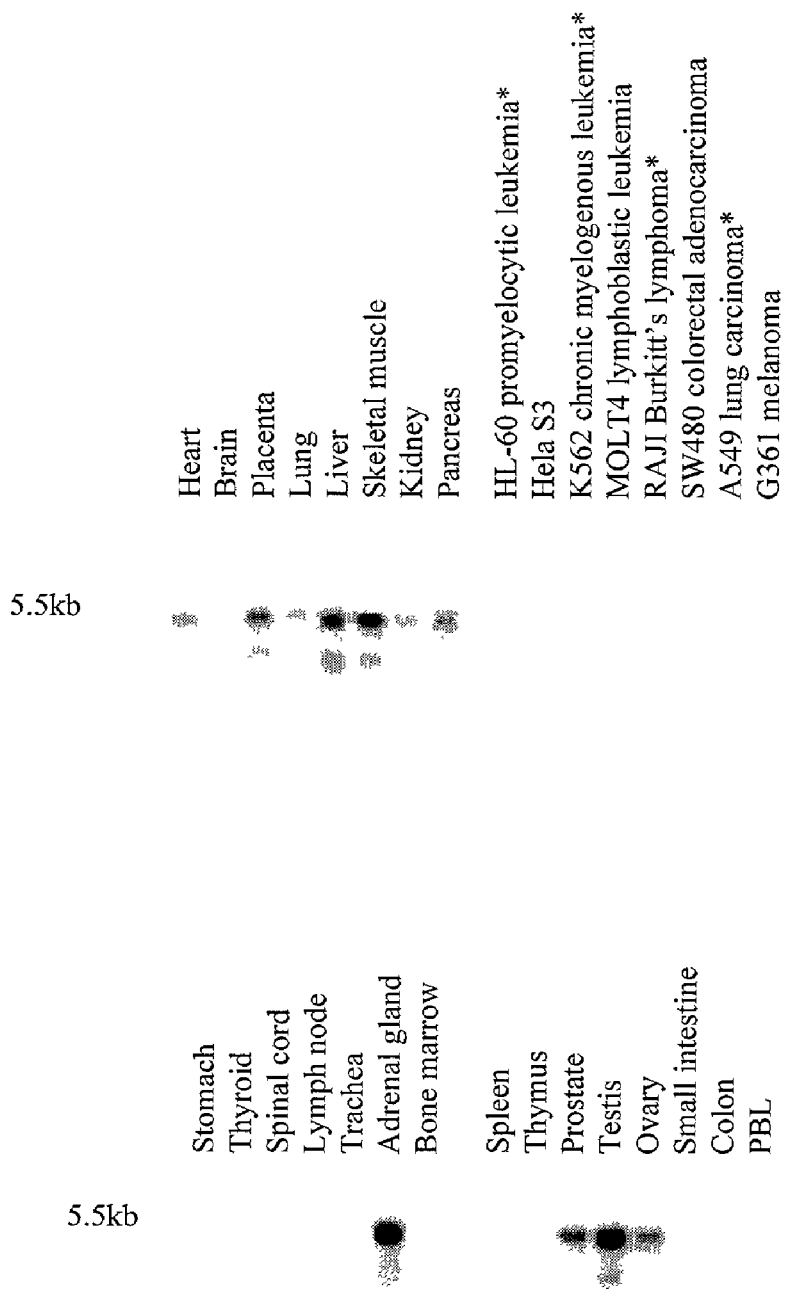

FIG. 15 shows the results of a northern hybridization illustrating the expression profile of the novel human phosphatase protein RET31. The figure illustrates the relative expression level of RET31 amongst various mRNA tissue sources. As shown, the RET31 polypeptide was expressed predominately in adrenal gland, testis, and skeletal muscle; to a significant extent, in the liver, prostate ovary, and to a lesser extent, in placenta, pancreas, thymus, small intestine, thyroid, heart, kidney and liver. Expression data was obtained by the hybridization of a 408 bp $P^{32}$-labeled RET31 polynucleotide fragment corresponding to SEQ ID NO:108 (specifically the RsaI fragment of SEQ ID NO:115) to several multiple tissue northern mRNA blots as described herein.

FIGS. 16A–C show the polynucleotide sequence (SEQ ID NO: 113) and deduced amino acid sequence (SEQ ID NO:114) of the novel full-length mouse phosphatase, mRET31, of the present invention. The standard one-letter abbreviation for amino acids is used to illustrate the deduced amino acid sequence. The polynucleotide sequence of this protein contains a sequence of 2756 nucleotides (SEQ ID NO:113), encoding 660 amino acids (SEQ ID NO:114) of the full-length mRET31 polypeptide. An analysis of the mRET31 polypeptide determined that it comprised the following features: a dual specificity phosphatase catalytic domain located from about amino acid 158 to about amino acid 297 (SEQ ID NO:135) of SEQ ED NO:114 represented by double underlining.

Figure 17:
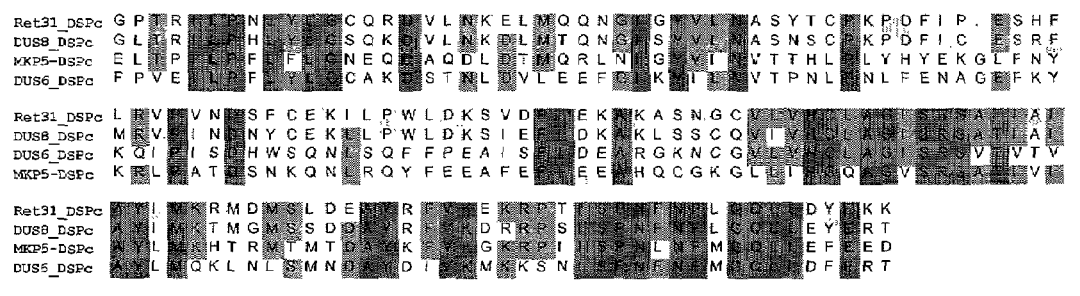

FIG. 17 shows the regions of identity between the dual specificity phosphatase catalytic (DSPc) domain of the encoded human phosphatase protein of RET31 (SEQ ID NO:109) to the dual specificity phosphatase catalytic (DSPc) domain of other phosphatase proteins, specifically, the DSPc domain of the human protein-tyrosine phosphatase DUS8 protein, also referred to as hVH-5 (DUS8_DSPc; Genbank Accession No:gi|U27193; SEQ ID NO:110); the DSPc domain of the human dual specificity MAP kinase DUSP6 protein (DUSP6_DSPc; Genbank Accession No:gi|AB013382; SEQ ID NO:111); and the DSPc domain of the human map kinase phosphatase MKP-5 protein (MKP-5_DSPc; Genbank Accession No:gi|AB026436; SEQ ID NO:112. Red boxes indicate conservation among all four DSPc domains, blue boxes indicate conservation among three DSPc domains, and green boxes indicate conservation between RET31 and one of the other protein domains. Dots ("•") between residues indicate gapped regions of non-identity for the aligned polypeptides.

Figure 18:
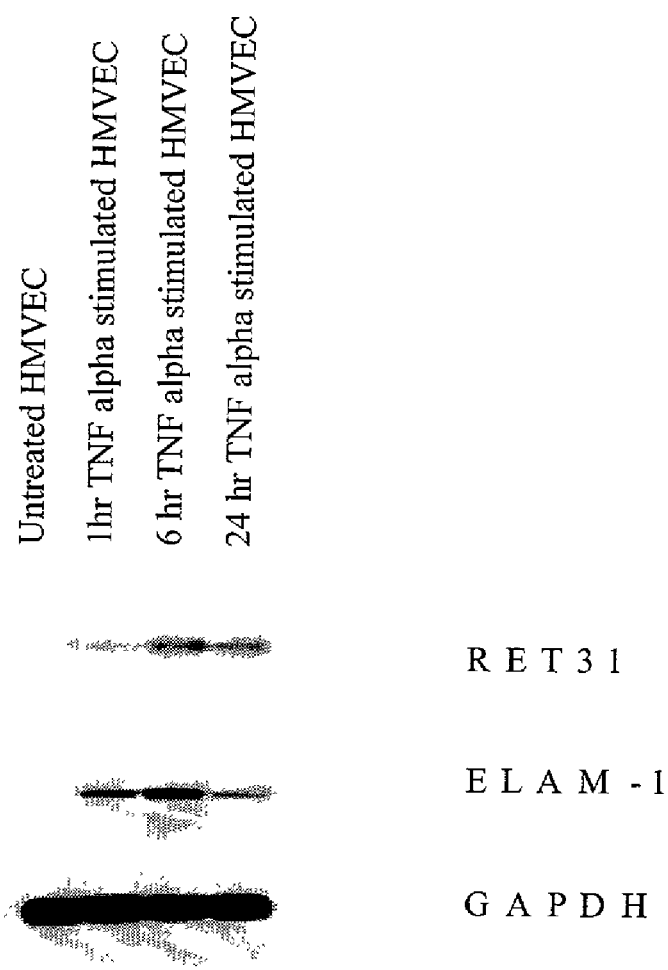

FIG. 18 shows the results of a northern hybridization illustrating the expression profile of the novel human phosphatase protein RET31 in human lung microvascular endothelial cells (HMCEC) after the administration of TNF-alpha for 0, 1, 6, and 24 hours. As shown, the RET31 polypeptide is up-regulated by TNF-α, reaching a peak of expression of about 6 hours. Expression data was obtained by the hybridization of a 408 bp $P^{32}$-labeled RET31 polynucleotide fragment corresponding to SEQ ID NO:108 (specifically the RsaI fragment of SEQ ID NO:115) to northern blots containing the isolated HMVEC mRNA for each indicated sample as described herein.

FIGS. 19A–F show the predicted polynucleotide sequence (SEQ ID NO:147) and deduced amino acid sequence (SEQ ID NO:148) of the novel full-length human phosphatase, RET31, of the present invention. The standard one-letter abbreviation for amino acids is used to illustrate the deduced amino acid sequence. The polynucleotide sequence of this protein contains a sequence of 5450 nucleotides (SEQ ID NO:147), encoding 665 amino acids (SEQ ID NO:148) of the full-length RET31 polypeptide. A portion of the sequence was determined based upon the sequence provided from the Incyte gene cluster 1026659.7 using bioinformatic methods.

FIGS. 20A–D show the predicted polynucleotide sequence (SEQ ID NO:149) and deduced amino acid sequence (SEQ ID NO:150) of the novel full-length human phosphatase, BMY_HPP1, of the present invention. The standard one-letter abbreviation for amino acids is used to illustrate the deduced amino acid sequence. The polynucleotide sequence of this protein contains a sequence of 4393 nucleotides (SEQ ID NO:149), encoding 607 amino acids (SEQ ID NO:150) of the full-length BMY_HPP1 polypeptide. An analysis of the BMY_HPP1 polypeptide determined that it comprised the following features: a predicted dual specificity phosphatase catalytic domain located from about amino acid 41 to about amino acid 49 of SEQ ID NO:150 represented by shading; and conserved phosphatase catalytic residues at amino acid 14, at amino acid 42, and at amino acid 48 of SEQ ID NO:150 (FIGS. 20A–D).

FIG. 21 shows the polynucleotide sequence (SEQ ID NO:151) and deduced amino acid sequence (SEQ ID NO:152) of the novel full-length human phosphatase, BMY_ HPP2, of the present invention. The standard one-letter abbreviation for amino acids is used to illustrate the deduced amino acid sequence. The polynucleotide sequence of this protein contains a sequence of 878 nucleotides (SEQ ID NO:151), encoding 150 amino acids (SEQ ID NO:152) of the full-length BMY_HPP2 polypeptide. An analysis of the BMY_HPP2 polypeptide determined that it comprised the following features: a predicted dual specificity phosphatase catalytic domain located from about amino acid 93 and 94, and from about amino acid 100 and 101 of SEQ ID NO:152 represented by shading; and conserved phosphatase catalytic residues located at amino acid 65, 94, and 100 of SEQ ID NO:152 represented in bold.

Figure 22:
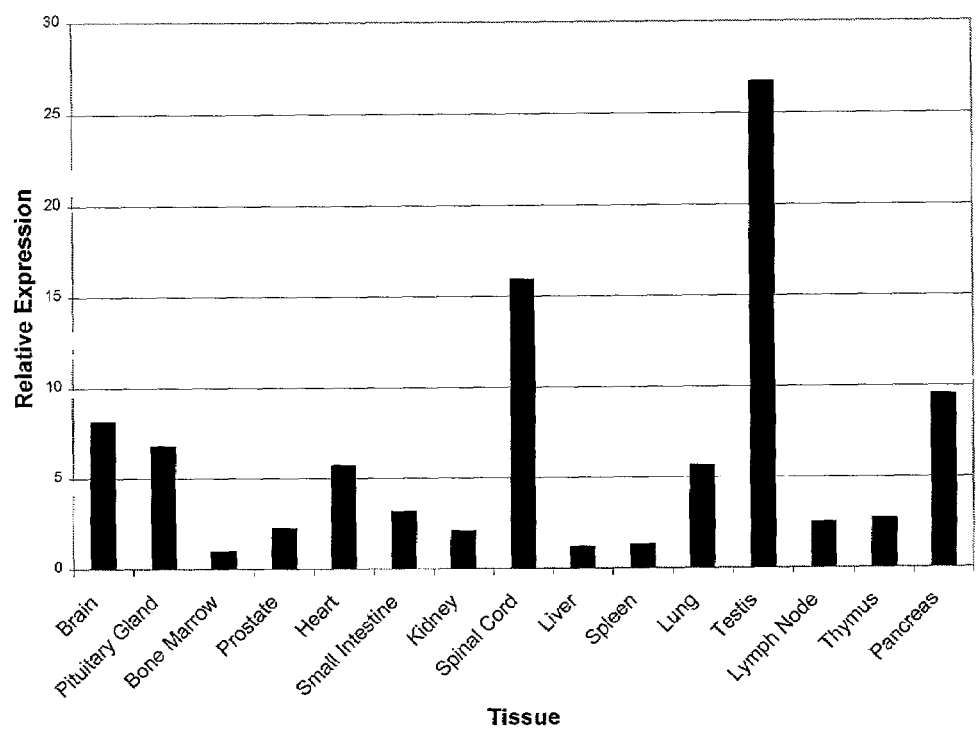

FIG. 22 shows an expression profile of the novel full-length human phosphatase protein BMY_HPP1. The figure illustrates the relative expression level of BMY_HPP1 amongst various mRNA tissue sources. As shown, the BMY_HPP1 polypeptide was expressed predominately in testis; to a significant extent, in the spinal cord, and to a lesser extent, in pancreas, brain, pituitary, heart, and lung. Expression data was obtained by measuring the steady state BMY_HPP1 mRNA levels by quantitative PCR using the PCR primer pair provided as SEQ ID NO:154 and 155 as described herein.

Figure 23:
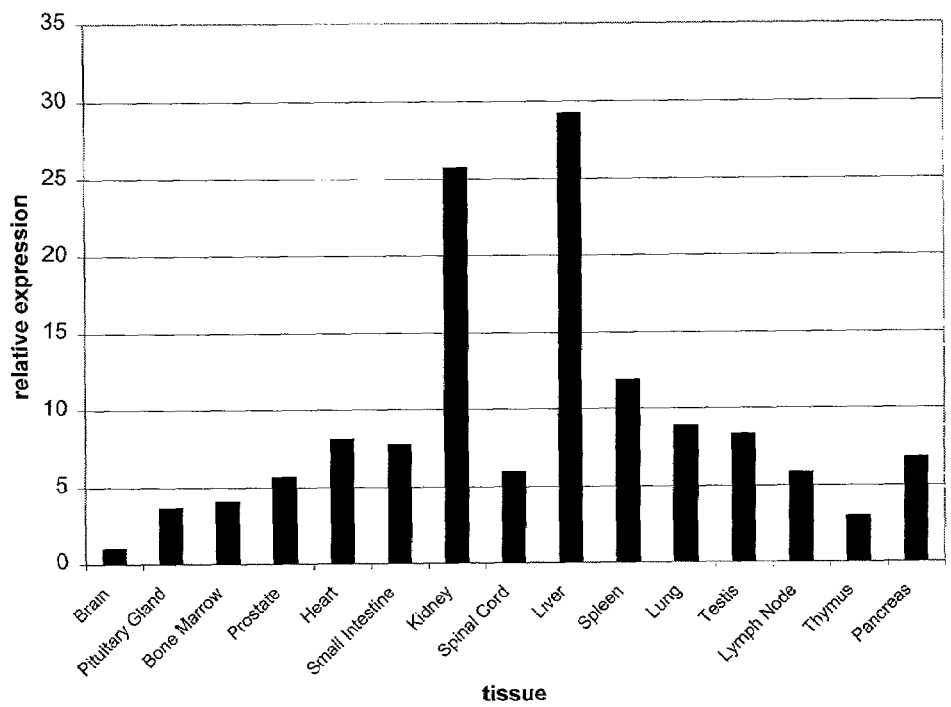

FIG. 23 shows an expression profile of the novel full-length human phosphatase protein BMY_HPP2. The figure illustrates the relative expression level of BMY_HPP2 amongst various mRNA tissue sources. As shown, the BMY_HPP2 polypeptide was expressed predominately in liver and kidney; to a significant extent, in the spleen, and to a lesser extent, in lung, testis, heart, intestine, pancreas, lymph node, spinal cord, and prostate. Expression data was obtained by measuring the steady state BMY_HPP2 mRNA levels by quantitative PCR using the PCR primer pair provided as SEQ ID NO:156 and 157 as described herein.

FIG. 24 shows a table illustrating the percent identity and percent similarity between the full-length BMY_HPP1 polypeptide (SEQ ID NO:150), and the full-length BMY_ HPP2 polypeptide (SEQ ID NO:152) of the present invention with other phosphatase proteins. The percent identity and percent similarity values were determined based upon the GAP algorithm (GCG suite of programs; and Henikoff, and Henikoff, J. G., Proc. Natl. Acad. Sci. USA 89: 10915–10919(1992)) using the following parameters: gap weight=8, and length weight=2.

FIG. 25 shows a table illustrating the percent identity and percent similarity between the full-length RET31 polypeptide (SEQ ID NO:109) of the present invention with other phosphatase proteins. The percent identity and percent similarity values were determined based upon the GAP algorithm (GCG suite of programs; and Henikoff, and Henikoff, J. G., Proc. Natl. Acad. Sci. USA 89: 10915–10919(1992)) using the following parameters: gap weight=8, and length weight=2.

FIG. 26 shows an expanded expression profile of the novel full-length human phosphatase protein BMY_HPP1. The figure illustrates the relative expression level of BMY_ HPP1 amongst various mRNA tissue sources. As shown, the BMY_HPP1 polypeptide was expressed predominately in brain subregions and other central nervous system tissues, in particular the caudate, hippocampus and nucleus accumbens of the brain. Significant expression was observed in the in the adrenal, pineal and pituitary glands, the atrium of the heart, in the testis, and to a lesser extent in a number of other tissues as shown. Expression data was obtained by measuring the steady state BMY_HPP1 mRNA levels by quantitative PCR using the PCR primer pair provided as SEQ ID NO:194 and 195, and Taqman probe (SEQ ID NO:196) as described in Example 59 herein.

FIG. 27 shows the regions of identity between amino acid residues M1 to E301 of the BMY_HPP1 polypeptide (amino acids M1 to E301 of SEQ ID NO:150) to amino acid residues D11 to N321 of the human tyrosine specific phosphatase 1 aax (Protein Data Bank, PDB entry 1 aax chain A; Genbank Accession No. gi|2981942; SEQ ID NO:206) which was used as the basis for building the BMY_HPP1 homology model as represented in Table VIII and visualized in FIG. 28. Amino acids defining active site residues are highlighted with asterisks ("*"). The alignment was created using the FASTA algorithm (Pearson, et. al. 1990).

FIG. 28 shows a three-dimensional homology model of amino acid residues M1 to E301 of the BMY_HPP1 polypeptide based upon the homologous structure of amino acid residues D11 to N321 of the human tyrosine specific phosphatase 1 aax (Protein Data Bank, PDB entry 1 aax chain A; Genbank Accession No. gi|2981942; SEQ ID NO:206). The structural coordinates of the BMY_HPP1 polypeptide are provided in Table VIII herein. The homology model of BMY_HPP1 was derived from generating a sequence alignment with the human tyrosine specific phosphatase 1 aax (Protein Data Bank, PDB entry 1 aax chain A; Genbank Accession No. gi|2981942; SEQ ID NO:206) using the INSIGHTII (Accelrys Inc., San Diego, Calif.) version 2000 as described herein.

Figure 29:
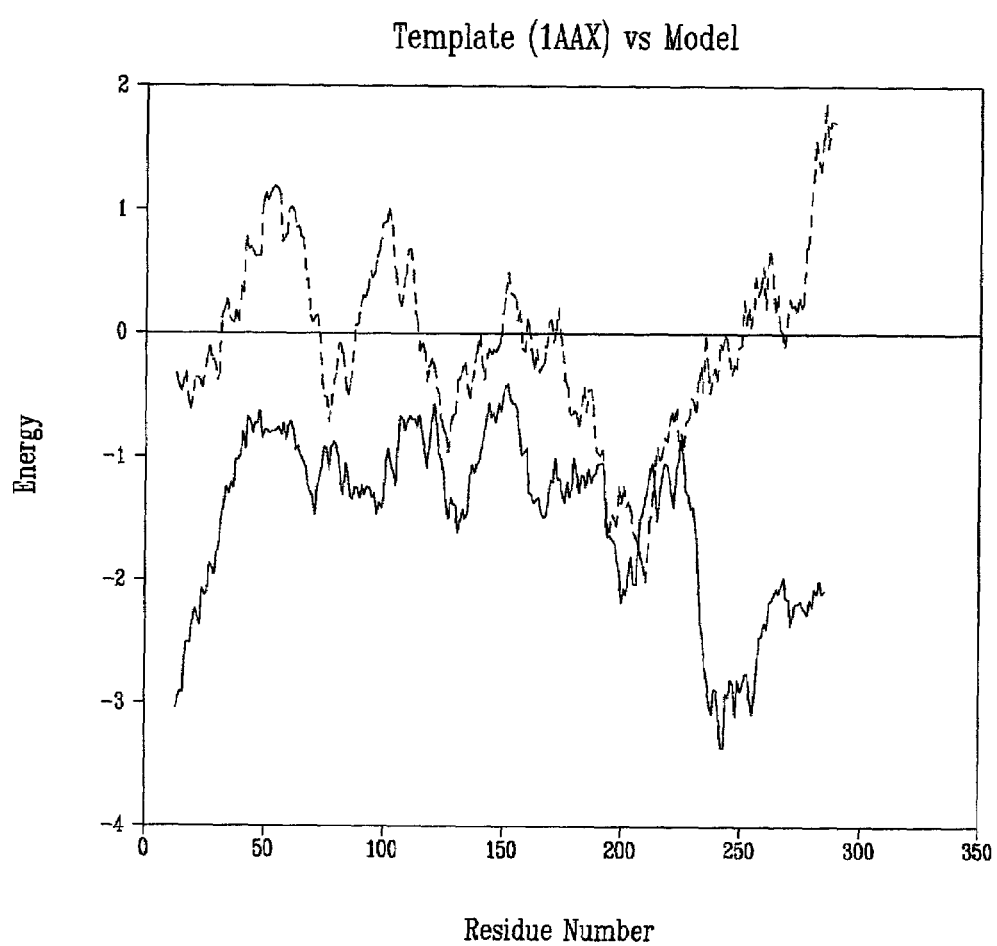

FIG. 29 shows an energy graph for the BMY_HPP1 model of the present invention (dotted line) and the tyrosine specific phosphatase 1 aax template (solid line) from which the model was generated. The energy distribution for each protein fold is displayed on the y-axis, while the amino acid residue position of the protein fold is displayed on the x-axis. As shown, the BMY_HPP1 model has slightly higher energies in the C-terminal region while the N-terminal region of the structural model appears to represent a "native-like" conformation of the BMY_HPP1 polypeptide. This graph supports the motif and sequence alignments in confirming that the three dimensional structure coordinates of BMY_HPP1 are an accurate and useful representation of the structure of the BMY_HPP1 polypeptide.

Figure 30:
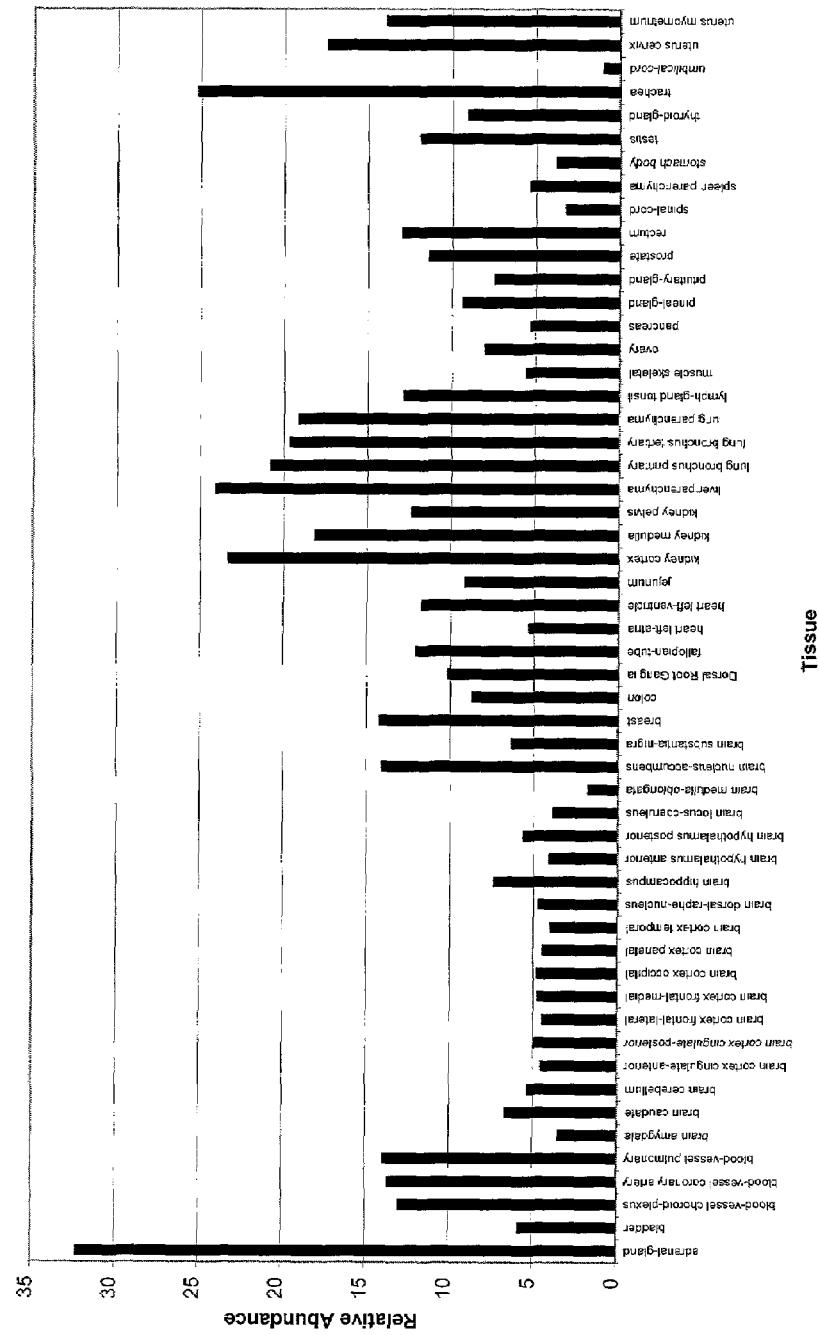

FIG. 30 shows an expanded expression profile of the novel full-length human phosphatase protein BMY_HPP2. The figure illustrates the relative expression level of BMY_ HPP2 amongst various mRNA tissue sources. As shown, the BMY_HPP2 polypeptide was expressed predominately in adrenal gland; significantly in the pineal and pituitary gland, lung parenchyma, bronchi, kidney, liver, blood vessels from the choroid plexus, coronary artery, pulmonary artery, the nucleus accumbens of the brain, and to a lesser extent in the trachea, breast and uterus and in other tissues as shown. Expression data was obtained by measuring the steady state BMY_HPP2 mRNA levels by quantitative PCR using the PCR primer pair provided as SEQ ID NO:197 and 198, and Taqman probe (SEQ ID NO:199) as described in Example 59 herein.

FIG. 31 shows the regions of identity between amino acid residues M1 to K150 of the BMY_HPP2 polypeptide (amino acids M1 to K150 of SEQ ID NO:152) to amino acid residues N31 to K179 of the N-terminus of the human dual specificity phosphatase, 1 vhr (vaccinia H1-related phosphatase VN1) (residues N31-K179; Protein Data Bank, PDB entry 1 vhr chain A; Genbank Accession No. gi|1633321; SEQ ID NO:207) which was used as the basis for building the BMY_HPP2 homology model as represented in Table IX and visualized in FIG. 32. Amino acids defining active site residues are highlighted in bold. The alignment was created using the FASTA algorithm (Pearson, et. al. 1990).

FIG. 32 shows a three-dimensional homology model of amino acid residues M1 to K150 of the BMY_HPP2 polypeptide based upon the homologous structure of amino acid residues N31 to K179 of the N-terminus of the human dual specificity phosphatase, 1 vhr (vaccinia H1-related phosphatase VN1) (residues N31-K179; Protein Data Bank, PDB entry 1 vhr chain A; Genbank Accession No. gi|1633321; SEQ ID NO:207). The structural coordinates of the BMY_HPP2 polypeptide are provided in Table IX herein. The homology model of BMY_HPP2 was derived from generating a sequence alignment with the human dual specificity phosphatase, 1 vhr (vaccinia H1-related phosphatase VN1) (residues N31-K179; Protein Data Bank, PDB entry 1 vhr chain A; Genbank Accession No. gi|1633321; SEQ ID NO:207) using the INSIGHTII (Accelrys Inc., San Diego, Calif.) version 2000 as described herein.

Figure 33:
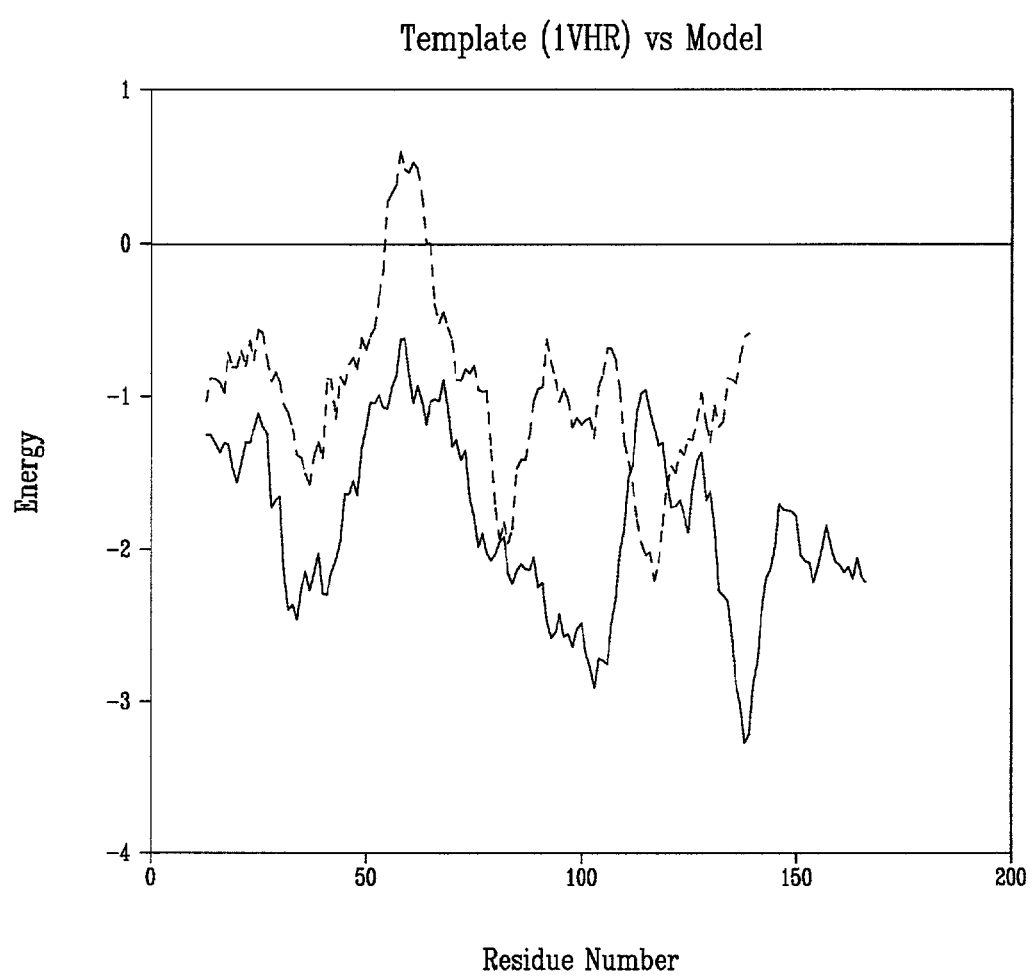

FIG. 33 shows an energy graph for the BMY_HPP2 model of the present invention (dotted line) and the phosphatase VHR template (PDB code 1 vhr) (solid line) from which the model was generated. The energy distribution for each protein fold is displayed on the y-axis, while the amino acid residue position of the protein fold is displayed on the x-axis. As shown, the BMY_HPP2 model and 1 vhr template have similar energies over the aligned region, suggesting that the structural model of BMY_HPP2 represents a "native-like" conformation of the BMY_HPP2 polypeptide. This graph supports the motif and sequence alignments in confirming that the three dimensional structure coordinates of BMY_HPP2 are an accurate and useful representation of the structure of the BMY_HPP1 polypeptide.

Figure 34:
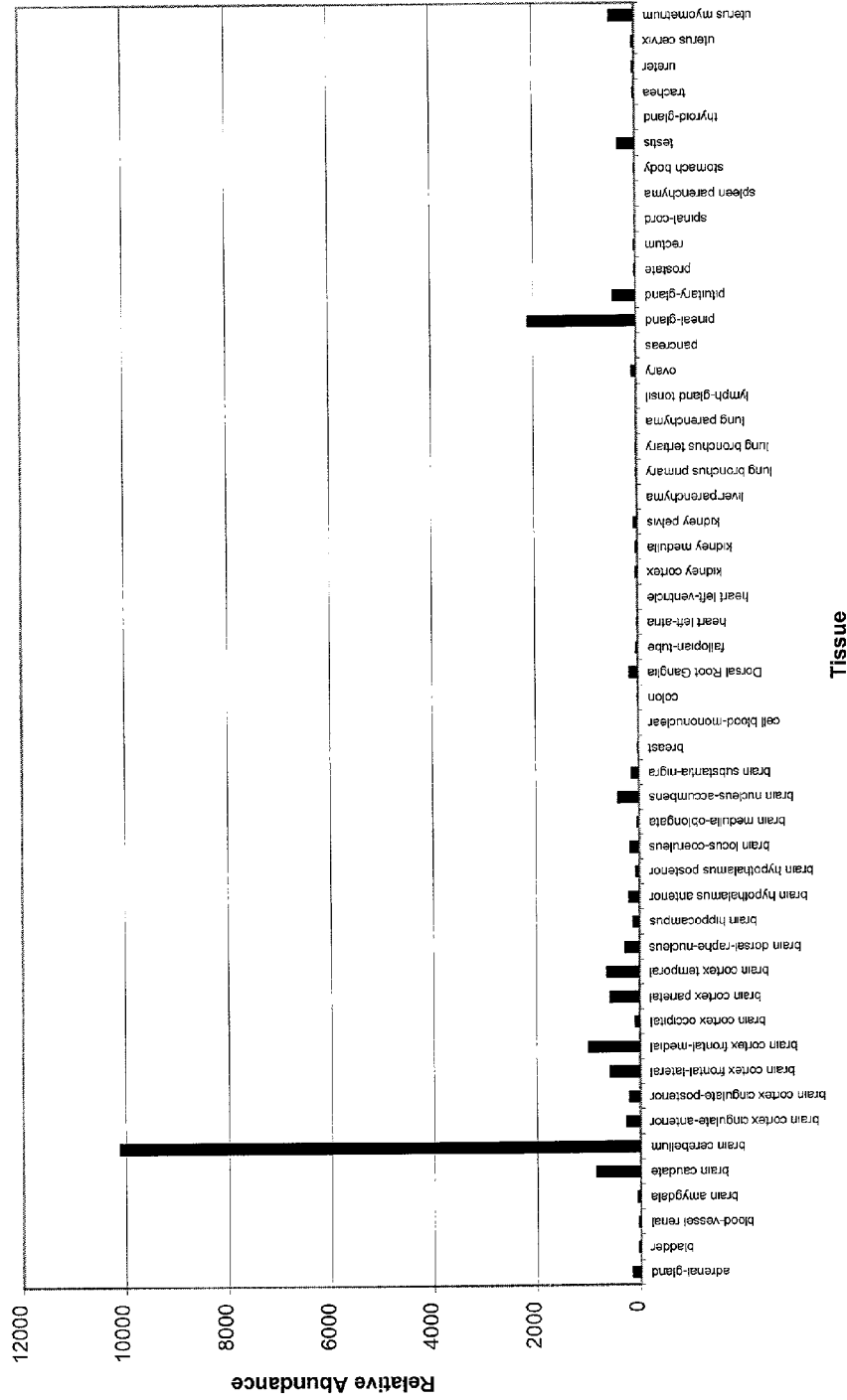

FIG. 34 shows an expanded expression profile of the novel full-length human phosphatase protein BMY_HPP4. The figure illustrates the relative expression level of BMY_HPP4 amongst various mRNA tissue sources. As shown, the BMY_HPP4 polypeptide was expressed predominately in cerebellum; significantly in other subregions of the brain, and in the pineal and pituitary glands. Expression data was obtained by measuring the steady state BMY_HPP4 mRNA levels by quantitative PCR using the PCR primer pair provided as SEQ ID NO:200 and 201, and Taqman probe (SEQ ID NO:202) as described in Example 59 herein.

Figure 35:
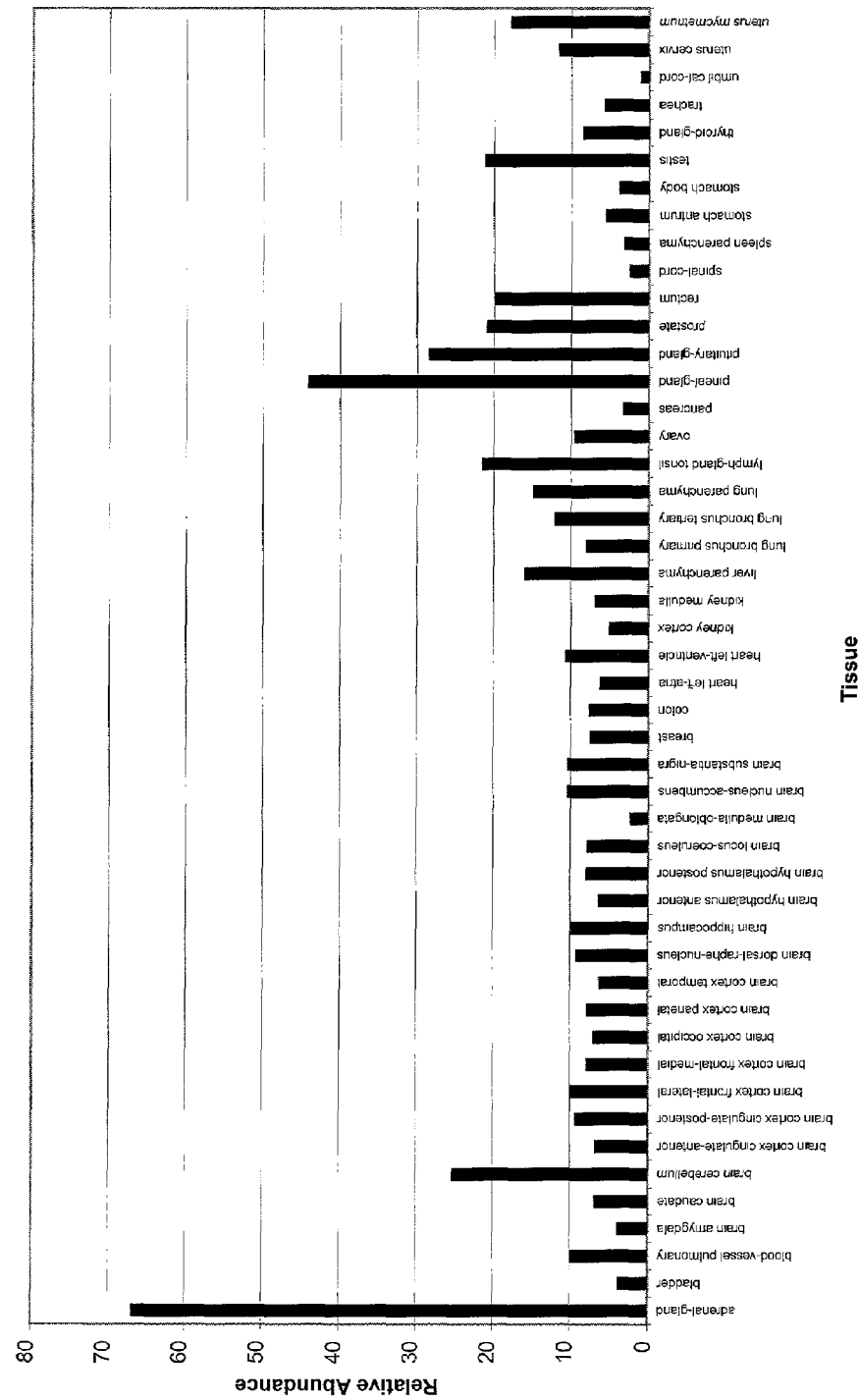

FIG. 35 shows an expanded expression profile of the novel full-length human phosphatase protein BMY_HPP5.

The figure illustrates the relative expression level of BMY_HPP5 amongst various mRNA tissue sources. As shown, the BMY_HPP5 polypeptide was expressed predominately in the adrenal, pineal and pituitary glands; significantly in the cerebellum, prostate, testis, and to a lesser extent in other tissues as shown. Expression data was obtained by measuring the steady state BMY_HPP5 mRNA levels by quantitative PCR using the PCR primer pair provided as SEQ ID NO:203 and 204, and Taqman probe (SEQ ID NO:205) as described in Example 59 herein.

Figure 36:
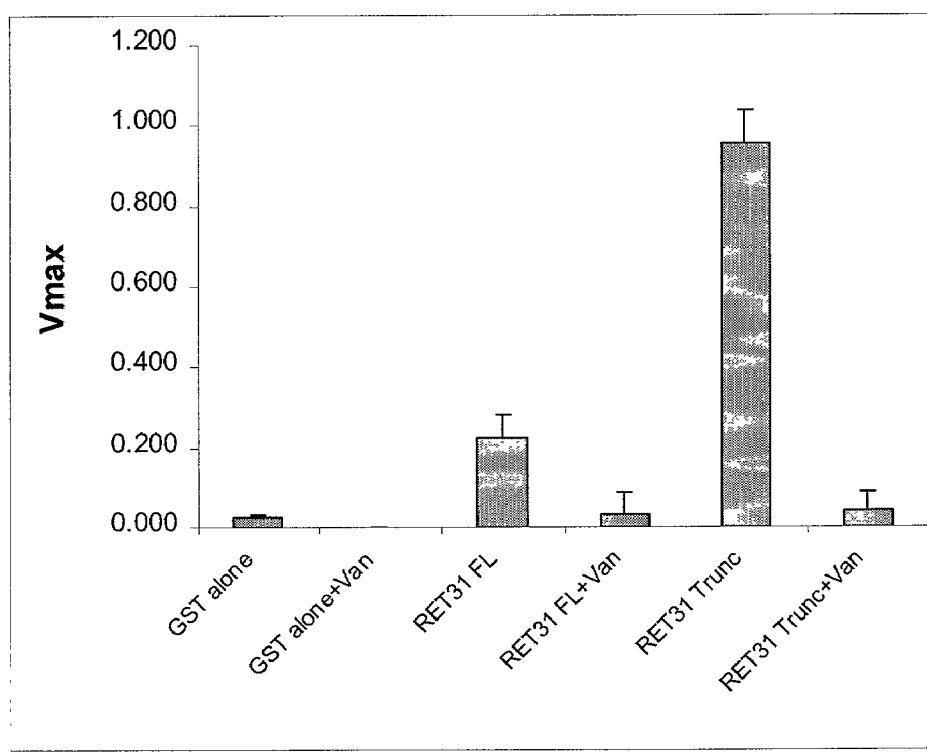

FIG. 36 shows the results of para-nitrophenylphosphate (pNPP) phosphatase activity assays of the purified RET31-GST full length (FL), and M1 to T302 RET31 C-terminal deletion mutant (trunc) fusion proteins, as compared to purified GST alone. The bars represent the average of triplicate determinations, and the standard deviations are as shown. Each protein preparation was assayed in the absence and presence of 2 mM orthovanadate ("-van"). As shown, both the full-length RET31 and M1 to T302 RET31 C-terminal deletion mutant demonstrated phosphatase activity via cleavage of the NPP substrate which was blocked by the phosphatase-specific inhibitor, vanadate. Of particular significance is the unexpected five fold increase in phosphatase activity of the M1 to T302 RET31 C-terminal deletion mutant relative to the full-length RET31 polypeptide. The phosphatase assays were performed as described in Example 57 herein. The full length and truncated versions clearly demonstrated phosphatase activity compared to the GST protein.

FIG. 37 shows the regions of identity between amino acid residues N157 to I300 of the BMY_HPP5 polypeptide (amino acids N157 to I300 of SEQ ID NO:42) to amino acid residues A204 to L347 of the human dual specificity phosphatase MAP Kinase phosphatase 3, also called PYST1, 1 mkp (residues A204-L347; Protein Data Bank, PDB entry 1 mkp chain A; Genbank Accession No. gi|5822131; SEQ ID NO:208) which was used as the basis for building the BMY_HPP5 homology model as represented in Table X and visualized in FIG. 38. Amino acids defining active site residues are highlighted in bold. The alignment was created using the FASTA algorithm (Pearson, et. al. 1990).

FIG. 38 shows a three-dimensional homology model of amino acid residues N157 to I300 of the BMY_HPP5 polypeptide based upon the homologous structure of amino acid residues A204 to L347 of the human dual specificity phosphatase MAP Kinase phosphatase 3, also called PYST1, 1 mkp (residues A204-L347; Protein Data Bank, PDB entry 1 mkp chain A; Genbank Accession No. gi|5822131; SEQ ID NO:208). The structural coordinates of the BMY_HPP2 polypeptide are provided in Table IX herein. The homology model of BMY_HPP2 was derived from generating a sequence alignment with the human dual specificity phosphatase MAP Kinase phosphatase 3, also called PYST1, 1 mkp (residues A204-L347; Protein Data Bank, PDB entry 1 mkp chain A; Genbank Accession No. gi|5822131; SEQ ID NO:208) using the INSIGHTII (Accelrys Inc., San Diego, Calif.) version 2000 as described herein.

Figure 39:
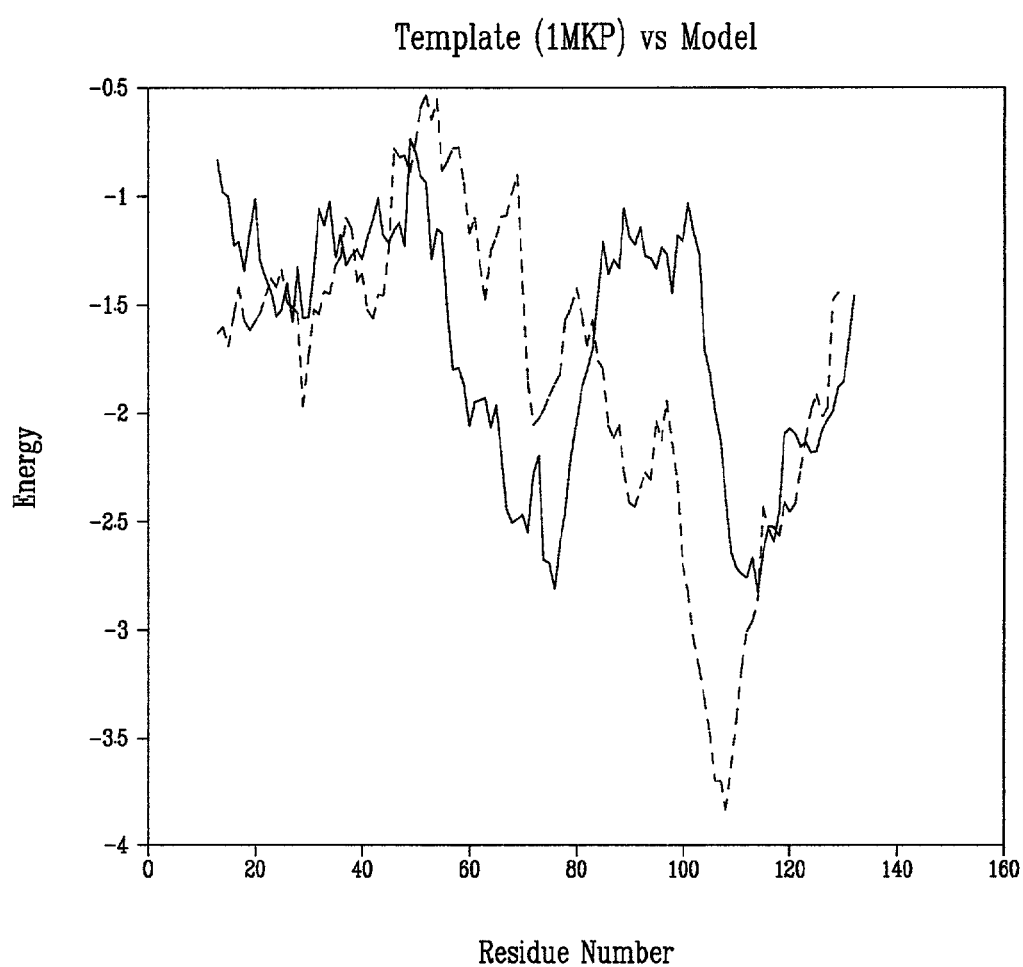

FIG. 39 shows an energy graph for the BMY_HPP5 model of the present invention (dotted line) and the phosphatase VHR template (PDB code 1 vhr) (solid line) from which the model was generated. The energy distribution for each protein fold is displayed on the y-axis, while the amino acid residue position of the protein fold is displayed on the x-axis. As shown, the BMY_HPP5 model and 1 vhr template have similar energies over the aligned region, suggesting that the structural model of BMY_HPP5 represents a "native-like" conformation of the BMY_HPP5 polypeptide.

This graph supports the motif and sequence alignments in confirming that the three dimensional structure coordinates of BMY_HPP5 are an accurate and useful representation of the structure of the BMY_HPP5 polypeptide.

Table I provides a summary of the novel polypeptides and their encoding polynucleotides of the present invention.

Table II illustrates the preferred hybridization conditions for the polynucleotides of the present invention. Other hybridization conditions may be known in the art or are described elsewhere herein.

Table III provides the amino acid sequences of known phosphatases that were used to identify the novel human phosphatases of the present invention using the BLAST algorithm as described herein.

Table IV provides the PFAM motifs that were used in Hidden Markov Model (HMM) searches to identify the novel human phosphatase of the present invention as described herein.

Table V provides the predicted exon structure of the BMY_HPP4 gene. The 'Start' and 'End' designations refer to the respective nucleotide positions of the BMY_HPP4 as they appear for the corresponding genomic sequence in BAC AL 354751. The numbering begins at the start of BAC AL354751; nucleotide 71352 in the BAC is equivalent to nucleotide 1 of the BMY_HPP4 transcript (SEQ ID NO:9; FIG. 4).

Table VI provides representative primers for sequencing and/or cloning any one of the human phosphatases of the present invention in conjunction with the teachings described herein. 'Left Cloning Primer', and 'Right Cloning Primer' represent the forward and reverse sequencing primers, while the 'Internal RevComp Cloning Primer' and/or 'Internal Cloning Primer' represent antisense cloning primers as described in the Examples herein.

Table VII provides a summary of various conservative substitutions encompassed by the present invention.

Table VIII provides the structural coordinates of the homology model of the BMY_HPP1 polypeptide provided in FIG. 28. A description of the headings are as follows: "Atom No" refers to the atom number within the BMY_HPP1 homology model; "Atom name" refers to the element whose coordinates are measured, the first letter in the column defines the element; "Residue" refers to the amino acid of the BMY_HPP1 polypeptide within which the atom resides; "Residue No" refers to the amino acid position in which the atom resides, "X Coord", "Y Coord", and "Z Coord" structurally define the atomic position of the element measured in three dimensions.

Table IX provides the structural coordinates of the homology model of the BMY_HPP2 polypeptide provided in FIG. 32. A description of the headings are as follows: "Atom No" refers to the atom number within the BMY_HPP2 homology model; "Atom name" refers to the element whose coordinates are measured, the first letter in the column defines the element; "Residue" refers to the amino acid of the BMY_HPP2 polypeptide within which the atom resides; "Residue No" refers to the amino acid position in which the atom resides, "X Coord", "Y Coord", and "Z Coord" structurally define the atomic position of the element measured in three dimensions.

Table X provides the structural coordinates of the homology model of the BMY_HPP5 polypeptide provided in FIG. 38. A description of the headings are as follows: "Atom No" refers to the atom number within the BMY_HPP5 homology model; "Atom name" refers to the element whose coordinates are measured, the first letter in the column defines the element; "Residue" refers to the amino acid of the BMY_HPP5 polypeptide within which the atom resides; "Residue No" refers to the amino acid position in which the atom resides, "X Coord", "Y Coord", and "Z Coord" structurally define the atomic position of the element measured in three dimensions.

DETAILED DESCRIPTION OF THE INVENTION

The present invention may be understood more readily by reference to the following detailed description of the preferred embodiments of the invention and the Examples included herein. All references to "phosphatase" and/or "human phosphatases" shall be construed to apply to BMY_HPP1, BMY_HPP2, BMY_HPP3, BMY_HPP4, BMY_HPP5, RET31, mouse RET31, and/or fragments thereof unless otherwise specified herein. Moreover, since BMY_HPP5 is believed to represent a splice variant of the RET31 polypeptide, all references to "BMY_HPP5" shall be construed to apply to RET31, and all references to "RET31" shall be construed to apply to "BMY_HPP5".

The invention provides human polynucleotide sequences encoding novel human phosphatases with substantial homology to the class of phosphatases known as phosphotyrosine or dual-specificity (P-Tyr, P-Ser and P-Thr) phosphatases. Members of this class of phosphatases have been implicated in a number of diseases and/or disorders, which include, but are not limited to, bone disorders, (Yoon, H K., Baylink, D J., Lau, K H, Am. J. Nephrol., 20(2):153–62, (2000)), disease resistance to pathogens, reproductive disorders (Gloria, Bottini, F., Nicotra, M., Lucarini, N., Borgiani, P., La, Torre, M., Amante, A., Gimelfarb, A., Bottini, E, Dis. Markers., 12(4):261–9, (1996)), neural disorders (Shimohama, S., Fujimoto, S., Taniguchi, T., Kameyama, M., Kimura, J. Ann, Neurol., 33(6):616–21, (1993)), prostate cancer (Nguyen, L., Chapdelaine, A., and Chevalier, S., Clin. Chem. 36(8 Pt 1): 1450–5 (1990)), immune disorders, particularly those relating to haematopoietic cell development, apoptosis, activation, and nonresponsiveness (Frearson, J A., Alexander, D R, Bioessays., 19(5): 417–27 (1997)), etc.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:7, 9, 41, 108, 149, 151 or the cDNA contained within the clone deposited with the ATCC. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO: 7, 9, 41, 108, 149, 151 was often generated by overlapping sequences contained in one or more clones (contig analysis). A representative clone containing all or most of the sequence for SEQ ID NO:149, 151, 7, 9, 41, or 108 was deposited with the American Type Culture Collection ("ATCC"). As shown in Table I, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. The deposited clone is inserted in the pSport plasmid (Life Technologies) using SalI and NotI restriction sites as described herein.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence provided as SEQ ID NO: 7, 9, 41, 108, 149, 151, a nucleic acid molecule of the present invention encoding a human phosphatase polypeptide may be obtained using standard cloning and screening procedures, such as those for cloning cDNAs using mRNA as starting material.

A "polynucleotide" of the present invention also includes those polynucleotides capable of hybridizing, under stringent hybridization conditions, to sequences contained in SEQ ID NO:149, 151, 7, 9, 41, or 108, the complement thereof, or the cDNA within the clone deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20×SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art.

Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).) "SEQ ID NO:149, 151, 7, 9, 41, or 108" refers to a polynucleotide sequence while "SEQ ID NO:150, 152, 8, 10, 42, or 109" refers to a polypeptide sequence, both sequences are identified by an integer specified in Table I.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

The term "organism" as referred to herein is meant to encompass any organism referenced herein, though preferably to eukaryotic organisms, more preferably to mammals, and most preferably to humans.

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol Endocrinol., 9(10):1321–9, (1995); and Ann. N. Y. Acad. Sci., 7;766:279–81, (1995)).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

As used herein the terms "modulate or modulates" refer to an increase or decrease in the amount, quality or effect of a particular activity, DNA, RNA, or protein.

Polynucleotides and Polypeptides of the Invention

Features of the Polypeptide Encoded by Gene No:1

Polypeptide fragments A and B corresponding to this gene provided as SEQ ID NO:2 and 4 (FIG. 1), encoded by the polynucleotide sequence according to SEQ ID NO:1 and 3 (FIG. 1), the predicted full-length polypeptide sequence corresponding to this gene provided as SEQ ID NO:150 (FIGS. 20A–D), encoded by the full-length polynucleotide sequence according to SEQ ID NO:149 (FIGS. 20A–D), and/or encoded by the polynucleotide contained within the deposited clone, BMY_HPP1, has significant homology at the nucleotide and amino acid level to a number of phosphatases, which include, for example, the *Schizosacchromyces* Pombe protein tyrosine phosphatase PYP3 protein (PYP3_SP; Genbank Accession No:gi|P32587; SEQ ID NO:29); the mouse protein tyrosine phosphatase, receptor type, O, protein (MM_RPTPO; Genbank Accession No:gi|

NP_035346; SEQ ID NO:28); and the human protein tyrosine phosphatase, receptor type, O, protein (HS_RPTPO; Genbank Accession No:gi| NP_002839; SEQ ID NO:27); as determined by BLASTP. An alignment of the human phosphatase polypeptide with these proteins is provided in FIGS. 6A–D. The conserved catalytic residues are noted.

BMY_HPP1 is a novel phosphoprotein phosphatase encoded by a human genomic BAC clone, Genbank accession AL360020. Aside from the predicted full-length BMY_HPP1 polypeptide sequence, two separate homologous regions in BAC AL360020 have been identified. Fragment A of BMY_HPP1 includes key conserved phosphatase catalytic residues: an Aspartate ("D") at amino acid 11 of SEQ ID NO:2 (FIG. 1), a Cysteine ("C") at amino acid 40 of SEQ ID NO:2 (FIG. 1), and an Arginine ("R") at amino acid 46 of SEQ ID NO:2 (FIG. 1). Fragment B of BMY_HPP1 represents a more N-terminal fragment and is not predicted to include any catalytic residues. The predicted conserved phosphatase catalytic residues for the predicted full-length BMY_HPP1 polypeptide are as follows: conserved phophatase catalytic residues: an Aspartate ("D") at amino acid 14 of SEQ ID NO:150 (FIGS. 20A–D), a Cysteine ("C") at amino acid 42 of SEQ ID NO:150 (FIGS. 20A–D), and an Arginine ("R") at amino acid 48 of SEQ ID NO:150 (FIGS. 20A–D).

An alignment of the BMY_HPP1 polypeptide fragments and predicted full-length polypeptide with other phosphatase proteins (FIGS. 6A–D) illustrates the conserved phosphatase catalytic residues.

Based upon the strong homology to members of the phosphatase proteins, the polypeptide encoded by the human BMY_HPP1 phosphatase of the present invention is expected to share at least some biological activity with phosphatase proteins, preferably with members of the novel phosphotyrosine/dual-specificity (P-Tyr, P-Ser and P-Thr) phosphatases, particularly the novel phosphotyrosine/dual-specificity (P-Tyr, P-Ser and P-Thr) phosphatases referenced herein.

The present invention encompasses the use of BMY_HPP1 inhibitors and/or activators of BMY_HPP1 activity for the treatment, detection, amelioration, or prevention of phosphatase associated disorders, including but not limited to metabolic diseases such as diabetes, in addition to neural and/or cardiovascular diseases and disorders. The present invention also encompasses the use of BMY_HPP1 inhibitors and/or activators of BMY_HPP1 activity as immunosuppressive agents, anti-inflammatory agents, and/or anti-tumor agents The present invention encompasses the use of BMY_HPP1 phosphatase inhibitors, including, antagonists such as antisense nucleic acids, in addition to other antagonists, as described herein, in a therapeutic regimen to diagnose, prognose, treat, ameliorate, and/or prevent diseases where a kinase activity is insufficient. One, non-limiting example of a disease which may occur due to insufficient kinase activity are certain types of diabetes, where one or more kinases involved in the insulin receptor signal pathway may have insufficient activity or insufficient expression, for example.

Moreover, the present invention encompasses the use of BMY_HPP1 phosphatase activators, and/or the use of the BMY_HPP1 phosphatase gene or protein in a gene therapy regimen, as described herein, for the diagnoses, prognoses, treatment, amelioration, and/or prevention of diseases and/or disorders where a kinase activity is overly high, such as a cancer where a kinase oncogene product has excessive activity or excessive expression.

The present invention also encompasses the use of catalytically inactive variants of BMY_HPP1 proteins, including fragments thereof, such as a protein therapeutic, or the use of the encoding polynucleotide sequence or as gene therapy, for example, in the diagnoses, prognosis, treatment, amelioration, and/or prevention of diseases or disorders where phosphatase activity is overly high.

The present invention encompasses the use of antibodies directed against the BMY_HPP1 polypeptides, including fragment and/or variants thereof, of the present invention in diagnostics, as a biomarkers, and/or as a therapeutic agents.

The present invention encompasses the use of an inactive, non-catalytic, mutant of the BMY_HPP1 phosphatase as a substrate trapping mutant to bind cellular phosphoproteins or a library of phosphopeptides to identify substrates of the BMY_HPP1 polypeptides.

The present invention encompasses the use of the BMY_HPP1 polypeptides, to identify inhibitors or activators of the BMY_HPP1 phosphatase activity, using either in vitro or 'virtual' (in silico) screening methods.

One embodiment of the invention relates to a method for identifying a compound as an activator or inhibitor of the BMY_HPP1 phosphatase comprising the steps of: i.) contacting a BMY_HPP1 phosphatase inhibitor or activator labeled with an analytically detectable reagent with the BMY_HPP1 phosphatase under conditions sufficient to form a complex with the inhibitor or activator; ii.) contacting said complex with a sample containing a compound to be identified; iii) and identifying the compound as an inhibitor or activator by detecting the ability of the test compound to alter the amount of labeled known BMY_HPP1 phosphatase inhibitor or activator in the complex.

Another embodiment of the invention relates to a method for identifying a compound as an activator or inhibitor of a BMY_HPP1 phosphatase comprising the steps of: i.) contacting the BMY_HPP1 phosphatase with a compound to be identified; and ii.) and measuring the ability of the BMY_HPP1 phosphatase to remove phosphate from a substrate.

The present invention also encompasses a method for identifying a ligand for the BMY_HPP1 phosphatase comprising the steps of: i.) contacting the BMY_HPP1 phosphatase with a series of compounds under conditions to permit binding; and ii.) detecting the presence of any ligand-bound protein.

Preferably, the above referenced methods comprise the BMY_HPP1 phosphatase in a form selected from the group consisting of whole cells, cytosolic cell fractions, membrane cell fractions, purified or partially purified forms. The invention also relates to recombinantly expressed BMY_HPP1 phosphatase in a purified, substantially purified, or unpurified state. The invention further relates to BMY_HPP1 phosphatase fused or conjugated to a protein, peptide, or other molecule or compound known in the art, or referenced herein.

The present invention also encompasses pharmaceutical composition of the BMY_HPP1 phosphatase polypeptide comprising a compound identified by above referenced methods and a pharmaceutically acceptable carrier.

Expression profiling designed to measure the steady state mRNA levels encoding the BMY_HPP1 polypeptide showed predominately high expression levels in testis; to a significant extent, in the spinal cord, and to a lesser extent, in pancreas, brain, pituitary, heart, and lung (as shown in FIG. 22).

Moreover, additional expression profiling of the BMY_HPP1 polypeptide in normal tissues showed strong expression in a number of brain subregions and other central nervous system tissues, in particular the caudate, hippocampus and nucleus accumbens of the brain (as shown in FIG. 26). These regions are known to be involved in a number of neurological disorders such as depression, bipolar disorder, schizophrenia, dementia, cognitive disorders and obesity. This data suggests a role for modulators of BMY_HPP1 activity in the treatment of neural disorders. In addition, BMY_HPP1 is strongly expressed in the adrenal, pineal and pituitary glands, suggesting a role for modulators of BMY_HPP1 activity in the treatment of endocrine disorders; in the atrium of the heart, suggesting a role for modulators of BMY_HPP1 activity in the treatment of cardiac failure or other diseases of the heart; and in the testis, suggesting a role for modulators of BMY_HPP1 activity in the treatment of male infertility caused by defective or insufficient spermatogenesis, as a contraceptive agent, or in the treatment of testicular cancer. In addition, BMY_HPP1 was expressed at lower levels across a number of tissues as well.

The strong homology to dual specificity phosphatases, combined with the predominate localized expression in testis tissue emphasizes the potential utility for BMY_HPP1 polynucleotides and polypeptides in treating, diagnosing, prognosing, and/or preventing testicular, in addition to reproductive disorders.

In preferred embodiments, BMY_HPP1 polynucleotides and polypeptides including agonists and fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The BMY_HPP1 polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Nonseminoma, seminona, and testicular germ cell tumors).

Likewise, the predominate localized expression in testis tissue also emphasizes the potential utility for BMY_HPP1 polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

The strong homology to dual specificity phosphatase proteins, combined with the localized expression in spinal cord, brain subregions, and other central nervous system tissues, suggests the BMY_HPP1 polynucleotides and polypeptides may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The BMY_HPP1 polypeptide has been shown to comprise one glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673–702(1972); Pless D. D., Lennarz W. J., Proc. Natl. Acad. Sci. U.S.A. 74:134–138(1977); Bause E., Biochem. J. 209:331–336(1983); Gavel Y., von Heijne G., Protein Eng. 3:433–442(1990); and Miletich J. P., Broze G. J. Jr., J. Biol. Chem. 265:11397–11404(1990).

In preferred embodiments, the following asparagine glycosylation site polypeptide is encompassed by the present invention: LTPLRNISCCDPKA (SEQ ID NO:158). Polynucleotides encoding this polypeptide are also provided. The present invention also encompasses the use of this BMY_HPP1 asparagine glycosylation site polypeptide as an immunogenic and/or antigenic epitope as described elsewhere herein.

The BMY_HPP1 polypeptides of the present invention were determined to comprise several phosphorylation sites based upon the Motif algorithm (Genetics Computer Group, Inc.). The phosphorylation of such sites may regulate some biological activity of the BMY_HPP1 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the BMY_HPP1 polypeptide to associate with other potassium channel alpha subunits, beta subunits, or its ability to modulate potassium channel function.

The BMY_HPP1 polypeptide was predicted to comprise four PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. 260:12492–12499(1985); which are hereby incorporated by reference herein.

In preferred embodiments, the following PKC phosphorylation site polypeptides are encompassed by the present invention: TLSFWSQKFGGLE (SEQ ID NO:159), VQNSRTPRSPLDC (SEQ ID NO:160), PLDCGSSKAQFLV (SEQ ID NO:161), and/or PTVYNTKKIFKHT (SEQ ID NO:162). Polynucleotides encoding these polypeptides are also provided. The present invention also encompasses the use of these BMY_HPP1 PKC phosphorylation site polypeptides as immunogenic and/or antigenic epitopes as described elsewhere herein.

In further confirmation of the human BMY_HPP1 polypeptide representing a novel human phosphatase polypeptide, the BMY_HPP1 polypeptide has been shown to comprise a tyrosine specific protein phosphatase active site domain according to the Motif algorithm (Genetics Computer Group, Inc.).

Tyrosine specific protein phosphatases (EC 3.1.3.48) (PTPase) are enzymes that catalyze the removal of a phosphate group attached to a tyrosine residue. These enzymes are very important in the control of cell growth, proliferation, differentiation and transformation. Multiple forms of PTPase have been characterized and can be classified into two categories: soluble PTPases and transmembrane receptor proteins that contain PTPase domain(s).

The currently known PTPases are listed below: Soluble PTPases, PTPN1 (PTP-1B), PTPN2 (T-cell PTPase; TC-PTP), PTPN3 (H1) and PTPN4 (MEG), enzymes that contain an N-terminal band 4.1-like domain and could act at junctions between the membrane and cytoskeleton, PTPN5 (STEP), PTPN6 (PTP-1C; HCP; SHP) and PTPN11 (PTP-2C; SH-PTP3; Syp), enzymes which contain two copies of the SH2 domain at its N-terminal extremity (e.g., the *Drosophila* protein corkscrew (gene csw) also belongs to this subgroup), PTPN7 (LC-PTP; Hematopoietic protein-tyrosine phosphatase; HePTP), PTPN8 (70Z-PEP), PTPN9 (MEG2), PTPN12 (PTP-G1; PTP-P19), Yeast PTP1, Yeast PTP2 which may be involved in the ubiquitin-mediated protein degradation pathway, Fission yeast pyp1 and pyp2 which play a role in inhibiting the onset of mitosis, Fission yeast pyp3 which contributes to the dephosphorylation of cdc2, Yeast CDC14 which may be involved in chromosome segregation, Yersinia virulence plasmid PTPAses (gene yopH), Autographa californica nuclear polyhedrosis virus 19 Kd PTPase, Dual specificity PTPases, DUSP1 (PTPN10; MAP kinase phosphatase-1; MKP-1); which dephosphorylates MAP kinase on both Thr-183 and Tyr-185, DUSP2 (PAC-1), a nuclear enzyme that dephosphorylates MAP kinases ERK1 and ERK2 on both Thr and Tyr residues, DUSP3 (VHR), DUSP4 (HVH2), DUSP5 (HVH3), DUSP6 (Pyst1; MKP-3), DUSP7 (Pyst2; MKP-X), Yeast MSG5, a PTPase that dephosphorylates MAP kinase FUS3, Yeast YVH1, Vaccinia virus H1PTPase—a dual specificity phosphatase, Structurally, all known receptor PTPases, are made up of a variable length extracellular domain, followed by a transmembrane region and a C-terminal catalytic cytoplasmic domain. Some of the receptor PTPases contain fibronectin type III (FN-III) repeats, immunoglobulin-like domains, MAM domains or carbonic anhydrase-like domains in their extracellular region. The cytoplasmic region generally contains two copies of the PTPAse domain. The first seems to have enzymatic activity, while the second is inactive but seems to affect substrate specificity of the first. In these domains, the catalytic cysteine is generally conserved but some other, presumably important, residues are not.

PTPase domains consist of about 300 amino acids. There are two conserved cysteines, the second one has been shown to be absolutely required for activity. Furthermore, a number of conserved residues in its immediate vicinity have also been shown to be important.

A consensus sequence for tyrosine specific protein phosphatases is provided as follows:

[LIVMF]—H—C-x(2)-G-x(3)-[STC]-[STAGP]-x-[LIVMFY], wherein C is the active site residue and "X" represents any amino acid.

Additional information related to tyrosine specific protein phosphatase domains and proteins may be found in reference to the following publications Fischer E. H., Charbonneau H., Tonks N. K., Science 253:401–406(1991); Charbonneau H., Tonks N. K., Annu. Rev. Cell Biol. 8:463–493 (1992); Trowbridge I. S., J. Biol. Chem. 266:23517–23520 (1991); Tonks N. K., Charbonneau H., Trends Biochem. Sci. 14:497–500(1989); and Hunter T., Cell 58:1013–1016(1989); which are hereby incorporated herein by reference in their entirety.

In preferred embodiments, the following tyrosine specific protein phosphatase active site domain polypeptide is encompassed by the present invention: QEGKVIHCHAGLGRTGVLIAYLV (SEQ ID NO:163). Polynucleotides encoding these polypeptides are also provided. The present invention also encompasses the use of this tyrosine specific protein phosphatase active site domain polypeptide as an immunogenic and/or antigenic epitope as described elsewhere herein.

In preferred embodiments, the following N-terminal BMY_HPP1 deletion polypeptides are encompassed by the present invention: M1-L607, E2-L607, A3-L607, G4-L607, I5-L607, Y6-L607, F7-L607, Y8-L607, N9-L607, F10-L607, G11-L607, W12-L607, K13-L607, D14-L607, Y15-L607, G16-L607, V17-L607, G11-L607, S19-L607, L20-L607, T21-L607, T22-L607, I23-L607, L24-L607, D25-L607, M26-L607, V27-L607, K28-L607, V29-L607, M30-L607, T31-L607, F32-L607, A33-L607, L34-L607, Q35-L607, E36-L607, G37-L607, K38-L607, V39-L607, A40-L607, I41-L607, H42-L607, C43-L607, H44-L607, A45-L607, G46-L607, L47-L607, G48-L607, R49-L607, T50-L607, G51-L607, V52-L607, L53-L607, I54-L607, A55-L607, C56-L607, Y57-L607, L58-L607, V59-L607, F60-L607, A61-L607, T62-L607, R63-L607, M64-L607, T65-L607, A66-L607, D67-L607, Q68-L607, A69-L607, I70-L607, I71-L607, F72-L607, V73-L607, R74-L607, A75-L607, K76-L607, R77-L607, P78-L607, N79-L607, S80-L607, I81-L607, Q82-L607, T83-L607, R84-L607, G85-L607, Q86-L607, L87-L607, L88-L607, C89-L607, V90-

L607, R91-L607, E92-L607, F93-L607, T94-L607, Q95-L607, F96-L607, L97-L607, T98-L607, P99-L607, L100-L607, R101-L607, N102-L607, I103-L607, F104-L607, S105-L607, C106-L607, C107-L607, D108-L607, P109-L607, K110-L607, A111-L607, H112-L607, A113-L607, V114-L607, T115-L607, L116-L607, P117-L607, Q118-L607, Y119-L607, L120-L607, I121-L607, R122-L607, Q123-L607, R124-L607, H125-L607, L126-L607, L127-L607, H128-L607, G129-L607, Y130-L607, E131-L607, A132-L607, R133-L607, L134-L607, L135-L607, K136-L607, H137-L607, V138-L607, P139-L607, K140-L607, I141-L607, I142-L607, H143-L607, L144-L607, V145-L607, C146-L607, K147-L607, L148-L607, L149-L607, L150-L607, D151-L607, L152-L607, A153-L607, E154-L607, N155-L607, R156-L607, P157-L607, V158-L607, M159-L607, M160-L607, K161-L607, D162-L607, V163-L607, S164-L607, E165-L607, G166-L607, P167-L607, G168-L607, L169-L607, S170-L607, A171-L607, E172-L607, I173-L607, E174-L607, K175-L607, T176-L607, M177-L607, S178-L607, E179-L607, M180-L607, V181-L607, T182-L607, M183-L607, Q184-L607, L185-L607, D186-L607, K187-L607, E188-L607, L189-L607, L190-L607, R191-L607, H192-L607, D193-L607, S194-L607, D195-L607, V196-L607, S197-L607, N198-L607, P199-L607, P200-L607, N201-L607, P202-L607, T203-L607, A204-L607, V205-L607, A206-L607, A207-L607, D208-L607, F209-L607, D210-L607, N211-L607, R212-L607, G213-L607, M214-L607, I215-L607, F216-L607, S217-L607, N218-L607, E219-L607, Q220-L607, Q221-L607, F222-L607, D223-L607, P224-L607, L225-L607, W226-L607, K227-L607, R228-L607, R229-L607, N230-L607, V231-L607, E232-L607, C233-L607, L234-L607, Q235-L607, P236-L607, L237-L607, T238-L607, H239-L607, L240-L607, K241-L607, R242-L607, R243-L607, L244-L607, S245-L607, Y246-L607, S247-L607, D248-L607, S249-L607, D250-L607, L251-L607, K252-L607, R253-L607, A254-L607, E255-L607, N256-L607, L257-L607, L258-L607, E259-L607, Q260-L607, G261-L607, E262-L607, T263-L607, P264-L607, Q265-L607, T266-L607, V267-L607, P268-L607, A269-L607, Q270-L607, I271-L607, L272-L607, V273-L607, G274-L607, H275-L607, K276-L607, P277-L607, R278-L607, Q279-L607, Q280-L607, K281-L607, L282-L607, I283-L607, S284-L607, H285-L607, C286-L607, Y287-L607, I288-L607, P289-L607, Q290-L607, S291-L607, P292-L607, E293-L607, P294-L607, D295-L607, L296-L607, H297-L607, K298-L607, E299-L607, A300-L607, L301-L607, V302-L607, R303-L607, S304-L607, T305-L607, L306-L607, S307-L607, F308-L607, W309-L607, S310-L607, Q311-L607, S312-L607, K313-L607, F314-L607, G315-L607, G316-L607, L317-L607, E318-L607, G319-L607, L320-L607, K321-L607, D322-L607, N323-L607, G324-L607, S325-L607, P326-L607, I327-L607, F328-L607, H329-L607, G330-L607, R331-L607, I332-L607, I333-L607, P334-L607, K335-L607, E336-L607, A337-L607, Q338-L607, Q339-L607, S340-L607, G341-L607, A342-L607, F343-L607, S344-L607, A345-L607, D346-L607, V347-L607, S348-L607, G349-L607, S350-L607, H351-L607, S352-L607, P353-L607, G354-L607, E355-L607, P356-L607, V357-L607, S358-L607, P359-L607, S360-L607, F361-L607, A362-L607, N363-L607, V364-L607, H365-L607, K366-L607, D367-L607, P368-L607, N369-L607, P370-L607, A371-L607, H372-L607, Q373-L607, Q374-L607, V375-L607, S376-L607, H377-L607, C378-L607, Q379-L607, C380-L607, K381-L607, T382-L607, H383-L607, G384-L607, V385-L607, G386-L607, S387-L607, P388-L607, G389-L607, S390-L607, V391-L607, R392-L607, Q393-L607, N394-L607, S395-L607, R396-L607, T397-L607, P398-L607, R399-L607, S400-L607, P401-L607, L402-L607, D403-L607, C404-L607, G405-L607, S406-L607, S407-L607, P408-L607, K409-L607, A410-L607, Q411-L607, F412-L607, L413-L607, V414-L607, E415-L607, H416-L607, E417-L607, T418-L607, Q419-L607, D420-L607, S421-L607, K422-L607, D423-L607, L424-L607, S425-L607, E426-L607, A427-L607, A428-L607, S429-L607, H430-L607, S431-L607, A432-L607, L433-L607, Q434-L607, S435-L607, E436-L607, L437-L607, S438-L607, A439-L607, E440-L607, A441-L607, R442-L607, R443-L607, I444-L607, L445-L607, A446-L607, A447-L607, K448-L607, A449-L607, L450-L607, A451-L607, N452-L607, I453-L607, N454-L607, E455-L607, S456-L607, V457-L607, E458-L607, K459-L607, E460-L607, E461-L607, L462-L607, K463-L607, R464-L607, K465-L607, V466-L607, E467-L607, M468-L607, W469-L607, Q470-L607, K471-L607, E472-L607, L473-L607, N474-L607, S475-L607, R476-L607, D477-L607, G478-L607, A479-L607, W480-L607, E481-L607, R482-L607, I483-L607, C484-L607, G485-L607, E486-L607, R487-L607, D488-L607, P489-L607, F490-L607, I491-L607, L492-L607, C493-L607, S494-L607, L495-L607, M496-L607, W497-L607, S498-L607, W499-L607, V500-L607, E501-L607, Q502-L607, L503-L607, K504-L607, E505-L607, P506-L607, V507-L607, I508-L607, T509-L607, K510-L607, E511-L607, D512-L607, V513-L607, D514-L607, M515-L607, L516-L607, V517-L607, D518-L607, R519-L607, R520-L607, A521-L607, D522-L607, A523-L607, A524-L607, E525-L607, A526-L607, L527-L607, F528-L607, L529-L607, L530-L607, E531-L607, K532-L607, G533-L607, Q534-L607, H535-L607, Q536-L607, T537-L607, I538-L607, L539-L607, C540-L607, V541-L607, L542-L607, H543-L607, C544-L607, I545-L607, V546-L607, N547-L607, L548-L607, Q549-L607, T550-L607, I551-L607, P552-L607, V553-L607, D554-L607, V555-L607, E556-L607, E557-L607, A558-L607, F559-L607, L560-L607, A561-L607, H562-L607, A563-L607, I564-L607, K565-L607, A566-L607, F567-L607, T568-L607, K569-L607, V570-L607, N571-L607, F572-L607, D573-L607, S574-L607, E575-L607, N576-L607, G577-L607, P578-L607, T579-L607, V580-L607, Y581-L607, N582-L607, T583-L607, L584-L607, K585-L607, K586-L607, I587-L607, F588-L607, K589-L607, H590-L607, T591-L607, L592-L607, E593-L607, E594-L607, K595-L607, R596-L607, K597-L607, M598-L607, T599-L607, K600-L607, and/or D601-L607 of SEQ ID NO:150. Polynucleotide sequences encoding these polypeptides are also provided. The present invention also encompasses the use of these N-terminal BMY_HPP1 deletion polypeptides as immunogenic and/or antigenic epitopes as described elsewhere herein.

In preferred embodiments, the following C-terminal BMY_HPP1 deletion polypeptides are encompassed by the present invention: M1-L607, M1-G606, M1-P605, M1-K604, M1-P603, M1-G602, M1-D601, M1-K600, M1-T599, M598, M1-K597, M1-R596, M1-K595, M1-E594, M1-E593, M1-L592, M1-T591, M1-H590, M1-K589, M1-F588, M1-I587, M1-K586, M1-K585, M1-L584, M1-T583, M1-N582, M1-Y581, M1-V580, M1-T579, M1-P578, M1-G577, M1-N576, M1-E575, M1-S574, M1-D573, M1-F572, M1-N571, M1-V570, M1-K569, M1-T568, M1-F567, M1-A566, M1-K565, M1-I564, M1-A563, M1-H562, M1-A561, M1-L560, M1-F559, M1-A558, M1-E557, M1-E556, M1-V555, M1-D554, M1-V553, M1-P552, M1-I551, M1-T550, M1-Q549, M1-L548, M1-N547, M1-V546, M1I545, M1-C544, M1-H543, M1-L542, M1-V541, M1-C540, M1-L539, M1-I538, M1-T537, M1-Q536, M1-H535, M1-Q534, M1-G533, M1-K532, M1-E531, M1-L530, M1-L529, M1-F528, M1-L527, M1-A526, M1-E525, M1-A524, M1-A523, M1-D5222, M1-A521, M1-R520, M1-R519, M1-D518, M1-V517, M1-L516, M1-M515, M1-D514, M1-V513, M1-D512, M1-E511, M1-K510, M1-T509, M1-I508, M1-V507, M1-P506, M1-E505, M1-K504, M1-L503, M1-Q502, M1-E501, M1-V500, M1-W499, M1-S498, M1-W497, M1-M496, M1-L495, M1-S494, M1-C493, M1-L492, M1-I491, M1-F490, M1-P489, M1-D488, M1-R487, M1-E486, M1-G485, M1-C484, M1-I483, M1-R482, M1-E481, M1-W480, M1-A479, M1-G478, M1-D477, M1-R476, M1-S475, M1-N474, M1-L473, M1-E472, M1-K471, M1-Q470, M1-W469, M1-M468, M1-E467, M1-V466, M1-K465, M1-R464, M1-K463, M1-L462, M1-E461, M1-E460, M1-K459, M1-E458, M1-V457, M1-S456, M1-E455, M1-N454, M1-L453, M1-N452, M1-A451, M1-L450, M1-A449, M1-K448, M1-A447, M1-A446, M1-L445, M1-I444, M1-R443, M1-R442, M1-A441, M1-E440, M1-A439, M1-S438, M1-L437, M1-E436, M1-S435, M1-Q434, M1-L433, M1-A432, M1-S431, M1-H430, M1-S429, M1-A428, M1-A427, M1-E426, M1-S425, M1-L424, M1-D423, M1-K422, M1-S421, M1-D420, M1-Q419, M1-T418, M1-E417, M1-H416, M1-E415, M1-V414, M1-L413, M1-F412, M1-Q411, M1-A410, M1-K409, M1-P408, M1-S407, M1-S406, M1-G405, M1-C404, M1-D403, M1-L402, M1-P401, M1-S400, M1-R399, M1-P398, M1-T397, M1-R396, M1-S395, M1-N394, M1-Q393, M1-R392, M1-V391, M1-S390, M1-G389, M1-P388, M1-S387, M1-G386, M1-V385, M1-G384, M1-H383, M1-T382, M1-K381, M1-C380, M1-Q379, M1-C378, M1-H377, M1-S376, M1-V375, M1-Q374, M1-Q373, M1-H372, M1-A371, M1-P370, M1-N369, M1-P368, M1-D367, M1-K366, M1-H365, M1-V364, M1-N363, M1-A362, M1-F361, M1-S360, M1-P359, M1-S358, M1-V357, M1-P356, M1-E355, M1-G354, M1-P353, M1-S352, M1-H351, M1-S350, M1-G349, M1-S348, M1-V347, M1-D346, M1-A345, M1-S344, M1-F343, M1-A342, M1-G341, M1-S340, M1-Q339, M1-Q338, M1-A337, M1-E336, M1-K335, M1-P334, M1-I333, M1-I332, M1-R331, M1-G330, M1-H329, M1-F328, M1-I327, M1-P326, M1-S325, M1-G324, M1-N323, M1-D322, M1-K321, M1-L320, M1-G319, M1-E318, M1-L317, M1-G316, M1-G315, M1-F314, M1-K313, M1-S312, M1-Q311, M1-S310, M1-W309, M1-F308, M1-S307, M1-L306, M1-T305, M1-S304, M1-R303, M1-V302, M1-L301, M1-A300, M1-E299, M1-K298, M1-H297, M1-L296, M1-D295, M1-P294, M1-E293, M1-P292, M1-S291, M1-Q290, M1-P289, M1-I288, M1-Y287, M1-C286, M1-H285, M1-S284, M1-I283, M1-L282, M1-K281, M1-Q280, M1-Q279, M1-R278, M1-P277, M1-K276, M1-H275, M1-G274, M1-V273, M1-L272, M1-I271, M1-Q270, M1-A269, M1-P268, M1-V267, M1-T266, M1-Q265, M1-P264, M1-T263, M1-E262, M1-G261, M1-Q260, M1-E259, M1-L258, M1-L257, M1-N256, M1-E255, M1-A254, M1-R253, M1-K252, M1-L251, M1-D250, M1-S249, M1-D248, M1-S247, M1-Y246, M1-S245, M1-L244, M1-R243, M1-R242, M1-K241, M1-L240, M1-H239, M1-T238, M1-L237, M1-P236, M1-Q235, M1-L234, M1-C233, M1-E232, M1-V231, M1-N230, M1-R229, M1-R228, M1-K227, M1-W226, M1-I225, M1-P224, M1-D223, M1-F222, M1-Q221, M1-Q220, M1-E219, M1-N218, M1-S217, M1-F216, M1-I215, M1-M214, M1-G213, M1-R212, M1-N211, M1-D210, M1-F209, M1-D208, M1-A207, M1-A206, M1-V205, M1-A204, M1-T203, M1-P202, M1-N201, M1-P200, M1-P199, M1-N198, M1-S197, M1-V196, M1-D195, M1-S194, M1-D193, M1-H192, M1-R191, M1-L190, M1-L189, M1-E188, M1-K187, M1-D186, M1-L185, M1-Q184, M1-M183, M1-T182, M1-V181, M1-M180, M1-E179, M1-S178, M1-M177, M1-T176, M1-K175, M1-E174, M1-I173, M1-E172, M1-A171, M1-S170, M1-L169, M1-G168, M1-P167, M1-G166, M1-E165, M1-S164, M1-V163, M1-D162, M1-K161, M1-M160, M1-M159, M1-V158, M1-P157, M1-R156, M1-N155, M1-E154, M1-A153, M1-L152, M1-D151, M1-L150, M1-L149, M1-L148, M1-K147, M1-C146, M1-V145, M1-L144, M1-H143, M1-I142, M1-I141, M1-K140, M1-P139, M1-V138, M1-H137, M1-K136, M1-L135, M1-L134, M1-R133, M1-A132, M1-E131, M1-Y130, M1-G129, M1-H128, M1-L127, M1-L126, M1-H125, M1-R124, M1-Q123, M1-R122, M1-I121, M1-L120, M1-Y119, M1-Q118, M1-P117, M1-L116, M1-T115, M1-V114, M1-A113, M1-H112, M1-A111, M1-K110, M1-P109, M1-D108, M1-C107, M1-C106, M1-S105, M1-F104, M1-I103, M1-N102, M1-R101, M1-L100, M1-P99, M1-T98, M1-L97, M1-F96, M1-Q95, M1-T94, M1-F93, M1-E92, M1-R91, M1-V90, M1-C89, M1-L88, M1-L87, M1-Q86, M1-G85, M1-R84, M1-T83, M1-Q82, M1-I81, M1-S80, M1-N79, M1-P78, M1-R77, M1-K76, M1-A75, M1-R74, M1-V73, M1-F72, M1-F72, M1-I71, M1-I70, M1-A69, M1-Q68, M1-D67, M1-A66, M1-T65, M1-M64, M1-R63, M1-T62, M1-A61, M1-F60, M1-V59, M1-L58, M1-Y57, M1-C56, M1-A55, M1-I54, M1-L53, M1-V52, M1-G51, M1-T50, M1-R49, M1-G48, M1-L47, M1-G46, M1-A45, M1-H44, M1-C43, M1-H42, M1-I41, M1-A40, M1V39, M1-K38, M1-G37, M1-E36, M1-Q35, M1-L34, M1-A33, M1-F32, M1-T31, M1-M30, M1-V29, M1-K28, M1-V27, M1-M26, M1-D25, M1-L24, M1-I23, M11-T22, M1-T21, M1-L20, M1-S19, M1-A18, M1-V17, M1-G16, M1-Y15, M1-D14, M1-K13, M1-W12, M1-G11, M1-F10, M1-N9, M1-Y8, and/or M1-F7 of SEQ ID NO:150. Polynucleotide sequences encoding these polypeptides are also provided. The present invention also encompasses the use of these C-terminal BMY_HPP1 deletion polypeptides as immunogenic and/or antigenic epitopes as described elsewhere herein.

In preferred embodiments, the following polypeptide is encompassed by the present invention: MEAGIYFNFG-WKDYGVASLTTIDMVKVMTFALQEGKVI-HCHAGLGRTGVLI AYLVFATRMTADQAIIVRAKRPN-SIQTRGQLCVREFTQFLTPLRNISCCDPKA HAVTLPQYIRQRHLLHGYEARLLHVPKI-IHLVCKLLLDAENRPVMMKDVSEG PLSAEIEKTM-SEMVTMLDKELLRHDSDVSNP-NPTAVAADFDNRGMISNEQQF DPLWKRRNVCLQPLTHLKRRLSYSS-DLKRAENLLEQGETQTVPAQILVGHKP RQKLISHCY-IPQSPEPDHKEALVRSTLSFWSQKFG-GLEGLKDNGSPIHGRIIPKE AQQSGAFADVSGSHSPGEPVSPFANVH-KDPNPAHQQVHCQCKTHGVGSPGS VQNSRT-PRSPLDCGSSKAQFLVEHETQDSKD-SEAASHSALQSELSAARRILAA KALANLNEVEKEELKRKVEMWQKLNSRD-GAWERICGERPFILCSLMWSWVE (SEQ ID NO:153). Polynucleotides encoding these polypeptides are also provided. The present invention also encompasses the use of this polypeptide as an immunogenic and/or antigenic epitope as described elsewhere herein.

In preferred embodiments, the following BMY_HPP1 phosphatase active site domain amino acid substitutions are encompassed by the present invention: wherein M1 is substituted with either an A, C, D, E, F, G, H, I, K, L, N, P, Q, R, S, T, V, W, or Y; wherein E2 is substituted with either an A, C, D, F, G, H, I, K, L, M, N, P, Q, R, S, T, V, W, or Y; wherein A3 is substituted with either a C, D, E, F, G, H, I, K, L, M, N, P, Q, R, S, T, V, W, or Y; wherein G4 is substituted with either an A, C, D, E, F, H, I, K, L, M, N, P, Q, R, S, T, V, W, or Y; wherein I5 is substituted with either an A, C, D, E, F, G, H, K, L, M, N, P, Q, R, S, T, V, W, or Y; wherein Y6 is substituted with either an A, C, D, E, F, G, H, I, K, L, M, N, P, Q, R, S, T, V, or W; wherein F7 is substituted with either an A, C, D, E, G, H, I, K, L, M, N, P, Q, R, S, T, V, W, or Y; wherein N8 is substituted with either an A, C, D, E, F, G, H, I, K, L, M, P, Q, R, S, T, V, W, or Y; wherein F9 is substituted with either an A, C, D, E, G, H, I, K, L, M, N, P, Q, R, S, T, V, W, or Y; wherein G10 is substituted with either an A, C, D, E, F, H, I, K, L, M, N, P, Q, R, S, T, V, W, or Y; wherein W 11 is substituted with either an A, C, D, E, F, G, H, I, K, L, M, N, P, Q, R, S, T, V, or Y; wherein K12 is substituted with either an A, C, D, E, F, G, H, I, L, M, N, P, Q, R, S, T, V, W, or Y; wherein D13 is substituted with either an A, C, E, F, G, H, I, K, L, M, N, P, Q, R, S, T, V, W, or Y; wherein Y14 is substituted with either an A, C, D, E, F, G, H, I, K, L, M, N, P, Q, R, S, T, V, or W; wherein G15 is substituted with either an A, C, D, E, F, H, I, K, L, M, N, P, Q, R, S, T, V, W, or Y; wherein V16 is substituted with either an A, C, D, E, F, G, H, I, K, L, M, N, P, Q, R, S, T, W, or Y; wherein A17 is substituted with either a C, D, E, F, G, H, I, K, L, M, N, P, Q, R, S, T, V, W, or Y; wherein S18 is substituted with either an A, C, D, E, F, G, H, I, K, L, M, N, P, Q, R, T, V, W, or Y; wherein L19 is substituted with either an A, C, D, E, F, G, H, I, K, M, N, P, Q, R, S, T, V, W, or Y; wherein T20 is substituted with either an A, C, D, E, F, G, H, I, K, L, M, N, P, Q, R, S, V, W, or Y; wherein T21 is substituted with either an A, C, D, E, F, G, H, I, K, L, M, N, P, Q, R, S, V, W, or Y; wherein I22 is substituted with either an A, C, D, E, F, G, H, K, L, M, N, P, Q, R, S, T, V, W, or Y; wherein D23 is substituted with either an A, C, E, F, G, H, I, K, L, M, N, P, Q, R, S, T, V, W, or Y; wherein M24 is substituted with either an A, C, D, E, F, G, H, I, K, L, N, P, Q, R, S, T, V, W, or Y; wherein V25 is substituted with either an A, C, D, E, F, G, H, I, K, L, M, N, P, Q, R, S, T, W, or Y; wherein K26 is substituted with either an A, C, D, E, F, G, H, I, L, M, N, P, Q, R, S, T, V, W, or Y; wherein V27 is substituted with either an A, C, D, E, F, G, H, I, K, L, M, N, P, Q, R, S, T, W, or Y; wherein M28 is substituted with either an A, C, D, E, F, G, H, I, K, L, N, P, Q, R, S, T, V, W, or Y; wherein T29 is substituted with either an A, C, D, E, F, G, H, I, K, L, M, N, P, Q, R, S, V, W, or Y; wherein F30 is substituted with either an A, C, D, E, G, H, I, K, L, M, N, P, Q, R, S, T, V, W, or Y; wherein A31 is substituted with either a C, D, E, F, G, H, I, K, L, M, N, P, Q, R, S, T, V, W, or Y; wherein L32 is substituted with either an A, C, D, E, F, G, H, I, K, M, N, P, Q, R, S, T, V, W, or Y; wherein Q33 is substituted with either an A, C, D, E, F, G, H, I, K, L, M, N, P, R, S, T, V, W, or Y; wherein E34 is substituted with either an A, C, D, F, G, H, I, K, L, M, N, P, Q, R, S, T, V, W, or Y; wherein G35 is substituted with either an A, C, D, E, F, H, I, K, L, M, N, P, Q, R, S, T, V, W, or Y; wherein K36 is substituted with either an A, C, D, E, F, G, H, I, L, M, N, P, Q, R, S, T, V, W, or Y; wherein V37 is substituted with either an A, C, D, E, F, G, H, I, K, L, M, N, P, Q, R, S, T, W, or Y; wherein I38 is substituted with either an A, C, D, E, F, G, H, K, L, M, N, P, Q, R, S, T, V, W, or Y; wherein H39 is substituted with either an A, C, D, E, F, G, I, K, L, M, N, P, Q, R, S, T, V, W, or Y; wherein C40 is substituted with either an A, D, E, F, G, H, I, K, L, M, N, P, Q, R, S, T, V, W, or Y; wherein H41 is substituted with either an A, C, D, E, F, G, I, K, L, M, N, P, Q, R, S, T, V, W, or Y; wherein A42 is substituted with either a C, D, E, F, G, H, I, K, L, M, N, P, Q, R, S, T, V, W, or Y; wherein G43 is substituted with either an A, C, D, E, F, H, I, K, L, M, N, P, Q, R, S, T, V, W, or Y; wherein L44 is substituted with either an, A, C, D, E, F, G, H, I, K, M, N, P, Q, R, S, T, V, W, or Y; wherein G45 is substituted with either an A, C, D, E, F, H, I, K, L, M, N, P, Q, R, S, T, V, W, or Y; wherein R46 is substituted with either an A, C, D, E, F, G, H, I, K, L, M, N, P, Q, S, T, V, W, or Y; wherein T47 is substituted with either an A, C, D, E, F, G, H, I, K, L, M, N, P, Q, R, S, V, W, or Y; wherein G48 is substituted with either an A, C, D, E, F, H, I, K, L, M, N, P, Q, R, S, T, V, W, or Y; wherein V49 is substituted with either an A, C, D, E, F, G, H, I, K, L, M, N, P, Q, R, S, T, W, or Y; wherein L50 is substituted with either an A, C, D, E, F, G, H, I, K, M, N, P, Q, R, S, T, V, W, or Y; wherein I51 is substituted with either an A, C, D, E, F, G, H, K, L, M, N, P, Q, R, S, T, V, W, or Y; wherein A52 is substituted with either a C, D, E, F, G, H, I, K, L, M, N, P, Q, R, S, T, V, W, or Y; wherein Y53 is substituted with either an A, C, D, E, F, G, H, I, K, L, M, N, P, Q, R, S, T, V, or W; wherein L54 is substituted with either an A, C, D, E, F, G, H, I, K, M, N, P, Q, R, S, T, V, W, or Y; wherein V55 is substituted with either an A, C, D, E, F, G, H, I, K, L, M, N, P, Q, R, S, T, W, or Y; wherein F56 is substituted with either an A, C, D, E, G, H, I, K, L, M, N, P, Q, R, S, T, V, W, or Y; and/or wherein A57 is substituted with either a C, D, E, F, G, H, I, K, L, M, N, P, Q, R, S, T, V, W, or Y of SEQ ID NO:150, in addition to any combination thereof. The present invention also encompasses the use of these BMY_HPP1 phosphatase active site domain amino acid substituted polypeptides as immunogenic and/or antigenic epitopes as described elsewhere herein.

In preferred embodiments, the following BMY_HPP1 phosphatase active site domain conservative amino acid substitutions are encompassed by the present invention: wherein M1 is substituted with either an A, G, S, or T; wherein E2 is substituted with a D; wherein A3 is substituted with either a G, I, L, M, S, T, or V; wherein G4 is substituted with either an A, M, S, or T; wherein I5 is substituted with either an A, V, or L; wherein Y6 is either an F, or W; wherein F7 is substituted with either a W, or Y; wherein N8 is substituted with a Q; wherein F9 is substituted with either a W, or Y; wherein G10 is substituted with either an A, M, S, or T; wherein W11 is either an F, or Y; wherein K12 is substituted with either a R, or H; wherein D13 is substituted with an E; wherein Y14 is either an F, or W; wherein G15 is substituted with either an A, M, S, or T; wherein V16 is substituted with either an A, I, or L; wherein A17 is substituted with either a G, I, L, M, S, T, or V; wherein S18 is substituted with either an A, G, M, or T; wherein L19 is substituted with either an A, I, or V; wherein T20 is substituted with either an A, G, M, or S; wherein T21 is substituted with either an A, G, M, or S; wherein I22 is substituted with either an A, V, or L; wherein D23 is substituted with an E; wherein M24 is substituted with either an A, G, S, or T; wherein V25 is substituted with either an A, I, or L; wherein K26 is substituted with either a R, or H; wherein V27 is substituted with either an A, I, or L; wherein M28 is substituted with either an A, G, S, or T; wherein T29 is substituted with either an A, G, M, or S; wherein F30 is substituted with either a W, or Y; wherein A31 is substituted with either a G, I, L, M, S, T, or V; wherein L32 is substituted with either an A, I, or V; wherein Q33 is substituted with a N; wherein E34 is substituted with a D; wherein G35 is substituted with either an A, M, S, or T; wherein K36 is substituted with either a R, or H; wherein V37 is substituted with either an A, I, or L; wherein I38 is substituted with either an A, V, or L; wherein H39 is substituted with either a K, or R; wherein C40 is a C; wherein H41 is substituted with either a K, or R; wherein A42 is substituted with either a G, I, L, M, S, T, or V; wherein G43 is substituted with either an A, M, S, or T; wherein L44 is substituted with either an A, I, or V; wherein G45 is substituted with either an A, M, S, or T; wherein R46 is substituted with either a K, or H; wherein T47 is substituted with either an A, G, M, or S; wherein G48 is substituted with either an A, M, S, or T; wherein V49 is substituted with either an A, I, or L; wherein L50 is substituted with either an A, I, or V; wherein I51 is substituted with either an A, V, or L; wherein A52 is substituted with either a G, I, L, M, S, T, or V; wherein Y53 is either an F, or W; wherein L54 is substituted with either an A, I, or V; wherein V55 is substituted with either an A, I, or L; wherein F56 is substituted with either a W, or Y; and/or wherein A57 is substituted with either a G, I, L, M, S, T, or V of SEQ ID NO:150 in addition to any combination thereof. Other suitable substitutions within the BMY_HPP1 phosphatase active site domain are encompassed by the present invention and are referenced elsewhere herein. The present invention also encompasses the use of these BMY_HPP1 phosphatase active site domain conservative amino acid substituted polypeptides as immunogenic and/or antigenic epitopes as described elsewhere herein.

In addition, the present invention also encompasses BMY_HPP1 polypeptides resulting from alternative initiating start codon positions of the BMY_HPP1 polynucleotide (SEQ ID NO:149).

In preferred embodiments, the following polypeptide resulting from the start codon beginning at nucleotide 31 of SEQ ID NO:149 is encompassed by the present invention:

```
MQVQDATRRPSAVRFLSSFLQGRRHSTSDPVLRLQQARRGSGLGSGSATKLLSSSSLQVMVAV    (SEQ ID NO: 175)

SSVSHAEGNPTFPERKRNLERPTPKYTKVGERLRHVIPGHMACSMACGGRACKYENPARWSE

QEQAIKGVYSSWVTDNILAMARPSSELLEKYHIIDQFLSHGIKTIINLQRPGEHASCGNPLEQES

GFTYLPEAFMEAGIYFYNFGWKDYGVASLTTILDMVKVMTFALQEGKVAIHCHAGLGRTGVL

IACYLVFATRMTADQAIIFVRAKRPNSIQTRGQLLCVREFTQFLTPLRNIFSCCDPKAHAVTLPQ

YLIRQRHLLHGYEARLLKHVPKIIHLVCKLLLDLAENRPVMMKDVSEGPGLSAEIEKTMSEMV

TMQLDKELLRHDSDVSNPPNPTAVAADFDNRGMIFSNEQQFDPLWKRRNVECLQPLTHLKRR

LSYSDSDLKRAENLLEQGETPQTVPAQILVGHKPRQQKLISHCYIPQSPEPDLHKEALVRSTLSF

WSQSKFGGLEGLKDNGSPIFHGRIIPKEAQQSGAFSADVSGSHSPGEPVSPSFANVHKDPNAH

QQVSHCQCKTHGVGSPGSVRQNSRTPRSPLDCGSSPKAQFLVEHETQDSKDLSEAASHSALQS

ELSAEARRILAAKALANLNESVEKEELKRKVEMWQKELNSRDGAWERICGERDPFILCSLMW

SWVEQLKEPVITKEDVDMLVDRRADAAEALFLLEKGQHQTILCVLHCIVNLQTIPVDVEEAFL

AHAIKAFTKVNFDSENGPTVYNTLKKIFKHTLEEKRKMTKDGPKPGL.
```

Polynucleotides encoding these polypeptides are also provided. The present invention also encompasses the use of this polypeptide as an immunogenic and/or antigenic epitope as described elsewhere herein.

In preferred embodiments, the following polypeptide resulting from the start codon beginning at nucleotide 208 of SEQ ID NO:149 is encompassed by the present invention:

MVAVSSVSHAEGNPTFPERKRNLERPTPKYTKVGERLRHVIPGHMACSMACG GRACKYENPARWSEQEQAIKGVYSSWVTDNILAMARPSSELLEKYHIIDQFLS HGIKTIINLQRPGEHASCGNPLEQESGFTYLPEAFMEAGIYFYNFGWKDYGVA SLTTILDMVKVMTFALQEGKVAIHCHAGLGRTGVLIACYLVFATRMTADQAI IFVRAKRPNSIQTRGQLLCVREFTQFLTPLRNIFSCCDPKAHAVTLPQYLIRQR HLLHGYEARLLKHVPKIIHLVCKLLLDLAENRPVMMKDVSEGPGLSAEIEKT MSEMVTMQLDKELLRHDSDVSNPPNPTAVAADFDNRGMIFSNEQQFDPLWK RRNVECLQPLTHLKRRLSYSDSDLKRAENLLEQGETPQTVPAQILVGHKPRQ QKLISHCYIPQSPEPDLHKEALVRSTLSFWSQSKFGGLEGLKDNGSPIFHGRIIP KEAQQSGAFSADVSGSHSPGEPVSPSFANVHKDPNPAHQQVSHCQCKTHGVG SPGSVRQNSRTPRSPLDCGSSPKAQFLVEHETQDSKDLSEAASHSALQSELSAE ARRILAAKALANLNESVEKEELKRKVEMWQKELNSRDGAWERICGERDPFIL CSLMWSWVEQLKEPVITKEDVDMLVDRRADAAEALFLLEKGQHQTILCVLH CIVNLQTIPVDVEEAFLAHAIKAFTKVNFDSENGPTVYNTLKKIFKHTLEEKRK MTKDGPKPGL (SEQ ID NO:176). Polynucleotides encoding these polypeptides are also provided. The present invention also encompasses the use of this polypeptide as an immunogenic and/or antigenic epitope as described elsewhere herein.

In preferred embodiments, the following polypeptide resulting from the start codon beginning at nucleotide 352 of SEQ ID NO:149 is encompassed by the present invention:

MACGGRACKYENPARWSEQEQAIKGVYSSWVTDNILAMARPSSELLEKYHII DQFLSHGIKTIINLQRPGEHASCGNPLEQESGFTYLPEAFMEAGIYFYNFGWK DYGVASLTTILDMVKVMTFALQEGKVAIHCHAGLGRTGVLIACYLVFATRM TADQAIIFVRAKRPN-

SIQTRGQLLCVREFTQFLTPLRNIFSC-
CDPKAHAVTLPQ YLIRQRHLLHGYEARLLKHVPKI-
IHLVCKLLLDLAENRPVMMKDVSEGPGLS
AEIEKTMSEMVTMQLDKELLRHDSDVSN-
PPNPTAVAADFDNRGMIFSNEQQF DPLWKRRNVE-
CLQPLTHLKRRLSYSDSDLKRAEN-
LLEQGETPQTVPAQILVG
HKPRQQKLISHCYIPQSPEPDLH-
KEALVRSTLSFWSQSKFGGLEGLKDNGSPIF HGRIIP-
KEAQQSGAFSADVSGSHSPGEPVSPS-
FANVHKDPNPAHQQVSHCQCK
THGVGSPGSVRQNSRTPRSPLDCGSSP-
KAQFLVEHETQDSKDLSEAASHSALQ SELSAEARRI-
LAAKALANLNESVEKEELKRKVEM-
WQKELNSRDGAWERICGE
RDPFILCSLMWSWVEQLKEPVITKEDVD-
MLVDRRADAAEALFLLEKGQHQTI LCVLHCIVN-
LQTIPVDVEEAFLAHAIKAFTKVNFD-
SENGPTVYNTLKKIFKHTL EEKRKMTKDGPKPGL
(SEQ ID NO:177). Polynucleotides encoding these polypeptides are also provided. The present invention also encompasses the use of this polypeptide as an immunogenic and/or antigenic epitope as described elsewhere herein.

In preferred embodiments, the following polypeptide resulting from the start codon beginning at nucleotide 463 of SEQ ID NO:149 is encompassed by the present invention:

MARPSSELLEKYHIIDQFLSHGIKTIIN-
LQRPGEHASCGNPLEQESGFTYLPEAF MEAGIYFYN-
FGWKDYGVASLTTILDMVKVMT-
FALQEGKVAIHCHAGLGRTG
VLIACYLVFATRMTADQAIIFVRAKRPN-
SIQTRGQLLCVREFTQFLTPLRNIFSC CDPKA-
HAVTLPQYLIRQRHLLHGYEARLLKHVP-
KIIHLVCKLLLDLAENRPV
MMKDVSEGPGLSAEIEKTMSEMVTMQLD-
KELLRHDSDVSNPPNPTAVAADF DNRGMIFS-
NEQQFDPLWKRRNVECLQPLTHLKRRL-
SYSDSDLKRAENLLEQG
ETPQTVPAQILVGHKPRQQKLISHCY-
IPQSPEPDLHKEALVRSTLSFWSQSKFG GLEGLKD-
NGSPIFHGRIIPKEAQQSGAFSADVSG-
SHSPGEPVSPSFANVHKDPN
PAHQQVSHCQCKTHGVGSPGSVRQNSRT-
PRSPLDCGSSPKAQFLVEHETQDS KDLSEAASH-
SALQSELSAEARRILAAKALANLNESVE-
KEELKRKVEMWQKEL
NSRDGAWERICGERDPFILCSLM-
WSWVEQLKEPVITKEDVDMLVDRRADAA
EALFLLEKGQHQTILCVLHCIVN-
LQTIPVDVEEAFLAHAIKAFTKVNFDSENGP TVYN-
TLKKIFKHTLEEKRKMTKDGPKPGL (SEQ ID
NO:178). Polynucleotides encoding these polypeptides are also provided. The present invention also encompasses the use of this polypeptide as an immunogenic and/or antigenic epitope as described elsewhere herein.

In preferred embodiments, the present invention encompasses a polynucleotide lacking the initiating start codon, in addition to, the resulting encoded polypeptide of BMY_HPP1. Specifically, the present invention encompasses the polynucleotide corresponding to nucleotides 631 thru 2448 of SEQ ID NO:149, and the polypeptide corresponding to amino acids 2 thru 607 of SEQ ID NO:150. Also encompassed are recombinant vectors comprising said encoding sequence, and host cells comprising said vector.

The present invention also provides a three-dimensional homology model of the BMY_HPP1 polypeptide (see FIG. 28) representing amino acids M1 to E301 of BMY_HPP1 (SEQ ID NO:150). A three-dimensional homology model can be constructed on the basis of the known structure of a homologous protein (Greer et al, 1991, Lesk, et al, 1992, Cardozo, et al, 1995, Yuan, et al, 1995). The homology model of the BMY_HPP1 polypeptide, corresponding to amino acid residues M1 to E301 of SEQ ID NO:150, was based upon the homologous structure of 1aax, a Human Protein Tyrosine Phosphatase Complex (residues D 11-N321; Protein Data Bank, PDB entry 1aax chain A; Genbank Accession No. gi|2981942; SEQ ID NO:206) and is defined by the set of structural coordinates set forth in Table VIII herein.

Homology models are useful when there is no experimental information available on the protein of interest. A 3-dimensional model can be constructed on the basis of the known structure of a homologous protein (Greer et. al., 1991, Lesk, et. al., 1992, Cardozo, et. al., 1995, Sali, et. al., 1995).

Those of skill in the art will understand that a homology model is constructed on the basis of first identifying a template, or, protein of known structure which is similar to the protein without known structure. This can be accomplished through pairwise alignment of sequences using such programs as FASTA (Pearson, et. al. 1990) and BLAST (Altschul, et. al., 1990). In cases where sequence similarity is high (greater than 30%), these pairwise comparison methods may be adequate. Likewise, multiple sequence alignments or profile-based methods can be used to align a query sequence to an alignment of multiple (structurally and biochemically) related proteins. When the sequence similarity is low, more advanced techniques are used such as fold recognition (protein threading; Hendlich, et. al., 1990), where the compatibility of a particular sequence with the 3-dimensional fold of a potential template protein is gauged on the basis of a knowledge-based potential. Following the initial sequence alignment, the query template can be optimally aligned by manual manipulation or by incorporation of other features (motifs, secondary structure predictions, and allowed sequence conservation). Next, structurally conserved regions can be identified and are used to construct the core secondary structure (Sali, et. al., 1995) elements in the three dimensional model. Variable regions, called "unconserved regions" and loops can be added using knowledge-based techniques. The complete model with variable regions and loops can be refined performing forcefield calculations (Sali, et. al., 1995, Cardozo, et. al., 1995).

Protein threading and molecular modeling of BMY_HPP1 suggested that a portion of BMY_HPP1 (residues M1 to E301) had a three dimensional fold similar to that of 1aax, a Human Protein Tyrosine Phosphatase Complex (residues D11-N321; Protein Data Bank, PDB entry 1 aax chain A; Genbank Accession No. gi|2981942; SEQ ID NO:206). Based on sequence, structure and known phosphatase signature sequences, BMY_HPP1 is a novel tyrosine specific phosphatase.

For BMY_HPP1, the pairwise alignment method FASTA (Pearson, et. al. 1990) and fold recognition methods (protein threading) generated identical sequence alignments for a portion (residues M1 to E301) of BMY_HPP1 aligned with the sequence of 1aax a tyrosine specific phosphatase (residues D11-N321; Protein Data Bank, PDB entry 1aax chain A; Genbank Accession No. gi|2981942; SEQ ID NO:206). The alignment of BMY_HPP1 with PDB entry 1aax is set forth in FIG. 27. In this invention, the homology model of BMY_HPP1 was derived from the sequence alignment set forth in FIG. 27 (residues D11-N321 of SEQ ID NO:206).

An overall atomic model including plausible sidechain orientations was generated using the program LOOK (Levitt 1992). The three dimensional model for BMY_HPP1 is defined by the set of structure coordinates as set forth in Table VIII and is shown in FIG. 28 rendered by backbone secondary structures.

In order to recognize errors in three-dimensional structure, knowledge based mean fields can be used to judge the quality of protein folds (Sippl 1993). The methods can be used to recognize misfolded structures as well as faulty parts of structural models. The technique generates an energy graph where the energy distribution for a given protein fold is displayed on the y-axis and residue position in the protein fold is displayed on the x-axis. The knowledge based mean fields compose a force field derived from a set of globular protein structures taken as a subset from the Protein Data Bank (Bernstein et. al. 1977). To analyze the quality of a model the energy distribution is plotted and compared to the energy distribution of the template from which the model was generated. FIG. 29 shows the energy graph for the BMY_HPP1 model (dotted line) and, the template (1aax, a tyrosine specific phosphatase) from which the model was generated. It is clear that the model has slightly higher energies in the C-terminal region while the N-terminal region appears to be "native-like". This graph supports the motif and sequence alignments in confirming that the three dimensional structure coordinates of BMY_HPP1 are an accurate and useful representation for the polypeptide.

The term "structure coordinates" refers to Cartesian coordinates generated from the building of a homology model. Those of skill in the art will understand that a set of structure coordinates for a protein is a relative set of points that define a shape in three dimensions. Thus, it is possible that an entirely different set of coordinates could define a similar or identical shape. Moreover, slight variations in the individual coordinates, as emanate from generation of similar homology models using different alignment templates (i.e., other than the structure coordinates of 1 aax), and/or using different methods in generating the homology model, will have minor effects on the overall shape. Variations in coordinates may also be generated because of mathematical manipulations of the structure coordinates. For example, the structure coordinates set forth in Table III and shown in FIG. 28 could be manipulated by fractionalization of the structure coordinates; integer additions or subtractions to sets of the structure coordinates, inversion of the structure coordinates or any combination of the above.

Various computational analyses are therefore necessary to determine whether a molecule or a portion thereof is sufficiently similar to all or parts of BMY_HPP1 described above as to be considered the same. Such analyses may be carried out in current software applications, such as INSIGHTII (Accelrys Inc., San Diego, Calif.) version 2000 as described in the User's Guide, or software applications available in the SYBYL software suite (Tripos Inc., St. Louis, Mo.).

Using the superimposition tool in the program INSIGHTII comparisons can be made between different structures and different conformations of the same structure. The procedure used in INSIGHTII to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. Since atom equivalency within INSIGHTII is defined by user input, for the purpose of this invention we will define equivalent atoms as protein backbone atoms (N, Cα, C and O) for all conserved residues between the two structures being compared. We will also consider only rigid fitting operations. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by INSIGHTII. For the purpose of this invention, any homology model of a BMY_HPP1 that has a root mean square deviation of conserved residue backbone atoms (N, Cα, C, O) of less than 3.0 A when superimposed on the relevant backbone atoms described by structure coordinates listed in Table VIII and shown in FIG. 28 are considered identical. More preferably, the root mean square deviation is less than 2.0 Å.

This invention as embodied by the homology model enables the structure-based design of modulators of the biological function of BMY_HPP1, as well as mutants with altered biological function and/or specificity.

There is 18% sequence identity between catalytic domain of BMY_HPP1 and the Human Protein Tyrosine Phosphatase 1B (PTP1B; PDB code 1 aax) as determined using the GAP program within GCG (Genetics Computing Group, Wisconsin). The structure was used as the template to generate the three dimensional model for BMY_HPP1. For BMY_HPP1, the functionally important residues are located in a cleft near the site that in other phosphatases is shown to be the active site. The active site residues are defined by: H189-C190-G193-R196 and D 161 as well as Y162. All these residues are conserved in PTP1B (denoted by the "*" in FIG. 27) and other known phosphatases. In the 1 aax polypeptide, the Cysteine was mutated to a Serine to facilitate structural analysis (Jia, Z., et al., 1995). These active site residues play critical roles in the mechanism of catalysis and substrate specificity and binding.

In a preferred embodiment of the present invention, the molecule comprises the active site region defined by structure coordinates of BMY_HPP1 amino acids described above according to Table VIII, or a mutant of said molecule. The active site is defined by residues H189-C190-G193-R196 and D 161 as well as Y162 of SEQ ID NO:150. Based on the sequence alignment disclosed in FIG. 27 and the structural model disclosed in Table VIII and visualized in FIG. 28, D161 is identified as a general acid, Y162 as a key determinant of substrate specificity which interacts with the phosphotyrosine substrate, C190 as the catalytic Cysteine nucleophile which cleaves the phosphodiester bond, and R196 as the essential Argenine which activates the bond for cleavage as described in the literature (reviewed by Fauman and .Saper, 1996).

More preferred are molecules comprising all or any part of the active site region or a mutant or homologue of said molecule or molecular complex. By mutant or homologue of the molecule it is meant a molecule that has a root mean square deviation from the backbone atoms of said BMY_HPP1 amino acids of not more than 3.5 Angstroms.

More preferred are molecules comprising all or any part of the active site region defined as residues above or a mutant or homologue of said molecule or molecular complex. By mutant or homologue of the molecule it is meant a molecule that has a root mean square deviation from the backbone atoms of said residues in the active site region of said BMY_HPP1 of not more than 3.5 Angstroms.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the relevant portion of the backbone of BMY_HPP1 as defined by the structure coordinates described herein.

The structure coordinates of a BMY_HPP1 homology model portion thereof are stored in a machine-readable storage medium. Such data may be used for a variety of purposes, such as drug discovery and target prioritization and validation.

Accordingly, in one embodiment of this invention is provided a machine-readable data storage medium comprising a data storage material encoded with the structure coordinates set forth in Table VIII and visualized in FIG. 28.

One embodiment utilizes System 10 as disclosed in WO 98/11134, the disclosure of which is incorporated herein by reference in its entirety. Briefly, one version of these embodiments comprises a computer comprising a central processing unit ("CPU"), a working memory which may be, e.g., RAM (random-access memory) or "core" memory, mass storage memory (such as one or more disk drives or CD-ROM drives), one or more cathode-ray tube ("CRT") display terminals, one or more keyboards, one or more input lines, and one or more output lines, all of which are interconnected by a conventional bidirectional system bus.

Input hardware, coupled to the computer by input lines, may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, keyboard may also be used as an input device.

Output hardware, coupled to the computer by output lines, may similarly be implemented by conventional devices. By way of example, output hardware may include a CRT display terminal for displaying a graphical representation of a region or domain of the present invention using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage, and accesses to and from the working memory, and determines the sequence of data processing steps. A number of programs may be used to process the machine-readable data of this invention. Such programs are discussed in reference to the computational methods of drug discovery as described herein. Specific references to components of the hardware system are included as appropriate throughout the following description of the data storage medium.

For the purpose of the present invention, any magnetic data storage medium which can be encoded with machine-readable data would be sufficient for carrying out the storage requirements of the system. The medium could be a conventional floppy diskette or hard disk, having a suitable substrate, which may be conventional, and a suitable coating, which may be conventional, on one or both sides, containing magnetic domains whose polarity or orientation could be altered magnetically, for example. The medium may also have an opening for receiving the spindle of a disk drive or other data storage device.

The magnetic domains of the coating of a medium may be polarized or oriented so as to encode in a manner which may be conventional, machine readable data such as that described herein, for execution by a system such as the system described herein.

Another example of a suitable storage medium which could also be encoded with such machine-readable data, or set of instructions, which could be carried out by a system such as the system described herein, could be an optically-readable data storage medium. The medium could be a conventional compact disk read only memory (CD-ROM) or a rewritable medium such as a magneto-optical disk which is optically readable and magneto-optically writable. The medium preferably has a suitable substrate, which may be conventional, and a suitable coating, which may be conventional, usually of one side of substrate.

In the case of a CD-ROM, as is well known, the coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Thus, in accordance with the present invention, data capable of displaying the three dimensional structure of the BMY_HPP1 homology model, or portions thereof and their structurally similar homologues is stored in a machine-readable storage medium, which is capable of displaying a graphical three-dimensional representation of the structure. Such data may be used for a variety of purposes, such as drug discovery.

For the first time, the present invention permits the use, through homology modeling based upon the sequence of BMY_HPP1 (FIGS. 20A–D) of structure-based or rational drug design techniques to design, select, and synthesizes chemical entities that are capable of modulating the biological function of BMY_HPP1. Comparison of the BMY_HPP1 homology model with the structures of template phosphatases enable the use of rational or structure based drug design methods to design, select or synthesize specific chemical modulators of BMY_HPP1.

Accordingly, the present invention is also directed to the entire sequence in FIG. 20A–D or any portion thereof for the purpose of generating a homology model for the purpose of three dimensional structure-based drug designs.

For purposes of this invention, we include mutants or homologues of the sequence in FIGS. 20A–D or any portion thereof. In a preferred embodiment, the mutants or homologues have at least 25% identity, more preferably 50% identity, more preferably 75% identity, and most preferably 90% identity to the amino acid residues in FIGS. 20A–D (SEQ ID NO:150).

The three-dimensional model structure of the BMY_HPP1 will also provide methods for identifying modulators of biological function. Various methods or combination thereof can be used to identify these compounds.

Structure coordinates of the active site region defined above can also be used to identify structural and chemical features. Identified structural or chemical features can then be employed to design or select compounds as potential BMY_HPP1 modulators. By structural and chemical features it is meant to include, but is not limited to, van der Waals interactions, hydrogen bonding interactions, charge interaction, hydrophobic interactions, and dipole interaction. Alternatively, or in conjunction, the three-dimensional structural model can be employed to design or select compounds as potential BMY_HPP1 modulators. Compounds identified as potential BMY_HPP1 modulators can then be synthesized and screened in an assay characterized by binding of a test compound to the BMY_HPP1, or in characterizing BMY_HPP1 deactivation in the presence of a small molecule. Examples of assays useful in screening of potential BMY_HPP1 modulators include, but are not limited to, screening in silico, in vitro assays and high throughput assays. Finally, these methods may also involve modifying or replacing one or more amino acids from BMY_HPP1 according to Table VIII.

However, as will be understood by those of skill in the art upon this disclosure, other structure based design methods can be used. Various computational structure based design methods have been disclosed in the art.

For example, a number of computer modeling systems are available in which the sequence of the BMY_HPP1 and the BMY_HPP1 structure (i.e., atomic coordinates of BMY_HPP1 and/or the atomic coordinates of the active site region as provided in Table VIII) can be input. The computer system then generates the structural details of one or more these regions in which a potential BMY_HPP1 modulator binds so that complementary structural details of the potential modulators can be determined. Design in these modeling systems is generally based upon the compound being capable of physically and structurally associating with BMY_HPP1. In addition, the compound must be able to assume a conformation that allows it to associate with BMY_HPP1. Some modeling systems estimate the potential inhibitory or binding effect of a potential BMY_HPP1 modulator prior to actual synthesis and testing.

Methods for screening chemical entities or fragments for their ability to associate with a given protein target are well known. Often these methods begin by visual inspection of the binding site on the computer screen. Selected fragments or chemical entities are then positioned in one or more positions and orientations within the active site region in BMY_HPP1. Molecular docking is accomplished using software such as INSIGHTII, ICM (Molsoft LLC, La Jolla, Calif.), and SYBYL, following by energy minimization and molecular dynamics with standard molecular mechanic forcefields such as CHARMM and MMFF. Examples of computer programs which assist in the selection of chemical fragment or chemical entities useful in the present invention include, but are not limited to, GRID (Goodford, 1985), AUTODOCK (Goodsell, 1990), and DOCK (Kuntz et. al. 1982).

Alternatively, compounds may be designed de novo using either an empty active site or optionally including some portion of a known inhibitor. Methods of this type of design include, but are not limited to LUDI (Bohm 1992), LeapFrog (Tripos Associates, St. Louis Mo.) and DOCK (Kuntz et. al., 1982). Programs such as DOCK (Kuntz et. al. 1982) can be used with the atomic coordinates from the homology model to identify potential ligands from databases or virtual databases which potentially bind the in the active site region, and which may therefore be suitable candidates for synthesis and testing. The computer programs may utilize a combination of the following steps:

(a) Selection of fragments or chemical entities from a database and then positioning the chemical entity in one or more orientations within the BMY_HPP1 active site defined by residues D161-Y162 and H189-C190-G193-R196. Characterization of the structural and chemical features of the chemical entity and active site including van der Waals interactions, hydrogen bonding interactions, charge interaction, hydrophobic bonding interaction, and dipole interactions;

(b) Search databases for molecular fragments which can be joined to or replace the docked chemical entity and spatially fit into regions defined by the said BMY_HPP1 active site;

(c) Evaluate the docked chemical entity and fragments using a combination of scoring schemes which account for van der Waals interactions, hydrogen bonding interactions, charge interaction, hydrophobic interactions; or (d) Databases that may be used include ACD (Molecular Designs Limited), Aldrich (Aldrich Chemical Company), NCI (National Cancer Institute), Maybridge(Maybridge Chemical Company Ltd), CCDC (Cambridge Crystallographic Data Center), CAST (Chemical Abstract Service), and Derwent (Derwent Information Limited).

Upon selection of preferred chemical entities or fragments, their relationship to each other and BMY_HPP1 can be visualized and then assembled into a single potential modulator. Programs useful in assembling the individual chemical entities include, but are not limited to SYBYL and LeapFrog (Tripos Associates, St. Louis Mo.), LUDI (Bohm 1992) as well as 3D Database systems (Martin 1992).

Additionally, the three-dimensional homology model of BMY_HPP1 will aid in the design of mutants with altered biological activity. Site directed mutagenesis can be used to generate proteins with similar or varying degrees of biological activity compared to native BMY_HPP1. This invention also relates to the generation of mutants or homologues of BMY_HPP1. It is clear that molecular modeling using the three dimensional structure coordinates set forth in Table VIII and visualization of the BMY_HPP1 model, FIG. 28 can be utilized to design homologues or mutant polypeptides of BMY_HPP1 that have similar or altered biological activities, function or reactivities.

Many polynucleotide sequences, such as EST sequences, are publicly available and accessible through sequence databases. Some of these sequences are related to SEQ ID NO:149 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 4379 of SEQ ID NO:149, b is an integer between 15 to 4393, where both a and b correspond to the positions of nucleotide residues shown in SEQ ID NO:149, and where b is greater than or equal to a+14.

Features of the Polypeptide Encoded by Gene No:2

The polypeptide fragment corresponding to this gene provided as SEQ ID NO:6 (FIG. 2), encoded by the polynucleotide sequence according to SEQ ID NO:5 (FIG. 2), and/or encoded by the polynucleotide contained within the deposited clone, BMY_HPP2, has significant homology at the nucleotide and amino acid level to a number of phosphatases, which include, for example, the human CDC14 (also known as the cell division cycle 14, *S. cerevisiae* Gene A protein) homologue A (HS_CDC14A; Genbank Accession No:gi| NP_003663; SEQ ID NO:30); the human *S. cerevisiae* CDC14 homolog, gene B (HS_CDC14B; Genbank Accession No:gi| NP_003662; SEQ ID NO:31); and the yeast soluble tyrosine-specific protein phosphatase Cdc14p protein (SC_CDC14; Genbank Accession No:gi| NP_002839; SEQ ID NO:32) as determined by BLASTP An alignment of the human phosphatase polypeptide with these proteins is provided in FIG. 7.

BMY_HPP2 is predicted, to be a phosphoprotein phosphatase based on its homology to human CDC14B as determined by BLASTP. BMY_HPP2 shows significant homology to the catalytic domains of human CDC14A and CDC14B and to yeast CDC14 including a conserved Aspartate at AA 76, a Cysteine at AA106 and an Arginine at AA 112 of BMY_HPP2 (shown in FIG. 2).

Polypeptide sequences corresponding to portions of the encoded BMY_HPP2 polypeptide sequence have been described as BAA91172 (Genbank Accession No:gi 7020545). However, conceptual translation of BAA91172 indicates that the phosphatase homology is in an open reading frame that begins before the 5' end of the provided polynucleotide EST sequence, in addition to regions of the polypeptide that are homologous to known phosphatases. Thus, the Genbank record, or the sequence, provided for BAA91172 does not provide any suggestion that this clone partially encodes a phosphatase protein.

Based upon the strong homology to members of the phosphatase proteins, the polypeptide encoded by the human BMY_HPP2 phosphatase of the present invention is expected to share at least some biological activity with phosphatase proteins, preferably with members of the novel phosphotyrosine/dual-specificity (P-Tyr, P-Ser and P-Thr) phosphatases, particularly the novel phosphotyrosine/dual-specificity (P-Tyr, P-Ser and P-Thr) phosphatases referenced herein.

The present invention encompasses the use of BMY_HPP2 inhibitors and/or activators of BMY_HPP2 activity for the treatment, detection, amelioration, or prevention of phosphatase associated disorders, including but not limited to metabolic diseases such as diabetes, in addition to neural and/or cardiovascular diseases and disorders. The present invention also encompasses the use of BMY_HPP2 inhibitors and/or activators of BMY_HPP2 activity as immunosuppressive agents, anti-inflammatory agents, and/or anti-tumor agents The present invention encompasses the use of BMY_HPP2 phosphatase inhibitors, including, antagonists such as antisense nucleic acids, in addition to other antagonists, as described herein, in a therapeutic regimen to diagnose, prognose, treat, ameliorate, and/or prevent diseases where a kinase activity is insufficient. One, non-limiting example of a disease which may occur due to insufficient kinase activity are certain types of diabetes, where one or more kinases involved in the insulin receptor signal pathway may have insufficient activity or insufficient expression, for example.

Moreover, the present invention encompasses the use of BMY_HPP2 phosphatase activators, and/or the use of the BMY_HPP2 phosphatase gene or protein in a gene therapy regimen, as described herein, for the diagnoses, prognoses, treatment, amelioration, and/or prevention of diseases and/ or disorders where a kinase activity is overly high, such as a cancer where a kinase oncogene product has excessive activity or excessive expression.

The present invention also encompasses the use of catalytically inactive variants of BMY_HPP2 proteins, including fragments thereof, such as a protein therapeutic, or the use of the encoding polynucleotide sequence or as gene therapy, for example, in the diagnoses, prognosis, treatment, amelioration, and/or prevention of diseases or disorders where phosphatase activity is overly high.

The present invention encompasses the use of antibodies directed against the BMY_HPP2 polypeptides, including fragment and/or variants thereof, of the present invention in diagnostics, as a biomarkers, and/or as a therapeutic agents.

The present invention encompasses the use of an inactive, non-catalytic, mutant of the BMY_HPP2 phosphatase as a substrate trapping mutant to bind cellular phosphoproteins or a library of phosphopeptides to identify substrates of the BMY_HPP2 polypeptides.

The present invention encompasses the use of the BMY_HPP2 polypeptides, to identify inhibitors or activators of the BMY_HPP2 phosphatase activity using either in vitro or 'virtual' (in silico) screening methods.

One embodiment of the invention relates to a method for identifying a compound as an activator or inhibitor of the BMY_HPP2 phosphatase comprising the steps of: i.) contacting a BMY_HPP2 phosphatase inhibitor or activator labeled with an analytically detectable reagent with the BMY_HPP2 phosphatase under conditions sufficient to form a complex with the inhibitor or activator; ii.) contacting said complex with a sample containing a compound to be identified; iii) and identifying the compound as an inhibitor or activator by detecting the ability of the test compound to alter the amount of labeled known BMY_HPP2 phosphatase inhibitor or activator in the complex.

Another embodiment of the invention relates to a method for identifying a compound as an activator or inhibitor of a BMY_HPP2 phosphatase comprising the steps of: i.) contacting the BMY_HPP2 phosphatase with a compound to be identified; and ii.) and measuring the ability of the BMY_HPP2 phosphatase to remove phosphate from a substrate.

The present invention also encompasses a method for identifying a ligand for the BMY_HPP2 phosphatase comprising the steps of: i.) contacting the BMY_HPP2 phosphatase with a series of compounds under conditions to permit binding; and ii.) detecting the presence of any ligand-bound protein.

Preferably, the above referenced methods comprise the BMY_HPP2 phosphatase in a form selected from the group consisting of whole cells, cytosolic cell fractions, membrane cell fractions, purified or partially purified forms. The invention also relates to recombinantly expressed BMY_HPP2 phosphatase in a purified, substantially purified, or unpurified state. The invention further relates to BMY_HPP2 phosphatase fused or conjugated to a protein, peptide, or other molecule or compound known in the art, or referenced herein.

The present invention also encompasses pharmaceutical composition of the BMY_HPP2 phosphatase polypeptide comprising a compound identified by above referenced methods and a pharmaceutically acceptable carrier.

Expression profiling designed to measure the steady state mRNA levels encoding the BMY_HPP2 polypeptide showed predominately high expression levels in liver and kidney; to a significant extent, in the spleen, and to a lesser extent, in lung, testis, heart, intestine, pancreas, lymph node, spinal cord, and prostate (as shown in FIG. 23).

Moreover, BLAST2 searches of the LifeSeq database (Incyte Pharmaceuticals) using the full-length BMY_HPP2 polynucleotide sequence (SEQ ID NO:151) led to the determination that the BMY_HPP2 sequence is expressed significantly in lung libraries which include patients with emphysema and other pulmonary diseases. The BMY_HPP2 polynucleotide was also found to be expressed in aorta and endothelial cells stimulated with IL-1 and TNF-alpha. These findings suggest a potential involvement of the BMY_HPP2 polynucleotides and polypeptides in the incidence of pulmonary disease and upregulation by IL-1 and TNF-alpha.

In addition, expanded expression profiling of the BMY_HPP2 polypeptide in normal tissues showed the highest level of expression in the adrenal gland, with lower but significant expression in the pineal pituitary glands suggesting a role for modulators of BMY_HPP2 activity in the treatment of endocrine disorders (as shown in FIG. 30). Consistent with the expression pattern in lung libraries from the Incyte database above, high relative levels of expression were also seen in the parenchyma and bronchi of the lung, suggesting a role for modulators of BMY_HPP2 activity in the treatment of respiratory diseases such as asthma or COPD; in the kidney, suggesting a role for modulators of BMY_HPP2 activity in the treatment of kidney disorders; in the liver, suggesting a role for modulators of BMY_HPP2 activity in the treatment of liver disorders such as hepatitis or cirrhosis; in blood vessels from the choroid plexus, coronary artery and pulmonary artery, suggesting a role for modulators of BMY_HPP2 activity in the treatment of circulatory disorders such as hypertension; and in the nucleus accumbens of the brain, suggesting a role for modulators of BMY_HPP2 activity in the treatment of affective disorders such as bipolar disorder, schizophrenia and depression. In addition, the BMY_HPP2 was highly expressed in the trachea, breast and uterus and significantly expressed in many other tissues within the human body.

The strong homology to phosphatases, particularly dual-specificity phosphatases, combined with the predominate localized expression in adrenal gland tissue suggests the human BMY_HPP2 phosphatase polynucleotides and polypeptides, including agonists, antagonists, and/or fragments thereof, may be useful for treating, diagnosing, prognosing, ameliorating, and/or preventing endocrine disorders, which include, but are not limited to adrenocortical hyperfunction, adrenocortical hypofunction, lethargy, Congenital adrenal hyperplasia, aberrant ACTH regulation, aberrant adrenaline regulation, disorders associated with defects in P450C21, P450C18, P450C17, and P450C11 hydroxylases and in 3-hydroxysteroid dehydrogenase (3-HSD), hirsutism, oligomenorrhea, acne, virilization, oligomenorrhea, female pseudohermaphroditism, disorders associated with the incidence of aberrant sexual characterisitics, disorders associated with aberrant cortisol secretion, hypertension, hypokalemia, hypogonadism, disorders associated with aberrant androgen secretion, adrenal virilism, Adrenal adenomas, Adrenal carcinomas, disorders associated with aberrant aldosterone secretion, aldosteronism, disorders associated with aberrant steriod biosynthesis, disorders associated with aberrant steriod transport, disorders associated with aberrant steriod secretion, disorders associated with aberrant steriod excretion, Addison's syndrome, and Cushing's syndrome.

The strong homology to phosphatases, particularly dual-specificity phosphatases, combined with the significant expression in liver indicates the BMY_HPP2 polynucleotides and polypeptides, in addition to, fragments and variants thereof, would be useful for the detection and treatment of liver disorders and cancers. Representative uses are described in the "Hyperproliferative Disorders", "Infectious Disease", and "Binding Activity" sections below, and elsewhere herein. Briefly, the protein can be used for the detection, treatment, amelioration, and/or prevention of hepatoblastoma, jaundice, hepatitis, liver metabolic diseases and conditions that are attributable to the differentiation of hepatocyte progenitor cells, cirrhosis, hepatic cysts, pyrogenic abscess, amebic abcess, hydatid cyst, cystadenocarcinoma, adenoma, focal nodular hyperplasia, hemangioma, hepatocellulae carcinoma, cholangiocarcinoma, and angiosarcoma, granulomatous liver disease, liver transplantation, hyperbilirubinemia, jaundice, parenchymal liver disease, portal hypertension, hepatobiliary disease, hepatic parenchyma, hepatic fibrosis, anemia, gallstones, cholestasis, carbon tetrachloride toxicity, beryllium toxicity, vinyl chloride toxicity, choledocholithiasis, hepatocellular necrosis, aberrant metabolism of amino acids, aberrant metabolism of carbohydrates, aberrant synthesis proteins, aberrant synthesis of glycoproteins, aberrant degradation of proteins, aberrant degradation of glycoproteins, aberrant metabolism of drugs, aberrant metabolism of hormones, aberrant degradation of drugs, aberrant degradation of drugs, aberrant regulation of lipid metabolism, aberrant regulation of cholesterol metabolism, aberrant glycogenesis, aberrant glycogenolysis, aberrant glycolysis, aberrant gluconeogenesis, hyperglycemia, glucose intolerance, hyperglycemia, decreased hepatic glucose uptake, decreased hepatic glycogen synthesis, hepatic resistance to insulin, portal-systemic glucose shunting, peripheral insulin resistance, hormonal abnormalities, increased levels of systemic glucagon, decreased levels of systemic cortisol, increased levels of systemic insulin, hypoglycemia, decreased gluconeogenesis, decreased hepatic glycogen content, hepatic resistance to glucagon, elevated levels of systemic aromatic amino acids, decreased levels of systemic branched-chain amino acids, hepatic encephalopathy, aberrant hepatic amino acid transamination, aberrant hepatic amino acid oxidative deamination, aberrant ammonia synthesis, aberrant albumin secretion, hypoalbuminemia, aberrant cytochromes b5 function, aberrant P450 function, aberrant glutathione S-acyltransferase function, aberrant cholesterol synthesis, and aberrant bile acid synthesis.

Moreover, polynucleotides and polypeptides, including fragments, agonists and/or antagonists thereof, have uses which include, directly or indirectly, treating, preventing, diagnosing, and/or prognosing the following, non-limiting, hepatic infections: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaries' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by Spirochete infection, liver disease caused by *Treponema pallidum* infection, liver disease caused by *Brrelia burgdorferi* infection, liver disease caused by Leptospirosis, liver disease caused by *Coxiella burnetii* infection, liver disease caused by *Rickettsia richettsii* infection, liver disease caused by *Chlamydia trachomatis* infection, liver disease caused by *Chlamydia psittaci* infection, liver disease caused by hepatitis virus infection, liver disease caused by Epstein-Barr virus infection in addition to any other hepatic disease and/or disorder implicated by the causative agents listed above or elsewhere herein.

The strong homology to dual specificity phophatases, combined with the localized expression in kidney tissue suggests the BMY_HPP2 polynucleotides and polypeptides may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention, slowing of urinary stream, large prostate, flank tenderness, full bladder sensation after voiding, enuresis, dysuria,bacteriuria, kideny stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome for example.

The strong homology to dual specificity phosphatases, combined with the localized expression in spleen tissue, in addition to the expression in endothelial cells stimulated with IL-1 and TNF-alpha, suggests the BMY_HPP2 polynucleotides and polypeptides may be useful in treating, diagnosing, prognosing, and/or preventing immune diseases and/or disorders. Representative uses are described in the "Immune Activity", "Chemotaxis", and "Infectious Disease" sections below, and elsewhere herein. Briefly, the strong expression in immune tissue indicates a role in regulating the proliferation; survival; differentiation; and/or activation of hematopoietic cell lineages, including blood stem cells.

The BMY_HPP2 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. The BMY_HPP2 polypeptide may be useful for modulating cytokine production, antigen presentation, or other processes, such as for boosting immune responses, etc.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissuemarkers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The significant expression of BMY_HPP2 transcripts in lung libraries as observed from electronic Northern's from the Incyte LifeSeq database suggests the potential utility for BMY_HPP2 polynucleotides and polypeptides in treating, diagnosing, prognosing, and/or preventing pulmonary diseases and disorders which include the following, not limiting examples: ARDS, emphysema, cystic fibrosis, interstitial lung disease, chronic obstructive pulmonary disease, bronchitis, lymphangioleiomyomatosis, pneumonitis, eosinophilic pneumonias, granulomatosis, pulmonary infarction, pulmonary fibrosis, pneumoconiosis, alveolar hemorrhage, neoplasms, lung abscesses, empyema, and increased susceptibility to lung infections (e.g., immumocompromised, HIV, etc.), for example.

Moreover, polynucleotides and polypeptides, including fragments, agonists and/or antagonists thereof, have uses which include, directly or indirectly, treating, preventing, diagnosing, and/or prognosing the following, non-limiting, pulmonary infections: pneumonia, bacterial pneumonia, viral pneumonia (for example, as caused by Influenza virus, Respiratory syncytial virus, Parainfluenza virus, Adenovirus, Coxsackievirus, Cytomegalovirus, Herpes simplex virus, Hantavirus, etc.), mycobacteria pneumonia (for example, as caused by Mycobacterium tuberculosis, etc.) mycoplasma pneumonia, fungal pneumonia (for example, as caused by Pneumocystis carinii, Histoplasma capsulatum, *Coccidioides immitis, Blastomyces* dermatitidis, *Candida* sp., *Cryptococcus* neoformans, *Aspergillus* sp., Zygomycetes, etc.), Legionnaires' Disease, *Chlamydia* pneumonia, aspiration pneumonia, *Nocordia* sp. Infections, parasitic pneumonia (for example, as caused by *Strongyloides, Toxoplasma gondii*, etc.) necrotizing pnemonia, in addition to any other pulmonary disease and/or disorder (e.g., non-pneumonia) implicated by the causative agents listed above or elsewhere herein.

Antisense oligonucleotides directed against BMY_HPP2 provided evidence suggesting its involvement in the regulation of mammalian cell cycle progression (see Example 56). Subjecting cells with an effective amount of a pool of five antisense oligoncleotides resulted in a significant increase in Cyclin D expression/activity providing convincing evidence that BMY_HPP2 at least regulates the activity and/or expression of Cyclin D either directly, or indirectly. Moreover, the results suggest the physiological role of BMY_HPP2 is the negative regulation of Cyclin D activity and/or expression, either directly or indirectly.

In preferred embodiments, BMY_HPP2 polynucleotides and polypeptides, including fragments thereof, are useful for treating, diagnosing, and/or ameliorating cell cycle defects, disorders related to aberrant phosphorylation, disorders related to aberrant signal transduction, proliferating disorders, and/or cancers.

Moreover, BMY_HPP2 polynucleotides and polypeptides, including fragments thereof, are useful for decreasing cellular proliferation, decreasing cellular proliferation in rapidly proliferating cells, increasing the number of cells in the G1 phase of the cell cycle, and decreasing the number of cells that progress to the S phase of the cell cycle.

In preferred embodiments, agonists directed to BMY_HPP2 are useful for decreasing cellular proliferation, decreasing cellular proliferation in rapidly proliferating cells, increasing the number of cells in the G1 phase of the cell cycle, and decreasing the number of cells that progress to the S phase of the cell cycle.

Moreover, antagonists directed against BMY_HPP2 are useful for increasing cellular proliferation, increasing cellular proliferation in rapidly proliferating cells, decreasing the number of cells in the G1 phase of the cell cycle, and increasing the number of cells that progress to the S phase of the cell cycle. Such antagonists would be particularly useful for transforming normal cells into immortalized cell lines, stimulating hematopoietic cells to grow and divide, increasing recovery rates of cancer patients that have undergone chemotherapy or other therapeutic regimen, by boosting their immune responses, etc.

The BMY_HPP2 polypeptide has been shown to comprise one glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N—{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673–702(1972); Pless D. D., Lennarz W. J., Proc. Natl. Acad. Sci. U.S.A. 74:134–138(1977); Bause E., Biochem. J. 209:331–336(1983); Gavel Y., von Heijne G., Protein Eng. 3:433–442(1990); and Miletich J. P., Broze G. J. Jr., J. Biol. Chem. 265:11397–11404(1990).

In preferred embodiments, the following asparagine glycosylation site polypeptide is encompassed by the present invention: GVQPPNFSWVLPGR (SEQ ID NO:164). Polynucleotides encoding this polypeptide are also provided. The present invention also encompasses the use of this BMY_HPP2 asparagine glycosylation site polypeptide as an immunogenic and/or antigenic epitope as described elsewhere herein.

The BMY_HPP2 polypeptides of the present invention were determined to comprise several phosphorylation sites based upon the Motif algorithm (Genetics Computer Group, Inc.). The phosphorylation of such sites may regulate some biological activity of the BMY_HPP2 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the BMY_HPP2 polypeptide to associate with other potassium channel alpha subunits, beta subunits, or its ability to modulate potassium channel function.

The BMY_HPP2 polypeptide was predicted to comprise one PKC phosphorylation site using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. 260:12492–12499(1985); which are hereby incorporated by reference herein.

In preferred embodiments, the following PKC phosphorylation site polypeptide is encompassed by the present invention: HLVSLTERGPPHS (SEQ ID NO:165). Polynucleotides encoding these polypeptides are also provided.

The present invention also encompasses the use of these BMY_HPP2 PKC phosphorylation site polypeptides as immunogenic and/or antigenic epitopes as described elsewhere herein.

In further confirmation of the human BMY_HPP2 polypeptide representing a novel human phosphatase polypeptide, the BMY_HPP2 polypeptide has been shown to comprise a tyrosine specific protein phosphatase active site domain according to the Motif algorithm (Genetics Computer Group, Inc.).

Tyrosine specific protein phosphatases (EC 3.1.3.48) (PTPase) are enzymes that catalyze the removal of a phosphate group attached to a tyrosine residue. These enzymes are very important in the control of cell growth, proliferation, differentiation and transformation. Multiple forms of PTPase have been characterized and can be classified into two categories: soluble PTPases and transmembrane receptor proteins that contain PTPase domain(s).

The currently known PTPases are listed below: Soluble PTPases, PTPN1 (PTP-1B), PTPN2 (T-cell PTPase; TC-PTP), PTPN3 (H1) and PTPN4 (MEG), enzymes that contain an N-terminal band 4.1-like domain and could act at junctions between the membrane and cytoskeleton, PTPN5 (STEP), PTPN6 (PTP-1C; HCP; SHP) and PTPN11 (PTP-2C; SH-PTP3; Syp), enzymes which contain two copies of the SH2 domain at its N-terminal extremity (e.g., the *Drosophila* protein corkscrew (gene csw) also belongs to this subgroup), PTPN7 (LC-PTP; Hematopoietic protein-tyrosine phosphatase; HePTP), PTPN8 (70Z-PEP), PTPN9 (MEG2), PTPN12 (PTP-G1; PTP-P19), Yeast PTP1, Yeast PTP2 which may be involved in the ubiquitin-mediated protein degradation pathway, Fission yeast pyp1 and pyp2 which play a role in inhibiting the onset of mitosis, Fission yeast pyp3 which contributes to the dephosphorylation of cdc2, Yeast CDC14 which may be involved in chromosome segregation, *Yersinia virulence* plasmid PTPAses (gene yopH), Autographa californica nuclear polyhedrosis virus 19 Kd PTPase, Dual specificity PTPases, DUSP1 (PTPN10; MAP kinase phosphatase-1; MKP-1); which dephosphorylates MAP kinase on both Thr-183 and Tyr-185, DUSP2 (PAC-1), a nuclear enzyme that dephosphorylates MAP kinases ERK1 and ERK2 on both Thr and Tyr residues, DUSP3 (VHR), DUSP4 (HVH2), DUSP5 (HVH3), DUSP6 (Pyst1; MKP-3), DUSP7 (Pyst2; MKP-X), Yeast MSG5, a PTPase that dephosphorylates MAP kinase FUS3, Yeast YVH1, Vaccinia virus H1PTPase—a dual specificity phosphatase, Structurally, all known receptor PTPases, are made up of a variable length extracellular domain, followed by a transmembrane region and a C-terminal catalytic cytoplasmic domain. Some of the receptor PTPases contain fibronectin type III (FN-III) repeats, immunoglobulin-like domains, MAM domains or carbonic anhydrase-like domains in their extracellular region. The cytoplasmic region generally contains two copies of the PTPAse domain. The first seems to have enzymatic activity, while the second is inactive but seems to affect substrate specificity of the first. In these domains, the catalytic cysteine is generally conserved but some other, presumably important, residues are not.

PTPase domains consist of about 300 amino acids. There are two conserved cysteines, the second one has been shown to be absolutely required for activity. Furthermore, a number of conserved residues in its immediate vicinity have also been shown to be important.

A consensus sequence for tyrosine specific protein phophatases is provided as follows:

[LIVMF]—H—C-x(2)-G-x(3)-[STC]-[STAGP]-x-[LIVMFY], wherein C is the active site residue and "X" represents any amino acid.

Additional information related to tyrosine specific protein phosphatase domains and proteins may be found in reference to the following publications Fischer E. H., Charbonneau H., Tonks N. K., Science 253:401–406(1991); Charbonneau H., Tonks N. K., Annu. Rev. Cell Biol. 8:463–493 (1992); Trowbridge I. S., J. Biol. Chem. 266:23517–23520 (1991); Tonks N. K., Charbonneau H., Trends Biochem. Sci. 14:497–500(1989); and Hunter T., Cell 58:1013–1016(1989); which are hereby incorporated herein by reference in their entirety.

In preferred embodiments, the following tyrosine specific protein phosphatase active site domain polypeptide is encompassed by the present invention: GEAVGVHCALGFGRTGT-MLACYL (SEQ ID NO:166). Polynucleotides encoding these polypeptides are also provided. The present invention also encompasses the use of this tyrosine specific protein phosphatase active site domain polypeptide as an immunogenic and/or antigenic epitope as described elsewhere herein.

In preferred embodiments, the following N-terminal BMY_HPP2 deletion polypeptides are encompassed by the present invention: M1-K150, G2-K150, V3-K150, Q4-K150, P5-K150, P6-K150, N7-K150, F8-K150, S9-K150, W10-K150, V11-K150, L12-K150, P13-K150, G14-K150, R15-K150, L16-K150, A17-K150, G18-K150, L19-K150, A20-K150, L21-K150, P22-K150, R23-K150, L24-K150, P25-K150, A26-K150, H27-K150, Y28-K150, Q29-K150, F30-K150, L31-K150, L32-K150, D33-K150, L34-K150, G35-K150, V36-K150, R37-K150, H38-K150, L39-K150, V40-K150, S41-K150, L42-K150, T43-K150, E44-K150, R45-K150, G46-K150, P47-K150, P48-K150, H49-K150, S50-K150, D51-K150, S52-K150, C53-K150, P54-K150, G55-K150, L56-K150, T57-K150, L58-K150, H59-K150, R60-K150, L61-K150, R62-K150, I63-K150, P64-K150, D65-K150, F66-K150, C67-K150, P68-K150, P69-K150, A70-K150, P71-K150, D72-K150, Q73-K150, I74-K150, D75-K150, R76-K150, F77-K150, V78-K150, Q79-K150, I80-K150, V81-K150, D82-K150, E83-K150, A84-K150, N85-K150, A86-K150, R87-K150, G88-K150, E89-K150, A90-K150, V91-K150, G92-K150, V93-K150, H94-K150, C95-K150, A96-K150, L97-K150, G98-K150, F99-K150, G100-K150, R101-K150, T102-K150, G103-K150, T104-K150, M105-K150, L106-K150, A107-K150, C108-K150, Y109-K150, L110-K150, V111-K150, K112-K150, E113-K150, R114-K150, G115-K150, L116-K150, A117-K150, A118-K150, G119-K150, D120-K150, A121-K150, I122-K150, A123-K150, E124-K150, I125-K150, R126-K150, R127-K150, L128-K150, R129-K150, P130-K150, G131-K150, S132-K150, I133-K150, E134-K150, T135-K150, Y136-K150, E137-K150, Q138-K150, E139-K150, K140-K150, A141-K150, V142-K150, F143-K150, and/or Q144-K150 of SEQ ID NO:152. Polynucleotide sequences encoding these polypeptides are also provided. The present invention also encompasses the use of these N-terminal BMY_HPP2 deletion polypeptides as immunogenic and/or antigenic epitopes as described elsewhere herein.

In preferred embodiments, the following C-terminal BMY_HPP2 deletion polypeptides are encompassed by the present invention: M1-K150, M1-T149, M1-R148, M1-Q147, M1-Y146, M1-F145, M1-Q144, M1-F143, M1-V142, M1-A141, M1-K140, M1-E139, M1-Q138, M1-E137, M1-Y136, M1-T135, M1-E134, M1-I133, M1-S132, M1-G131, M1-P130, M1-R129, M1-L128, M1-R127, M1-R126, M1-I125, M1-E124, M1-A123, M1-I122, M1-A121, M1-D120, M1-G119, M1-A118, M1-A117, M1-L116, M1-G115, M1-R114, M1-E113, M1-K112, M1-V111, M1-L110, M1-Y109, M1-C108, M1-A107, M1-L106, M1-M105, M1-T104, M1-G103, M1-T102, M1-R101, M1-G100, M1-F99, M1-G98, M1-L97, M1-A96, M1-C95, M1-H94, M1-V93, M1-G92, M1-V91, M1-A90, M1-E89, M1-G88, M1-R87, M1-A86, M1-N85, M1-A84, M1-E83, M1-D82, M1-V81, M1-I80, M1-Q79, M1-V78, M1-F77, M1-R76, M1-D75, M1-I74, M1-Q73, M1-D72, M1-P71, M1-A70, M1-P69, M1-P68, M1-C67, M1-F66, M1-D65, M1-P64, M1-I63, M1-R62, M1-L61, M1-R60, M1-H59, M1-L58, M1-T57, M1-L56, M1-G55, M1-P54, M1-C53, M1-S52, M1-D51, M1-S50, M1-H49, M1-P48, M1-P47, M1-G46, M1-R45, M1-E44, M1-T43, M1-L42, M1-S41, M1-V40, M1-L39, M1-H38, M1-R37, M1-V36, M1-G35, M1-L34, M1-D33, M1-L32, M1-L31, M1-F30, M1-Q29, M1-Y28, M1-H27, M1-A26, M1-P25, M1-L24, M1-R23, M1-P22, M1-L21, M1-A20, M1-L19, M1-G18, M1-A17, M1-L16, M1-R15, M1-G14, M1-P13, M1-L12, M1-V11, M1-W10, M1-S9, M1-F8, and/or M1-N7 of SEQ ID NO:152. Polynucleotide sequences encoding these polypeptides are also provided. The present invention also encompasses the use of these C-terminal BMY_HPP2 deletion polypeptides as immunogenic and/or antigenic epitopes as described elsewhere herein.

In preferred embodiments, the following BMY_HPP2 phosphatase active site domain amino acid substitutions are encompassed by the present invention: wherein M1 is substituted with either an A, C, D, E, F, G, H, I, K, L, N, P, Q, R, S, T, V, W, or Y; wherein G2 is substituted with either an A, C, D, E, F, H, I, K, L, M, N, P, Q, R, S, T, V, W, or Y; wherein V3 is substituted with either an A, C, D, E, F, G, H, I, K, L, M, N, P, Q, R, S, T, W, or Y; wherein Q4 is substituted with either an A, C, D, E, F, G, H, I, K, L, M, N, P, R, S, T, V, W, or Y; wherein P5 is substituted with either an A, C, D, E, F, G, H, I, K, L, M, N, Q, R, S, T, V, W, or Y; wherein P6 is substituted with either an A, C, D, E, F, G, H, I, K, L, M, N, Q, R, S, T, V, W, or Y; wherein N7 is substituted with either an A, C, D, E, F, G, H, I, K, L, M, P, Q, R, S, T, V, W, or Y; wherein F8 is substituted with either an A, C, D, E, G, H, I, K, L, M, N, P, Q, R, S, T, V, W, or Y; wherein S9 is substituted with either an A, C, D, E, F, G, H, I, K, L, M, N, P, Q, R, T, V, W, or Y; wherein W10 is substituted with either an A, C, D, E, F, G, H, I, K, L, M, N, P, Q, R, S, T, V, or Y; wherein V11 is substituted with either an A, C, D, E, F, G, H, I, K, L, M, N, P, Q, R, S, T, W, or Y; wherein L12 is substituted with either an A, C, D, E, F, G, H, I, K, M, N, P, Q, R, S, T, V, W, or Y; wherein P13 is substituted with either an A, C, D, E, F, G, H, I, K, L, M, N, Q, R, S, T, V, W, or Y; wherein G14 is substituted with either an A, C, D, E, F, H, I, K, L, M, N, P, Q, R, S, T, V, W, or Y; wherein R15 is substituted with either an A, C, D, E, F, G, H, I, K, L, M, N, P, Q, S, T, V, W, or Y; wherein L16 is substituted with either an A, C, D, E, F, G, H, I, K, M, N, P, Q, R, S, T, V, W, or Y; wherein A17 is substituted with either a C, D, E, F, G, H, I, K, L, M, N, P, Q, R, S, T, V, W, or Y; wherein G18 is substituted with either an A, C, D, E, F, H, I, K, L, M, N, P, Q, R, S, T, V, W, or Y; wherein L19 is substituted with either an A, C, D, E, F, G, H, I, K, M, N, P, Q, R, S, T, V, W, or Y; wherein A20 is substituted with either a C, D, E, F, G, H, I, K, L, M, N, P, Q, R, S, T, V, W, or Y; wherein L21 is substituted with either an A, C, D, E, F, G, H, I, K, M, N, P, Q, R, S, T, V, W, or Y; wherein P22 is substituted with either an A, C, D, E, F, G, H, I, K, L, M, N, Q, R, S, T, V, W, or Y; wherein R23 is substituted with either an A, C, D, E, F, G, H, I, K, L, M, N, P, Q, S, T, V, W, or Y; wherein L24 is substituted with either an A, C, D, E, F, G, H, I, K, M, N, P, Q, R, S, T, V, W, or Y; wherein P25 is substituted with either an A, C, D, E, F, G, H, I, K, L, M, N, Q, R, S, T, V, W, or Y; wherein A26 is substituted with either a C, D, E, F, G, H, I, K, L, M, N, P, Q, R, S, T, V, W, or Y; wherein H27 is substituted with either an A, C, D, E, F, G, I, K, L, M, N, P, Q, R, S, T, V, W, or Y; wherein Y28 is substituted with either an A, C, D, E, F, G, H, I, K, L, M, N, P, Q, R, S, T, V, or W; wherein Q29 is substituted with either an A, C, D, E, F, G, H, I, K, L, M, N, P, R, S, T, V, W, or Y; wherein F30 is substituted with either an A, C, D, E, G, H, I, K, L, M, N, P, Q, R, S, T, V, W, or Y; wherein L31 is substituted with either an A, C, D, E, F, G, H, I, K, M, N, P, Q, R, S, T, V, W, or Y; wherein L32 is substituted with either an A, C, D, E, F, G, H, I, K, M, N, P, Q, R, S, T, V, W, or Y; wherein D33 is substituted with either an A, C, E, F, G, H, I, K, L, M, N, P, Q, R, S, T, V, W, or Y; wherein L34 is substituted with either an A, C, D, E, F, G, H, I, K, M, N, P, Q, R, S, T, V, W, or Y; wherein G35 is substituted with either an A, C, D, E, F, H, I, K, L, M, N, P, Q, R, S, T, V, W, or Y; wherein V36 is substituted with either an A, C, D, E, F, G, H, I, K, L, M, N, P, Q, R, S, T, W, or Y; wherein R37 is substituted with either an A, C, D, E, F, G, H, I, K, L, M, N, P, Q, S, T, V, W, or Y; wherein H38 is substituted with either an A, C, D, E, F, G, I, K, L, M, N, P, Q, R, S, T, V, W, or Y; wherein L39 is substituted with either an A, C, D, E, F, G, H, I, K, M, N, P, Q, R, S, T, V, W, or Y; wherein V40 is substituted with either an A, C, D, E, F, G, H, I, K, L, M, N, P, Q, R, S, T, W, or Y; wherein S41 is substituted with either an A, C, D, E, F, G, H, I, K, L, M, N, P, Q, R, T, V, W, or Y; wherein L2 is substituted with either an A, C, D, E, F, G, H, I, K, M, N, P, Q, R, S, T, V, W, or Y; wherein T43 is substituted with either an A, C, D, E, F, G, H, I, K, L, M, N, P, Q, R, S, V, W, or Y; wherein E44 is substituted with either an A, C, D, F, G, H, I, K, L, M, N, P, Q, R, S, T, V, W, or Y; wherein R45 is substituted with either an A, C, D, E, F, G, H, I, K, L, M, N, P, Q, S, T, V, W, or Y; wherein G46 is substituted with either an A, C, D, E, F, H, I, K, L, M, N, P, Q, R, S, T, V, W, or Y; wherein P47 is substituted with either an A, C, D, E, F, G, H, I, K, L, M, N, Q, R, S, T, V, W, or Y; wherein P48 is substituted with either an A, C, D, E, F, G, H, I, K, L, M, N, Q, R, S, T, V, W, or Y; wherein H49 is substituted with either an A, C, D, E, F, G, I, K, L, M, N, P, Q, R, S, T, V, W, or Y; wherein S50 is substituted with either an A, C, D, E, F, G, H, I, K, L, M, N, P, Q, R, T, V, W, or Y; wherein D51 is substituted with either an A, C, E, F, G, H, I, K, L, M, N, P, Q, R, S, T, V, W, or Y; wherein S52 is substituted with either an A, C, D, E, F, G, H, I, K, L, M, N, P, Q, R, T, V, W, or Y; wherein C53 is substituted with either an A, D, E, F, G, H, I, K, L, M, N, P, Q, R, S, T, V, W, or Y; wherein P54 is substituted with either an A, C, D, E, F, G, H, I, K, L, M, N, Q, R, S, T, V, W, or Y; wherein G55 is substituted with either an A, C, D, E, F, H, I, K, L, M, N, P, Q, R, S, T, V, W, or Y; wherein L56 is substituted with either an A, C, D, E, F, G, H, I, K, M, N, P, Q, R, S, T, V, W, or Y; wherein T57 is substituted with either an A, C, D, E, F, G, H, I, K, L, M, N, P, Q, R, S, V, W, or Y; wherein L58 is substituted with either an A, C, D, E, F, G, H, I, K, M, N, P, Q, R, S, T, V, W, or Y; wherein H59 is substituted with either an A, C, D, E, F, G, I, K, L, M, N, P, Q, R, S, T, V, W, or Y; wherein R60 is substituted with either an A, C, D, E, F, G, H, I, K, L, M, N, P, Q, S, T, V, W, or Y; wherein L61 is substituted with either an A, C, D, E, F, G, H, I, K, M, N, P, Q, R, S, T, V, W, or Y; wherein R62 is substituted with either an A, C, D, E, F, G, H, I, K, L, M, N, P, Q, S, T, V, W, or Y; wherein I63 is substituted with either an A, C, D, E, F, G, H, K, L, M, N, P, Q, R, S, T, V, W, or Y; wherein P64 is substituted with either an A, C, D, E, F, G, H, I, K, L, M, N, Q, R, S, T, V, W, or Y; wherein D65 is substituted with either an A, C, E, F, G, H, I, K, L, M, N, P, Q, R, S, T, V, W, or Y; wherein F66 is substituted with either an A, C, D, E, G, H, I, K, L, M, N, P, Q, R, S, T, V, W, or Y; wherein C67 is substituted with either an A, D, E, F, G, H, I, K, L, M, N, P, Q, R, S, T, V, W, or Y; wherein P68 is substituted with either an A, C, D, E, F, G, H, I, K, L, M, N, Q, R, S, T, V, W, or Y; wherein P69 is substituted with either an A, C, D, E, F, G, H, I, K, L, M, N, Q, R, S, T, V, W, or Y; wherein A70 is substituted with either a C, D, E, F, G, H, I, K, L, M, N, P, Q, R, S, T, V, W, or Y; wherein P71 is substituted with either an A, C, D, E, F, G, H, I, K, L, M, N, Q, R, S, T, V, W, or Y; wherein D72 is substituted with either an A, C, E, F, G, H, I, K, L, M, N, P, Q, R, S, T, V, W, or Y; wherein Q73 is substituted with either an A, C, D, E, F, G, H, I, K, L, M, N, P, R, S, T, V, W, or Y; wherein I74 is substituted with either an A, C, D, E, F, G, H, K, L, M, N, P, Q, R, S, T, V, W, or Y; wherein D75 is substituted with either an A, C, E, F, G, H, I, K, L, M, N, P, Q, R, S, T, V, W, or Y; wherein R76 is substituted with either an A, C, D, E, F, G, H, I, K, L, M, N, P, Q, S, T, V, W, or Y; wherein F77 is substituted with either an A, C, D, E, G, H, I, K, L, M, N, P, Q, R, S, T, V, W, or Y; wherein V78 is substituted with either an A, C, D, E, F, G, H, I, K, L, M, N, P, Q, R, S, T, W, or Y; wherein Q79 is substituted with either an A, C, D, E, F, G, H, I, K, L, M, N, P, R, S, T, V, W, or Y; wherein I80 is substituted with either an A, C, D, E, F, G, H, K, L, M, N, P, Q, R, S, T, V, W, or Y; wherein V81 is substituted with either an A, C, D, E, F, G, H, I, K, L, M, N, P, Q, R, S, T, W, or Y; wherein D82 is substituted with either an A, C, E, F, G, H, I, K, L, M, N, P, Q, R, S, T, V, W, or Y; wherein E83 is substituted with either an A, C, D, F, G, H, I, K, L, M, N, P, Q, R, S, T, V, W, or Y; wherein A84 is substituted with either a C, D, E, F, G, H, I, K, L, M, N, P, Q, R, S, T, V, W, or Y; wherein N85 is substituted with either an A, C, D, E, F, G, H, I, K, L, M, P, Q, R, S, T, V, W, or Y; wherein A86 is substituted with either a C, D, E, F, G, H, I, K, L, M, N, P, Q, R, S, T, V, W, or Y; wherein R87 is substituted with either an A, C, D, E, F, G, H, I, K, L, M, N, P, Q, S, T, V, W, or Y; wherein G88 is substituted with either an A, C, D, E, F, H, I, K, L, M, N, P, Q, R, S, T, V, W, or Y; wherein E89 is substituted with either an A, C, D, F, G, H, I, K, L, M, N, P, Q, R, S, T, V, W, or Y; wherein A90 is substituted with either a C, D, E, F, G, H, I, K, L, M, N, P, Q, R, S, T, V, W, or Y; wherein V91 is substituted with either an A, C, D, E, F, G, H, I, K, L, M, N, P, Q, R, S, T, W, or Y; wherein G92 is substituted with either an A, C, D, E, F, H, I, K, L, M, N, P, Q, R, S, T, V, W, or Y; wherein V93 is substituted with either an A, C, D, E, F, G, H, I, K, L, M, N, P, Q, R, S, T, W, or Y; wherein H94 is substituted with either an A, C, D, E, F, G, I, K, L, M, N, P, Q, R, S, T, V, W, or Y; wherein C95 is substituted with either an A, D, E, F, G, H, I, K, L, M, N, P, Q, R, S, T, V, W, or Y; wherein A96 is substituted with either a C, D, E, F, G, H, I, K, L, M, N, P, Q, R, S, T, V, W, or Y; wherein L97 is substituted with either an A, C, D, E, F, G, H, I, K, M, N, P, Q, R, S, T, V, W, or Y; wherein G98 is substituted with either an A, C, D, E, F, H, I, K, L, M, N, P, Q, R, S, T, V, W, or Y; wherein F99 is substituted with either an A, C, D, E, G, H, I, K, L, M, N, P, Q, R, S, T, V, W, or Y; wherein G100 is substituted with either an A, C, D, E, F, H, I, K, L, M, N, P, Q, R, S, T, V, W, or Y; wherein R101 is substituted with either an A, C, D, E, F, G, H, I, K, L, M, N, P, Q, S, T, V, W, or Y; wherein T102 is substituted with either an A, C, D, E, F, G, H, I, K, L, M, N, P, Q, R, S, V, W, or Y; wherein G103 is substituted with either an A, C, D, E, F, H, I, K, L, M, N, P, Q, R, S, T, V, W, or Y; wherein T104 is substituted with either an A, C, D, E, F, G, H, I, K, L, M, N, P, Q, R, S, V, W, or Y; wherein M105 is substituted with either an A, C, D, E, F, G, H, I, K, L, N, P, Q, R, S, T, V, W, or Y; wherein L106 is substituted with either an A, C, D, E, F, G, H, I, K, M, N, P, Q, R, S, T, V, W, or Y; wherein A107 is substituted with either a C, D, E, F, G, H, I, K, L, M, N, P, Q, R, S, T, V, W, or Y; wherein C108 is substituted with either an A, D, E, F, G, H, I, K, L, M, N, P, Q, R, S, T, V, W, or Y; wherein Y109 is substituted with either an A, C, D, E, F, G, H, I, K, L, M, N, P, Q, R, S, T, V, or W; wherein L110 is substituted with either an A, C, D, E, F, G, H, I, K, M, N, P, Q, R, S, T, V, W, or Y; and/or wherein V111 is substituted with either an A, C, D, E, F, G, H, I, K, L, M, N, P, Q, R, S, T, W, or Y of SEQ ID NO:152, in addition to any combination thereof. The present invention also encompasses the use of these BMY_HPP2 phosphatase active site domain amino acid substituted polypeptides as immunogenic and/or antigenic epitopes as described elsewhere herein.

In preferred embodiments, the following BMY_HPP2 phosphatase active site domain conservative amino acid substitutions are encompassed by the present invention: wherein M1 is substituted with either an A, G, S, or T; wherein G2 is substituted with either an A, M, S, or T; wherein V3 is substituted with either an A, I, or L; wherein Q4 is substituted with a N; wherein P5 is a P; wherein P6 is a P; wherein N7 is substituted with a Q; wherein F8 is substituted with either a W, or Y; wherein S9 is substituted with either an A, G, M, or T; wherein W10 is either an F, or Y; wherein V11 is substituted with either an A, I, or L; wherein L12 is substituted with either an A, I, or V; wherein P13 is a P; wherein G14 is substituted with either an A, M, S, or T; wherein R15 is substituted with either a K, or H; wherein L16 is substituted with either an A, I, or V; wherein A17 is substituted with either a G, I, L, M, S, T, or V; wherein G18 is substituted with either an A, M, S, or T; wherein L19 is substituted with either an A, I, or V; wherein A20 is substituted with either a G, I, L, M, S, T, or V; wherein L21 is substituted with either an A, I, or V; wherein P22 is a P; wherein R23 is substituted with either a K, or H; wherein L24 is substituted with either an A, I, or V; wherein P25 is a P; wherein A26 is substituted with either a G, I, L, M, S, T, or V; wherein H27 is substituted with either a K, or R; wherein Y28 is either an F, or W; wherein Q29 is substituted with a N; wherein F30 is substituted with either a W, or Y; wherein L31 is substituted with either an A, I, or V; wherein L32 is substituted with either an A, I, or V; wherein D33 is substituted with an E; wherein L34 is substituted with either an A, I, or V; wherein G35 is substituted with either an A, M, S, or T; wherein V36 is substituted with either an A, I, or L; wherein R37 is substituted with either a K, or H; wherein H38 is substituted with either a K, or R; wherein L39 is substituted with either an A, I, or V; wherein V40 is substituted with either an A, I, or L; wherein S41 is substituted with either an A, G, M, or T; wherein L42 is substituted with either an A, I, or V; wherein T43 is substituted with either an A, G, M, or S; wherein E44 is substituted with a D; wherein R45 is substituted with either a K, or H; wherein G46 is substituted with either an A, M, S, or T; wherein P47 is a P; wherein P48 is a P; wherein H49 is substituted with either a K, or R; wherein S50 is substituted with either an A, G, M, or T; wherein D51 is substituted with an E; wherein S52 is substituted with either an A, G, M, or T; wherein C53 is a C; wherein P54 is a P; wherein G55 is substituted with either an A, M, S, or T; wherein L56 is substituted with either an A, I, or V; wherein T57 is substituted with either an A, G, M, or S; wherein L58 is substituted with either an A, I, or V; wherein H59 is substituted with either a K, or R; wherein R60 is substituted with either a K, or H; wherein L61 is substituted with either an A, I, or V; wherein R62 is substituted with either a K, or H; wherein I63 is substituted with either an A, V, or L; wherein P64 is a P; wherein D65 is substituted with an E; wherein F66 is substituted with either a W, or Y; wherein C67 is a C; wherein P68 is a P; wherein P69 is a P; wherein A70 is substituted with either a G, I, L, M, S, T, or V; wherein P71 is a P; wherein D72 is substituted with an E; wherein Q73 is substituted with a N; wherein I74 is substituted with either an A, V, or L; wherein D75 is substituted with an E; wherein R76 is substituted with either a K, or H; wherein F77 is substituted with either a W, or Y; wherein V78 is substituted with either an A, I, or L; wherein Q79 is substituted with a N; wherein I80 is substituted with either an A, V, or L; wherein V81 is substituted with either an A, I, or L; wherein D82 is substituted with an E; wherein E83 is substituted with a D; wherein A84 is substituted with either a G, I, L, M, S, T, or V; wherein N85 is substituted with a Q; wherein A86 is substituted with either a G, I, L, M, S, T, or V; wherein R87 is substituted with either a K, or H; wherein G88 is substituted with either an A, M, S, or T; wherein E89 is substituted with a D; wherein A90 is substituted with either a G, I, L, M, S, T, or V; wherein V91 is substituted with either an A, I, or L; wherein G92 is substituted with either an A, M, S, or T; wherein V93 is substituted with either an A, I, or L; wherein H94 is substituted with either a K, or R; wherein C95 is a C; wherein A96 is substituted with either a G, I, L, M, S, T, or V; wherein L97 is substituted with either an A, I, or V; wherein G98 is substituted with either an A, M, S, or T; wherein F99 is substituted with either a W, or Y; wherein G100 is substituted with either an A, M, S, or T; wherein R101 is substituted with either a K, or H; wherein T102 is substituted with either an A, G, M, or S; wherein G103 is substituted with either an A, M, S, or T; wherein T104 is substituted with either an A, G, M, or S; wherein M105 is substituted with either an A, G, S, or T; wherein L106 is substituted with either an A, I, or V; wherein A107 is substituted with either a G, I, L, M, S, T, or V; wherein C108 is a C; wherein Y109 is either an F, or W; wherein L110 is substituted with either an A, I, or V; and/or wherein V111 is substituted with either an A, I, or L of SEQ ID NO:152 in addition to any combination thereof. Other suitable substitutions within the BMY_HPP2 phosphatase active site domain are encompassed by the present invention and are referenced elsewhere herein. The present invention also encompasses the use of these BMY_HPP2 phosphatase active site domain conservative amino acid substituted polypeptides as immunogenic and/or antigenic epitopes as described elsewhere herein.

In preferred embodiments, the present invention encompasses a polynucleotide lacking the initiating start codon, in addition to, the resulting encoded polypeptide of BMY_HPP2. Specifically, the present invention encompasses the polynucleotide corresponding to nucleotides 92 thru 538 of SEQ ID NO:151, and the polypeptide corresponding to amino acids 2 thru 150 of SEQ ID NO:152. Also encompassed are recombinant vectors comprising said encoding sequence, and host cells comprising said vector.

The present invention also provides a three-dimensional homology model of the BMY_HPP2 polypeptide (see FIG. 32) representing amino acid residues M1 to K150 of the polypeptide sequence of BMY_HPP2 (amino acid residues M1 to K150 of SEQ ID NO:152). A three-dimensional homology model can be constructed on the basis of the known structure of a homologous protein (Greer et al, 1991, Lesk, et al, 1992, Cardozo, et al, 1995, Yuan, et al, 1995). The homology model of the BMY_HPP2 polypeptide sequence (SEQ ID NO:152), was based upon the homologous structure of 1 vhr from the N-terminus of the human dual specificity phosphatase (vaccinia H1-related phosphatase VN1) (residues N31-K179; Protein Data Bank, PDB entry 1 vhr chain A; Genbank Accession No. gi|1633321; SEQ ID NO:207) and is defined by the set of structural coordinates set forth in Table IX herein.

Homology models are useful when there is no experimental information available on the protein of interest. A 3-dimensional model can be constructed on the basis of the known structure of a homologous protein (Greer et al, 1991, Lesk, et al, 1992, Cardozo, et al, 1995, Sali, et al, 1995).

Those of skill in the art will understand that a homology model is constructed on the basis of first identifying a template, or, protein of known structure which is similar to the protein without known structure. This can be accomplished by through pairwise alignment of sequences using such programs as FASTA (Pearson, et al 1990) and BLAST (Altschul, et al, 1990). In cases where sequence similarity is high (greater than 30%) these pairwise comparison methods may be adequate. Likewise, multiple sequence alignments or profile-based methods can be used to align a query sequence to an alignment of multiple (structurally and biochemically) related proteins. When the sequence similarity is low, more advanced techniques are used such as fold recognition (protein threading; Hendlich, et al, 1990), where the compatibility of a particular sequence with the 3-dimensional fold of a potential template protein is gauged on the basis of a knowledge-based potential. Following the initial sequence alignment, the query template can be optimally aligned by manual manipulation or by incorporation of other features (motifs, secondary structure predictions, and allowed sequence conservation). Next, structurally conserved regions can be identified and used to construct the core secondary structure (Sali, et al, 1995). Loops can be added using knowledge-based techniques, and refined performing forcefield calculations (Sali, et al, 1995, Cardozo, et al, 1995).

For BMY_HPP2 the pairwise alignment method FASTA (Pearson, et al 1990) and fold recognition methods (protein threading) generated identical sequence alignments for a portion (residues M1 to K150 of SEQ ID NO:152) of BMY_HPP2 aligned with the sequence of 1 vhr from the N-terminus of the human dual specificity phosphatase (vaccinia H1-related phosphatase VN1) (residues N31-K179; Protein Data Bank, PDB entry 1 vhr chain A; Genbank Accession No. gi|1633321; SEQ ID NO:207). The alignment of BMY_HPP2 with PDB entry 1 vhr is set forth in FIG. 31. In this invention, the homology model of BMY_HPP2 was derived from the sequence alignment set forth in FIG. 31, and hence an overall atomic model including plausible sidechain orientations using the program LOOK (Levitt, 1992). The three dimensional model for BMY-HPP2 is defined by the set of structure coordinates as set forth in Table IX and visualized in FIG. 32.

In order to recognize errors in three-dimensional structures knowledge based mean fields can be used to judge the quality of protein folds (Sippl 1993). The methods can be used to recognize misfolded structures as well as faulty parts of structural models. The technique generates an energy graph where the energy distribution for a given protein fold is displayed on the y-axis and residue position in the protein fold is displayed on the x-axis. The knowledge based mean fields compose a force field derived from a set of globular protein structures taken as a subset from the Protein Data Bank (Bernstein et. al. 1977). To analyze the quality of a model the energy distribution is plotted and compared to the energy distribution of the template from which the model was generated. FIG. 33 shows the energy graph for theBMY_HPP2 model (dotted line) and the template (1vhr, a dual-specificity phosphatase) from which the model was generated. It is clear that the model and template have similar energies over the aligned region, suggesting thatBMY_HPP2 is in a "native-like" conformation. This graph supports the motif and sequence alignments in confirming that the three dimensional structure coordinates ofBMY_HPP2 are an accurate and useful representation for the polypeptide.

The term "structure coordinates" refers to Cartesian coordinates generated from the building of a homology model.

Those of skill in the art will understand that a set of structure coordinates for a protein is a relative set of points that define a shape in three dimensions. Thus, it is possible that an entirely different set of coordinates could define a similar or identical shape. Moreover, slight variations in the individual coordinates, as emanate from generation of similar homology models using different alignment templates (i.e., other than the structure coordinates of 1 vhr), and/or using different methods in generating the homology model, will have minor effects on the overall shape. Variations in coordinates may also be generated because of mathematical manipulations of the structure coordinates. For example, the structure coordinates set forth in Table IX and visualized in FIG. 32 could be manipulated by fractionalization of the structure coordinates; integer additions or subtractions to sets of the structure coordinates, inversion of the structure coordinates or any combination of the above.

Various computational analyses are therefore necessary to determine whether a molecule or a portion thereof is sufficiently similar to all or parts of BMY_HPP2 described above as to be considered the same. Such analyses may be carried out in current software applications, such as INSIGHTII (Molecular Simulations Inc., San Diego, Calif.) version 2000 and as described in the accompanying User's Guide.

Using the superimposition tool in the program INSIGHTII comparisons can be made between different structures and different conformations of the same structure. The procedure used in INSIGHTII to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. Since atom equivalency within INSIGHTII is defined by user input, for the purpose of this invention we will define equivalent atoms as protein backbone atoms (N, $C\alpha$, C and O) for all conserved residues between the two structures being compared. We will also consider only rigid fitting operations. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by INSIGHTII. For the purpose of this invention, any homology model of a BMY_HPP2 that has a root mean square deviation of conserved residue backbone atoms (N, $C\alpha$, C, O) of less than 3.0 A when superimposed on the relevant backbone atoms described by structure coordinates listed in Table IX and visualized in FIG. 32 are considered identical. More preferably, the root mean square deviation is less than 2.0 Å.

This invention as embodied by the homology model enables the structure-based design of modulators of the biological function of BMY_HPP2, as well as mutants with altered biological function and/or specificity.

There is 23% sequence identity between catalytic domain of BMY_HPP2 and the human dual specificity phosphatase VHR (Yuvaniyama, J., et al., 1996; PDB identifier 1 vhr) which was used as the template for 3D model generation as determined by the GAP program within GCG (Genetics Computer Group, Wisconsin). For the BMY_HPP2 the functionally important residues are located in a cleft comprised of residues D65, H94-C95-X—X-G98-X—X—R101 (the 'active site'). All these residues are conserved in 1 vhr (D92, H123-C124-X—X-G127-X—X—R130). Based on the sequence alignment disclosed in FIG. 31 and the structural model disclosed in Table IX and visualized in FIG. 32, D65 is identified as a general acid, C95 as the catalytic Cysteine nucleophile which cleaves the phosphodiester bond, and R101 as the essential Argenine which activates the bond for cleavage as described in the literature (reviewed by Fauman and Saper, 1996).

In a preferred embodiment of the present invention, the molecule comprises the cleft region defined by structure coordinates of BMY_HPP2 amino acids described above according to Table IX, or a mutant of said molecule.

More preferred are molecules comprising all or any part of the cleft or a mutant or homologue of said molecule or molecular complex. By mutant or homologue of the molecule it is meant a molecule that has a root mean square deviation from the backbone atoms of said BMY_HPP2 amino acids of not more than 3.5 Angstroms.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the relevant portion of the backbone of BMY_HPP2 as defined by the structure coordinates described herein.

The structure coordinates of a BMY_HPP2 homology model portions thereof are stored in a machine-readable storage medium. Such data may be used for a variety of purposes, such as drug discovery.

Accordingly, in one embodiment of this invention is provided a machine-readable data storage medium comprising a data storage material encoded with the structure coordinates set forth in Table IX One embodiment utilizes System 10 as disclosed in WO 98/11134, the disclosure of which is incorporated herein by reference in its entirety. Briefly, one version of these embodiments comprises a computer comprising a central processing unit ("CPU"), a working memory which may be, e.g., RAM (random-access memory) or "core" memory, mass storage memory (such as one or more disk drives or CD-ROM drives), one or more cathode-ray tube ("CRT") display terminals, one or more keyboards, one or more input lines, and one or more output lines, all of which are interconnected by a conventional bidirectional system bus.

Input hardware, coupled to the computer by input lines, may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, keyboard may also be used as an input device.

Output hardware, coupled to the computer by output lines, may similarly be implemented by conventional devices. By way of example, output hardware may include a CRT display terminal for displaying a graphical representation of a region or domain of the present invention using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage, and accesses to and from the working memory, and determines the sequence of data processing steps. A number of programs may be used to process the machine-readable data of this invention. Such programs are discussed in reference to the computational methods of drug discovery as described herein. Specific references to components of the hardware system are included as appropriate throughout the following description of the data storage medium.

For the purpose of the present invention, any magnetic data storage medium which can be encoded with machine-readable data would be sufficient for carrying out the storage requirements of the system. The medium could be a conventional floppy diskette or hard disk, having a suitable substrate, which may be conventional, and a suitable coating, which may be conventional, on one or both sides, containing magnetic domains whose polarity or orientation could be altered magnetically, for example. The medium may also have an opening for receiving the spindle of a disk drive or other data storage device.

The magnetic domains of the coating of a medium may be polarized or oriented so as to encode in a manner which may be conventional, machine readable data such as that described herein, for execution by a system such as the system described herein.

Another example of a suitable storage medium which could also be encoded with such machine-readable data, or set of instructions, which could be carried out by a system such as the system described herein, could be an optically-readable data storage medium. The medium could be a conventional compact disk read only memory (CD-ROM) or a rewritable medium such as a magneto-optical disk which is optically readable and magneto-optically writable. The medium preferably has a suitable substrate, which may be conventional, and a suitable coating, which may be conventional, usually of one side of substrate.

In the case of a CD-ROM, as is well known, the coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Thus, in accordance with the present invention, data capable of displaying the three dimensional structure of the BMY_HPP2 homology model, or portions thereof and their structurally similar homologues is stored in a machine-readable storage medium, which is capable of displaying a graphical three-dimensional representation of the structure. Such data may be used for a variety of purposes, such as drug discovery.

For the first time, the present invention permits the use, through homology modeling based upon the sequence of BMY_HPP2 (FIG. 21; SEQ ID NO:152) of structure-based or rational drug design techniques to design, select, and synthesize chemical entities that are capable of modulating the biological function of BMY_HPP2.

Accordingly, the present invention is also directed to the entire sequence in FIG. 21 or any portion thereof for the purpose of generating a homology model for the purpose of 3D structure-based drug design.

For purposes of this invention, we include mutants or homologues of the sequence in FIG. 21 or any portion thereof. In a preferred embodiment, the mutants or homologues have at least 25% identity, more preferably 50% identity, more preferably 75% identity, and most preferably 90% identity to the amino acid residues in FIG. 21.

The three-dimensional model structure of the BMY_HPP2 will also provide methods for identifying modulators of biological function. Various methods or combination thereof can be used to identify these compounds.

Structure coordinates of the catalytic region defined above can also be used to identify structural and chemical features. Identified structural or chemical features can then be employed to design or select compounds as potential BMY_HPP2 modulators. By structural and chemical features it is meant to include, but is not limited to, van der Waals interactions, hydrogen bonding interactions, charge interaction, hydrophobic bonding interaction, and dipole interaction. Alternatively, or in conjunction, the three-dimensional structural model can be employed to design or select compounds as potential BMY_HPP2 modulators. Compounds identified as potential BMY_HPP2 modulators can then be synthesized and screened in an assay characterized by binding of a test compound to the BMY_HPP2, or in characterizing BMY_HPP2 deactivation in the presence of a small molecule. Examples of assays useful in screening of potential BMY_HPP2 modulators include, but are not limited to, screening in silico, in vitro assays and high throughput assays. Finally, these methods may also involve modifying or replacing one or more amino acids from BMY_HPP2 according to Table IX.

However, as will be understood by those of skill in the art upon this disclosure, other structure based design methods can be used. Various computational structure based design methods have been disclosed in the art.

For example, a number of computer modeling systems are available in which the sequence of the BMY_HPP2 and the BMY_HPP2 structure (i.e., atomic coordinates of BMY_HPP2 and/or the atomic coordinates of the active site as provided in Table IX) can be input. This computer system then generates the structural details of one or more these regions in which a potential BMY_HPP2 modulator binds so that complementary structural details of the potential modulators can be determined. Design in these modeling systems is generally based upon the compound being capable of physically and structurally associating with BMY_HPP2. In addition, the compound must be able to assume a conformation that allows it to associate with BMY_HPP2. Some modeling systems estimate the potential inhibitory or binding effect of a potential BMY_HPP2 modulator prior to actual synthesis and testing.

Methods for screening chemical entities or fragments for their ability to associate with a given protein target are also well known. Often these methods begin by visual inspection of the binding site on the computer screen. Selected fragments or chemical entities are then positioned in one or more of the active site region in BMY_HPP2. Docking is accomplished using software such as INSIGHTII, QUANTA and SYBYL, following by energy minimization and molecular dynamics with standard molecular mechanic forcefields such as CHARMM and AMBER. Examples of computer programs which assist in the selection of chemical fragment or chemical entities useful in the present invention include, but are not limited to, GRID (Goodford, 1985), AUTODOCK (Goodsell, 1990), and DOCK (Kuntz et al. 1982).

Upon selection of preferred chemical entities or fragments, their relationship to each other and BMY_HPP2 can be visualized and then assembled into a single potential modulator. Programs useful in assembling the individual chemical entities include, but are not limited to SYBYL and LeapFrog (Tripos Associates, St. Louis Mo.), LUDI (Bohm 1992) and 3D Database systems (Martin 1992).

Alternatively, compounds may be designed de novo using either an empty active site or optionally including some portion of a known inhibitor. Methods of this type of design include, but are not limited to LUDI (Bohm 1992) and LeapFrog (Tripos Associates, St. Louis Mo.).

In addition, BMY_HPP2 is overall well suited to modern methods including combinatorial chemistry.

Programs such as DOCK (Kuntz et al. 1982) can be used with the atomic coordinates from the homology model to identify potential ligands from databases or virtual databases which potentially bind the in the metal binding region, and which may therefore be suitable candidates for synthesis and testing.

Additionally, the three-dimensional homology model of BMY_HPP2 will aid in the design of mutants with altered biological activity.

Many polynucleotide sequences, such as EST sequences, are publicly available and accessible through sequence databases. Some of these sequences are related to SEQ ID NO:151 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 864 of SEQ ID NO:151, b is an integer between 15 to 878, where both a and b correspond to the positions of nucleotide residues shown in SEQ ID NO:151, and where b is greater than or equal to a+14.

Features of the Polypeptide Encoded by Gene No:3

The polypeptide fragment corresponding to this gene provided as SEQ ID NO:8 (FIG. 3), encoded by the polynucleotide sequence according to SEQ ID NO:7 (FIG. 3), and/or encoded by the polynucleotide contained within the deposited clone, BMY_HPP3, has significant homology at the nucleotide and amino acid level to a number of phosphatases, which include, for example, the human protein tyrosine phosphatase PTPCAAX1 protein (HS_PTPCAAX1; Genbank Accession No:gil AAB40597; SEQ ID NO:33); the human protein tyrosine phosphatase PTPCAAX2 (HS_PTPCAAX2; Genbank Accession No:gil AAB40598; SEQ ID NO:34); the mouse prenylated protein tyrosine phosphatase (MM_PTPCAAX; Genbank Accession No:gil JC5981; SEQ ID NO:35); and the *Drosophila*

PRL-1 protein (DM_PRL1; Genbank Accession No:gi| AAF53506; SEQ ID NO:36) as determined by BLASTP. An alignment of the human phosphatase polypeptide with these proteins is provided in FIG. 8.

BMY_HPP3 is predicted to be a prenylated phosphoprotein phosphatase based on its similarity to drosophila, mouse and human prenylated phosphotyrosine phosphatases (PTP-CAAX proteins). Among the conserved catalytic residues, there is a conserved Aspartate ("D") and a conserved nucleophilic Cysteine ("C") as shown in FIG. 8. At the C-terminus, a consensus prenylation site is conserved in BMY_HPP3 suggesting that the protein could be post-translationally modified by farnesylation or geranylation.

Preferred polynucleotides of the present invention comprise the following nucleic acid sequence:

ATGGCTAGAATGAACCTCCCTGCTTCTGTGGACATTGCATACAAAAATGT GAGATTTCTTATTACACACAACCCAACCAATACCTACTTTAATAGATTCTT ACAGGAACTTAAGCAGGATGGAGTTACCACCATAGTAAGAGTATGAAAA GCAACTTACAACATTGCTCTTTTAGAGAAGGGAAGCATCCAGGTTCCGGA CTGGCCTTTTGATGATGGTACAGCACCATCCAGCCAGATAATTGATAACTG GTTAAAACTTATGAAAAATAAATTTCATGAAGATCCTGGTTGTTGTATTGC AATTCACTGTGTTGTAGGTTTTGGGTGAGCTCCAGTTGCTAGTTGCCCTAG CTTTAATTGAAGGTGGAATGAAATATGAAAATGTAGTACAGTTCATCAGA TAAAAGTGACATGGAACTTTTAACAGCAAACAACTTTTGTATTTGGAGAA ATATTGTCTTAAAATATGCTTGCACCTCAGAAATCCCAGAAATAACTGTTT CCTTCAG (SEQ ID NO: 83). Polypeptides encoding by these polynucleotides are also provided.

Preferred polypeptides of the present invention comprise the following amino acid sequence:

MARMNLPASVDIAYKNVRFLITHNPTNTYFNRFLQELKQDGVTTIVRVKATY NIALLEKGSIQVPDWPFDDGTAPSSQIIDNWLKLMKNKFHEDPGCCIAIHCVV GFGELQLLVALALIEGGMKYENVVQFIRKHGTFNSKQLLYLEKYCLKICLHLR NPRNNCFLQ (SEQ ID NO:84). Polynucleotides encoding these polypeptides are also provided.

Based upon the strong homology to members of the phosphatase proteins, the polypeptide encoded by the human BMY_HPP3 phosphatase of the present invention is expected to share at least some biological activity with phosphatase proteins, preferably with members of the novel phosphotyrosine/dual-specificity (P-Tyr, P-Ser and P-Thr) phosphatases, particularly the novel phosphotyrosine/dual-specificity (P-Tyr, P-Ser and P-Thr) phosphatases referenced herein.

The present invention encompasses the use of BMY_HPP3 inhibitors and/or activators of BMY_HPP3 activity for the treatment, detection, amelioration, or prevention of phosphatase associated disorders, including but not limited to metabolic diseases such as diabetes, in addition to neural and/or cardiovascular diseases and disorders. The present invention also encompasses the use of BMY_HPP3 inhibitors and/or activators of BMY_HPP3 activity as immunosuppressive agents, anti-inflammatory agents, and/or anti-tumor agents The present invention encompasses the use of BMY_HPP3 phosphatase inhibitors, including, antagonists such as antisense nucleic acids, in addition to other antagonists, as described herein, in a therapeutic regimen to diagnose, prognose, treat, ameliorate, and/or prevent diseases where a kinase activity is insufficient. One, non-limiting example of a disease which may occur due to insufficient kinase activity are certain types of diabetes, where one or more kinases involved in the insulin receptor signal pathway may have insufficient activity or insufficient expression, for example.

Moreover, the present invention encompasses the use of BMY_HPP3 phosphatase activators, and/or the use of the BMY_HPP3 phosphatase gene or protein in a gene therapy regimen, as described herein, for the diagnoses, prognoses, treatment, amelioration, and/or prevention of diseases and/or disorders where a kinase activity is overly high, such as a cancer where a kinase oncogene product has excessive activity or excessive expression.

The present invention also encompasses the use of catalytically inactive variants of BMY_HPP3 proteins, including fragments thereof, such as a protein therapeutic, or the use of the encoding polynucleotide sequence or as gene therapy, for example, in the diagnoses, prognosis, treatment, amelioration, and/or prevention of diseases or disorders where phosphatase activity is overly high.

The present invention encompasses the use of antibodies directed against the BMY_HPP3 polypeptides, including fragment and/or variants thereof, of the present invention in diagnostics, as a biomarkers, and/or as a therapeutic agents.

The present invention encompasses the use of an inactive, non-catalytic, mutant of the BMY_HPP3 phosphatase as a substrate trapping mutant to bind cellular phosphoproteins or a library of phosphopeptides to identify substrates of the BMY_HPP3 polypeptides.

The present invention encompasses the use of the BMY_HPP3 polypeptides, to identify inhibitors or activators of the BMY_HPP3 phosphatase activity using either in vitro or 'virtual' (in silico) screening methods.

One embodiment of the invention relates to a method for identifying a compound as an activator or inhibitor of the BMY_HPP3 phosphatase comprising the steps of: i.) contacting a BMY_HPP3 phosphatase inhibitor or activator labeled with an analytically detectable reagent with the BMY_HPP3 phosphatase under conditions sufficient to form a complex with the inhibitor or activator; ii.) contacting said complex with a sample containing a compound to be identified; iii) and identifying the compound as an inhibitor or activator by detecting the ability of the test compound to alter the amount of labeled known BMY_HPP3 phosphatase inhibitor or activator in the complex.

Another embodiment of the invention relates to a method for identifying a compound as an activator or inhibitor of a BMY_HPP3 phosphatase comprising the steps of: i.) contacting the BMY_HPP3 phosphatase with a compound to be identified; and ii.) and measuring the ability of the BMY_HPP3 phosphatase to remove phosphate from a substrate.

The present invention also encompasses a method for identifying a ligand for the BMY_HPP3 phosphatase comprising the steps of: i.) contacting the BMY_HPP3 phosphatase with a series of compounds under conditions to permit binding; and ii.) detecting the presence of any ligand-bound protein.

Preferably, the above referenced methods comprise the BMY_HPP3 phosphatase in a form selected from the group consisting of whole cells, cytosolic cell fractions, membrane cell fractions, purified or partially purified forms. The invention also relates to recombinantly expressed BMY_HPP3 phosphatase in a purified, substantially purified, or unpurified state. The invention further relates to BMY_HPP3 phosphatase fused or conjugated to a protein, peptide, or other molecule or compound known in the art, or referenced herein.

The present invention also encompasses pharmaceutical composition of the BMY_HPP3 phosphatase polypeptide comprising a compound identified by above referenced methods and a pharmaceutically acceptable carrier.

Features of the Polypeptide Encoded by Gene No:4

The polypeptide fragment corresponding to this gene provided as SEQ ID NO:10 (FIG. 4), encoded by the polynucleotide sequence according to SEQ ID NO:9 (FIG. 4), and/or encoded by the polynucleotide contained within the deposited clone, BMY_HPP4, has significant homology at the nucleotide and amino acid level to a number of phosphatases, which include, for example, the mouse osteotesticular protein tyrosine phosphatase (MM_OST-PTP; Genbank Accession No:gi| AAG28768; SEQ ID NO:37); and the rat protein-tyrosine-phosphatase (RN_PTP-OST; Genbank Accession No:gi| A55148; SEQ ID NO:38) as determined by BLASTP. An alignment of the human phosphatase polypeptide with these proteins is provided in FIG. 9.

BMY_HPP4 is predicted to be a phosphoprotein phosphatase based on its homology to rat osteotesticular receptor protein-tyrosine-phosphatase precursor (Genbank ID 1083770) and to mouse receptor protein-tyrosine-phosphatase precursor (Genbank ID 11066925). The BMY_HPP4 polypeptide has been shown to comprise a conserved Aspartate ("D") at amino acid 182 of SEQ ID NO:10 (FIG. 4), a catalytic Cysteine ("C") at amino acid 216 of SEQ ID NO:10 (FIG. 4), and a conserved Argenine ("R") at amino acid 227 of SEQ ID NO:10 (FIG. 4).

The predicted exon structure of the BMY_HPP4 gene is provided in Table V. The 'Start' and 'End' designations refer to the respective nucleotide positions of the BMY_HPP4 as they appear for BAC AL 354751. The numbering begins at the start of BAC AL354751; nucleotide 71352 in the BAC is equivalent to nucleotide 1 of the BMY_HPP4 transcript (SEQ ID NO:9; FIG. 4).

Based upon the strong homology to members of the phosphatase proteins, the polypeptide encoded by the human BMY_HPP4 phosphatase of the present invention is expected to share at least some biological activity with phosphatase proteins, preferably with members of the novel phosphotyrosine/dual-specificity (P-Tyr, P-Ser and P-Thr) phosphatases, particularly the novel phosphotyrosine/dual-specificity (P-Tyr, P-Ser and P-Thr) phosphatases referenced herein.

The present invention encompasses the use of BMY_HPP4 inhibitors and/or activators of BMY_HPP4 activity for the treatment, detection, amelioration, or prevention of phosphatase associated disorders, including but not limited to metabolic diseases such as diabetes, in addition to neural and/or cardiovascular diseases and disorders. The present invention also encompasses the use of BMY_HPP4 inhibitors and/or activators of BMY_HPP4 activity as immunosuppressive agents, anti-inflammatory agents, and/or anti-tumor agents The present invention encompasses the use of BMY_HPP4 phosphatase inhibitors, including, antagonists such as antisense nucleic acids, in addition to other antagonists, as described herein, in a therapeutic regimen to diagnose, prognose, treat, ameliorate, and/or prevent diseases where a kinase activity is insufficient. One, non-limiting example of a disease which may occur due to insufficient kinase activity are certain types of diabetes, where one or more kinases involved in the insulin receptor signal pathway may have insufficient activity or insufficient expression, for example.

Moreover, the present invention encompasses the use of BMY_HPP4 phosphatase activators, and/or the use of the BMY_HPP4 phosphatase gene or protein in a gene therapy regimen, as described herein, for the diagnoses, prognoses, treatment, amelioration, and/or prevention of diseases and/or disorders where a kinase activity is overly high, such as a cancer where a kinase oncogene product has excessive activity or excessive expression.

The present invention also encompasses the use of catalytically inactive variants of BMY_HPP4 proteins, including fragments thereof, such as a protein therapeutic, or the use of the encoding polynucleotide sequence or as gene therapy, for example, in the diagnoses, prognosis, treatment, amelioration, and/or prevention of diseases or disorders where phosphatase activity is overly high.

The present invention encompasses the use of antibodies directed against the BMY_HPP4 polypeptides, including fragment and/or variants thereof, of the present invention in diagnostics, as a biomarkers, and/or as a therapeutic agents.

The present invention encompasses the use of an inactive, non-catalytic, mutant of the BMY_HPP4 phosphatase as a substrate trapping mutant to bind cellular phosphoproteins or a library of phosphopeptides to identify substrates of the BMY_HPP4 polypeptides.

The present invention encompasses the use of the BMY_HPP4 polypeptides, to identify inhibitors or activators of the BMY_HPP4 phosphatase activity using either in vitro or 'virtual' (in silico) screening methods.

One embodiment of the invention relates to a method for identifying a compound as an activator or inhibitor of the BMY_HPP4 phosphatase comprising the steps of: i.) contacting a BMY_HPP4 phosphatase inhibitor or activator labeled with an analytically detectable reagent with the BMY_HPP4 phosphatase under conditions sufficient to form a complex with the inhibitor or activator; ii.) contacting said complex with a sample containing a compound to be identified; iii) and identifying the compound as an inhibitor or activator by detecting the ability of the test compound to alter the amount of labeled known BMY_HPP4 phosphatase inhibitor or activator in the complex.

Another embodiment of the invention relates to a method for identifying a compound as an activator or inhibitor of a BMY_HPP4 phosphatase comprising the steps of: i.) contacting the BMY_HPP4 phosphatase with a compound to be identified; and ii.) and measuring the ability of the BMY_HPP4 phosphatase to remove phosphate from a substrate.

The present invention also encompasses a method for identifying a ligand for the BMY_HPP4 phosphatase comprising the steps of: i.) contacting the BMY_HPP4 phosphatase with a series of compounds under conditions to permit binding; and ii.) detecting the presence of any ligand-bound protein.

Preferably, the above referenced methods comprise the BMY_HPP4 phosphatase in a form selected from the group consisting of whole cells, cytosolic cell fractions, membrane cell fractions, purified or partially purified forms. The invention also relates to recombinantly expressed BMY_HPP4 phosphatase in a purified, substantially purified, or unpurified state. The invention further relates to BMY_HPP4 phosphatase fused or conjugated to a protein, peptide, or other molecule or compound known in the art, or referenced herein.

The present invention also encompasses pharmaceutical composition of the BMY_HPP4 phosphatase polypeptide comprising a compound identified by above referenced methods and a pharmaceutically acceptable carrier.

Expression profiling of the BMY_HPP4 polypeptide in normal tissues showed that BMY_HPP4 is expressed at higher levels in the cerebellum than in any other tissue, suggesting a role for modulators of BMY_HPP4 activity in the treatment of neurological disorders such as depression, bipolar disorder, schizophrenia, dementia and cognitive disorders (as shown in FIG. 34). BMY_HPP4 was also expressed at lower levels in other subregions of the brain. In addition, BMY_HPP4 was expressed at significant levels in the pineal and pituitary glands, suggesting a role for modulators of BMY_HPP4 activity in endocrine disorders.

The strong homology to dual specificity phophatases, combined with the localized expression in cerebellum suggests the BMY_HPP4 polynucleotides and polypeptides may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to dual specificity phophatases, combined with the localized expression in pineal and pituitary glands suggests the BMY_HPP4 polynucleotides and polypeptides may be useful in treating, diagnosing, prognosing, and/or preventing endocrine diseases and/or disorders, which include, but are not limited to, the following: aberrant growth hormone synthesis and/or secretion, aberrant prolactin synthesis and/or secretion, aberrant luteinizing hormone synthesis and/or secretion, aberrant follicle-stimulating hormone synthesis and/or secretion, aberrant thyroid-stimulating hormone synthesis and/or secretion, aberrant adrenocorticotropin synthesis and/or secretion, aberrant vasopressin secretion, aberrant oxytocin secretion, aberrant growth, aberrant lactation, aberrant sexual characteristic development, aberrant testosterone synthesis and/or secretion, aberrant estrogen synthesis and/or secretion, aberrant water homeostasis, hypogonadism, Addison's disease, hypothyroidism, Cushing's disease, agromegaly, gigantism, lethargy, osteoporosis, aberrant calcium homeostasis, aberrant potassium homeostasis, reproductive disorders, and developmental disorders.

Features of the Polypeptide Encoded by Gene No:5

The polypeptide corresponding to this gene provided as SEQ ID NO:42 (FIG. 5), encoded by the polynucleotide sequence according to SEQ ID NO:41 (FIG. 5), and/or encoded by the polynucleotide contained within the deposited clone, BMY_HPP5, has significant homology at the nucleotide and amino acid level to a number of phosphatases, which include, for example, the human dual specificity phosphatase 8 (hs_dspp8; Genbank Accession No:gi| NP_004411; SEQ ID NO:39); and the mouse neuronal tyrosine/threonine phosphatase 1 (r mm_npp1; Genbank Accession No:gi| NP_032774; SEQ ID NO:40) as determined by BLASTP. An alignment of the human phosphatase polypeptide with these proteins is provided in FIGS. 10A–B.

The determined nucleotide sequence of the BMY_HPP5 cDNA in FIGS. 5A–E (SEQ ID NO:41) contains an open reading frame encoding a protein of about 665 amino acid residues, with a deduced molecular weight of about 73 kDa. The amino acid sequence of the predicted BMY_HPP5 polypeptide is shown in FIGS. 5A–E (SEQ ID NO:42). The BMY_HPP5 protein shown in FIGS. 5A–E was determined to share significant identity and similarity to several known phosphatases, particularly, dual-specificity protein phosphatases. Specifically, the BMY_HPP5 protein shown in FIGS. 5A–E was determined to be about 46% identical and 58% similar to the human dual specificity phosphatase 8 (HS_DSPP8; Genbank Accession No: gi| NP_004411; SEQ ID NO:39); and about 43% identical and 56% similar to the mouse neuronal tyrosine/threonine phosphatase 1 (MM_NPP1; Genbank Accession No: gi| NP_032774; SEQ ID NO:40), as shown in FIG. 12.

BMY_HPP5 is predicted to encode a phosphoprotein phosphatase based on its homology to known dual-specificity protein phosphatases including human dual-specificity protein phosphatase 8 (GI 4758212) and mouse neuronal tyrosine/threonine phosphatase 1 (GI 6679156) (FIGS. 10A–B). The BMY_HPP5 polypeptide was determined to comprise conserved residues, which include, the catalytic Aspartate ("D") at amino acid 212, and a conserved Cysteine ("C") at amino acid 244, and Arginine ("R") at amino acid 249 of SEQ ID NO:42 (FIGS. 5A–E).

Based upon the strong homology to members of the phosphatase proteins, the polypeptide encoded by the human BMY_HPP5 phosphatase of the present invention is expected to share at least some biological activity with phosphatase proteins, preferably with members of the novel phosphotyrosine/dual-specificity (P-Tyr, P-Ser and P-Thr) phosphatases, particularly the novel phosphotyrosine/dual-specificity (P-Tyr, P-Ser and P-Thr) phosphatases referenced herein.

Expression profiling designed to measure the steady state mRNA levels encoding the human phosphatase polypeptide, BMY_HPP5, showed predominately high expression levels in the testis and spinal cord, and to a lesser extent, in bone marrow, brain, liver, and thymus. (See FIG. 11).

Moreover, expanded expression profiling of the BMY_HPP5 polypeptide in normal human tissues showed the highest levels of expression in the adrenal, pineal and pituitary glands suggesting that modulators of BMY_HPP5 activity could be useful in the treatment of endocrine disorders (as shown in FIG. 35). BMY_HPP5 also expressed at high levels in the cerebellum, suggesting a role for modulators of BMY_HPP5 activity in the treatment of neurological disorders such as depression, bipolar disorder, schizophrenia, dementia and cognitive disorders; in the prostate, suggesting a role for modulators of BMY_HPP5 activity in the treatment of prostate cancer or benign prostatic hyperplasia; in the testis, suggesting a role for modulators of BMY_HPP5 activity in the treatment of male infertility caused by defective or insufficient spermatogenesis, as a contraceptive agent, or in the treatment of testicular cancer. BMYBMY_HPP5 was also expressed at a lower but significant level in many other normal human tissues.

The strong homology to phosphatases, particularly dual-specificity phosphatases, combined with the predominate localized expression in adrenal gland tissue suggests the human BMY_HPP5 phosphatase polynucleotides and polypeptides, including antagonists, and/or fragments thereof, may be useful for treating, diagnosing, prognosing, ameliorating, and/or preventing endocrine disorders, which include, but are mot limited to adrenocortical hyperfunction, adrenocortical hypofunction, lethargy. Congenital adrenal hyperplasia, aberrant ACTH regulation, aberrant adrenaline regulation, disorders associated with defects in P450C21, P450C18, P450C17, and P450C11 hydroxylases and in 3-hydroxysteroid dehydrogenase (3-HSD), hirsutism, oligomenorrhea, acne, virilization, oligomenorrhea, female pseudohermaphroditism, disorders associated with the incidence of aberrant sexual characterisitics, disorders associated with aberrant cortisol secretion, hypertension, hypokalemia, hypogonadism, disorders associated with aberrant androgen secretion, adrenal virilism, Adrenal adenomas, Adrenal carcinomas, disorders associated with aberrant aldosterone secretion, aldosteronism, disorders associated with aberrant steriod biosynthesis, disorders associated with aberrant steriod transport, disorders associated with aberrant steriod secretion, disorders associated with aberrant steriod excretion, Addison's syndrome, and Cushing's syndrome.

The strong homology to phosphatases, particularly dual-specificity phosphatases, combined with the predominate localized expression in pituitary gland tissue suggests the BMY_HPP5 polynucleotides and polypeptides may be useful in treating, diagnosing, prognosing, and/or preventing endocrine diseases and/or disorders, which include, but are not limited to, the following: aberrant growth hormone synthesis and/or secretion, aberrant prolactin synthesis and/ or secretion, aberrant luteinizing hormone synthesis and/or secretion, aberrant follicle-stimulating hormone synthesis and/or secretion, aberrant thyroid-stimulating hormone synthesis and/or secretion, aberrant adrenocorticotropin synthesis and/or secretion, aberrant vasopressin secretion, aberrant oxytocin secretion, aberrant growth, aberrant lactation, aberrant sexual characteristic development, aberrant testosterone synthesis and/or secretion, aberrant estrogen synthesis and/ or secretion, aberrant water homeostasis, hypogonadism, Addison's disease, hypothyroidism, Cushing's disease, agromegaly, gigantism, lethargy, osteoporosis, aberrant calcium homeostasis, aberrant potassium homeostasis, reproductive disorders, developmental disorders, and depression related to low incident light levels.

The strong homology to phosphatases, particularly dual-specificity phosphatases, combined with the predominate localized expression in testis tissue suggests the human BMY_HPP5 phosphatase polynucleotides and polypeptides, including antagonists, and/or fragments thereof, may be useful for treating, diagnosing, prognosing, and/or preventing male reproductive disorders, such as, for example, male infertility, impotence, and/or testicular cancer. This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. If fact, increased expression of certain phosphatases have been identified as tumor markers for testicular cancer (see, for example, Koshida, K., Nishino, A., Yamamoto, H., Uchibayashi, T., Naito, K., Hisazumi, H., Hirano, K., Hayashi, Y., Wahren, B., Andersson, L, J. Urol., 146(1): 57–60, (1991); and Klein, E A, Urol. Clin. North. Am., 20(1):67–73, (1993)).

Alternatively, the strong homology to phosphatases, particularly dual-specificity phosphatases, combined with the significant localized expression in spinal cord and brain tissue suggests the human phosphatase polynucleotides and polypeptides may be useful in treating, diagnosing, prognosing, and/or preventing neural diseases and/or disorders. Representative uses are described in the "Neurological Diseases" section below, and elsewhere herein. Briefly, the expression in neural tissue indicates a role in Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal dyphida, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Moreover, the tissue distribution in liver indicates the protein product of this clone would be useful for the detection and treatment of liver disorders and cancers. Representative uses are described in the "Hyperproliferative Disorders", "Infectious Disease", and "Binding Activity" sections below, and elsewhere herein. Briefly, the protein can be used for the detection, treatment, and/or prevention of hepatoblastoma, jaundice, hepatitis, liver metabolic diseases and conditions that are attributable to the differentiation of hepatocyte progenitor cells. In addition the expression in fetus would suggest a useful role for the protein product in developmental abnormalities, fetal deficiencies, pre-natal disorders and various would-healing diseases and/or tissue trauma.

Moreover, human phosphatase polynucleotides and polypeptides, including fragments and agonists thereof, may have uses which include treating, diagnosing, prognosing, and/or preventing hyperproliferative disorders, particularly of the renal, neural, and reproductive systems. Such disorders may include, for example, cancers, and metastasis.

The human phosphatase polynucleotides and polypeptides, including fragments and agonists thereof, may have uses which include, either directly or indirectly, for boosting immune responses.

The human phosphatase polynucleotides and polypeptides, including fragments and/or antagonists thereof, may have uses which include identification of modulators of human phosphatase function including antibodies (for detection or neutralization), naturally-occurring modulators and small molecule modulators. Antibodies to domains of the human phosphatase protein could be used as diagnostic agents of cardiovascular and inflammatory conditions in patients, are useful in monitoring the activation of signal transduction pathways, and can be used as a biomarker for the involvement of phosphatases in disease states, and in the evaluation of inhibitors of phosphatases in vivo.

Human phosphatase polypeptides and polynucleotides have additional uses which include diagnosing diseases related to the over and/or under expression of human phosphatase by identifying mutations in the human phosphatase gene by using human phosphatase sequences as probes or by determining human phosphatase protein or mRNA expression levels. Human phosphatase polypeptides may be useful for screening compounds that affect the activity of the protein. Human phosphatase peptides can also be used for the generation of specific antibodies and as bait in yeast two hybrid screens to find proteins the specifically interact with human phosphatase (described elsewhere herein).

Although it is believed the encoded polypeptide may share at least some biological activities with phosphatase proteins (particularly dual specificity proteins), a number of methods of determining the exact biological function of this clone are either known in the art or are described elsewhere herein. Briefly, the function of this clone may be determined by applying microarray methodology. Nucleic acids corresponding to the human phosphatase polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from diseased heart tissue, as compared to, normal tissue might indicate a function in modulating cardiac function, for example. In the case of human BMY_HPP5 phosphatase, testis, spinal cord, brain, liver, bone marrow, and thymus tissue should be used, for example, to extract RNA to prepare the probe.

In addition, the function of the protein may be assessed by applying quantitative PCR methodology, for example. Real time quantitative PCR would provide the capability of following the expression of the human phosphatase gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of human phosphatase, a disease correlation related to human phosphatase may be made by comparing the mRNA expression level of human phosphatase in normal tissue, as compared to diseased tissue (particularly diseased tissue isolated from the following: testis, spinal cord, brain, liver, bone marrow, and thymus tissue). Significantly higher or lower levels of human phosphatase expression in the diseased tissue may suggest human phosphatase plays a role in disease progression, and antagonists against human phosphatase polypeptides would be useful therapeutically in treating, preventing, and/or ameliorating the disease. Alternatively, significantly higher or lower levels of human phosphatase expression in the diseased tissue may suggest human phosphatase plays a defensive role against disease progression, and agonists of human phosphatase polypeptides may be useful therapeutically in treating, preventing, and/or ameliorating the disease. Also encompassed by the present invention are quantitative PCR probes corresponding to the polynucleotide sequence provided as SEQ ID NO:41 (FIGS. 4A–D).

The function of the protein may also be assessed through complementation assays in yeast. For example, in the case of the human phosphatase, transforming yeast deficient in purinergic receptor activity, for example, and assessing their ability to grow would provide convincing evidence the human phosphatase polypeptide has purinergic receptor activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype. Such knock-out experiments are known in the art, some of which are disclosed elsewhere herein.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a kidney, lung, spinal cord, or testes tissue specific promoter), or it can be expressed at a specified time of development using an inducible and/or a developmentally regulated promoter.

In the case of human phosphatase transgenic mice or rats, if no phenotype is apparent in normal growth conditions, observing the organism under diseased conditions (renal, pulmonary, neurological, or reproductive disorders, in addition to cancers, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal deletion mutants are encompassed by the present invention: M1-S665, A2-S665, H3-S665, E4-S665, M5-S665, I6-S665, G7-S665, T8-S665, Q9-S665, I10-S665, V11-S665, T12-S665, E13-S665, R14-S665, L15-S665, V16-S665, A17-S665, L18-S665, L19-S665, E20-S665, S21-S665, G22-S665, T23-S665, E24-S665, K25-S665, V26-S665, L27-S665, L28-S665, I29-S665, D30-S665, S31-S665, R32-S665, P33-S665, F34-S665, V35-S665, E36-S665, Y37-S665, N38-S665, T39-S665, S40-S665, H41-S665, I42-S665, L43-S665, E44-S665, A45-S665, I46-S665, N47-S665, I48-S665, N49-S665, C50-S665, S51-S665, K52-S665, L53-S665, M54-S665, K55-S665, R56-S665, R57-S665, L58-S665, Q59-S665, Q60-S665, D61-S665, K62-S665, V63-S665, L64-S665, I65-S665, T66-S665, E67-S665, L68-S665, I69-S665, Q70-S665, H71-S665, S72-S665, A73-S665, K74-S665, H75-S665, K76-S665, V77-S665, D78-S665, I79-S665, D80-S665, C81-S665, S82-S665, Q83-S665, K84-S665, V85-S665, V86-S665, V87-S665, A73-S665, D89-S665, Q90-S665, S91-S665, S92-

S665, Q93-S665, D94-S665, V95-S665, A96-S665, S97-S665, L98-S665, S99-S665, S100-S665, D101-S665, C102-S665, F103-S665, L104-S665, T105-S665, V106-S665, L107-S665, L108-S665, G109-S665, K110-S665, L111-S665, E112-S665, K113-S665, S114-S665, F115-S665, N116-S665, S117-S665, V118-S665, H119-S665, L120-S665, L121-S665, A122-S665, G123-S665, G124-S665, F125-S665, A126-S665, E127-S665, F128-S665, S129-S665, R130-S665, C131-S665, F132-S665, P133-S665, G134-S665, L135-S665, C136-S665, E137-S665, G138-S665, K139-S665, S140-S665, T141-S665, L142-S665, V143-S665, P144-S665, T145-S665, C146-S665, I147-S665, S148-S665, Q149-S665, P150-S665, C151-S665, L152-S665, P153-S665, V154-S665, A155-S665, N156-S665, I157-S665, G158-S665, P159-S665, T160-S665, R161-S665, I162-S665, L163-S665, P164-S665, N165-S665, L166-S665, Y167-S665, L168-S665, G169-S665, C170-S665, Q171-S665, R172-S665, D173-S665, V174-S665, L175-S665, N176-S665, K177-S665, E178-S665, L179-S665, M180-S665, Q181-S665, Q182-S665, N183-S665, G184-S665, I185-S665, G186-S665, Y187-S665, V188-S665, L189-S665, N190-S665, A191-S665, S192-S665, N193-S665, T194-S665, C195-S665, P196-S665, K197-S665, P198-S665, D199-S665, F200-S665, I201-S665, P202-S665, E203-S665, S204-S665, H205-S665, F206-S665, L207-S665, R208-S665, V209-S665, P210-S665, V211-S665, N212-S665, D213-S665, S214-S665, F215-S665, C216-S665, E217-S665, K218-S665, I219-S665, L220-S665, P221-S665, W222-S665, L223-S665, D224-S665, K225-S665, S226-S665, V227-S665, D228-S665, F229-S665, I230-S665, E231-S665, K232-S665, A233-S665, K234-S665, A235-S665, S236-S665, N237-S665, G238-S665, C239-S665, V240-S665, L241-S665, V242-S665, H243-S665, C244-S665, L245-S665, A246-S665, G247-S665, I248-S665, S249-S665, R250-S665, S251-S665, A252-S665, T253-S665, I254-S665, A255-S665, I256-S665, A257-S665, Y258-S665, I259-S665, M260-S665, K261-S665, R262-S665, M263-S665, D264-S665, M265-S665, S266-S665, L267-S665, D268-S665, E269-S665, A270-S665, Y271-S665, R272-S665, F273-S665, V274-S665, K275-S665, E276-S665, K277-S665, R278-S665, P279-S665, T280-S665, I281-S665, S282-S665, P283-S665, N284-S665, F285-S665, N286-S665, F287-S665, L288-S665, G289-S665, Q290-S665, L291-S665, L292-S665, A293-S665, Y294-S665, E295-S665, K296-S665, K297-S665, I298-S665, K299-S665, N300-S665, Q301-S665, T302-S665, G303-S665, A304-S665, S305-S665, G306-S665, P307-S665, K308-S665, S309-S665, K310-S665, L311-S665, K312-S665, L313-S665, L314-S665, P315-S665, L316-S665, E317-S665, K318-S665, P319-S665, N320-S665, E321-S665, P322-S665, V323-S665, P324-S665, A325-S665, V326-S665, S327-S665, E328-S665, G329-S665, G330-S665, Q331-S665, K332-S665, S333-S665, E334-S665, T335-S665, P336-S665, L337-S665, S338-S665, P339-S665, P340-S665, C341-S665, A342-S665, D343-S665, S344-S665, A345-S665, T346-S665, S347-S665, E348-S665, A349-S665, A350-S665, G351-S665, Q352-S665, R353-S665, P354-S665, V355-S665, H356-S665, P357-S665, A358-S665, S359-S665, V360-S665, P361-S665, S362-S665, V363-S665, P364-S665, S365-S665, V366-S665, Q367-S665, P368-S665, S369-S665, L370-S665, L371-S665, E372-S665, D373-S665, S374-S665, P375-S665, L376-S665, V377-S665, Q378-S665, A379-S665, L380-S665, S381-S665, G382-S665, L383-S665, H384-S665, L385-S665, S386-S665, A387-S665, D388-S665, R389-S665, L390-S665, E391-S665, D392-S665, S393-S665, N394-S665, K395-S665, L396-S665, K397-S665, R398-S665, S399-S665, F400-S665, S401-S665, L402-S665, D403-S665, I404-S665, K405-S665, S406-S665, V407-S665, S408-S665, Y409-S665, S410-S665, A411-S665, S412-S665, M413-S665, A414-S665, A415-S665, S416-S665, L417-S665, H418-S665, G419-S665, F420-S665, S421-S665, S422-S665, S423-S665, E424-S665, D425-S665, A426-S665, L427-S665, E428-S665, Y429-S665, Y430-S665, K431-S665, P432-S665, S433-S665, T434-S665, T435-S665, L436-S665, D437-S665, G438-S665, T439-S665, N440-S665, K441-S665, L442-S665, C443-S665, Q444-S665, F445-S665, S446-S665, P447-S665, V448-S665, Q449-S665, E450-S665, L451-S665, S452-S665, E453-S665, Q454-S665, T455-S665, P456-S665, E457-S665, T458-S665, S459-S665, P460-S665, D461-S665, K462-S665, E463-S665, E464-S665, A465-S665, S466-S665, I467-S665, P468-S665, K469-S665, K470-S665, L471-S665, Q472-S665, T473-S665, A474-S665, R475-S665, P476-S665, S477-S665, D478-S665, S479-S665, Q480-S665, S481-S665, K482-S665, R483-S665, L484-S665, H485-S665, S486-S665, V487-S665, R488-S665, T489-S665, S490-S665, S491-S665, S492-S665, G493-S665, T494-S665, A495-S665, Q496-S665, R497-S665, S498-S665, L499-S665, L500-S665, S501-S665, P502-S665, L503-S665, H504-S665, R505-S665, S506-S665, G507-S665, S508-S665, V509-S665, E510-S665, D511-S665, N512-S665, Y513-S665, H514-S665, T515-S665, S516-S665, F517-S665, L518-S665, F519-S665, G520-S665, L521-S665, S522-S665, T523-S665, S524-S665, Q525-S665, Q526-S665, H527-S665, L528-S665, T529-S665, K530-S665, S531-S665, A532-S665, G533-S665, L534-S665, G535-S665, L536-S665, K537-S665, G538-S665, W539-S665, H540-S665, S541-S665, D542-S665, I543-S665, L544-S665, A545-S665, P546-S665, Q547-S665, T548-S665, S549-S665, T550-S665, P551-S665, S552-S665, L553-S665, T554-S665, S555-S665, S556-S665, W557-S665, Y558-S665, F559-S665, A560-S665, T561-S665, E562-S665, S563-S665, S564-S665, H565-S665, F566-S665, Y567-S665, S568-S665, A569-S665, S570-S665, A571-S665, I572-S665, Y573-S665, G574-S665, G575-S665, S576-S665, A577-S665, S578-S665, Y579-S665, S580-S665, A581-S665, Y582-S665, S583-S665, C584-S665, S585-S665, Q586-S665, L587-S665, P588-S665, T589-S665, C590-S665, G591-S665, D592-S665, Q593-S665, V594-S665, Y595-S665, S596-S665, V597-S665, R598-S665, R599-S665, R600-S665, Q601-S665, K602-S665, P603-S665, S604-S665, D605-S665, R606-S665, A607-S665, D608-S665, S609-S665, R610-S665, R611-S665, S612-S665, W613-S665, H614-S665, E615-S665, E616-S665, S617-S665, P618-S665, F619-S665, E620-S665, K621-S665, Q622-S665, F623-S665, K624-S665, R625-S665, R626-S665, S627-S665, C628-S665, Q629-S665, M630-S665, E631-S665, F632-S665, G633-S665, E634-S665, S635-S665, I636-S665, M637-S665, S638-S665, E639-S665, N640-S665, R641-S665, S642-S665, R643-S665, E644-S665, E645-S665, L646-S665, G647-S665, K648-S665, V649-S665, G650-S665, S651-S665, Q652-S665, S653-S665, S654-S665, F655-S665, S656-S665, G657-S665, S658-S665, and/or M659-S665 of SEQ ID NO:42. Polynucleotide sequences encoding these polypeptides are also provided. The present invention also encompasses the use of the human BMY_HPP5 phosphatase N-terminal deletion polypeptides as immunogenic and/or antigenic epitopes as described elsewhere herein.

In preferred embodiments, the following C-terminal deletion mutants are encompassed by the present invention: M1-S665, M1-V664, M1-E663, M1-I662, M1-I661, M1-E660, M1-M659, M1-S658, M1-G657, M1-S656, M1-F655, M1-S654, M1-S653, M1-Q652, M1-S651, M1-G650, M1-V649, M1-K648, M1-G647, M1-L646, M1-E645, M1-E644, M1-R643, M1-S642, M1-R641, M1-N640, M1-E639, M1-S638, M1-M637, M1-I636, M1-S635, M1-E634, M1-G633, M1-F632, M1-E631, M1-M630, M1-Q629, M1-C628, M1-S627, M1-R626, M1-R625, M1-K624, M1-F623, M1-Q622, M1-K621, M1-E620, M1-F619, M1-P618, M1-S617, M1-E616, M1-E615, M1-H614, M1-W613, M1-S612, M1-R611, M1-R610, M1-S609, M1-D608, M1-A607, M1-R606, M1-D605, M1-S604, M1-P603, M1-K602, M1-Q601, M1-R600, M1-R599, M1-R598, M1-V597, M1-S596, M1-Y595, M1-V594, M1-Q593, M1-D592, M1-G591, M1-C590, M1-T589, M1-P588, M1-L587, M1-Q586, M1-S585, M1-C584, M1-S583, M1-Y582, M1-A581, M1-S580, M1-Y579, M1-S578, M1-A577, M1-S576, M1-G575, M1-G574, M1-Y573, M1-I572, M1-A571, M1-S570, M1-A569, M1-S568, M1-Y567, M1-F566, M1-H565, M1-S564, M1-S563, M1-E562, M1-T561, M1-A560, M1-F559, M1-Y558, M1-W557, M1-S556, M1-S555, M1-T554, M1-L553, M1-S552, M1-P551, M1-T550, M1-S549, M1-T548, M1-Q547, M1-P546, M1-A545, M1-L544, M1-I543, M1-D542, M1-S541, M1-H540, M1-W539, M1-G538, M1-K537, M1-L536, M1-G535, M1-L534, M1-G533, M1-A532, M1-S531, M1-K530, M1-T529, M1-L528, M1-H527, M1-Q526, M1-Q525, M1-S524, M1-T523, M1-S522, M1-L521, M1-G520, M1-F519, M1-L518, M1-F517, M1-S516, M1-T515, M1-H514, M1-Y513, M1-N512, M1-D511, M1-E510, M1-V509, M1-S508, M1-G507, M1-S506, M1-R505, M1-H504, M1-L503, M1-P502, M1-S501, M1-L500, M1-L499, M1-S498, M1-R497, M1-Q496, M1-A495, M1-T494, M1-G493, M1-S492, M1-S491, M1-S490, M1-T489, M1-R488, M1-V487, M1-S486, M1-H485, M1-L484, M1-R483, M1-K482, M1-S481, M1-Q480, M1-S479, M1-D478, M1-S477, M1-P476, M1-R475, M1-A474, M1-T473, M1-Q472, M1-L471, M1-K470, M1-K469, M1-P468, M1-I467, M1-S466, M1-A465, M1-E464, M1-E463, M1-K462, M1-D461, M1-P460, M1-S459, M1-T458, M1-E457, M1-P456, M1-T455, M1-Q454, M1-E453, M1-S452, M1-L451, M1-E450, M1-Q449, M1-V448, M1-P447, M1-S446, M1-F445, M1-Q444, M1-C443, M1-L442, M1-K441, M1-N440, M1-T439, M1-G438, M1-D437, M1-L436, M1-T435, M1-T434, M1-S433, M1-P432, M1-K431, M1-Y430, M1-Y429, M1-E428, M1-L427, M1-A426, M1-D425, M1-E424, M1-S423, M1-S422, M1-S421, M1-F420, M1-G419, M1-H418, M1-L417, M1-S416, M1-A415, M1-A414, M1-M413, M1-S412, M1-A411, M1-S410, M1-Y409, M1-S408, M1-V407, M1-S406, M1-K405, M1-I404, M1-D403, M1-L402, M1-S401, M1-F400, M1-S399, M1-R398, M1-K397, M1-L396, M1-K395, M1-N394, M1-S393, M1-D392, M1-E391, M1-L390, M1-R389, M1-D388, M1-A387, M1-S386, M1-L385, M1-H384, M1-L383, M1-G382, M1-S381, M1-L380, M1-A379, M1-Q378, M1-V377, M1-L376, M1-P375, M1-S374, M1-D373, M1-E372, M1-L371, M1-L370, M1-S369, M1-P368, M1-Q367, M1-V366, M1-S365, M1-P364, M1-V363, M1-S362, M1-P361, M1-V360, M1-S359, M1-A358, M1-P357, M1-H356, M1-V355, M1-P354, M1-R353, M1-Q352, M1-G351, M1-A350, M1-A349, M1-E348, M1-S347, M1-T346, M1-A345, M1-S344, M1-D343, M1-A342, M1-C341, M1-P340, M1-P339, M1-S338, M1-L337, M1-P336, M1-T335, M1-E334, M1-S333, M1-K332, M1-Q331, M1-G330, M1-G329, M1-E328, M1-S327, M1-V326, M1-A325, M1-P324, M1-V323, M1-P322, M1-E321, M1-N320, M1-P319, M1-K318, M1-E317, M1-L316, M1-P315, M1-L314, M1-L313, M1-K312, M1-L311, M1-K310, M1-S309, M1-K308, M1-P307, M1-G306, M1-S305, M1-A304, M1-G303, M1-T302, M1-Q301, M1-N300, M1-K299, M1-I298, M1-K297, M1-K296, M1-E295, M1-Y294, M1-A293, M1-L292, M1-L291, M1-Q290, M1-G289, M1-L288, M1-F287, M1-N286, M1-F285, M1-N284, M1-P283, M1-S282, M1-I281, M1-T280, M1-P279, M1-R278, M1-K277, M1-E276, M1-K275, M1-V274, M1-F273, M1-R272, M1-Y271, M1-A270, M1-E269, M1-D268, M1-L267, M1-S266, M1-M265, M1-D264, M1-M263, M1-R262, M1-K261, M1-M260, M1-I259, M1-Y258, M1-A257, M1-I256, M1-A255, M1-I254, M1-T253, M1-A252, M1-S251, M1-R250, M1-S249, M1-I248, M1-G247, M1-A246, M1-L245, M1-C244, M1-H243, M1-V242, M1-L241, M1-V240, M1-C239, M1-G238, M1-N237, M1-S236, M1-A235, M1-K234, M1-A233, M1-K232, M1-E231, M1-I230, M1-F229, M1-D228, M1-V227, M1-S226, M1-K225, M1-D224, M1-L223, M1-W222, M1-P221, M1-L220, M1-I219, M1-K218, M1-E217, M1-C216, M1-F215, M1-S214, M1-D213, M1-N212, M1-V211, M1-P210, M1-V209, M1-R208, M1-L207, M1-F206, M1-H205, M1-S204, M1-E203, M1-P202, M1-I201, M1-F200, M1-D99, M1-P198, M1-K197, M1-P196, M1-C195, M1-T194, M1-N193, M1-S192, M1-A191, M1-N190, M1-L189, M1-V188, M1-Y187, M1-G186, M1-I185, M1-G184, M1-N183, M1-Q182, M1-Q181, M1-M180, M1-L179, M1-E178, M1-K177, M1-N176, M1-L175, M1-V174, M1-D173, M1-R172, M1-Q171, M1-C170, M1-G169, M1-L168, M1-Y167, M1-L166, M1-N165, M1-P164, M1-L163, M1-I162, M1-R161, M1-T160, M1-P159, M1-G158, M1-I157, M1-N156, M1-A155, M1-V154, M1-P153, M1-L152, M1-C151, M1-P150, M1-Q149, M1-S148, M1-I147, M1-C146, M1-T145, M1-P144, M1-V143, M1-L142, M1-T141, M1-S140, M1-K139, M1-G138, M1-E137, M1-C136, M1-L135, M1-G134, M1-P133, M1-F132, M1-C131, M1-R130, M1-S129, M1-F128, M1-E127, M1-A126, M1-F125, M1-G124, M1-G123, M1-A122, M1-L121, M1-L120, M1-H119, M1-V118, M1-S117, M1-N116, M1-F115, M1-S114, M1-K113, M1-E112, M1-L111, M1-K110, M1-G109, M1-L108, M1-L107, M1-V106, M1-T105, M1-L104, M1-F103, M1-C102, M1-D101, M1-S100, M1-S99, M1-L98, M1-S97, M1-A96, M1-V95, M1-D94, M1-Q93, M1-S92, M1-S91, M1-Q90, M1-D89, M1-Y88, M1-V87, M1-V86, M1-V85, M1-K84, M1-Q83, M1-S82, M1-C81, M1-D80, M1-I79, M1-D78, M1-V77, M1-K76, M1-H75, M1-K74, M1-A73, M1-S72, M1-K71, M1-Q70, M1-I69, M1-L68, M1-E67, M1-T66, M1-I65, M1-L64, M1-V63, M1-K62, M1-D61, M1-Q60, M1-Q59, M1-L58, M1-R57, M1-R56, M1-K55, M1-M54, M1-L53, M1-K52, M1-S51, M1-C50, M1-N49, M1-I48, M1-N47, M1-I46, M1-A45, M1-E44, M1-L43, M1-I42, M1-H41, M1-S40, M1-T39, M1-N38, M1-Y37, M1-E36, M1-V35, M1-F34, M1-P33, M1-R32, M1-S31, M1-D30, M1-I29, M1-L28, M1-L27, M1-V26, M1-K25, M1-E24, M1-T23, M1-G22, M1-S21, M1-E20, M1-L19, M1-L18, M1-A17, M1-V16, M1-L15, M1-R14, M1-E13, M1-T12, M1-V11, M1-I10, M1-Q9, M1-T8, and/or M1-G7 of SEQ ID NO:42. Polynucleotide sequences encoding these polypeptides are also provided. The present invention also encompasses the use of the human BMY_HPP5 phosphatase C-terminal deletion polypeptides as immunogenic and/or antigenic epitopes as described elsewhere herein.

The present invention also encompasses immunogenic and/or antigenic epitopes of the human BMY_HPP5 phosphatase polypeptide.

The human phosphatase polypeptides of the present invention were determined to comprise several phosphorylation sites based upon the Motif algorithm (Genetics Computer Group, Inc.). The phosphorylation of such sites may regulate some biological activity of the human phosphatase polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the human phosphatase polypeptide to associate with other polypeptides, particularly cognate ligand for human phosphatase, or its ability to modulate certain cellular signal pathways.

Specifically, the BMY_HPP5 polypeptide was predicted to comprise one tyrosine phosphorylation site using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973–977 (1982); Hunter T., J. Biol. Chem. 257:4843–4848(1982), and Cooper J. A., Esch F. S., Taylor S. S., Hunter T., J. Biol. Chem. 259:7835–7841(1984), which are hereby incorporated herein by reference.

In preferred embodiments, the following tyrosine phosphorylation site polypeptides are encompassed by the present invention: NGCVLVHCLAGISRSATIAIAYI (SEQ ID NO:103). Polynucleotides encoding these polypeptides are also provided. The present invention also encompasses the use of the human BMY_HPP5 tyrosine phosphorylation site polypeptides as immunogenic and/or antigenic epitopes as described elsewhere herein.

The human phosphatase polypeptide was predicted to comprise twelve PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. 260:12492–12499(1985); which are hereby incorporated by reference herein.

In preferred embodiments, the following PKC phosphorylation site polypeptides are encompassed by the present invention: GTQIVTERLVALL (SEQ ID NO:91), LLESGTEKVLLID (SEQ ID NO:92), ELIQHSAKHKVDI (SEQ ID NO:93), VDIDCSQKVVVYD (SEQ ID NO:94), DRLEDSNKLKRSF (SEQ ID NO:95), TTLDGTNKLCQFS (SEQ ID NO:96), PKKLQTARPSDSQ (SEQ ID NO:97), PSDSQSKRLHSVR (SEQ ID NO:98), SKRLHSVRTSSSG (SEQ ID NO:99), GDQVYSVRRRQKP (SEQ ID NO:100), RRQKPSDRADSRR (SEQ ID NO:101), and/or SDRADSRRSWHEE (SEQ ID NO:102). Polynucleotides encoding these polypeptides are also provided. The present invention also encompasses the use of the human BMY_HPP5 phosphatase PKC phosphorylation site polypeptides as immunogenic and/or antigenic epitopes as described elsewhere herein.

The human phosphatase polypeptide has been shown to comprise six glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine phosphorylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673–702(1972); Pless D. D., Lennarz W. J., Proc. Natl. Acad. Sci. U.S.A. 74:134–138(1977); Bause E., Biochem. J. 209:331–336(1983); Gavel Y., von Heijne G., Protein Eng. 3:433–442(1990); and Miletich J. P., Broze G. J. Jr., J. Biol. Chem. 265:11397–11404(1990).

In preferred embodiments, the following asparagine glycosylation site polypeptides are encompassed by the present invention: PFVEYNTSHILEAI (SEQ ID NO:85), EAININCSKLMKRR (SEQ ID NO:86), IGYVLNASNTCPKP (SEQ ID NO:87), LRVPVNDSFCEKIL (SEQ ID NO:88), EKKIKNQTGASGPK (SEQ ID. NO:89), and/or SIMSENRSREELGK (SEQ ID NO:90). Polynucleotides encoding these polypeptides are also provided. The present invention also encompasses the use of the human BMY_HPP5 phosphatase asparagine glycosylation site polypeptides as immunogenic and/or antigenic epitopes as described elsewhere herein.

The present invention encompasses the use of BMY_HPP5 inhibitors and/or activators of BMY_HPP5 activity for the treatment, detection, amelioration, or prevention of phosphatase associated disorders, including but not limited to metabolic diseases such as diabetes, in addition to neural and/or cardiovascular diseases and disorders. The present invention also encompasses the use of BMY_HPP5 inhibitors and/or activators of BMY_HPP5 activity as immunosuppressive agents, anti-inflammatory agents, and/or anti-tumor agents The present invention encompasses the use of BMY_HPP5 phosphatase inhibitors, including, antagonists such as antisense nucleic acids, in addition to other antagonists, as described herein, in a therapeutic regimen to diagnose, prognose, treat, ameliorate, and/or prevent diseases where a kinase activity is insufficient. One, non-limiting example of a disease which may occur due to insufficient kinase activity are certain types of diabetes, where one or more kinases involved in the insulin receptor signal pathway may have insufficient activity or insufficient expression, for example.

Moreover, the present invention encompasses the use of BMY_HPP5 phosphatase activators, and/or the use of the BMY_HPP5 phosphatase gene or protein in a gene therapy regimen, as described herein, for the diagnoses, prognoses, treatment, amelioration, and/or prevention of diseases and/or disorders where a kinase activity is overly high, such as a cancer where a kinase oncogene product has excessive activity or excessive expression.

The present invention also encompasses the use of catalytically inactive variants of BMY_HPP5 proteins, including fragments thereof, such as a protein therapeutic, or the use of the encoding polynucleotide sequence or as gene therapy, for example, in the diagnoses, prognosis, treatment, amelioration, and/or prevention of diseases or disorders where phosphatase activity is overly high.

The present invention encompasses the use of antibodies directed against the BMY_HPP5 polypeptides, including fragment and/or variants thereof, of the present invention in diagnostics, as a biomarkers, and/or as a therapeutic agents.

The present invention encompasses the use of an inactive, non-catalytic, mutant of the BMY_HPP5 phosphatase as a substrate trapping mutant to bind cellular phosphoproteins or a library of phosphopeptides to identify substrates of the BMY_HPP5 polypeptides.

The present invention encompasses the use of the BMY_HPP5 polypeptides, to identify inhibitors or activators of the BMY_HPP5 phosphatase activity using either in vitro or 'virtual' (in silico) screening methods.

One embodiment of the invention relates to a method for identifying a compound as an activator or inhibitor of the BMY_HPP5 phosphatase comprising the steps of: i.) contacting a BMY_HPP5 phosphatase inhibitor or activator labeled with an analytically detectable reagent with the BMY_HPP5 phosphatase under conditions sufficient to form a complex with the inhibitor or activator; ii.) contacting said complex with a sample containing a compound to be identified; iii) and identifying the compound as an inhibitor or activator by detecting the ability of the test compound to alter the amount of labeled known BMY_HPP5 phosphatase inhibitor or activator in the complex.

Another embodiment of the invention relates to a method for identifying a compound as an activator or inhibitor of a BMY_HPP5 phosphatase comprising the steps of: i.) contacting the BMY_HPP5 phosphatase with a compound to be identified; and ii.) and measuring the ability of the BMY_HPP5 phosphatase to remove phosphate from a substrate.

The present invention also encompasses a method for identifying a ligand for the BMY_HPP5 phosphatase comprising the steps of: i.) contacting the BMY_HPP5 phosphatase with a series of compounds under conditions to permit binding; and ii.) detecting the presence of any ligand-bound protein.

Preferably, the above referenced methods comprise the BMY_HPP5 phosphatase in a form selected from the group consisting of whole cells, cytosolic cell fractions, membrane cell fractions, purified or partially purified forms. The invention also relates to recombinantly expressed BMY_HPP5 phosphatase in a purified, substantially purified, or unpurified state. The invention further relates to BMY_HPP5 phosphatase fused or conjugated to a protein, peptide, or other molecule or compound known in the art, or referenced herein.

The present invention also encompasses a pharmaceutical composition of the BMY_HPP5 phosphatase polypeptide comprising a compound identified by above referenced methods and a pharmaceutically acceptable carrier.

In preferred embodiments, the present invention encompasses a polynucleotide lacking the initiating start codon, in addition to, the resulting encoded polypeptide of BMY_HPP5. Specifically, the present invention encompasses the polynucleotide corresponding to nucleotides 473 thru 2464 of SEQ ID NO:41, and the polypeptide corresponding to amino acids 2 thru 665 of SEQ ID NO:42. Also encompassed are recombinant vectors comprising said encoding sequence, and host cells comprising said vector.

The present invention also provides a three-dimensional homology model of the BMY_HPP5 polypeptide (see FIG. 38) representing amino acids N157 to I300 of BMY_HPP5 (SEQ ID NO:42). A three-dimensional homology model can be constructed on the basis of the known structure of a homologous protein (Greer et al, 1991, Lesk, et al, 1992, Cardozo, et al, 1995, Yuan, et al, 1995). The homology model of the BMY_HPP5 polypeptide, corresponding to amino acid residues N157 to I300 of SEQ ID NO:42, was based upon the homologous structure of 1vhr from the N-terminus of human dual specificity phosphatase MAP Kinase phosphatase 3 (also called PYST1) (residues A204-L347; Protein Data Bank, PDB entry 1mkp chain A Genbank Accession No. gi|5822131; SEQ ID NO:208) (Stewart, A. E. , et al., 1999) and is defined by the set of structural coordinates set forth in Table X herein.

Homology models are useful when there is no experimental information available on the protein of interest. A 3-dimensional model can be constructed on the basis of the known structure of a homologous protein (Greer et al, 1991, Lesk, et al, 1992, Cardozo, et al, 1995, Sali, et al, 1995).

Those of skill in the art will understand that a homology model is constructed on the basis of first identifying a template, or, protein of known structure which is similar to the protein without known structure. This can be accomplished by through pairwise alignment of sequences using such programs as FASTA (Pearson, et al 1990) and BLAST (Altschul, et al, 1990). In cases where sequence similarity is high (greater than 30%) these pairwise comparison methods may be adequate. Likewise, multiple sequence alignments or profile-based methods can be used to align a query sequence to an alignment of multiple (structurally and biochemically) related proteins. When the sequence similarity is low, more advanced techniques are used such as fold recognition (protein threading; Hendlich, et al, 1990), where the compatibility of a particular sequence with the 3-dimensional fold of a potential template protein is gauged on the basis of a knowledge-based potential. Following the initial sequence alignment, the query template can be optimally aligned by manual manipulation or by incorporation of other features (motifs, secondary structure predictions, and allowed sequence conservation). Next, structurally conserved regions can be identified and used to construct the core secondary structure (Sali, et al, 1995). Loops can be added using knowledge-based techniques, and refined performing force field calculations (Sali, et al, 1995; Cardozo, et al, 1995).

For BMY_HPP5 the pairwise alignment method FASTA (Pearson, et al 1990) and fold recognition methods (protein threading) generated identical sequence alignments for a portion (residues N157 to I300 of SEQ ID NO:42) of BMY_HPP5 aligned with the sequence of the human dual specificity phosphatase MAP Kinase phosphatase 3 (also called PYST1) (residues A204-L347; Protein Data Bank, PDB entry 1mkp chain A; Genbank Accession No. gi|5822131; SEQ ID NO:208) (Stewart, A. E. , et al., 1999). The alignment of BMY_HPP5 with PDB entry 1mkp is set forth in FIG. 37. In this invention, the homology model of BMY_HPP5 was derived from the sequence alignment set forth in FIG. 37, and thence an overall atomic model including plausible sidechain orientations using the program LOOK (Levitt, 1992). The three dimensional model for BMY_HPP5 is defined by the set of structure coordinates as set forth in Table X and visualized in FIG. 38.

In order to recognize errors in three-dimensional structures knowledge based mean fields can be used to judge the quality of protein folds (Sippl 1993). The methods can be used to recognize misfolded structures as well as faulty parts of structural models. The technique generates an energy graph where the energy distribution for a given protein fold is displayed on the y-axis and residue position in the protein fold is displayed on the x-axis. The knowledge based mean fields compose a force field derived from a set of globular protein structures taken as a subset from the Protein Data Bank (Bernstein et. al. 1977). To analyze the quality of a model the energy distribution is plotted and compared to the energy distribution of the template from which the model was generated. FIG. 39 shows the energy graph for the BMY_HPP5 model (dotted line) and the template (1mkp, a dual-specificity phosphatase) from which the model was generated. It is clear that the model and template have similar energies over the aligned region, suggesting that BMY_HPP5 is in a "native-like" conformation. This graph supports the motif and sequence alignments in confirming that the three dimensional structure coordinates of BMY_HPP5 are an accurate and useful representation for the polypeptide.

The term "structure coordinates" refers to Cartesian coordinates generated from the building of a homology model.

Those of skill in the art will understand that a set of structure coordinates for a protein is a relative set of points that define a shape in three dimensions. Thus, it is possible that an entirely different set of coordinates could define a similar or identical shape. Moreover, slight variations in the individual coordinates, as emanate from generation of similar homology models using different alignment templates (i.e., other than the structure coordinates of 1 mkp), and/or using different methods in generating the homology model, will have minor effects on the overall shape. Variations in coordinates may also be generated because of mathematical manipulations of the structure coordinates. For example, the structure coordinates set forth in Table X and visualized in FIG. 38 could be manipulated by fractionalization of the structure coordinates; integer additions or subtractions to sets of the structure coordinates, inversion of the structure coordinates or any combination of the above.

Various computational analyses are therefore necessary to determine whether a molecule or a portion thereof is sufficiently similar to all or parts of BMY_HPP5 described above as to be considered the same. Such analyses may be carried out in current software applications, such as INSIGHTII (Molecular Simulations Inc., San Diego, Calif.) version 2000 and as described in the accompanying User's Guide.

Using the superimposition tool in the program INSIGHTII comparisons can be made between different structures and different conformations of the same structure. The procedure used in INSIGHTII to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. Since atom equivalency within INSIGHTII is defined by user input, for the purpose of this invention we will define equivalent atoms as protein backbone atoms (N, Cα, C and O) for all conserved residues between the two structures being compared. We will also consider only rigid fitting operations. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by INSIGHTII. For the purpose of this invention, any homology model of a BMY_HPP5 that has a root mean square deviation of conserved residue backbone atoms (N, Cα, C, O) of less than 3.0 Å when superimposed on the relevant backbone atoms described by structure coordinates listed in Table X and visualized in FIG. 38 are considered identical. More preferably, the root mean square deviation is less than 2.0 Å.

This invention as embodied by the homology model enables the structure-based design of modulators of the biological function of BMY_HPP5, as well as mutants with altered biological function and/or specificity.

There is 40% sequence identity between catalytic domain of BMY_HPP5 and 1mkp which was used as the template for 3D model generation. For the BMY_HPP5 the functionally important residues are located in a cleft comprised of residues D213, H243, C244, R250, and S251. All these residues are conserved in 1 mkp (for structure determination studies the cysteine was mutated to a serine in 1 mkp). Based on the sequence alignment disclosed in FIG. 37 and the structural model disclosed in Table X and visualized in FIG. 38, D213 is identified as a general acid, C244 as the catalytic Cysteine nucleophile which cleaves the phosphodiester bond, and R250 as the essential Argenine which activates the bond for cleavage as described in the literature (reviewed by Fauman and .Saper, 1996). Other important residues include F287 which imparts substrate specificity onto the enzyme. All of these residues are conserved.

In a preferred embodiment of the present invention, the molecule comprises the cleft region defined by structure coordinates of BMY_HPP5 amino acids described above according to Table X, or a mutant of said molecule.

More preferred are molecules comprising all or any part of the cleft or a mutant or homologue of said molecule or molecular complex. By mutant or homologue of the molecule it is meant a molecule that has a root mean square deviation from the backbone atoms of said BMY_HPP5 amino acids of not more than 3.5 Angstroms.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the relevant portion of the backbone of BMY_HPP5 as defined by the structure coordinates described herein.

The structure coordinates of a BMY_HPP5 homology model portions thereof are stored in a machine-readable storage medium. Such data may be used for a variety of purposes, such as drug discovery.

Accordingly, in one embodiment of this invention is provided a machine-readable data storage medium comprising a data storage material encoded with the structure coordinates set forth in Table X.

One embodiment utilizes System 10 as disclosed in WO 98/11134, the disclosure of which is incorporated herein by reference in its entirety. Briefly, one version of these embodiments comprises a computer comprising a central processing unit ("CPU"), a working memory which may be, e.g, RAM (random-access memory) or "core" memory, mass storage memory (such as one or more disk drives or CD-ROM drives), one or more cathode-ray tube ("CRT") display terminals, one or more keyboards, one or more input lines, and one or more output lines, all of which are interconnected by a conventional bidirectional system bus.

Input hardware, coupled to the computer by input lines, may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, keyboard may also be used as an input device.

Output hardware, coupled to the computer by output lines, may similarly be implemented by conventional devices. By way of example, output hardware may include a CRT display terminal for displaying a graphical representation of a region or domain of the present invention using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage, and accesses to and from the working memory, and determines the sequence of data processing steps. A number of programs may be used to process the machine-readable data of this invention. Such programs are discussed in reference to the computational methods of drug discovery as described herein. Specific references to components of the hardware system are included as appropriate throughout the following description of the data storage medium.

For the purpose of the present invention, any magnetic data storage medium which can be encoded with machine-readable data would be sufficient for carrying out the storage requirements of the system. The medium could be a conventional floppy diskette or hard disk, having a suitable substrate, which may be conventional, and a suitable coating, which may be conventional, on one or both sides, containing magnetic domains whose polarity or orientation could be altered magnetically, for example. The medium may also have an opening for receiving the spindle of a disk drive or other data storage device.

The magnetic domains of the coating of a medium may be polarized or oriented so as to encode in a manner which may be conventional, machine readable data such as that described herein, for execution by a system such as the system described herein.

Another example of a suitable storage medium which could also be encoded with such machine-readable data, or set of instructions, which could be carried out by a system such as the system described herein, could be an optically-readable data storage medium. The medium could be a conventional compact disk read only memory (CD-ROM) or a rewritable medium such as a magneto-optical disk which is optically readable and magneto-optically writable. The medium preferably has a suitable substrate, which may be conventional, and a suitable coating, which may be conventional, usually of one side of substrate.

In the case of a CD-ROM, as is well known, the coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Thus, in accordance with the present invention, data capable of displaying the three dimensional structure of the BMY_HPP5 homology model, or portions thereof and their structurally similar homologues is stored in a machine-readable storage medium, which is capable of displaying a graphical three-dimensional representation of the structure. Such data may be used for a variety of purposes, such as drug discovery.

For the first time, the present invention permits the use, through homology modeling based upon the sequence of BMY_HPP5 (FIGS. 5A–D; SEQ ID NO:42) of structure-based or rational drug design techniques to design, select, and synthesize chemical entities that are capable of modulating the biological function of BMY_HPP5.

Accordingly, the present invention is also directed to the entire sequence in FIGS. 5A–D or any portion thereof for the purpose of generating a homology model for the purpose of 3D structure-based drug design.

For purposes of this invention, we include mutants or homologues of the sequence in FIGS. 5A–D or any portion thereof. In a preferred embodiment, the mutants or homologues have at least 25% identity, more preferably 50% identity, more preferably 75% identity, and most preferably 90% identity to the amino acid residues in FIGS. 5A–D.

The three-dimensional model structure of the BMY_HPP5 will also provide methods for identifying modulators of biological function. Various methods or combination thereof can be used to identify these compounds.

Structure coordinates of the catalytic region defined above can also be used to identify structural and chemical features. Identified structural or chemical features can then be employed to design or select compounds as potential BMY_HPP5 modulators. By structural and chemical features it is meant to include, but is not limited to, van der Waals interactions, hydrogen bonding interactions, charge interaction, hydrophobic bonding interaction, and dipole interaction. Alternatively, or in conjunction, the three-dimensional structural model can be employed to design or select compounds as potential BMY_HPP5 modulators. Compounds identified as potential BMY_HPP5 modulators can then be synthesized and screened in an assay characterized by binding of a test compound to the BMY_HPP5, or in characterizing BMY_HPP5 deactivation in the presence of a small molecule. Examples of assays useful in screening of potential BMY_HPP5 modulators include, but are not limited to, screening in silico, in vitro assays and high throughput assays. Finally, these methods may also involve modifying or replacing one or more amino acids from BMY_HPP5 according to Table X.

However, as will be understood by those of skill in the art upon this disclosure, other structure based design methods can be used. Various computational structure based design methods have been disclosed in the art.

For example, a number of computer modeling systems are available in which the sequence of the BMY_HPP5 and the BMY_HPP5 structure (i.e., atomic coordinates of BMY_HPP5 and/or the atomic coordinates of the active site as provided in Table X) can be input. This computer system then generates the structural details of one or more these regions in which a potential BMY_HPP5 modulator binds so that complementary structural details of the potential modulators can be determined. Design in these modeling systems is generally based upon the compound being capable of physically and structurally associating with BMY_HPP5. In addition, the compound must be able to assume a conformation that allows it to associate with BMY_HPP5. Some modeling systems estimate the potential inhibitory or binding effect of a potential BMY_HPP5 modulator prior to actual synthesis and testing.

Methods for screening chemical entities or fragments for their ability to associate with a given protein target are also well known. Often these methods begin by visual inspection of the binding site on the computer screen. Selected fragments or chemical entities are then positioned in one or more of the active site region in BMY_HPP5. Docking is accomplished using software such as INSIGHTII, QUANTA and SYBYL, following by energy minimization and molecular dynamics with standard molecular mechanic forcefields such as CHARMM and AMBER. Examples of computer programs which assist in the selection of chemical fragment or chemical entities useful in the present invention include, but are not limited to, GRID (Goodford, 1985), AUTODOCK (Goodsell, 1990), and DOCK (Kuntz et al. 1982).

Upon selection of preferred chemical entities or fragments, their relationship to each other and BMY_HPP5 can be visualized and then assembled into a single potential modulator. Programs useful in assembling the individual chemical entities include, but are not limited to SYBYL and LeapFrog (Tripos Associates, St. Louis Mo.), LUDI (Bohm 1992) and 3D Database systems (Martin 1992).

Alternatively, compounds may be designed de hovo using either an empty active site or optionally including some portion of a known inhibitor. Methods of this type of design include, but are not limited to LUDI (Bohm 1992) and LeapFrog (Tripos Associates, St. Louis Mo.).

In addition, BMY_HPP5 is overall well suited to modern methods including combinatorial chemistry.

Programs such as DOCK (Kuntz et al. 1982) can be used with the atomic coordinates from the homology model to identify potential ligands from databases or virtual databases which potentially bind the in the metal binding region, and which may therefore be suitable candidates for synthesis and testing.

Additionally, the three-dimensional homology model of BMY_HPP5 will aid in the design of mutants with altered biological activity.

Many polynucleotide sequences, such as EST sequences, are publicly available and accessible through sequence databases. Some of these sequences are related to SEQ ID NO: 41 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 5097 of SEQ ID NO:41, b is an integer between 15 to 5111, where both a and b correspond to the positions of nucleotide residues shown in SEQ ID NO:41, and where b is greater than or equal to a+14.

Features of the Polypeptide Encoded by Gene No:6

The development of inflammatory disease is characterized by infiltration of circulating blood cells across the endothelium into the tissue. A number of key events occur in the endothelial cells that mediate this "gateway" function. The endothelial cells express receptors and chemokines that sequentially tether the leukocytes, activate them, cause them to tightly adhere, and aid in their transmigration through endothelial cell junctions. This process is initiated by the production of early inflammatory mediators such as TNF-α. The coordinated expression of receptors and chemokines is mediated by intracellular signaling molecules including kinases, scaffolding proteins, and transcription factors. These molecules thus form a signaling cascade that may be a "master switch" for the development of inflammatory processes. Components of this cascade such as the transcription factor NF-κB are known. However, there are many other components that have not yet been identified. The analysis of genes that are differentially expressed in TNF-α-activated endothelium may help to identify other components of this "master switch" cascade.

To this end, the RNA expressed in TNF-α-stimulated human lung microvascular endothelial cells has been analyzed to identify gene products involved in regulatory events. Resting cells were stimulated for 1 h with TNF-α, and the RNA was isolated from the cells. Complementary DNA (cDNA) was created from the isolated RNA. The cDNAs that were upregulated in response to TNFα were identified using subtractive hybridization methodology.

A novel dual specificity phosphatase (DSP), RET31 (Regulated in Endothelial cells treated with TNF-α clone 31) (FIGS. 13A–F) was identified from the TNF-α treated endothelial subtraction library. The dual specificity phosphatase catalytic (DSPc) domain for RET 31 was identified using the DSPc PFAM-HMM (PF00782). A search for homologues identified three other DSPs that contain extensive homology to RET31 (FIGS. 14A–C). RET31, DUS8, DUSP6 and MAP-kinase phosphatase 5 are shown in a multiple sequence alignment comparing the DSPc domains of these four proteins (FIG. 17).

RET31 was confirmed to be up-regulated by TNF-α, reaching a peak of expression at 6 h by northern blot analysis (FIG. 15). RET31 mRNA was virtually undetectable in brain, spleen, and peripheral blood leukocytes by Northern blot analysis.

RET31 is believed to represent a novel splice variant of the BMY_HPP5 polypeptide of the present invention. The sequence for RET31 differs in the 5' end from that of BMY_HPP5. However, comparison of the tissue expression of RET31 and BMY_HPP5 showed significant differential expression despite their significant identity. Specifically, the tissue expression of BMY_HPP5 by PCR analysis (as described elsewhere herein) suggested that there were significant levels of RET31 in the brain. The reason for such disparate expression profiles is unclear but may be related to the use of separate pools of RNA or to the use of alternate probes.

In all tissues that expressed significant levels of RET31, there was a primary hybridizing band and a secondary band of lower molecular weight. It is not clear whether this represents splice variants of the same gene or whether there is a homologue present.

The polypeptide corresponding to this gene provided as SEQ ID NO:108 (FIGS. 13A–F), encoded by the polynucleotide sequence according to SEQ ID NO:109 (FIGS. 13A–F), and/or encoded by the polynucleotide contained within the deposited clone, RET31, has significant homology at the nucleotide and amino acid level to a number of phosphatases, which include, for example, the human protein-tyrosine phosphatase DUS8 protein, also referred to as hVH-5 (DUS8; Genbank Accession No:gi|U27193; SEQ ID NO:110); the human dual specificity MAP kinase DUSP6 protein (DUSP6; Genbank Accession No:gi|AB013382; SEQ ID NO:111);

and the human map kinase phosphatase MKP-5 protein (MKP-5; Genbank Accession No:gi|AB026436; SEQ ID NO:112) as determined by BLASTP. An alignment of the human phosphatase polypeptide with these proteins is provided in FIGS. 14A–C.

The human protein-tyrosine phosphatase DUS8 protein (also referred to as hVH-5) is thought to be a member of a subset of protein tyrosine phosphatases that regulate mitogen-activated protein kinase. The catalytic region of hVH-5 was expressed as a fusion protein and was shown to hydrolyze p-nitrophenylphosphate and inactivate mitogen-activated protein kinase, thus proving that hVH-5 possessed phosphatase activity. Moreover, expression of hVH-5 transcripts were induced in PC12 cells upon nerve growth factor and insulin treatment in a manner characteristic of an immediate-early gene, suggesting a possible role in the signal transduction cascade (The J. Neurochem. 65 (4), 1823–1833 (1995)).

The dual specificity MAP kinase DUSP6 protein is believed to be implicated in pancreatic carcinogensis based upon its encoding polynucleotide mapping to chromosome locus12q21, one of the regions of frequent allelic loss in pancreatic cancer, in addition to, its reduced expressions amongst several pancreatic cancer cell lines (Cytogenet. Cell Genet. 82 (3–4), 156–159 (1998)).

The human map kinase phosphatase MKP-5 protein was determined to belong to a group of dual specificity protein phosphatases that negatively regulate members of the mitogen-activated protein kinase (MAPK) superfamily, which consists of three major subfamilies, MAPK/extracellular signal-regulated kinase (ERK), stress-activated protein kinase (SAPK)/c-Jun N-terminal kinase (JNK), and p38. Members of this group show distinct substrate specificities for MAPKs, different tissue distribution and subcellular localization, and different modes of inducibility of their expression by extracellular stimuli. MKP-5 was shown to bind to p38 and SAPK/JNK, but not to MAPK/ERK, and inactivate p38 and SAPK/JNK, but not MAPK/ERK. p38 was determined to be the preferred substrate for MKP-5. MKP-5 mRNA was widely expressed in various tissues and organs, and its expression in cultured cells was inducible by stress stimuli. Thus, MKP-5 is thought to represent a type of dual specificity phosphatase specific for p38 and SAPK/JNK (J Biol Chem., 274(28):19949–56, (1999)).

The determined nucleotide sequence of the RET31 cDNA in FIGS. 13A–F (SEQ ID NO:41) contains an open reading frame encoding a protein of about 665 amino acid residues, with a deduced molecular weight of about 73.1 kDa. The amino acid sequence of the predicted RET31 polypeptide is shown in FIGS. 13A–F (SEQ ID NO:42). The RET31 protein shown in FIGS. 13A–F was determined to share significant identity and similarity to several known phosphatases, particularly, dual-specificity protein phosphatases. Specifically, the RET31 protein shown in FIGS. 13A–F was determined to be about 50.3% identical and 56.8% similar to human protein-tyrosine phosphatase DUS8 protein (DUS8; Genbank Accession No:gi|U27193; SEQ ID NO:110); to be about 36.5% identical and 48.3% similar to the human dual specificity MAP kinase DUSP6 protein (DUSP6; Genbank Accession No:gi|AB013382; SEQ ID NO:111); and to be about 34.3% identical and 47.2% similar to the human map kinase phosphatase MKP-5 protein (MKP-5; Genbank Accession No:gi|AB026436; SEQ ID NO:112), as shown in FIG. 12.

Based upon the strong homology to members of the phosphatase proteins, the polypeptide encoded by the human RET31 phosphatase of the present invention is expected to share at least some biological activity with phosphatase proteins, preferably with members of the novel phosphotyrosine/dual-specificity (P-Tyr, P-Ser and P-Thr) phosphatases, particularly the novel phosphotyrosine/dual-specificity (P-Tyr, P-Ser and P-Thr) phosphatases referenced herein.

The strong homology to phosphatases, particularly dual-specificity phosphatases, combined with the predominant localized expression in adrenal gland tissue suggests the human RET31 phosphatase polynucleotides and polypeptides, including antagonists, and/or fragments thereof, may be useful for treating, diagnosing, prognosing, ameliorating, and/or preventing endocrine disorders, which include, but are mot limited to adrenocortical hyperfunction, adrenocortical hypofunction, lethargy. Congenital adrenal hyperplasia, aberrant ACTH regulation, aberrant adrenaline regulation, disorders associated with defects in P450C21, P450C18, P450C17, and P450C11 hydroxylases and in 3-hydroxysteroid dehydrogenase (3-HSD), hirsutism, oligomenorrhea, acne, virilization, female pseudohermaphroditism, disorders associated with the incidence of aberrant sexual characterisitics, disorders associated with aberrant cortisol secretion, hypertension, hypokalemia, hypogonadism, disorders associated with aberrant androgen secretion, adrenal virilism, Adrenal adenomas, Adrenal carcinomas, disorders associated with aberrant aldosterone secretion, aldosteronism, disorders associated with aberrant steriod biosynthesis, disorders associated with aberrant steriod transport, disorders associated with aberrant steriod secretion, disorders associated with aberrant steriod excretion, Addison's syndrome, and Cushing's syndrome.

The strong homology to phosphatases, particularly dual-specificity phosphatases, combined with the localized expression in testis and prostate tissue suggests the human RET31 phosphatase polynucleotides and polypeptides, including antagonists, and/or fragments thereof, may be useful for treating, diagnosing, prognosing, and/or preventing male reproductive disorders, such as, for example, male infertility, impotence, prostate cancer, ejaculatory disorders, and/or testicular cancer. This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. If fact, increased expression of certain phosphatases have been identified as tumor markers for testicular cancer (see, for example, Koshida, K., Nishino, A., Yamamoto, H., Uchibayashi, T., Naito, K., Hisazumi, H., Hirano, K., Hayashi, Y., Wahren, B., Andersson, L, J. Urol., 146(1):57–60, (1991); and Klein, E A, Urol. Clin. North. Am., 20(1):67–73, (1993)).

The strong homology to phosphatases, particularly dual-specificity phosphatases, combined with the significant localized expression in ovary and placental tissue suggests the human phosphatase polynucleotides and polypeptides may be useful in treating, diagnosing, prognosing, and/or preventing reproductive disorders.

In preferred embodiments, RET31 polynucleotides and polypeptides including agonists and fragments thereof, have uses which include treating, diagnosing, prognosing, and/or preventing the following, non-limiting, diseases or disorders of the uterus: dysfunctional uterine bleeding, amenorrhea, primary dysmenorrhea, sexual dysfunction, infertility, pelvic inflammatory disease, endometriosis, placental aromatase deficiency, premature menopause, and placental dysfunction.

The strong homology to phosphatases, particularly dual-specificity phosphatases, combined with the significant localized expression in skeletal tissue suggests the human phosphatase polynucleotides and polypeptides may be useful in treating, diagnosing, prognosing, and/or preventing muscle diseases and/or disorders, which include but are not limited to, musculodegenerative disorders, multiple sclerosis, atrophy, ticks.

Alternatively, the strong homology to phosphatases, particularly dual-specificity phosphatases, combined with the significant localized expression in liver tissue suggests the human phosphatase polynucleotides and polypeptides may be useful in treating, diagnosing, prognosing, and/or preventing hepatic diseases and/or disorders. Representative uses are described in the "Hyperproliferative Disorders", "Infectious Disease", and "Binding Activity" sections below, and elsewhere herein. Briefly, the protein can be used for the detection, treatment, and/or prevention of hepatoblastoma, jaundice, hepatitis, liver metabolic diseases and conditions that are attributable to the differentiation of hepatocyte progenitor cells, cirrhosis, hepatic cysts, pyrogenic abscess, amebic abcess, hydatid cyst, cystadenocarcinoma, adenoma, focal nodular hyperplasia, hemangioma, hepatocellulae carcinoma, cholangiocarcinoma, angiosarcoma, and granulomatous liver disease. In addition the protein product is useful for treating developmental abnormalities, fetal deficiencies, pre-natal disorders and various would-healing diseases and/or tissue trauma.

Moreover, polynucleotides and polypeptides, including fragments and/or antagonists thereof, have uses which include, directly or indirectly, treating, preventing, diagnosing, and/or prognosing the following, non-limiting, hepatic infections: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaries' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by Spirochete infection, liver disease caused by *Treponema pallidum* infection, liver disease caused by *Brrelia burgdorferi* infection, liver disease caused by Leptospirosis, liver disease caused by *Coxiella burnetii* infection, liver disease caused by *Rickettsia richettsii* infection, liver disease caused by *Chlamydia trachomatis* infection, liver disease caused by *Chlamydia psittaci* infection, in addition to any other hepatic disease and/or disorder implicated by the causative agents listed above or elsewhere herein.

The strong homology to phosphatases, particularly dual-specificity phosphatases, combined with the significant localized expression in placental tissue suggests the human phosphatase polynucleotides and polypeptides may be useful in treating, diagnosing, prognosing, and/or preventing a variety of vascular disorders and conditions, which include, but are not limited to miscrovascular disease, vascular leak syndrome, aneurysm, stroke, embolism, thrombosis, coronary artery disease, arteriosclerosis, and/or atherosclerosis. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to phosphatases, particularly dual-specificity phosphatases, combined with the predominate localized expression in pancreas tissue suggests the human RET31 phosphatase polynucleotides and polypeptides, including antagonists, and/or fragments thereof, may be useful for treating, diagnosing, prognosing, and/or preventing pancreatic, in addition to metabolic and gastrointestinal disorders.

In preferred embodiments, RET31 polynucleotides and polypeptides including agonists, antagonists, and fragments thereof, have uses which include treating, diagnosing, prognosing, and/or preventing the following, non-limiting, diseases or disorders of the pancreas: diabetes mellitus, diabetes, type 1 diabetes, type 2 diabetes, adult onset diabetes, indications related to islet cell transplantation, indications related to pancreatic transplantation, pancreatitis, pancreatic cancer, pancreatic exocrine insufficiency, alcohol induced pancreatitis, maldigestion of fat, maldigestion of protein, hypertriglyceridemia, vitamin b12 malabsorption, hypercalcemia, hypocalcemia, hyperglycemia, ascites, pleural effusions, abdominal pain, pancreatic necrosis, pancreatic abscess, pancreatic pseudocyst, gastrinomas, pancreatic islet cell hyperplasia, multiple endocrine neoplasia type 1 (men 1) syndrome, insulitis, amputations, diabetic neuropathy, pancreatic auto-immune disease, genetic defects of—cell function, HNF-1 aberrations (formerly MODY3), glucokinase aberrations (formerly MODY2), HNF-4 aberrations (formerly MODY1), mitochondrial DNA aberrations, genetic defects in insulin action, type a insulin resistance, leprechaunism, Rabson-Mendenhall syndrome, lipoatrophic diabetes, pancreatectomy, cystic fibrosis, hemochromatosis, fibrocalculous pancreatopathy, endocrinopathies, acromegaly, Cushing's syndrome, glucagonoma, pheochromocytoma, hyperthyroidism, somatostatinoma, aldosteronoma, drug- or chemical-induced diabetes such as from the following drugs: Vacor, Pentamdine, Nicotinic acid, Glucocorticoids, Thyroid hormone, Diazoxide, Adrenergic agonists, Thiazides, Dilantin, and Interferon, pancreatic infections, congenital rubella, cytomegalovirus, uncommon forms of immune-mediated diabetes, "stiff-man" syndrome, anti-insulin receptor antibodies, in addition to other genetic syndromes sometimes associated with diabetes which include, for example, Down's syndrome, Klinefelter's syndrome, Turner's syndrome, Wolfram's syndrome, Friedrich's ataxia, Huntington's chorea, Lawrence Moon Beidel syndrome, Myotonic dystrophy, Porphyria, and Prader Willi syndrome, and/or Gestational diabetes mellitus (GDM).

The strong homology to phosphatases, particularly dual-specificity phosphatases, combined with the predominate localized expression in thymus tissue suggests the human RET31 phosphatase polynucleotides and polypeptides, including antagonists, and/or fragments thereof, may be useful for treating, diagnosing, prognosing, and/or preventing immune and hematopoietic disorders. Representative uses are described in the "Immune Activity", "Chemotaxis", and "Infectious Disease" sections below, and elsewhere herein. Briefly, the strong expression in immune tissue indicates a role in regulating the proliferation; survival; differentiation; and/or activation of hematopoietic cell lineages, including blood stem cells.

The RET31 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product may be useful in the expansion of stem cells and committed progenitors of various blood lineages, and in the differentiation and/or proliferation of various cell types.

The RET31 polypeptide may be useful for modulating cytokine production, antigen presentation, or other processes, such as for boosting immune responses, etc. Expression in cells of lymphoid origin, indicates the natural gene product would be involved in immune functions.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissuemarkers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The human phosphatase polynucleotides and polypeptides, including fragments and agonists thereof, may have uses which include, either directly or indirectly, for boosting immune responses.

The strong homology to phosphatases, particularly dual-specificity phosphatases, suggests the human phosphatase polynucleotides and polypeptides may be useful in treating, diagnosing, prognosing, and/or preventing a variety of disorders and conditions, particularly inflammatory conditions, which include, but are not limited to rheumatoid arthritis, juvenile arthritis, psoriasis, asthma, ischemia-repurfusion, multiple sclerosis, rejection of organ or tissue transplants, chronic obstructive pulmonary disease, inflammatory bowel disease, Chrohn's disease, ulcerative colitis, inacute respiratory distress syndrome, systemic lupus erythematosis, cystic fibrosis, autoimmune diseases, cancers, tumors, and neoplasms.

The human phosphatase polynucleotides and polypeptides, including fragments and/or antagonists thereof, may have uses which include identification of modulators of human phosphatase function including antibodies (for detection or neutralization), naturally-occurring modulators and small molecule modulators. Antibodies to domains of the human phosphatase protein could be used as diagnostic agents of cardiovascular and inflammatory conditions in patients, are useful in monitoring the activation of signal transduction pathways, and can be used as a biomarker for the involvement of phosphatases in disease states, and in the evaluation of inhibitors of phosphatases in vivo.

Human phosphatase polypeptides and polynucleotides have additional uses which include diagnosing diseases related to the over and/or under expression of human phosphatase by identifying mutations in the human phosphatase gene by using human phosphatase sequences as probes or by determining human phosphatase protein or mRNA expression levels. Human phosphatase polypeptides may be useful for screening compounds that affect the activity of the protein. Human phosphatase peptides can also be used for the generation of specific antibodies and as bait in yeast two hybrid screens to find proteins the specifically interact with human phosphatase (described elsewhere herein).

Immunohistochemistry analysis of the protein localization of the RET31 polypeptide (see Example 58) in normal and diseased tissues determined that RET31 was strongly expressed in normal respiratory epithelial cell bodies, type I and II pneumocytes, lung neutrophils, lung mast cells, lung macrophages, in comparison to the same in asthmatic patients which showed less staining. These results suggest that RET31 polypeptides and polynucleotides, including fragments thereof, may be useful for the treatment of pulmonary disorders. The decreased staining in diseased lung tissues suggests RET31 is essential for normal cell maintenance and homeostasis, and is downregulated in transformed, or rapidly proliferating cells. Thus, agonists of RET31 polypeptides and polynucleotides may be particularly useful for the treatment of pulmonary disorders.

Immunohistochemistry analysis of the protein localization of the RET31 polypeptide (see Example 58) in normal and diseased tissues determined that RET31 was also strongly expressed in chondrocytes and rimming osteoblasts in degenerative arthritis, in addition to hematopoeitic cell tissue. Moreover, melanocytes were strongly positive, as was skin with psoriasis. These results suggest that RET31 may be involved in inflammatory responses of certain diseases and/or disorders. Thus, RET31 polypeptides and polynucleotides, including fragments thereof, may be useful for the treatment of inflammatory disorders, particularly inflammatory disorders of the skin and bone, such as, psoriasis and arthritis, for example. Moreover, antagonists of RET31 polypeptides and polynucleotides may be useful for the treatment of inflammatory disorders, particularly inflammatory disorders of the skin and bone, such as, psoriasis and arthritis, for example.

Assays designed to assess the phosphatase activity of the RET31 polypeptide have been performed and prove that RET31 does indeed have phosphatase activity as described in Example 57 herein (see FIG. 36). The observed phosphatase activity was specific to RET31 as GST alone did not result in any observed activity. In addition, the observed phosphatase activity was specifically inhibited by the known phosphatase active site inhibitor, vanadate.

In addition to assaying the full-length RET31 polypeptide (SEQ ID NO:109), a C-terminal deletion of RET31 was also assayed corresponding to amino acids M1 to T302 of SEQ ID NO:109). The M1 to T302 deletion mutant had an unexpected five fold increase in phosphatase activity relative to the full-length protein.

A phosphatase with a sequence similar to the RET31 polypeptide has been reported as MKP7 (Masuda et al., JBC 276, 39002–39011; and Tanoue et al., JBC., 276, 26269–26639). These authors reported that the phosphatase could bind to and dephosphorylate the p38 kinase and the Jnk kinase in cells, resulting in the inactivation of these kinases. Activation of p38 kinase is known to be important in the induction of apoptosis (Herlaar and Brown, Molecular Medicine Today 5, 439–447). One pathway where p38 has been reported to be important is in paclitaxel (Taxol®) induced apoptosis in tumor cells (Seidman et al., Experimental Cell Research 268, 84–92). Similarly, activation of the Jnk kinase has also been reported to be important in the induction of apoptosis (Chang and Karin, Nature 410, 37–40), including in paclitaxel induced apoptosis (Lee et al., JBC., 273, 28253–28260). Therefore, inhibitors of RET31 should induce apoptosis in tumor cells by increasing the activation of p38 and Jnk kinases in the cells by preventing the dephosphorylation of these kinases. This would be particularly advantageous when combined with a chemotherapeutic drug, such as paclitaxel, that activates p38 and/or Jnk kinases to help induce apoptosis. Such a use represents a novel utility of RET31 antagonists and which has not been appreciated by Masuda et al., nor by Tanoue et al. Indeed, Masuda et al. teach that MKP7 may be a tumor suppressor gene, in which case inhibition of MKP7 would increase malignancies, which teaches away from our intended use for RET31 inhibitors.

In preferred embodiments, the present invention encompasses the use of inhibitors of RET31 for the treatment of cancer. Per the teachings described herein, inhibitors of RET31 may include small molecule inhibitors of RET31 activity, inhibitors that prevent RET31 from binding to p38 and/or Jnk kinases, antisense oligonucleotides to RET31, and antibodies directed against RET31. Such RET31 inhibitors would be particularly useful in malignancies where RET31 was overexpressed relative to normal tissues. In addition to the use of RET31 inhibitors as single agents, inhibitors of RET31 would be of particular use in combination with paclitaxel and other chemotherapeutic agents that induce Jnk and/or p38 dependent apoptosis in tumor cells for the treatment of malignancies. Other chemotherapeutic agents that may induce the activation of Jnk and/or p38 leading to apoptosis that would be of use in combination with inhibitors of RET31 include but are not limited to RRR-alpha-tocopherol succinate, DA-125 [(8S,10S)-8-(3-aminopropanoyloxyacetyl)-10-[(2,6-dideoxy-2-fluoro-alpha-L-talopyranosyl)oxy]-7,8,9,10-tetrahydro-6,8,11-trihydroxy-1-methoxy-5,12-naphthacene-dione hydrochloride] a novel anthracycline derivative, cisplatin, tamoxifen, sulindac sulfone, sulindac, arsenic trioxide, actinomycin D, docetaxel (Taxotere), vinblastine, vincristine, nocodazole, colchicines, and other microtubule-interfering agents.

Although it is believed the encoded polypeptide may share at least some biological activities with phosphatase proteins (particularly dual specificity proteins), a number of methods of determining the exact biological function of this clone are either known in the art or are described elsewhere herein. Briefly, the function of this clone may be determined by applying microarray methodology. Nucleic acids corresponding to the human phosphatase polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from diseased testis tissue, as compared to, normal tissue might indicate a function in modulating testis function, for example. In the case of human RET31 phosphatase, adrenal gland, testis, prostate, ovary, skeletal muscle, liver, placenta, pancreas, thymus, small intestine, thyroid, heart, kidney, and/or lung tissue should be used, for example, to extract RNA to prepare the probe.

In addition, the function of the protein may be assessed by applying quantitative PCR methodology, for example. Real time quantitative PCR would provide the capability of following the expression of the human phosphatase gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of human phosphatase, a disease correlation related to human phosphatase may be made by comparing the mRNA expression level of human phosphatase in normal tissue, as compared to diseased tissue (particularly diseased tissue isolated from the following: adrenal gland, testis, prostate, ovary, skeletal muscle, liver, placenta, pancreas, thymus, small intestine, thyroid, heart, kidney, and/or lung tissue). Significantly higher or lower levels of human phosphatase expression in the diseased tissue may suggest human phosphatase plays a role in disease progression, and antagonists against human phosphatase polypeptides would be useful therapeutically in treating, preventing, and/or ameliorating the disease. Alternatively, significantly higher or lower levels of human phosphatase expression in the diseased tissue may suggest human phosphatase plays a defensive role against disease progression, and agonists of human phosphatase polypeptides may be useful therapeutically in treating, preventing, and/or ameliorating the disease. Also encompassed by the present invention are quantitative PCR probes corresponding to the polynucleotide sequence provided as SEQ ID NO:108 (FIGS. 13A–F).

The function of the protein may also be assessed through complementation assays in yeast. For example, in the case of the human phosphatase, transforming yeast deficient in dual-specificity phosphatase activity, for example, and assessing their ability to grow would provide convincing evidence the human phosphatase polypeptide has dual-specificity phosphatase activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype. Such knock-out experiments are known in the art, some of which are disclosed elsewhere herein.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a adrenal gland, testis, prostate, ovary, skeletal muscle, liver, placenta, pancreas, thymus, small intestine, thyroid, heart, kidney, and/or lung tissue specific promoter), or it can be expressed at a specified time of development using an inducible and/or a developmentally regulated promoter.

In the case of human phosphatase transgenic mice or rats, if no phenotype is apparent in normal growth conditions, observing the organism under diseased conditions (metabolic, reproductive, immune, hematopoietic, cardiovascular, hepatic, or pulmonary disorders, in addition to cancers, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal RET31 deletion polypeptides are encompassed by the present invention: M1-S665, A2-S665, H3-S665, E4-S665, M5-S665, I6-S665, G7-S665, T8-S665, Q9-S665, I10-S665, V11-S665, T12-S665, E13-S665, R14-S665, L15-S665, V16-S665, A17-S665, L18-S665, L19-S665, E20-S665, S21-S665, G22-S665, T23-S665, E24-S665, K25-S665, V26-S665, L27-S665, L28-S665, I29-S665, D30-S665, S31-S665, R32-S665, P33-S665, F34-S665, V35-S665, E36-S665, Y37-S665, N38-S665, T39-S665, S40-S665, H41-S665, I42-S665, L43-S665, E44-S665, A45-S665, I46-S665, N47-S665, I48-S665, N49-S665, C50-S665, S51-S665, K52-S665, L53-S665, M54-S665, K55-S665, R56-S665, R57-S665, L58-S665, Q59-S665, Q60-S665, D61-S665, K62-S665, V63-S665, L64-S665, I65-S665, T66-S665, E67-S665, L68-S665, I69-S665, Q70-S665, H71-S665, S72-S665, A73-S665, K74-S665, H75-S665, K76-S665, V77-S665, D78-S665, I79-S665, D80-S665, C81-S665, S82-S665, Q83-S665, K84-S665, V85-S665, V86-S665, V87-S665, Y88-S665, D89-S665, Q90-S665, S91-S665, S92-S665, Q93-S665, D94-S665, V95-S665, A96-S665, S97-S665, L98-S665, S99-S665, S100-S665, D101-S665, C102-S665, F103-S665, L104-S665, T105-S665, V106-S665, L107-S665, L108-S665, G109-S665, K110-S665, L111-S665, E112-S665, K113-S665, S114-S665, F115-S665, N116-S665, S117-S665, V118-S665, H119-S665, L120-S665, L121-S665, A122-S665, G123-S665, G124-S665, F125-S665, A126-S665, E127-S665, F128-S665, S129-S665, R130-S665, C131-S665, F132-S665, P133-S665, G134-S665, L135-S665, C136-S665, E137-S665, G138-S665, K139-S665, S140-S665, T141-S665, L142-S665, V143-S665, P144-S665, T145-S665, C146-S665, I147-S665, S148-S665, Q149-S665, P150-S665, C151-S665, L152-S665, P153-S665, V154-S665, A155-S665, N156-S665, I157-S665, G158-S665, P159-S665, T160-S665, R161-S665, I162-S665, L163-S665, P164-S665, N165-S665, L166-S665, Y167-S665, L168-S665, G169-S665, C170-S665, Q171-S665, R172-S665, D173-S665, V174-S665, L175-S665, N176-S665, K177-S665, E178-S665, L179-S665, I180-S665, Q181-S665, Q182-S665, N183-S665, G184-S665, I185-S665, G186-S665, Y187-S665, V188-S665, L189-S665, N190-S665, A191-S665, S192-S665, Y193-S665, T194-S665, C195-S665, P196-S665, K197-S665, P198-S665, D199-S665, F200-S665, I201-S665, P202-S665, E203-S665, S204-S665, H205-S665, F206-S665, L207-S665, R208-S665, V209-S665, P210-S665, V211-S665, N212-S665, D213-S665, S214-S665, F215-S665, C216-S665, E217-S665, K218-S665, I219-S665, L220-S665, P221-S665, W222-S665, L223-S665, D224-S665, K225-S665, S226-S665, V227-S665, D228-S665, F229-S665, I230-S665, E231-S665, K232-S665, A233-S665, K234-S665, A235-S665, S236-S665, N237-S665, G238-S665, C239-S665, V240-S665, L241-S665, V242-S665, H243-S665, C244-S665, L245-S665, A246-S665, G247-S665, I248-S665, S249-S665, R250-S665, S251-S665, A252-S665, T253-S665, I254-S665, A255-S665, I256-S665, A257-S665, Y258-S665, I259-S665, M260-S665, K261-S665, R262-S665, M263-S665, D264-S665, M265-S665, S266-S665, L267-S665, D268-S665, E269-S665, A270-S665, Y271-S665, R272-S665, F273-S665, V274-S665, K275-S665, E276-S665, K277-S665, R278-S665, P279-S665, T280-S665, I281-S665, S282-S665, P283-S665, N284-S665, F285-S665, N286-S665, F287-S665, L288-S665, G289-S665, Q290-S665, L291-S665, L292-S665, D293-S665, Y294-S665, E295-S665, K296-S665, K297-S665, I298-S665, K299-S665, N300-S665, Q301-S665, T302-S665, G303-S665, A304-S665, S305-S665, G306-S665, P307-S665, K308-S665, S309-S665, K310-S665, L311-S665, K312-S665, L313-S665, L314-S665, H315-S665, L316-S665, E317-S665, K318-S665, P319-S665, N320-S665, E321-S665, P322-S665, V323-S665, P324-S665, A325-S665, V326-S665, S327-S665, E328-S665, G329-S665, G330-S665, Q331-S665, K332-S665, S333-S665, E334-S665, T335-S665, P336-S665, L337-S665, S338-S665, P339-S665, P340-S665, C341-S665, A342-S665, D343-S665, S344-S665, A345-S665, T346-S665, S347-S665, E348-S665, A349-S665, A350-S665, G351-S665, Q352-S665, R353-S665, S354-S665, V355-S665, H356-S665, P357-S665, A358-S665, S359-S665, V360-S665, P361-S665, S362-S665, V363-S665, P364-S665, S365-S665, V366-S665, Q367-S665, P368-S665, S369-S665, L370-S665, L371-S665, E372-S665, D373-S665, S374-S665, P375-S665, L376-S665, V377-S665, Q378-S665, A379-S665, L380-S665, S381-S665, G382-S665, L383-S665, H384-S665, L385-S665, S386-S665, A387-S665, D388-S665, R389-S665, L390-S665, E391-S665, D392-S665, S393-S665, N394-S665, K395-S665, L396-S665, K397-S665, R398-S665, S399-S665, F400-S665, S401-S665, L402-S665, D403-S665, I404-S665, K405-S665, S406-S665, V407-S665, S408-S665, Y409-S665, S410-S665, A411-S665, S412-S665, M413-S665, A414-S665, A415-S665, S416-S665, IA17-S665, H418-S665, G419-S665, F420-S665, S421-S665, S422-S665, S423-S665, E424-S665, D425-S665, A426-S665, L427-S665, E428-S665, Y429-S665, Y430-S665, K431-S665, P432-S665, S433-S665, T434-S665, T435-S665, L436-S665, D437-S665, G438-S665, T439-S665, N440-S665, K441-S665, L442-S665, C443-S665, Q444-S665, F445-S665, S446-S665, P447-S665, V448-S665, Q449-S665, E450-S665, L451-S665, S452-S665, E453-S665, Q454-S665, T455-S665, P456-S665, E457-S665, T458-S665, S459-S665, P460-S665, D461-S665, K462-S665, E463-S665, E464-S665, A465-S665, S466-S665, I467-S665, P468-S665, K469-S665, K470-S665, L471-S665, Q472-S665, T473-S665, A474-S665, R475-S665, P476-S665, S477-S665, D478-S665, S479-S665, Q480-S665, S481-S665, K482-S665, R483-S665, L484-S665, H485-S665, S486-S665, V487-S665, R488-S665, T489-S665, S490-S665, S491-S665, S492-S665, G493-S665, T494-S665, A495-S665, Q496-S665, R497-S665, S498-S665, L499-S665, L500-S665, S501-S665, P502-S665, L503-S665, H504-S665, R505-S665, S506-S665, G507-S665, S508-S665, V509-S665, E510-S665, D511-S665, N512-S665, Y513-S665, H514-S665, T515-S665, S516-S665, F517-S665, L518-S665, F519-S665, G520-S665, L521-S665, S522-S665, T523-S665, S524-S665, Q525-S665, Q526-S665, H527-S665, L528-S665, T529-S665, K530-S665, S531-S665, A532-S665, G533-S665, L534-S665, G535-S665, L536-S665, K537-S665, G538-S665, W539-S665, H540-S665, S541-S665, D542-S665, I543-S665, L544-S665, A545-S665, P546-S665, Q547-S665, T548-S665, S549-S665, T550-S665, P551-

S665, S552-S665, L553-S665, T554-S665, S555-S665, S556-S665, W557-S665, Y558-S665, F559-S665, A560-S665, T561-S665, E562-S665, S563-S665, S564-S665, H565-S665, F566-S665, Y567-S665, S568-S665, A569-S665, S570-S665, A571-S665, I572-S665, Y573-S665, G574-S665, G575-S665, S576-S665, A577-S665, S578-S665, Y579-S665, S580-S665, A581-S665, Y582-S665, S583-S665, C584-S665, S585-S665, Q586-S665, L587-S665, P588-S665, T589-S665, C590-S665, G591-S665, D592-S665, Q593-S665, V594-S665, Y595-S665, S596-S665, V597-S665, R598-S665, R599-S665, R600-S665, Q601-S665, K602-S665, P603-S665, S604-S665, D605-S665, R606-S665, A607-S665, D608-S665, S609-S665, R610-S665, R611-S665, S612-S665, W613-S665, H614-S665, E615-S665, E616-S665, S617-S665, P618-S665, F619-S665, E620-S665, K621-S665, Q622-S665, F623-S665, K624-S665, R625-S665, R626-S665, S627-S665, C628-S665, Q629-S665, M630-S665, E631-S665, F632-S665, G633-S665, E634-S665, S635-S665, I636-S665, M637-S665, S638-S665, E639-S665, N640-S665, R641-S665, S642-S665, R643-S665, E644-S665, E645-S665, L646-S665, G647-S665, K648-S665, V649-S665, G650-S665, S651-S665, Q652-S665, S653-S665, S654-S665, F655-S665, S656-S665, G657-S665, S658-S665, and/or M659-S665 of SEQ ID NO:109. Polynucleotide sequences encoding these polypeptides are also provided.

The present invention also encompasses the use of these N-terminal RET31 deletion polypeptides as immunogenic and/or antigenic epitopes as described elsewhere herein.

In preferred embodiments, the following C-terminal RET31 deletion polypeptides are encompassed by the present invention: M1-S665, M1-V664, M1-E663, M1-I662, M1-I661, M1-E660, M1-M659, M1-S658, M1-G657, M1-S656, M1-F655, M1-S654, M1-S653, M1-Q652, M1-S651, M1-G650, M1-V649, M1-K648, M1-G647, M1-L646, M1-E645, M1-E644, M1-R643, M1-S642, M1-R641, M1-M1-F632, M1-E631, M1-M630, M1-Q629, M1-C628, M1-S627, M1-R626, M1-R625, M1-K624, M1-F623, M1-Q622, M1-K621, M1-E620, M1-F619, M1-P618, M1-S617, M1-E616, M1-E615, M1-H614, M1-W613, M1-S612, M1-R611, M1-R610, M1-S609, M1-D608, M1-A607, M1-R606, M1-D605, M1-S604, M1-P603, M1-K602, M1-Q601, M1-R600, M1-R599, M1-R598, M1-V597, M1-S596, M1-Y595, M1-V594, M1-Q593, M1-D592, M1-G591, M1-C590, M1-T589, M1-P588, M1-L587, M1-Q586, M1-S585, M1-C584, M1-S583, M1-Y582, M1-A581, M1-S580, M1-Y579, M1-S578, M1-A577, M1-S576, M1-G575, M1-G574, M1-Y573, M1-I572, M1-A571, M1-S570, M1-A569, M1-S568, M1-Y567, M1-F566, M1-H565, M1-S564, M1-S563, M1-E562, M1-T561, M1-A560, M1-F559, M1-Y558, M1-W557, M1-S556, M1-S555, M1-T554, M1-L553, M1-S552, M1-P551, M1-T550, M1-S549, M1-T548, M1-Q547, M1-P546, M1-A545, M1-L544, M1-I543, M1-H527, M1-S541, M1-H540, M1-W539, M1-G538, M1-K537, M1-L536, M1-G535, M1-L534, M1-G533, M1-A532, M1-S531, M1-K530, M1-T529, M1-L528, M1-H527, M1-Q526, M1-Q525, M1-S524, M1-T523, M1-S522, M1-L521, M1-G520, M1-F519, M1-L518, M1-F517, M1-S516, M1-T515, M1-H514, M1-Y513, M1-N512, M1-D511, M1-E510, M1-V509, M1-S508, M1-G507, M1-S506, M1-R505, M1-H504, M1-L503, M1-P502, M1-S501, M1-L500, M1-L499, M1-S498, M1-R497, M1-Q496, M1-A495, M1-T494, M1-G493, M1-S492, M1-S491, M1-S490, M1-T489, M1-R488, M1-V487, M1-S486, M1-H485, M1-L484, M1-R483, M1-K482, M1-S481, M1-Q480, M1-S479, M1-D478, M1-S477, M1-P476, M1-R475, M1-A474, M1-T473, M1-Q472, M1-L471, M1-K470, M1-K469, M1-P468, M1-I467, M1-S466, M1-A465, M1-E464, M1-E463, M1-K462, M1-D461, M1-P460, M1-S459, M1-T458, M1-E457, M1-P456, M1-T455, M1-Q454, M1-E453, M1-S452, M1-L451, M1-E450, M1-Q449, M1-V448, M1-P447, M1-S446, M1-F445, M1-Q444, M1-C443, M1-L442, M1-K441, M1-N440, M1-T439, M1-G438, M1-D437, M1-L436, M1-T435, M1-T434, M1-S433, M1-P432, M1-K431, M1-Y430, M1-Y429, M1-E428, M1-L427, M1-A426, M1-D425, M1-E424, M1-S423, M1-S422, M1-S421, M1-F420, M1-G419, M1-H418, M1-L417, M1-S416, M1-A415, M1-A414, M1-M413, M1-S412, M1-A411, M1-S410, M1-Y409, M1-S408, M1-V407, M1-S406, M1-K405, M1-I404, M1-D403, M1-L402, M1-S401, M1-F400, M1-S399, M1-R398, M1-K397, M1-L396, M1-K395, M1-N394, M1-S393, M1-D392, M1-E391, M1-L390, M1-R389, M1-D388, M1-A387, M1-S386, M1-L385, M1-H384, M1-L383, M1-G382, M1-S381, M1-L380, M1-A379, M1-Q378, M1-V377, M1-L376, M1-P375, M1-S374, M1-D373, M1-E372, M1-L371, M1-L370, M1-S369, M1-P368, M1-Q367, M1-V366, M1-S365, M1-P364, M1-V363, M1-S362, M1-P361, M1-V360, M1-S359, M1-A358, M1-P357, M1-H356, M1-V355, M1-P354, M1-R353, M1-Q352, M1-G351, M1-A350, M1-A349, M1-E348, M1-S347, M1-T346, M1-A345, M1-S344, M1-D343, M1-A342, M1-C341, M1-P340, M1-P339, M1-S338, M1-L337, M1-P336, M1-T335, M1-E334, M1-S333, M1-K332, M1-Q331, M1-G330, M1-G329, M1-E328, M1-S327, M1-V326, M1-A325, M1-P324, M1-V323, M1-P322, M1-E321, M1-N320, M1-P319, M1-K318, M1-E317, M1-L316, M1-H315, M1-L314, M1-L313, M1-K312, M1-L311, M1-K310, M1-S309, M1-K308, M1-P307, M1-G306, M1-S305, M1-A304, M1-G303, M1-T302, M1-Q301, M1-N300, M1-K299, M1-I298, M1-K297, M1-K296, M1-E295, M1-Y294, M1-D293, M1-L292, M1-L291, M1-Q290, M1-G289, M1-L288, M1-F287, M1-N286, M1-F285, M1-N284, M1-P283, M1-S282, M1-I281, M1-T280, M1-P279, M1-R278, M1-K277, M1-E276, M1-K275, M1-V274, M1-F273, M1-R272, M1-Y271, M1-A270, M1-E269, M1-D268, M1-L267, M1-S266, M1-M265, M1-D264, M1-M263, M1-R262, M1-K261, M1-M260, M1-I259, M1-Y258, M1-A257, M1-I256, M1-A255, M1-I254, M1-T253, M1-A252, M1-S251, M1-R250, M1-S249, M1-I248, M1-G247, M1-A246, M1-L245, M1-C244, M1-H243, M1-V242, M1-L241, M1-V240, M1-C239, M1-G238, M1-N237, M1-S236, M1-A235, M1-K234, M1-A233, M1-K232, M1-E231, M1-I230, M1-F229, M1-D228, M1-V227, M1-S226, M1-K225, M1-D224, M1-L223, M1-W222, M1-P221, M1-L220, M1-I219, M1-K218, M1-E217, M1-C216, M1-F215, M1-S214, M1-D213, M1-N212, M1-V211, M1-P210, M1-V209, M1-R208, M1-L207, M1-F206, M1-H205, M1-S204, M1-E203, M1-P202, M1-I201, M1-F200, M1-D199, M1-P198, M1-K197, M1-P196, M1-C195, M1-T194, M1-Y193, M1-S192, M1-A191, M1-N190, M1-L189, M1-V188, M1-Y187, M1-G186, M1-I185, M1-G184, M1-N183, M1-Q182, M1-Q181, M1-I180, M1-L179, M1-E178, M1-K177, M1-N176, M1-L175, M1-V174, M1-D173, M1-R172, M1-Q171, M1-C170, M1-G169, M1-L168, M1-Y167, M1-L166, M1-N165, M1-P164, M1-L163, M1-I162, M1-R161, M1-T160, M1-P159, M1-G158, M1-I157, M1-N156, M1-A155, M1-V154, M1-P153, M1-L152, M1-C151, M1-P150, M1-Q149, M1-S148, M1-I147, M1-C146, M1-T145, M1-P144, M1-V143, M1-L142, M1-T141, M1-S140, M1-K139, M1-G138, M1-E137, M1-C136, M1-L135, M1-G134, M1-P133, M1-F132, M1-C131, M1-R130, M1-S129, M1-F128, M1-E127, M1-A126, M1-F125, M1-G124, M1-G123, M1-A122, M1-L121, M1-L120, M1-H119, M1-V118, M1-S117, M1-N116, M1-F115, M1-S114, M1-K113, M1-E112, M1-L111, M1-K110, M1-G109, M1-L108, M1-L107, M1-V106, M1-T105, M1-L104, M1-F103, M1-C102, M1-D10, M1-S100, M1-S99, M1-L98, M1-S97, M1-A96, M1-V95, M1-D94, M1-Q93, M1-S92, M1-S91, M1-Q90, M1-D89, M1-Y88, M1-V87, M1-V86, M1-V85, M1-K84, M1-Q83, M1-S82, M1-C81, M1-D80, M1-I79, M1-D78, M1-V77, M1-K76, M1-H75, M1-K74, M1-A73, M1-S72, M1-H71, M1-Q70, M1-I69, M1-L68, M1-E67, M1-T66, M1-I65, M1-L64, M1-V63, M1-K62, M1-D61, M1-Q60, M1-Q59, M1-L58, M1-R57, M1-R56, M1-K55, M1-M54, M1-L53, M1-K52, M1-S51, M1-C50, M1-N49, M1-I48, M1-N47, M1-I46, M1-A45, M1-E44, M1-L43, M1-I42, M1-H41, M1-S40, M1-T39, M1-N38, M1-Y37, M1-E36, M1-V35, M1-F34, M1-P33, M1-R32, M1-S31, M1-D30, M1-I29, M1-L28, M1-L27, M1-V26, M1-K25, M1-E24, M1-T23, M1-G22, M1-S21, M1-E20, M1-L19, M1-L18, M1-A17, M1-V16, M1-L15, M1-R14, M1-E13, M1-T12, M1-V11, M1-I10, M1-Q9, M1-T8, and/or M1-G7 of SEQ ID NO:109. Polynucleotide sequences encoding these polypeptides are also provided. The present invention also encompasses the use of these C-terminal RET31 deletion polypeptides as immunogenic and/or antigenic epitopes as described elsewhere herein.

The present invention also encompasses immunogenic and/or antigenic epitopes of the human RET31 phosphatase polypeptide.

The human phosphatase polypeptides of the present invention were determined to comprise several phosphorylation sites based upon the Motif algorithm (Genetics Computer Group, Inc.). The phosphorylation of such sites may regulate some biological activity of the human phosphatase polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the human phosphatase polypeptide to associate with other polypeptides, particularly cognate ligand for human phosphatase, or its ability to modulate certain cellular signal pathways.

The human phosphatase polypeptide was predicted to comprise twelve PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. 260:12492–12499(1985); which are hereby incorporated by reference herein.

In preferred embodiments, the following PKC phosphorylation site polypeptides are encompassed by the present invention: GTQIVTERLVALL (SEQ ID NO:116), LLESGTEKVLLID (SEQ ID NO:117), ELIQHSAKHKVDI (SEQ ID NO:118), VDIDCSQKVVVYD (SEQ ID NO:119), DRLEDSNKLKRSF (SEQ ID NO:120), TTLDGTNKLCQFS (SEQ ID NO:121), PKKLQTARPSDSQ (SEQ ID NO:122), PSDSQSKRLHSVR (SEQ ID NO:123), SKRLHSVRTSSSG (SEQ ID NO:124), GDQVYSVRRRQKP (SEQ ID NO:125), RRQKPSDRADSRR (SEQ ID NO:126), and/or SDRADSRRSWHEE (SEQ ID NO:127). Polynucleotides encoding these polypeptides are also provided. The present invention also encompasses the use of the human RET31 phosphatase PKC phosphorylation site polypeptides as immunogenic and/or antigenic epitopes as described elsewhere herein.

The human phosphatase polypeptide has been shown to comprise six glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine phosphorylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673–702(1972); Pless D. D., Lennarz W. J., Proc. Natl. Acad. Sci. U.S.A. 74:134–138(1977); Bause E., Biochem. J. 209:331–336(1983); Gavel Y., von Heijne G., Protein Eng. 3:433–442(1990); and Miletich J. P., Broze G. J. Jr., J. Biol. Chem. 265:11397–11404(1990).

In preferred embodiments, the following asparagine glycosylation site polypeptides are encompassed by the present invention: PFVEYNTSHILEAI (SEQ ID NO:128), EAININCSKLMKRR (SEQ ID NO:129), IGYVLNASYTCPKP (SEQ ID NO:130), LRVPVNDSFCEKIL (SEQ ID NO:131), EKKIKNQTGASGPK (SEQ ID NO:132), and/or SIMSENRSREELGK (SEQ ID NO:133). Polynucleotides encoding these polypeptides are also provided. The present invention also encompasses the use of the human RET31 phosphatase asparagine glycosylation site polypeptides as immunogenic and/or antigenic epitopes as described elsewhere herein.

In confirmation of the human RET31 representing a novel human phosphatase polypeptide, the RET31 polypeptide has been shown to comprise a dual specificity phosphatase catalytic domain as identified by the BLAST2 algorithm using the DSPc PFAM HMM (PF00782) as a query sequence.

The catalytic residue of the human RET31 polypeptide is represented by an active site cysteine located at amino acid residue 244 of SEQ ID NO:109 (FIGS. 13A–F).

In preferred embodiments, the following human RET31 DSPc domain polypeptide is encompassed by the present invention:

GPTRILPNLYLGCQRDVLNKELIQQNGIGYVLNASYTCPKPDFIPESHFLRVPV (SEQ ID NO: 134)
NDSFCEKILPWLDKSVDFIEKAKASNGCVLVHCLAGISRSATIAIAYIMKRMD
MSLDEAYRFVKEKRPTISPNFNFLGQLLDYEKK.

Polynucleotides encoding this polypeptide are also provided. The present invention also encompasses the use of this human RET31 DSPc domain polypeptide as an immunogenic and/or antigenic epitope as described elsewhere herein.

In preferred embodiments, the following human RET31 DSPc domain amino acid substitutions are encompassed by the present invention: wherein G158 is substituted with either an A, C, D, E, F, H, I, K, L, M, N, P, Q, R, S, T, V, W, or Y; wherein P159 is substituted with either an A, C, D, E, F, G, H, I, K, L, M, N, Q, R, S, T, V, W, or Y; wherein T160 is substituted with either an A, C, D, E, F, G, H, I, K, L, M, N, P, Q, R, S, V, W, or Y; wherein R161 is substituted with either an A, C, D, E, F, G, H, I, K, L, M, N, P, Q, S, T, V, W, or Y; wherein I162 is substituted with either an A, C, D, E, F, G, H, K, L, M, N, P, Q, R, S, T, V, W, or Y; wherein L163 is substituted with either an A, C, D, E, F, G, H, I, K, M, N, P, Q, R, S, T, V, W, or Y; wherein P164 is substituted with either an A, C, D, E, F, G, H, I, K, L, M, N, Q, R, S, T, V, W, or Y; wherein N165 is substituted with either an A, C, D, E, F, G, H, I, K, L, M, P, Q, R, S, T, V, W, or Y; wherein L166 is substituted with either an A, C, D, E, F, G, H, I, K, M, N, P, Q, R, S, T, V, W, or Y; wherein Y167 is substituted with either an A, C, D, E, F, G, H, 1, K, L, M, N, P, Q, R, S, T, V, or W; wherein L168 is substituted with either an A, C, D, E, F, G, H, I, K, M, N, P, Q, R, S, T, V, W, or Y; wherein G169 is substituted with either an A, C, D, E, F, H, I, K, L, M, N, P, Q, R, S, T, V, W, or Y; wherein C170 is substituted with either an A, D, E, F, G, H, I, K, L, M, N, P, Q, R, S, T, V, W, or Y; wherein Q171 is substituted with either an A, C, D, E, F, G, H, I, K, L, M, N, P, R, S, T, V, W, or Y; wherein R172 is substituted with either an A, C, D, E, F, G, H, I, K, L, M, N, P, Q, S, T, V, W, or Y; wherein D173 is substituted with either an A, C, E, F, G, H, I, K, L, M, N, P, Q, R, S, T, V, W, or Y; wherein V174 is substituted with either an A, C, D, E, F, G, H, I, K, L, M, N, P, Q, R, S, T, W, or Y; wherein L175 is substituted with either an A, C, D, E, F, G, H, I, K, M, N, P, Q, R, S, T, V, W, or Y; wherein N176 is substituted with either an A, C, D, E, F, G, H, I, K, L, M, P, Q, R, S, T, V, W, or Y; wherein K177 is substituted with either an A, C, D, E, F, G, H, I, L, M, N, P, Q, R, S, T, V, W, or Y; wherein E178 is substituted with either an A, C, D, F, G, H, I, K, L, M, N, P, Q, R, S, T, V, W, or Y; wherein L179 is substituted with either an A, C, D, E, F, G, H, I, K, M, N, P, Q, R, S, T, V, W, or Y; wherein I180 is substituted with either an A, C, D, E, F, G, H, K, L, M, N, P, Q, R, S, T, V, W, or Y; wherein Q181 is substituted with either an A, C, D, E, F, G, H, I, K, L, M, N, P, R, S, T, V, W, or Y; wherein Q182 is substituted with either an A, C, D, E, F, G, H, I, K, L, M, N, P, R, S, T, V, W, or Y; wherein N183 is substituted with either an A, C, D, E, F, G, H, I, K, L, M, P, Q, R, S, T, V, W, or Y; wherein G184 is substituted with either an A, C, D, E, F, H, I, K, L, M, N, P, Q, R, S, T, V, W, or Y; wherein I185 is substituted with either an A, C, D, E, F, G, H, K, L, M, N, P, Q, R, S, T, V, W, or Y; wherein G186 is substituted with either an A, C, D, E, F, H, I, K, L, M, N, P, Q, R, S, T, V, W, or Y; wherein Y187 is substituted with either an A, C, D, E, F, G, H, I, K, L, M, N, P, Q, R, S, T, V, or W; wherein V188 is substituted with either an A, C, D, E, F, G, H, I, K, L, M, N, P, Q, R, S, T, W, or Y; wherein L189 is substituted with either an A, C, D, E, F, G, H, I, K, M, N, P, Q, R, S, T, V, W, or Y; wherein N190 is substituted with either an A, C, D, E, F, G, H, I, K, L, M, P, Q, R, S, T, V, W, or Y; wherein A191 is substituted with either a C, D, E, F, G, H, I, K, L, M, N, P, Q, R, S, T, V, W, or Y; wherein S192 is substituted with either an A, C, D, E, F, G, H, I, K, L, M, N, P, Q, R, T, V, W, or Y; wherein Y193 is substituted with either an A, C, D, E, F, G, H, I, K, L, M, N, P, Q, R, S, T, V, or W; wherein T194 is substituted with either an A, C, D, E, F, G, H, I, K, L, M, N, P, Q, R, S, V, W, or Y; wherein C195 is substituted with either an A, D, E, F, G, H, I, K, L, M, N, P, Q, R, S, T, V, W, or Y; wherein P196 is substituted with either an A, C, D, E, F, G, H, I, K, L, M, N, Q, R, S, T, V, W, or Y; wherein K197 is substituted with either an A, C, D, E, F, G, H, I, L, M, N, P, Q, R, S, T, V, W, or Y; wherein P198 is substituted with either an A, C, D, E, F, G, H, I, K, L, M, N, Q, R, S, T, V, W, or Y; wherein D199 is substituted with either an A, C, E, F, G, H, I, K, L, M, N, P, Q, R, S, T, V, W, or Y; wherein F200 is substituted with either an A, C, D, E, G, H, I, K, L, M, N, P, Q, R, S, T, V, W, or Y; wherein I201 is substituted with either an A, C, D, E, F, G, H, K, L, M, N, P, Q, R, S, T, V, W, or Y; wherein P202 is substituted with either an A, C, D, E, F, G, H, I, K, L, M, N, Q, R, S, T, V, W, or Y; wherein E203 is substituted with either an A, C, D, F, G, H, I, K, L, M, N, P, Q, R, S, T, V, W, or Y; wherein S204 is substituted with either an A, C, D, E, F, G, H, I, K, L, M, N, P, Q, R, T, V, W, or Y; wherein H205 is substituted with either an A, C, D, E, F, G, I, K, L, M, N, P, Q, R, S, T, V, W, or Y; wherein F206 is substituted with either an A, C, D, E, G, H, I, K, L, M, N, P, Q, R, S, T, V, W, or Y; wherein L207 is substituted with either an A, C, D, E, F, G, H, I, K, M, N, P, Q, R, S, T, V, W, or Y; wherein R208 is substituted with either an A, C, D, E, F, G, H, I, K, L, M, N, P, Q, S, T, V, W, or Y; wherein V209 is substituted with either an A, C, D, E, F, G, H, I, K, L, M, N, P, Q, R, S, T, W, or Y; wherein P210 is substituted with either an A, C, D, E, F, G, H, I, K, L, M, N, Q, R, S, T, V, W, or Y; wherein V211 is substituted with either an A, C, D, E, F, G, H, I, K, L, M, N, P, Q, R, S, T, W, or Y; wherein N212 is substituted with either an A, C, D, E, F, G, H, I, K, L, M, P, Q, R, S, T, V, W, or Y; wherein D213 is substituted with either an A, C, E, F, G, H, I, K, L, M, N, P, Q, R, S, T, V, W, or Y; wherein S214 is substituted with either an A, C, D, E, F, G, H, I, K, L, M, N, P, Q, R, T, V, W, or Y; wherein F215 is substituted with either an A, C, D, E, G, H, I, K, L, M, N, P, Q, R, S, T, V, W, or Y; wherein C216 is substituted with either an A, D, E, F, G, H, I, K, L, M, N, P, Q, R, S, T, V, W, or Y; wherein E217 is substituted with either an A, C, D, F, G, H, I, K, L, M, N, P, Q, R, S, T, V, W, or Y; wherein K218 is substituted with either an A, C, D, E, F, G, H, I, L, M, N, P, Q, R, S, T, V, W, or Y; wherein I219 is substituted with either an A, C, D, E, F, G, H, K, L, M, N, P, Q, R, S, T, V, W, or Y; wherein L220 is substituted with either an A, C, D, E, F, G, H, I, K, M, N, P, Q, R, S, T, V, W, or Y; wherein P221 is substituted with either an A, C, D, E, F, G, H, I, K, L, M, N, Q, R, S, T, V, W, or Y; wherein W222 is substituted with either an A, C, D, E, F, G, H, I, K, L, M, N, P, Q, R, S, T, V, or Y; wherein L223 is substituted with either an A, C, D, E, F, G, H, I, K, M, N, P, Q, R, S, T, V, W, or Y; wherein D224 is substituted with either an A, C, E, F, G, H, I, K, L, M, N, P, Q, R, S, T, V, W, or Y; wherein K225 is substituted with either an A, C, D, E, F, G, H, I, L, M, N, P, Q, R, S, T, V, W, or Y; wherein S226 is substituted with either an A, C, D, E, F, G, H, I, K, L, M, N, P, Q, R, T, V, W, or Y; wherein V227 is substituted with either an A, C, D, E, F, G, H, I, K, L, M, N, P, Q, R, S, T, W, or Y; wherein D228 is substituted with either an A, C, E, F, G, H, I, K, L, M, N, P, Q, R, S, T, V, W, or Y; wherein F229 is substituted with either an A, C, D, E, G, H, I, K, L, M, N, P, Q, R, S, T, V, W, or Y; wherein I230 is substituted with either an A, C, D, E, F, G, H, K, L, M, N, P, Q, R, S, T, V, W, or Y; wherein E231 is substituted with either an A, C, D, F, G, H, I, K, L, M, N, P, Q, R, S, T, V, W, or Y; wherein K232 is substituted with either an A, C, D, E, F, G, H, I, L, M, N, P, Q, R, S, T, V, W, or Y; wherein A233 is substituted with either a C, D, E, F, G, H, I, K, L, M, N, P, Q, R, S, T, V, W, or Y; wherein K234 is substituted with either an A, C, D, E, F, G, H, I, L, M, N, P, Q, R, S, T, V, W, or Y; wherein A235 is substituted with either a C, D, E, F, G, H, I, K, L, M, N, P, Q, R, S, T, V, W, or Y; wherein S236 is substituted with either an A, C, D, E, F, G, H, I, K, L, M, N, P, Q, R, T, V, W, or Y; wherein N237 is substituted with either an A, C, D, E, F, G, H, I, K, L, M, P, Q, R, S, T, V, W, or Y; wherein G238 is substituted with either an A, C, D, E, F, H, I, K, L, M, N, P, Q, R, S, T, V, W, or Y; wherein C239 is substituted with either an A, D, E, F, G, H, I, K, L, M, N, P, Q, R, S, T, V, W, or Y; wherein V240 is substituted with either an A, C, D, E, F, G, H, I, K, L, M, N, P, Q, R, S, W, or Y; wherein L241 is substituted with either an A, C, D, E, F, G, H, I, K, M, N, P, Q, R, S, T, V, W, or Y; wherein V242 is substituted with either an A, C, D, E, F, G, H, I, K, L, M, N, P, Q, R, S, T, W, or Y; wherein H243 is substituted with either an A, C, D, E, F, G, I, K, L, M, N, P, Q, R, S, T, V, W, or Y; wherein C244 is substituted with either an A, D, E, F, G, H, I, K, L, M, N, P, Q, R, S, T, V, W, or Y; wherein L245 is substituted with either an A, C, D, E, F, G, H, I, K, M, N, P, Q, R, S, T, V, W, or Y; wherein A246 is substituted with either a C, D, E, F, G, H, I, K, L, M, N, P, Q, R, S, T, V, W, or Y; wherein G247 is substituted with either an A, C, D, E, F, H, I, K, L, M, N, P, Q, R, S, T, V, W, or Y; wherein I248 is substituted with either an A, C, D, E, F, G, H, K, L, M, N, P, Q, R, S, T, V, W, or Y; wherein S249 is substituted with either an A, C, D, E, F, G, H, I, K, L, M, N, P, Q, R, T, V, W, or Y; wherein R250 is substituted with either an A, C, D, E, F, G, H, I, K, L, M, N, P, Q, S, T, V, W, or Y; wherein S251 is substituted with either an A, C, D, E, F, G, H, I, K, L, M, N, P, Q, R, T, V, W, or Y; wherein A252 is substituted with either a C, D, E, F, G, H, I, K, L, M, N, P, Q, R, S, T, V, W, or Y; wherein T253 is substituted with either an A, C, D, E, F, G, H, I, K, L, M, N, P, Q, R, S, V, W, or Y;

wherein I254 is substituted with either an A, C, D, E, F, G, H, K, L, M, N, P, Q, R, S, T, V, W, or Y; wherein A255 is substituted with either a C, D, E, F, G, H, I, K, L, M, N, P, Q, R, S, T, V, W, or Y; wherein I256 is substituted with either an A, C, D, E, F, G, H, K, L, M, N, P, Q, R, S, T, V, W, or Y; wherein A257 is substituted with either a C, D, E, F, G, H, I, K, L, M, N, P, Q, R, S, T, V, W, or Y; wherein Y258 is substituted with either an A, C, D, E, F, G, H, I, K, L, M, N, P, Q, R, S, T, V, or W; wherein I259 is substituted with either an A, C, D, E, F, G, H, K, L, M, N, P, Q, R, S, T, V, W, or Y; wherein M260 is substituted with either an A, C, D, E, F, G, H, I, K, L, N, P, Q, R, S, T, V, W, or Y; wherein K261 is substituted with either an A, C, D, E, F, G, H, I, L, M, N, P, Q, R, S, T, V, W, or Y; wherein R262 is substituted with either an A, C, D, E, F, G, H, I, K, L, M, N, P, Q, S, T, V, W, or Y; wherein M263 is substituted with either an A, C, D, E, F, G, H, I, K, L, N, P, Q, R, S, T, V, W, or Y; wherein D264 is substituted with either an A, C, E, F, G, H, I, K, L, M, N, P, Q, R, S, T, V, W, or Y; wherein M265 is substituted with either an A, C, D, E, F, G, H, I, K, L, N, P, Q, R, S, T, V, W; or Y; wherein S266 is substituted with either an A, C, D, E, F, G, H, I, K, L, M, N, P, Q, R, T, V, W, or Y; wherein L267 is substituted with either an A, C, D, E, F, G, H, I, K, M, N, P, Q, R, S, T, V, W, or Y; wherein D268 is substituted with either an A, C, E, F, G, H, I, K, L, M, N, P, Q, R, S, T, V, W, or Y; wherein E269 is substituted with either an A, C, D, F, G, H, I, K, L, M, N, P, Q, R, S, T, V, W, or Y; wherein A270 is substituted with either a C, D, E, F, G, H, I, K, L, M, N, P, Q, R, S, T, V, W, or Y; wherein Y271 is substituted with either an A, C, D, E, F, G, H, I, K, L, M, N, P, Q, R, S, T, V, or W; wherein R272 is substituted with either an A, C, D, E, F, G, H, I, K, L, M, N, P, Q, S, T, V, W, or Y; wherein F273 is substituted with either an A, C, D, E, G, H, I, K, L, M, N, P, Q, R, S, T, V, W, or Y; wherein V274 is substituted with either an A, C, D, E, F, G, H, I, K, L, M, N, P, Q, R, S, T, W, or Y; wherein K275 is substituted with either an A, C, D, E, F, G, H, I, L, M, N, P, Q, R, S, T, V, W, or Y; wherein E276 is substituted with either an A, C, D, F, G, H, I, K, L, M, N, P, Q, R, S, T, V, W, or Y; wherein K277 is substituted with either an A, C, D, E, F, G, H, I, L, M, N, P, Q, R, S, T, V, W, or Y; wherein R278 is substituted with either an A, C, D, E, F, G, H, I, K, L, M, N, P, Q, S, T, V, W, or Y; wherein P279 is substituted with either an A, C, D, E, F, G, H, I, K, L, M, N, Q, R, S, T, V, W, or Y; wherein T280 is substituted with either an A, C, D, E, F, G, H, I, K, L, M, N, P, Q, R, S, V, W, or Y; wherein I281 is substituted with either an A, C, D, E, F, G, H, K, L, M, N, P, Q, R, S, T, V, W, or Y; wherein S282 is substituted with either an A, C, D, E, F, G, H, I, K, L, M, N, P, Q, R, T, V, W, or Y; wherein P283 is substituted with either an A, C, D, E, F, G, H, I, K, L, M, N, Q, R, S, T, V, W, or Y; wherein N284 is substituted with either an A, C, D, E, F, G, H, I, K, L, M, P, Q, R, S, T, V, W, or Y; wherein F285 is substituted with either an A, C, D, E, G, H, I, K, L, M, N, P, Q, R, S, T, V, W, or Y; wherein N286 is substituted with either an A, C, D, E, F, G, H, I, K, L, M, P, Q, R, S, T, V, W, or Y; wherein F287 is substituted with either an A, C, D, E, G, H, I, K, L, M, N, P, Q, R, S, T, V, W, or Y; wherein L288 is substituted with either an A, C, D, E, F, G, H, I, K, M, N, P, Q, R, S, T, V, W, or Y; wherein G289 is substituted with either an A, C, D, E, F, H, I, K, L, M, N, P, Q, R, S, T, V, W, or Y; wherein Q290 is substituted with either an A, C, D, E, F, G, H, I, K, L, M, N, P, R, S, T, V, W, or Y; wherein L291 is substituted with either an A, C, D, E, F, G, H, I, K, M, N, P, Q, R, S, T, V, W, or Y; wherein L292 is substituted with either an A, C, D, E, F, G, H, I, K, M, N, P, Q, R, S, T, V, W, or Y; wherein D293 is substituted with either an A, C, E, F, G, H, I, K, L, M, N, P, Q, R, S, T, V, W, or Y; wherein Y294 is substituted with either an A, C, D, E, F, G, H, I, K, L, M, N, P, Q, R, S, T, V, or W; wherein E295 is substituted with either an A, C, D, F, G, H, I, K, L, M, N, P, Q, R, S, T, V, W, or Y; wherein K296 is substituted with either an A, C, D, E, F, G, H, I, L, M, N, P, Q, R, S, T, V, W, or Y; and/or wherein K297 is substituted with either an A, C, D, E, F, G, H, I, L, M, N, P, Q, R, S, T, V, W, or Y of SEQ ID NO:109, in addition to any combination thereof. The present invention also encompasses the use of these human RET31 DSPc domain amino acid substituted polypeptides as immunogenic and/or antigenic epitopes as described elsewhere herein.

In preferred embodiments, the following human RET31 DSPc domain conservative amino acid substitutions are encompassed by the present invention: wherein G158 is substituted with either an A, M, S, or T; wherein P159 is a P; wherein T160 is substituted with either an A, G, M, or S; wherein R161 is substituted with either a K, or H; wherein I162 is substituted with either an A, V, or L; wherein L163 is substituted with either an A, I, or V; wherein P164 is a P; wherein N165 is substituted with a Q; wherein L166 is substituted with either an A, I, or V; wherein Y167 is either an F, or W; wherein L168 is substituted with either an A, I, or V; wherein G169 is substituted with either an A, M, S, or T; wherein C170 is a C; wherein Q171 is substituted with a N; wherein R172 is substituted with either a K, or H; wherein D173 is substituted with an E; wherein V174 is substituted with either an A, I, or L; wherein L175 is substituted with either an A, I, or V; wherein N176 is substituted with a Q; wherein K177 is substituted with either a R, or H; wherein E178 is substituted with a D; wherein L179 is substituted with either an A, I, or V; wherein I180 is substituted with either an A, V, or L; wherein Q181 is substituted with a N; wherein Q182 is substituted with a N; wherein N183 is substituted with a Q; wherein G184 is substituted with either an A, M, S, or T; wherein I185 is substituted with either an A, V, or L; wherein G186 is substituted with either an A, M, S, or T; wherein Y187 is either an F, or W; wherein V188 is substituted with either an A, I, or L; wherein L189 is substituted with either an A, I, or V; wherein N190 is substituted with a Q; wherein A191 is substituted with either a G, I, L, M, S, T, or V; wherein S192 is substituted with either an A, G, M, or T; wherein Y193 is either an F, or W; wherein T194 is substituted with either an A, G, M, or S; wherein C195 is a C; wherein P196 is a P; wherein K197 is substituted with either a R, or H; wherein P198 is a P; wherein D199 is substituted with an E; wherein F200 is substituted with either a W, or Y; wherein I201 is substituted with either an A, V, or L; wherein P202 is a P; wherein E203 is substituted with a D; wherein S204 is substituted with either an A, G, M, or T; wherein H205 is substituted with either a K, or R; wherein F206 is substituted with either a W, or Y; wherein L207 is substituted with either an A, I, or V; wherein R208 is substituted with either a K, or H; wherein V209 is substituted with either an A, I, or L; wherein P210 is a P; wherein V211 is substituted with either an A, I, or L; wherein N212 is substituted with a Q; wherein D213 is substituted with an E; wherein S214 is substituted with either an A, G, M, or T; wherein F215 is substituted with either a W, or Y; wherein C216 is a C; wherein E217 is substituted with a D; wherein K218 is substituted with either a R, or H; wherein I219 is substituted with either an A, V, or L; wherein L220 is substituted with either an A, I, or V; wherein P221 is a P; wherein W222 is either an F, or Y; wherein L223 is substituted with either an A, I, or V; wherein D224 is substituted with an E; wherein K225 is substituted with either a R, or H; wherein S226 is substituted with either an A, G, M, or T; wherein V227 is substituted with either an A, I, or L; wherein D228 is substituted with an E; wherein F229 is substituted with either a W, or Y; wherein I230 is substituted with either an A, V, or L; wherein E231 is substituted with a D; wherein K232 is substituted with either a R, or H; wherein A233 is substituted with either a G, I, L, M, S, T, or V; wherein K234 is substituted with either a R, or H; wherein A235 is substituted with either a G, I, L, M, S, T, or V; wherein S236 is substituted with either an A, G, M, or T; wherein N237 is substituted with a Q; wherein G238 is substituted with either an A, M, S, or T; wherein C239 is a C; wherein V240 is substituted with either an A, I, or L; wherein L241 is substituted with either an A, I, or V; wherein V242 is substituted with either an A, I, or L; wherein H243 is substituted with either a K, or R; wherein C244 is a C; wherein L245 is substituted with either an A, I, or V; wherein A246 is substituted with either a G, I, L, M, S, T, or V; wherein G247 is substituted with either an A, M, S, or T; wherein I248 is substituted with either an A, V, or L; wherein S249 is substituted with either an A, G, M, or T; wherein R250 is substituted with either a K, or H; wherein S251 is substituted with either an A, G, M, or T; wherein A252 is substituted with either a G, I, L, M, S, T, or V; wherein T253 is substituted with either an A, G, M, or S; wherein I254 is substituted with either an A, V, or L; wherein A255 is substituted with either a G, I, L, M, S, T, or V; wherein I256 is substituted with either an A, V, or L; wherein A257 is substituted with either a G, I, L, M, S, T, or V; wherein Y258 is either an F, or W; wherein I259 is substituted with either an A, V, or L; wherein M260 is substituted with either an A, G, S, or T; wherein K261 is substituted with either a R, or H; wherein R262 is substituted with either a K, or H; wherein M263 is substituted with either an A, G, S, or T; wherein D264 is substituted with an E; wherein M265 is substituted with either an A, G, S, or T; wherein S266 is substituted with either an A, G, M, or T; wherein L267 is substituted with either an A, I, or V; wherein D268 is substituted with an E; wherein E269 is substituted with a D; wherein A270 is substituted with either a G, I, L, M, S, T, or V; wherein Y271 is either an F, or W; wherein R272 is substituted with either a K, or H; wherein F273 is substituted with either a W, or Y; wherein V274 is substituted with either an A, I, or L; wherein K275 is substituted with either a R, or H; wherein E276 is substituted with a D; wherein K277 is substituted with either a R, or H; wherein R278 is substituted with either a K, or H; wherein P279 is a P; wherein T280 is substituted with either an A, G, M, or S; wherein I281 is substituted with either an A, V, or L; wherein S282 is substituted with either an A, G, M, or T; wherein P283 is a P; wherein N284 is substituted with a Q; wherein F285 is substituted with either a W, or Y; wherein N286 is substituted with a Q; wherein F287 is substituted with either a W, or Y; wherein L288 is substituted with either an A, I, or V; wherein G289 is substituted with either an A, M, S, or T; wherein Q290 is substituted with a N; wherein L291 is substituted with either an A, I, or V; wherein L292 is substituted with either an A, I, or V; wherein D293 is substituted with an E; wherein Y294 is either an F, or W; wherein E295 is substituted with a D; wherein K296 is substituted with either a R, or H; and/or wherein K297 is substituted with either a R, or H of SEQ ID NO:109 in addition to any combination thereof. Other suitable substitutions within the human RET31 DSPc domain are encompassed by the present invention and are referenced elsewhere herein. The present invention also encompasses the use of these human RET31 DSPc domain conservative amino acid substituted polypeptides as immunogenic and/or antigenic epitopes as described elsewhere herein.

In further confirmation of the human RET31 polypeptide representing a novel human phosphatase polypeptide, the RET31 polypeptide has been shown to comprise a tyrosine specific protein phosphatase active site domain according to the Motif algorithm (Genetics Computer Group, Inc.).

Tyrosine specific protein phosphatases (EC 3.1.3.48) (PTPase) are enzymes that catalyze the removal of a phosphate group attached to a tyrosine residue. These enzymes are very important in the control of cell growth, proliferation, differentiation and transformation. Multiple forms of PTPase have been characterized and can be classified into two categories: soluble PTPases and transmembrane receptor proteins that contain PTPase domain(s).

The currently known PTPases are listed below: Soluble PTPases, PTPN1 (PTP-1B), PTPN2 (T-cell PTPase; TC- PTP), PTPN3 (H1) and PTPN4 (MEG), enzymes that contain an N-terminal band 4.1-like domain and could act at junctions between the membrane and cytoskeleton, PTPN5 (STEP), PTPN6 (PTP-1C; HCP; SHP) and PTPN11 (PTP-2C; SH-PTP3; Syp), enzymes which contain two copies of the SH2 domain at its N-terminal extremity (e.g., the *Drosophila* protein corkscrew (gene csw) also belongs to this subgroup), PTPN7 (LC-PTP; Hematopoietic protein-tyrosine phosphatase; HePTP), PTPN8 (70Z-PEP), PTPN9 (MEG2), PTPN12 (PTP-G1; PTP-P19), Yeast PTP1, Yeast PTP2 which may be involved in the ubiquitin-mediated protein degradation pathway, Fission yeast pyp1 and pyp2 which play a role in inhibiting the onset of mitosis, Fission yeast pyp3 which contributes to the dephosphorylation of cdc2, Yeast CDC14 which may be involved in chromosome segregation, *Yersinia* virulence plasmid PTPAses (gene yopH), *Autographa californica* nuclear polyhedrosis virus 19 Kd PTPase, Dual specificity PTPases, DUSP1 (PTPN10; MAP kinase phosphatase-1; MKP-1); which dephosphorylates MAP kinase on both Thr-183 and Tyr-185, DUSP2 (PAC-1), a nuclear enzyme that dephosphorylates MAP kinases ERK1 and ERK2 on both Thr and Tyr residues, DUSP3 (VHR), DUSP4 (HVH2), DUSP5 (HVH3), DUSP6 (Pyst1; MKP-3), DUSP7 (Pyst2; MKP-X), Yeast MSG5, a PTPase that dephosphorylates MAP kinase FUS3, Yeast YVH1, Vaccinia virus H1 PTPase—a dual specificity phosphatase.

Structurally, all known receptor PTPases, are made up of a variable length extracellular domain, followed by a transmembrane region and a C-terminal catalytic cytoplasmic domain. Some of the receptor PTPases contain fibronectin type III (FN-III) repeats, immunoglobulin-like domains, MAM domains or carbonic anhydrase-like domains in their extracellular region. The cytoplasmic region generally contains two copies of the PTPAse domain. The first seems to have enzymatic activity, while the second is inactive but seems to affect substrate specificity of the first. In these domains, the catalytic cysteine is generally conserved but some other, presumably important, residues are not.

PTPase domains consist of about 300 amino acids. There are two conserved cysteines, the second one has been shown to be absolutely required for activity. Furthermore, a number of conserved residues in its immediate vicinity have also been shown to be important.

A consensus sequence for tyrosine specific protein phophatases is provided as follows:

[LIVMF]—H—C-x(2)-G-x(3)-[STC]—[STAGP]-x-[LIVMFY], wherein C is the active site residue and "X" represents any amino acid.

Additional information related to tyrosine specific protein phosphatase domains and proteins may be found in reference to the following publications Fischer E. H., Charbonneau H., Tonks N. K., Science 253:401–406(1991); Charbonneau H., Tonks N. K., Annu. Rev. Cell Biol. 8:463–493 (1992); Trowbridge I. S., J. Biol. Chem. 266:23517–23520 (1991); Tonks N. K., Charbonneau H., Trends Biochem. Sci. 14:497–500(1989); and Hunter T., Cell 58:1013–1016(1989); which are hereby incorporated herein by reference in their entirety.

In preferred embodiments, the following tyrosine specific protein phosphatase active site domain polypeptide is encompassed by the present invention: NGCVLVHCLAG-ISRSATIAIAYI (SEQ ID NO:144). Polynucleotides encoding these polypeptides are also provided. The present invention also encompasses the use of this tyrosine specific protein phosphatase active site domain polypeptide as an immunogenic and/or antigenic epitope as described elsewhere herein.

In addition to the human RET31 polynucleotide and polypeptide sequence, the present invention also relates to the isolated mouse ortholog of the RET31 olypeptide.

The polypeptide corresponding to the mouse RET31 gene provided as SEQ ID NO:113 (FIGS. 16A–C), encoded by the polynucleotide sequence according to SEQ ID NO:114 (FIGS. 16A–C), and/or encoded by the polynucleotide contained within the deposited clone, mRET31, has significant homology at the nucleotide and amino acid level to a number of phosphatases, which include, for example, the human RET31 protein of the present invention (SEQ ID NO:109); the human DUS8 (DUS8; Genbank Accession No:gi|U27193; SEQ ID NO:110); the human DUSP6 protein (DUSP6; Genbank Accession No: gi|AB013382; SEQ ID NO:111); and the human map kinase phosphatase MKP-5 protein (MKP-5; Genbank Accession No: gi|AB026436; SEQ ID NO:112) as determined by BLASTP. An alignment of the human phosphatase polypeptide with these proteins is provided in FIGS. 14A–C.

The determined nucleotide sequence of the mRET31 cDNA in FIGS. 16A–C (SEQ ID NO:114) contains an open reading frame encoding a protein of about 660 amino acid residues, with a deduced molecular weight of about 73 kDa. The amino acid sequence of the predicted mRET31 polypeptide is shown in FIGS. 16A–C (SEQ ID NO:114). The mRET31 protein shown in FIGS. 16A–C was determined to share significant identity and similarity to several known phosphates, particularly, dual-specificity protein phosphatases. Specifically, the mRET31 protein shown in FIGS. 16A–C was determined to be about 90% identical and 92% similar to the human RET31 protein of the present invention (SEQ ID NO:109); to be about 48.5% identical and 55.7% similar to the human DUS8 (DUS8; Genbank Accession No: gi|U27193; SEQ ID NO:110); to be about 37.4% identical and 49.7% similar to the human DUSP6 protein(DUSP6; Genbank Accession No: gi|AB013382; SEQ ID NO:111); and to be about 35.2% identical and 46.9% similar to the human map kinase phosphatase MKP-5 protein (MKP-5; Genbank Accession No: gi|AB026436; SEQ ID NO:112), as shown in FIG. 12.

The translational start nucleotide position of the mRET31 polynucleotide has been determined to begin at nucleotide 369 of SEQ ID NO:113 (FIGS. 16A–C), and the translational stop nucleotide position has been determined to be at nucleotide 2348 of SEQ ID NO:113 (FIGS. 16A–C).

In preferred embodiments, the following N-terminal mRET31 deletion polypeptides are encompassed by the present invention: M1-S660, A2-S660, H3-S660, E4-S660, M5-S660, I6-S660, G7-S660, T8-S660, Q9-S660, I10-S660, V11-S660, T12-S660, E13-S660, S14-S660, L15-S660, V16-S660, A17-S660, L18-S660, L19-S660, E20-S660, S21-S660, G22-S660, T23-S660, E24-S660, K25-S660, V26-S660, L27-S660, L28-S660, I29-S660, D30-S660, S31-S660, R32-S660, P33-S660, F34-S660, V35-S660, E36-S660, Y37-S660, N38-S660, T39-S660, S40-S660, H41-S660, I42-S660, L43-S660, E44-S660, A45-S660, I46-S660, N47-S660, I48-S660, N49-S660, C50-S660, S51-S660, K52-S660, L53-S660, M54-S660, K55-S660, R56-S660, R57-S660, L58-S660, Q59-S660, Q60-S660, D61-S660, K62-S660, V63-S660, L64-S660, I65-S660, T66-S660, E67-S660, L68-S660, I69-S660, H70-S660, Q71-S660, S72-S660, T73-S660, K74-S660, H75-S660, K76-S660, V77-S660, D78-S660, I79-S660, D80-S660, C81-S660, N82-S660, Q83-S660, R84-S660, V85-S660, V86-

S660, V87-S660, Y88-S660, D89-S660, H90-S660, S91-S660, S92-S660, Q93-S660, D94-S660, V95-S660, G96-S660, S97-S660, L98-S660, S99-S660, S100-S660, D101-S660, C102-S660, F103-S660, L104-S660, T105-S660, V106-S660, L107-S660, L108-S660, G109-S660, K110-S660, L111-S660, E112-S660, R113-S660, S114-S660, F115-S660, N116-S660, S117-S660, V118-S660, H119-S660, L120-S660, L121-S660, A122-S660, G123-S660, G124-S660, F125-S660, A126-S660, E127-S660, F128-S660, S129-S660, R130-S660, C131-S660, F132-S660, P133-S660, G134-S660, L135-S660, C136-S660, E137-S660, G138-S660, K139-S660, S140-S660, T141-S660, L142-S660, V143-S660, P144-S660, T145-S660, C146-S660, I147-S660, S148-S660, Q149-S660, P150-S660, C151-S660, L152-S660, P153-S660, V154-S660, A155-S660, N156-S660, I157-S660, G158-S660, P159-S660, T160-S660, R161-S660, I162-S660, L163-S660, P164-S660, N165-S660, L166-S660, Y167-S660, L168-S660, G169-S660, C170-S660, Q171-S660, R172-S660, D173-S660, V174-S660, L175-S660, N176-S660, K177-S660, D178-S660, L179-S660, M180-S660, Q181-S660, Q182-S660, N183-S660, G184-S660, I185-S660, G186-S660, Y187-S660, V188-S660, L189-S660, N190-S660, A191-S660, S192-S660, N193-S660, T194-S660, C195-S660, P196-S660, K197-S660, P198-S660, D199-S660, F200-S660, I201-S660, P202-S660, E203-S660, S204-S660, H205-S660, F206-S660, L207-S660, R208-S660, V209-S660, P210-S660, V211-S660, N212-S660, D213-S660, S214-S660, F215-S660, C216-S660, E217-S660, K218-S660, I219-S660, L220-S660, P221-S660, W222-S660, L223-S660, D224-S660, K225-S660, S226-S660, V227-S660, D228-S660, F229-S660, I230-S660, E231-S660, K232-S660, A233-S660, K234-S660, A235-S660, S236-S660, N237-S660, G238-S660, C239-S660, V240-S660, L241-S660, I242-S660, H243-S660, C244-S660, L245-S660, A246-S660, G247-S660, I248-S660, S249-S660, R250-S660, S251-S660, A252-S660, T253-S660, I254-S660, A255-S660, I256-S660, A257-S660, Y258-S660, I259-S660, M260-S660, K261-S660, R262-S660, M263-S660, D264-S660, M265-S660, S266-S660, L267-S660, D268-S660, E269-S660, A270-S660, Y271-S660, R272-S660, F273-S660, V274-S660, K275-S660, E276-S660, K277-S660, R278-S660, P279-S660, T280-S660, I281-S660, S282-S660, P283-S660, N284-S660, F285-S660, N286-S660, F287-S660, M288-S660, G289-S660, Q290-S660, L291-S660, M292-S660, D293-S660, Y294-S660, E295-S660, K296-S660, T297-S660, I298-S660, N299-S660, N300-S660, Q301-S660, T302-S660, G303-S660, M304-S660, S305-S660, G306-S660, P307-S660, K308-S660, S309-S660, K310-S660, L311-S660, K312-S660, L313-S660, L314-S660, H315-S660, L316-S660, D317-S660, K318-S660, P319-S660, S320-S660, E321-S660, P322-S660, V323-S660, P324-S660, A325-S660, A326-S660, S327-S660, E328-S660, G329-S660, G330-S660, W331-S660, K332-S660, S333-S660, A334-S660, L335-S660, S336-S660, L337-S660, S338-S660, P339-S660, P340-S660, C341-S660, A342-S660, N343-S660, S344-S660, T345-S660, S346-S660, E347-S660, A348-S660, S349-S660, G350-S660, Q351-S660, R352-S660, L353-S660, V354-S660, H355-S660, P356-S660, A357-S660, S358-S660, V359-S660, P360-S660, R361-S660, L362-S660, Q363-S660, P364-S660, S365-S660, L366-S660, L367-S660, E368-S660, D369-S660, S370-S660, P371-S660, L372-S660, V373-S660, Q374-S660, A375-S660, L376-S660, S377-S660, G378-S660, L379-S660, Q380-S660, L381-S660, S382-S660, S383-S660, E384-S660, K385-S660, L386-S660, E387-S660, D388-S660, S389-S660, T390-S660, K391-S660, L392-S660, K393-S660, R394-S660, S395-S660, F396-S660, S397-S660, L398-S660, D399-S660, I400-S660, K401-S660, S402-S660, V403-S660, S404-S660, Y405-S660, S406-S660, A407-S660, S408-S660, M409-S660, A410-S660, A411-S660, S412-S660, L413-S660, H414-S660, G415-S660, F416-S660, S417-S660, S418-S660, E419-S660, E420-S660, A421-S660, L422-S660, D423-S660, Y424-S660, C425-S660, K426-S660, P427-S660, S428-S660, A429-S660, T430-S660, L431-S660, D432-S660, G433-S660, T434-S660, N435-S660, K436-S660, L437-S660, C438-S660, Q439-S660, F440-S660, S441-S660, P442-S660, V443-S660, Q444-S660, E445-S660, V446-S660, S447-S660, E448-S660, Q449-S660, S450-S660, P451-S660, E452-S660, T453-S660, S454-S660, P455-S660, D456-S660, K457-S660, E458-S660, E459-S660, A460-S660, H461-S660, I462-S660, P463-S660, K464-S660, Q465-S660, P466-S660, Q467-S660, P468-S660, P469-S660, R470-S660, P471-S660, S472-S660, E473-S660, S474-S660, Q475-S660, V476-S660, T477-S660, R478-S660, L479-S660, H480-S660, S481-S660, V482-S660, R483-S660, T484-S660, G485-S660, S486-S660, S487-S660, G488-S660, S489-S660, T490-S660, Q491-S660, R492-S660, P493-S660, F494-S660, F495-S660, S496-S660, P497-S660, L498-S660, H499-S660, R500-S660, S501-S660, G502-S660, S503-S660, V504-S660, E505-S660, D506-S660, N507-S660, Y508-S660, H509-S660, T510-S660, N511-S660, F512-S660, L513-S660, F514-S660, G515-S660, L516-S660, S517-S660, T518-S660, S519-S660, Q520-S660, Q521-S660, H522-S660, L523-S660, T524-S660, K525-S660, S526-S660, A527-S660, G528-S660, L529-S660, G530-S660, L531-S660, K532-S660, G533-S660, W534-S660, H535-S660, S536-S660, D537-S660, I538-S660, L539-S660, A540-S660, P541-S660, Q542-S660, S543-S660, S544-S660, A545-S660, P546-S660, S547-S660, L548-S660, T549-S660, S550-S660, S551-S660, W534-S660, Y553-S660, F554-S660, A555-S660, T556-S660, E557-S660, P558-S660, S559-S660, H560-S660, L561-S660, Y562-S660, S563-S660, A564-S660, S565-S660, A566-S660, I567-S660, Y568-S660, G569-S660, G570-S660, N571-S660, S572-S660, S573-S660, Y574-S660, S575-S660, A576-S660, Y577-S660, S578-S660, C579-S660, G580-S660, Q581-S660, L582-S660, P583-S660, T584-S660, C585-S660, S586-S660, D587-S660, Q588-S660, I589-S660, Y590-S660, S591-S660, V592-S660, R593-S660, R594-S660, R595-S660, Q596-S660, K597-S660, P598-S660, T599-S660, D600-S660, R601-S660, A602-S660, D603-S660, S604-S660, R605-S660, R606-S660, S607-S660, W608-S660, H609-S660, E610-S660, E611-S660, S612-S660, P613-S660, F614-S660, E615-S660, K616-S660, Q617-S660, F618-S660, K619-S660, R620-S660, R621-S660, S622-S660, C623-S660, Q624-S660, M625-S660, E626-S660, F627-S660, G628-S660, E629-S660, S630-S660, I631-S660, M632-S660, S633-S660, E634-S660, N635-S660, R636-S660, S637-S660, R638-S660, E639-S660, E640-S660, L641-S660, G642-S660, K643-S660, V644-S660, G645-S660, S646-S660, Q647-S660, S648-S660, S649-S660, F650-S660, S651-S660, G652-S660, S653-S660, and/or M654-S660 of SEQ ID NO:114. Polynucleotide sequences encoding these polypeptides are also provided. The present invention also encompasses the use of these N-terminal mRET31 deletion polypeptides as immunogenic and/or antigenic epitopes as described elsewhere herein.

In preferred embodiments, the following C-terminal mRET31 deletion polypeptides are encompassed by the present invention: M1-S660, M1-V659, M1-E658, M1-I657, M1-I656, M1-E655, M1-M654, M1-S653, M1-G652, M1-S651, M1-F650, M1-S649, M1-S648, M1-Q647, M1-S646, M1-G645, M1-V644, M1-K643, M1-G642, M1-L641, M1-E640, M1-E639, M1-R638, M1-S637, M1-R636, M1-N635, M1-E634, M1-S633, M1-M632, M1-I631, M1-S630, M1-E629, M1-G628, M1-F627, M1-E626, M1-M625, M1-Q624, M1-C623, M1-S622, M1-R621, M1-R620, M1-K619, M1-F618, M1-Q617, M1-K616, M1-E615, M1-F614, M1-P613, M1-S612, M1-E611, M1-E610, M1-H609, M1-W608, M1-S607, M1-R606, M1-R605, M1-S604, M1-D603, M1-A602, M1-R601, M1-D600, M1-T599, M1-P598, M1-K597, M1-Q596, M1-R595, M1-R594, M1-R593, M1-V592, M1-S591, M1-Y590, M1-I589, M1-Q588, M1-D587, M1-S586, M1-C585, M1-T584, M1-P583, M1-L582, M1-Q581, M1-G580, M1-C579, M1-S578, M1-Y577, M1-A576, M1-S575, M1-Y574, M1-S573, M1-S572, M1-N571, M1-G570, M1-G569, M1-Y568, M1-I567, M1-A566, M1-S565, M1-A564, M1-S563, M1-Y562, M1-L561, M1-Y568, M1-S559, M1-P558, M1-E557, M1-T556, M1-A555, M1-F554, M1-Y553, M1-W552, M1-S551, M1-S550, M1-T549, M1-L548, M1-S547, M1-P546, M1-A545, M1-S544, M1-S543, M1-Q542, M1-P541, M1-A540, M1-L539, M1-I538, M1-D537, M1-S536, M1-H535, M1-W534, M1-G533, M1-K532, M1-L531, M1-G530, M1-L529, M1-G528, M1-A527, M1-S526, M1-K525, M1-T524, M1-L523, M1-H522, M1-Q521, M1-Q520, M1-S519, M1-T518, M1-S517, M1-L516, M1-G515, M1-F514, M1-L513, M1-F512, M1-N511, M1-T510, M1-H509, M1-Y508, M1-N507, M1-D506, M1-E505, M1-V504, M1-S503, M1-G502, M1-S501, M1-R500, M1-H499, M1-L498, M1-P497, M1-S496, M1-F495, M1-F494, M1-P493, M1-R492, M1-Q491, M1-T490, M1-S489, M1-G488, M1-S487, M1-S486, M1-G485, M1-T484, M1-R483, M1-V482, M1-S481, M1-H480, M1-LA479, M1-R478, M1-T477, M1-V476, M1-Q475, M1-S474, M1-E473, M1-S472, M1-P471, M1-R470, M1-P469, M1-P468, M1-Q467, M1-P466, M1-Q465, M1-K464, M1-P463, M1-I462, M1-H461, M1-A460, M1-E459, M1-E458, M1-K457, M1-D456, M1-P455, M1-S454, M1-T453, M1-E452, M1-P451, M1-S450, M1-Q449, M1-E448, M1-S447, M1-V446, M1-E445, M1-Q444, M1-V443, M1-P442, M1-S441, M1-F440, M1-Q439, M1-C438, M1-L437, M1-K436, M1-N435, M1-T434, M1-G433, M1-D432, M1-L431, M1-T430, M1-A429, M1-S428, M1-P427, M1-K426, M1-C425, M1-Y424, M1-D423, M1-L422, M1-A421, M1-E420, M1-E419, M1-S418, M1-S417, M1-F416, M1-G415, M1-H414, M1-L413, M1-S412, M1-A411, M1-A410, M1-M409, M1-S408, M1-A407, M1-S406, M1-Y405, M1-S404, M1-V403, M1-S402, M1-K401, M1-I400, M1-D399, M1-L398, M1-S397, M1-F396, M1-S395, M1-R394, M1-K393, M1-L392, M1-K391, M1-T390, M1-S389, M1-D388, M1-E387, M1-L386, M1-K385, M1-E384, M1-S383, M1-S382, M1-L381, M1-Q380, M1-L379, M1-G378, M1-S377, M1-L376, M1-A375, M1-Q374, M1-V373, M1-L372, M1-P371, M1-S370, M1-D369, M1-E368, M1-L367, M1-L366, M1-S365, M1-P364, M1-Q363, M1-L362, M1-R361, M1-P360, M1-V359, M1-S358, M1-A357, M1-P356, M1-H355, M1-V354, M1-L353, M1-R352, M1-Q351, M1-G350, M1-S349, M1-A348, M1-E347, M1-S346, M1-T345, M1-S344, M1-N343, M1-A342, M1-C341, M1-P340, M1-P339, M1-S338, M1-L337, M1-S336, M1-L335, M1-A334, M1-S333, M1-K332, M1-W331, M1-G330, M1-G329, M1-E328, M1-S327, M1-A326, M1-A325, M1-P324, M1-V323, M1-P322, M1-E321, M1-S320, M1-P319, M1-K318, M1-D317, M1-L316, M1-H315, M1-L314, M1-L313, M1-K312, M1-L311, M1-K310, M1-S309, M1-K308, M1-P307, M1-G306, M1-S305, M1-M304, M1-G303, M1-T302, M1-Q301, M1-N300, M1-N299, M1-I298, M1-T297, M1-K296, M1-E295, M1-Y294, M1-D293, M1-M292, M1-L291, M1-Q290, M1-G289, M1-M288, M1-F287, M1-N286, M1-F285, M1-N284, M1-P283, M1-S282, M1-I281, M1-T280, M1-P279, M1-R278, M1-K277, M1-E276, M1-K275, M1-V274, M1-F273, M1-R272, M1-Y271, M1-A270, M1-E269, M1-D268, M1-L267, M1-S266, M1-M265, M1-D264, M1-M263, M1-R262, M1-K261, M1-M260, M1-I259, M1-Y258, M1-A257, M1-I256, M1-A255, M1-I254, M1-T253, M1-A252, M1-S251, M1-R250, M1-S249, M1-I248, M1-G247, M1-A246, M1-L245, M1-C244, M1-H243, M1-I242, M1-L241, M1-V240, M1-C239, M1-G238, M1-N237, M1-S236, M1-A235, M1-K234, M1-A233, M1-K232, M1-E231, M1-I230, M1-F229, M1-D228, M1-V227, M1-S226, M1-K225, M1-D224, M1-L223, M1-W222, M1-P221, M1-L220, M1-I219, M1-K218, M1-E217, M1-C216, M1-F215, M1-S214, M1-D213, M1-N212, M1-V211, M1-P210, M1-V209, M1-R208, M1-L207, M1-F206, M1-M205, M1-S204, M1-E203, M1-P202, M1-I201, M1-F200, M1-D199, M1-P198, M1-K197, M1-P196, M1-C195, M1-T194, M1-N193, M1-S192, M1-A191, M1-N190, M1-L189, M1-V188, M1-Y187, M1-G186, M1-I185, M1-G184, M1-N183, M1-Q182, M1-Q181, M1-M180, M1-L179, M1-D178, M1-K177, M1-N176, M1-L175, M1-V174, M1-D173, M1-R172, M1-Q171, M1-C170, M1-G169, M1-L168, M1-Y167, M1-L166, M1-N165, M1-P164, M1-L163, M1-I162, M1-R161, M1-T160, M1-P159, M1-G158, M1-I157, M1-N156, M1-A155, M1-V154, M1-P153, M1-L152, M1-C151, M1-P150, M1-Q149, M1-S148, M1-I147, M1-C146, M1-T145, M1-P144, M1-V143, M1-L142, M1-T141, M1-S140, M1-K139, M1-G138, M1-E137, M1-C136, M1-L135, M1-G134, M1-P133, M1-F132, M1-C131, M1-R130, M1-S129, M1-F128, M1-E127, M1-A126, M1-F125, M1-G124, M1-G123, M1-A122, M1-L121, M1-L120, M1-H119, M1-V118, M1-S117, M1-N116, M1-F115, M1-S114, M1-R113, M1-E112, M1-L111, M1-K110, M1-G109, M1-L108, M1-L107, M1-V106, M1-T105, M1-L104, M1-F103, M1-C102, M1-D101, M1-S100, M1-S99, M1-L98, M1-S97, M1-G96, M1-V95, M1-D94, M1-Q93, M1-S92, M1-S91, M1-H90, M1-D89, M1-Y88, M1-V87, M1-V86, M1-V85, M1-R84, M1-Q83, M1-N82, M1-C81, M1-D80, M1-I79, M1-D78, M1-V77, M1-K76, M1-H75, M1-K74, M1-T73, M1-S72, M1-Q71, M1-H70, M1-I69, M1-L68, M1-E67, M1-T66, M1-I65, M1-L64, M1-V63, M1-K62, M1-D61, M1-Q60, M1-Q59, M1-L58, M1-R57, M1-R56, M1-K55, M1-M54, M1-L53, M1-K52, M1-S51, M1-C50, M1-N49, M1-I48, M1-N47, M1-I46, M1-A45, M1-E44, M1-L43, M1-I42, M1-H41, M1-S40, M1-T39, M1-N38, M1-Y37, M1-E36, M1-V35, M1-F34, M1-P33, M1-R32, M1-S31, M1-D30, M1-I29, M1-L28, M1-L27, M1-V26, M1-K25, M1-E24, M1-T23, M1-G22, M1-S21, M1-E20, M1-L19, M1-L18, M1-A17, M1-V16, M1-L15, M1-S14, M1-E13, M1-T12, M1-V11, M1-I10, M1-Q9, M1-T8, and/or M1-G7 of SEQ ID NO:114. Polynucleotide sequences encoding these polypeptides are also provided. The present invention also encompasses the use of these C-terminal mRET31 deletion polypeptides as immunogenic and/or antigenic epitopes as described elsewhere herein.

In confirmation of the mouse RET31 representing a novel mouse phosphatase polypeptide, the mRET31 polypeptide has been shown to comprise a dual specificity phosphatase catalytic domain as identified by the BLAST2 algorithm using the DSPc PFAM HMM (PF00782) as a query sequence.

In preferred embodiments, the following mouse RET31 DSPc domain polypeptide is encompassed by the present invention:

```
GPTRILPNLYLGCQRDVLNKDLMQQNGIGYVLNASNTCPKPDFIPESHFLRVP   (SEQ ID NO: 135)
VNDSFCEKILPWLDKSVDFIEKAKASNGCVLIHCLAGISRSATIAIAYIMKRMD
MSLDEAYRFVKEKRPTISPNFNFMGQLMDYEKT.
```

Polynucleotides encoding this polypeptide are also provided. The present invention also encompasses the use of this mouse RET31 DSPc domain polypeptide as an immunogenic and/or antigenic epitope as described elsewhere herein.

The present invention encompasses the use of RET31 inhibitors and/or activators of RET31 activity for the treatment, detection, amelioration, or prevention of phosphatase associated disorders, including but not limited to metabolic diseases such as diabetes, in addition to neural and/or cardiovascular diseases and disorders. The present invention also encompasses the use of RET31 inhibitors and/or activators of RET31 activity as immunosuppressive agents, anti-inflammatory agents, and/or anti-tumor agents The present invention encompasses the use of RET31 phosphatase inhibitors, including, antagonists such as antisense nucleic acids, in addition to other antagonists, as described herein, in a therapeutic regimen to diagnose, prognose, treat, ameliorate, and/or prevent diseases where a kinase activity is insufficient. One, non-limiting example of a disease which may occur due to insufficient kinase activity are certain types of diabetes, where one or more kinases involved in the insulin receptor signal pathway may have insufficient activity or insufficient expression, for example.

Moreover, the present invention encompasses the use of RET31 phosphatase activators, and/or the use of the RET31 phosphatase gene or protein in a gene therapy regimen, as described herein, for the diagnoses, prognoses, treatment, amelioration, and/or prevention of diseases and/or disorders where a kinase activity is overly high, such as a cancer where a kinase oncogene product has excessive activity or excessive expression.

The present invention also encompasses the use of catalytically inactive variants of RET31 proteins, including fragments thereof, such as a protein therapeutic, or the use of the encoding polynucleotide sequence or as gene therapy, for example, in the diagnoses, prognosis, treatment, amelioration, and/or prevention of diseases or disorders where phosphatase activity is overly high.

The present invention encompasses the use of antibodies directed against the RET31 polypeptides, including fragment and/or variants thereof, of the present invention in diagnostics, as a biomarkers, and/or as a therapeutic agents.

The present invention encompasses the use of an inactive, non-catalytic, mutant of the RET31 phosphatase as a substrate trapping mutant to bind cellular phosphoproteins or a library of phosphopeptides to identify substrates of the RET31 polypeptides.

The present invention encompasses the use of the RET31 polypeptides, to identify inhibitors or activators of the RET31 phosphatase activity using either in vitro or 'virtual' (in silico) screening methods.

One embodiment of the invention relates to a method for identifying a compound as an activator or inhibitor of the RET31 phosphatase comprising the steps of: i.) contacting a RET31 phosphatase inhibitor or activator labeled with an analytically detectable reagent with the RET31 phosphatase under conditions sufficient to form a complex with the inhibitor or activator; ii.) contacting said complex with a sample containing a compound to be identified; iii) and identifying the compound as an inhibitor or activator by detecting the ability of the test compound to alter the amount of labeled known RET31 phosphatase inhibitor or activator in the complex.

Another embodiment of the invention relates to a method for identifying a compound as an activator or inhibitor of a RET31 phosphatase comprising the steps of: i.) contacting the RET31 phosphatase with a compound to be identified; and ii.) and measuring the ability of the RET31 phosphatase to remove phosphate from a substrate.

The present invention also encompasses a method for identifying a ligand for the RET31 phosphatase comprising the steps of: i.) contacting the RET31 phosphatase with a series of compounds under conditions to permit binding; and ii.) detecting the presence of any ligand-bound protein.

Preferably, the above referenced methods comprise the RET31 phosphatase in a form selected from the group consisting of whole cells, cytosolic cell fractions, membrane cell fractions, purified or partially purified forms. The invention also relates to recombinantly expressed RET31 phosphatase in a purified, substantially purified, or unpurified state. The invention further relates to RET31 phosphatase fused or conjugated to a protein, peptide, or other molecule or compound known in the art, or referenced herein.

The present invention also encompasses pharmaceutical composition of the RET31 phosphatase polypeptide comprising a compound identified by above referenced methods and a pharmaceutically acceptable carrier.

In preferred embodiments, the present invention encompasses a polynucleotide lacking the initiating start codon, in addition to, the resulting encoded polypeptide of RET31. Specifically, the present invention encompasses the polynucleotide corresponding to nucleotides 541 thru 2532 of SEQ ID NO:108, and the polypeptide corresponding to amino acids 2 thru 665 of SEQ ID NO:109. Also encompassed are recombinant vectors comprising said encoding sequence, and host cells comprising said vector.

Many polynucleotide sequences, such as EST sequences, are publicly available and accessible through sequence databases. Some of these sequences are related to SEQ ID NO: 108 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 5436 of SEQ ID NO:108, b is an integer between 15 to 5450, where both a and b correspond to the positions of nucleotide residues shown in SEQ ID NO:108, and where b is greater than or equal to a+14.

Many polynucleotide sequences, such as EST sequences, are publicly available and accessible through sequence databases. Some of these sequences are related to SEQ ID NO: 113 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 2742 of SEQ ID NO:113, b is an integer between 15 to 2756, where both a and b correspond to the positions of nucleotide residues shown in SEQ ID NO:113, and where b is greater than or equal to a+14.

duced by these alternative open reading frames are specifically contemplated by the present invention.

The total number of amino acids within the open reading frame of SEQ ID NO:150, 152, 8, 10, 42, or 109 is identified as "Total AA of ORF".

SEQ ID NO:149, 151, 7, 9, 41, or 108 and the translated SEQ ID NO:150, 152, 8, 10, 42, or 109 are sufficiently accurate and otherwise suitable for a variety of uses well known in the art and described further herein. For instance, SEQ ID NO:149, 151, 7, 9, 41, or 108 is useful for designing nucleic acid hybridization probes that will detect nucleic acid sequences contained in SEQ ID NO:149, 151, 7, 9, 41, or 108 or the cDNA contained in the deposited clone. These probes will also hybridize to nucleic acid molecules in biological samples, thereby enabling a variety of forensic and diagnostic methods of the invention. Similarly, polypeptides identified from SEQ ID NO:150, 152, 8, 10, 42, or 109 may be used, for example, to generate antibodies which bind

TABLE I

| Gene No. | CDNA CloneID | ATCC Deposit No. and Date | Vector | NT SEQ ID. No. | Total NT Seq of Clone | 5' NT of Start Codon of ORF | 3' NT of ORF | AA Seq ID No. | Total AA of ORF |
|---|---|---|---|---|---|---|---|---|---|
| 1. | BMY_HPP1_FL | PTA-3949 Dec. 22, 2001 | | 149 | 4393 | 628 | 2448 | 150 | 607 |
| 1. | BMY_HPP1 - Fragment A | N/A | | 1 | 144 | 1 | 144 | 2 | 48 |
| 1. | BMY_HPP1 - Fragment B | N/A | | 3 | 33 | 1 | 33 | 4 | 11 |
| 2. | BMY_HPP2_FL | PTA-3949 Dec. 22, 2001 | | 151 | 878 | 89 | 538 | 152 | 150 |
| 2. | BMY_HPP2_partial | N/A | | 5 | 746 | 2 | 745 | 6 | 248 |
| 3. | BMY_HPP3 | N/A | | 7 | 511 | 1 | 510 | 8 | 170 |
| 4. | BMY_HPP4 | N/A | | 9 | 1710 | 1 | 1710 | 10 | 570 |
| 5. | BMY_HPP5 (7IC-5-E2) | PTA-2966 Jan. 24, 2001 | pSport | 41 | 5111 | 470 | 2464 | 42 | 665 |
| 6. | RET31 (also referred to as 1 hr TNF031, and/or Clone 31 | PTA-3434 Jun. 07, 2001 | PTAdv | 108 | 5450 | 538 | 2532 | 109 | 665 |

Table I summarizes the information corresponding to each "Gene No." described above. The nucleotide sequence identified as "NT SEQ ID NO:" was assembled from partially homologous ("overlapping") sequences obtained from the "cDNA clone ID" identified in Table I and, in some cases, from additional related DNA clones. The overlapping sequences were assembled into a single contiguous sequence of high redundancy (usually several overlapping sequences at each nucleotide position), resulting in a final sequence identified as SEQ ID NO:149, 151, 7, 9, 41, or 108.

The cDNA Clone ID was deposited on the date and given the corresponding deposit number listed in "ATCC Deposit No: and Date." "Vector" refers to the type of vector contained in the cDNA Clone ID.

"Total NT Seq. Of Clone" refers to the total number of nucleotides in the clone contig identified by "Gene No." The deposited clone may contain all or most of the sequence of SEQ ID NO:149, 151, 7, 9, 41, or 108. The nucleotide position of SEQ ID NO:149, 151, 7, 9, 41, or 108 of the putative start codon (methionine) is identified as "5' NT of Start Codon of ORF."

The translated amino acid sequence, beginning with the methionine, is identified as "AA SEQ ID NO:," although other reading frames can also be easily translated using known molecular biology techniques. The polypeptides pro-specifically to proteins containing the polypeptides and the proteins encoded by the cDNA clones identified in Table I.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:149, 151, 7, 9, 41, or 108 and the predicted translated amino acid sequence identified as SEQ ID NO:150, 152, 8, 10, 42, or 109, but also a sample of plasmid DNA containing a cDNA of the invention deposited with the ATCC, as set forth in Table I. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited cDNA, collecting the protein, and determining its sequence. The present invention also relates to the genes corresponding to SEQ ID NO:149, 151, 7, 9, 41, or 108, SEQ ID NO:150, 152, 8, 10, 42, or 109, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologues of genes corresponding to SEQ ID NO:149, 151, 7, 9, 41, or 108, SEQ ID NO:150, 152, 8, 10, 42, or 109, or a deposited clone, relying on the sequence from the sequences disclosed herein or the clones deposited with the ATCC. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner.

Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31–40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:149, 151, 7, 9, 41, or 108, and/or a cDNA provided in ATCC Deposit No:PTA-2966, PTA-3434, and/or PTA-3949. The present invention also provides a polypeptide comprising, or alternatively consisting of, the sequence identified as SEQ ID NO:150, 152, 8, 10, 42, or 109, and/or a polypeptide encoded by the cDNA provided in ATCC Deposit NO:PTA-2966, PTA-3434, and/or PTA-3949. The present invention also provides polynucleotides encoding a polypeptide comprising, or alternatively consisting of the polypeptide sequence of SEQ ID NO:150, 152, 8, 10, 42, or 109, and/or a polypeptide sequence encoded by the cDNA contained in ATCC Deposit No:PTA-2966, PTA-3434, and/or PTA-3949.

Preferably, the present invention is directed to a polynucleotide comprising, or alternatively consisting of, the sequence identified as SEQ ID NO:149, 151, 7, 9, 41, or 108, and/or a cDNA provided in ATCC Deposit No:PTA-2966, PTA-3434. and/or PTA-3949 that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:149, 151, 7, 9, 41, or 108, the sequence contained in a deposit, and/or the nucleic acid sequence encoding the sequence disclosed as SEQ ID NO:150, 152, 8, 10, 42, or 109.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table II below: highly stringent conditions are those that are at least as stringent as, for example, conditions A–F; stringent conditions are at least as stringent as, for example, conditions G–L; and reduced stringency conditions are at least as stringent as, for example, conditions M–R.

TABLE II

| Stringency Condition | Polynucleotide Hybrid± | Hybrid Length (bp) ‡ | Hybridization Temperature and Buffer † | Wash Temperature and Buffer † |
|---|---|---|---|---|
| A | DNA:DNA | > or equal to 50 | 65° C.; 1xSSC -or- 42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC -or- 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC -or- 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC -or- 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC -or- 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC -or- 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC -or- 40° C. 6xSSC, 50% formamide | 50° C.; 2xSSC |

TABLE II-continued

| Stringency Condition | Poly-nucleotide Hybrid± | Hybrid Length (bp) ‡ | Hybridization Temperature and Buffer † | Wash Temperature and Buffer † |
|---|---|---|---|---|
| N | DNA:DNA | <50 | Tn*; 6xSSC | Tn*; 6xSSC |
| O | DNA:RNA | > or equal to 50 | 55° C.; 4xSSC -or- 42° C.; 6xSSC, 50% formamide | 55° C.; 2xSSC |
| P | DNA:RNA | <50 | Tp*; 6xSSC | Tp*; 6xSSC |
| Q | RNA:RNA | > or equal to 50 | 60° C.; 4xSSC -or- 45° C.; 6xSSC, 50% formamide | 60° C.; 2xSSC |
| R | RNA:RNA | <50 | Tr*; 4xSSC | Tr*; 4xSSC |

‡: The "hybrid length" is the anticipated length for the hybridized region (s) of the hybridizing polynucleotides. When hybridizing a polynucleotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions or optimal sequence complementarity. Methods of aligning two or more polynucleotide sequences and/or determining the present identity between two polynucleotide sequences are well known in the art (e.g., MegAlign program of the DNA*Star suite of programs, etc).
†: SSPE (1 × SSPE is 0.15 M NaCl, 10 mM NaH2PO4, and 1.25 mM EDTA, pH 7.4) can be substituted for SSC (1 × SSC is 0.15 M NaCl and 15 mM sodium citrate) in the hybridization and wash buffers; washes are performed for 15 minutes after hybridization is complete. The hydridizations and washes may additionally include 5x Denhardt's reagent, .5–1.0% SDS, 100 ug/ml denatured, fragmented salmon sperm DNA, 0.5% sodium pyrophosphate, and up to 50% formamide.
*Tb—Tr: The hybridization temperature for hybrids anticipated to be less than 50 base pairs in length should be 5–10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length, Tm(° C.) = 81.5 + 16.6(log$_{10}$[Na+]) + 0.41(% G + C) − (600/N), where N is the number of bases in the hybrid, and [Na+] is the concentration of sodium ions in the hybridization buffer ([NA+] for 1 × SSC = .165 M).
±: The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3–6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, the clone deposited with the ATCC, and/or the cDNA encoding the polypeptides of the present invention. PCR techniques for the amplification of nucleic acids are described in U.S. Pat. No. 4,683,195 and Saiki et al., Science, 239:487–491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643–1650, (1991); and "PCR Protocols, A Guide to Methods and Applications", Eds., Innis et al., Academic Press, New York, (1990).

Signal Sequences

The present invention also encompasses mature forms of the polypeptide comprising, or alternatively consisting of, the polypeptide sequence of SEQ ID NO:150, 152, 8, 10, 42, or 109, the polypeptide encoded by the polynucleotide described as SEQ ID NO:149, 151, 7, 9, 41, or 108, and/or the polypeptide sequence encoded by a cDNA in the deposited clone. The present invention also encompasses polynucleotides encoding mature forms of the present invention, such as, for example the polynucleotide sequence of SEQ ID NO:149, 151, 7, 9, 41, or 108, and/or the polynucleotide sequence provided in a cDNA of the deposited clone.

According to the signal hypothesis, proteins secreted by eukaryotic cells have a signal or secretary leader sequence which is cleaved from the mature protein once export of the growing protein chain across the rough endoplasmic reticulum has been initiated. Most eukaryotic cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available; For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

The established method for identifying the location of signal sequences, in addition, to their cleavage sites has been the SignalP program (v1.1) developed by Henrik Nielsen et al., Protein Engineering 10:1–6 (1997). The program relies upon the algorithm developed by von Heinje, though provides additional parameters to increase the prediction accuracy.

More recently, a hidden Markov model has been developed (H. Neilson, et al., Ismb 1998; 6:122–30), which has been incorporated into the more recent SignalP (v2.0). This new method increases the ability to identify the cleavage site by discriminating between signal peptides and uncleaved signal anchors. The present invention encompasses the application of the method disclosed therein to the prediction of the signal peptide location, including the cleavage site, to any of the polypeptide sequences of the present invention.

As one of ordinary skill would appreciate, however, cleavage sites sometimes vary from organism to organism and cannot be predicted with absolute certainty. Accordingly, the polypeptide of the present invention may contain a signal sequence. Polypeptides of the invention which comprise a signal sequence have an N-terminus beginning within 5 residues (i.e., + or −5 residues, or preferably at the −5, −4, −3, −2, −1, +1, +2, +3, +4, or +5 residue) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:149, 151, 7, 9, 41, or 108 and/or the polynucleotide sequence contained in the cDNA of a deposited clone, in a mammalian cell (e.g., COS cells, as described below). These polypeptides, and the polynucleotides encoding such polypeptides, are contemplated by the present invention.

Polynucleotide and Polypeptide Variants

The present invention also encompasses variants (e.g., allelic variants, orthologs, etc.) of the polynucleotide sequence disclosed herein in SEQ ID NO:149, 151, 7, 9, 41, or 108, the complementary strand thereto, and/or the cDNA sequence contained in the deposited clone.

The present invention also encompasses variants of the polypeptide sequence, and/or fragments therein, disclosed in SEQ ID NO:150, 152, 8, 10, 42, or 109, a polypeptide encoded by the polynucleotide sequence in SEQ ID NO:149, 151, 7, 9, 41, or 108, and/or a polypeptide encoded by a cDNA in the deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a human phosphatase related polypeptide having an amino acid sequence as shown in the sequence listing and described in SEQ ID NO:149, 151, 7, 9, 41, or 108 or the cDNA contained in ATCC deposit No:PTA-2966, PTA-3434, and/or PTA-3949; (b) a nucleotide sequence encoding a mature human phosphatase related polypeptide having the amino acid sequence as shown in the sequence listing and described in SEQ ID NO:149, 151, 7, 9, 41, or 108 or the cDNA contained in ATCC deposit No:PTA-2966, PTA-3434, and/or PTA-3949; (c) a nucleotide sequence encoding a biologically active fragment of a human phosphatase related polypeptide having an amino acid sequence shown in the sequence listing and described in SEQ ID NO:149, 151, 7, 9, 41, or 108 or the cDNA contained in ATCC deposit No:PTA-2966, PTA-3434, and/or PTA-3949; (d) a nucleotide sequence encoding an antigenic fragment of a human phosphatase related polypeptide having an amino acid sequence sown in the sequence listing and described in SEQ ID NO:149, 151, 7, 9, 41, or 108 or the cDNA contained in ATCC deposit No:PTA-2966, PTA-3434, and/or PTA-3949; (e) a nucleotide sequence encoding a human phosphatase related polypeptide comprising the complete amino acid sequence encoded by a human cDNA plasmid contained in SEQ ID NO:149, 151, 7, 9, 41, or 108 or the cDNA contained in ATCC deposit No:PTA-2966, PTA-3434, and/or PTA-3949; (f) a nucleotide sequence encoding a mature human phosphatase related polypeptide having an amino acid sequence encoded by a human cDNA plasmid contained in SEQ ID NO:149, 151, 7, 9, 41, or 108 or the cDNA contained in ATCC deposit No:PTA-2966, PTA-3434, and/or PTA-3949; (g) a nucleotide sequence encoding a biologically active fragment of a human phosphatase related polypeptide having an amino acid sequence encoded by a human cDNA plasmid contained in SEQ ID NO:149, 151, 7, 9, 41, or 108 or the cDNA contained in ATCC deposit No:PTA-2966, PTA-3434, and/or PTA-3949; (h) a nucleotide sequence encoding an antigenic fragment of a human phosphatase related polypeptide having an amino acid sequence encoded by a human cDNA plasmid contained in SEQ ID NO:149, 151, 7, 9, 41, or 108 or the cDNA contained in ATCC deposit No:PTA-2966, PTA-3434, and/or PTA-3949; (l) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least 80%, 85%, 90%, 91%, 92%, 93%, 94%, 95%, 96%, 97%, 98%, or 99% identical to, for example, any of the nucleotide sequences in (a), (b), (c), (d), (e), (f), (g), or (h), above. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a human phosphatase related polypeptide having an amino acid sequence as shown in the sequence listing and descried in Table I; (b) a nucleotide sequence encoding a mature human phosphatase related polypeptide having the amino acid sequence as shown in the sequence listing and descried in Table I; (c) a nucleotide sequence encoding a biologically active fragment of a human phosphatase related polypeptide having an amino acid sequence as shown in the sequence listing and descried in Table I; (d) a nucleotide sequence encoding an antigenic fragment of a human phosphatase related polypeptide having an amino acid sequence as shown in the sequence listing and described in Table I; (e) a nucleotide sequence encoding a human phosphatase related polypeptide comprising the complete amino acid sequence encoded by a human cDNA in a cDNA plasmid contained in the ATCC Deposit and described in Table I; (f) a nucleotide sequence encoding a mature human phosphatase related polypeptide having an amino acid sequence encoded by a human cDNA in a cDNA plasmid contained in the ATCC Deposit and described in Table I: (g) a nucleotide sequence encoding a biologically active fragment of a human phosphatase related polypeptide having an amino acid sequence encoded by a human cDNA in a cDNA plasmid contained in the ATCC Deposit and described in Table I; (h) a nucleotide sequence encoding an antigenic fragment of a human phosphatase related polypeptide having an amino acid sequence encoded by a human cDNA in a cDNA plasmid contained in the ATCC deposit and described in Table I; (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least 80%, 85%, 90%, 91%, 92%, 93%, 94%, 95%, 96%, 97%, 98%, or 99% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least 80%, 98%, 90%, 91%, 92%, 93%, 94%, 95%, 96%, 97%, 98%, or 99% identical to, the following non-limited examples, the polypeptide sequence identified as SEQ ID NO:150, 152, 8, 10, 42, or 109, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least 80%, 98%, 90%, 91%, 92%, 93%, 94%, 95%, 96%, 97%, 98%, or 99% identical to, for example, the polypeptide sequence shown in SEQ ID NO:150, 152, 8, 10, 42, or 109, a polypeptide sequence encoded by the nucleotide sequence in SEQ ID NO:149, 151, 7, 9, 41, or 108, a polypeptide sequence encoded by the cDNA in cDNA plasmid:PTA-2966, PTA-3434, and/or PTA-3949, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table I, the ORF (open reading frame), or any fragment specified as described herein.

As a practical matter, whether any particular nucleic acid molecule or polypeptide is at least 80%, 85%, 90%, 91%, 92%, 93%, 94%, 95%, 96%, 97%, 98% or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2):189–191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multiple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed.

However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modified CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein (Dobeli et al., J. Biotechnology 7:199–216 (1988)).

Moreover, ample evidence demonstrates that variants often retain a biological activity similar to that of the naturally occurring protein. For example, Gayle and coworkers (J. Biol. Chem. 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N— or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

Thus, the invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247: 1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306–1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table VII below.

TABLE VII

| For Amino Acid | Code | Replace with any of: |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |

TABLE VII-continued

| For Amino Acid | Code | Replace with any of: |
| --- | --- | --- |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

Moreover, the invention further includes polypeptide variants created through the application of molecular evolution ("DNA Shuffling") methodology to the polynucleotide disclosed as SEQ ID NO:149, 151, 7, 9, 41, or 108, the sequence of the clone submitted in a deposit, and/or the cDNA encoding the polypeptide disclosed as SEQ ID NO:150, 152, 8, 10, 42, or 109. Such DNA Shuffling technology is known in the art and more particularly described elsewhere herein (e.g., W P C, Stemmer, PNAS, 91:10747, (1994)), and in the Examples provided herein).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:149, 151, 7, 9, 41, or 108 or the complementary strand thereto, or is a portion of a polynucleotide sequence encoding the polypeptide of SEQ ID NO:150, 152, 8, 10, 42, or 109. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:149, 151, 7, 9, 41, or 108. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:149, 151, 7, 9, 41, or 108, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:150, 152, 8, 10, 42, or 109 or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both.

For example, any number of amino acids, ranging from 1–60, can be deleted from the amino terminus of the full-length polypeptide. Similarly, any number of amino acids, ranging from 1–30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:150, 152, 8, 10, 42, or 109 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:150, 152, 8, 10, 42, or 109, or an epitope of the polypeptide sequence encoded by a polynucleotide sequence contained in ATCC deposit No:PTA-2966, PTA-3434, and/ or PTA-3949 or encoded by a polynucleotide that hybridizes to the complement of the sequence of SEQ ID NO:149, 151, 7, 9, 41, or 108 or contained in ATCC deposit No:PTA-2966, PTA-3434, and/or PTA-3949 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605, 793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:149, 151, 7, 9, 41, or 108 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:150, 152, 8, 10, 42, or 109, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24:316–325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7):3170–3179 (1998); Prat et al., J. Cell. Sci. 111(Pt2): 237–247 (1998); Pitard et al., J. Immunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, 2$^{nd}$ ed. (1988), which is hereby incorporated herein by reference in its entirety). For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, 2$^{nd}$ ed. (1988), by Hammerling, et al., Monoclonal Antibodies and T-Cell Hybridomas (Elsevier, N.Y., (1981)), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59–103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51–63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoadsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,861,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize, specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182: 41–50 (1995); Ames et al., J. Immunol. Methods 184: 177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489–498 (1991); Studnicka et al., Protein Engineering 7(6):805–814 (1994); Roguska. et al., PNAS 91:969–973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522–525 (1986); Reichmann et al., Nature, 332:323–327 (1988); Verhoeyen et al., Science, 239:1534–1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522–525 (1986); Riechmann et al., Nature 332:323–329 (1988)1 and Presta, Curr. Op. Struct. Biol., 2:593–596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boemer et al., J. Immunol., 147(1):86–95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779–783 (1992); Lonberg et al., Nature 368:856–859 (1994); Fishwild et al., Nature Biotechnol., 14:845–51 (1996); Neuberger, Nature Biotechnol., 14:826 (1996); Lonberg and Huszer, Intern. Rev. Immunol., 13:65–93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The antibodies of the present invention may be bispecific antibodies. Bispecific antibodies are monoclonal, preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:150, 152, 8, 10, 42, or 109.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide-probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide.

Techniques for the assembly of functional Fv fragments in *E. coli* may also be used (Skerra et al., Science 242: 1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:150, 152, 8, 10, 42, or 109 may be fused or conjugated to the above antibody portions to increase the in vivo half life of the polypeptides or for use in immunoassays using methods known in the art. Further, the polypeptides corresponding to SEQ ID NO:150, 152, 8, 10, 42, or 109 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Uses for Antibodies Directed Against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123–131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp147–158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219(1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $5 \times 10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-15}$ M, and $10^{-15}$ M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or genes, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Antibody-based Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342: 435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92 m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue-sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Compositions

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging with Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331: 84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270: 9459–9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-hitidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existence of other "tags" which could be readily substituted for the tags referred to supra for purification and/or identification of polypeptides of the present invention (Jones C., et al., J Chromatogr A. 707(1):3–22 (1995)). For example, the c-myc tag and the 8F9, 3C7, 6E10, G4m B7 and 9E10 antibodies thereto (Evan et al., Molecular and Cellular Biology 5:3610–3616 (1985)); the Herpes Simplex virus glycoprotein D (gD) tag and its antibody (Paborsky et al., Protein Engineering, 3(6):547–553 (1990), the Flag-peptide—i.e., the octapeptide sequence DYKDDDDK (SEQ ID NO:75), (Hopp et al., Biotech. 6:1204–1210 (1988); the KT3 epitope peptide (Martin et al., Science, 255:192–194 (1992)); a-tubulin epitope peptide (Skinner et al., J. Biol. Chem., 266:15136–15166, (1991)); the T7 gene 10 protein peptide tag (Lutz-Freyermuth et al., Proc. Natl. Sci. USA, 87:6363–6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann. N. Y. Acad. Sci. 1999; 886:233–5), or HC toxin (Tonukari N J, et al., Plant Cell. 2000 February; 12(2): 237–248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. Imm. 11:548–557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/ GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast Pichia pastoris is used to express the polypeptide of the present invention in a eukaryotic system. Pichia pastoris is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, Pichia pastoris must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in Pichia pastoris. See, Ellis, S. B., et al., Mol. Cell. Biol. 5:1111–21 (1985); Koutz, P. J, et al., Yeast 5:167–77 (1989); Tschopp, J. F., et al., Nucl. Acids Res. 15:3859–76 (1987). Thus, a heterologous coding sequence, such as, for example, a polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the Pichia pastoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHWL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Nati. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105–111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation-or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, to mannuronic acid, glucosamine, galactosamine, and neuraminic acid, and naturally occurring derivatives thereof Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics.RTM., commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:150, 152, 8, 10, 42, or 109 or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences).

In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers.

Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:149, 151, 7, 9, 41, or 108. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:149, 151, 7, 9, 41, or 108 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or MRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may Preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat.

Nos. 5,858,659 and 5,856,104. The US Patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point ($T_m$) by 8°–20° C., vs. 4°–16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991) ) or to the mRNA itself (antisense—Okano, J. Neurochem. 56:560 (1991); Oligodeoxynucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300–303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615–622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific MRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell . Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($125I$, $121I$), carbon ($14C$), sulfur ($35S$), tritium ($3H$), indium ($112In$), and technetium ($99mTc$), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, $131I$, $112In$, $99mTc$), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $99mTc$. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207–216 (1993); Ferrantini et al., Cancer Research, 53:107–1112 (1993); Ferrantini et al., J. Immunology 153: 4604–4615 (1994); Kaido, T., et al., Int. J. Cancer 60: 221–229 (1995); Ogura et al., Cancer Research 50: 5102–5106 (1990); Santodonato, et al., Human Gene Therapy 7:1–10 (1996); Santodonato, et al., Gene Therapy 4:1246–1255 (1997); and Zhang, et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413–7416 (1987), which is herein incorporated by reference); MRNA (Malone et al., Proc. Natl. Acad. Sci. USA , 86:6077–6081 (1989), which is herein incorporated by reference); and purified transcription factors (Debs et al., J. Biol. Chem., 265:10189–10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA , 84:7413–7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512–527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include Ca2+-EDTA chelation (Papahadjopoulos et al., Biochim. Biophys. Acta, 394:483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, 1:5–14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle.

Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartzet al., Am. Rev. Respir. Dis., 109:233–238 (1974)). Finally, adenovirus mediated gene transfer has been demonstrated in a number of instances including transfer of alpha-1-antitrypsin and CFTR to the lungs of cotton rats (Rosenfeld et al., Science, 252:431–434 (1991); Rosenfeld et al., Cell, 68:143–155 (1992)). Furthermore, extensive studies to attempt to establish adenovirus as a causative agent in human cancer were uniformly-negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499–503 (1993); Rosenfeld et al., Cell, 68:143–155 (1992); Engelhardt et al., Human Genet. Ther., 4:759–769 (1993); Yang et al., Nature Genet., 7:362–369 (1994); Wilson et al., Nature 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding angiogenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189:11277–11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinogenemia, factor deficiencies, arterial thrombosis, venous thrombosis, etc.), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. Polynucleotides or polypeptides, or agonists or antagonists of the present invention are may also be useful for the detection, prognosis, treatment, and/or prevention of heart attacks (infarction), strokes, scarring, fibrinolysis, uncontrolled bleeding, uncontrolled coagulation, uncontrolled complement fixation, and/or inflammation.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more Preferably an adenoviral vector (See G J. Nabel, et. al., PNAS 1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, $10^{-15}$M.

Moreover, polypeptides of the present invention may be useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, anti-inflammatory proteins (See for example, Mutat. Res. 400 (1–2):447–55 (1998), Med Hypotheses. 50(5):423–33 (1998), Chem. Biol. Interact. Apr. 24; 111–112:23–34 (1998), J Mol Med. 76(6):402–12 (1998), Int. J. Tissue React. 20(1):3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998; 231:125–41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm; myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Anti-Angiogenesis Activity

The naturally occurring balance between endogenous stimulators and inhibitors of angiogenesis is one in which inhibitory influences predominate. Rastinejad et al., Cell 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormnal neovascularization including solid tumor growth and metastases, arthritis, some types of eye diseases, disorders, and/or conditions, and psoriasis. See, e.g., reviews by Moses et al., Biotech. 9:630–634 (1991); Folkman et al., N. Engl. J. Med., 333:1757–1763 (1995); Auerbach et al., J. Microvasc. Res. 29:401–411 (1985); Folkman, Advances in Cancer Research, eds. Klein and Weinhouse, Academic Press, New York, pp. 175–203 (1985); Patz, Am. J. Opthalmol. 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, Science 235:442–447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)).Thus, the present invention provides a method of treating, preventing, and/or diagnosing an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat or prevent a cancer or tumor. Cancers which may be treated, prevented, and/or diagnosed with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating, preventing, and/or diagnosing other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating, preventing, and/or diagnosing hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating, preventing, and/or diagnosing neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated, prevented, and/or diagnosed with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., Am. J. Ophthal. 85:704–710 (1978) and Gartner et al., Surv. Ophthal. 22:291–312 (1978).

Thus, within one aspect of the present invention methods are provided for treating or preventing neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating or preventing neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating or preventing proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating or preventing retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated, prevented, and/or diagnosed with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated, prevented, and/or diagnosed with the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (*Rochele minalia quintosa*), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metastasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intestine, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Neurological Diseases

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B 12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., Anthrax, *Clostridium*), Bacteroidaceae, Blastomycosis, *Bordetella, Borrelia* (e.g., *Borrelia burgdorferi*), Brucellosis, Candidiasis, *Campylobacter*, Coccidioidomycosis, Cryptococcosis, Dermatocycoses, *E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), Erysipelothrix, *Helicobacter*, Legionellosis, Leptospirosis, *Listeria*, Mycoplasmatales, *Mycobacterium leprae, Vibrio cholerae*, Neisseriaceae (e.g., *Acinetobacter*, Gonorrhea, Menigococcal), Meisseria meningitidis, Pasteurellacea Infections (e.g., *Actinobacillus, Heamophilus* (e.g., *Heamophilus* influenza type B), *Pasteurella*), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., Plasmodium virax, Plasmodium falciparium, Plasmodium malariae and Plasmodium ovale). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Chemotaxis

A polynucleotide or polypeptide and/or agonist or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polynucleotide or polypeptide and/or agonist or antagonist of the present invention may inhibit chemotactic activity. These molecules could also be used to treat, prevent, and/or diagnose diseases, disorders, and/or conditions. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors),or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or E. coli. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605, 793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human phosphatase polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a phosphatase polypeptide, or a bindable peptide fragment, of this invention, comprising providing a plurality of compounds, combining the phosphatase polypeptide, or a bindable peptide fragment, with each of a plurality of compounds for a time sufficient to allow binding under suitable conditions and detecting binding of the phosphatase polypeptide or peptide to each of the plurality of test compounds, thereby identifying the compounds that specifically bind to the phosphatase polypeptide or peptide.

Methods of identifying compounds that modulate the activity of the novel human phosphatase polypeptides and/or peptides are provided by the present invention and comprise combining a potential or candidate compound or drug modulator of phosphatase activity with a phosphatase polypeptide or peptide, for example, the phosphatase amino acid sequence as set forth in SEQ ID NO:42, 109, 150, or 152, and measuring an effect of the candidate compound or drug modulator on the biological activity of the phosphatase polypeptide or peptide. Such measurable effects include, for example, physical binding interaction; the ability to phosphorylate a suitable calpain substrate; effects on native and cloned phosphatase-expressing cell line; and effects of modulators or other phosphatase-mediated physiological measures.

Another method of identifying compounds that modulate the biological activity of the novel phosphatase polypeptides of the present invention comprises combining a potential or candidate compound or drug modulator of a phosphatase activity with a host cell that expresses the phosphatase polypeptide and measuring an effect of the candidate compound or drug modulator on the biological activity of the phosphatase polypeptide. The host cell can also be capable of being induced to express the phosphatase polypeptide, e.g., via inducible expression. Physiological effects of a given modulator candidate on the phosphatase polypeptide can also be measured. Thus, cellular assays for particular phosphatase modulators may be either direct measurement or quantification of the physical biological activity of the phosphatase polypeptide, or they may be measurement or quantification of a physiological effect. Such methods preferably employ a phosphatase polypeptide as described herein, or an overexpressed recombinant phosphatase polypeptide in suitable host cells containing an expression vector as described herein, wherein the phosphatase polypeptide is expressed, overexpressed, or undergoes upregulated expression.

Another aspect of the present invention embraces a method of screening for a compound that is capable of modulating the biological activity of a phosphatase polypeptide, comprising providing a host cell containing an expression vector harboring a nucleic acid sequence encoding a phosphatase polypeptide, or a functional peptide or portion thereof (e.g., SEQ ID NO:42, 109, 150, or 152); determining the biological activity of the expressed phosphatase polypeptide in the absence of a modulator compound; contacting the cell with the modulator compound and determining the biological activity of the expressed phosphatase polypeptide in the presence of the modulator compound. In such a method, a difference between the activity of the phosphatase polypeptide in the presence of the modulator compound and in the absence of the modulator compound indicates a modulating effect of the compound.

Essentially any chemical compound can be employed as a potential modulator or ligand in the assays according to the present invention. Compounds tested as phosphatase modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel phosphatase polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.*, 37:487–493; and Houghton et al., 1991, *Nature*, 354:84–88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA*, 90:6909–6913), vinylogous polypeptides (Hagihara et al., 1992, *J. Amer. Chem. Soc.*, 114:6568), nonpeptidal peptidomimetics with glucose scaffolding (Hirschmann et al., 1992, *J. Amer. Chem. Soc.*, 114:9217–9218), analogous organic synthesis of small compound libraries (Chen et al., 1994, *J. Amer. Chem. Soc.*, 116:2661), oligocarbamates (Cho et al., 1993, *Science*, 261:1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3):309–314) and PCT/US96/10287), carbohydrate libraries (e.g., Liang et al., 1996, *Science*, 274–1520–1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000–20,000 different compounds are possible using the described integrated systems.

In another of its aspects, the present invention encompasses screening and small molecule (e.g., drug) detection assays which involve the detection or identification of small molecules that can bind to a given protein, i.e., a phosphatase polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a phosphatase polypeptide or peptide to measure a biological binding or ligand binding activity, the source may be a whole cell lysate that can be prepared by successive freeze-thaw cycles (e.g., one to three) in the presence of standard protease inhibitors. The phosphatase polypeptide may be partially or completely purified by standard protein purification methods, e.g., affinity chromatography using specific antibody described infra, or by ligands specific for an epitope tag engineered into the recombinant phosphatase polypeptide molecule, also as described herein. Binding activity can then be measured as described.

Compounds which are identified according to the methods provided herein, and which modulate or regulate the biological activity or physiology of the phosphatase polypeptides according to the present invention are a preferred embodiment of this invention. It is contemplated that such modulatory compounds may be employed in treatment and therapeutic methods for treating a condition that is mediated by the novel phosphatase polypeptides by administering to an individual in need of such treatment a therapeutically effective amount of the compound identified by the methods described herein.

In addition, the present invention provides methods for treating an individual in need of such treatment for a disease, disorder, or condition that is mediated by the phosphatase polypeptides of the invention, comprising administering to the individual a therapeutically effective amount of the phosphatase-modulating compound identified by a method provided herein.

Antisense and Ribozyme (Antagonists)

In specific embodiments, antagonists according to the present invention are nucleic acids-corresponding to the sequences contained in SEQ ID NO:149, 151, 7, 9, 41, or 108, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251: 1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304–310 (1981), the promoter contained in the 3' long terminal repeat of Rous sarcoma virus (Yamamoto et al., Cell, 22:787–797 (1980), the herpes thymidine promoter (Wagner et al., Proc. Natl. Acad. Sci. U.S.A., 78:1441–1445 (1981), the regulatory sequences of the metallothionein gene (Brinster et al., Nature, 296:39–42 (1982)), etc.

The antisense nucleic acids of the invention comprise a sequence complementary to at least a portion of an RNA transcript of a gene of interest.

However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372: 333–335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci., 84:648–652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958–976 (1988)) or intercalating agents. (See, e.g., Zon, Pharm. Res., 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625–6641 (1987)). The oligonucleotide is a 2-0-methylribonucleotide (Inoue et al., Nucl. Acids Res., 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448–7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222–1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585–591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

invention, and/or (b) a ribozyme directed to the polynucleotide of the present invention.

Biotic Associations

A polynucleotide or polypeptide and/or agonist or antagonist of the present invention may increase the organisms ability, either directly or indirectly, to initiate and/or maintain biotic associations with other organisms. Such associations may be symbiotic, nonsymbiotic, endosymbiotic, macrosymbiotic, and/or microsymbiotic in nature. In general, a polynucleotide or polypeptide and/or agonist or antagonist of the present invention may increase the organisms ability to form biotic associations with any member of the fungal, bacterial, lichen, mycorrhizal, cyanobacterial, dinoflaggellate, and/or algal, kingdom, phylums, families, classes, genuses, and/or species.

The mechanism by which a polynucleotide or -polypeptide and/or agonist or antagonist of the present invention may increase the host organisms ability, either directly or indirectly, to initiate and/or maintain biotic associations is variable, though may include, modulating osmolarity to desirable levels for the symbiont, modulating pH to desirable levels for the symbiont, modulating secretions of organic acids, modulating the secretion of specific proteins, phenolic compounds, nutrients, or the increased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

In an alternative embodiment, a polynucleotide or polypeptide and/or agonist or antagonist of the present invention may decrease the host organisms ability to form biotic associations with another organism, either directly or indirectly. The mechanism by which a polynucleotide or polypeptide and/or agonist or antagonist of the present invention may decrease the host organisms ability, either directly or indirectly, to initiate and/or maintain biotic associations with another organism is variable, though may include, modulating osmolarity to undesirable levels, modulating pH to undesirable levels, modulating secretions of organic acids, modulating the secretion of specific proteins, phenolic compounds, nutrients, or the decreased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

The hosts ability to maintain biotic associations with a particular pathogen has significant implications for the overall health and fitness of the host. For example, human hosts have symbiosis with enteric bacteria in their gastrointestinal tracts, particularly in the small and large intestine. In fact, bacteria counts in feces of the distal colon often approach $10^{12}$ per milliliter of feces. Examples of bowel flora in the gastrointestinal tract are members of the Enterobacteriaceae, Bacteriodes, in addition to a-hemolytic *streptococci, E. coli, Bifobacteria, Anaerobic cocci, Eubacteria, Costridia, lactobacilli*, and yeasts. Such bacteria, among other things, assist the host in the assimilation of nutrients by breaking down food stuffs not typically broken down by the hosts digestive system, particularly in the hosts bowel. Therefore, increasing the hosts ability to maintain such a biotic association would help assure proper nutrition for the host.

Aberrations in the enteric bacterial population of mammals, particularly humans, has been associated with the following disorders: diarrhea, ileus, chronic inflammatory disease, bowel obstruction, duodenal diverticula, biliary calculous disease, and malnutrition. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant enteric flora population.

The composition of the intestinal flora, for example, is based upon a variety of factors, which include, but are not limited to, the age, race, diet, malnutrition, gastric acidity, bile salt excretion, gut motility, and immune mechanisms. As a result, the polynucleotides and polypeptides, including agonists, antagonists, and fragments thereof, may modulate the ability of a host to form biotic associations by affecting, directly or indirectly, at least one or more of these factors.

Although the predominate intestinal flora comprises anaerobic organisms, an underlying percentage represents aerobes (e.g., *E. coli*). This is significant as such aerobes rapidly become the predominate organisms in intraabdominal infections—effectively becoming opportunistic early in infection pathogenesis. As a result, there is an intrinsic need to control aerobe populations, particularly for immune compromised individuals.

In a preferred embodiment, a polynucleotides and polypeptides, including agonists, antagonists, and fragments thereof, are useful for inhibiting biotic associations with specific enteric symbiont organisms in an effort to control the population of such organisms.

Biotic associations occur not only in the gastrointestinal tract, but also on an in the integument. As opposed to the gastrointestinal flora, the cutaneous flora is comprised almost equally with aerobic and anaerobic organisms. Examples of cutaneous flora are members of the gram-positive cocci (e.g., *S. aureus*, coagulase-negative *staphylococci, micrococcus, M. sedentarius*), gram-positive bacilli (e.g., *Corynebacterium* species, *C. minutissimum, Brevibacterium* species, *Propoionibacterium* species, *P. acnes*), gram-negative bacilli (e.g., *Acinebacter* species), and fungi (*Pityrosporum orbiculare*). The relatively low number of flora associated with the integument is based upon the inability of many organisms to adhere to the skin. The organisms referenced above have acquired this unique ability. Therefore, the polynucleotides and polypeptides of the present invention may have uses which include modulating the population of the cutaneous flora, either directly or indirectly.

Aberrations in the cutaneous flora are associated with a number of significant diseases and/or disorders, which include, but are not limited to the following: impetigo, ecthyma, blistering distal dactulitis, pustules, folliculitis, cutaneous abscesses, pitted keratolysis, trichomycosis axcillaris, dermatophytosis complex, axillary odor, erthyrasma, cheesy foot odor, acne, tinea versicolor, seborrheic dermititis, and *Pityrosporum folliculitis*, to name a few. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant cutaneous flora population.

Additional biotic associations, including diseases and disorders associated with the aberrant growth of such associations, are known in the art and are encompassed by the invention. See, for example, "Infectious Disease", Second Edition, Eds., S. L., Gorbach, J. G., Bartlett, and N. R., Blacklow, W. B. Saunders Company, Philadelphia, (1998); which is hereby incorporated herein by reference).

Pheromones

In another embodiment, a polynucleotide or polypeptide and/or agonist or antagonist of the present invention may increase the organisms ability to synthesize and/or release a pheromone. Such a pheromone may, for example, alter the organisms behavior and/or metabolism.

A polynucleotide or polypeptide and/or agonist or antagonist of the present invention may modulate the biosynthesis and/or release of pheromones, the organisms ability to respond to pheromones (e.g., behaviorally, and/or metabolically), and/or the organisms ability to detect pheromones. Preferably, any of the pheromones, and/or volatiles released from the organism, or induced, by a polynucleotide or polypeptide and/or agonist or antagonist of the invention have behavioral effects the organism.

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The polypeptide of the invention may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

OTHER PREFERRED EMBODIMENTS

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:149, 151, 7, 9, 41, or 108.

Also preferred is a nucleic acid molecule wherein said sequence of contiguous nucleotides is included in the nucleotide sequence of SEQ ID NO:149, 151, 7, 9, 41, or 108 in the range of positions beginning with the nucleotide at about the position of the "5' NT of Start Codon of ORF" and ending with the nucleotide at about the position of the "3' NT of ORF" as defined for SEQ ID NO:149, 151, 7, 9, 41, or 108 in Table I.

Also preferred is an isolated nucleic acid molecule comprising a nucleotide sequence which is at least 95% identical to a sequence of at least about 150 contiguous nucleotides in the nucleotide sequence of SEQ ID NO:149, 151, 7, 9, 41, or 108.

Further preferred is an isolated nucleic acid molecule comprising a nucleotide sequence which is at least 95% identical to a sequence of at least about 500 contiguous nucleotides in the nucleotide sequence of SEQ ID NO:149, 151, 7, 9, 41, or 108.

A further preferred embodiment is a nucleic acid molecule comprising a nucleotide sequence which is at least 95% identical to the nucleotide sequence of SEQ ID NO:149, 151, 7, 9, 41, or 108 beginning with the nucleotide at about the position of the "5' NT of ORF" and ending with the nucleotide at about the position of the "3' NT of ORF" as defined for SEQ ID NO:149, 151, 7, 9, 41, or 108 in Table I.

A further preferred embodiment is an isolated nucleic acid molecule comprising a nucleotide sequence which is at least 95% identical to the complete nucleotide sequence of SEQ ID NO:149, 151, 7, 9, 41, or 108.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a cDNA clone identified by a cDNA Clone Identifier in Table I, which DNA molecule is contained in the material deposited with the American Type Culture Collection and given the ATCC Deposit Number shown in Table I for said cDNA Clone Identifier.

Also preferred is an isolated nucleic acid molecule comprising a nucleotide sequence which is at least 95% identical to a sequence of at least 50 contiguous nucleotides in the nucleotide sequence of a cDNA clone identified by a cDNA Clone Identifier in Table I, which DNA molecule is contained in the deposit given the ATCC Deposit Number shown in Table I.

Also preferred is an isolated nucleic acid molecule, wherein said sequence of at least 50 contiguous nucleotides is included in the nucleotide sequence of the complete open reading frame sequence encoded by said cDNA clone.

Also preferred is an isolated nucleic acid molecule comprising a nucleotide sequence which is at least 95% identical to sequence of at least 150 contiguous nucleotides in the nucleotide sequence encoded by said cDNA clone.

A further preferred embodiment is an isolated nucleic acid molecule comprising a nucleotide sequence which is at least 95% identical to sequence of at least 500 contiguous nucleotides in the nucleotide sequence encoded by said cDNA clone.

A further preferred embodiment is an isolated nucleic acid molecule comprising a nucleotide sequence which is at least 95% identical to the complete nucleotide sequence encoded by said cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:149, 151, 7, 9, 41, or 108; and a nucleotide sequence encoded by a cDNA clone identified by a cDNA Clone Identifier in Table I and contained in the deposit with the ATCC Deposit Number shown for said cDNA clone in Table I; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:149, 151, 7, 9, 41, or 108; and a nucleotide sequence encoded by a cDNA clone identified by a cDNA Clone Identifier in Table I and contained in the deposit with the ATCC Deposit Number shown for said cDNA clone in Table I.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a protein identified in Table I, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:149, 151, 7, 9, 41, or 108; and a nucleotide sequence encoded by a cDNA clone identified by a cDNA Clone Identifier in Table I and contained in the deposit with the ATCC Deposit Number shown for said cDNA clone in Table I.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:149, 151, 7, 9, 41, or 108; and a nucleotide sequence encoded by a cDNA clone identified by a cDNA Clone Identifier in Table I and contained in the deposit with the ATCC Deposit Number shown for said cDNA clone in Table I. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:150, 152, 8, 10, 42, or 109.

Also preferred is a polypeptide, wherein said sequence of contiguous amino acids is included in the amino acid sequence of SEQ ID NO:150, 152, 8, 10, 42, or 109 in the range of positions "Total AA of the Open Reading Frame (ORF)" as set forth for SEQ ID NO:150, 152, 8, 10, 42, or 109 in Table I.

Also preferred is an isolated polypeptide comprising an amino acid sequence at least 95% identical to a sequence of at least about 30 contiguous amino acids in the amino acid sequence of SEQ ID NO:150, 152, 8, 10, 42, or 109.

Further preferred is an isolated polypeptide comprising an amino acid sequence at least 95% identical to a sequence of at least about 100 contiguous amino acids in the amino acid sequence of SEQ ID NO:150, 152, 8, 10, 42, or 109.

Further preferred is an isolated polypeptide comprising an amino acid sequence at least 95% identical to the complete amino acid sequence of SEQ ID NO:150, 152, 8, 10, 42, or 109.

Further preferred is an isolated polypeptide comprising an amino acid sequence at least 90% identical to a sequence of at least about 10 contiguous amino acids in the complete amino acid sequence of a protein encoded by a cDNA clone identified by a cDNA Clone Identifier in Table I and contained in the deposit with the ATCC Deposit Number shown for said cDNA clone in Table I.

Also preferred is a polypeptide wherein said sequence of contiguous amino acids is included in the amino acid sequence of the protein encoded by a cDNA clone identified by a cDNA Clone Identifier in Table I and contained in the deposit with the ATCC Deposit Number shown for said cDNA clone in Table I.

Also preferred is an isolated polypeptide comprising an amino acid sequence at least 95% identical to a sequence of at least about 30 contiguous amino acids in the amino acid sequence of the protein encoded by a cDNA clone identified by a cDNA Clone Identifier in Table I and contained in the deposit with the ATCC Deposit Number shown for said cDNA clone in Table I.

Also preferred is an isolated polypeptide comprising an amino acid sequence at least 95% identical to a sequence of at least about 100 contiguous amino acids in the amino acid sequence of the protein encoded by a cDNA clone identified by a cDNA Clone Identifier in Table I and contained in the deposit with the ATCC Deposit Number shown for said cDNA clone in Table I.

Also preferred is an isolated polypeptide comprising an amino acid sequence at least 95% identical to the amino acid sequence of the protein encoded by a cDNA clone identified by a cDNA Clone Identifier in Table I and contained in the deposit with the ATCC Deposit Number shown for said cDNA clone in Table I.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:150, 152, 8, 10, 42, or 109; and a complete amino acid sequence of a protein encoded by a cDNA clone identified by a cDNA Clone Identifier in Table I and contained in the deposit with the ATCC Deposit Number shown for said cDNA clone in Table I.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:150, 152, 8, 10, 42, or 109; and a complete amino acid sequence of a protein encoded by a cDNA clone identified by a cDNA Clone Identifier in Table I and contained in the deposit with the ATCC Deposit Number shown for said cDNA clone in Table I; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:150, 152, 8, 10, 42, or 109; and a complete amino acid sequence of a protein encoded by a cDNA clone identified by a cDNA Clone Identifier in Table I and contained in the deposit with the ATCC Deposit Number shown for said cDNA clone in Table I.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:150, 152, 8, 10, 42, or 109; and a complete amino acid sequence of a protein encoded by a cDNA clone identified by a cDNA Clone Identifier in Table I and contained in the deposit with the ATCC Deposit Number shown for said cDNA clone in Table I.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing a pathological condition associated with an organism with abnormal structure or expression of a gene encoding a protein identified in Table I, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:150, 152, 8, 10, 42, or 109; and a complete amino acid sequence of a protein encoded by a cDNA clone identified by a cDNA Clone Identifier in Table I and contained in the deposit with the ATCC Deposit Number shown for said cDNA clone in Table I.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:150, 152, 8, 10, 42, or 109; and a complete amino acid sequence of a protein encoded by a cDNA clone identified by a cDNA Clone Identifier in Table I and contained in the deposit with the ATCC Deposit Number shown for said cDNA clone in Table I.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:150, 152, 8, 10, 42, or 109; and a complete amino acid sequence of a protein encoded by a cDNA clone identified by a cDNA Clone Identifier in Table I and contained in the deposit with the ATCC Deposit Number shown for said cDNA clone in Table I.

Further preferred is a method of making a recombinant vector comprising inserting any of the above isolated nucleic acid molecule(s) into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a protein comprising an amino acid sequence selected from the group consisting of: an amino acid sequence of SEQ ID NO:150, 152, 8, 10, 42, or 109 and said position of the "Total AA of ORF" of SEQ ID NO:150, 152, 8, 10, 42, or 109 is defined in Table I; and an amino acid sequence of a protein encoded by a cDNA clone identified by a cDNA Clone Identifier in Table I and contained in the deposit with the ATCC Deposit Number shown for said cDNA clone in Table I. The isolated polypeptide produced by this method is also preferred.

Also preferred is a method of treatment of an individual in need of an increased level of a protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

REFERENCES

Altschul, S. F., T. L. Madden, et al. (1997). "Gapped BLAST and PSI-BLAST: a new generation of protein database search programs." *Nucleic Acids Res* 25(17): 3389–402.

Bateman, A., E. Birney, et al. (2000). *Nucleic Acids Res* 28(1): 263–6.

Burge, C. and S. Karlin (1997)., *J Mol Biol* 268(1): 78–94.

Fauman, E. B. and M. A. Saper (1996)., *Trends Biochem Sci* 21(11): 413–7.

Sonnhammer, E. L., S. R. Eddy, et al. (1997), *Proteins* 28(3): 405–20.

Bernstein, F C, Koetzle, T F, Williams, G J B, Meyer, E F Jr., Brice, M D, Rodgers, J R, Kennard, O, Simanouchi, T, Tasumi, M. 1977. The Protein Data Bank: A computer-based archival file for macromolecular structures. J. Mol. Biol. 112:535–542.

Bohm H-J, LUDI: rule-based automatic design of new substituents for enzyme inhibitor leads. J. Comp. Aid. Molec. Design 6:61–78 (1992)

Cabral, J. H. M., Lee, A., Cardozo T; Totrov M; Abagyan R Homology modeling by the ICM method. Proteins 23, 403–14(1995).

Cardozo, T., Totrov, M., Abagyan, R. Homology modeling by the ICM method. Proteins 23:403–14, 1995.

Fauman, E. and Saper, M. Structure and function of the protein tyrosine phosphatases. Trends Biochem. Sci. 21:413–7 (1996).

Goodford, P. J. A computational procedure for determining energetically favorable binding sites on biologically important macromolecules. J. Med. Chem. 28:849–857 (1985)

Goodsell, D. S. and Olsen, A. J. Automated docking of substrates to proteins by simulated annealing. Proteins 8:195–202 (1990)

Greer J Comparative modeling of homologous proteins. Meth. Enzymol. 202:239–52 (1991).

Hendlich M; Lackner P; Weitckus S; Floeckner H; Froschauer R; Gottsbacher K; Casari G; Sippl M J Identification of native protein folds amongst a large number of incorrect models. The calculation of low energy conformations from potentials of mean force. J Mol. Biol. 216, 167–80 (1990).

Jia, Z., Badford, D., Flint, A. J., and Tonks, N. K. Structural basis for phosphotyrosine peptide recognition by protein tyrosine phosphatase 1B. Science 268:1754–8, 1995.

Kuntz I D, Blaney J M, Oatley S J, Langridge R, Ferrin T E. A geometric approach to macromolecule-ligand interactions. J. Mol. Biol. 161:269–288 (1982)

Lesk, A. M., Boswell, D. R., Homology Modeling: Inferences from Tables of Aligned Sequences. Curr. Op. Struc. Biol. 2: 242–247 (1992)

Levitt, M. Accurate modeling of protein conformation by automatic segment matching. J Mol Biol 226:507–33 (1992)

Martin, Y. C. 3D database searching in drug design. J. Med. Chem. 35:2145–2154 (1992)

Novotny J; Rashin A A; Bruccoleri R E. Criteria that discriminate between native proteins and incorrectly folded models. Proteins, 4:19–30 (1988).

Pearson W R Rapid and sensitive sequence comparison with FASTP and FASTA. Methods In Enzymology 18363–98 (1990).

Pearson, W. R. Rapid and sensitive sequence comparison with FASTP and FASTA. Meth. Enzymol. 183:63–98, 1990.

Sali A; Potterton L; Yuan F; van Vlijmen H; Karplus M Evaluation of comparative protein modeling by MODELLER. Proteins 23:318–26 (1995).

Stewart, A. E., Dowd, S., Keyse, S. M. and McDonald, N. Q. Crystal structure of the MAPK phosphatase Pyst1 catalytic domain and implications for regulated activation. Nat. Struct. Biol. 6:174–80 (1999).

Yuvaniyama, J.; Denu, J. M.; Dixon, J. E. and Saper, M. A. Crystal structure of the dual specificity protein phosphatase vhr. Science 272:1328–31 (1996).

EXAMPLES

Description of the Preferred Embodiments

Example 1

Method of Identifying the Novel BMY_HPP Human Phosphatases of the Present Invention Polynucleotide sequences encoding the novel BMY_HPP phosphoprotein phosphatases of the present invention were identified by a combination of the following methods:

Homology-based searches using the TBLASTN program [Altschul, 1997] to compare known phosphoprotein phosphatases with human genomic (gDNA) and EST sequences. EST or gDNA sequences having significant homology to one or more of the known phosphatases listed in Table III (expect score less than or equal to $1 \times 10^{-3}$) were retained for further analysis.

Hidden Markov Model (HMM) searches using PFAM motifs (listed in Table IV) [Bateman, 2000 #9; Sonnhammer, 1997] were used to search human genomic sequence using the Genewise program. EST or gDNA sequences having a significant score (greater than or equal to 10) with any of the following motifs were retained for further analysis.

HMM searches using PFAM motifs (listed in Table IV) were used to search predicted protein sequences identified by GENSCAN analysis of human genomic sequence [Burge, 1997 #10]. gDNA sequences having a significant score (greater than or equal to 10) with any of the following motifs were retained for further analysis.

TABLE IV

PFAM motifs used to identify phosphoprotein phosphatases

| Motif Name | PFAM Accession No. | Description |
| --- | --- | --- |
| DSPc | PF00782 | Dual specificity phosphatase, catalytic domain |
| ST_phosphatase | PF00149 | Ser/Thr protein phosphatase |
| Y_phosphatase | PF00102 | Protein-tyrosine phosphatase |

Once a bacterial artificial chromosomes (Backs) encoding a novel phosphoprotein phosphatase was identified by any one of the methods above, additional potential axons were identified using GENSCAN analysis of all nearby Backs (identified by the Golden Path tiling map, UCSC). Intron/exon boundaries, transcript cDNA sequence and protein sequence were determined using GENSCAN. The predicted protein sequence were used to identify the most closely related known phosphatase using the BLASTP program as described in herein.

In the case of BMY_HPP5, BMY_HPP5 was identified as an Incyte EST (ID 4155374) with homology to known protein phosphatases and significant expression in the central nervous system. The Incyte clone sequence was used to design oligonucleotides for isolation of additional cDNAs. Such cDNAs have been recovered and sequenced and compared to a full-length Incyte template (assembly of EST sequences) (ID1026659.7). The BMY_HPP5 cDNA has significant identity to Incyte 1026659.7 but diverges at the five-prime and three-prime ends, suggesting that it may be an alternatively spliced product of the same gene.

Example 2

Cloning of the Novel Human BMY_HPP Phosphatases of the Present Invention

A variety of methods known in the art may be used for cloning the novel BMY_HPP phosphatases of the present invention. Briefly, using the predicted or observed cDNA sequences for the BMY-HPP genes of the present invention, antisense oligonucleotides with biotin on the 5' end could be designed (the sequences of these oligos are provided in Table VI). These oligos will be used to isolate cDNA clones according to the following procedure:

One microliter (one hundred and fifty nanograms) of a biotinylated oligo is added to six microliters (six micrograms) of a mixture of single-stranded covalently closed circular cDNA libraries (such libraries are commercially available from Life Technologies, Rockville, Md., or may be created using routine methods known in the art) and seven microliters of 100% formamide in a 0.5 ml PCR tube. The cDNA libraries used for specific BMY_HPP genes will be determined by the results of the expression patterns as described herein.

The mixture is heated in a thermal cycler to 95° C. for 2 mins.

Fourteen microliters of 2× hybridization buffer (50% formamide, 1.5 M NaCl, 0.04 M NaPO$_4$, pH 7.2, 5 mM EDTA, 0.2% SDS) wis added to the heated probe/cDNA library mixture and incubated at 42° C. for 26 hours.

Hybrids between the biotinylated oligo and the circular cDNA are isolated by diluting the hybridization mixture to 220 microliters in a solution containing 1 M NaCl, 10 mM Tris-HCl pH 7.5, 1 mM EDTA, pH 8.0 and adding 125 microliters of streptavidin magnetic beads. This solution is incubated at 42° C. for 60 mins, mixing every 5 mins to resuspend the beads.

The beads are separated from the solution with a magnet and the beads washed three times in 200 microliters of 0.1×SSPE, 0.1% SDS at 45° C.

The single stranded cDNAs are released from the biotinlyated oligo/streptavidin magnetic bead complex by adding 50 microliters of 0.1 N NaOH and incubating at room temperature for 10 mins.

The cDNAs are precipitated by adding six microliters of 3 M Sodium Acetate, 5 micrograms of glycogen and 120 microliters of 100% ethanol followed by centrifugation.

The cDNAs are resuspended in 12 microliters of TE (10 mM Tris-HCl, pH 8.0), 1 mM EDTA, pH 8.0).

The single stranded cDNAs are converted into double stranded molecules in a thermal cycler by mixing 5 microliters of the captured DNA with 1.5 microliters of a standard SP6 primer (homologous to a sequence on the cDNA cloning vector) at 10 micromolar concentration and 1.5 microliters of 10×PCR buffer. The mixture is heated to 95° C. for 20 seconds, then ramped down to 59° C. At this time 15 microliters of a repair mix preheated to 70° C. is added (repair mix contains 4 microliters of 5 mM dNTPs (1.25 mM each), 1.5 microliters of 10×PCR buffer, 9.25 microliters of water, and 0.25 microliters of Taq polymerase). The solution is ramped back to 73° C. and incubated for 23 mins.

The repaired DNA was precipitated as described above and resuspended in 10 microliters of TE.

Two microliters of double-stranded cDNA are used to transform *E. coli* DH12S cells by electroporation.

The resulting colonies are screened by PCR, using a primer pair designed to identify the proper cDNAs (primer sequences, as provided in Table VI, may be used).

Those cDNA clones that are positive by PCR are then assessed to determine the inserts size. Two clones for each BMY_HPP gene are chosen for DNA sequencing using standard methods known in the art and described herein.

The polynucleotide(s) of the present invention, the polynucleotide encoding the polypeptide of the present invention, or the polypeptide encoded by the deposited clone may represent partial, or incomplete versions of the complete coding region (i.e., full-length gene). Several methods are known in the art for the identification of the 5' or 3' non-coding and/or coding portions of a gene which may not be present in the deposited clone. The methods that follow are exemplary and should not be construed as limiting the scope of the invention. These methods include but are not limited to, filter probing, clone enrichment using specific probes, and protocols similar or identical to 5' and 3' "RACE" protocols that are well known in the art. For instance, a method similar to 5' RACE is available for generating the missing 5' end of a desired full-length transcript. (Fromont-Racine et al., Nucleic Acids Res. 21(7): 1683–1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full-length gene.

This above method starts with total RNA isolated from the desired source, although poly-A+ RNA can be used. The RNA preparation can then be treated with phosphatase if necessary to eliminate 5' phosphate groups on degraded or damaged RNA that may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene. Moreover, it may be advantageous to optimize the RACE protocol to increase the probability of isolating additional 5' or 3' coding or non-coding sequences. Various methods of optimizing a RACE protocol are known in the art, though a detailed description summarizing these methods can be found in B.C. Schaefer, Anal. Biochem., 227:255–273, (1995).

An alternative method for carrying out 5' or 3' RACE for the identification of coding or non-coding sequences is provided by Frohman, M. A., et al., Proc. Nat'l. Acad. Sci. USA, 85:8998–9002 (1988). Briefly, a cDNA clone missing either the 5' or 3' end can be reconstructed to include the absent base pairs extending to the translational start or stop codon, respectively. In some cases, cDNAs are missing the start of translation. The following briefly describes a modification of this original 5' RACE procedure. Poly A+ or total RNAs reverse transcribed with Superscript II (Gibco/BRL) and an antisense or I complementary primer specific to the cDNA sequence. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoIJ SaiI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as pBluescript SKII (Stratagene) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length genes. A second kit is available from Clontech which is a modification of a related technique, SLIC (single-stranded ligation to single-stranded cDNA), developed by Dumas et al., Nucleic Acids Res., 19:5227–32(1991). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Generating the 5' or 3+ End Sequences to Obtain Full Length Genes Once a gene of interest is identified, several methods are available for the identification of the 5' or 3' portions of the gene which may not be present in the original cDNA plasmid. These methods include, but are not limited to, filter probing, clone enrichment using specific probes and protocols similar and identical to 5' and 3'RACE. While the full-length gene may be present in the library and can be identified by probing, a useful method for generating the 5' or 3' end is to use the existing sequence information from the original cDNA to generate the missing information. A method similar to 5'RACE is available for generating the missing 5' end of a desired full-length gene. (This method was published by Fromont-Racine et al., Nucleic Acids Res., 21(7): 1683–1684 (1993)). Briefly, a specific RNA oligonucleotide is ligated to the 5' ends of a population of RNA presumably 30 containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis reaction can then be used as a template for PCR amplification of the desired 5' end using a primer specific to the ligated RNA oligonucleotide and a primer specific to the known sequence of interest. The resultant product is then sequenced and analyzed to confirm that the 5' end sequence belongs to the relevant family.

Representative primers for cloning any one of the human phosphatases of the present invention are provided in Table VI herein as 'Left Cloning Primer', 'Right Cloning Primer', 'Internal RevComp Cloning Primer', and/or 'Internal Cloning Primer'. Other primers could be substituted for any of the above as would be appreciated by one skilled in the art.

In the case of the full-length BMY_HPP1, BMY_HPP1 was cloned using the polynucleotide sequences of the identified BMY_HPP1 fragments BMY_HPP1_A (SEQ ID NO:1) and BMY_HPP1_B (SEQ ID NO:3) to design the following antisense 80 bp oligo with biotin on the 5' end:

| Name | Sequence |
|---|---|
| Phos4-80b | 5'bTGACAATGGATAGCTACTTTTCCTTCCTGTAAGGCAAATGTCATC (SEQ ID NO: 45) ACCTTCACCATATCTAGGATAGTAGTAAGAGACGC -3 |

One microliter (one hundred and fifty nanograms) of the gel-purified biotinylated PCR fragment was added to six microliters (six micrograms) of a single-stranded covalently closed circular brain, fetal brain, bone marrow, prostate, spleen, testis, and thymus cDNA libraries and seven microliters of 100% formamide in a 0.5 ml PCR tube. The mixture was heated in a thermal cycler to 95° C. for 2 mins. Fourteen microliters of 2× hybridization buffer (50% formamide, 1.5 M NaCl, 0.04 M NaPO$_4$, pH 7.2, 5 mM EDTA, 0.2% SDS) was added to the heated probe/cDNA library mixture and incubated at 42° C. for 26 hours. Hybrids between the biotinylated oligo and the circular cDNA were isolated by diluting the hybridization mixture to 220 microliters in a solution containing 1 M NaCl, 10 mM Tris-HCl pH 7.5, 1 mM EDTA, pH 8.0 and adding 125 microliters of streptavidin magnetic beads. This solution was incubated at 42° C. for 60 mins, mixing every 5 mins to resuspend the beads. The beads were separated from the solution with a magnet and the beads washed three times in 200 microliters of 0.1×SSPE, 0.1% SDS at 45° C.

The single stranded cDNAs were released from the biotinlyated probe/streptavidin magnetic bead complex by adding 50 microliters of 0.1 N NaOH and incubating at room temperature for 10 mins. Six microliters of 3 M Sodium Acetate was added along with 15 micrograms of glycogen and the solution ethanol precipitated with 120 microliters of 100% ethanol. The DNA was resuspend in 12 microliters of TE (10 mM Tris-HCl, pH 8.0), 1 mM EDTA, pH 8.0). The single stranded cDNA was converted into double strands in a thermal cycler by mixing 5 microliters of the captured DNA with 1.5 microliters 10 micromolar standard SP6 primer (homologous to a sequence on the cDNA cloning vector) and 1.5 microliters of 10×PCR buffer. The mixture was heated to 95° C. for 20 seconds, then ramped down to 59° C. At this time 15 microliters of a repair mix, that was preheated to 70° C. (Repair mix contains 4 microliters of 5 mM dNTPs (1.25 mM each), 1.5 microliters of 10×PCR buffer, 9.25 microliters of water, and 0.25 microliters of Taq polymerase). The solution was ramped back to 73° C. and incubated for 23 mins. The repaired DNA was ethanol precipitated and resuspended in 10 microliters of TE. Two microliters were electroporated in *E. coli* DH12S cells and resulting colonies were screened by PCR, using the following primer pair number:

| Name | Sequence | |
|---|---|---|
| Phos2-2s | TACAATTTCGGATGGAAGGATTAT | (SEQ ID NO: 154) |
| Phos2-2a | GCATGACAATGGATAGCTACTTT | (SEQ ID NO: 155) |

The sequence of the BMY_HPP1 polynucleotide was sequenced and is provided in FIGS. 20A–D (SEQ ID NO:149).

In the case of the full-length BMY_HPP2, BMY_HPP1 was cloned using the polynucleotide sequences of the identified BMY_HPP2 fragment (SEQ ID NO:5) to design the following antisense 80 bp oligo with biotin on the 5' end:

| Name | Sequence | |
|---|---|---|
| Phos2-80b | 5'bGTGCCGCACGCCCAGGTCCAACAGGAACTGGTAGTGGGCGGGG | (SEQ ID NO: 51) |
| | AGCCGCGGCAGCGCCAGTCCCGCCAGCCGGCCCGGA -3 | |

One microliter (one hundred and fifty nanograms) of the gel-purified biotinylated PCR fragment was added to six microliters (six micrograms) of a single-stranded covalently closed circular brain, fetal brain, bone marrow, prostate, spleen, testis, and thymus cDNA libraries and seven microliters of 100% formamide in a 0.5 ml PCR tube. The mixture was heated in a thermal cycler to 95° C. for 2 mins. Fourteen microliters of 2× hybridization buffer (50% formamide, 1.5 M NaCl, 0.04 M NaPO$_4$, pH 7.2, 5 mM EDTA, 0.2% SDS) was added to the heated probe/cDNA library mixture and incubated at 42° C. for 26 hours. Hybrids between the biotinylated oligo and the circular cDNA were isolated by diluting the hybridization mixture to 220 microliters in a solution containing 1 M NaCl, 10 mM Tris-HCl pH 7.5, 1 mM EDTA, pH 8.0 and adding 125 microliters of streptavidin magnetic beads. This solution was incubated at 42° C. for 60 mins, mixing every 5 mins to resuspend the beads. The beads were separated from the solution with a magnet and the beads washed three times in 200 microliters of 0.1×SSPE, 0.1% SDS at 45° C.

The single stranded cDNAs were released from the biotinlyated probe/streptavidin magnetic bead complex by adding 50 microliters of 0.1 N NaOH and incubating at room temperature for 10 mins. Six microliters of 3 M Sodium Acetate was added along with 15 micrograms of glycogen and the solution ethanol precipitated with 120 microliters of 100% ethanol. The DNA was resuspend in 12 microliters of TE (10 mM Tris-HCl, pH 8.0), 1 mM EDTA, pH 8.0). The single stranded cDNA was converted into double strands in a thermal cycler by mixing 5 microliters of the captured DNA with 1.5 microliters 10 micromolar standard SP6 primer (homologous to a sequence on the cDNA cloning vector) and 1.5 microliters of 10×PCR buffer. The mixture was heated to 95° C. for 20 seconds, then ramped down to 59° C. At this time 15 microliters of a repair mix, that was preheated to 70° C. (Repair mix contains 4 microliters of 5 mM dNTPs (1.25 mM each), 1.5 microliters of 10×PCR buffer, 9.25 microliters of water, and 0.25 microliters of Taq polymerase). The solution was ramped back to 73° C. and incubated for 23 mins. The repaired DNA was ethanol precipitated and resuspended in 10 microliters of TE. Two microliters were electroporated in *E. coli* DH12S cells and resulting colonies were screened by PCR, using the following primer pair number:

| Name | Sequence | |
|---|---|---|
| Phos2-2s | GAGAAAGCAGTCTTCCAGTTCTAC | (SEQ ID NO: 156) |
| Phos2-2a | ATGGGAGCTAGAGGGTTTAATACT | (SEQ ID NO: 157) |

The sequence of the BMY_HPP2 polynucleotide was sequenced and is provided in FIG. 21 (SEQ ID NO:151).

In the case of BMY_HPP5, BMY_HPP5 was cloned using the sequence of Incyte clone 4155374 to design the following PCR oligos:

```
Oligo
number  Name          Sequence 686     4155374-C3.s  5'-GGCCAAAGAGCAAACTCAAG-3  (SEQ ID NO: 69)

687     4155374-C3.Ba 5'-bGCATAGCTTGTTGGTCCCAT-3 (SEQ ID NO: 70)
```

A biotinylated nucleotide was included on the 5' end of oligo 687. Using the PCR primer pair, a 414bp biotinylated fragment was amplified using the Incyte clone as the template. The fragment was gel purified by agarose electrophoresis and stored at 4° C. The same PCR primer pair was used to screen cDNA libraries for the presence of homologous sequences. Positive PCR results were obtained in our HPLC-size fractionated brain and testis libraries. One microliter (one hundred and fifty nanograms) of the gel-purified biotinylated PCR fragment was added to six microliters (six micrograms) of a single-stranded covalently closed circular testis cDNA library and seven microliters of 100% formamide in a 0.5 ml PCR tube. The mixture was heated in a thermal cycler to 95° C. for 2 mins. Fourteen microliters of 2× hybridization buffer (50% formamide, 1.5 M NaCl, 0.04 M NaPO$_4$, pH 7.2, 5 mM EDTA, 0.2% SDS) was added to the heated probe/cDNA library mixture and incubated at 42° C. for 26 hours. Hybrids between the biotinylated oligo and the circular cDNA were isolated by diluting the hybridization mixture to 220 microliters in a solution containing 1 M NaCl, 10 mM Tris-HCl pH 7.5, 1 mM EDTA, pH 8.0 and adding 125 microliters of streptavidin magnetic beads. This solution was incubated at 42° C. for 60 mins, mixing every 5 mins to resuspend the beads. The beads were separated from the solution with a magnet and the beads washed three times in 200 microliters of 0.1×SSPE, 0.1% SDS at 45° C.

The single stranded cDNAs were released from the biotinlyated probe/streptavidin magnetic bead complex by adding 50 microliters of 0.1 N NaOH and incubating at room temperature for 10 mins. Six microliters of 3 M Sodium Acetate was added along with 15 micrograms of glycogen and the solution ethanol precipitated with 120 microliters of 100% ethanol. The DNA was resuspend in 12 microliters of TE (10 mM Tris-HCl, pH 8.0), 1 mM EDTA, pH 8.0). The single stranded cDNA was converted into double strands in a thermal cycler by mixing 5 microliters of the captured DNA with 1.5 microliters 10 micromolar standard SP6 primer (homologous to a sequence on the cDNA cloning vector) and 1.5 microliters of 10×PCR buffer. The mixture was heated to 95° C. for 20 seconds, then ramped down to 59° C. At this time 15 microliters of a repair mix, that was preheated to 70° C. (Repair mix contains 4 microliters of 5 mM dNTPs (1.25 mM each), 1.5 microliters of 10×PCR buffer, 9.25 microliters of water, and 0.25 microliters of Taq polymerase). The solution was ramped back to 73° C. and incubated for 23 mins. The repaired DNA was ethanol precipitated and resuspended in 10 microliters of TE. Two microliters were electroporated in E. coli DH12S cells and resulting colonies were screened by PCR, using the primer pair number 686/687. The sequence of the BMY_HPP5 polynucleotide was sequenced and is provided in FIGS. 5A–E (SEQ ID NO:41).

Example 3

Expression Profiling of the Novel Human BMY_HPP Phosphatase Polypeptides of the Present Invention PCR primers designed from the predicted or observed cDNA sequences (described elsewhere herein) will be used in a real-time PCR assay to determine relative steady state mRNA expression levels of BMY_HPP1, BMY_HPP2, BMY_HPP3, and BMY_HPP4 across a panel of human tissues according to the following protocol.

First strand cDNA may be synthesized from commercially available mRNA (Clontech) and subjected to real time quantitative PCR using a PE 5700 instrument (Applied Biosystems, Foster City, Calif.) using the manufacturers recommended protocol. This instrument detects the amount of DNA amplified during each cycle by the fluorescent output of SYBR green, a DNA binding dye specific for double strands. The specificity of the primer pair for its target may be verified by performing a thermal denaturation profile at the end of the run which provides an indication of the number of different DNA sequences present by determining melting Tm. Only primer pairs giving a single PCR product are considered. Contributions of contaminating genomic DNA to the assessment of tissue abundance may be controlled by performing the PCR with first strand made with and without reverse transcriptase. Only samples where the contribution of material amplified in the no reverse transcriptase controls was negligible are considered.

Small variations in the amount of cDNA used in each tube can be determined by performing a parallel experiment using a primer pair for the cyclophilin gene, which is expressed in equal amounts in all tissues. The data is then used to normalize the data obtained with each primer pair. The PCR data was converted into a relative assessment of the difference in transcript abundance amongst the tissues tested.

Representative primers for expression profiling analysis for each gene are provided in Table VI herein as 'EP Sense' and 'EP Anti-sense Primer', though may also include one or more of the following: 'Left Cloning Primer', 'Right Cloning Primer', 'Internal RevComp Cloning Primer', and/or 'Internal Cloning Primer'. Other primers could be substituted for any of the above as would be appreciated by one skilled in the art.

In the case of BMY_HPP1, the following PCR primer pair was used to measure the steady state levels of BMY_HPP1 mRNA by quantitative PCR:

```
Sense:
5'- TACAATTTCGGATGGAAGGATTAT -3'   (SEQ ID NO: 154)

Antisense:
5'- GCATGACAATGGATAGCTACTTT -3'   (SEQ ID NO: 155)
```

Briefly, first strand cDNA was made from commercially available mRNA. The relative amount of cDNA used in each assay was determined by performing a parallel experiment using a primer pair for a gene expressed in equal amounts in all tissues, cyclophilin. The cyclophilin primer pair detected small variations in the amount of cDNA in each sample and these data were used for normalization of the data obtained with the primer pair for the novel BMY_HPP1. The PCR data was converted into a relative assessment of the difference in transcript abundance amongst the tissues tested and the data is presented in FIG. 22. Transcripts corresponding to BMY_HPP1 were expressed highly in testis; to a significant extent, in the spinal cord, and to a lesser extent, in pancreas, brain, pituitary, heart, and lung.

In the case of BMY HPP2, the following PCR primer pair was used to measure the steady state levels of BMY HPP2 mRNA by quantitative PCR:

```
Sense:
5'- GAGAAAGCAGTCTTCCAGTTCTAC -3'   (SEQ ID NO: 156)

Antisense:
5'- ATGGGAGCTAGAGGGTTTAATACT -3'   (SEQ ID NO: 157)
```

Briefly, first strand cDNA was made from commercially available mRNA. The relative amount of cDNA used in each assay was determined by performing a parallel experiment using a primer pair for a gene expressed in equal amounts in all tissues, cyclophilin. The cyclophilin primer pair detected small variations in the amount of cDNA in each sample and these data were used for normalization of the data obtained with the primer pair for the novel BMY_HPP2. The PCR data was converted into a relative assessment of the difference in transcript abundance amongst the tissues tested and the data is presented in FIG. 23. Transcripts corresponding to BMY_HPP2 were expressed highly in liver and kidney; to a significant extent, in the spleen, and to a lesser extent, in lung, testis, heart, intestine, pancreas, lymph node, spinal cord, and prostate.

In the case of BMY HPP5, the following PCR primer pair was used to measure the steady state levels of BMY HPP5 mRNA by quantitative PCR:

```
Sense:
5'- ATGGGACCAACAAGCTATGC -3'   (SEQ ID NO: 67)

Antisense:
5'- TTATCAGGACTGGTTTCGGG -3'   (SEQ ID NO: 68)
```

Briefly, first strand cDNA was made from commercially available mRNA. The relative amount of cDNA used in each assay was determined by performing a parallel experiment using a primer pair for a gene expressed in equal amounts in all tissues, cyclophilin. The cyclophilin primer pair detected small variations in the amount of cDNA in each sample and these data were used for normalization of the data obtained with the primer pair for the novel BMY_HPP5. The PCR data was converted into a relative assessment of the difference in transcript abundance amongst the tissues tested and the data is presented in FIG. 11. Transcripts corresponding to BMY_HPP5 were expressed highly in the testis, spinal cord, an to a lesser extent in bone marrow, brain, thymus, and liver.

Example 4

Method of Assaying the Phosphatase Activity of the BMY_HPP Polypeptides of the Present Invention The Phosphatase Activity of the BMY_HPP Polypeptides of the present invention may be assessed through the application of various biochemical assays known in the art and described herein.

Hydrolysis of Para-nitrophenyl Phosphate

The phosphatase activity for BMY_HPP proteins may be measured by assaying the ability of the proteins to hydrolyze para-nitrophenyl phosphate, a compound known to be a substrate for phosphatases, as described in Krejsa, C. et al., J. Biol. Chem. Vol. 272, p. 11541–11549, 1997 (which is hereby incorporated in its entirety herein). The proteins are incubated in 3 mg/ml para-nitrophenyl phosphate in a solution containing 60 mM MES, pH 6.0, 5% glycerol, 5 mM dithiothreitol, and 0.1% Triton X-100 for 15 min, or such other time as may be desired. The pH of the reaction may be varied to provide an optimal pH for each individual BMY_HPP protein by those with ordinary skill in the art of enzyme assays. The phosphatase reaction is stopped by the addition of 3 N NaOH to give a final NaOH concentration of 0.7 M. The product of the reaction is measured by reading the absorbance of the solution at 405 nm.

Two Dimensional Gel Electrophoresis

The BMY_HPP polynucleotides of the present invention may be subcloned into appropriate vectors for expression in host cells. Representative vectors are known in the art and described herein. 2-D gel electrophoresis (IEF followed by SDS-PAGE) will be used to assay BMY_HPP-dependent dephosphorylation of host cell proteins. These proteins can be recovered from the gel and identified by mass spectrometric or other protein sequencing techniques known in the art.

Briefly, Methods for 2-dimensional gel analysis and labeling cells with proteins are well known in the art. Cells would be labeled with 32P orthophosphate, cellular proteins would be resolved on 2D gels and their positions determined by autoradiography. Proteins of interest would be identified by excising the spots and analyzing their sequence by mass spectroscopy. The following paper and the references therein describe the methods of labeling cells, analyzing the proteins on 2D gels and mass spec identification: Gerner, C. et al., J. Biol. Chem., Vol. 275, p. 39018–39026, 2000. Substrates affected by the phosphatase would be identified by comparing wild type cells to cells where expression of the phosphatase is inhibited by deletion, anti-sense, or other means. Proteins whose phosphorylation increased would be either direct substrates or indirectly regulated by the phosphatase. Conversely, in cells where the active phosphatase was overexpressed, proteins whose phosphorylation decreased would either be direct substrates or indirectly regulated by the phosphatase.

Example 5

Method of Identifying the Substrate of the BMY_HPP Phosphatase Polypeptides of the Present Invention Substrate Identification Protein substrates for BMY_HPP polypeptides of the present invention may be identified by recovery of proteins dephosphorylated in the 2-D gel electrophoresis assay described above. Phosphopeptide substrates may also be identified as proteins whose phosphorylation increases when the activity or expression of a BMY_HPP protein is decreased (for example; by an antibody, antisense or double-stranded inhibitory RNA or by a small molecule inhibitor of BMY_HPP activity). In either case, mass spectrometry can be used to identify the recovered proteins.

Phosphopeptide substrates for BMY-HPP polypeptides may also be identified by incubation of a phosphopeptide library with a catalytically inactive version of the protein, recovery of the complex, and peptide sequencing by standard methods such as Edman degradation or mass spectrometry.

Phosphopeptide substrates can also be identified by expressing a substrate trapping mutant phosphatase (one that is catalytically inactive due to active site mutation) and isolating the proteins that bind preferentially to the substrate trapping phosphatase relative to the wild type phosphatase.

Example 6

Method of Identifying RET31 of the Present Invention

In an effort to identify gene products involved in regulatory events, the RNA expressed in TNF-α-stimulated human lung microvascular endothelial cells was analyzed. Resting cells were stimulated for 1 h with TNF-α, and the RNA was isolated from the cells. Complementary DNA (cDNA) was created from the isolated RNA using methods known in the art. The cDNA that were upregulated in response to TNFα were identified using subtractive hybridization. A clone corresponding to a portion of the RET31 polynucleotide was identified and used to identify the full-length (SEQ ID NO:115). Additional methods are provided below.

HMVEC Cell Culture

Primary cultures of human lung microvascular endothelial cells (HMVEC), from a single donor, were obtained from Clonetics (Walkersville, Md.). The cells were grown in the endothelial cell growth medium-2 kit (CC-3202) with 5% Fetal Bovine Serum (Hyclone). Initially, the cells were seeded into a T-25 flask and, after reaching approximately 90% confluence, they were trypsinized and transferred into T-225 flasks at $1.2 \times 10^6$/flask in 80 mls of medium. For normal growth conditions, the medium was changed each 48 h. When the cells reached approximately 90% confluence, they were passaged again and seeded into T-225 flasks at $1.8 \times 10^6$/ml in 80 mls of medium.

HMVEC Cell Treatment for RNA Isolation

Subconfluent (90% confluent) T-225 flasks of HMVEC were adjusted to 40 ml of medium per flask by removing excess medium. HMVEC were either left untreated (time 0) or treated with 10 ng/ml TNF-α for 1, 6 or 24 h. The medium was not changed at the time of TNF-α addition.

RNA Isolation

At the designated time points, The flasks of HMVEC were trypsinized briefly to remove cells from the flasks and trypsinization was terminated by the addition of fetal calf serum. The cells were removed from the flasks and the flasks rinsed with PBS. The cells were pelleted, rinsed once in PBS and re-pelleted. The supernatant was removed and the cell pellet used for RNA isolation. Poly A+RNA was isolated directly using Fast Track 2.0™ (Invitrogen, Carlsbad, Calif.).

Construction of the Subtraction Library

The PCR-select cDNA subtraction kit™ (Clontech, Palo Alto, Calif.) was used to generate a subtraction library from untreated HMVEC poly A+ RNA (tester) and 1 h TNF-α-treated HMVEC poly A+ RNA (driver), according to the manufacturer's protocols. Ten secondary PCR reactions were combined and run on a 2% agarose gel. Fragments ranging from approximately 0.3 kb–10 kb were gel purified using the QIAgen gel extraction kit (QIAgen Inc., Valencia, Calif.) and inserted into the TA cloning vector, pCR2.1 (Invitrogen). TOP10F' competent *E. coli* (Invitrogen) were transformed and plated on LB plates containing 50 micrograms/ml ampicillin. Clones were isolated and grown in LB broth containing similar concentrations of ampicillin. Plasmids were sequenced using methods known in the art or described elsewhere herein.

As referenced above, the methods utilized for constructing the subtraction library followed the PCR-Select cDNA Subtraction Kit (Clonetech; Protocol # PT1117-1; Version # PR85431) which is hereby incorporated herein by reference in its entirety. Additional references to this method-may be found in Diatchenko, L., et al., PNAS 93:6025–6030 (1996), which is hereby incorporated herein by reference in its entirety.

Example 7

Method of Cloning RET31 of the Present Invention

A clone containing the predicted coding sequence of RET31 was isolated from human microvascular endothelial cells (HMVECs) treated with tumor necrosis factor alpha (TNFα) for 6 hours using reverse transcription/polymerase chain reaction (RT/PCR). RNA was purified from the TNFa stimulated HMVEC cells according to methods known in the art. A primer set (each at 400 nM final concentration) was used to amplify a 3 kb sequence using the following primers and conditions:

```
primer JNF388:
CACACCACCATTACATCATCGTGGC          (SEQ ID NO: 145)

primer JNF525:
TGCTGCTCTGCTACCAACCC               (SEQ ID NO: 146)
``` with 200 μM dNTP's, 1× Advantage 2 polymerase, and 2.0 μl DNA in 25.0 μl reaction. The experiment was cycled 35 times through the following sequence: 94° C. for 30 sec, 68° C. for 30 sec. then 72° C. for 3.5 min. At the completion of the reaction, 6.0 μl of loading dye was added and the entire reaction was separated by gel electrophoresis in a 1.2% agarose gel containing ethidium bromide. An ~3 kb size band was excised from the gel and purified using the QIAgen extraction kit (QIAgen, Valencia, Calif.). This fragment was ligated into the pTAdv cloning vector (Clontech, Palo Alto, Calif.) and sequenced using standard methods.

The RET31 clone (SEQ ID NO:108; FIGS. 13A–F) contains about a 3 kb sequence corresponding to nucleotides 472 to 3513 of the predicted RET31 coding sequence (SEQ ID NO:147). The predicted RET31 coding sequence (SEQ ID NO:147) was derived from Incyte gene cluster 1026659.7.

A nucleic acid sequence corresponding to the nucleic acid sequence encoding the RET31 polypeptide was first identified in a subtraction library from TNF-α stimulated human lung microvascular endothelial cells (HMVEC). This subtraction clone sequence encoded a 408 bp partial cDNA sequence, as shown:

agarose gel containing 3.0% formaldehyde and transferred to Hybond N+ nucleic acid transfer membrane (Amersham, Piscataway, N.J.) using standard blotting techniques (see Maniatis et al. referenced herein). Membranes were auto cross-linked using Stratalinker (Stratagene) and prehybridized in ExpressHyb hybridization solution for 1 h and probed in parallel with the multiple tissue northern blots.

After hybridization, membranes were washed by continuous shaking for 30 minutes with low stringency solution (2×SSC/0.05% SDS) at room temperature with 2 changes of solution. Membranes were then washed for 30 minutes with

```
RET31 subtraction clone                                              (SEQ ID NO: 115)
ACAATGGAGTGGCTGAGCCTTTGAGCACACCACCATTACATCATCGTGGCAAATTAAAGAAGGAGGTGG

GAAAAGAGGACTTATTGTTGTCATGGCCCATGAGATGATTGGAACTCAAATTGTTACTGAGAGGTTGGT

GGCTCTGCTGGAAAGTGGAACGGAAAAAGTGCTGCTAATTGATAGCCGGCCATTTGTGGAATACAATAC

ATCCCACATTTTGGAAGCCATTAATATCAACTGCTCCAAGCTTATGAAGCGAAGGTTGCAACAGGACAA

AGTGTTAATTACAGAGCTCATCCAGCATTCAGCGAAACATAAGGTTGACATTGATTGCAGTCAGAAGGT

TGTAGTTTACGATCAAAGCTCCCAAGATGTTGCCTCTCTCTCTTCAGACTGTTTTCTCACTGT
```

Example 8

Method of Determining the mRNA Expression Profile of RET31 Using Northern Hybridization Multiple tissue northern blots (MTN) were purchased from Clontech Laboratories (Palo Alto, Calif.) and hybridized with $P^{32}$-labeled RET31. Briefly, a 408 bp RET31 fragment (RET31/RsaI) was isolated from subtraction clone 1 hrTNF031 (SEQ ID NO:115) using RsaI restriction endonuclease, run on a 2.0% agarose gel, and purified using the QIAgen Gel Extraction Kit (QIAgen, Valencia, Calif.). Approximately 30 ng of RET31/RsaI was radiolabeled (6000 Ci/mmol $P^{32}$-dCTP) using the Random Primed DNA Labeling Kit (Roche, Indianapolis, Ind.). Unincorporated nucleotides were removed using NucTrap Probe Purification Columns (Stratgene, La Jolla, Calif.). Radiolabeled RET31/RsaI probe was added at a specific activity of $1.5 \times 10^6$ cpm/ml of ExpressHyb hybridization solution (Clontech) and incubated overnight at 65° C. Blots were washed to 2.0×SSC/0.05% SDS at 50° C. and exposed to film for 24 and 48 h. The MTN's used were human MTN (#7760-1), human MTN II (#7759-1), human MTN III (#7767-1), and human cancer cell line MTN (#7757-1).

The results show the RET31 polypeptide was expressed predominately in adrenal gland, testis, and skeletal muscle; to a significant extent, in the liver, prostate ovary, and to a lesser extent, in placenta, pancreas, thymus, small intestine, thyroid, heart, kidney and liver (see FIG. 15).

Example 9

Method of Assessing the Affect of TNF-alpha on RET31 mRNA Expression

In an effort to confirm the TNF-alpha dependent regulation of RET31 expression, HMVEC cells were treated with TNF-alpha over several time periods and the mRNA subsequently harvested and probed by northern hybridization. Briefly, untreated HMVEC, 1 h TNF-α stimulated HMVEC, 6 h TNF-α stimulated HMVEC, 24 h TNF-α stimulated HMVEC poly A+RNA (2 µg each) were run on a 1.2% high stringency solution (0.1×SSC/0.1% SDS) at 50° C. with 1 change of solution. The membranes were exposed with intensifying screens to X-ray film at −70° C. for 10 days.

The endothelial cell blot was reprobed for E-selectin and GAPDH.

The results confirmed RET31 is up-regulated by TNF-α, reaching a peak of expression at 6 h by northern blot analysis (see FIG. 18).

Example 10

Method of Assessing the Physiological Function of the Human Phosphatase Polypeptide at the Cellular Level The physiological function of the human phosphatase polypeptide may be assessed by expressing the sequences encoding human phosphatase at physiologically elevated levels in mammalian cell culture systems. cDNA is subcloned into a mammalian expression vector containing a strong promoter that drives high levels of cDNA expression (examples are provided elsewhere herein). Vectors of choice include pCMV SPORT (Life Technologies) and pCR3.1 (Invitrogen, Carlsbad Calif.), both of which contain the cytomegalovirus promoter. 5–10, ug of recombinant vector are transiently transfected into a human cell line, preferably of endothelial or hematopoietic origin, using either liposome formulations or electroporation. 1–2 ug of an additional plasmid containing sequences encoding a marker protein are cotransfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cytometry, Oxford, New York N.Y.

The influence of human phosphatase polypeptides on gene expression can be assessed using highly purified populations of cells transfected with sequences encoding human phosphatase and either CD64 or CD64-GFP. CD64 and CD64-GFP are expressed on the surface of transfected cells and bind to conserved regions of human immunoglobulin G (IgG). Transfected cells are efficiently separated from non-transfected cells using magnetic beads coated with either human IgG or antibody against CD64 (DYNAL, Lake Success N.Y.). mRNA can be purified from the cells using methods well known by those of skill in the art. Expression of mRNA encoding human phosphatase polypeptides and other genes of interest can be analyzed by northern analysis or microarray techniques.

Example 11

Method of Screening for Compounds that Interact with the Human Phosphatase Polypeptide The following assays are designed to identify compounds that bind to the human phosphatase polypeptide, bind to other cellular proteins that interact with the human phosphatase polypeptide, and to compounds that interfere with the interaction of the human phosphatase polypeptide with other cellular proteins.

Such compounds can include, but are not limited to, other cellular proteins. Specifically, such compounds can include, but are not limited to, peptides, such as, for example, soluble peptides, including, but not limited to Ig-tailed fusion peptides, comprising extracellular portions of human phosphatase polypeptide transmembrane receptors, and members of random peptide libraries (see, e.g., Lam, K. S. et al., 1991, Nature 354:82–84; Houghton, R. et al., 1991, Nature 354: 84–86), made of D-and/or L-configuration amino acids, phosphopeptides (including, but not limited to, members of random or partially degenerate phosphopeptide libraries; see, e.g., Songyang, Z., et al., 1993, Cell 72:767–778), antibodies (including, but not limited to, polyclonal, monoclonal, humanized, anti-idiotypic, chimeric or single chain antibodies, and FAb, F(ab').sub.2 and FAb expression libary fragments, and epitope-binding fragments thereof), and small organic or inorganic molecules.

Compounds identified via assays such as those described herein can be useful, for example, in elaborating the biological function of the human phosphatase polypeptide, and for ameliorating symptoms of tumor progression, for example. In instances, for example, whereby a tumor progression state or disorder results from a lower overall level of human phosphatase expression, human phosphatase polypeptide, and/or human phosphatase polypeptide activity in a cell involved in the tumor progression state or disorder, compounds that interact with the human phosphatase polypeptide can include ones which accentuate or amplify the activity of the bound human phosphatase polypeptide. Such compounds would bring about an effective increase in the level of human phosphatase polypeptide activity, thus ameliorating symptoms of the tumor progression disorder or state. In instances whereby mutations within the human phosphatase polypeptide cause aberrant human phosphatase polypeptides to be made which have a deleterious effect that leads to tumor progression, compounds that bind human phosphatase polypeptide can be identified that inhibit the activity of the bound human phosphatase polypeptide. Assays for testing the effectiveness of such compounds are known in the art and discussed, elsewhere herein.

Example 12

Method of Screening, In Vitro, Compounds that Bind to the Human Phosphatase Polypeptide In vitro systems can be designed to identify compounds capable of binding the human phosphatase polypeptide of the invention. Compounds identified can be useful, for example, in modulating the activity of wild type and/or mutant human phosphatase polypeptide, preferably mutant human phosphatase polypeptide, can be useful in elaborating the biological function of the human phosphatase polypeptide, can be utilized in screens for identifying compounds that disrupt normal human phosphatase polypeptide interactions, or can in themselves disrupt such interactions.

The principle of the assays used to identify compounds that bind to the human phosphatase polypeptide involves preparing a reaction mixture of the human phosphatase polypeptide and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring human phosphatase polypeptide or the test substance onto a solid phase and detecting human phosphatase polypeptide/test compound complexes anchored on the solid phase at the end of the reaction. In one embodiment of such a method, the human phosphatase polypeptide can be anchored onto a solid surface, and the test compound, which is not anchored, can be labeled, either directly or indirectly.

In practice, microtitre plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for human phosphatase polypeptide or the test compound to anchor any complexes formed in solution, and a labeled antibody specific for the other component of the possible complex to detect anchored complexes.

Example 13

Method of Identifying Compounds that Interfere with Human Phosphatase Polypeptide/Cellular Product Interaction The human phosphatase polypeptide of the invention can, in vivo, interact with one or more cellular or extracellular macromolecules, such as proteins. Such macromolecules include, but are not limited to, polypeptides, particularly ligands, and those products identified via screening methods described, elsewhere herein. For the purposes of this discussion, such cellular and extracellular macromolecules are referred to herein as "binding partner(s)". For the purpose of the present invention, "binding partner" may also encompass polypeptides, small molecule compounds, polysaccarides, lipids, and any other molecule or molecule type referenced herein. Compounds that disrupt such interactions can be useful in regulating the activity of the human phosphatase polypeptide, especially mutant human phosphatase polypeptide. Such compounds can include, but are not limited to molecules such as antibodies, peptides, and the like described in elsewhere herein.

The basic principle of the assay systems used to identify compounds that interfere with the interaction between the human phosphatase polypeptide and its cellular or extracellular binding partner or partners involves preparing a reaction mixture containing the human phosphatase polypeptide, and the binding partner under conditions and for a time sufficient to allow the two products to interact and bind, thus forming a complex. In order to test a compound for inhibitory activity, the reaction mixture is prepared in the presence and absence of the test compound. The test compound can be initially included in the reaction mixture, or can be added at a time subsequent to the addition of human phosphatase polypeptide and its cellular or extracellular binding partner. Control reaction mixtures are incubated without the test compound or with a placebo. The formation of any complexes between the human phosphatase polypeptide and the cellular or extracellular binding partner is then detected. The formation of a complex in the control reaction, but not in the reaction mixture containing the test compound, indicates that the compound interferes with the interaction of the human phosphatase polypeptide and the interactive binding partner. Additionally, complex formation within reaction mixtures containing the test compound and normal human phosphatase polypeptide can also be compared to complex formation within reaction mixtures containing the test compound and mutant human phosphatase polypeptide. This comparison can be important in those cases wherein it is desirable to identify compounds that disrupt interactions of mutant but not normal human phosphatase polypeptide.

The assay for compounds that interfere with the interaction of the human phosphatase polypeptide and binding partners can be conducted in a heterogeneous or homogeneous format. Heterogeneous assays involve anchoring either the human phosphatase polypeptide or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the human phosphatase polypeptide and the binding partners, e.g., by competition, can be identified by conducting the reaction in the presence of the test substance; i.e., by adding the test substance to the reaction mixture prior to or simultaneously with the human phosphatase polypeptide and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the human phosphatase polypeptide or the interactive cellular or extracellular binding partner, is anchored onto a solid surface, while the non-anchored species is labeled, either directly or indirectly. In practice, microtitre plates are conveniently utilized. The anchored species can be immobilized by non-covalent or covalent attachments. Non-covalent attachment can be accomplished simply by coating the solid surface with a solution of the human phosphatase polypeptide or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the human phosphatase polypeptide and the interactive cellular or extracellular binding partner product is prepared in which either the human phosphatase polypeptide or their binding partners are labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt human phosphatase polypeptide -cellular or extracellular binding partner interaction can be identified.

In a particular embodiment, the human phosphatase polypeptide can be prepared for immobilization using recombinant DNA techniques known in the art. For example, the human phosphatase polypeptide coding region can be fused to a glutathione-S-transferase (GST) gene using a fusion vector such as pGEX-5X-1, in such a manner that its binding activity is maintained in the resulting fusion product. The interactive cellular or extracellular product can be purified and used to raise a monoclonal antibody, using methods routinely practiced in the art and described above. This antibody can be labeled with the radioactive isotope .sup.125 I, for example, by methods routinely practiced in the art. In a heterogeneous assay, e.g., the GST-human phosphatase polypeptide fusion product can be anchored to glutathione-agarose beads. The interactive cellular or extracellular binding partner product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the human phosphatase polypeptide and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-human phosphatase polypeptide fusion product and the interactive cellular or extracellular binding partner product can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the human phosphatase polypeptide product and the interactive cellular or extracellular binding partner (in case where the binding partner is a product), in place of one or both of the full length products.

Any number of methods routinely practiced in the art can be used to identify and isolate the protein's binding site. These methods include, but are not limited to, mutagenesis of one of the genes encoding one of the products and screening for disruption of binding in a co-immunoprecipitation assay. Compensating mutations in the gene encoding the second species in the complex can be selected. Sequence analysis of the genes encoding the respective products will reveal the mutations that correspond to the region of the product involved in interactive binding. Alternatively, one product can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing.

Also, once the gene coding for the cellular or extracellular binding partner product is obtained, short gene segments can be engineered to express peptide fragments of the product, which can then be tested for binding activity and purified or synthesized.

Example 14

Isolation of a Specific Clone from the Deposited Sample

The deposited material in the sample assigned the ATCC Deposit Number cited in Table I for any given cDNA clone also may contain one or more additional plasmids, each comprising a cDNA clone different from that given clone. Thus, deposits sharing the same ATCC Deposit Number contain at least a plasmid for each cDNA clone identified in Table I. Typically, each ATCC deposit sample cited in Table I comprises a mixture of approximately equal amounts (by weight) of about 1–10 plasmid DNAs, each containing a different cDNA clone and/or partial cDNA clone; but such a deposit sample may include plasmids for more or less than 2 cDNA clones.

Two approaches can be used to isolate a particular clone from the deposited sample of plasmid DNA(s) cited for that clone in Table I. First, a plasmid is directly isolated by screening the clones using a polynucleotide probe corresponding to SEQ ID NO:149, 151, 7, 9, 41, or 108.

Particularly, a specific polynucleotide with 30–40 nucleotides is synthesized using an Applied Biosystems DNA synthesizer according to the sequence reported. The oligonucleotide is labeled, for instance, with 32P-(-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:149, 151, 7, 9, 41, or 108 (i.e., within the region of SEQ ID NO:149, 151, 7, 9, 41, or 108 bounded by the 5' NT and the 3' NT of the clone defined in Table I) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5–5 mM MgCl2, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Example 15

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 10 is labeled with p32 using the rediprime ™ DNA labeling system (Amersham Life Science), according to manufacturer's instructions. After labeling, the probe is purified using CHROMA SPIN0-100 column (Clontech Laboratories, Inc.) according to manufacturer's protocol number PT1200-1. The purified labeled probe is then used to examine various tissues for mRNA expression.

Tissue Northern blots containing the bound mRNA of various tissues are examined with the labeled probe using ExpressHybtm hybridization solution (Clonetech according to manufacturers protocol number PT1190-1. Northern blots can be produced using various protocols well known in the art (e.g., Sambrook et al). Following hybridization and washing, the blots are mounted and exposed to film at −70 C overnight, and the films developed according to standard procedures.

Example 16

Chromosomal Mapping of the Polynucleotides

An oligonucleotide primer set is designed according to the sequence at the 5' end of SEQ ID NO:149, 151, 7, 9, 41, or 108. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Mammalian DNA, preferably human DNA, is used as template in addition to a somatic cell hybrid panel containing individual chromosomes or chromosome fragments (Bios, Inc). The reactions are analyzed on either 8% polyacrylamide gels or 3.5% agarose gels. Chromosome mapping is determined by the presence of an approximately 100 bp PCR fragment in the particular somatic cell hybrid.

Example 17

Bacterial Expression of a Polypeptide

A polynucleotide encoding a polypeptide of the present invention is amplified using PCR oligonucleotide primers corresponding to the 5' and 3' ends of the DNA sequence, as outlined in Example 10, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 18

Purification of a Polypeptide from an Inclusion Body

The following alternative method can be used to purify a polypeptide expressed in E coli when it is present in the form of inclusion bodies. Unless otherwise specified, all of the following steps are conducted at 4–10 degree C.

Upon completion of the production phase of the E. coli fermentation, the cell culture is cooled to 4–10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perceptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perceptive Biosystems) and weak anion (Poros CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 19

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

A polynucleotide encoding a polypeptide of the present invention is amplified using PCR oligonucleotide primers corresponding to the 5' and 3' ends of the DNA sequence, as outlined in Example 10, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described in Example 10. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 20

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five μg of an expression plasmid is cotransformed with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of the desired gene product is analyzed, for instance, by SDS-PAGE and Western blot or by reversed phase HPLC analysis.

Example 21

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84–86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

Example 22

Production of an Antibody from a Polypeptide

The antibodies of the present invention can be prepared by a variety of methods. (See, Current Protocols, Chapter 2.) As one example of such methods, cells expressing a polypeptide of the present invention are administered to an animal to induce the production of sera containing polyclonal antibodies. In a preferred method, a preparation of the protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The

```
Human IgG Fc region:                                            (SEQ ID NO: 76)
    GGGATCCGGAGCCCAAATCTTCTGACAAAACTCACACATGCCCACC

GTGCCCAGCACCTGAATTCGAGGGTGCACCGTCAGTCTTCCTCTTCCCCCC

AAAACCCAAGGACACCCTCATGATCTCCCGGACTCCTGAGGTCACATGCG

TGGTGGTGGACGTAAGCCACGAAGACCCTGAGGTCAAGTTCAACTGGTAC

GTGGACGGCGTGGAGGTGCATAATGCCAAGACAAAGCCGCGGGAGGAGC

AGTACAACAGCACGTACCGTGTGGTCAGCGTCCTCACCGTCCTGCACCAG

GACTGGCTGAATGGCAAGGAGTACAAGTGCAAGGTCTCCAACAAAGCCCT

CCCAACCCCCATCGAGAAAACCATCTCCAAAGCCAAAGGGCAGCCCCGAG

AACCACAGGTGTACACCCTGCCCCCATCCCGGGATGAGCTGACCAAGAAC

CAGGTCAGCCTGACCTGCCTGGTCAAAGGCTTCTATCCAAGCGACATCGC

CGTGGAGTGGGAGAGCAATGGGCAGCCGGAGAACAACTACAAGACCACG

CCTCCCGTGCTGGACTCCGACGGCTCCTTCTTCCTCTACAGCAAGCTCACC

GTGGACAAGAGCAGGTGGCAGCAGGGGAACGTCTTCTCATGCTCCGTGAT

GCATGAGGCTCTGCACAACCACTACACGCAGAAGAGCCTCTCCCTGTCTC

CGGGTAAATGAGTGCGACGGCCGCGACTCTAGAGGAT
``` hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 23

Regulation of Protein Expression Via Controlled Aggregation in the Endoplasmic Reticulum As described more particularly herein, proteins regulate diverse cellular processes in higher organisms, ranging from rapid metabolic changes to growth and differentiation. Increased production of specific proteins could be used to prevent certain diseases and/or disease states. Thus, the ability to modulate the expression of specific proteins in an organism would provide significant benefits.

Numerous methods have been developed to date for introducing foreign genes, either under the control of an inducible, constitutively active, or endogenous promoter, into organisms. Of particular interest are the inducible promoters (see, M. Gossen, et al., Proc. Natl. Acad. Sci. USA., 89:5547 (1992); Y. Wang, et al., Proc. Natl. Acad. Sci. USA, 91:8180 (1994), D. No., et al., Proc. Natl. Acad. Sci. USA, 93:3346 (1996); and V. M. Rivera, et al., Nature Med, 2:1028 (1996); in addition to additional examples disclosed elsewhere herein). In one example, the gene for erthropoietin (Epo) was transferred into mice and primates under the control of a small molecule inducer for expression (e.g., tetracycline or rapamycin) (see, D. Bohl, et al., Blood, 92:1512, (1998); K. G. Rendahl, et al., Nat. Biotech, 16:757, (1998); V. M. Rivera, et al., Proc. Natl. Acad. Sci. USA, 96:8657 (1999); and X. Ye et al., Science, 283:88 (1999). Although such systems enable efficient induction of the gene of interest in the organism upon addition of the inducing agent (i.e., tetracycline, rapamycin, etc,.), the levels of expression tend to peak at 24 hours and trail off to background levels after 4 to 14 days. Thus, controlled transient expression is virtually impossible using these systems, though such control would be desirable.

A new alternative method of controlling gene expression levels of a protein from a transgene (i.e., includes stable and transient transformants) has recently been elucidated (V. M. Rivera., et al., Science, 287:826–830, (2000)). This method does not control gene expression at the level of the mRNA like the aforementioned systems. Rather, the system controls the level of protein in an active secreted form. In the absence of the inducing agent, the protein aggregates in the ER and is not secreted. However, addition of the inducing agent results in dis-aggregation of the protein and the subsequent secretion from the ER. Such a system affords low basal secretion, rapid, high level secretion in the presence of the inducing agent, and rapid cessation of secretion upon removal of the inducing agent. In fact, protein secretion reached a maximum level within 30 minutes of induction, and a rapid cessation of secretion within 1 hour of removing the inducing agent. The method is also applicable for controlling the level of production for membrane proteins.

Detailed methods are presented in V. M. Rivera., et al., Science, 287:826–830, (2000)), briefly:

Fusion protein constructs are created using polynucleotide sequences of the present invention with one or more copies (preferably at least 2, 3, 4, or more) of a conditional aggregation domain (CAD) a domain that interacts with itself in a ligand-reversible manner (i.e., in the presence of an inducing agent) using molecular biology methods known in the art and discussed elsewhere herein. The CAD domain may be the mutant domain isolated from the human FKBP12 (Phe$^{36}$ to Met) protein (as disclosed in V. M. Rivera., et al., Science, 287:826–830, (2000), or alternatively other proteins having domains with similar ligand-reversible, self-aggregation properties. As a principle of design the fusion protein vector would contain a furin cleavage sequence operably linked between the polynucleotides of the present invention and the CAD domains. Such a cleavage site would enable the proteolytic cleavage of the CAD domains from the polypeptide of the present invention subsequent to secretion from the ER and upon entry into the trans-Golgi (J. B. Denault, et al., FEBS Lett., 379:113, (1996)). Alternatively, the skilled artisan would recognize that any proteolytic cleavage sequence could be substituted for the furin sequence provided the substituted sequence is cleavable either endogenously (e.g., the furin sequence) or exogenously (e.g., post secretion, post purification, pbst production, etc.). The preferred sequence of each feature of the fusion protein construct, from the 5' to 3' direction with each feature being operably linked to the other, would be a promoter, signal sequence, "X" number of (CAD)x domains, the furin sequence (or other proteolytic sequence), and the coding sequence of the polypeptide of the present invention.

The artisan would appreciate that the promotor and signal sequence, independent from the other, could be either the endogenous promotor or signal sequence of a polypeptide of the present invention, or alternatively, could be a heterologous signal sequence and promotor.

The specific methods described herein for controlling protein secretion levels through controlled ER aggregation are not meant to be limiting are would be generally applicable to any of the polynucleotides and polypeptides of the present invention, including variants, homologues, orthologs, and fragments therein.

Example 24

Alteration of Protein Glycosylation Sites to Enhance Characteristics of Polypeptides of the Invention Many eukaryotic cell surface and proteins are post-translationally processed to incorporate N-linked and O-linked carbohydrates (Kornfeld and Kornfeld (1985) Annu. Rev. Biochem. 54:631–64; Rademacher et al., (1988) Annu. Rev. Biochem. 57:785–838). Protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldler and Simons (1995) Cell, 81:309–312; Helenius (1994) Mol. Biol. Of the Cell 5:253–265; Olden et al., (1978) Cell, 13:461–473; Caton et al., (1982) Cell, 37:417–427; Alexander and Elder (1984), Science, 226:1328–1330; and Flack et al., (1994), J. Biol. Chem., 269:14015–14020). In higher organisms, the nature and extent of glycosylation can markedly affect the circulating half-life and bio-availability of proteins by mechanisms involving receptor mediated uptake and clearance (Ashwell and Morrell, (1974), Adv. Enzymol., 41:99–128; Ashwell and Harford (1982), Ann. Rev. Biochem., 51:531–54). Receptor systems have been identified that are thought to play a major role in the clearance of serum proteins through recognition of various carbohydrate structures on the glycoproteins (Stockert (1995), Physiol. Rev., 75:591–609; Kery et al., (1992), Arch. Biochem. Biophys., 298:49–55). Thus, production strategies resulting in incomplete attachment of terminal sialic acid residues might provide a means of shortening the bioavailability and half-life of glycoproteins. Conversely, expression strategies resulting in saturation of terminal sialic acid attachment sites might lengthen protein bioavailability and half-life.

In the development of recombinant glycoproteins for use as pharmaceutical products, for example, it has been speculated that the pharmacodynamics of recombinant proteins can be modulated by the addition or deletion of glycosylation sites from a glycoproteins primary structure (Berman and Lasky (1985a) Trends in Biotechnol., 3:51–53). However, studies have reported that the deletion of N-linked glycosylation sites often impairs intracellular transport and results in the intracellular accumulation of glycosylation site variants (Machamer and Rose (1988), J. Biol Chem., 263: 5955–5960; Gallagher et al., (1992), J. Virology., 66:7136–7145; Collier et al., (1993), Biochem., 32:7818–7823; Claffey et al., (1995) Biochemica et Biophysica Acta, 1246:1–9; Dube et al., (1988), J. Biol. Chem. 263:17516–17521). While glycosylation site variants of proteins can be expressed intracellularly, it has proved difficult to recover useful quantities from growth conditioned cell culture medium.

Moreover, it is unclear to what extent a glycosylation site in one species will be recognized by another species glycosylation machinery. Due to the importance of glycosylation in protein metabolism, particularly the secretion and/or expression of the protein, whether a glycosylation signal is recognized may profoundly determine a proteins ability to be expressed, either endogenously or recombinately, in another organism (i.e., expressing a human protein in E.coli, yeast, or viral organisms; or an E.coli, yeast, or viral protein in human, etc.). Thus, it may be desirable to add, delete, or modify a glycosylation site, and possibly add a glycosylation site of one species to a protein of another species to improve the proteins functional, bioprocess purification, and/or structural characteristics (e.g., a polypeptide of the present invention).

A number of methods may be employed to identify the location of glycosylation sites within a protein. One preferred method is to run the translated protein sequence through the PROSITE computer program (Swiss Institute of Bioinformatics). Once identified, the sites could be systematically deleted, or impaired, at the level of the DNA using mutagenesis methodology known in the art and available to the skilled artisan, Preferably using PCR-directed mutagenesis (See Maniatis, Molecular Cloning: A Laboratory Manual, Cold Spring Harbor Press, Cold Spring, N.Y. (1982)). Similarly, glycosylation sites could be added, or modified at the level of the DNA using similar methods, preferably PCR methods (See, Maniatis, supra). The-results of modifying the glycosylation sites for a particular protein (e.g., solubility, secretion potential, activity, aggregation, proteolytic resistance, etc.) could then be analyzed using methods know in the art.

The skilled artisan would acknowledge the existence of other computer algorithms capable of predicting the location of glycosylation sites within a protein. For example, the Motif computer program (Genetics Computer Group suite of programs) provides this function, as well.

Example 25

Method of Enhancing the Biological Activity/Functional Characteristics of Invention through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

For example, an engineered phosphatase may be constitutively active. Alternatively, an engineered phosphatase may be constitutively active in the absence of ligand binding. In yet another example, an engineered phosphatase may be capable of being activated with less than all of the regulatory factors and/or conditions typically required for phosphatase activation (e.g., ligand binding, phosphorylation, conformational changes, etc.). Alternatively, an engineered phosphatase may have altered substrate specificity. Such phosphatases would be useful in screens to identify phosphatase modulators, among other uses described herein.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145–152, (1986), and Hill, D E, et al, Methods Enzymol., 55:559–568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (W P C, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments—further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2–4 ug of the DNA substrate(s) would be digested with 0.0015 units of Dnase I (Sigma) per ul in 100 ul of 50 mM Tris-HCL, pH 7.4/1 mM MgCl2 for 10–20 min. at room temperature. The resulting fragments of 10–50 bp could then be purified by running them through a 2% low-melting point agarose gel by electrophoresis onto DE81 ion-exchange paper (Whatmann) or could be purified using Microcon concentrators (Amicon) of the appropriate molecular weight cutoff, or could use oligonucleotide purification columns (Qiagen), in addition to other methods known in the art. If using DE81 ion-exchange paper, the 10–50 bp fragments could be eluted from said paper using 1M NaCl, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris.HCL, pH 9.0, and 0.1% Triton X-100, at a final fragment concentration of 10–30 ng/ul. No primers are added at this point. Taq DNA polymerase (Promega) would be used at 2.5 units per 100 ul of reaction mixture. A PCR program of 94 C for 60 s; 94 C for 30 s, 50–55 C for 30 s, and 72 C for 30 s using 30–45 cycles, followed by 72 C for 5 min using an MJ Research (Cambridge, Mass.)

PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6):1307–1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336–347, (1997), F. R., Cross, et al., Mol. Cell. Biol., 18:2923–2931, (1998), and A. Crameri., et al., Nat. Biotech., 15:436–438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436–438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 26

Method of Determining Alterations in a Gene Corresponding to a Polynucleotide RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:149, 151, 7, 9, 41, or 108. Suggested PCR conditions consist of 35 cycles at 95 degrees C. for 30 seconds; 60–120 seconds at 52–58 degrees C.; and 60–120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 27

Method of Detecting Abnormal Levels of a Polypeptide in a Biological Sample A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described elsewhere herein. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 28

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention may also be suitably administered by sustained-release systems. Suitable examples of sustained-release Therapeutics include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly(2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see, generally, Langer, Science 249:1527–1533 (1990); Treat et al., in Liposomes in the Therapy of Infectious Disease and Cancer, Lopez-Berestein and Fidler (eds.), Liss, New York, pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci.(USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose; or dextrins; chelating agents such as EDTA; sugar alcohols such as mannitol or sorbitol; counterions such as sodium; and/or nonionic surfactants such as polysorbates, poloxamers, or PEG.

The Therapeutic will typically be formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4–1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR (zidovudine/AZT), VIDEX(didanosine/ddI), HIVID(zalcitabine/ddC), ZERIT(stavudine/d4T), EPIVIR(lamivudine/3TC), and COMBIVIR(zidovudine/lamivudine). Non-nucleoside reverse transcriptase inhibitors that may be administered in combination with the Therapeutics of the invention, include, but are not limited to, VIRAMUNE (nevirapine), RESCRIPTOR(delavirdine), and SUSTIVA(efavirenz). Protease inhibitors that may be administered in combination with the Therapeutics of the invention, include, but are not limited to, CRIXIVAN(indinavir), NORVIR (ritonavir), INVIRASE(saquinavir), and VIRACEPT(nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE, DAPSONE, PENTAMIDINE, ATOVAQUONE, ISONIAZID, RIFAMPIN, PYRAZINAMIDE, ETHAMBUTOL, RIFABUTIN, CLARITHROMYCIN, AZITHROMYCIN, GANCICLOVIR, FOSCARNET, CIDOFOVIR, FLUCONAZOLE, ITRACONAZOLE, KETOCONAZOLE, ACYCLOVIR, FAMCICOLVIR, PYRIMETHAMINE, LEUCOVORIN, NEUPOGEN (filgrastim/G-CSF), and LEUKINE((sargramostim/GM-CSF). In a specific embodiment, Therapeutics of the invention are used in any combination with TRIMETHOPRIM-SULFAMETHOXAZOLE, DAPSONE, PENTAMIDINE, and/or ATOVAQUONE(to prophylactically treat or prevent an opportunistic *Pneumocystis carinii* pneumonia infection. In another specific embodiment, Therapeutics of the invention are used in any combination with ISONIAZID, RIFAMPIN, PYRAZINAMIDE, and/or ETHAMBUTOL to prophylactically treat or prevent an opportunistic *Mycobacterium avium* complex infection. In another specific embodiment, Therapeutics of the invention are used in any combination with RIFABUTIN, CLARITHROMYCIN, and/or AZITHROMYCIN to prophylactically treat or prevent an opportunistic *Mycobacterium tuberculosis* infection. In another specific embodiment, Therapeutics of the invention are used in any combination with GANCICLOVIR, FOSCARNET, and/or CIDOFOVIR to prophylactically treat or prevent an opportunistic cytomegalovirus infection. In another specific embodiment, Therapeutics of the invention are used in any combination with FLUCONAZOLE, ITRACONAZOLE, and/or KETOCONAZOLE to prophylactically treat or prevent an opportunistic fungal infection. In another specific embodiment, Therapeutics of the invention are used in any combination with ACYCLOVIR and/or FAMCICOLVIR to prophylactically treat or prevent an opportunistic herpes simplex virus type I and/or type II infection. In another specific embodiment, Therapeutics of the invention are used in any combination with PYRIMETHAMINE and/or LEUCOVORIN to prophylactically treat or prevent an opportunistic *Toxoplasma gondii* infection. In another specific embodiment, Therapeutics of the invention are used in any combination with LEUCOVORIN and/or NEUPOGEN to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE((OKT3), SANDIMMUNE/ NEORAL/SANGDYA(cyclosporin), PROGRAF(tacrolimus), CELLCEPT(mycophenolate), Azathioprine, glucorticosteroids, and RAPAMUNE(sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR, IVEEGAM, SANDOGLOBULIN, GAMMAGARD S/D, and GAMIMUNE. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, formulations of the present invention may further comprise antagonists of P-glycoprotein (also referred to as the multiresistance protein, or PGP), including antagonists of its encoding polynucleotides (e.g., antisense oligonucleotides, ribozymes, zinc-finger proteins, etc.). P-glycoprotein is well known for decreasing the efficacy of various drug administrations due to its ability to export intracellular levels of absorbed drug to the cell exterior. While this activity has been particularly pronounced in cancer cells in response to the administration of chemotherapy regimens, a variety of other cell types and the administration of other drug classes have been noted (e.g., T-cells and anti-HIV drugs). In fact, certain mutations in the PGP gene significantly reduces PGP function, making it less able to force drugs out of cells. People who have two versions of the mutated gene—one inherited from each parent—have more than four times less PGP than those with two normal versions of the gene. People may also have one normal gene and one mutated one. Certain ethnic populations have increased incidence of such PGP mutations. Among individuals from Ghana, Kenya, the Sudan, as well as African Americans, frequency of the normal gene ranged from 73% to 84%. In contrast, the frequency was 34% to 59% among British whites, Portuguese, Southwest Asian, Chinese, Filipino and Saudi populations. As a result, certain ethnic populations may require increased administration of PGP antagonist in the formulation of the present invention to arrive at the an efficacious dose of the therapeutic (e.g., those from African descent). Conversely, certain ethnic populations, particularly those having increased frequency of the mutated PGP (e.g., of Caucasian descent, or non-African descent) may require less pharmaceutical compositions in the formulation due to an effective increase in efficacy of such compositions as a result of the increased effective absorption (e.g., less PGP activity) of said composition.

Moreover, in another specific embodiment, formulations of the present invention may further comprise antagonists of OATP2 (also referred to as the multiresistance protein, or MRP2), including antagonists of its encoding polynucleotides (e.g., antisense oligonucleotides, ribozymes, zinc-finger proteins, etc.). The invention also further comprises any additional antagonists known to inhibit proteins thought to be attributable to a multidrug resistant phenotype in proliferating cells.

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, ILA, IL5, IL6, IL7, IL10, WL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE((SARGRAMOSTIM( ) and NEUPOGEN((FILGRASTIM( ).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the Therapeutics of the invention are administered in combination with other therapeutic or prophylactic regimens, such as, for example, radiation therapy.

Example 29

Method of Treating Decreased Levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided herein.

Example 30

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided herein.

Example 31

Method of Treatment Using Gene Therapy-Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 10 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 32

Gene Therapy Using Endogenous Genes Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately 3×106 cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHI site on the 3'end. Two non-coding sequences are amplified via PCR: one non-coding sequence (fragment 1) is amplified with a HindIII site at the 5' end and an Xba site at the 3'end; the other non-coding sequence (fragment 2) is amplified with a BamHI site at the 5'end and a HindIII site at the 3'end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately 1.5.×106 cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 33

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata et al., Cardiovasc. Res. 35(3):470–479 (1997); Chao et al., Pharmacol. Res. 35(6):517–522 (1997); Wolff, Neuromuscul. Disord. 7(5): 314–318 (1997); Schwartz et al., Gene Ther. 3(5):405–411 (1996); Tsurumi et al., Circulation 94(12):3281–3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught by Felgner P. L. et al. (1995) Ann. NY Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 34

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR(RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 35

Knock-Out Animals

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or 10 regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 36

Production of an Antibody a) Hybridoma Technology

The antibodies of the present invention can be prepared by a variety of methods. (See, Current Protocols, Chapter 2.) As one example of such methods, cells expressing human phosphatase are administered to an animal to induce the production of sera containing polyclonal antibodies. In a preferred method, a preparation of human phosphatase protein is prepared and purified to render it substantially free of natural contaminants. Such a preparation is then introduced into an animal in order to produce polyclonal antisera of greater specific activity.

Monoclonal antibodies specific for protein human phosphatase are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with human phosphatase polypeptide or, more preferably, with a secreted human phosphatase polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the human phosphatase polypeptide.

Alternatively, additional antibodies capable of binding to human phosphatase polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the human phosphatase protein-specific antibody can be blocked by human phosphatase. Such antibodies comprise anti-idiotypic antibodies to the human phosphatase protein-specific antibody and are used to immunize an animal to induce formation of further human phosphatase protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation of Antibody Fragments Directed
Against Human Phosphatase from a Library of scFvs Naturally occurring V-genes isolated from human PBLs are constructed into a library of antibody fragments which contain reactivities against human phosphatase to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 $E.$ $coli$ harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 μg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 μg/mi or 10 μg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.OM Tris-HCl, pH 7.4. Phage are then used to infect 10 ml of mid-log $E.$ $coli$ TG1 by incubating eluted phage with bacteria for 30 minutes at 37° C. The $E.$ $coli$ are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect $E.$ $coli$ HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 37

Assays Detecting Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay-Purified polypeptides of the invention, or truncated forms thereof, is assessed for its ability to induce activation, proliferation, differentiation or inhibition and/or death in B-cell populations and their precursors. The activity of the polypeptides of the invention on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added 105 B-cells suspended in culture medium (RPMI 1640 containing 10% FBS, 5×10-5M 2ME, 100 U/ml penicillin, 10 ug/ml streptomycin, and 10–5 dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay-BALB/c mice are injected (i.p.) twice per day with buffer only, or 2 mg/Kg of a polypeptide of the invention, or truncated forms thereof. Mice receive this treatment for 4 consecutive days, at which time they are sacrificed and various tissues and serum collected for analyses. Comparison of H&E sections from normal spleens and spleens treated with polypeptides of the invention identify the results of the activity of the polypeptides on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from mice treated with polypeptide is used to indicate whether the polypeptide specifically increases the proportion of ThB+, CD45R (B220)dull B cells over that which is observed in control mice.

Likewise, a predicted consequence of increased mature B-cell representation in vivo is a relative increase in serum Ig titers. Accordingly, serum IgM and IgA levels are compared between buffer and polypeptide-treated mice.

One skilled in the art could easily modify the exemplified studies to test the activity of polynucleotides of the invention (e.g., gene therapy), agonists, and/or antagonists of polynucleotides or polypeptides of the invention.

Example 38

T Cell Proliferation Assay

A CD3-induced proliferation assay is performed on PBMCs and is measured by the uptake of 3H-thymidine. The assay is performed as follows. Ninety-six well plates are coated with 100 (1/well of mAb to CD3 (HIT3a, Pharmingen) or isotype-matched control mAb (B33.1) overnight at 4 degrees C. (1 (g/ml in 0.05M bicarbonate buffer, pH 9.5), then washed three times with PBS. PBMC are isolated by F/H gradient centrifugation from human peripheral blood and added to quadruplicate wells (5×104/well) of mAb coated plates in RPMI containing 10% FCS and P/S in the presence of varying concentrations of polypeptides of the invention (total volume 200 ul). Relevant protein buffer and medium alone are controls. After 48 hr. culture at 37 degrees C., plates are spun for 2 min. at 1000 rpm and 100 (1 of supernatant is removed and stored –20 degrees C. for measurement of IL-2 (or other cytokines) if effect on proliferation is observed. Wells are supplemented with 100 ul of medium containing 0.5 uCi of 3H-thymidine and cultured at 37 degrees C. for 18–24 hr. Wells are harvested and incorporation of 3H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of polypeptides of the invention.

One skilled in the art could easily modify the exemplified studies to test the activity of polynucleotides of the invention (e.g., gene therapy), agonists, and/or antagonists of polynucleotides or polypeptides of the invention.

Example 39

Effect of Polypeptides of the Invention on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-(, causes a rapid change in surface phenotype (increased expression of MHC class I and II, costimulatory and adhesion molecules, downregulation of FC(RII, upregulation of CD83). These changes correlate with increased antigen-presenting capacity and with functional maturation of the dendritic cells.

FACS analysis of surface antigens is performed as follows. Cells are treated 1–3 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. EL-12 strongly influences the development of Th1 helper T-cell immune response, and induces cytotoxic T and NK cell function. An ELISA is used to measure the IL-12 release as follows. Dendritic cells (106/ml) are treated with increasing concentrations of polypeptides of the invention for 24 hours. LPS (100 ng/ml) is added to the cell culture as positive control. Supernatants from the cell cultures are then collected and analyzed for IL-12 content using commercial ELISA kit(e.g., R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved, in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Polypeptides, agonists, or antagonists of the invention can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of 2×106/ml in PBS containing PI at a final concentration of 5 (g/ml, and then incubated at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of 5×105 cells/ml with increasing concentrations of the a polypeptide of the invention and under the same conditions, but in the absence of the polypeptide. For IL-12 production, the cells are primed overnight with IFN (100 U/ml) in presence of a polypeptide of the invention. LPS (10 ng/ml) is then added. Conditioned media are collected after 24 h and kept frozen until use. Measurement of TNF-alpha, IL-10, MCP-1 and IL-8 is then performed using a commercially available ELISA kit(e.g., R & D Systems (Minneapolis, Minn.)) and applying the standard protocols provided with the kit.

Oxidative burst. Purified monocytes are plated in 96-w plate at 2-1×105 cell/well. Increasing concentrations of polypeptides of the invention are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37(C for 2 hours and the reaction is stopped by adding 20 μl 1N NaOH per well. The absorbance is read at 610 nm. To calculate the amount of H2O2 produced by the macrophages, a standard curve of a H2O2 solution of known molarity is performed for each experiment.

One skilled in the art could easily modify the exemplified studies to test the activity of polynucleotides of the invention (e.g., gene therapy), agonists, and/or antagonists of polynucleotides or polypeptides of the invention.

Example 40

Biological Effects of Human Phosphatase Polypeptides of the Invention

Astrocyte and Neuronal Assays

Recombinant polypeptides of the invention, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate a polypeptide of the invention's activity on these cells.

Moreover, previous reports describing the biological effects of FGF-2 (basic FGF) on cortical or hippocampal neurons in vitro have demonstrated increases in both neuron survival and neurite outgrowth (Walicke et al., "Fibroblast growth factor promotes survival of dissociated hippocampal neurons and enhances neurite extension." Proc. Natl. Acad. Sci. USA 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of a polypeptide of the invention to induce neurite outgrowth can be compared to the response achieved with FGF-2 using, for example, a thymidine incorporation assay.

Fibroblast and Endothelial Cell Assays

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the PGE2 assays, the human lung fibroblasts are cultured at 5,000 cells/well in a 96-well plate for one day. After a medium change to 0.1% BSA basal medium, the cells are incubated with FGF-2 or polypeptides of the invention with or without IL-1(for 24 hours. The supernatants are collected and assayed for PGE2 by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or with or without polypeptides of the invention WIL-1(for 24 hours. The supernatants are collected and assayed for IL-6 by ELISA kit (Endogen, Cambridge, Mass.).

Human lung fibroblasts are cultured with FGF-2 or polypeptides of the invention for 3 days in basal medium before the addition of Alamar Blue to assess effects on growth of the fibroblasts. FGF-2 should show a stimulation at 10–2500 ng/ml which can be used to compare stimulation with polypeptides of the invention.

Parkinson Models

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine (MPP+) and released. Subsequently, MPP+ is actively accumulated in dopaminergic neurons by the high-affinity reuptake transporter for dopamine. MPP+ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, polypeptides of the invention can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of a polypeptide of the invention is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/cm2 on polyorthinine-laminin coated glass coverslips. The cells are maintained in Dulbecco's Modified Eagle's medium and F12 medium containing hormonal supplements (Ni). The cultures are fixed with paraformaldehyde after 8 days in vitro and are processed for tyrosine hydroxylase, a specific marker for dopaminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if a polypeptide of the invention acts to prolong the survival of dopaminergic neurons, it would suggest that the polypeptide may be involved in Parkinson's Disease.

One skilled in the art could easily modify the exemplified studies to test the activity of polynucleotides of the invention (e.g., gene therapy), agonists, and/or antagonists of polynucleotides or polypeptides of the invention.

Example 41

The Effect of the Human Phosphatase Polypeptides of the Invention on the Growth of Vascular Endothelial Cells On day 1, human umbilical vein endothelial cells (HUVEC) are seeded at 2-5×104 cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. A polypeptide having the amino acid sequence of SEQ ID NO:150, 152, 8, 10, 42, or 109, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that the polypeptide of the invention may proliferate vascular endothelial cells.

One skilled in the art could easily modify the exemplified studies to test the activity of polynucleotides of the invention (e.g., gene therapy), agonists, and/or antagonists of polynucleotides or polypeptides of the invention.

Example 42

Stimulatory Effect of Polypeptides of the Invention on the Proliferation of Vascular Endothelial Cells For evaluation of mitogenic activity of growth factors, the colorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, VEGF165 or a polypeptide of the invention in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. In Vitro Cell. Dev. Biol. 30A:512–518 (1994).

One skilled in the art could easily modify the exemplified studies to test the activity of polynucleotides of the invention (e.g., gene therapy), agonists, and/or antagonists of polynucleotides or polypeptides of the invention.

Example 43

Inhibition of PDGF—Induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4 degrees C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem. 6:271(36): 21985–21992 (1996).

One skilled in the art could easily modify the exemplified studies to test the activity of polynucleotides of the invention (e.g., gene therapy), agonists, and/or antagonists of polynucleotides or polypeptides of the invention.

Example 44

Stimulation of Endothelial Migration

This example will be used to explore the possibility that a polypeptide of the invention may stimulate lymphatic endothelial cell migration.

Endothelial cell migration assays are performed using a 48 well microchemotaxis chamber (Neuroprobe Inc., Cabin John, M D; Falk, W., et al., J. Immunological Methods 1980; 33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, 2.5×105 cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

One skilled in the art could easily modify the exemplified studies to test the activity of polynucleotides of the invention (e.g., gene therapy), agonists, and/or antagonists of polynucleotides or polypeptides of the invention.

Example 45

Stimulation of Nitric Oxide Production by Endothelial Cells

Nitric oxide released by the vascular endothelium is believed to be a mediator of vascular endothelium relaxation. Thus, activity of a polypeptide of the invention can be assayed by determining nitric oxide production by endothelial cells in response to the polypeptide.

Nitric oxide is measured in 96-well plates of confluent microvascular endothelial cells after 24 hours starvation and a subsequent 4 hr exposure to various levels of a positive control (such as VEGF-1) and the polypeptide of the invention. Nitric oxide in the medium is determined by use of the Griess reagent to measure total nitrite after reduction of nitric oxide-derived nitrate by nitrate reductase. The effect of the polypeptide of the invention on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

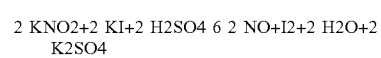

The standard calibration curve is obtained by adding graded concentrations of KNO2 (0, 5, 10, 25, 50, 100, 250, and 500 nmol/L) into the calibration solution containing KI and H2SO4. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per 1×106 endothelial cells. All values reported are means of four to six measurements in each group (number of cell culture wells). See, Leak et al. Biochem. and Biophys. Res. Comm. 217: 96–105 (1995).

One skilled in the art could easily modify the exemplified studies to test the activity of polynucleotides of the invention (e.g., gene therapy), agonists, and/or antagonists of polynucleotides or polypeptides of the invention.

Example 46

Effect of Human Phosphatase Polypeptides of the Invention on Cord Formation in Angiogenesis Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or a polypeptide of the invention (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

One skilled in the art could easily modify the exemplified studies to test the activity of polynucleotides of the invention (e.g., gene therapy), agonists, and/or antagonists of polynucleotides or polypeptides of the invention.

Example 47

Angiogenic Effect on Chick Chorioallantoic Membrane

Chick chorioallantoic membrane (CAM) is a well-established system to examine angiogenesis. Blood vessel formation on CAM is easily visible and quantifiable. The ability of polypeptides of the invention to stimulate angiogenesis in CAM can be examined.

Fertilized eggs of the White Leghorn chick (Gallus gallus) and the Japanese qual (Coturnix coturnix) are incubated at 37.8° C. and 80% humidity. Differentiated CAM of 16-day-old chick and 13-day-old qual embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

One skilled in the art could easily modify the exemplified studies to test the activity of polynucleotides of the invention (e.g., gene therapy), agonists, and/or antagonists of polynucleotides or polypeptides of the invention.

Example 48

Angiogenesis Assay Using a Matrigel Implant in Mouse

In vivo angiogenesis assay of a polypeptide of the invention measures the ability of an existing capillary network to form new vessels in an implanted capsule of murine extracellular matrix material (Matrigel). The protein is mixed with the liquid Matrigel at 4 degree C. and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 degree C. the Matrigel material is a liquid. The Matrigel is mixed with a polypeptide of the invention at 150 ng/ml at 4 degrees C. and drawn into cold 3 ml syringes. Female C57B1/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

One skilled in the art could easily modify the exemplified studies to test the activity of polynucleotides of the invention (e.g., gene therapy), agonists, and/or antagonists of polynucleotides or polypeptides of the invention.

Example 49

Rescue of Ischemia in Rabbit Lower Limb Model

To study the in vivo effects of polynucleotides and polypeptides of the invention on ischemia, a rabbit hindlimb ischemia model is created by surgical removal of one femoral arteries as described previously (Takeshita et al., Am J. Pathol 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshitaet al. Am J. Pathol 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked expression plasmid containing a polynucleotide of the invention by arterial gene transfer technology using a hydrogel-coated balloon catheter as described (Riessen et al. Hum Gene Ther. 4:749–758 (1993); Leclerc et al. J. Clin. Invest. 90: 936–944 (1992)). When a polypeptide of the invention is used in the treatment, a single bolus of 500 mg polypeptide of the invention or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

One skilled in the art could easily modify the exemplified studies to test the activity of polynucleotides of the invention (e.g., gene therapy), agonists, and/or antagonists of polynucleotides or polypeptides of the invention.

Example 50

Effect of Polypeptides of the Invention on Vasodilation

Since dilation of vascular endothelium is important in reducing blood pressure, the ability of polypeptides of the invention to affect the blood pressure in spontaneously hypertensive rats (SHR) is examined. Increasing doses (0, 10, 30, 100, 300, and 900 mg/kg) of the polypeptides of the invention are administered to 13–14 week old spontaneously hypertensive rats (SHR). Data are expressed as the mean ± SEM. Statistical analysis are performed with a paired t-test and statistical significance is defined as $p<0.05$ vs. the response to buffer alone.

One skilled in the art could easily modify the exemplified studies to test the activity of polynucleotides of the invention (e.g., gene therapy), agonists, and/or antagonists of polynucleotides or polypeptides of the invention.

Example 51

Rat Ischemic Skin Flap Model

The evaluation parameters include skin blood flow, skin temperature, and factor VIII immunohistochemistry or endothelial alkaline phosphatase reaction. Expression of polypeptides of the invention, during the skin ischemia, is studied using in situ hybridization.

The study in this model is divided into three parts as follows:
  a) Ischemic skin
  b) Ischemic skin wounds
  c) Normal wounds The experimental protocol includes:
  a) Raising a 3×4 cm, single pedicle full-thickness random skin flap (myocutaneous flap over the lower back of the animal).
  b) An excisional wounding (4–6 mm in diameter) in the ischemic skin (skin-flap).
  c) Topical treatment with a polypeptide of the invention of the excisional wounds (day 0, 1, 2, 3, 4 post-wounding) at the following various dosage ranges: 1 mg to 100 mg.
  d) Harvesting the wound tissues at day 3, 5, 7, 10, 14 and 21 post-wounding for histological, immunohistochemical, and in situ studies.

One skilled in the art could easily modify the exemplified studies to test the activity of polynucleotides of the invention (e.g., gene therapy), agonists, and/or antagonists of polynucleotides or polypeptides of the invention.

Example 52

Peripheral Arterial Disease Model

Angiogenic therapy using a polypeptide of the invention is a novel therapeutic strategy to obtain restoration of blood flow around the ischemia in case of peripheral arterial diseases. The experimental protocol includes:

a) One side of the femoral artery is ligated to create ischemic muscle of the hindlimb, the other side of hindlimb serves as a control.
  b) a polypeptide of the invention, in a dosage range of 20 mg–500 mg, is delivered intravenously and/or intramuscularly 3 times (perhaps more) per week for 2–3 weeks.
  c) The ischemic muscle tissue is collected after ligation of the femoral artery at 1, 2, and 3 weeks for the analysis of expression of a polypeptide of the invention and histology. Biopsy is also performed on the other side of normal muscle of the contralateral hindlimb.

One skilled in the art could easily modify the exemplified studies to test the activity of polynucleotides of the invention (e.g., gene therapy), agonists, and/or antagonists of polynucleotides or polypeptides of the invention.

Example 53

Ischemic Myocardial Disease Model

A polypeptide of the invention is evaluated as a potent mitogen capable of stimulating the development of collateral vessels, and restructuring new vessels after coronary artery occlusion. Alteration of expression of the polypeptide is investigated in situ. The experimental protocol includes:

a) The heart is exposed through a left-side thoracotomy in the rat. Immediately, the left coronary artery is occluded with a thin suture (6-0) and the thorax is closed.
  b) a polypeptide of the invention, in a dosage range of 20 mg–500 mg, is delivered intravenously and/or intramuscularly 3 times (perhaps more) per week for 2–4 weeks.
  c) Thirty days after the surgery, the heart is removed and cross-sectioned for morphometric and in situ analyzes.

One skilled in the art could easily modify the exemplified studies to test the activity of polynucleotides of the invention (e.g., gene therapy), agonists, and/or antagonists of polynucleotides or polypeptides of the invention.

Example 54

Rat Corneal Wound Healing Model

This animal model shows the effect of a polypeptide of the invention on neovascularization. The experimental protocol includes:

a) Making a 1–1.5 mm long incision from the center of cornea into the stromal layer.
  b) Inserting a spatula below the lip of the incision facing the outer corner of the eye.
  c) Making a pocket (its base is 1–1.5 mm form the edge of the eye).
  d) Positioning a pellet, containing 50 ng-5 ug of a polypeptide of the invention, within the pocket.
  e) Treatment with a polypeptide of the invention can also be applied topically to the corneal wounds in a dosage range of 20 mg–500 mg (daily treatment for five days).

One skilled in the art could easily modify the exemplified studies to test the activity of polynucleotides of the invention (e.g., gene therapy), agonists, and/or antagonists of polynucleotides or polypeptides of the invention.

Example 55

Diabetic Mouse and Glucocorticoid-Impaired Wound Healing Models

A. Diabetic db+/db+ Mouse Model

To demonstrate that a polypeptide of the invention accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., J. Surg. Res. 52:389 (1992); Greenhalgh, D. G. et al., Am. J. Pathol. 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. Proc. Natl. Acad. Sci. USA 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., J. Immunol. 120:1375 (1978); Debray-Sachs, M. et al., Clin. Exp. Immunol. 51(1):1–7 (1983); Leiter et al., Am. J. of Pathol. 114:46–55 (1985)). Peripheral neuropathy, myocardial complications, and microvascular lesions, basement membrane thickening and glomerular filtration abnormalities have been described in these animals (Norido, F. et al., Exp. Neurol. 83(2):221–232 (1984); Robertson et al., Diabetes 29(1):60–67 (1980); Giacomelli et al., Lab Invest. 40(4):460–473 (1979); Coleman, D. L., Diabetes 31 (Suppl): 1–6 (1982)). These homozygous diabetic mice develop hyperglycemia that is resistant to insulin analogous to human type II diabetes (Mandel et al., J. Immunol. 120:1375–1377 (1978)).

The characteristics observed in these animals suggests that healing in this model may be similar to the healing observed in human diabetes (Greenhalgh, et al., Am. J. of Pathol. 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Bristol-Myers Squibb Company's Institutional Animal Care and Use Committee and the Guidelines for the Care and Use of Laboratory Animals.

Wounding protocol is performed according to previously reported methods (Tsuboi, R. and Rifkin, D. B., J. Exp. Med. 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

A polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated group, and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 mm2, the corresponding size of the dermal punch. Calculations are made using the following formula:

[Open area on day 8]–[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with a polypeptide of the invention. This assessment included verification of the presence of cell accumulation, inflammatory cells, capillaries, fibroblasts, re-epithelialization and epidermal maturity (Greenhalgh, D. G. et al., Am. J. Pathol. 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, Glucocorticoids and Wound healing. In: Anti-Inflammatory Steroid Action: Basic and Clinical Aspects. 280–302 (1989); Wahl et al., J. Immunol. 115: 476–481 (1975); Werb et al., J. Exp. Med. 147:1684–1694 (1978)). Glucocorticoids retard wound healing by inhibiting angiogenesis, decreasing vascular permeability (Ebert et al., An. Intern. Med. 37:701–705 (1952)), fibroblast proliferation, and collagen synthesis (Beck et al., Growth Factors. 5: 295–304 (1991); Haynes et al., J. Clin. Invest. 61: 703–797 (1978)) and producing a transient reduction of circulating monocytes (Haynes et al., J. Clin. Invest. 61: 703–797 (1978); Wahl, "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck et al., Growth Factors. 5: 295–304 (1991); Haynes et al., J. Clin. Invest. 61: 703–797 (1978); Wahl, "Glucocorticoids and wound healing", In: Antiinflammatory Steroid Action: Basic and Clinical Aspects, Academic Press, New York, pp. 280–302 (1989); Pierce et al., Proc. Natl. Acad. Sci. USA 86: 2229–2233 (1989)).

To demonstrate that a polypeptide of the invention can accelerate the healing process, the effects of multiple topical applications of the polypeptide on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study would be conducted according to the rules and guidelines of Bristol-Myers Squibb Corporations Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

The polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 mm2, the corresponding size of the dermal punch. Calculations are made using the following formula:

$$[\text{Open area on day 8}] - [\text{Open area on day 1}]/[\text{Open area on day 1}]$$

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with a polypeptide of the invention. A calibrated lens micrometer is used by a blinded observer to determine the distance of the wound gap.

Experimental data are analyzed using an unpaired t test. A p value of <0.05 is considered significant.

One skilled in the art could easily modify the exemplified studies to test the activity of polynucleotides of the invention (e.g., gene therapy), agonists, and/or antagonists of polynucleotides or polypeptides of the invention.

Example 56

Lymphedema Animal Model

The purpose of this experimental approach is to create an appropriate and consistent lymphedema model for testing the therapeutic effects of a polypeptide of the invention in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (A J Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements: Blood is drawn, spun, and serum separated prior to surgery and then at conclusion for total protein and Ca2+ comparison.

Limb Weight Comparison: After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations: The transverse muscle located behind the knee (popliteal) area is dissected and arranged in a metal mold, filled with freezeGel, dipped into cold methylbutane, placed into labeled sample bags at—80EC until sectioning. Upon sectioning, the muscle is observed under fluorescent microscopy for lymphatics.

One skilled in the art could easily modify the exemplified studies to test the activity of polynucleotides of the invention (e.g., gene therapy), agonists, and/or antagonists of polynucleotides or polypeptides of the invention.

Example 57

Suppression of TNF Alpha-Induced Adhesion Molecule Expression by a Polypeptide of the Invention The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of a polypeptide of the invention to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% CO2. HUVECs are seeded in 96-well plates at concentrations of 1×104 cells/well in EGM medium at 37 degree C. for 18–24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either5 h (selectin and integrin expression) or 24 h (integrin expression only). Plates are aspirated to remove medium and 100 μl of 0.1% paraformaldehyde-PBS(with Ca++ and Mg++) is added to each well. Plates are held at 4° C. for 30 min.

Fixative is then removed from the wells and wells are washed 1× with PBS(+Ca,Mg)+0.5% BSA and drained. Do not allow the wells to dry. Add 10 μl of diluted primary antibody to the test and control wells. Anti-ICAM-1-Biotin, Anti-VCAM-1-Biotin and Anti-E-selectin-Biotin are used at a concentration of 10 μg/ml (1:10 dilution of 0.1 mg/ml stock antibody). Cells are incubated at 37° C. for 30 min. in a humidified environment. Wells are washed ×3 with PBS (+Ca,Mg)+0.5% BSA.

Then add 20 μl of diluted ExtrAvidin-Alkaline Phosphatase (1:5,000 dilution) to each well and incubated at 37° C. for 30 min. Wells are washed ×3 with PBS(+Ca,Mg)+ 0.5% BSA. 1 tablet of p-Nitrophenol Phosphate pNPP is dissolved in 5 ml of glycine buffer (pH 10.4). 100 μl of pNPP substrate in glycine buffer is added to each test well. Standard wells in triplicate are prepared from the working dilution of the ExtrAvidin-Alkaline Phosphatase in glycine buffer: 1:5,000 (100)>10–0.5>10–1>10–1.5. 5 μl of each dilution is added to triplicate wells and the resulting AP content in each well is 5.50 ng, 1.74 ng, 0.55 ng, 0.18 ng. 100 μl of pNNP reagent must then be added to each of the standard wells. The plate must be incubated at 37° C. for 4 h. A volume of 50 μl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

Example 58
Method of Creating N- and C-Terminal Deletion Mutants Corresponding to the Human Phosphatase Polypeptides of the Present Invention As described elsewhere herein, the present invention encompasses the creation of N- and C-terminal deletion mutants, in addition to any combination of N- and C-terminal deletions thereof, corresponding to the human phosphatase polypeptides of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below using specific BMY_HPP1, BMY_HPP2, BMY_HPP5 and human RET31 deletions as examples.

Briefly, using the isolated cDNA clone encoding the full-length human BMY_HPP1, BMY_HPP2, BMY_HPP5 or RET31 phosphatase polypeptide sequence (as described elsewhere herein, for example), appropriate primers of about 15–25 nucleotides derived from the desired 5' and 3' positions of SEQ ID NO:41, SEQ ID NO:108, SEQ ID NO:149, or SEQ ID NO:151 may be designed to PCR amplify, and subsequently clone, the intended N- and/or C-terminal deletion mutant. Such primers could comprise, for example, an inititation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the N9 to L606 BMY_HPP1 N-terminal deletion mutant, the following primers could be used to amplify a cDNA fragment corresponding to this deletion mutant:

```
5' Primer 5'-GCAGCA GCGGCCGC AATTTCGGATGGAAGGATTATGGTG-3'   (SEQ ID NO: 167)
                   NotI 3' Primer 5'-GCAGCA GTCGAC GAGGCCAGGCTTAGGGCCATC-3'         (SEQ ID NO: 168)
                   SalI
```

For example, in the case of the M1 to E500 BMY_HPP1 C-terminal deletion mutant, the following primers could be used to amplify a cDNA fragment corresponding to this deletion mutant:

```
5' Primer 5'-GCAGCA GCGGCCGC ATGGAGGCTGGCATTTACTTCTAC-3'    (SEQ ID NO: 169)
                   NotI 3' Primer 5'-GCAGCA GTCGAC CACCCAAGACCACATCAAGCTGC-3'       (SEQ ID NO: 170)
                   SalI
```

For example, in the case of the L31 to K150 BMY_HPP2 N-terminal deletion mutant, the following primers could be used to amplify a cDNA fragment corresponding to this deletion mutant:

```
5' Primer 5'-GCAGCA GCGGCCGC CTGTTGGACCTGGGCGTGCGGCACC-3'   (SEQ ID NO: 171)
                   NotI 3' Primer 5'-GCAGCA GTCGAC TTTCGTTCGCTGGTAGAACTGGAAG-3'     (SEQ ID NO: 172)
                   SalI
```

For example, in the case of the M1 to V111 BMY_HPP2 C-terminal deletion mutant, the following primers could be used to amplify a cDNA fragment corresponding to this deletion mutant:

```
5' Primer  5'-GCAGCA GCGGCCGC ATGGGCGTGCAGCCCCCAACTTC-3'   (SEQ ID NO: 173)
           NotI 3' Primer  5'-GCAGCA GTCGAC CACCAGGTAACAGGCCAGCATGGTG-3'   (SEQ ID NO: 174)
           SalI
```

For example, in the case of the I256 to S665 BMY_HPP5 N-terminal deletion mutant, the following primers could be used to amplify a cDNA fragment corresponding to this deletion mutant:

```
5' Primer  5'-GCAGCA GCGGCCGC ATCGCCTACATCATGAAGAGGATGG-3'  (SEQ ID NO: 104)
           NotI 3' Primer  5'-GCAGCA GTCGAC GGAGACCTCAATGA1TTCCATGCTG-3'    (SEQ ID NO: 105)
           SalI
```

For example, in the case of the M1 to Q367 BMY_HPP5 C-terminal deletion mutant, the following primers could be used to amplify a cDNA fragment corresponding to this deletion mutant:

```
5' Primer  5'-GCAGCA GCGGCCGC ATGGCCCATGAGATGATTGGAACTC-3'  (SEQ ID NO: 106)
           NotI 3' Primer  5'-GCAGCA GTCGAC CTGCACGCTGGGCACGCTGGGCACG-3'    (SEQ ID NO: 107)
           SalI
```

For example, in the case of the I157 to S665 RET31 N-terminal deletion mutant, the following primers could be used to amplify a cDNA fragment corresponding to this deletion mutant:

```
5' Primer  5'-GCAGCA GCGGCCGC ATTGGGCCAACCCGAATTCTTCCC-3'   (SEQ ID NO: 136)
           NotI 3' Primer  5'-GCAGCA GTCGAC GGAGACCTCAATGATTTCCATGCTG-3'    (SEQ ID NO: 137)
           SalI
```

For example, in the case of the M1 to K297 RET31 C-terminal deletion mutant, the following primers could be used to amplify a cDNA fragment corresponding to this deletion mutant:

```
5' Primer  5'-GCAGCA GCGGCCGC ATGGCCCATGAGATGATTGGAACTC-3'  (SEQ ID NO: 138)
           NotI 3' Primer  5'-GCAGCA GTCGAC CTTCTTCTCATAGTCCAGGAGTTGG-3'    (SEQ ID NO: 139)
           SalI
```

For example, in the case of the I157 to S660 mRET31 N-terminal deletion mutant, the following primers could be used to amplify a cDNA fragment corresponding to this deletion mutant:

```
5' Primer  5'-GCAGCA GCGGCCGC ATTGGGCCAACTCGAATTCTTCCC-3'   (SEQ ID NO: 140)
           NotI 3' Primer  5'-GCAGCA GTCGAC AGAGACCTCGATGATCTCCATGCTG-3'    (SEQ ID NO: 141)
           SalI
```

For example, in the case of the M1 to T297 mRET31 C-terminal deletion mutant, the following primers could be used to amplify a cDNA fragment corresponding to this deletion mutant:

```
5' Primer 5'-GCAGCA GCGGCCGC ATGGCCCATGAGATGATTGGAACTC-3'  (SEQ ID NO: 142)
                NotI 3' Primer 5'-GCAGCA GTCGAC CGTCTTCTCATAGTCCATGAGTTGG-3'    (SEQ ID NO: 143)
                SalI
```

Representative PCR amplification conditions are provided below, although the skilled artisan would appreciate that other conditions may be required for efficient amplification. A 100 ul PCR reaction mixture may be prepared using 10 ng of the template DNA (cDNA clone of Human phosphatase polypeptides), 200 uM 4 dNTPs, 1 uM primers, 0.25 U Taq DNA polymerase (PE), and standard Taq DNA polymerase buffer. Typical PCR cycling condition are as follows:

| 20–25 cycles: | 45 sec, 93 degrees |
| --- | --- |
|  | 2 min, 50 degrees |
|  | 2 min, 72 degrees |
| 1 cycle: | 10 min, 72 degrees |

After the final extension step of PCR, 5 U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E.coli cells using methods provided herein and/or otherwise known in the art.

The 5' primer sequence for amplifying any additional N-terminal deletion mutants may be determined by reference to the following formula:

(S+(X*3)) to ((S+(X*3))+25), wherein 'S' is equal to the nucleotide position of the initiating start codon of the human BMY_HPP1, BMY_HPP2, BMY_HPP5 or RET31 phosphatase gene (SEQ ID NO:41, SEQ ID NO:149, SEQ ID NO:151, or SEQ ID NO:108, respectively), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand SEQ ID NO:41, SEQ ID NO:149, SEQ ID NO:151, or SEQ ID NO:108, respectively. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula:

(S+(X*3)) to ((S+(X*3))−25), wherein 'S' is equal to the nucleotide position of the initiating start codon of the human BMY_HPP1, BMY_HPP2, BMY_HPP5 or RET31 phosphatase genes (SEQ SEQ ID NO:41, SEQ ID NO:149, SEQ ID NO:151, or SEQ ID NO:108, respectively), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ SEQ ID NO:41, SEQ ID NO:149, SEQ ID NO:151, or SEQ ID NO:108, respectively. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

As mentioned above, the same methodology described for BMY_HPP1, BMY_HPP2, BMY_HPP5 or RET31 N- and C-terminal deletion mutants could be applied to creating N- and C-terminal deletion mutants corresponding to HPP_BMY1, HPP_BMY2, HPP_BMY3, HPP_BMY4, HPP_BMY5, RET31, and/or mRET31 as would be appreciated by the skilled artisan.

One skilled in the art could easily modify the exemplified studies to test the activity of polynucleotides of the invention (e.g., gene therapy), agonists, and/or antagonists of polynucleotides or polypeptides of the invention.

Example 59

Method of Mutating the Human Phosphatases of the Present Invention Using Site Directed/Site-Specific Mutagenesis In vitro site-directed mutagenesis is an invaluable technique for studying protein structure-function relationships and gene expression, for example, as well as for vector modification. Approaches utilizing single stranded DNA (ssDNA) as the template have been reported (e.g., T. A. Kunkel et al., 1985, *Proc. Natl. Acad. Sci. USA)*, 82:488–492; M. A. Vandeyar et al., 1988, *Gene*, 65(1): 129–133; M. Sugimoto et al., 1989, *Anal. Biochem.*, 179 (2):309–311; and J. W. Taylor et al., 1985, *Nuc. Acids. Res.*, 13(24):8765–8785).

The use of PCR in site-directed mutagenesis accomplishes strand separation by using a denaturing step to separate the complementary strands and to allow efficient polymerization of the PCR primers. PCR site-directed mutagenesis methods thus permit site specific mutations to be incorporated in virtually any double stranded plasmid, thus eliminating the need for re-subcloning into M13-based bacteriophage vectors or single-stranded rescue. (M. P. Weiner et al., 1995, *Molecular Biology: Current Innovations and Future Trends*, Eds. A. M. Griffin and H. G. Griffin, Horizon Scientific Press, Norfolk, UK; and C. Papworth et al., 1996, *Strategies*, 9(3):3–4).

A protocol for performing site-directed mutagenesis, particularly employing the QuikChange™ site-directed mutagenesis kit (Stratagene, La Jolla, Calif.; U.S. Pat. Nos. 5,789,166 and 5,923,419) is provided for making point mutations, to switch or substitute amino acids, and to delete or insert single or multiple amino acids in the RATL1d6 amino acid sequence of this invention.

Primer Design

For primer design using this protocol, the mutagenic oligonucleotide primers are designed individually according to the desired mutation. The following considerations should be made for designing mutagenic primers: 1) Both of the mutagenic primers must contain the desired mutation and anneal to the same sequence on opposite strands of the plasmid; 2) Primers should be between 25 and 45 bases in length, and the melting temperature ($T_m$) of the primers should be greater than, or equal to, 78° C. The following formula is commonly used for estimating the $T_m$ of primers: $T=81.5+0.41$ (% GC)$-675/N-$% mismatch. For calculating $T_m$, N is the primer length in bases; and values for % GC and % mismatch are whole numbers. For calculating $T_m$ for primers intended to introduce insertions or deletions, a modified version of the above formula is employed: $T=81.5+0.41$ (% GC)$-675/N$, where N does not include the bases which are being inserted or deleted; 3) The desired mutation (deletion or insertion) should be in the middle of the primer with approximately 10–15 bases of correct sequence on both sides; 4) The primers optimally should have a minimum GC content of 40%, and should terminate in one or more C or G bases; 5) Primers need not be 5'-phosphorylated, but must be purified either by fast polynucleotide liquid chromatography (FPLC) or by polyacrylamide gel electrophoresis (PAGE). Failure to purify the primers results in a significant decrease in mutation efficiency; and 6) It is important that primer concentration is in excess. It is suggested to vary the amount of template while keeping the concentration of the primers constantly in excess (QuikChange™ Site-Directed Mutagenesis Kit, Stratagene, La Jolla, Calif.).

Protocol for Setting Up the Reactions

Using the above-described primer design, two complimentary oligonucleotides containing the desired mutation, flanked by unmodified nucleic acid sequence, are synthesized. The resulting oligonucleotide primers are purified.

A control reaction is prepared using 5 µl 10× reaction buffer (100 mM KCl; 100 mM (NH$_4$)$_2$SO$_4$; 200 mM Tris-HCl, pH 8.8; 20 mM MgSO$_4$; 1% Triton® X-100; 1 mg/ml nuclease-free bovine serum albumin, BSA); 2 µl (10 ng) of pWhitescript™, 4.5-kb control plasmid (5 ng/L); 1.25 µl (125 ng) of oligonucleotide control primer #1 (34-mer, 100 ng/µl); 1.25 µl (125 ng) of oligonucleotide control primer #2 (34-mer, 100 ng/µl); 1 µl of dNTP mix; double distilled H$_2$O; to a final volume of 50 µl. Thereafter, 1 µl of DNA polymerase (PfuTurbo® DNA Polymerase, Stratagene), (2.5 U/µl) is added. PfuTurbo® DNA Polymerase is stated to have 6-fold higher fidelity in DNA synthesis than does Taq polymerase. To maximize temperature cycling performance, use of thin-walled test tubes is suggested to ensure optimum contact with the heating blocks of the temperature cycler.

The sample reaction is prepared by combining 5 µl of 10× reaction buffer; x µl (5–50 ng) of dsDNA template; x µl (125 ng) of oligonucleotide primer #1; x µl (5–50 ng) of dsDNA template; x µl (125 ng) of oligonucleotide primer #2; 1 µl of dNTP mix; and ddH$_2$O to a final volume of 50 µl. Thereafter, 1 µl of DNA polymerase (PfuTurbo DNA Polymerase, Stratagene), (2.5 U/µl) is added.

It is suggested that if the thermal cycler does not have a hot-top assembly, each reaction should be overlaid with approximately 30 µl of mineral oil.

Cycling the Reactions

Each reaction is cycled using the following cycling parameters:

| Segment | Cycles | Temperature | Time |
| --- | --- | --- | --- |
| 1 | 1 | 95° C. | 30 seconds |
| 2 | 12–18 | 95° C. | 30 seconds |
|  |  | 55° C. | 1 minute |
|  |  | 68° C. | 2 minutes/kb of plasmid length |

For the control reaction, a 12-minute extension time is used and the reaction is run for 12 cycles. Segment 2 of the above cycling parameters is adjusted in accordance with the type of mutation desired. For example, for point mutations, 12 cycles are used; for single amino acid changes, 16 cycles are used; and for multiple amino acid deletions or insertions, 18 cycles are used. Following the temperature cycling, the reaction is placed on ice for 2 minutes to cool the reaction to $\leq 37°$ C.

Digesting the Products and Transforming Competent Cells

One µl of the DpnI restriction enzyme (10 U/µl) is added directly (below mineral oil overlay) to each amplification reaction using a small, pointed pipette tip. The reaction mixture is gently and thoroughly mixed by pipetting the solution up and down several times. The reaction mixture is then centrifuged for 1 minute in a microcentrifuge. Immediately thereafter, each reaction is incubated at 37° C. for 1 hour to digest the parental (i.e., the non-mutated) supercoiled dsDNA.

Competent cells (i.e., XL1-Blue supercompetent cells, Stratagene) are thawed gently on ice. For each control and sample reaction to be transformed, 50 µl of the supercompetent cells are aliquotted to a prechilled test tube (Falcon 2059 polypropylene). Next, 1 µl of the DpnI-digested DNA is transferred from the control and the sample reactions to separate aliquots of the supercompetent cells. The transformation reactions are gently swirled to mix and incubated for 30 minutes on ice. Thereafter, the transformation reactions are heat-pulsed for 45 seconds at 42° C. for 2 minutes.

0.5 ml of NZY+ broth, preheated to 42° C. is added to the transformation reactions which are then incubated at 37° C. for 1 hour with shaking at 225–250 rpm. An aliquot of each transformation reaction is plated on agar plates containing the appropriate antibiotic for the vector. For the mutagenesis and transformation controls, cells are spread on LB-ampicillin agar plates containing 80 µg/ml of X-gal and 20 mM MIPTG. Transformation plates are incubated for >16 hours at 37° C.

Example 60

Complementary Polynucleotides of the BMY_HPP2 Phosphatase of the Present Invention Antisense molecules or nucleic acid sequences complementary to the BMY_HPP2 protein-encoding sequence, or any part thereof, is used to decrease or to inhibit the expression of naturally occurring BMY_HPP2. Although the use of antisense or complementary oligonucleotides comprising about 15 to 35 base-pairs is described, essentially the same procedure is used with smaller or larger nucleic acid sequence fragments. An oligonucleotide based on the coding sequence of BMY_HPP2 protein, as shown in FIG. 21, or as depicted in SEQ ID NO:151, for example, is used to inhibit expression of naturally occurring BMY_HPP2. The complementary oligonucleotide is typically designed from the most unique 5' sequence and is used either to inhibit transcription by preventing promoter binding to the coding sequence, or to inhibit translation by preventing the ribosome from binding to the BMY_HPP2 protein-encoding transcript. However, other regions may also be targeted.

Using an appropriate portion of the signal and/or 5' sequence of SEQ ID NO:151, an effective antisense oligonucleotide includes any of about 15–35 nucleotides spanning the region which translates into the signal or 5' coding sequence, among other regions, of the polypeptide as shown in FIG. 21 (SEQ ID NO:152). Appropriate oligonucleotides are designed using OLIGO 4.06 software and the BMY_HPP2 protein coding sequence (SEQ ID NO:151). Preferred oligonucleotides are dideoxy based and are provided below. The oligonucleotides were synthesized using chemistry essentially as described in U.S. Pat. No. 5,849,902; which is hereby incorporated herein by reference in its entirety.

| ID # | Sequence | |
|---|---|---|
| 13600 | GGAUAUCACUACUGCAUUGCCUGGA | (SEQ ID NO: 179) |
| 13601 | UACAGCAGAUCUGUGCAGGCCAGGU | (SEQ ID NO: 180) |
| 13602 | UGAUCACACAGUAGCGGAAGAUGCU | (SEQ ID NO: 181) |
| 13603 | AGGAGUAGCAGAAUGGUUAGCCUUC | (SEQ ID NO: 182) |
| 13604 | UGAAAGCAGGCGAGAUUCGAUCCGA | (SEQ ID NO: 183) |

The BMY-HPP2 polypeptide has been shown to be involved in the regulation of the mammalian cell cycle. Subjecting cells with an effective amount of a pool of all five of the above antisense oligoncleotides resulted in a significant increase in Cyclin D expression/activity providing convincing evidence that BMY_HPP2 at least regulates the activity and/or expression of Cyclin D either directly, or indirectly. Moreover, the results suggest the physiological role of BMY_HPP2 is the negative regulation of Cyclin D activity and/or expression, either directly or indirectly. The Cyclin D assay used is described below and was based upon the analysis of Cyclin D activity as a downstream marker for proliferative signal transduction events.

Transfection of Post-quiescent A549 Cells with AntiSense Oligonucleotides.

Materials needed:
  A549 cells maintained in DMEM with high glucose (Gibco-BRL) supplemented with 10% Fetal Bovine Serum, 2 mM L-Glutamine, and 1× penicillin/streptomycin.
  Opti-MEM (Gibco-BRL)
  Lipofectamine 2000 (Invitrogen)
  Antisense oligomers (Sequitur)
  Polystyrene tubes.
  Tissue culture treated plates.
  Quiescent cells were prepared as follows:
Day 0: 300, 000 A549 cells were seeded in a T75 tissue culture flask in 10 ml of A549 media, and incubated in at 37° C., 5% $CO_2$ in a humidified incubator for 48 hours.
Day 2: The T75 flasks were rocked to remove any loosely adherent cells, and the A549 growth media removed and replenished with 10 ml of fresh A549 media. The cells were cultured for six days without changing the media to create a quiescent cell population.
Day 8: Quiescent cells were plated in multi-well format and transfected with antisense oligonucleotides.
  A549 cells were transfected according to the following:
1. Trypsinize T75 flask containing quiescent population of A549 cells.
2. Count the cells and seed 24-well plates with 60K quiescent A549 cells per well.
3. Allow the cells to adhere to the tissue culture plate (approximately 4 hours).
4. Transfect the cells with antisense and control oligonucleotides according to the following:
   a. A 10× stock of lipofectamine 2000 (10 ug/mi is 10×) was prepared, and diluted lipid was allowed to stand at RT for 15 minutes.
      Stock solution of lipofectamine 2000 was 1 mg/ml.
      10× solution for transfection was 10 ug/ml.
      To prepare 10× solution, dilute 10 ul of lipofectamine 2000 stock per 1 ml of Opti-MEM (serum free media).
   b. A 10× stock of each oligomer was prepared to be used in the transfection.
      Stock solutions of oligomers were at 100 uM in 20 mM HEPES, pH 7.5.
      10× concentration of oligomer was 0.25 uM.
      To prepare the 10× solutions, dilute 2.5 ul of oligomer per 1 ml of Opti-MEM.
   c. Equal volumes of the 10× lipofectamine 2000 stock and the 10× oligomer solutions were mixed well, and incubated for 15 minutes at RT to allow complexation of the oligomer and lipid. The resulting mixture was 5×.
   d. After the 15 minute complexation, 4 volumes of full growth media was added to the oligomer/lipid complexes (solution was 1×).
   e. The media was aspirated from the cells, and 0.5 ml of the 1× oligomer/lipid complexes added to each well.
   f. The cells were incubated for 16–24 hours at 37° C. in a humidified $CO_2$ incubator.
   g. Cell pellets were harvested for RNA isolation and TaqMan analysis of downstream marker genes.

TaqMan Reactions

Quantitative RT-PCR analysis was performed on total RNA preps that had been treated with DNaseI or poly A selected RNA. The Dnase treatment may be performed using methods known in the art, though preferably using a Qiagen Rneasy kit to purify the RNA samples, wherein DNAse I treatment is performed on the column.

Briefly, a master mix of reagents was prepared according to the following table:

Dnase I Treatment

| Reagent | Per r'xn (in uL) |
|---|---|
| 10× Buffer | 2.5 |
| Dnase I (1 unit/ul @ 1 unit per ug sample) | 2 |
| DEPC H₂O | 0.5 |
| RNA sample @ 0.1 ug/ul (2–3 ug total) | 20 |
| Total | 25 |

Next, 5 ul of master mix was aliquoted per well of a 96-well PCR reaction plate (PE part # N801-0560). RNA samples were adjusted to 0.1 ug/ul with DEPC treated H$_2$O (if necessary), and 20 ul was added to the aliquoted master mix for a final reaction volume of 25 ul.

The wells were capped using strip well caps (PE part # N801-0935), placed in a plate, and briefly spun in a centrifuge to collect all volume in the bottom of the tubes. Generally, a short spin up to 500 rpm in a Sorvall RT is sufficient The plates were incubated at 37° C. for 30 mins. Then, an equal volume of 0.1 mM EDTA in 10 mM Tris was added to each well, and heat inactivated at 70° C. for 5 min. The plates were stored at −80° C. upon completion.

RT reaction

A master mix of reagents was prepared according to the following table:

RT reaction

| Reagent | RT Per Rx'n (in ul) | No RT Per Rx'n (in ul) |
|---|---|---|
| 10× RT buffer | 5 | 2.5 |
| MgCl$_2$ | 11 | 5.5 |
| DNTP mixture | 10 | 5 |
| Random Hexamers | 2.5 | 1.25 |
| Rnase inhibitors | 1.25 | 0.625 |
| RT enzyme | 1.25 | — |
| Total RNA 500 ng (100 ng no RT) | 19.0 max | 10.125 max |
| DEPC H$_2$O | — | — |
| Total | 50 uL | 25 uL |

Samples were adjusted to a concentration so that 500 ng of RNA was added to each RT rx'n (100 ng for the no RT). A maximum of 19 ul can be added to the RT rx'n mixture (10.125 ul for the no RT.) Any remaining volume up to the maximum values was filled with DEPC treated H$_2$O, so that the total reaction volume was 50 ul (RT) or 25 ul (no RT).

On a 96-well PCR reaction plate (PE part # N801-0560), 37.5 ul of master mix was aliquoted (22.5 ul of no RT master mix), and the RNA sample added for a total reaction volume of 50 ul (25 ul, no RT). Control samples were loaded into two or even three different wells in order to have enough template for generation of a standard curve.

The wells were capped using strip well caps (PE part # N801-0935), placed in a plate, and spin briefly in a centrifuge to collect all volume in the bottom of the tubes.

Generally, a short spin up to 500 rpm in a Sorvall RT is sufficient.

For the RT-PCR reaction, the following thermal profile was used:

25° C. for 10 min
48° C. for 30 min
95° C. for 5 min
4° C. hold (for 1 hour)
Store plate @-20° C. or lower upon completion.

TaqMan Reaction (Template Comes from RT Plate.)

A master mix was prepared according to the following table:

TaqMan reaction (per well)

| Reagent | Per Rx'n (in ul) |
|---|---|
| TaqMan Master Mix | 4.17 |
| 100 uM Probe (SEQ ID NO: 186) | .025 |
| 100 uM Forward primer (SEQ ID NO: 184) | .05 |
| 100 uM Reverse primer (SEQ ID NO: 185) | .05 |
| Template | — |
| DEPC H$_2$O | 18.21 |
| Total | 22.5 |

The primers used for the RT-PCR reaction is as follows:

```
Cyclin D primer and probes:
Forward Primer:
ACTACCGCCTCACACGCTTC        (SEQ ID NO: 184)

Reverse Primer:
CTTGACTCCAGCAGGGCTTC        (SEQ ID NO: 185)

TaqMan Probe:
ATCAAGTGTGACCCAGACTGCCTCCG  (SEQ ID NO: 186)
```

Using a Gilson P-10 repeat pipetter, 22.5 ul of master mix was aliqouted per well of a 96-well optical plate. Then, using P-10 pipetter, 2.5 ul of sample was added to individual wells. Generally, RT samples are run in triplicate with each primer/probe set used, and no RT samples are run once and only with one primer/probe set, often gapdh (or other internal control).

A standard curve is then constructed and loaded onto the plate. The curve has five points plus one no template control (NTC, =DEPC treated H$_2$O). The curve was made with a high point of 50 ng of sample (twice the amount of RNA in unknowns), and successive samples of 25, 10, 5, and 1 ng. The curve was made from a control sample(s) (see above).

The wells were capped using optical strip well caps (PE part # N801-0935), placed in a plate, and spun in a centrifuge to collect all volume in the bottom of the tubes. Generally, a short spin up to 500 rpm in a Sorvall RT is sufficient.

Plates were loaded onto a PE 5700 sequence detector making sure the plate is aligned properly with the notch in the upper right hand corner. The lid was tightened down and run using the 5700 and 5700 quantitation programes and the SYBR probe using the following thermal profile:

50° C. for 2 min
95° C. for 10 min
and the following for 40 cycles:

95° C. for 15 sec
60° C. for 1 min

Change the reaction volume to 25 ul.

Once the reaction was complete, a manual threshold of around 0.1 was set to minimize the background signal. Additional information relative to operation of the Gene-Amp 5700 machine may be found in reference to the following manuals: "GeneAmp 5700 Sequence Detection System Operator Training CD"; and the "User's Manual for 5700 Sequence Detection System"; available from Perkin-Elmer and hereby incorporated by reference herein in their entirety.

Cyclin D1 is a critical regulator of the process of cell division. It has been identified as an early modulator of the G1 phase of the cell cycle, and cyclin D1 expression increases as cells enter that phase of the cell cycle. It has long been thought that an ability to pharmacologically block cancerous cells in any part of the cell cycle will have a negative impact on the tumor and be beneficial for managing the disease. Support for this rationale comes from the observation that effective drugs such as Taxol block the cell cycle in G2 phase. Importantly, the rapidly dividing cells found in the cancerous state require abundant levels of cyclin D1 to maintain an accelerated rate of proliferation and proceed to S-phase. Most notably, overexpression of cyclinD1 is a hallmark of several types of human tumors, especially breast tumors (J Mammary Gland Biol Neoplasia 1996April ; 1(2):153–62). As such, it is thought that drugs that affect cyclin D1, directly or indirectly, would block cancer cells from dividing and have a beneficial effect for patients. Such drug targets could lie within the signal transduction pathway between the oncogene ras and the nucleus, where cell cycle modulators control DNA synthesis (J. Biol Chem, 2000, Oct. 20; 275 (42):32649–57). Even more evidence exists suggesting that the Wnt pathway, mediated by the tumor suppressor betacatenin, regulates the cell cycle via transcriptional control of cyclinD1 (Oncogene 2001 Aug. 23; 20(37):5093–9: PNAS 2000 Apr. 11; 97(8): 4262–6). Thus targets influencing beta catenin/TCF4 function could also affect cyclin D1 transcript levels. As mutations in oncogenes such as ras, and tumor suppressors such as beta catenin are common to may cancers, it is obvious that cyclinD1 levels are indicative of the condition of the cell and its preparedness to proliferate, and affecting cyclinD1 levels and activity could be achieved by numerous mechanisms embodied in multiple pathways.

Antisense inhibition of the HPP_BMY2 phosphatase levels provokes a O0 response in A549 cells that indicates the regulatory pathways controlling cydlinD1 levels are affected. This implicates HPP_BMY2 in pathways important for maintenance of the proliferative state and progression through the cell cycle. As stated above, there are numerous pathways that could have either indirect or direct affects on the transcriptional levels of cyclin D1. Importantly, a major part of the pathways implicated involve the regulation of protein activity through phosphorylation. In as much as HPP_BMY2 is a phosphatase enzyme, it is readily conceivable that dephosphorylation of proteins, the counter activity to the kinases in the signal transduction cascades, contributes to the signals determining cell cycle regulation and proliferation, including regulating cyclin D1 levels. Additionally, the complexity of the interactions between proteins in the pathways described also allow for affects on the pathway eliciting compensatory responses. That is, inhibition of one pathway affecting cyclinD1 activity could provoke a more potent response and signal from another pathway of the same end, resulting in upregulation of cyclin D1. Thus, the effect of inhibition of HPP_BMY2 resulting in slight increases in cyclin D1 levels could indicate that one pathway important to cancer is effected in a way to implicate HPP_BMY2 as a potential target for pharmacologic inhibition for cancer treatment, yet a parallel pathway in the context of the experiment would replace HPP_BMY2 and propagate dysregulation of Cyclin D1.

Example 61

Method of Creating RET31 and Truncated RET31 Fusion Protein Constructs and Methods of Expression and Purification of the Same The GST fusion proteins were designed to contain the full-length RET31 protein sequence (SEQ ID NO:109), as well as a C-terminal deletion mutant of the RET31 protein sequence corresponding to amino acids M1 to T302 of SEQ ID NO:109 which was truncated after the phosphatase homology domain ending at about amino acid residue 297 of SEQ ID NO:109.

In order to generate the RET31 fusion proteins, three PCR primers were designed and received from Life Technologies (Gaithersburg, Md.). The oligos were:

| Oligo number | Name | Sequence | |
|---|---|---|---|
| S5972B08 | RET31for | 5'-CATATGGGATCCATGGCCCATGAGATTG | (SEQ ID NO: 187) |
| S5972B09 | RET31rev | 5'-GGTACCCTCGAGTCAGGAGACCTCAATGAT | (SEQ ID NO: 188) |
| S6311A01 | RET31rev2-2 | 5'-GGTACCCTCGAGTCAAGTCTGGTTCTTAAT | (SEQ ID NO: 189) |

Clones containing the original gene sequence of the full-length RET 31 polynucleotide (SEQ ID NO:108) were used as a template for the subsequent PCR.

The clone was linearized using a restriction enzyme prior to PCR. PCR was performed using random hexamers and the Expand High Fidelity PCR System (ROCHE). Amplification was achieved using RET31 forward primer (SEQ ID NO:187) paired with either RET31 Rev (SEQ ID NO:188) or Rev2-2 (SEQ ID NO:189), for the full-length cDNA or truncated cDNA respectively. The thermocycler settings were 94° C. for 30 sec, 55° C. for 30 sec and 72° C. for 60 seconds for 25 cycles. The amplimers were gel purified by the QIAgen Extraction kit (QIAgen, Valencia, Calif.) and ligated, using T4 DNA ligase, into the pGEX 4T3 Vector (Amersham Pharmacia Biotech) and sequenced using standard methods.

Appropriate clones were chosen based upon the sequencing data, and were used for subsequent steps. Protein expression was induced with 0.1 mM IPTG over a 5-hour period. The fusion protein was isolated following the methods outlined in Ausubel, et al., 1992, Short Protocols in Molecular Biology, John Wiley and Sons, Inc., pp. 16–28 to 16–31, using GST beads (Pierce) and reduced Glutathione (Sigma). The predicted proteins were approximately 100 kD for the full-length protein and 60 kD for the truncated protein. To confirm that GST fusion protein was present, the proteins, along with appropriate markers, were run on a 4–12% NuPage BIS TRIS Gel with Mops buffer and transferred to a PVD membrane at 4° C. The membrane was blocked with 5% nonfat dry milk in TBS, and probed with a rabbit anti-GST antibody (developed in house). A goat anti-rabbit conjugated to HRP secondary antibody (Biorad) was used and the blot was developed with ECL reagent (Amersham Pharmacia Biotech)—data not shown.

Example 62

Method of Assaying the Phosphatase Activity of the RET31 Polypeptide

The phosphatase activity for the full-length RET31 and the M1 to T302 C-terminal RET31 GST fusion proteins were measured by assaying the ability of the proteins to hydrolyze para-nitrophenylphosphate, a compound known to be a substrate for phosphatases, as described in Krejsa, C. et al., J. Biol. Chem. Vol. 272, p. 11541–11549, 1997 (which is hereby incorporated in its entirety herein). The proteins are incubated with para-nitrophenylphosphate in a solution containing 10 mM imidazole, pH 7.0, 1 mM EDTA, 2 mM dithiothreitol, and 5 µg/ml BSA for 2 hours with and without sodium orthovanadate (Fisher) prepared in distilled water. The progress of the phosphatase reaction in a 96-well format was monitored by the OD405 nm on a plate reader (Molecular Devices) at 10-minute intervals in the kinetic mode.

The RET31-GST full length (FL), M1 to T302 C-terminal RET31-GST (trunc), or GST alone were purified and assayed for cleavage of para-nitrophenylphosphate (pNPP). The bars represent the average of triplicate determinations, and the standard deviations are as shown. Each protein preparation was assayed in the absence and presence of 2 mM of the phosphatase inhibitor orthovanadate. The full length and truncated versions clearly demonstrated activity compared to the GST protein as shown in FIG. 36. In addition, the full length and truncated protein phosphatase activity was blocked by the phosphatase inhibitor vanadate, as shown.

Of particular significance is the unexpected five fold increase in phosphatase activity of the M1 to T302 C-terminal RET31-GST (trunc) fusion protein relative to the RET31-GST full length (FL) fusion protein.

While the described phosphatase assay elucidated the phosphatase activity of the full-length RET31 (SEQ ID NO:109) and M1 to T302 RET31 C-terminal deletion mutant (amino acids 1 to 302 of SEQ ID NO:109), subsequent sequencing of the RET31-GST full length (FL) and M1 to T302 C-terminal RET31-GST (trunc) fusion protein constructs determined that several amino acid mutations were unintentionally introduced during their construction. The sequences of the RET31 portions of both fusion proteins are provided below. Since the location of these mutations are not within the conserved phosphatase domain nor near any active site residues, it is not believed they would have any effect on the phosphatase activity of either construct. Rather, the observed phosphatase activity is believed to be representative of the wild type RET31 polypeptide sequence (SEQ ID NO:109) for the RET31-GST full length (FL), while the observed phosphatase activity of the M1 to T302 C-terminal RET31-GST (trunc) fusion protein is believed to be representative of the wild type M1 to T302 C-terminal RET31 C-terminal deletion (amino acids M1 to T302 of SEQ ID NO:109). One skilled in the art of molecular biology could easily correct the mutations of both constructs using known methods in conjunction with the information and teachings described herein. Nonetheless, the polypeptide sequences of the RET31 portion of both fusion proteins are encompassed by the present invention.

In preferred embodiments, the following RET31 polypeptide is encompassed by the present invention: MAHEIGT-QIVTERLVALLESGTEKVLLIDSR-PFVEYNTSHILEAININCSKLMKR RLQQDKVLrIELIQHSAKHKVDIDC-SQKVVVYDQSSQDVASLSSDCFLTVLLG KLEKSFNS-VHLLAGGFAEFSRCFPGLCEGKSTLVPT-CISQPCLPVANIGPTRILP NLYLGCQRDVLNKELMQQNGIGYVL-NASNTCPKPDFIPESHFLRVPVNDSFCE KILPWLDKS-VDFIEKAKASNGCVLVHCLAGISRSA-TIAIAYIMKRMDMSLDEA YRFVKEKRPTISPSFNFLGQLLDYEK-KIKNQAGASGPKS KLKLLHLEKPNEPVP AVSEG-GQKSETPLSPPCADSATSEAAGQRPVH-PASVPSVPSVQPSLLEDSPLVQ ALSGLHLSADRLEDSNKLKRSFSLDIKS-VSYSASMAASLHGFSSSEDALEYYK PSTTLDGT-NKLCQFSPVQELSEQTPETSPDKEEA-SIPKKLQTARPSDSQSKRLH SVRTSSSGTAQRSLLSPLHRSGSVED-NYHTSFLFGLSTSQQHLTKSAGLGLKG WHSDI-LAPQTSTPSLTSSWYFATESSHFYSA-SAIYGGSASYSAYSRSQLPTCGD QVYSVRRRQKPSDRADSRRS-WHEESPFEKQFKRRSCQMEFGESIMSENRSREE LGKVGSQSSFSGSMEIIEVS (SEQ ID NO:190). Polynucleotides encoding this polypeptide are also provided.

In preferred embodiments, the following M1 to T302 RET31 polypeptide is encompassed by the present invention:

```
MAHEIVGTQIVTERLVALLESGTEKVLLIDSRPFVEYNTSHILEAININCSKLMKRRLQQDKVLI   (SEQ ID NO: 191)

TELIQHSAKHKVDIDCSQKVVVYDQSSQDVASLSSDCFLTVLLGKLEKSFNSVHLLAGGFAEF

SRCFPGLCEGKSTLVPTCISQPCLPVANIGPTRILPNLYLGCQRDVLNKELMQQNGIGYVLNAS

NTCPKPDFIPESHFLRVPVNDSFCEKILPWLDKSVDFIEKAKASNGCVLVHCLAGISRSATIAIA

YIMKRMDMSLDEAYRFVKEKRPTISPSFNFLGQLLDYEKKIKNQT.
```

Polynucleotides encoding this polypeptide are also provided.

The present invention encompasses the application of this phosphatase activity assay to the other phosphatases of the present invention.

Example 63

Method of Assessing the Expression Profile of the RET31 Phosphatase Polypeptides of the Present Invention at the Level of the Protein Using Immunohistochemistry Peptide Selection and Antibody Production The sequence for the RET31 polypeptide (SEQ ID NO:109) was analyzed by the algorithm of Hopp and Woods to determine potential peptides for synthesis and antibody production. The peptides were then BLASTed against the SWISS-PROT database to determine the uniqueness of the identified peptide and to help predict the specificity of the resulting antibodies. The following RET31 polypeptide fragments were selected according to the methods above for peptide synthesis: KNQTGASGPKSKKLKLLHLE (SEQ ID NO:192); and CKKLQTARPSDSQSKRLHS (SEQ ID NO:193). Rabbit polyclonal antisera was generated for both synthesized RET31 peptides. In order to allow for peptide conjugation to the carrier protein, a cysteine residue was added to the N-terminus of the SEQ ID NO:193 peptide. The third bleeds were subjected to peptide affinity purification, and the resulting antisera were then used as primary antibodies in immunohistochemistry experiments. The antisera for the SEQ ID NO:192 peptide was labeled RET31 antibody 299, while the antisera for the SEQ ID NO:193 peptide was labeled RET31 antibody 469 antibody.

Antibody Titration Protocol and Positive Control Study Results

Antibody titration experiments were conducted with RET31 antibodies 299 and 469 (both rabbit polyclonals) to establish concentrations that would result in minimal background and maximal detection of signal. Serial dilutions were performed at 1:50. 1:100, 1:250, 1:500, and 1:1000. The serial dilution study demonstrated the highest signal-to-noise ratios at dilutions 1:250 and 1:400, on paraffin-embedded, formalin-fixed tissues for both antibodies. These concentrations were used for the study. RET3 1 antibodies 299 and 469 were used as primary antibodies, and the principal detection system consisted of a Vector anti-rabbit secondary (BA-1000; DAKO Corp.), a Vector ABC-AP Kit (AK-5000; DAKO Corp.) with a Vector Red substrate kit (SK-5100; DAKO Corp.), which was used to produce a fuchsia-colored deposit. Tissues were also stained with a positive control antibody (CD31) to ensure that the tissue antigens were preserved and accessible for immunohistochemical analysis. Only tissues that stained positive for CD31 were chosen for the remainder of the study. The negative control consisted of performing the entire immunohistochemistry procedure on adjacent sections in the absence of primary antibody. Slides were imaged using a DVC 1310C digital camera coupled to a Nikon microscope. Images were stored as TIFF files using Adobe PhotoShop.

Immunohistochemistry Procedure

Slides containing paraffin sections (LifeSpan Bio-Sciences, Inc.; Seattle, Wash.) were deparaffinized through xylene and alcohol, rehydrated, and then subjected to the steam method of target retrieval (#S1700; DAKO Corp.; Carpenteria, Calif.). Immunohistochemical assay techniques are commonly known in the art and are described briefly herein. Immunocytochemical (ICC) experiments were performed on a DAKO autostainer following the procedures and reagents developed by DAKO. Specifically, the slides were blocked with avidin, rinsed, blocked with biotin, rinsed, protein blocked with DAKO universal protein block, machine blown dry, primary antibody, incubated, and the slides rinsed. Biotinylated secondary antibody was applied using the manufacturer's instructions (1 drop/10 ml, or approximately 0.75 µg/mL), incubated, rinsed slides, and applied Vectastain ABC-AP reagent for 30 minutes. Vector Red was used as substrate and prepared according to the manufacturer's instructions just prior to use.

Immunohistochemistry Results

The immunohistochemistry results were consistent with the Northern Blot and RT-PCR expression profiles described elsewhere herein for the RET31 polypeptide. Specifically, moderate to strong staining was observed in normal respiratory epithelial cell bodies and cilia. Types I and II pneumocytes were also moderately positive, as were neutrophils, mast cells, and macrophages in normal lung. In asthmatic patients, respiratory epithelial cell bodies stained less intensely, but cilia continued to stain strongly. Pneumocytes also stained less intensely than normal tissue. Inflammatory cell staining did not differ from normal tissue. Bronchial smooth muscle stained faintly in normal and asthmatic lungs. Cytoplasmic, diffuse nucleoplasmic, and nucleolar staining was observed in several cell types, including vascular endothelial and respiratory epithelial cells.

Moderate to strong staining was seen in chondrocytes and rimming osteoblasts in degenerative arthritis. In contrast, osteocytes were negative, as was the osteoid matrix. Hematopoetic tissue showed strongly positive cytoplasm and nucleus in myeloid series cells at all stages of maturation. Megakaryocytic and erythroid cells were negative.

Schwann cells and vascular endothelial cells were moderately to strongly positive in normal colon, in contrast to epithelial cells and ganglion cells, which were negative. Inflammatory cells, such as neutrophils, eosinophils, macrophages, and mast wells were strongly positive. Plasma cells showed blush to faint staining. Lymphocytes in normal colon showed strong punctate nuclear and nucleolar staining. In contrast to normal colon, the colon sections with ulcerative colitis showed less prominent nucleolar staining in lymphocytes. Neuroendocrine cells in the epithelium were faintly positive.

Normal lung showed strong cilial staining in the respiratory epithelial cells, with only blush, diffuse, nuclear staining in the cell body of these cells. Pneumocytes were faintly to moderately positive, as were alveolar macrophages and vascular endothelium. Asthmatic lungs continued to show strong cilial staining, but showed blush positivity in normal lung, and were predominately negative in diseased lung. Pneumocyte staining varied from blush to moderately positive in asthmatic lungs. Pneumocyte staining was unchanged from normal lung. Inflammatory cell staining was similar to normal tissue.

Moderate staining was seen in the stratum granulosum in normal skin, whereas the other layers were negative or showed blush positivity. Melanocytes were moderately to strongly positive, as were hair follicles and eccrine and sebaceous glands. Skin with psoriasis showed strong staining in the stratum granulosum, increased from normal skin. In contrast to normal skin, melanocytes in skin were negative. In the psoriasisform dermatitis sample, the staining pattern was similar to that observed in normal skin.

In synovium, the reactive synoviocytes in one sample of rheumatoid arthritis were faintly to moderately positive, in contrast to normal synoviocytes, which were negative or showed blush staining. In the second sample of rheumatoid arthritis, the difference in synoviocyte staining was smaller than in the first sample.

Interesting observations in this study included the very prominent staining of the nucleolus of lymphocytes and other cell types. In inflammatory bowel disease, the lymphocytes did not show nucleolar staining as prominately as in normal colon. Skin with psorisis had very prominent staining of the stratum granulosum, in comparison to normal skin or to the psoriasiform dermatitis sample.

The present invention encompasses the application of this phosphatase activity assay to the other phosphatases of the present invention.

Example 64

Method of Assessing the Expression Profile of the Novel Phosphatases of Polypeptides of the Present Invention using Expanded mRNA Tissue and Cell Sources Total RNA from tissues was isolated using the TriZol protocol (Invitrogen) and quantified by determining its absorbance at 260 nM. An assessment of the 18 s and 28 s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For BMY_HPP1, the primer probe sequences were as follows

```
Forward Primer
5'-TCAGAGAATGGGCCAACAAGA-3'        (SEQ ID NO: 194)

Reverse Primer
5'-CGAAAACGCTCGAGGAATGA-3'         (SEQ ID NO: 195)

TaqMan Probe
5'-CAGGCCTAGGTTCCTCCTCTCGGAAA-3'   (SEQ ID NO: 196)
```

For BMY_HPP2, the primer probe sequences were as follows

```
Forward Primer
5'-TCAGAGAATGGGCCAACAAGA-3'        (SEQ ID NO: 197)

Reverse Primer
5'-CGAAAACGCTCGAGGAATGA-3'         (SEQ ID NO: 198)

TaqMan Probe
5'-CAGGCCTAGGTTCCTCCTCTCGGAAA-3'   (SEQ ID NO: 199)
```

For BMY_HPP4, the primer probe sequences were as follows

```
Forward Primer
5'-TCAGAGAATGGGCCAACAAGA-3'        (SEQ ID NO: 200)

Reverse Primer
5'-CGAAAACGCTCGAGGAATGA-3'         (SEQ ID NO: 201)

TaqMan Probe
5'-CAGGCCTAGGTTCCTCCTCTCGGAAA-3'   (SEQ ID NO: 202)
```

For BMY_HPP5 (RET31), the primer probe sequences were as follows

```
Forward Primer
5'-TCAGAGAATGGGCCAACAAGA-3'        (SEQ ID NO: 203)

Reverse Primer
5'-CGAAAACGCTCGAGGAATGA-3'         (SEQ ID NO: 204)

TaqMan Probe
5'-CAGGCCTAGGTTCCTCCTCTCGGAAA-3'   (SEQ ID NO: 205)
```

The same BMY_HPP5 primer probe sequences hybridize to the RET31 mRNA sequences as well. Therefore, the expression profiling for BMY_HPP5 is also representative of the RET31 expression profile as well.

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TaqMan assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+ RNA. If not the RNA was not used in actual experiments.

Reverse Transcription Reaction and Sequence Detection 100 ng of Dnase-treated total RNA was annealed to 2.5 μM of the respective gene-specific reverse primer in the presence of 5.5 mM Magnesium Chloride by heating the sample to 72° C. for 2 min and then cooling to 55° C. for 30 min. 1.25 U/μl of MuLv reverse transcriptase and 500 μM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 μM forward and reverse primers, 500 μM of each dNTP, buffer and 5 U AmpliTaq Gold™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ mRNA levels were assayed in samples from three individual donors for each tissue for each human phosphatase polypeptide. Values presented represent the average abundance of each human phosphatase polypeptide for each tissue divided by the average abundance of said polypeptide in the tissue with the lowest level of expression. For example, the lowest expression level detected for each polypeptide is as follows: BMY_HPP1=blood mononuclear cells; BMY_HPP2=umbilical cord; BMY_HPP4=blood mononuclear cells; and BMY_HPP5 (RET31)=umbilical cord.

The expanded expression profile of BMY_HPP1, BMY_HPP2, BMY_HPP4, and BMY_HPP5 (RET31), are provided in FIGS. 26, 30, 34, and 35 and are described elsewhere herein.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated nucleic acid molecule comprising a polynucleotide sequence selected from the group consisting of:
   (a) an isolated polynucleotide encoding a polypeptide comprising amino acids 1 to 665 of SEQ ID NO:109; and
   (b) an isolated polynucleotide encoding a polypeptide comprising amino acids 2 to 665 of SEQ ID NO:109.

2. The isolated nucleic acid molecule of claim 1, wherein said polynucleotide is (a).

3. The isolated nucleic acid molecule of claim 2, wherein said polynucleotide comprises nucleotides 538 to 2532 of SEQ ID NO:108.

4. The isolated nucleic acid molecule of claim 1, wherein said polynucleotide is (b).

5. The isolated nucleic acid molecule of claim 4, wherein said polynucleotide comprises nucleotides 541 to 2532 of SEQ ID NO:108.

6. A recombinant vector comprising the isolated nucleic acid molecule of claim 1.

7. A recombinant host cell comprising the vector sequence of claim 6.

8. A method of making an isolated polypeptide comprising:
   (a) culturing the recombinant host cell of claim 7 under conditions such that said polypeptide is expressed; and
   (b) recovering said polypeptide.

9. The isolated polynucleotide of claim 1 wherein said nucleic acid sequence further comprises a heterologous nucleic acid sequence.

10. The isolated polynucleotide of claim 9 wherein said heterologous nucleic acid sequence encodes a heterologous polypeptide.

11. The isolated polynucleotide of claim 10 wherein said heterologous polypeptide is the Fc domain of immunoglobulin.

12. An isolated nucleic acid molecule comprising a polynucleotide selected from the group consisting of:
   (a) a polynucleotide comprising the cDNA clone contained in plasmid RET31 in ATCC Deposit No. PTA-3434; and
   (b) a polynucleotide comprising the cDNA clone contained in plasmid BMY_HPP5 in ATCC Deposit No. PTA-2966.

13. The isolated polynucleotide of claim 12 wherein said nucleic acid sequence further comprises a heterologous nucleic acid sequence.

14. The isolated polynucleotide of claim 13 wherein said heterologous nucleic acid sequence encodes a heterologous polypeptide.

15. The isolated polynucleotide of claim 14 wherein said heterologous polypeptide is the Fc domain of immunoglobulin.

16. An isolated polynucleotide comprising a polynucleotide encoding amino acids 2 to 665 of SEQ ID NO:109 comprising amino acid substitutions at amino acid residue 180; at amino acid residue 193; at amino acid residue 293; and at amino acid residue 315; wherein the substitute amino acid at amino acid residue 180 is methionine; the substitute amino acid at amino acid residue 193 is asparagine; the substitute amino acid at amino acid residue 293 is alanine; and the substitute amino acid at amino acid residue 315 is proline; and wherein said polypeptide has phosphatase activity, or is catalytically inactive yet retains ability to bind to a phosphoprotein substrate.

17. An isolated polynucleotide comprising a polynucleotide encoding amino acids 2 to 665 of SEQ ID NO:109 comprising amino acid substitutions at amino acid residue 5, at amino acid residue 180; at amino acid residue 193, at amino acid residue 284, at amino acid residue 302, at amino acid residue 584, wherein the substitute amino acid at amino acid residue 5 represents an amino acid deletion at this position, the substitute amino acid at amino acid residue 180 is methionine, the substitute amino acid at amino acid residue 193 is asparagine, the substitute amino acid at amino acid residue 284 is serine, the substitute amino acid at amino acid residue 302, and the substitute amino acid at amino acid residue 584 is arginine; and wherein said polypeptide has phosphatase activity.

18. An isolated polynucleotide comprising a polynucleotide encoding amino acids 2 to 665 of SEQ ID NO:109 comprising amino acid substitutions at amino acid residue 5, at amino acid residue 6, at amino acid residue 180; at amino acid residue 193, and at amino acid residue 284, wherein the substitute amino acid at amino acid residue 5 is isoleucine, the substitute amino acid at amino acid residue 6 is valine, the substitute amino acid at amino acid residue 180 is methionine, the substitute amino acid at amino acid residue 193 is asparagine, and the substitute amino acid at amino residue 284 is serine; and wherein said polypeptide has phosphatase activity.

19. An isolated polynucleotide encoding a polypeptide comprising amino acids 1 to 302 of SEQ ID NO:109.

20. The isolated nucleic acid molecule of claim 19, wherein said polynucleotide comprises nucleotides 538 to 1443 of SEQ ID NO:108.

21. An isolated polynucleotide encoding a polypeptide comprising amino acids 2 to 302 of SEQ ID NO:109.

22. The isolated nucleic acid molecule of claim 21, wherein said polynucleotide comprises nucleotides 541 to 1443 of SEQ ID NO:108.

23. An isolated polynucleotide encoding a polypeptide comprising at least 473 contiguous amino acids of SEQ ID NO:109, wherein said at least 473 contiguous amino acids of SEQ ID NO:109 has phosphatase activity.

24. The isolated nucleic acid molecule of claim 23, wherein said polynucleotide comprises at least 1419 contiguous nucleotides of SEQ ID NO:108.

25. An isolated polynucleotide which represents the complementary sequence:
 (a) the isolated polynucleotide (a) of claim 1;
 (b) the isolated polynucleotide (b) of claim 1;
 (c) the isolated polynucleotide of claim 19;
 (d) the isolated polynucleotide of claim 21; and
 (e) the isolated polynucleotide of claim 23.

26. The isolated polynucleotide encoding a polypeptide comprising amino acids 1 to 302 of SEQ ID NO:109, wherein said encoded polypeptide comprises amino acid substitutions at amino acid residue 5, at amino acid residue 6, at amino acid residue 180; at amino acid residue 193, and at amino acid residue 284, wherein the substitute amino acid at amino acid residue 5 is isoleucine, the substitute amino acid at amino acid residue 6 is valine, the substitute amino acid at amino acid residue 180 is methionine, the substitute amino acid at amino acid residue 193 is asparagine, and the substitute amino acid at amino residue 284 is serine, wherein said polypeptide has phosphatase activity.

27. The isolated polynucleotide encoding a polypeptide comprising amino acids 2 to 302 of SEQ ID NO:109, wherein said encoded polypeptide comprises amino acid substitutions at amino acid residue 5, at amino acid residue 6, at amino acid residue 180, at amino acid residue 193, and at amino acid residue 284, wherein the substitute amino acid at amino acid residue 5 is isoleucine, the substitue amino acid at amino acid residue 6 is valine, the substitue amino acid at amino acid residue 180 is methionine, the substitute amino acid at amino acid residue 193 is asparagine, and the substitue amino acid at amino residue 284 is serine, wherein said polypeptide has phosphatase activity.

28. The isolated polynucleotide encoding a polypeptide comprising amino acids 2 to 302 of SEQ ID NO:109, wherin said encoded polypeptide comprises amino acid substitutions at amino acid residue 180, at amino acid residue 193, and at amino acid residue 293, wherein the substitue amino acid at amino acid residue 180 is methionine, the substitue amino acid at amino acid residue 193 is asparagine, and the substitute amino acid at amino residue 293 is alanine, wherein said polypeptide has phosphatase activity.

* * * * *

UNITED STATES PATENT AND TRADEMARK OFFICE
CERTIFICATE OF CORRECTION

PATENT NO. : 7,153,678 B2 Page 1 of 1
APPLICATION NO. : 10/029345
DATED : December 26, 2006
INVENTOR(S) : Donald G. Jackson et al.

It is certified that error appears in the above-identified patent and that said Letters Patent is hereby corrected as shown below:

On Title Page
Item (75) Inventors: Remove "John N. Feder" and "Thomas C. Nelson"

Column 530
    Claim 17, line 49 - add --and-- immediately prior to "at amino acid residue 584"
        line 56 - add --is alanine-- after "acid residue 302"

Column 531
    Claim 25, line 22 - add --of a member of the group consisting of-- after "complementary sequence"

Column 532
    Claim 27, line 15 - substitute "substitue" with --substitute--
        line 16 - substitute "substitue" with --substitute--
        line 19 - substitute "substitue" with --substitute--

Claim 28, line 22, substitute "wherin" with --wherein--
        line 25, substitute "substitue" with --substitute--
        line 26, substitute "substitue" with --substitute--

Signed and Sealed this

Twenty-fourth Day of July, 2007

JON W. DUDAS
*Director of the United States Patent and Trademark Office*

SEQUENCE LISTING

```
<160> NUMBER OF SEQ ID NOS: 208

<210> SEQ ID NO 1
<211> LENGTH: 144
<212> TYPE: DNA
<213> ORGANISM: HOMO SAPIENS

<400> SEQUENCE: 1
ctagtttact tctacaattt cggatggaag gattatggtg tagcgtctct tactactatc      60
ctagatatgg tgaaggtgat gacatttgcc ttacaggaag gaaaagtagc tatccattgt     120
catgcagggc ttggtcgaac aggt                                            144

<210> SEQ ID NO 2
<211> LENGTH: 48
<212> TYPE: PRT
<213> ORGANISM: HOMO SAPIENS

<400> SEQUENCE: 2

Leu Val Tyr Phe Tyr Asn Phe Gly Trp Lys Asp Tyr Gly Val Ala Ser
1               5                   10                  15

Leu Thr Thr Ile Leu Asp Met Val Lys Val Met Thr Phe Ala Leu Gln
            20                  25                  30

Glu Gly Lys Val Ala Ile His Cys His Ala Gly Leu Gly Arg Thr Gly
        35                  40                  45

<210> SEQ ID NO 3
<211> LENGTH: 33
<212> TYPE: DNA
<213> ORGANISM: HOMO SAPIENS

<400> SEQUENCE: 3
gatgtcttct gggccctcct gtggaacaca gtt                                   33

<210> SEQ ID NO 4
<211> LENGTH: 11
<212> TYPE: PRT
<213> ORGANISM: HOMO SAPIENS

<400> SEQUENCE: 4

Asp Val Phe Trp Ala Leu Leu Trp Asn Thr Val
1               5                   10

<210> SEQ ID NO 5
<211> LENGTH: 746
<212> TYPE: DNA
```

-continued

<213> ORGANISM: HOMO SAPIENS

<400> SEQUENCE: 5

```
gtggcccggg aggcgccgag gccaggtagg tgcgatgggc gtgcagcccc ccaacttctc      60
ctgggtgctt ccggccggc tggcgggact ggcgctgccg cggctcccg cccactacca      120
gttcctgttg gacctgggcg tgcggcacct ggtgtccctg acggagcgcg ggccccctca     180
cagcgacagc tgccccggcc tcaccctgca ccgcctgcga atcccgact tctgcccgcc     240
ggccccgac cagatcgacc gcttcgtgca gatcgtggac gaggccaacg cacggggaga     300
ggctgtggga gtgcactgtg ctctgggctt tggccgcact ggcaccatgc tggcctgtta     360
cctggtgaag gagcggggct tggctgcagg agatgccatt gctgaaatcc gacgactacg     420
acccggcccc atcgagacct atgagcagga gaaagcagtc ttccagttct accagcgaac     480
gaaataaggg gccttagtac ccttctacca ggccctcact ccccttcccc atgttgtcga     540
tggggccaga gatgaaggga agtggactaa agtattaaac cctctagctc ccattggctg     600
aagacactga agtagcccac ccctgcaggc aggtcctgat tgaaggggag cttgtactg      660
ctttgttgaa taaatgagtt ttacgaacca gggaaaaaaa aaaaaaaaaa aaagaaaaaa     720
aaaaaaaaaa aaaaaaaaaa aaagaa                                          746
```

<210> SEQ ID NO 6
<211> LENGTH: 248
<212> TYPE: PRT
<213> ORGANISM: HOMO SAPIENS
<220> FEATURE:
<221> NAME/KEY: VARIANT
<222> LOCATION: (162)..(162)
<223> OTHER INFORMATION: wherein 'Xaa' is any amino acid.
<220> FEATURE:
<221> NAME/KEY: VARIANT
<222> LOCATION: (200)..(200)
<223> OTHER INFORMATION: wherein 'Xaa' is any amino acid.
<220> FEATURE:
<221> NAME/KEY: VARIANT
<222> LOCATION: (203)..(203)
<223> OTHER INFORMATION: wherein 'Xaa' is any amino acid.
<220> FEATURE:
<221> NAME/KEY: VARIANT
<222> LOCATION: (214)..(214)
<223> OTHER INFORMATION: wherein 'Xaa' is any amino acid.
<220> FEATURE:
<221> NAME/KEY: VARIANT
<222> LOCATION: (224)..(224)
<223> OTHER INFORMATION: wherein 'Xaa' is any amino acid.

<400> SEQUENCE: 6

```
Trp Pro Gly Arg Arg Gly Gln Val Gly Ala Met Gly Val Gln Pro
1               5                   10                  15

Pro Asn Phe Ser Trp Val Leu Pro Gly Arg Leu Ala Gly Leu Ala Leu
                20                  25                  30

Pro Arg Leu Pro Ala His Tyr Gln Phe Leu Leu Asp Leu Gly Val Arg
            35                  40                  45

His Leu Val Ser Leu Thr Glu Arg Gly Pro Pro His Ser Asp Ser Cys
        50                  55                  60

Pro Gly Leu Thr Leu His Arg Leu Arg Ile Pro Asp Phe Cys Pro Pro
65                  70                  75                  80

Ala Pro Asp Gln Ile Asp Arg Phe Val Gln Ile Val Asp Glu Ala Asn
                85                  90                  95

Ala Arg Gly Glu Ala Val Gly Val His Cys Ala Leu Gly Phe Gly Arg
            100                 105                 110
```

-continued

```
Thr Gly Thr Met Leu Ala Cys Tyr Leu Val Lys Glu Arg Gly Leu Ala
        115                 120                 125
Ala Gly Asp Ala Ile Ala Glu Ile Arg Arg Leu Arg Pro Gly Pro Ile
    130                 135                 140
Glu Thr Tyr Glu Gln Glu Lys Ala Val Phe Gln Phe Tyr Gln Arg Thr
145                 150                 155                 160
Lys Xaa Gly Ala Leu Val Pro Phe Tyr Gln Ala Leu Thr Pro Leu Pro
                165                 170                 175
His Val Val Asp Gly Ala Arg Asp Glu Gly Lys Trp Thr Lys Val Leu
            180                 185                 190
Asn Pro Leu Ala Pro Ile Gly Xaa Arg His Xaa Ser Ser Pro Pro Leu
        195                 200                 205
Gln Ala Gly Pro Asp Xaa Arg Gly Gly Leu Tyr Cys Phe Val Glu Xaa
    210                 215                 220
Met Ser Phe Thr Asn Gln Gly Lys Lys Lys Lys Lys Arg Lys Lys
225                 230                 235                 240
Lys Lys Lys Lys Lys Lys Lys Arg
                245
```

<210> SEQ ID NO 7
<211> LENGTH: 511
<212> TYPE: DNA
<213> ORGANISM: HOMO SAPIENS

<400> SEQUENCE: 7

```
atggctagaa tgaacctccc tgcttctgtg gacattgcat acaaaaatgt gagatttctt      60
attacacaca acccaaccaa tacctacttt aatagattct tacaggaact taagcaggat     120
ggagttacca ccatagtaag agtatgaaaa gcaacttaca acattgctct tttagagaag     180
ggaagcatcc aggttccgga ctggcctttt gatgatggta cagcaccatc cagccagata     240
attgataact ggttaaaaact tatgaaaaat aaatttcatg aagatcctgg ttgttgtatt     300
gcaattcact gtgttgtagg ttttgggtga gctccagttg ctagttgccc tagctttaat     360
tgaaggtgga atgaaatatg aaaatgtagt acagttcatc agataaaagt gacatggaac     420
ttttaacagc aaacaacttt tgtatttgga gaaatattgt cttaaaatat gcttgcacct     480
cagaaatccc agaataaact gtttccttca g                                     511
```

<210> SEQ ID NO 8
<211> LENGTH: 170
<212> TYPE: PRT
<213> ORGANISM: HOMO SAPIENS
<220> FEATURE:
<221> NAME/KEY: Variant
<222> LOCATION: (49)..(49)
<223> OTHER INFORMATION: wherein 'Xaa' is any amino acid.
<220> FEATURE:
<221> NAME/KEY: Variant
<222> LOCATION: (166)..(166)
<223> OTHER INFORMATION: wherein 'Xaa' is any amino acid.
<220> FEATURE:
<221> NAME/KEY: Variant
<222> LOCATION: (142)..(142)
<223> OTHER INFORMATION: wherein 'Xaa' is any amino acid.
<220> FEATURE:
<221> NAME/KEY: Variant
<222> LOCATION: (110)..(110)
<223> OTHER INFORMATION: wherein 'Xaa' is any amino acid.
<220> FEATURE:
<221> NAME/KEY: Variant
<222> LOCATION: (121)..(121)
<223> OTHER INFORMATION: wherein 'Xaa' is any amino acid.
<220> FEATURE:

```
<221> NAME/KEY: Variant
<222> LOCATION: (127)..(127)
<223> OTHER INFORMATION: wherein 'Xaa' is any amino acid.
<220> FEATURE:
<221> NAME/KEY: Variant
<222> LOCATION: (155)..(155)
<223> OTHER INFORMATION: wherein 'Xaa' is any amino acid.

<400> SEQUENCE: 8
```

Met Ala Arg Met Asn Leu Pro Ala Ser Val Asp Ile Ala Tyr Lys Asn
1               5                   10                  15

Val Arg Phe Leu Ile Thr His Asn Pro Thr Asn Thr Tyr Phe Asn Arg
            20                  25                  30

Phe Leu Gln Glu Leu Lys Gln Asp Gly Val Thr Thr Ile Val Arg Val
        35                  40                  45

Xaa Lys Ala Thr Tyr Asn Ile Ala Leu Leu Glu Lys Gly Ser Ile Gln
    50                  55                  60

Val Pro Asp Trp Pro Phe Asp Asp Gly Thr Ala Pro Ser Ser Gln Ile
65              70                  75                  80

Ile Asp Asn Trp Leu Lys Leu Met Lys Asn Lys Phe His Glu Asp Pro
                85                  90                  95

Gly Cys Cys Ile Ala Ile His Cys Val Val Gly Phe Gly Xaa Ala Pro
            100                 105                 110

Val Ala Ser Cys Pro Ser Phe Asn Xaa Arg Trp Asn Glu Ile Xaa Lys
        115                 120                 125

Cys Ser Thr Val His Gln Ile Lys Val Thr Trp Asn Phe Xaa Gln Gln
    130                 135                 140

Thr Thr Phe Val Phe Gly Glu Ile Leu Ser Xaa Asn Met Leu Ala Pro
145                 150                 155                 160

Gln Lys Ser Gln Lys Xaa Leu Phe Pro Ser
                165                 170

```
<210> SEQ ID NO 9
<211> LENGTH: 1710
<212> TYPE: DNA
<213> ORGANISM: HOMO SAPIENS

<400> SEQUENCE: 9
ctcaggcaga actatgaggc caagagtgct catgcgcacc aggctttctt tttgaaattc     60
gaggagctga aggaggtgag caaggagcag cccagactgg aggctgagta ccctgccaac    120
accaccaaga actgttaacc acatgtgcta ccctatgacc actccagggt caggctgacc    180
cagctggagg gagagcctca ttctgactac atcaatgcca acttggtccc aggctacacc    240
cgcccacagg agttcattgc ctctcagggg cctctcaaga aaacactgga gaacttctgg    300
cggctggtgc gggagcagca ggtccgcatc atcatcatgc cgaccatcag catggagaac    360
gggagggtgc tgtgtgagca ttactggctg accgactcta ccccggacac ccatggtcac    420
atcaccatcc acctcctagc tgaggagcct gaggatgagt ggaccaagcg ggaattccag    480
ctgcagcacg ttgtccagca acatcaacgg agggtggagc aactgcagtt caccaccctga   540 tccgaccaca gcatccttga ggctcccagc tccctgctcg cctttatgga gctggtacag    600
tagcaggcaa gggccaccca gggcgtggga cccatcctgg tgcactgcag gggctgtccc    660
tgcggtgtgg gcatgggccg acaggcacc ttcgtggccc tgtcgaggct gctgcagcag    720
ctggaggagg agcagatggt agacgtgttc catgctgtgt atgcactccg gatgcaccag    780
cccctcatga tccagaccct gagccagtac gtcttcctgc acagctgcct actgaacaag    840
```

```
attctggaag dacccttcaa catctctgag tcttggccca tctctgtgac ggacctcccg      900
caggcgtgtg ccaagagggc agccagtgcc aatgctggct tcttgaagga gtacgaggcc      960
atcaaggacg aggctggctt ttccgcaccc ccgcctggct atgagcagga cagccccgtc     1020
tcctatgacc gttctcaggg gcagtttttct ccggtggagg agagcccccc tgacgacatg     1080
cctctctgga agccaatgat ctgtgctctg caggtgggc cctctggccg tgatcatacg     1140
gtgctgactg gccccgcagg gccaaaggag ctctgggagc tggtgtggca gcacagggct     1200
catgtgcttg tctctctttg cccacccaat gtcatggaga aggaattctg ccaacggag     1260 atgcagcccg tagtcacaga catggtgacg gtgcactggg tggctgagag cagcacagca     1320
ggctggttct gtaccctcct cagggtcaca catggggaga gcaggaagga aagggaggtg     1380
cagagactgc aatttccata cctggagcct gggcatgagc tgcccgccac caccctgctg     1440
cccttcctgg ctgctgtggg ccagtgctgc tctcggggca acaacaagaa gccgggcaca     1500
ctgctcagcc actccaacaa gggtgcaacc cagctgggca ccttcctggc catggagcag     1560
ctgctgcagc aggcagggtc tgagtgcacc gtggatatct ttaacgtggc cctgcagcag     1620
tctcaggcct gtggccttat gaccccaaca ctgaagcagt atgtctacct ctacaactgt     1680
ctgaacagcg cgctggcaga cgggctgccc                                      1710
```

<210> SEQ ID NO 10
<211> LENGTH: 570
<212> TYPE: PRT
<213> ORGANISM: HOMO SAPIENS
<220> FEATURE:
<221> NAME/KEY: Variant
<222> LOCATION: (46)..(46)
<223> OTHER INFORMATION: wherein 'Xaa' is any amino acid.
<220> FEATURE:
<221> NAME/KEY: Variant
<222> LOCATION: (180)..(180)
<223> OTHER INFORMATION: wherein 'Xaa' is any amino acid.
<220> FEATURE:
<221> NAME/KEY: Variant
<222> LOCATION: (201)..(201)
<223> OTHER INFORMATION: wherein 'Xaa' is any amino acid.

<400> SEQUENCE: 10

```
Leu Arg Gln Asn Tyr Glu Ala Lys Ser Ala His Ala His Gln Ala Phe
1               5                   10                  15

Phe Leu Lys Phe Glu Glu Leu Lys Glu Val Ser Lys Glu Gln Pro Arg
            20                  25                  30

Leu Glu Ala Glu Tyr Pro Ala Asn Thr Thr Lys Asn Cys Xaa Pro His
        35                  40                  45

Val Leu Pro Tyr Asp His Ser Arg Val Arg Leu Thr Gln Leu Glu Gly
    50                  55                  60

Glu Pro His Ser Asp Tyr Ile Asn Ala Asn Leu Val Pro Gly Tyr Thr
65                  70                  75                  80

Arg Pro Gln Glu Phe Ile Ala Ser Gln Gly Pro Leu Lys Lys Thr Leu
                85                  90                  95

Glu Asn Phe Trp Arg Leu Val Arg Glu Gln Gln Val Arg Ile Ile Ile
            100                 105                 110

Met Pro Thr Ile Ser Met Glu Asn Gly Arg Val Leu Cys Glu His Tyr
        115                 120                 125

Trp Leu Thr Asp Ser Thr Pro Asp Thr His Gly His Ile Thr Ile His
    130                 135                 140

Leu Leu Ala Glu Glu Pro Glu Asp Glu Trp Thr Lys Arg Glu Phe Gln
145                 150                 155                 160
```

```
Leu Gln His Val Val Gln Gln His Gln Arg Arg Val Glu Gln Leu Gln
            165                 170                 175
Phe Thr Thr Xaa Ser Asp His Ser Ile Leu Glu Ala Pro Ser Ser Leu
            180                 185                 190
Leu Ala Phe Met Glu Leu Val Gln Xaa Gln Ala Arg Ala Thr Gln Gly
            195                 200                 205
Val Gly Pro Ile Leu Val His Cys Arg Gly Cys Pro Cys Gly Val Gly
            210                 215                 220
Met Gly Arg Thr Gly Thr Phe Val Ala Leu Ser Arg Leu Leu Gln Gln
225                 230                 235                 240
Leu Glu Glu Glu Gln Met Val Asp Val Phe His Ala Val Tyr Ala Leu
                    245                 250                 255
Arg Met His Gln Pro Leu Met Ile Gln Thr Leu Ser Gln Tyr Val Phe
            260                 265                 270
Leu His Ser Cys Leu Leu Asn Lys Ile Leu Glu Gly Pro Phe Asn Ile
            275                 280                 285
Ser Glu Ser Trp Pro Ile Ser Val Thr Asp Leu Pro Gln Ala Cys Ala
            290                 295                 300
Lys Arg Ala Ala Ser Ala Asn Ala Gly Phe Leu Lys Glu Tyr Glu Ala
305                 310                 315                 320
Ile Lys Asp Glu Ala Gly Phe Ser Ala Pro Pro Gly Tyr Glu Gln
            325                 330                 335
Asp Ser Pro Val Ser Tyr Asp Arg Ser Gln Gly Gln Phe Ser Pro Val
            340                 345                 350
Glu Glu Ser Pro Pro Asp Asp Met Pro Leu Trp Lys Pro Met Ile Cys
            355                 360                 365
Ala Leu Gln Gly Gly Pro Ser Gly Arg Asp His Thr Val Leu Thr Gly
            370                 375                 380
Pro Ala Gly Pro Lys Glu Leu Trp Glu Leu Val Trp Gln His Arg Ala
385                 390                 395                 400
His Val Leu Val Ser Leu Cys Pro Pro Asn Val Met Glu Lys Glu Phe
                    405                 410                 415
Trp Pro Thr Glu Met Gln Pro Val Val Thr Asp Met Val Thr Val His
            420                 425                 430
Trp Val Ala Glu Ser Ser Thr Ala Gly Trp Phe Cys Thr Leu Leu Arg
            435                 440                 445
Val Thr His Gly Glu Ser Arg Lys Glu Arg Glu Val Gln Arg Leu Gln
            450                 455                 460
Phe Pro Tyr Leu Glu Pro Gly His Glu Leu Pro Ala Thr Thr Leu Leu
465                 470                 475                 480
Pro Phe Leu Ala Ala Val Gly Gln Cys Cys Ser Arg Gly Asn Asn Lys
                    485                 490                 495
Lys Pro Gly Thr Leu Leu Ser His Ser Asn Lys Gly Ala Thr Gln Leu
            500                 505                 510
Gly Thr Phe Leu Ala Met Glu Gln Leu Leu Gln Gln Ala Gly Ser Glu
            515                 520                 525
Cys Thr Val Asp Ile Phe Asn Val Ala Leu Gln Gln Ser Gln Ala Cys
            530                 535                 540
Gly Leu Met Thr Pro Thr Leu Lys Gln Tyr Val Tyr Leu Tyr Asn Cys
545                 550                 555                 560
Leu Asn Ser Ala Leu Ala Asp Gly Leu Pro
            565                 570
```

```
<210> SEQ ID NO 11
<211> LENGTH: 63
<212> TYPE: DNA
<213> ORGANISM: HOMO SAPIENS

<400> SEQUENCE: 11
ctcaggcaga actatgaggc caagagtgct catgcgcacc aggctttctt tttgaaattc     60
gag                                                                  63

<210> SEQ ID NO 12
<211> LENGTH: 91
<212> TYPE: DNA
<213> ORGANISM: HOMO SAPIENS

<400> SEQUENCE: 12
gagctgaagg aggtgagcaa ggagcagccc agactggagg ctgagtaccc tgccaacacc     60
accaagaact gttaaccaca tgtgctaccc t                                   91

<210> SEQ ID NO 13
<211> LENGTH: 77
<212> TYPE: DNA
<213> ORGANISM: HOMO SAPIENS

<400> SEQUENCE: 13
atgaccactc cagggtcagg ctgacccagc tggagggaga gcctcattct gactacatca     60
atgccaactt ggtccca                                                   77

<210> SEQ ID NO 14
<211> LENGTH: 135
<212> TYPE: DNA
<213> ORGANISM: HOMO SAPIENS

<400> SEQUENCE: 14
ggctacaccc gcccacagga gttcattgcc tctcagggc ctctcaagaa aacactggag     60
aacttctggc ggctggtgcg ggagcagcag gtccgcatca tcatcatgcc gaccatcagc    120
atggagaacg ggagg                                                    135

<210> SEQ ID NO 15
<211> LENGTH: 123
<212> TYPE: DNA
<213> ORGANISM: HOMO SAPIENS

<400> SEQUENCE: 15
gtgctgtgtg agcattactg gctgaccgac tctaccccgg acacccatgg tcacatcacc     60
atccacctcc tagctgagga gcctgaggat gagtggacca gcgggaatt ccagctgcag    120 cac                                                                 123

<210> SEQ ID NO 16
<211> LENGTH: 161
<212> TYPE: DNA
<213> ORGANISM: HOMO SAPIENS

<400> SEQUENCE: 16
gttgtccagc aacatcaacg gagggtggag caactgcagt tcaccacctg atccgaccac     60
agcatccttg aggctcccag ctccctgctc gcctttatgg agctggtaca gtagcaggca    120
agggccaccc agggcgtggg acccatcctg gtgcactgca g                       161
```

<210> SEQ ID NO 17
<211> LENGTH: 151
<212> TYPE: DNA
<213> ORGANISM: HOMO SAPIENS

<400> SEQUENCE: 17
gggctgtccc tgcggtgtgg gcatgggccg gacaggcacc ttcgtggccc tgtcgaggct    60
gctgcagcag ctggaggagg agcagatggt agacgtgttc catgctgtgt atgcactccg   120
gatgcaccag cccctcatga tccagaccct g                                   151

<210> SEQ ID NO 18
<211> LENGTH: 68
<212> TYPE: DNA
<213> ORGANISM: HOMO SAPIENS

<400> SEQUENCE: 18
agccagtacg tcttcctgca cagctgccta ctgaacaaga ttctggaagg acccttcaac    60
atctctga                                                             68

<210> SEQ ID NO 19
<211> LENGTH: 88
<212> TYPE: DNA
<213> ORGANISM: HOMO SAPIENS

<400> SEQUENCE: 19
gtcttggccc atctctgtga cggacctccc gcaggcgtgt gccaagaggg cagccagtgc    60
caatgctggc ttcttgaagg agtacgag                                       88

<210> SEQ ID NO 20
<211> LENGTH: 67
<212> TYPE: DNA
<213> ORGANISM: HOMO SAPIENS

<400> SEQUENCE: 20
gccatcaagg acgaggctgg cttttccgca ccccgcctg gctatgagca ggacagcccc     60
gtctcct                                                              67

<210> SEQ ID NO 21
<211> LENGTH: 58
<212> TYPE: DNA
<213> ORGANISM: HOMO SAPIENS

<400> SEQUENCE: 21
atgaccgttc tcaggggcag ttttctccgg tggaggagag ccccctgac gacatgcc       58

<210> SEQ ID NO 22
<211> LENGTH: 160
<212> TYPE: DNA
<213> ORGANISM: HOMO SAPIENS

<400> SEQUENCE: 22
tctctggaag ccaatgatct gtgctctgca gggtgggccc tctggccgtg atcatacggt    60
gctgactggc cccgcagggc caaggagct ctgggagctg gtgtggcagc acagggctca    120
tgtgcttgtc tctctttgcc cacccaatgt catggagaag                         160

<210> SEQ ID NO 23
<211> LENGTH: 111
<212> TYPE: DNA
<213> ORGANISM: HOMO SAPIENS

<400> SEQUENCE: 23

```
gaattctggc caacggagat gcagcccgta gtcacagaca tggtgacggt gcactgggtg      60
gctgagagca gcacagcagg ctggttctgt accctcctca gggtcacaca t             111
```

<210> SEQ ID NO 24
<211> LENGTH: 164
<212> TYPE: DNA
<213> ORGANISM: HOMO SAPIENS

<400> SEQUENCE: 24

```
ggggagagca ggaaggaaag ggaggtgcag agactgcaat tccatacct ggagcctggg      60
catgagctgc ccgccaccac cctgctgccc ttcctggctg ctgtgggcca gtgctgctct    120
cggggcaaca acaagaagcc gggcacactg ctcagccact ccaa                     164
```

<210> SEQ ID NO 25
<211> LENGTH: 136
<212> TYPE: DNA
<213> ORGANISM: HOMO SAPIENS

<400> SEQUENCE: 25

```
caagggtgca acccagctgg gcaccttcct ggccatggag cagctgctgc agcaggcagg     60
gtctgagtgc accgtggata tctttaacgt ggccctgcag cagtctcagg cctgtggcct   120
tatgacccca acactg                                                    136
```

<210> SEQ ID NO 26
<211> LENGTH: 57
<212> TYPE: DNA
<213> ORGANISM: HOMO SAPIENS

<400> SEQUENCE: 26

```
aagcagtatg tctacctcta caactgtctg aacagcgcgc tggcagacgg gctgccc        57
```

<210> SEQ ID NO 27
<211> LENGTH: 1188
<212> TYPE: PRT
<213> ORGANISM: HOMO SAPIENS

<400> SEQUENCE: 27

```
Met Gly His Leu Pro Thr Gly Ile His Gly Ala Arg Arg Leu Leu Pro
1               5                   10                  15

Leu Leu Trp Leu Phe Val Leu Phe Lys Asn Ala Thr Ala Phe His Val
            20                  25                  30

Thr Val Gln Asp Asp Asn Asn Ile Val Val Ser Leu Glu Ala Ser Asp
        35                  40                  45

Val Ile Ser Pro Ala Ser Val Tyr Val Val Lys Ile Thr Gly Glu Ser
    50                  55                  60

Lys Asn Tyr Phe Phe Glu Phe Glu Glu Phe Asn Ser Thr Leu Pro Pro
65                  70                  75                  80

Pro Val Ile Phe Lys Ala Ser Tyr His Gly Leu Tyr Tyr Ile Ile Thr
                85                  90                  95

Leu Val Val Val Asn Gly Asn Val Thr Lys Pro Ser Arg Ser Ile
            100                 105                 110

Thr Val Leu Thr Lys Pro Leu Pro Val Thr Ser Val Ser Ile Tyr Asp
        115                 120                 125

Tyr Lys Pro Ser Pro Glu Thr Gly Val Leu Phe Glu Ile His Tyr Pro
    130                 135                 140
```

-continued

```
Glu Lys Tyr Asn Val Phe Thr Arg Val Asn Ile Ser Tyr Trp Glu Gly
145                 150                 155                 160

Lys Asp Phe Arg Thr Met Leu Tyr Lys Asp Phe Phe Lys Gly Lys Thr
                165                 170                 175

Val Phe Asn His Trp Leu Pro Gly Met Cys Tyr Ser Asn Ile Thr Phe
            180                 185                 190

Gln Leu Val Ser Glu Ala Thr Phe Asn Lys Ser Thr Leu Val Glu Tyr
        195                 200                 205

Ser Gly Val Ser His Glu Pro Lys Gln His Arg Thr Ala Pro Tyr Pro
    210                 215                 220

Pro Gln Asn Ile Ser Val Arg Ile Val Asn Leu Asn Lys Asn Asn Trp
225                 230                 235                 240

Glu Glu Gln Ser Gly Asn Phe Pro Glu Glu Ser Phe Met Arg Ser Gln
                245                 250                 255

Asp Thr Ile Gly Lys Glu Lys Leu Phe His Phe Thr Glu Glu Thr Pro
            260                 265                 270

Glu Ile Pro Ser Gly Asn Ile Ser Ser Gly Trp Pro Asp Phe Asn Ser
        275                 280                 285

Ser Asp Tyr Glu Thr Thr Ser Gln Pro Tyr Trp Trp Asp Ser Ala Ser
    290                 295                 300

Ala Ala Pro Glu Ser Glu Asp Glu Phe Val Ser Val Leu Pro Met Glu
305                 310                 315                 320

Tyr Glu Asn Asn Ser Thr Leu Ser Glu Thr Glu Lys Ser Thr Ser Gly
                325                 330                 335

Ser Phe Ser Phe Phe Pro Val Gln Met Ile Leu Thr Trp Leu Pro Pro
            340                 345                 350

Lys Pro Pro Thr Ala Phe Asp Gly Phe His Ile His Ile Glu Arg Glu
        355                 360                 365

Glu Asn Phe Thr Glu Tyr Leu Met Val Asp Glu Glu Ala His Glu Phe
    370                 375                 380

Val Ala Glu Leu Lys Glu Pro Gly Lys Tyr Lys Leu Ser Val Thr Thr
385                 390                 395                 400

Phe Ser Ser Ser Gly Ser Cys Glu Thr Arg Lys Ser Gln Ser Ala Lys
                405                 410                 415

Ser Leu Ser Phe Tyr Ile Ser Pro Ser Gly Glu Trp Ile Glu Glu Leu
            420                 425                 430

Thr Glu Lys Pro Gln His Val Ser Val His Val Leu Ser Ser Thr Thr
        435                 440                 445

Ala Leu Met Ser Trp Thr Ser Ser Gln Glu Asn Tyr Asn Ser Thr Ile
    450                 455                 460

Val Ser Val Val Ser Leu Thr Cys Gln Lys Gln Lys Glu Ser Gln Arg
465                 470                 475                 480

Leu Glu Lys Gln Tyr Cys Thr Gln Val Asn Ser Ser Lys Pro Ile Ile
                485                 490                 495

Glu Asn Leu Val Pro Gly Ala Gln Tyr Gln Val Ile Tyr Leu Arg
            500                 505                 510

Lys Gly Pro Leu Ile Gly Pro Ser Asp Pro Val Thr Phe Ala Ile
        515                 520                 525

Val Pro Thr Gly Ile Lys Asp Leu Met Leu Tyr Pro Leu Gly Pro Thr
    530                 535                 540

Ala Val Val Leu Ser Trp Thr Arg Pro Tyr Leu Gly Val Phe Arg Lys
545                 550                 555                 560

Tyr Val Val Glu Met Phe Tyr Phe Asn Pro Ala Thr Met Thr Ser Glu
```

-continued

```
                565                 570                 575
Trp Thr Thr Tyr Tyr Glu Ile Ala Ala Thr Val Ser Leu Thr Ala Ser
            580                 585                 590
Val Arg Ile Ala Asn Leu Leu Pro Ala Trp Tyr Tyr Asn Phe Arg Val
            595                 600                 605
Thr Met Val Thr Trp Gly Asp Pro Glu Leu Ser Cys Cys Asp Ser Ser
            610                 615                 620
Thr Ile Ser Phe Ile Thr Ala Pro Val Ala Pro Glu Ile Thr Ser Val
625                 630                 635                 640
Glu Tyr Phe Asn Ser Leu Leu Tyr Ile Ser Trp Thr Tyr Gly Asp Asp
                645                 650                 655
Thr Thr Asp Leu Ser His Ser Arg Met Leu His Trp Met Val Val Ala
                660                 665                 670
Glu Gly Lys Lys Lys Ile Lys Lys Ser Val Thr Arg Asn Val Met Thr
            675                 680                 685
Ala Ile Leu Ser Leu Pro Pro Gly Asp Ile Tyr Asn Leu Ser Val Thr
            690                 695                 700
Ala Cys Thr Glu Arg Gly Ser Asn Thr Ser Met Leu Arg Leu Val Lys
705                 710                 715                 720
Leu Glu Pro Ala Pro Pro Lys Ser Leu Phe Ala Val Asn Lys Thr Gln
                725                 730                 735
Thr Ser Val Thr Leu Leu Trp Val Glu Gly Val Ala Asp Phe Phe
                740                 745                 750
Glu Val Phe Cys Gln Gln Val Gly Ser Ser Gln Lys Thr Lys Leu Gln
            755                 760                 765
Glu Pro Val Ala Val Ser Ser His Val Val Thr Ile Ser Ser Leu Leu
            770                 775                 780
Pro Ala Thr Ala Tyr Asn Cys Ser Val Thr Ser Phe Ser His Asp Ser
785                 790                 795                 800
Pro Ser Val Pro Thr Phe Ile Ala Val Ser Thr Met Val Thr Glu Met
                805                 810                 815
Asn Pro Asn Val Val Val Ile Ser Val Leu Ala Ile Leu Ser Thr Leu
                820                 825                 830
Leu Ile Gly Leu Leu Leu Val Thr Leu Ile Ile Leu Arg Lys Lys His
                835                 840                 845
Leu Gln Met Ala Arg Glu Cys Gly Ala Gly Thr Phe Val Asn Phe Ala
            850                 855                 860
Ser Leu Glu Arg Asp Gly Lys Leu Pro Tyr Asn Trp Ser Lys Asn Gly
865                 870                 875                 880
Leu Lys Lys Arg Lys Leu Thr Asn Pro Val Gln Leu Asp Asp Phe Asp
                885                 890                 895
Ala Tyr Ile Lys Asp Met Ala Lys Asp Ser Asp Tyr Lys Phe Ser Leu
                900                 905                 910
Gln Phe Glu Glu Leu Lys Leu Ile Gly Leu Asp Ile Pro His Phe Ala
            915                 920                 925
Ala Asp Leu Pro Leu Asn Arg Cys Lys Asn Arg Tyr Thr Asn Ile Leu
            930                 935                 940
Pro Tyr Asp Phe Ser Arg Val Arg Leu Val Ser Met Asn Glu Glu Glu
945                 950                 955                 960
Gly Ala Asp Tyr Ile Asn Ala Asn Tyr Ile Pro Gly Tyr Asn Ser Pro
                965                 970                 975
Gln Glu Tyr Ile Ala Thr Gln Gly Pro Leu Pro Glu Thr Arg Asn Asp
            980                 985                 990
```

-continued

```
Phe Trp Lys Met Val Gln Gln  Lys Ser Gln Ile Ile  Val Met Leu
        995               1000              1005

Thr Gln  Cys Asn Glu Lys Arg  Arg Val Lys Cys  Asp His Tyr Trp
    1010              1015              1020

Pro Phe  Thr Glu Glu Pro Ile  Ala Tyr Gly Asp  Ile Thr Val Glu
    1025              1030              1035

Met Ile  Ser Glu Glu Glu Gln  Asp Asp Trp Ala  Cys Arg His Phe
    1040              1045              1050

Arg Ile  Asn Tyr Ala Asp Glu  Met Gln Asp Val  Met His Phe Asn
    1055              1060              1065

Tyr Thr  Ala Trp Pro Asp His  Gly Val Pro Thr  Ala Asn Ala Ala
    1070              1075              1080

Glu Ser  Ile Leu Gln Phe Val  His Met Val Arg  Gln Gln Ala Thr
    1085              1090              1095

Lys Ser  Lys Gly Pro Met Ile  Ile His Cys Ser  Ala Gly Val Gly
    1100              1105              1110

Arg Thr  Gly Thr Phe Ile Ala  Leu Asp Arg Leu  Leu Gln His Ile
    1115              1120              1125

Arg Asp  His Glu Phe Val Asp  Ile Leu Gly Leu  Val Ser Glu Met
    1130              1135              1140

Arg Ser  Tyr Arg Met Ser Met  Val Gln Thr Glu  Gln Tyr Ile
    1145              1150              1155

Phe Ile  His Gln Cys Val Gln  Leu Met Trp Met  Lys Lys Lys Gln
    1160              1165              1170

Gln Phe  Cys Ile Ser Asp Val  Ile Tyr Glu Asn  Val Ser Lys Ser
    1175              1180              1185

<210> SEQ ID NO 28
<211> LENGTH: 405
<212> TYPE: PRT
<213> ORGANISM: Mus musculus

<400> SEQUENCE: 28

Met Val Thr Glu Val Asn Pro Asn Val Val Ile Ser Val Leu Ala
1               5                   10                  15

Ile Leu Ser Thr Leu Leu Ile Gly Leu Leu Val Thr Leu Val Ile
            20                  25                  30

Leu Arg Lys Lys His Leu Gln Met Ala Arg Glu Cys Gly Ala Gly Thr
        35                  40                  45

Phe Val Asn Phe Ala Ser Leu Glu Arg Glu Gly Lys Leu Pro Tyr Ser
    50                  55                  60

Trp Arg Arg Ser Val Phe Ala Leu Leu Thr Leu Leu Pro Ser Cys Leu
65                  70                  75                  80

Trp Thr Asp Tyr Leu Leu Ala Phe Tyr Ile Asn Pro Trp Ser Lys Asn
                85                  90                  95

Gly Leu Lys Lys Arg Lys Leu Thr Asn Pro Val Gln Leu Asp Asp Phe
            100                 105                 110

Asp Ser Tyr Ile Lys Asp Met Ala Lys Asp Ser Asp Tyr Lys Phe Ser
        115                 120                 125

Leu Gln Phe Glu Glu Leu Lys Leu Ile Gly Leu Asp Ile Pro His Phe
    130                 135                 140

Ala Ala Asp Leu Pro Leu Asn Arg Cys Lys Asn Arg Tyr Thr Asn Ile
145                 150                 155                 160

Leu Pro Tyr Asp Phe Ser Arg Val Arg Leu Val Ser Met Asn Glu Glu
```

```
                165                 170                 175
Glu Gly Ala Asp Tyr Ile Asn Ala Asn Tyr Ile Pro Gly Tyr Asn Ser
            180                 185                 190
Pro Gln Glu Tyr Ile Ala Thr Gln Gly Pro Leu Pro Glu Thr Arg Asn
            195                 200                 205
Asp Phe Trp Lys Met Val Leu Gln Gln Lys Ser His Ile Ile Val Met
210                 215                 220
Leu Thr Gln Cys Asn Glu Lys Arg Val Lys Cys Asp His Tyr Trp
225                 230                 235                 240
Pro Phe Thr Glu Pro Ile Ala Tyr Gly Asp Ile Thr Val Glu Met
            245                 250                 255
Val Ser Glu Glu Glu Glu Asp Trp Ala Ser Arg His Phe Arg Ile
            260                 265                 270
Asn Tyr Ala Asp Glu Ala Gln Asp Val Met His Phe Asn Tyr Thr Gly
            275                 280                 285
Trp Pro Asp His Gly Val Pro Pro Ala Asn Ala Ala Glu Ser Ile Leu
            290                 295                 300
Gln Phe Val Phe Thr Val Arg Gln Gln Ala Ala Lys Ser Lys Gly Pro
305                 310                 315                 320
Met Ile Ile His Cys Ser Ala Gly Val Gly Arg Thr Gly Thr Phe Ile
                325                 330                 335
Ala Leu Asp Arg Leu Leu Gln His Ile Arg Asp His Glu Phe Val Asp
            340                 345                 350
Ile Leu Gly Leu Val Ser Glu Met Arg Ser Tyr Arg Met Ser Met Val
            355                 360                 365
Gln Thr Glu Glu Gln Tyr Ile Phe Ile His Gln Cys Val Gln Leu Met
            370                 375                 380
Trp Leu Arg Lys Lys Gln Gln Phe Cys Ile Ser Asp Val Ile Tyr Glu
385                 390                 395                 400
Asn Val Ser Lys Ser
                405

<210> SEQ ID NO 29
<211> LENGTH: 303
<212> TYPE: PRT
<213> ORGANISM: Schizosaccharomyces pombe

<400> SEQUENCE: 29

Met Ser Phe Lys Glu Val Ser Thr Glu Asn Gly Val Leu Thr Pro Leu
1               5                   10                  15
Ile Thr Ile Lys Glu Lys Ala Tyr Met Ile Ile Glu Gly Leu Asn Glu
            20                  25                  30
Glu Glu Ile Glu Leu Leu Asn Thr Arg Leu Pro Lys Leu Ser Lys Lys
        35                  40                  45
Ala Leu Ala Arg Asn Arg Tyr Ser Asn Ile Val Pro Tyr Glu Asn Thr
    50                  55                  60
Arg Val Arg Leu Asp Pro Met Trp Lys Glu Ala Cys Asp Tyr Ile Asn
65                  70                  75                  80
Ala Ser Ile Val Lys Ile Pro Ser Gly Lys Thr Phe Ile Ala Thr Gln
                85                  90                  95
Gly Pro Thr Ser Asn Ser Ile Asp Val Phe Trp Lys Met Val Trp Gln
            100                 105                 110
Ser Val Pro Lys Ser Gly Ile Ile Val Met Leu Thr Lys Leu Arg Glu
            115                 120                 125
```

```
Arg His Arg Leu Lys Cys Asp Ile Tyr Trp Pro Val Glu Leu Phe Glu
    130                 135                 140

Thr Leu Asn Ile Gly Asp Leu Ser Val Ile Leu Val Lys Val Tyr Thr
145                 150                 155                 160

Leu Thr Ser Leu Asn Glu Val Gln Val Arg Glu Phe Glu Leu Asn Lys
                165                 170                 175

Asp Gly Val Lys Lys Ile Leu His Phe Tyr Asn Gly Trp Pro
            180                 185                 190

Asp Phe Gly Ala Pro His Thr Phe Ser Leu Leu Ser Leu Thr Arg Tyr
            195                 200                 205

Ile Lys Ser Leu Ser Tyr Ser Pro Asp Phe Glu Thr Ala Pro Ile Ile
    210                 215                 220

Val His Cys Ser Ala Gly Cys Gly Arg Thr Gly Thr Phe Met Ala Leu
225                 230                 235                 240

Phe Glu Ile Leu Ser Gln Thr Asp Asp Ser Thr Ser Thr Ser Lys Phe
                245                 250                 255

Glu Val Asp Asn Ile Ala Asn Ile Val Ser Ser Leu Arg Ser Gln Arg
            260                 265                 270

Met Gln Ser Val Gln Ser Val Asp Gln Leu Val Phe Leu Tyr Thr Val
                275                 280                 285

Ser Gln Glu Leu Leu Gln Gly Lys Glu Phe Leu Leu Pro Gln Leu
    290                 295                 300

<210> SEQ ID NO 30
<211> LENGTH: 580
<212> TYPE: PRT
<213> ORGANISM: homo sapiens

<400> SEQUENCE: 30

Met Lys Asp Arg Leu Tyr Phe Ala Thr Leu Arg Asn Arg Pro Lys Ser
1               5                   10                  15

Thr Val Asn Thr His Tyr Phe Ser Ile Asp Glu Glu Leu Val Tyr Glu
                20                  25                  30

Asn Phe Tyr Ala Asp Phe Gly Pro Leu Asn Leu Ala Met Val Tyr Arg
            35                  40                  45

Tyr Cys Cys Lys Leu Asn Lys Lys Leu Lys Ser Tyr Ser Leu Ser Arg
    50                  55                  60

Lys Lys Ile Val His Tyr Thr Cys Phe Asp Gln Arg Lys Arg Ala Asn
65                  70                  75                  80

Ala Ala Phe Leu Ile Gly Ala Tyr Ala Val Ile Tyr Leu Lys Lys Thr
                85                  90                  95

Pro Glu Glu Ala Tyr Arg Ala Leu Leu Ser Gly Ser Asn Pro Pro Tyr
            100                 105                 110

Leu Pro Phe Arg Asp Ala Ser Phe Gly Asn Cys Thr Tyr Asn Leu Thr
        115                 120                 125

Ile Leu Asp Cys Leu Gln Gly Ile Arg Lys Gly Leu Gln His Gly Phe
    130                 135                 140

Phe Asp Phe Glu Thr Ile Asp Val Asp Glu Tyr Glu His Tyr Glu Arg
145                 150                 155                 160

Val Glu Asn Gly Asp Phe Asn Cys Ile Val Pro Gly Lys Phe Leu Ala
                165                 170                 175

Phe Ser Gly Pro His Pro Lys Ser Lys Ile Glu Asn Gly Tyr Pro Leu
            180                 185                 190

His Ala Pro Glu Ala Tyr Phe Pro Tyr Phe Lys Lys His Asn Val Thr
        195                 200                 205
```

```
Ala Val Val Arg Leu Asn Lys Lys Ile Tyr Glu Ala Lys Arg Phe Thr
        210                 215                 220

Asp Ala Gly Phe Glu His Tyr Asp Leu Phe Phe Ile Asp Gly Ser Thr
225                 230                 235                 240

Pro Ser Asp Asn Ile Val Arg Arg Phe Leu Asn Ile Cys Glu Asn Thr
                245                 250                 255

Glu Gly Ala Ile Ala Val His Cys Lys Ala Gly Leu Gly Arg Thr Gly
            260                 265                 270

Thr Leu Ile Ala Cys Tyr Val Met Lys His Tyr Arg Phe Thr His Ala
        275                 280                 285

Glu Ile Ile Ala Trp Ile Arg Ile Cys Arg Pro Gly Ser Ile Ile Gly
290                 295                 300

Pro Gln Gln His Phe Leu Glu Glu Lys Gln Ala Ser Leu Trp Val Gln
305                 310                 315                 320

Gly Asp Ile Phe Arg Ser Lys Leu Lys Asn Arg Pro Ser Ser Glu Gly
                325                 330                 335

Ser Ile Asn Lys Ile Leu Ser Gly Leu Asp Asp Met Ser Ile Gly Gly
            340                 345                 350

Asn Leu Ser Lys Thr Gln Asn Met Glu Arg Phe Gly Glu Asp Asn Leu
        355                 360                 365

Glu Asp Asp Val Glu Met Lys Asn Gly Ile Thr Gln Gly Asp Lys
370                 375                 380

Leu Arg Ala Leu Lys Ser Gln Arg Gln Pro Arg Thr Ser Pro Ser Cys
385                 390                 395                 400

Ala Phe Arg Ser Asp Asp Thr Lys Gly His Pro Arg Ala Val Ser Gln
                405                 410                 415

Pro Phe Arg Leu Ser Ser Ser Leu Gln Gly Ser Ala Val Thr Leu Lys
            420                 425                 430

Thr Ser Lys Met Ala Leu Ser Pro Ser Ala Thr Ala Lys Arg Ile Asn
        435                 440                 445

Arg Thr Ser Leu Ser Ser Gly Ala Thr Val Arg Ser Phe Ser Ile Asn
450                 455                 460

Ser Arg Leu Ala Ser Ser Leu Gly Asn Leu Asn Ala Ala Thr Asp Asp
465                 470                 475                 480

Pro Glu Asn Lys Lys Thr Ser Ser Ser Lys Ala Gly Phe Thr Ala
                485                 490                 495

Ser Pro Phe Thr Asn Leu Leu Asn Gly Ser Ser Gln Pro Thr Thr Arg
            500                 505                 510

Asn Tyr Pro Glu Leu Asn Asn Gln Tyr Asn Arg Ser Ser Asn Ser
        515                 520                 525

Asn Gly Gly Asn Leu Asn Ser Pro Pro Gly Pro His Ser Ala Lys Thr
530                 535                 540

Glu Glu His Thr Thr Ile Leu Arg Pro Ser Tyr Thr Gly Leu Ser Ser
545                 550                 555                 560

Ser Ser Ala Arg Phe Leu Ser Arg Ser Ile Pro Ser Leu Gln Ser Glu
                565                 570                 575

Tyr Val His Tyr
            580

<210> SEQ ID NO 31
<211> LENGTH: 459
<212> TYPE: PRT
<213> ORGANISM: homo sapiens
```

```
<400> SEQUENCE: 31

Met Lys Arg Lys Ser Glu Arg Ser Ser Trp Ala Ala Pro Pro
1               5                   10                  15

Cys Ser Arg Arg Cys Ser Ser Thr Ser Pro Gly Val Lys Lys Ile Arg
                20                  25                  30

Ser Ser Thr Gln Gln Asp Pro Arg Arg Asp Pro Gln Asp Asp Val
            35                  40                  45

Tyr Leu Asp Ile Thr Asp Arg Leu Cys Phe Ala Ile Leu Tyr Ser Arg
        50                  55                  60

Pro Lys Ser Ala Ser Asn Val His Tyr Phe Ser Ile Asp Asn Glu Leu
65                  70                  75                  80

Glu Tyr Glu Asn Phe Tyr Ala Asp Phe Gly Pro Leu Asn Leu Ala Met
                85                  90                  95

Val Tyr Arg Tyr Cys Cys Lys Ile Asn Lys Lys Leu Lys Ser Ile Thr
                100                 105                 110

Met Leu Arg Lys Lys Ile Val His Phe Thr Gly Ser Asp Gln Arg Lys
            115                 120                 125

Gln Ala Asn Ala Ala Phe Leu Val Gly Cys Tyr Met Val Ile Tyr Leu
130                 135                 140

Gly Arg Thr Pro Glu Glu Ala Tyr Arg Ile Leu Ile Phe Gly Glu Thr
145                 150                 155                 160

Ser Tyr Ile Pro Phe Arg Asp Ala Ala Tyr Gly Ser Cys Asn Phe Tyr
                165                 170                 175

Ile Thr Leu Leu Asp Cys Phe His Ala Val Lys Ala Met Gln Tyr
            180                 185                 190

Gly Phe Leu Asn Phe Asn Ser Phe Asn Leu Asp Glu Tyr Glu His Tyr
            195                 200                 205

Glu Lys Ala Glu Asn Gly Asp Leu Asn Trp Ile Ile Pro Asp Arg Phe
210                 215                 220

Ile Ala Phe Cys Gly Pro His Ser Arg Ala Arg Leu Glu Ser Gly Tyr
225                 230                 235                 240

His Gln His Ser Pro Glu Thr Tyr Ile Gln Tyr Phe Lys Asn His Asn
                245                 250                 255

Val Thr Thr Ile Ile Arg Leu Asn Lys Arg Met Tyr Asp Ala Lys Arg
                260                 265                 270

Phe Thr Asp Ala Gly Phe Asp His His Asp Leu Phe Phe Ala Asp Gly
            275                 280                 285

Ser Thr Pro Thr Asp Ala Ile Val Lys Glu Phe Leu Asp Ile Cys Glu
            290                 295                 300

Asn Ala Glu Gly Ala Ile Ala Val His Cys Lys Ala Gly Leu Gly Arg
305                 310                 315                 320

Thr Gly Thr Leu Ile Ala Cys Tyr Ile Met Lys His Tyr Arg Met Thr
                325                 330                 335

Ala Ala Glu Thr Ile Ala Trp Val Arg Ile Cys Arg Pro Gly Ser Val
            340                 345                 350

Ile Gly Pro Gln Gln Gln Phe Leu Val Met Lys Gln Thr Asn Leu Trp
            355                 360                 365

Leu Glu Gly Asp Tyr Phe Arg Gln Lys Leu Lys Gly Gln Glu Asn Gly
            370                 375                 380

Gln His Arg Ala Ala Phe Ser Lys Leu Leu Ser Gly Val Asp Asp Ile
385                 390                 395                 400

Ser Ile Asn Gly Val Glu Asn Gln Asp Gln Gln Glu Pro Glu Pro Tyr
                405                 410                 415
```

Ser Asp Asp Asp Glu Ile Asn Gly Val Thr Gln Gly Asp Arg Leu Arg
        420                 425                 430

Ala Leu Lys Ser Arg Arg Gln Ser Lys Thr Asn Ala Ile Pro Leu Thr
        435                 440                 445

Leu Ser Ile Ser Arg Thr Lys Thr Val Leu Arg
        450                 455

<210> SEQ ID NO 32
<211> LENGTH: 551
<212> TYPE: PRT
<213> ORGANISM: Saccharomyces cerevisiae

<400> SEQUENCE: 32

Met Arg Arg Ser Val Tyr Leu Asp Asn Thr Ile Glu Phe Leu Arg Gly
1               5                   10                  15

Arg Val Tyr Leu Gly Ala Tyr Asp Tyr Thr Pro Glu Asp Thr Asp Glu
            20                  25                  30

Leu Val Phe Phe Thr Val Glu Asp Ala Ile Phe Tyr Asn Ser Phe His
        35                  40                  45

Leu Asp Phe Gly Pro Met Asn Ile Gly His Leu Tyr Arg Phe Ala Val
    50                  55                  60

Ile Phe His Glu Ile Leu Asn Asp Pro Glu Asn Ala Asn Lys Ala Val
65                  70                  75                  80

Val Phe Tyr Ser Ser Ala Ser Thr Arg Gln Arg Ala Asn Ala Ala Cys
                85                  90                  95

Met Leu Cys Cys Tyr Met Ile Leu Val Gln Ala Trp Thr Pro His Gln
            100                 105                 110

Val Leu Gln Pro Leu Ala Gln Val Asp Pro Pro Phe Met Pro Phe Arg
        115                 120                 125

Asp Ala Gly Tyr Ser Asn Ala Asp Phe Glu Ile Thr Ile Gln Asp Val
    130                 135                 140

Val Tyr Gly Val Trp Arg Ala Lys Glu Lys Gly Leu Ile Asp Leu His
145                 150                 155                 160

Ser Phe Asn Leu Glu Ser Tyr Glu Lys Tyr Glu His Val Glu Phe Gly
                165                 170                 175

Asp Phe Asn Val Leu Thr Pro Asp Phe Ile Ala Phe Ala Ser Pro Gln
            180                 185                 190

Glu Asp His Pro Lys Gly Tyr Leu Ala Thr Lys Ser Ser His Leu Asn
        195                 200                 205

Gln Pro Phe Lys Ser Val Leu Asn Phe Ala Asn Asn Val Gln
    210                 215                 220

Leu Val Val Arg Leu Asn Ser His Leu Tyr Asn Lys Lys His Phe Glu
225                 230                 235                 240

Asp Ile Gly Ile Gln His Leu Asp Leu Ile Phe Glu Asp Gly Thr Cys
                245                 250                 255

Pro Asp Leu Ser Ile Val Lys Asn Phe Val Gly Ala Ala Glu Thr Ile
            260                 265                 270

Ile Lys Arg Gly Gly Lys Ile Ala Val His Cys Lys Ala Gly Leu Gly
        275                 280                 285

Arg Thr Gly Cys Leu Ile Gly Ala His Leu Ile Tyr Thr Tyr Gly Phe
    290                 295                 300

Thr Ala Asn Glu Cys Ile Gly Phe Leu Arg Phe Ile Arg Pro Gly Met
305                 310                 315                 320

Val Val Gly Pro Gln Gln His Trp Leu Tyr Leu His Gln Asn Asp Phe

```
                    325                 330                 335
Arg Glu Trp Lys Tyr Thr Thr Arg Ile Ser Leu Lys Pro Ser Glu Ala
                340                 345                 350
Ile Gly Gly Leu Tyr Pro Leu Ile Ser Leu Glu Glu Tyr Arg Leu Gln
            355                 360                 365
Lys Lys Lys Leu Lys Asp Asp Lys Arg Val Ala Gln Asn Asn Ile Glu
        370                 375                 380
Gly Glu Leu Arg Asp Leu Thr Met Thr Pro Ser Asn Gly His Gly
385                 390                 395                 400
Ala Leu Ser Ala Arg Asn Ser Ser Gln Pro Ser Thr Ala Asn Asn Gly
                405                 410                 415
Ser Asn Ser Phe Lys Ser Ser Ala Val Pro Gln Thr Ser Pro Gly Gln
            420                 425                 430
Pro Arg Lys Gly Gln Asn Gly Ser Asn Thr Ile Glu Asp Ile Asn Asn
        435                 440                 445
Asn Arg Asn Pro Thr Ser His Ala Asn Arg Lys Val Val Ile Glu Ser
    450                 455                 460
Asn Asn Ser Asp Asp Glu Ser Met Gln Asp Thr Asn Gly Thr Ser Asn
465                 470                 475                 480
His Tyr Pro Lys Val Ser Arg Lys Lys Asn Asp Ile Ser Ser Ala Ser
                485                 490                 495
Ser Ser Arg Met Glu Asp Asn Glu Pro Ser Ala Thr Asn Ile Asn Asn
            500                 505                 510
Ala Ala Asp Asp Thr Ile Leu Arg Gln Leu Leu Pro Lys Asn Arg Arg
        515                 520                 525
Val Thr Ser Gly Arg Arg Thr Thr Ser Ala Ala Gly Gly Ile Arg Lys
    530                 535                 540
Ile Ser Gly Ser Ile Lys Lys
545                 550

<210> SEQ ID NO 33
<211> LENGTH: 173
<212> TYPE: PRT
<213> ORGANISM: homo sapiens

<400> SEQUENCE: 33

Met Ala Arg Met Asn Arg Pro Ala Pro Val Glu Val Thr Tyr Lys Asn
1               5                   10                  15
Met Arg Phe Leu Ile Thr His Asn Pro Thr Asn Ala Thr Leu Asn Lys
            20                  25                  30
Phe Ile Glu Glu Leu Lys Lys Tyr Gly Val Thr Thr Ile Val Arg Val
        35                  40                  45
Cys Glu Ala Thr Tyr Asp Thr Thr Leu Val Glu Lys Glu Gly Ile His
    50                  55                  60
Val Leu Asp Trp Pro Phe Asp Asp Gly Ala Pro Pro Ser Asn Gln Ile
65                  70                  75                  80
Val Asp Asp Trp Leu Ser Leu Val Lys Ile Lys Phe Arg Glu Glu Pro
                85                  90                  95
Gly Cys Cys Ile Ala Val His Cys Val Ala Gly Leu Gly Arg Ala Pro
            100                 105                 110
Val Leu Val Ala Leu Ala Leu Ile Glu Gly Gly Met Lys Tyr Glu Asp
        115                 120                 125
Ala Val Gln Phe Ile Arg Gln Lys Arg Arg Gly Ala Phe Asn Ser Lys
    130                 135                 140
```

```
Gln Leu Leu Tyr Leu Glu Lys Tyr Arg Pro Lys Met Arg Leu Arg Phe
145                 150                 155                 160

Lys Asp Ser Asn Gly His Arg Asn Asn Cys Cys Ile Gln
                165                 170

<210> SEQ ID NO 34
<211> LENGTH: 167
<212> TYPE: PRT
<213> ORGANISM: homo sapiens

<400> SEQUENCE: 34

Met Asn Arg Pro Ala Pro Val Glu Ile Ser Tyr Glu Asn Met Arg Phe
1               5                   10                  15

Leu Ile Thr His Asn Pro Thr Asn Ala Thr Leu Asn Lys Phe Thr Glu
            20                  25                  30

Glu Leu Lys Lys Tyr Gly Val Thr Thr Leu Val Arg Val Cys Asp Ala
        35                  40                  45

Thr Tyr Asp Lys Ala Pro Val Glu Lys Glu Gly Ile His Val Leu Asp
    50                  55                  60

Trp Pro Phe Asp Asp Gly Ala Pro Pro Asn Gln Ile Val Asp Asp
65                  70                  75                  80

Trp Leu Asn Leu Leu Lys Thr Lys Phe Arg Glu Glu Pro Gly Cys Cys
                85                  90                  95

Val Ala Val His Cys Val Ala Gly Leu Gly Arg Ala Pro Val Leu Val
            100                 105                 110

Ala Leu Ala Leu Ile Glu Cys Gly Met Lys Tyr Glu Asp Ala Val Gln
        115                 120                 125

Phe Ile Arg Gln Lys Arg Arg Gly Ala Phe Asn Ser Lys Gln Leu Leu
    130                 135                 140

Tyr Leu Glu Lys Tyr Arg Pro Lys Met Arg Leu Arg Phe Arg Asp Thr
145                 150                 155                 160

Asn Gly His Cys Cys Val Gln
                165

<210> SEQ ID NO 35
<211> LENGTH: 167
<212> TYPE: PRT
<213> ORGANISM: Mus musculus

<400> SEQUENCE: 35

Met Asn Arg Pro Ala Pro Val Glu Ile Ser Tyr Glu Asn Met Arg Phe
1               5                   10                  15

Leu Ile Thr His Asn Pro Thr Asn Ala Thr Leu Asn Lys Phe Thr Glu
            20                  25                  30

Glu Leu Lys Lys Tyr Gly Val Thr Thr Leu Val Arg Val Cys Asp Ala
        35                  40                  45

Thr Tyr Asp Lys Ala Pro Val Glu Lys Glu Gly Ile His Val Leu Asp
    50                  55                  60

Trp Pro Phe Asp Asp Gly Ala Pro Pro Asn Gln Ile Val Asp Asp
65                  70                  75                  80

Trp Leu Asn Leu Leu Lys Thr Leu Phe Arg Glu Glu Pro Gly Cys Cys
                85                  90                  95

Val Ala Val His Cys Val Ala Gly Ile Gly Arg Ala Pro Val Leu Val
            100                 105                 110

Ala Leu Ala Leu Ile Glu Cys Gly Met Lys Tyr Glu Asp Ala Val Gln
        115                 120                 125
```

```
Phe Ile Arg Gln Lys Arg Gly Ala Phe Asn Ser Lys Gln Leu Leu
    130                 135                 140
Tyr Leu Glu Lys Tyr Arg Pro Lys Met Arg Leu Arg Phe Arg Asp Thr
145                 150                 155                 160
Asn Gly His Cys Cys Val Gln
                165

<210> SEQ ID NO 36
<211> LENGTH: 178
<212> TYPE: PRT
<213> ORGANISM: Drosophila melanogaster

<400> SEQUENCE: 36

Met Ser Ile Thr Met Arg Gln Lys Asp Leu Arg Pro Ala Pro Ala Leu
1               5                   10                  15
Ile Glu Tyr Lys Gly Met Lys Phe Leu Ile Thr Asp Arg Pro Ser Asp
                20                  25                  30
Ile Thr Ile Asn His Tyr Ile Met Glu Leu Lys Lys Asn Asn Val Asn
            35                  40                  45
Thr Val Val Arg Val Cys Glu Pro Ser Tyr Asn Thr Asp Glu Leu Glu
    50                  55                  60
Thr Gln Gly Ile Thr Val Lys Asp Leu Ala Phe Glu Asp Gly Thr Phe
65                  70                  75                  80
Pro Pro Gln Gln Val Val Asp Glu Trp Phe Glu Phe Val Val Leu
                85                  90                  95
Tyr Arg Tyr Gln Gln Asn Pro Glu Ala Cys Val Ala Val His Cys Val
                100                 105                 110
Ala Gly Leu Gly Arg Ala Pro Val Leu Val Ala Leu Ala Leu Ile Glu
            115                 120                 125
Leu Gly Leu Lys Tyr Glu Ala Ala Val Glu Met Ile Arg Asp Lys Arg
        130                 135                 140
Arg Gly Ala Ile Asn Ala Lys Gln Leu Ser Phe Leu Glu Lys Tyr Lys
145                 150                 155                 160
Pro Lys Ala Arg Leu Lys His Lys Asn Gly His Lys Asn Ser Cys Ser
                165                 170                 175
Val Gln

<210> SEQ ID NO 37
<211> LENGTH: 1705
<212> TYPE: PRT
<213> ORGANISM: Mus musculus

<400> SEQUENCE: 37

Met Arg Pro Leu Ile Leu Leu Ala Ala Leu Leu Trp Leu Gln Asp Ser
1               5                   10                  15
Leu Ala Gln Glu Asp Val Cys Ser Ser Leu Asp Gly Ser Pro Asp Arg
                20                  25                  30
Gln Gly Gly Gly Pro Pro Leu Ser Val Asn Val Ser Ser Arg Gly Lys
            35                  40                  45
Pro Thr Ser Leu Phe Leu Ser Trp Val Ala Ala Glu Pro Gly Gly Phe
    50                  55                  60
Asp Tyr Ala Leu Cys Leu Arg Ala Met Asn Leu Ser Gly Phe Pro Glu
65                  70                  75                  80
Gly Gln Gln Leu Gln Ala His Thr Asn Glu Ser Ser Phe Glu Phe His
                85                  90                  95
Gly Leu Val Pro Gly Ser Arg Tyr Gln Leu Glu Leu Thr Val Leu Arg
```

-continued

```
            100                 105                 110
Pro Cys Trp Gln Asn Val Thr Ile Thr Leu Thr Ala Arg Thr Ala Pro
        115                 120                 125

Thr Val Val Arg Gly Leu Gln Leu His Ser Thr Gly Ser Pro Ala Ser
130                 135                 140

Leu Glu Ala Ser Trp Ser Asp Ala Ser Gly Asp Gln Asp Ser Tyr Gln
145                 150                 155                 160

Leu Leu Leu Tyr His Pro Glu Ser His Thr Leu Ala Cys Asn Val Ser
                165                 170                 175

Val Ser Pro Asp Thr Leu Ser Tyr Asn Phe Gly Asp Leu Leu Pro Gly
            180                 185                 190

Ser Gln Tyr Val Leu Glu Val Ile Thr Trp Ala Gly Ser Leu His Ala
        195                 200                 205

Lys Thr Ser Ile Leu Gln Trp Thr Glu Pro Val Pro Pro Asp His Leu
    210                 215                 220

Thr Leu Arg Ala Leu Gly Thr Ser Ser Leu Gln Ala Phe Trp Asn Ser
225                 230                 235                 240

Ser Glu Gly Ala Thr Trp Phe His Leu Ile Leu Thr Asp Leu Leu Glu
                245                 250                 255

Gly Thr Asn Leu Thr Lys Val Val Arg Gln Gly Ile Ser Thr His Thr
            260                 265                 270

Phe Leu Arg Leu Ser Pro Gly Thr Pro Tyr Gln Leu Lys Ile Cys Ala
        275                 280                 285

Ala Ala Gly Pro His Gln Ile Trp Gly Pro Asn Ala Thr Glu Trp Thr
    290                 295                 300

Tyr Pro Ser Tyr Pro Ser Asp Leu Val Leu Thr Pro Leu Trp Asn Glu
305                 310                 315                 320

Leu Trp Ala Ser Trp Lys Ala Gly Gln Gly Ala Arg Asp Gly Tyr Val
                325                 330                 335

Leu Lys Leu Ser Gly Pro Val Glu Asn Thr Thr Thr Leu Gly Pro Glu
            340                 345                 350

Glu Cys Asn Ala Val Phe Pro Gly Pro Leu Pro Pro Gly His Tyr Thr
        355                 360                 365

Leu Gly Leu Arg Val Leu Ala Gly Pro Tyr Asp Ala Trp Val Glu Gly
    370                 375                 380

Ser Ile Trp Leu Ala Glu Ser Ala Ala Arg Pro Met Glu Val Pro Gly
385                 390                 395                 400

Ala Arg Leu Trp Leu Glu Gly Leu Glu Ala Thr Lys Gln Pro Gly Arg
                405                 410                 415

Arg Ala Leu Leu Tyr Ser Val Asp Ala Pro Gly Leu Leu Gly Asn Ile
            420                 425                 430

Ser Val Ser Ser Gly Ala Thr His Val Thr Phe Cys Gly Leu Val Pro
        435                 440                 445

Gly Ala His Tyr Arg Val Asp Ile Ala Ser Ser Met Gly Asp Ile Thr
    450                 455                 460

Gln Ser Leu Thr Gly Tyr Thr Ser Pro Leu Pro Pro Gln Ser Leu Glu
465                 470                 475                 480

Ile Ile Ser Arg Asn Ser Pro Ser Asp Leu Thr Ile Gly Trp Ala Pro
                485                 490                 495

Ala Pro Gly Gln Met Glu Gly Tyr Lys Val Thr Trp His Gln Asp Gly
            500                 505                 510

Ser Gln Arg Ser Pro Gly Asp Leu Val Asp Leu Gly Pro Asp Ile Ser
        515                 520                 525
```

-continued

```
Ser Leu Thr Leu Lys Ser Leu Val Pro Gly Ser Cys Tyr Thr Val Ser
    530                 535                 540

Ala Trp Ala Trp Ser Gly Asn Leu Ser Ser Asp Ser Gln Lys Ile His
545                 550                 555                 560

Ser Cys Thr Arg Pro Ala Pro Thr Asn Leu Ser Leu Gly Phe Ala
                565                 570                 575

His Gln Pro Ala Thr Leu Arg Ala Ser Trp Cys His Pro Pro Gly Gly
                580                 585                 590

Arg Asp Ala Phe Gln Leu Arg Leu Tyr Arg Leu Arg Pro Leu Thr Leu
                595                 600                 605

Glu Ser Glu Lys Ile Leu Ser Gln Glu Ala Gln Asn Phe Ser Trp Ala
    610                 615                 620

Gln Leu Pro Ala Gly Tyr Glu Phe Gln Val Gln Leu Ser Thr Leu Trp
625                 630                 635                 640

Gly Ser Glu Glu Ser Gly Ser Ala Asn Thr Thr Gly Trp Thr Pro Pro
                645                 650                 655

Ser Ala Pro Thr Leu Val Asn Val Thr Ser Glu Ala Pro Thr Gln Leu
                660                 665                 670

His Val Ser Trp Val His Ala Ala Gly Asp Arg Ser Ser Tyr Gln Val
                675                 680                 685

Thr Leu Tyr Gln Glu Ser Thr Arg Thr Ala Thr Ser Ile Val Gly Pro
    690                 695                 700

Lys Ala Asp Ser Thr Ser Phe Trp Gly Leu Thr Pro Gly Thr Lys Tyr
705                 710                 715                 720

Lys Val Glu Ala Ile Ser Trp Ala Gly Pro Leu Tyr Thr Ala Ala Ala
                725                 730                 735

Asn Val Ser Ala Trp Thr Tyr Pro Leu Thr Pro Asn Glu Leu Leu Ala
                740                 745                 750

Ser Met Gln Ala Gly Ser Ala Val Val Asn Leu Ala Trp Pro Ser Gly
    755                 760                 765

Pro Leu Gly Gln Gly Thr Cys His Ala Gln Leu Ser Asp Ala Gly His
770                 775                 780

Leu Ser Trp Glu Gln Pro Leu Ser Leu Gly Gln Asp Leu Leu Met Leu
785                 790                 795                 800

Arg Asn Leu Ile Pro Gly His Thr Val Ser Leu Ser Val Lys Cys Arg
                805                 810                 815

Ala Gly Pro Leu Gln Ala Ser Thr His Pro Leu Val Leu Ser Val Glu
                820                 825                 830

Pro Gly Pro Val Glu Asp Val Phe Cys Gln Pro Glu Ala Thr Tyr Leu
                835                 840                 845

Ser Leu Asn Trp Thr Met Pro Thr Gly Asp Val Ala Val Cys Leu Val
    850                 855                 860

Glu Val Glu Gln Leu Val Pro Gly Gly Ser Ala His Phe Val Phe Gln
865                 870                 875                 880

Val Asn Thr Ser Glu Asp Ala Leu Leu Leu Pro Asn Leu Thr Pro Thr
                885                 890                 895

Thr Ser Tyr Arg Leu Ser Leu Thr Val Leu Gly Gly Asn Arg Gln Trp
                900                 905                 910

Ser Arg Ala Val Thr Leu Val Cys Thr Thr Ser Ala Glu Val Trp His
                915                 920                 925

Pro Pro Glu Leu Ala Glu Ala Pro Gln Val Glu Leu Gly Thr Gly Met
930                 935                 940
```

-continued

```
Gly Val Thr Val Thr Arg Gly Met Phe Gly Lys Asp Asp Gly Gln Ile
945                 950                 955                 960

Gln Trp Tyr Gly Ile Ile Ala Thr Ile Asn Met Thr Leu Ala Gln Pro
                965                 970                 975

Ser Gln Glu Ala Ile Asn His Thr Trp Tyr Asp His Tyr Tyr Arg Gly
            980                 985                 990

His Asp Ser Tyr Leu Ala Leu Leu Phe Pro Asn Pro Phe Tyr Pro Glu
        995                 1000                1005

Pro Trp Ala Val Pro Arg Ser Trp Thr Val Pro Val Gly Thr Glu
    1010                1015                1020

Asp Cys Asp Asn Thr Gln Glu Ile Cys Asn Gly His Leu Lys Pro
    1025                1030                1035

Gly Phe Gln Tyr Arg Phe Ser Ile Ala Ala Phe Ser Arg Leu Ser
    1040                1045                1050

Ser Pro Glu Thr Ile Leu Ala Phe Ser Ala Phe Ser Glu Pro Gln
    1055                1060                1065

Ala Ser Ile Ser Leu Val Ala Met Pro Leu Thr Val Met Met Gly
    1070                1075                1080

Thr Val Val Gly Cys Ile Ile Ile Val Cys Ala Val Leu Cys Leu
    1085                1090                1095

Leu Cys Arg Arg Arg Leu Lys Gly Pro Arg Ser Glu Lys Asn Gly
    1100                1105                1110

Phe Ser Gln Glu Leu Met Pro Tyr Asn Leu Trp Arg Thr His Arg
    1115                1120                1125

Pro Ile Pro Ser His Ser Phe Arg Gln Ser Tyr Glu Ala Lys Ser
    1130                1135                1140

Ala Arg Ala His Gln Ala Phe Phe Gln Glu Phe Glu Glu Leu Lys
    1145                1150                1155

Glu Val Gly Lys Asp Gln Pro Arg Leu Glu Ala Glu His Pro Ala
    1160                1165                1170

Asn Ile Thr Lys Asn Arg Tyr Pro His Val Leu Pro Tyr Asp His
    1175                1180                1185

Ser Arg Val Arg Leu Thr Gln Leu Ser Gly Glu Pro His Ser Asp
    1190                1195                1200

Tyr Ile Asn Ala Asn Phe Ile Pro Gly Tyr Ser His Pro Gln Glu
    1205                1210                1215

Ile Ile Ala Thr Gln Gly Pro Leu Lys Lys Thr Val Glu Asp Phe
    1220                1225                1230

Trp Arg Leu Val Trp Glu Gln Gln Val His Val Ile Ile Met Leu
    1235                1240                1245

Thr Val Gly Met Glu Asn Gly Arg Val Leu Cys Glu His Tyr Trp
    1250                1255                1260

Pro Val Asn Ser Thr Pro Val Thr His Gly His Ile Thr Thr His
    1265                1270                1275

Leu Leu Ala Glu Glu Ser Glu Asp Glu Trp Thr Arg Arg Glu Phe
    1280                1285                1290

Gln Leu Gln His Gly Ala Glu Gln Lys Gln Arg Arg Val Lys Gln
    1295                1300                1305

Leu Gln Phe Thr Thr Trp Pro Asp His Ser Val Pro Glu Ala Pro
    1310                1315                1320

Ser Ser Leu Leu Ala Phe Val Glu Leu Val Gln Glu Glu Val Lys
    1325                1330                1335

Ala Thr Gln Gly Lys Gly Pro Ile Leu Val His Cys Ser Ala Gly
```

```
                    1340                1345                1350
        Val Gly Arg Thr Gly Thr Phe Val Ala Leu Leu Pro Ala Val Arg
            1355                1360                1365

Gln Leu Glu Glu Glu Gln Val Val Asp Val Phe Asn Thr Val Tyr
            1370                1375                1380

Ile Leu Arg Leu His Arg Pro Leu Met Ile Gln Thr Leu Ser Gln
            1385                1390                1395

Tyr Ile Phe Leu His Ser Cys Leu Leu Asn Lys Ile Leu Glu Gly
            1400                1405                1410

Pro Ser Asp Ala Ser Asp Ser Gly Pro Ile Pro Val Met Asn Phe
            1415                1420                1425

Ala Gln Ala Cys Ala Lys Arg Ala Ala Asn Ala Asn Ala Gly Phe
            1430                1435                1440

Leu Lys Glu Tyr Arg Leu Leu Lys Gln Ala Ile Lys Asp Glu Thr
            1445                1450                1455

Gly Ser Leu Leu Pro Ser Pro Asp Tyr Asn Gln Asn Ser Ile Ala
            1460                1465                1470

Ser Cys His His Ser Gln Glu Gln Leu Ala Leu Val Glu Glu Ser
            1475                1480                1485

Pro Ala Asp Asn Met Leu Ala Ala Ser Leu Phe Pro Gly Gly Pro
            1490                1495                1500

Ser Gly Arg Asp His Val Val Leu Thr Gly Ser Ala Gly Pro Lys
            1505                1510                1515

Glu Leu Trp Glu Met Val Trp Glu His Gly Ala Tyr Val Leu Val
            1520                1525                1530

Ser Leu Gly Leu Pro Asp Thr Lys Glu Lys Pro Gln Asp Ile Trp
            1535                1540                1545

Pro Met Glu Met Gln Pro Ile Val Thr Asp Met Val Thr Val His
            1550                1555                1560

Arg Val Ala Glu Ser Asn Thr Ala Gly Trp Pro Ser Thr Leu Ile
            1565                1570                1575

Arg Val Ile His Gly Asp Ser Gly Thr Glu Arg Gln Val Gln Cys
            1580                1585                1590

Leu Gln Phe Pro His Cys Glu Thr Gly Ser Glu Leu Pro Ala Asn
            1595                1600                1605

Thr Leu Leu Thr Phe Leu Asp Ala Val Gly Gln Cys Cys Ser Arg
            1610                1615                1620

Gly Asn Ser Lys Lys Pro Gly Thr Leu Leu Ser His Ser Ser Lys
            1625                1630                1635

Val Thr Asn Gln Leu Ser Thr Phe Leu Ala Met Glu Gln Leu Leu
            1640                1645                1650

Gln Gln Ala Gly Thr Glu Arg Thr Val Asp Val Phe Ser Val Ala
            1655                1660                1665

Leu Lys Gln Thr Gln Ala Cys Gly Leu Lys Thr Pro Thr Leu Glu
            1670                1675                1680

Gln Tyr Ile Tyr Leu Tyr Asn Cys Leu Asn Ser Ala Leu Arg Asn
            1685                1690                1695

Arg Leu Pro Arg Ala Arg Lys
            1700                1705

<210> SEQ ID NO 38
<211> LENGTH: 1711
<212> TYPE: PRT
<213> ORGANISM: Rattus norvegicus
```

-continued

<400> SEQUENCE: 38

Met Arg Pro Leu Ile Leu Leu Ala Ala Leu Leu Trp Leu Gln Gly Phe
1               5                   10                  15

Leu Ala Glu Asp Asp Ala Cys Ser Ser Leu Gly Gly Ser Pro Asp Arg
            20                  25                  30

Gln Gly Gly Gly Pro Leu Leu Ser Val Asn Val Ser Ser His Gly Lys
        35                  40                  45

Ser Thr Ser Leu Phe Leu Ser Trp Val Ala Ala Glu Leu Gly Gly Phe
    50                  55                  60

Asp Tyr Ala Leu Ser Leu Arg Ser Val Asp Ser Ser Gly Ser Pro Glu
65                  70                  75                  80

Gly Gln Gln Leu Gln Ala His Thr Asn Glu Ser Gly Phe Glu Phe His
                85                  90                  95

Gly Leu Val Pro Gly Ser Arg Tyr Gln Leu Lys Leu Thr Val Leu Arg
            100                 105                 110

Pro Cys Trp Gln Asn Val Thr Ile Thr Leu Thr Ala Arg Thr Ala Pro
        115                 120                 125

Thr Val Val Arg Gly Leu Gln Leu His Ser Ala Gly Ser Pro Ala Arg
    130                 135                 140

Leu Glu Ala Ser Trp Ser Asp Ala Pro Gly Asp Gln Asp Ser Tyr Gln
145                 150                 155                 160

Leu Leu Leu Tyr His Leu Glu Ser Gln Thr Leu Ala Cys Asn Val Ser
                165                 170                 175

Val Ser Pro Asp Thr Leu Ser Tyr Ser Phe Gly Asp Leu Leu Pro Gly
            180                 185                 190

Thr Gln Tyr Val Leu Glu Val Ile Thr Trp Ala Gly Ser Leu His Ala
        195                 200                 205

Lys Thr Ser Ile Leu Gln Trp Thr Glu Pro Val Pro Pro Asp His Leu
    210                 215                 220

Ala Leu Arg Ala Leu Gly Thr Ser Ser Leu Gln Ala Phe Trp Asn Ser
225                 230                 235                 240

Ser Glu Gly Ala Thr Ser Phe His Leu Met Leu Thr Asp Leu Leu Gly
                245                 250                 255

Gly Thr Asn Thr Thr Ala Val Ile Arg Gln Gly Val Ser Thr His Thr
            260                 265                 270

Phe Leu His Leu Ser Pro Gly Thr Pro His Glu Leu Lys Ile Cys Ala
        275                 280                 285

Ser Ala Gly Pro His Gln Ile Trp Gly Pro Ser Ala Thr Glu Trp Thr
    290                 295                 300

Tyr Pro Ser Tyr Pro Ser Asp Leu Val Leu Thr Pro Leu Arg Asn Glu
305                 310                 315                 320

Leu Trp Ala Ser Trp Lys Ala Gly Leu Gly Ala Arg Asp Gly Tyr Val
                325                 330                 335

Leu Lys Leu Ser Gly Pro Met Glu Ser Thr Ser Thr Leu Gly Pro Glu
            340                 345                 350

Glu Cys Asn Ala Val Phe Pro Gly Pro Leu Pro Pro Gly His Tyr Thr
        355                 360                 365

Leu Gln Leu Lys Val Leu Ala Gly Pro Tyr Asp Ala Trp Val Glu Gly
    370                 375                 380

Ser Thr Trp Leu Ala Glu Ser Ala Ala Leu Pro Arg Glu Val Pro Gly
385                 390                 395                 400

Ala Arg Leu Trp Leu Asp Gly Leu Glu Ala Ser Lys Gln Pro Gly Arg

-continued

```
                405                 410                 415
Arg Ala Leu Leu Tyr Ser Asp Asp Ala Pro Gly Ser Leu Gly Asn Ile
            420                 425                 430
Ser Val Pro Ser Gly Ala Thr His Val Ile Phe Cys Gly Leu Val Pro
            435                 440                 445
Gly Ala His Tyr Arg Val Asp Ile Ala Ser Ser Thr Gly Asp Ile Ser
            450                 455                 460
Gln Ser Ile Ser Gly Tyr Thr Ser Pro Leu Pro Gln Ser Leu Glu
465                 470                 475                 480
Val Ile Ser Arg Ser Ser Pro Ser Asp Leu Thr Ile Ala Trp Gly Pro
                485                 490                 495
Ala Pro Gly Gln Leu Glu Gly Tyr Lys Val Thr Trp His Gln Asp Gly
            500                 505                 510
Ser Gln Arg Ser Pro Gly Asp Leu Val Asp Leu Gly Pro Asp Thr Leu
            515                 520                 525
Ser Leu Thr Leu Lys Ser Leu Val Pro Gly Ser Ser Tyr Thr Val Ser
            530                 535                 540
Ala Trp Ala Trp Ala Gly Asn Leu Gly Ser Asp Ser Gln Lys Ile His
545                 550                 555                 560
Ser Cys Thr Arg Pro Ala Pro Pro Thr Asn Leu Ser Leu Gly Phe Ala
                565                 570                 575
His Gln Pro Ala Ala Leu Lys Ala Ser Trp Tyr His Pro Pro Gly Gly
            580                 585                 590
Arg Asp Ala Phe His Leu Arg Leu Tyr Arg Leu Arg Pro Leu Thr Leu
            595                 600                 605
Glu Ser Glu Lys Val Leu Pro Arg Glu Ala Gln Asn Phe Ser Trp Ala
            610                 615                 620
Gln Leu Thr Ala Gly Cys Glu Phe Gln Val Gln Leu Ser Thr Leu Trp
625                 630                 635                 640
Gly Ser Glu Arg Ser Ser Ala Asn Ala Thr Gly Trp Thr Pro Pro
                645                 650                 655
Ser Ala Pro Thr Leu Val Asn Val Thr Ser Asp Ala Pro Thr Gln Leu
                660                 665                 670
Gln Val Ser Trp Ala His Val Pro Gly Gly Arg Ser Arg Tyr Gln Val
            675                 680                 685
Thr Leu Tyr Gln Glu Ser Thr Arg Thr Ala Thr Ser Ile Met Gly Pro
690                 695                 700
Lys Glu Asp Gly Thr Ser Phe Leu Gly Leu Thr Pro Gly Thr Lys Tyr
705                 710                 715                 720
Lys Val Glu Val Ile Ser Trp Ala Gly Pro Leu Tyr Thr Ala Ala Ala
                725                 730                 735
Asn Val Ser Ala Trp Thr Tyr Pro Leu Ile Pro Asn Glu Leu Leu Val
                740                 745                 750
Ser Met Gln Ala Gly Ser Ala Val Asn Leu Ala Trp Pro Ser Gly
            755                 760                 765
Pro Leu Gly Gln Gly Ala Cys His Ala Gln Leu Ser Asp Ala Gly His
            770                 775                 780
Leu Ser Trp Glu Gln Pro Leu Lys Leu Gly Gln Glu Leu Phe Met Leu
785                 790                 795                 800
Arg Asp Leu Thr Pro Gly His Thr Ile Ser Met Ser Val Arg Cys Arg
                805                 810                 815
Ala Gly Pro Leu Gln Ala Ser Thr His Leu Val Val Leu Ser Val Glu
            820                 825                 830
```

```
Pro Gly Pro Val Glu Asp Val Leu Cys His Pro Glu Ala Thr Tyr Leu
        835                 840                 845
Ala Leu Asn Trp Thr Met Pro Ala Gly Asp Val Asp Val Cys Leu Val
    850                 855                 860
Val Val Glu Arg Leu Val Pro Gly Gly Thr His Phe Val Phe Gln
865                 870                 875                 880
Val Asn Thr Ser Gly Asp Ala Leu Leu Leu Pro Asn Leu Met Pro Thr
                885                 890                 895
Thr Ser Tyr Arg Leu Ser Leu Thr Val Leu Gly Arg Asn Ser Arg Trp
            900                 905                 910
Ser Arg Ala Val Ser Leu Val Cys Ser Thr Ser Ala Glu Ala Trp His
            915                 920                 925
Pro Pro Glu Leu Ala Glu Pro Pro Gln Val Glu Leu Gly Thr Gly Met
    930                 935                 940
Gly Val Thr Val Met Arg Gly Met Phe Gly Lys Asp Asp Gly Gln Ile
945                 950                 955                 960
Gln Trp Tyr Gly Ile Ile Ala Thr Ile Asn Met Thr Leu Ala Gln Pro
                965                 970                 975
Ser Arg Glu Ala Ile Asn Tyr Thr Trp Tyr Asp His Tyr Tyr Arg Gly
            980                 985                 990
Cys Glu Ser Phe Leu Ala Leu Leu Phe Pro Asn Pro Phe Tyr Pro Glu
            995                 1000                1005
Pro Trp Ala Gly Pro Arg Ser Trp Thr Val Pro Val Gly Thr Glu
    1010                1015                1020
Asp Cys Asp Asn Thr Gln Glu Ile Cys Asn Gly Arg Leu Lys Ser
    1025                1030                1035
Gly Phe Gln Tyr Arg Phe Ser Val Val Ala Phe Ser Arg Leu Asn
    1040                1045                1050
Thr Pro Glu Thr Ile Leu Ala Phe Ser Ala Phe Ser Glu Pro Arg
    1055                1060                1065
Ala Ser Ile Ser Leu Ala Ile Ile Pro Leu Thr Val Met Leu Gly
    1070                1075                1080
Ala Val Val Gly Ser Ile Val Ile Val Cys Ala Val Leu Cys Leu
    1085                1090                1095
Leu Arg Trp Arg Cys Leu Lys Gly Pro Arg Ser Glu Lys Asp Gly
    1100                1105                1110
Phe Ser Lys Glu Leu Met Pro Tyr Asn Leu Trp Arg Thr His Arg
    1115                1120                1125
Pro Ile Pro Ile His Ser Phe Arg Gln Ser Tyr Glu Ala Lys Ser
    1130                1135                1140
Ala His Ala His Gln Thr Phe Phe Gln Glu Phe Glu Glu Leu Lys
    1145                1150                1155
Glu Val Gly Lys Asp Gln Pro Arg Leu Glu Ala Glu His Pro Asp
    1160                1165                1170
Asn Ile Ile Lys Asn Arg Tyr Pro His Val Leu Pro Tyr Asp His
    1175                1180                1185
Ser Arg Val Arg Leu Thr Gln Leu Pro Gly Glu Pro His Ser Asp
    1190                1195                1200
Tyr Ile Asn Ala Asn Phe Ile Pro Gly Tyr Ser His Thr Gln Glu
    1205                1210                1215
Ile Ile Ala Thr Gln Gly Pro Leu Lys Lys Thr Leu Glu Asp Phe
    1220                1225                1230
```

-continued

```
Trp Arg Leu Val Trp Glu Gln Gln Val His Val Ile Ile Met Leu
    1235                1240                1245

Thr Val Gly Met Glu Asn Gly Arg Val Leu Cys Glu His Tyr Trp
    1250                1255                1260

Pro Ala Asn Ser Thr Pro Val Thr His Gly His Ile Thr Ile His
    1265                1270                1275

Leu Leu Ala Glu Glu Pro Glu Asp Glu Trp Thr Arg Arg Glu Phe
    1280                1285                1290

Gln Leu Gln His Gly Thr Glu Gln Lys Gln Arg Arg Val Lys Gln
    1295                1300                1305

Leu Gln Phe Thr Thr Trp Pro Asp His Ser Val Pro Glu Ala Pro
    1310                1315                1320

Ser Ser Leu Leu Ala Phe Val Glu Leu Val Gln Glu Gln Val Gln
    1325                1330                1335

Ala Thr Gln Gly Lys Gly Pro Ile Leu Val His Cys Ser Ala Gly
    1340                1345                1350

Val Gly Arg Thr Gly Thr Phe Val Ala Leu Leu Arg Leu Leu Arg
    1355                1360                1365

Gln Leu Glu Glu Glu Lys Val Ala Asp Val Phe Asn Thr Val Tyr
    1370                1375                1380

Ile Leu Arg Leu His Arg Pro Leu Met Ile Gln Thr Leu Ser Gln
    1385                1390                1395

Tyr Ile Phe Leu His Ser Cys Leu Leu Asn Lys Ile Leu Glu Gly
    1400                1405                1410

Pro Pro Asp Ser Ser Asp Ser Gly Pro Ile Ser Val Met Asp Phe
    1415                1420                1425

Ala Gln Ala Cys Ala Lys Arg Ala Ala Asn Ala Asn Ala Gly Phe
    1430                1435                1440

Leu Lys Glu Tyr Lys Leu Leu Lys Gln Ala Ile Lys Asp Gly Thr
    1445                1450                1455

Gly Ser Leu Leu Pro Pro Pro Asp Tyr Asn Gln Asn Ser Ile Val
    1460                1465                1470

Ser Arg Arg His Ser Gln Glu Gln Phe Ala Leu Val Glu Glu Cys
    1475                1480                1485

Pro Glu Asp Ser Met Leu Glu Ala Ser Leu Phe Pro Gly Gly Pro
    1490                1495                1500

Ser Gly Cys Asp His Val Val Leu Thr Gly Ser Ala Gly Pro Lys
    1505                1510                1515

Glu Leu Trp Glu Met Val Trp Glu His Asp Ala His Val Leu Val
    1520                1525                1530

Ser Leu Gly Leu Pro Asp Thr Lys Glu Lys Pro Pro Asp Ile Trp
    1535                1540                1545

Pro Val Glu Met Gln Pro Ile Val Thr Asp Met Val Thr Val His
    1550                1555                1560

Arg Val Ser Glu Ser Asn Thr Thr Thr Gly Trp Pro Ser Thr Leu
    1565                1570                1575

Phe Arg Val Ile His Gly Glu Ser Gly Lys Glu Arg Gln Val Gln
    1580                1585                1590

Cys Leu Gln Phe Pro Cys Ser Glu Ser Gly Cys Glu Leu Pro Ala
    1595                1600                1605

Asn Thr Leu Leu Thr Phe Leu Asp Ala Val Gly Gln Cys Cys Phe
    1610                1615                1620

Arg Gly Lys Ser Lys Lys Pro Gly Thr Leu Leu Ser His Ser Ser
```

-continued

```
            1625                1630                1635

Lys Asn Thr Asn Gln Leu Gly Thr Phe Leu Ala Met Glu Gln Leu
        1640                1645                1650

Leu Gln Gln Ala Gly Thr Glu Arg Thr Val Asp Val Phe Asn Val
    1655                1660                1665

Ala Leu Lys Gln Ser Gln Ala Cys Gly Leu Met Thr Pro Thr Leu
    1670                1675                1680

Glu Gln Tyr Ile Tyr Leu Tyr Asn Cys Leu Asn Ser Ala Leu Leu
    1685                1690                1695

Asn Gly Leu Pro Arg Ala Gly Lys Trp Pro Ala Pro Cys
    1700                1705                1710

<210> SEQ ID NO 39
<211> LENGTH: 625
<212> TYPE: PRT
<213> ORGANISM: HOMO SAPIENS

<400> SEQUENCE: 39

Met Ala Gly Asp Arg Leu Pro Arg Lys Val Met Asp Ala Lys Lys Leu
1               5                   10                  15

Ala Ser Leu Leu Arg Gly Gly Pro Gly Gly Pro Leu Val Ile Asp Ser
                20                  25                  30

Arg Ser Phe Val Glu Tyr Asn Ser Trp His Val Leu Ser Ser Val Asn
            35                  40                  45

Ile Cys Cys Ser Lys Leu Val Lys Arg Leu Gln Gln Gly Lys Val
        50                  55                  60

Thr Ile Ala Glu Leu Ile Gln Pro Ala Ala Arg Ser Gln Val Glu Ala
65                  70                  75                  80

Thr Glu Pro Gln Asp Val Val Tyr Asp Gln Ser Thr Arg Asp Ala
                85                  90                  95

Ser Val Leu Ala Ala Asp Ser Phe Leu Ser Ile Leu Ser Lys Leu
                100                 105                 110

Asp Gly Cys Phe Asp Ser Val Ala Ile Leu Thr Gly Gly Phe Ala Thr
            115                 120                 125

Phe Ser Ser Cys Phe Pro Gly Leu Cys Glu Gly Lys Pro Ala Ala Leu
        130                 135                 140

Leu Pro Met Ser Leu Ser Gln Pro Cys Leu Pro Val Pro Ser Val Gly
145                 150                 155                 160

Leu Thr Arg Ile Leu Pro His Leu Tyr Leu Gly Ser Gln Lys Asp Val
                165                 170                 175

Leu Asn Lys Asp Leu Met Thr Gln Asn Gly Ile Ser Tyr Val Leu Asn
            180                 185                 190

Ala Ser Asn Ser Cys Pro Lys Pro Asp Phe Ile Cys Glu Ser Arg Phe
        195                 200                 205

Met Arg Val Pro Ile Asn Asp Asn Tyr Cys Glu Lys Leu Leu Pro Trp
    210                 215                 220

Leu Asp Lys Ser Ile Glu Phe Ile Asp Lys Ala Lys Leu Ser Ser Cys
225                 230                 235                 240

Gln Val Ile Val His Cys Leu Ala Gly Ile Ser Arg Ser Ala Thr Ile
                245                 250                 255

Ala Ile Ala Tyr Ile Met Lys Thr Met Gly Met Ser Ser Asp Asp Ala
            260                 265                 270

Tyr Arg Phe Val Lys Asp Arg Arg Pro Ser Ile Ser Pro Asn Phe Asn
        275                 280                 285
```

```
Phe Leu Gly Gln Leu Leu Glu Tyr Glu Arg Thr Leu Lys Leu Leu Ala
    290                 295                 300

Ala Leu Gln Gly Asp Pro Gly Thr Pro Ser Gly Thr Pro Glu Pro Pro
305                 310                 315                 320

Pro Ser Pro Ala Ala Gly Ala Pro Leu Pro Arg Leu Pro Pro Pro Thr
                325                 330                 335

Ser Glu Ser Ala Ala Thr Gly Asn Ala Ala Arg Glu Gly Gly Leu
            340                 345                 350

Ser Ala Gly Gly Glu Pro Pro Ala Pro Pro Thr Pro Ala Thr Ser
                355                 360                 365

Ala Leu Gln Gln Gly Leu Arg Gly Leu His Leu Ser Ser Asp Arg Leu
    370                 375                 380

Gln Asp Thr Asn Arg Leu Lys Arg Ser Phe Ser Leu Asp Ile Lys Ser
385                 390                 395                 400

Ala Tyr Ala Pro Ser Arg Arg Pro Asp Gly Pro Gly Pro Pro Asp Pro
                405                 410                 415

Gly Glu Ala Pro Lys Leu Cys Lys Leu Asp Ser Pro Ser Gly Ala Ala
                420                 425                 430

Leu Gly Leu Ser Ser Pro Ser Pro Asp Ser Pro Asp Ala Ala Pro Glu
    435                 440                 445

Ala Arg Pro Arg Pro Arg Arg Pro Arg Pro Ala Gly Ser Pro
450                 455                 460

Ala Arg Ser Pro Ala His Ser Leu Gly Leu Asn Phe Gly Asp Ala Ala
465                 470                 475                 480

Arg Gln Thr Pro Arg His Gly Leu Ser Ala Leu Ser Ala Pro Gly Leu
                485                 490                 495

Pro Gly Pro Gly Gln Pro Ala Gly Pro Gly Ala Trp Ala Pro Pro Leu
            500                 505                 510

Asp Ser Pro Gly Thr Pro Ser Pro Asp Gly Pro Trp Cys Phe Ser Pro
            515                 520                 525

Glu Gly Ala Gln Gly Ala Gly Gly Val Leu Phe Ala Pro Phe Gly Arg
    530                 535                 540

Ala Gly Ala Pro Gly Pro Gly Gly Ser Asp Leu Arg Arg Arg Glu
545                 550                 555                 560

Ala Ala Arg Ala Glu Pro Arg Asp Ala Arg Thr Gly Trp Pro Glu Glu
                565                 570                 575

Pro Ala Pro Glu Thr Gln Phe Lys Arg Arg Ser Cys Gln Met Glu Phe
            580                 585                 590

Glu Glu Gly Met Val Glu Gly Arg Ala Arg Gly Glu Glu Leu Ala Ala
        595                 600                 605

Leu Gly Lys Gln Ala Ser Phe Ser Gly Ser Val Glu Val Ile Glu Val
    610                 615                 620

Ser
625

<210> SEQ ID NO 40
<211> LENGTH: 663
<212> TYPE: PRT
<213> ORGANISM: Mus musculus

<400> SEQUENCE: 40

Met Ala Gly Asp Arg Leu Pro Arg Lys Val Met Asp Ala Lys Lys Leu
1               5                   10                  15

Ala Ser Leu Leu Arg Gly Gly Pro Gly Gly Pro Leu Val Ile Asp Ser
            20                  25                  30
```

-continued

```
Arg Ser Phe Val Glu Tyr Asn Ser Cys His Val Leu Ser Ser Val Asn
         35                  40                  45
Ile Cys Cys Ser Lys Leu Val Lys Arg Arg Leu Gln Gln Gly Lys Val
 50                  55                  60
Thr Ile Ala Glu Leu Ile Gln Pro Ala Thr Arg Ser Gln Val Asp Ala
 65                  70                  75                  80
Thr Glu Pro Gln Asp Val Val Tyr Asp Gln Ser Thr Arg Asp Ala
                 85                  90                  95
Ser Val Leu Ala Ala Asp Ser Phe Leu Ser Ile Leu Leu Ser Lys Leu
                100                 105                 110
Asp Gly Cys Phe Asp Ser Val Ala Ile Leu Thr Gly Phe Ala Thr
        115                 120                 125
Phe Ser Ser Cys Phe Pro Gly Leu Cys Glu Gly Lys Pro Ala Thr Leu
130                 135                 140
Pro Ser Met Ser Leu Ser Gln Pro Cys Leu Pro Val Pro Ser Val Gly
145                 150                 155                 160
Leu Thr Arg Ile Leu Pro His Leu Tyr Leu Gly Ser Gln Lys Asp Val
                165                 170                 175
Leu Asn Lys Asp Leu Met Thr Gln Asn Gly Ile Ser Tyr Val Leu Asn
                180                 185                 190
Ala Ser Asn Ser Cys Pro Lys Pro Asp Phe Ile Cys Glu Ser Arg Phe
            195                 200                 205
Met Arg Ile Pro Ile Asn Asp Asn Tyr Cys Glu Lys Leu Leu Pro Trp
    210                 215                 220
Leu Asp Lys Ser Ile Glu Phe Ile Asp Lys Ala Lys Leu Ser Ser Cys
225                 230                 235                 240
Gln Val Ile Val His Cys Leu Ala Gly Ile Ser Arg Ser Ala Thr Ile
                245                 250                 255
Ala Ile Ala Tyr Ile Met Lys Thr Met Gly Met Ser Ser Asp Asp Ala
                260                 265                 270
Tyr Arg Phe Val Lys Asp Arg Arg Pro Ser Ile Ser Pro Asn Phe Asn
            275                 280                 285
Phe Leu Gly Gln Leu Leu Glu Tyr Glu Arg Ser Leu Lys Leu Leu Ala
    290                 295                 300
Ala Leu Gln Thr Asp Gly Pro His Leu Gly Thr Pro Glu Pro Leu Met
305                 310                 315                 320
Gly Pro Ala Ala Gly Ile Pro Leu Pro Arg Leu Pro Pro Ser Thr Ser
                325                 330                 335
Glu Ser Ala Ala Thr Gly Ser Glu Ala Ala Thr Ala Ala Arg Glu Gly
                340                 345                 350
Ser Pro Ser Ala Gly Gly Asp Ala Pro Ile Pro Ser Thr Ala Pro Ala
            355                 360                 365
Thr Ser Ala Leu Gln Gln Gly Leu Arg Gly Leu His Leu Ser Ser Asp
    370                 375                 380
Arg Leu Gln Asp Thr Asn Arg Leu Lys Arg Ser Phe Ser Leu Asp Ile
385                 390                 395                 400
Lys Ser Ala Tyr Ala Pro Ser Arg Arg Pro Asp Phe Pro Gly Pro Pro
                405                 410                 415
Asp Pro Gly Glu Ala Pro Lys Leu Cys Lys Leu Asp Ser Pro Ser Gly
            420                 425                 430
Gly Thr Leu Gly Leu Pro Ser Pro Ser Pro Asp Ser Pro Asp Ser Val
    435                 440                 445
```

```
Pro Glu Cys Arg Pro Arg Pro Arg Arg Arg Pro Pro Ala Ser Ser
    450                 455                 460

Pro Ala Arg Ser Pro Ala His Gly Leu Gly Leu Asn Phe Gly Asp Thr
465                 470                 475                 480

Ala Arg Gln Thr Pro Arg His Gly Leu Ser Ala Leu Ser Ala Pro Gly
                485                 490                 495

Leu Pro Gly Pro Gly Gln Pro Ala Gly Pro Gly Gly Trp Val Pro Pro
            500                 505                 510

Leu Asp Ser Pro Gly Thr Pro Ser Pro Asp Gly Pro Trp Cys Phe Ser
            515                 520                 525

Pro Glu Gly Ala Gln Gly Pro Gly Ala Val Phe Ser Ala Phe Gly Arg
    530                 535                 540

Val Ser Ala Gly Ala Pro Gly Pro Gly Asn Ser Ser Ser Ser Gly Gly
545                 550                 555                 560

Gly Gly Gly Gly Gly Gly Gly Gly Gly Gly Gly Gly Gly Gly
                565                 570                 575

Ser Ser Ser Ser Asn Ser Ser Ser Ser Ser Ser Ser Ser Ser Ser Ser
            580                 585                 590

Ser Ser Ser Ser Ser Ser Ser Asp Leu Arg Arg Arg Asp Val Arg
    595                 600                 605

Thr Gly Trp Pro Glu Glu Pro Ala Ala Asp Ala Gln Phe Lys Arg Arg
610                 615                 620

Ser Cys Gln Met Glu Phe Glu Glu Gly Met Val Glu Gly Arg Ala Arg
625                 630                 635                 640

Gly Glu Glu Leu Ala Ala Leu Gly Lys Gln Thr Ser Phe Ser Gly Ser
                645                 650                 655

Val Glu Val Ile Glu Val Ser
            660

<210> SEQ ID NO 41
<211> LENGTH: 5111
<212> TYPE: DNA
<213> ORGANISM: HOMO SAPIENS

<400> SEQUENCE: 41
atgttcattt taaaaaactt caggatgggc acaaacacac agaagtggga aatgaataaa      60
agagtattga taaatttttg aaaattgttg aagctgagta atgggctttc agtccagtgt     120
aaagctgttg gagcgcggga gcaaaggtaa agaatgatgt aatgcgctgg ctgctccaaa     180
gcatcttttg ttgtggaatg gttattccag tcatctcttt atgaatcaaa tgtgaggggc     240
tgctttgtgg acggagtcct ttgcaagagc acatcaacgg gaaagagaaa gagacattca     300
cttggagggc tcttgctgaa aatgggttta actctccttt tgccagtcac caccagcctg     360
acctcataca cttttagtac aatggagtgg ctgagccttt gagcacacca ccattacatc     420
atcgtggcaa attaaagaag gaggtgggaa agaggactt attgttgtca tggcccatga     480
gatgattgga actcaaattg ttactgagag gttggtggct ctgctggaaa gtggaacgga     540
aaaagtgctg ctaattgata gccggccatt tgtggaatac aatacatccc acattttgga     600
agccattaat atcaactgct ccaagcttat gaagcgaagg ttgcaacagg acaaagtgtt     660
aattacagag ctcatccagc attcagcgaa acataaggtt gacattgatt gcagtcagaa     720
ggttgtagtt tacgatcaaa gctcccaaga tgttgcctct ctctcttcag actgttttct     780
cactgtactt ctgggtaaac tggagaagag cttcaactct gttcacctgc ttgcaggtgg     840
gtttgctgag ttctctcgtt gtttccctgg cctctgtgaa ggaaaatcca ctctagtccc     900
```

-continued

```
tacctgcatt tctcagcctt gcttacctgt tgccaacatt gggccaaccc gaattcttcc    960
caatctttat cttggctgcc agcgagatgt cctcaacaag gagctgatgc agcagaatgg   1020
gattggttat gtgttaaatg ccagcaatac ctgtccaaag cctgacttta tccccgagtc   1080
tcatttcctg cgtgtgcctg tgaatgacag cttttgtgag aaaattttgc cgtggttgga   1140
caaatcagta gatttcattg agaaagcaaa agcctccaat ggatgtgttc tagtgcactg   1200
tttagctggg atctcccgct ccgccaccat cgctatcgcc tacatcatga gaggatgga   1260
catgtcttta gatgaagctt acagatttgt gaaagaaaaa agacctacta tatctccaaa   1320
cttcaattt ctgggccaac tcctggccta tgagaagaag attaagaacc agactggagc   1380
atcagggcca aagagcaaac tcaagctgct gcccctggag aagccaaatg aacctgtccc   1440
tgctgtctca gagggtggac agaaaagcga gacgcccctc agtccaccct gtgccgactc   1500
tgctacctca gaggcagcag gacaaaggcc cgtgcatccc gccagcgtgc ccagcgtgcc   1560
cagcgtgcag ccgtcgctgt tagaggacag cccgctggta caggcgctca gtgggctgca   1620
cctgtccgca gacaggctgg aagacagcaa taagctcaag cgttccttct ctctggatat   1680
caaatcagtt tcatattcag ccagcatggc agcatcctta catggcttct cctcatcaga   1740
agatgctttg gaatactaca aaccttccac tactctggat gggaccaaca agctatgcca   1800
gttctcccct gttcaggaac tatcggagca gactcccgaa accagtcctg ataaggagga   1860
agccagcatc cccaagaagc tgcagaccgc caggccttca gacagccaga gcaagcgatt   1920
gcattcggtc agaaccagca gcagtggcac cgcccagagg tccctttat ctccactgca   1980
tcgaagtggg agcgtggagg acaattacca caccagcttc cttttcggcc tttccaccag   2040
ccagcagcac ctcacgaagt ctgctggcct gggccttaag ggctggcact cggatatctt   2100
ggccccccag acctctaccc cttccctgac cagcagctgg tattttgcca cagagtcctc   2160
acacttctac tctgcctcag ccatctacgg aggcagtgcc agttactctg cctacagctg   2220
cagccagctg cccacttgcg gagaccaagt ctattctgtg cgcaggcggc agaagccaag   2280
tgacagagct gactcgcggc ggagctggca tgaagagagc ccctttgaaa agcagtttaa   2340
acgcagaagc tgccaaatgg aatttggaga gagcatcatg tcagagaaca ggtcacggga   2400
agagctgggg aaagtgggca gtcagtctag cttttcgggc agcatggaaa tcattgaggt   2460
ctcctgagaa gaaagacact tgtgacttct atagacaatt ttttttttctt gttcacaaaa   2520
aaattccctg ggaatctgaa atatgtatgt gggcatacat atatatttt ggaaaatgga   2580
gctatggtgt aaaagcaaca ggtggatcaa cccagttgtt actctcttaa catctgcatt   2640
tcagagatca gctaatactt gctctcaaca aaaatggaag ggcagatgct agaatcccc   2700
ctagacggag gaaaaccatt ttattcagtg aattacacat cctcttgttc ttaaaaaagc   2760
aagtgtcttt ggtgttggag gacaaaatcc cctaccattt tcacgttgtg ctactaagag   2820
atctcaaata ttagtctttg tccggaccct tccatagtac accttagcgc tgagactgag   2880
ccagcttggg ggtcaggtag gtagaccctg ttagggacag agcctagtgg taaatccaag   2940
agaaatgatc ctatccaaag ctgattcaca aacccacgct cacctgacag ccgagggaca   3000
cgagcatcac tctgctggac ggaccattag gggccttgcc aaggtctacc ttagagcaaa   3060
cccagtacct cagacaggaa agtcggggct ttgaccacta ccatatctgg tagcccattt   3120
tctaggcatt gtgaataggt aggtagctag tcacactttt cagaccaatt caaactgtct   3180
atgcacaaaa ttcccgtggg cctagatgga gataattttt ttttcttctc agctttatga   3240
```

```
agagaaggga aactgtctag gattcagctg aaccaccagg aacctggcaa catcacgatt    3300
taagctaagg ttgggaggct aacgagtcta cctccctctt tgtaaatcaa agaattgttt    3360
aaaatgggat tgtcaatcct ttaaataaag atgaacttgg tttcaagcca aatgtgaatt    3420
tatttgggtt ggtagcagag cagcagcacc ttcaaattct cagccaaagc agatgttttt    3480 gcccttctg cttcactgca tggatacagt tggtaaaatg taataatatg gcagaatttt     3540
ataggaaact tcctagggag gtaaattatg ggaagattaa aaaggtaca aattgctgag     3600 gagaagcagg aaacctgttt ccttagtggc ttttatcccc tcggcatgcg atggggctga    3660
tgtttctata attgcctcag actttcacat ttactagtag ggctgagaga ggctttagtg    3720
aggaaagaat attcagaata aaacggttga gaaagctgag aagaccattg agttttgatc    3780
agttgtgaat agagtgcaaa gccatggcca agctgttttt ggaaacgctg gccggcgtgt    3840
cttcagtgga aaaagcaaat caaaatggag cgagagcaaa ggggcgtcct cagtcctcaa    3900
cctacaatca ctgtatggaa tcggtcctgg cagctgaaca taggaggtca ctggaacaag    3960
tgatagtgca gattggcttt caaacatcct cctggcttga gttttatcag ctacaatgtg    4020
ggtcctcttt tgaagcctta attcacaaca gcagctttt ggggggtgggg ctgggcgggt    4080 gttgtcattg ttcttccct tctgtaagt gtcgctagtt gctgcctcgt atctcaggtt      4140
tttctctgtt tttgagaaat ggacagtttt ttgaccagga tgtgacttca tgtttcctat    4200
ggtgacttct aaaaccagca cagaatgata tgactcaaca cagaccgact tggttatggg    4260
gatgatgagc cgcacagacc tcactagttg tgcacaaata atgtgctatg atggggtgta    4320
aagtgaaggc agaagagggt cagccgcatt gttatgatac tgggaaagtg ccggtcaacg    4380
atttgagtta gttttttagat atacattgaa atctttaatc agacattctc aagtttcaca    4440
cagtagtttt tgatgttatg tacacacaca ccaaatgtgt aacagttcac cacttccaga    4500
gtgtggtcat gcccaaaaca tgtttaagaa aggaaagcag tagctccttg ctaacgatgt    4560
ttcaggaggt ttggggcact tggttttaat gagcttctgt catttagggc ttctcttggc    4620
catggtcccc ttccttctgg aactgtgatg tagtcacatc ctacagcctt tagtgctggt    4680
tcactagtgt cagataatca gttcttggaa tcgagactgc cgtggcgaag gggtggcctc    4740
ggaggcaggc tctggagctg cttggatgtc tttaggtggg gtggtggctg gctctcttca    4800
gcatgtaatt ggggaaaccc tcgcgtctac tagggggtgat acagatggtg attttaaaga    4860
gcaaaactag acttctatgt gagaagtgct ggaaaatgat ttaggacgtg taaagttaga    4920
tggaaagact gtaaatgttt aatatgaata tagtgttctt ttgaagtaag gccagctgtt    4980
gaacggttaa actgtgcatt tctcattttg atgtgtcatg tatgttaatg tatgaaatga    5040
ttaaataaaa tcaaaactgg tacctgttta tccataaaaa aaaaaaaaaa aaaaaaaaa    5100 aaaaaaaaaa g                                                         5111
```

<210> SEQ ID NO 42
<211> LENGTH: 665
<212> TYPE: PRT
<213> ORGANISM: HOMO SAPIENS

<400> SEQUENCE: 42

```
Met Ala His Glu Met Ile Gly Thr Gln Ile Val Thr Glu Arg Leu Val
1               5                   10                  15

Ala Leu Leu Glu Ser Gly Thr Glu Lys Val Leu Leu Ile Asp Ser Arg
            20                  25                  30

Pro Phe Val Glu Tyr Asn Thr Ser His Ile Leu Glu Ala Ile Asn Ile
```

-continued

```
            35                  40                  45
Asn Cys Ser Lys Leu Met Lys Arg Leu Gln Gln Asp Lys Val Leu
 50                  55                  60
Ile Thr Glu Leu Ile Gln His Ser Ala Lys His Lys Val Asp Ile Asp
 65                  70                  75                  80
Cys Ser Gln Lys Val Val Tyr Asp Gln Ser Ser Gln Asp Val Ala
                 85                  90                  95
Ser Leu Ser Ser Asp Cys Phe Leu Thr Val Leu Leu Gly Lys Leu Glu
                100                 105                 110
Lys Ser Phe Asn Ser Val His Leu Leu Ala Gly Gly Phe Ala Glu Phe
                115                 120                 125
Ser Arg Cys Phe Pro Gly Leu Cys Glu Gly Lys Ser Thr Leu Val Pro
    130                 135                 140
Thr Cys Ile Ser Gln Pro Cys Leu Pro Val Ala Asn Ile Gly Pro Thr
145                 150                 155                 160
Arg Ile Leu Pro Asn Leu Tyr Leu Gly Cys Gln Arg Asp Val Leu Asn
                165                 170                 175
Lys Glu Leu Met Gln Gln Asn Gly Ile Gly Tyr Val Leu Asn Ala Ser
                180                 185                 190
Asn Thr Cys Pro Lys Pro Asp Phe Ile Pro Glu Ser His Phe Leu Arg
            195                 200                 205
Val Pro Val Asn Asp Ser Phe Cys Glu Lys Ile Leu Pro Trp Leu Asp
    210                 215                 220
Lys Ser Val Asp Phe Ile Glu Lys Ala Lys Ala Ser Asn Gly Cys Val
225                 230                 235                 240
Leu Val His Cys Leu Ala Gly Ile Ser Arg Ser Ala Thr Ile Ala Ile
                245                 250                 255
Ala Tyr Ile Met Lys Arg Met Asp Met Ser Leu Asp Glu Ala Tyr Arg
                260                 265                 270
Phe Val Lys Glu Lys Arg Pro Thr Ile Ser Pro Asn Phe Asn Phe Leu
            275                 280                 285
Gly Gln Leu Leu Ala Tyr Glu Lys Lys Ile Lys Asn Gln Thr Gly Ala
    290                 295                 300
Ser Gly Pro Lys Ser Lys Leu Lys Leu Pro Leu Glu Lys Pro Asn
305                 310                 315                 320
Glu Pro Val Pro Ala Val Ser Glu Gly Gly Gln Lys Ser Glu Thr Pro
                325                 330                 335
Leu Ser Pro Pro Cys Ala Asp Ser Ala Thr Ser Glu Ala Ala Gly Gln
            340                 345                 350
Arg Pro Val His Pro Ala Ser Val Pro Ser Val Pro Ser Val Gln Pro
    355                 360                 365
Ser Leu Leu Glu Asp Ser Pro Leu Val Gln Ala Leu Ser Gly Leu His
    370                 375                 380
Leu Ser Ala Asp Arg Leu Glu Asp Ser Asn Lys Leu Lys Arg Ser Phe
385                 390                 395                 400
Ser Leu Asp Ile Lys Ser Val Ser Tyr Ser Ala Ser Met Ala Ala Ser
                405                 410                 415
Leu His Gly Phe Ser Ser Glu Asp Ala Leu Glu Tyr Tyr Lys Pro
                420                 425                 430
Ser Thr Thr Leu Asp Gly Thr Asn Lys Leu Cys Gln Phe Ser Pro Val
            435                 440                 445
Gln Glu Leu Ser Glu Gln Thr Pro Glu Thr Ser Pro Asp Lys Glu Glu
    450                 455                 460
```

```
Ala Ser Ile Pro Lys Lys Leu Gln Thr Ala Arg Pro Ser Asp Ser Gln
465                 470                 475                 480

Ser Lys Arg Leu His Ser Val Arg Thr Ser Ser Gly Thr Ala Gln
            485                 490                 495

Arg Ser Leu Leu Ser Pro Leu His Arg Ser Gly Ser Val Glu Asp Asn
            500                 505                 510

Tyr His Thr Ser Phe Leu Phe Gly Leu Ser Thr Ser Gln Gln His Leu
            515                 520                 525

Thr Lys Ser Ala Gly Leu Gly Leu Lys Gly Trp His Ser Asp Ile Leu
            530                 535                 540

Ala Pro Gln Thr Ser Thr Pro Ser Leu Thr Ser Ser Trp Tyr Phe Ala
545                 550                 555                 560

Thr Glu Ser Ser His Phe Tyr Ser Ala Ser Ala Ile Tyr Gly Gly Ser
            565                 570                 575

Ala Ser Tyr Ser Ala Tyr Ser Cys Ser Gln Leu Pro Thr Cys Gly Asp
            580                 585                 590

Gln Val Tyr Ser Val Arg Arg Arg Gln Lys Pro Ser Asp Arg Ala Asp
            595                 600                 605

Ser Arg Arg Ser Trp His Glu Glu Ser Pro Phe Glu Lys Gln Phe Lys
610                 615                 620

Arg Arg Ser Cys Gln Met Glu Phe Gly Glu Ser Ile Met Ser Glu Asn
625                 630                 635                 640

Arg Ser Arg Glu Glu Leu Gly Lys Val Gly Ser Gln Ser Ser Phe Ser
            645                 650                 655

Gly Ser Met Glu Ile Ile Glu Val Ser
            660                 665
```

<210> SEQ ID NO 43
<211> LENGTH: 20
<212> TYPE: DNA
<213> ORGANISM: HOMO SAPIENS

<400> SEQUENCE: 43
cggatggaag gattatggtg                                               20

<210> SEQ ID NO 44
<211> LENGTH: 18
<212> TYPE: DNA
<213> ORGANISM: HOMO SAPIENS

<400> SEQUENCE: 44
ctgttcgacc aagccctg                                                 18

<210> SEQ ID NO 45
<211> LENGTH: 80
<212> TYPE: DNA
<213> ORGANISM: HOMO SAPIENS

<400> SEQUENCE: 45
tgacaatgga tagctacttt tccttcctgt aaggcaaatg tcatcacctt caccatatct    60
aggatagtag taagagacgc                                               80

<210> SEQ ID NO 46
<211> LENGTH: 20
<212> TYPE: DNA
<213> ORGANISM: HOMO SAPIENS

<400> SEQUENCE: 46

-continued ttcggatgga aggattatgg                                          20

<210> SEQ ID NO 47
<211> LENGTH: 18
<212> TYPE: DNA
<213> ORGANISM: HOMO SAPIENS

<400> SEQUENCE: 47
ctgttcgacc aagccctg                                            18

<210> SEQ ID NO 48
<211> LENGTH: 80
<212> TYPE: DNA
<213> ORGANISM: HOMO SAPIENS

<400> SEQUENCE: 48
tgacaatgga tagctacttt tccttcctgt aaggcaaatg tcatcacctt caccatatct    60
aggatagtag taagagacgc                                          80

<210> SEQ ID NO 49
<211> LENGTH: 19
<212> TYPE: DNA
<213> ORGANISM: HOMO SAPIENS

<400> SEQUENCE: 49
ccaacttctc ctgggtgct                                           19

<210> SEQ ID NO 50
<211> LENGTH: 18
<212> TYPE: DNA
<213> ORGANISM: HOMO SAPIENS

<400> SEQUENCE: 50
ctccgtcagg gacaccag                                            18

<210> SEQ ID NO 51
<211> LENGTH: 79
<212> TYPE: DNA
<213> ORGANISM: HOMO SAPIENS

<400> SEQUENCE: 51
gtgccgcacg cccaggtcca acaggaactg gtagtgggcg gggagccgcg gcagcgccag    60
tcccgccagc cggcccgga                                           79

<210> SEQ ID NO 52
<211> LENGTH: 20
<212> TYPE: DNA
<213> ORGANISM: HOMO SAPIENS

<400> SEQUENCE: 52
caacttctcc tgggtgcttc                                          20

<210> SEQ ID NO 53
<211> LENGTH: 18
<212> TYPE: DNA
<213> ORGANISM: HOMO SAPIENS

<400> SEQUENCE: 53
cagctgtcgc tgtgaggg                                            18

<210> SEQ ID NO 54

```
<211> LENGTH: 80
<212> TYPE: DNA
<213> ORGANISM: HOMO SAPIENS

<400> SEQUENCE: 54
ctccgtcagg gacaccaggt gccgcacgcc caggtccaac aggaactggt agtgggcggg    60
gagccgcggc agcgccagtc                                                80

<210> SEQ ID NO 55
<211> LENGTH: 20
<212> TYPE: DNA
<213> ORGANISM: HOMO SAPIENS

<400> SEQUENCE: 55
ctccctgctt ctgtggacat                                                20

<210> SEQ ID NO 56
<211> LENGTH: 20
<212> TYPE: DNA
<213> ORGANISM: HOMO SAPIENS

<400> SEQUENCE: 56
aacctggatg cttcccttct                                                20

<210> SEQ ID NO 57
<211> LENGTH: 80
<212> TYPE: DNA
<213> ORGANISM: HOMO SAPIENS

<400> SEQUENCE: 57
aaaagagcaa tgttgtaagt tgcttttcat actcttacta tggtggtaac tccatcctgc    60
ttaagttcct gtaagaatct                                                80

<210> SEQ ID NO 58
<211> LENGTH: 20
<212> TYPE: DNA
<213> ORGANISM: HOMO SAPIENS

<400> SEQUENCE: 58
tgcttctgtg gacattgcat                                                20

<210> SEQ ID NO 59
<211> LENGTH: 20
<212> TYPE: DNA
<213> ORGANISM: HOMO SAPIENS

<400> SEQUENCE: 59
aacctggatg cttcccttct                                                20

<210> SEQ ID NO 60
<211> LENGTH: 80
<212> TYPE: DNA
<213> ORGANISM: HOMO SAPIENS

<400> SEQUENCE: 60
aaaagagcaa tgttgtaagt tgcttttcat actcttacta tggtggtaac tccatcctgc    60
ttaagttcct gtaagaatct                                                80

<210> SEQ ID NO 61
<211> LENGTH: 20
<212> TYPE: DNA
<213> ORGANISM: HOMO SAPIENS
```

```
<400> SEQUENCE: 61
ggcagaacta tgaggccaag                                          20

<210> SEQ ID NO 62
<211> LENGTH: 20
<212> TYPE: DNA
<213> ORGANISM: HOMO SAPIENS

<400> SEQUENCE: 62
gaccctggag tggtcatagg                                          20

<210> SEQ ID NO 63
<211> LENGTH: 80
<212> TYPE: DNA
<213> ORGANISM: HOMO SAPIENS

<400> SEQUENCE: 63
gctcatgcgc accaggcttt cttttttgaaa ttcgaggagc tgaaggaggt gagcaaggag   60
cagcccagac tggaggctga                                          80

<210> SEQ ID NO 64
<211> LENGTH: 20
<212> TYPE: DNA
<213> ORGANISM: HOMO SAPIENS

<400> SEQUENCE: 64
gcaccaggct ttcttttttga                                         20

<210> SEQ ID NO 65
<211> LENGTH: 20
<212> TYPE: DNA
<213> ORGANISM: HOMO SAPIENS

<400> SEQUENCE: 65
gaccctggag tggtcatagg                                          20

<210> SEQ ID NO 66
<211> LENGTH: 80
<212> TYPE: DNA
<213> ORGANISM: HOMO SAPIENS

<400> SEQUENCE: 66
tcgaggagct gaaggaggtg agcaaggagc agcccagact ggaggctgag taccctgcca   60
acaccaccaa gaactgttaa                                          80

<210> SEQ ID NO 67
<211> LENGTH: 20
<212> TYPE: DNA
<213> ORGANISM: HOMO SAPIENS

<400> SEQUENCE: 67
atgggaccaa caagctatgc                                          20

<210> SEQ ID NO 68
<211> LENGTH: 20
<212> TYPE: DNA
<213> ORGANISM: HOMO SAPIENS

<400> SEQUENCE: 68
ttatcaggac tggtttcggg                                          20
```

```
<210> SEQ ID NO 69
<211> LENGTH: 20
<212> TYPE: DNA
<213> ORGANISM: HOMO SAPIENS

<400> SEQUENCE: 69
ggccaaagag caaactcaag                                               20

<210> SEQ ID NO 70
<211> LENGTH: 20
<212> TYPE: DNA
<213> ORGANISM: HOMO SAPIENS

<400> SEQUENCE: 70
gcatagcttg ttggtcccat                                               20

<210> SEQ ID NO 71
<211> LENGTH: 20
<212> TYPE: DNA
<213> ORGANISM: HOMO SAPIENS

<400> SEQUENCE: 71
aggcagaact atgaggccaa                                               20

<210> SEQ ID NO 72
<211> LENGTH: 20
<212> TYPE: DNA
<213> ORGANISM: HOMO SAPIENS

<400> SEQUENCE: 72
gaccctggag tggtcatagg                                               20

<210> SEQ ID NO 73
<211> LENGTH: 80
<212> TYPE: DNA
<213> ORGANISM: HOMO SAPIENS

<400> SEQUENCE: 73
gctcatgcgc accaggcttt cttttgaaa ttcgaggagc tgaaggaggt gagcaaggag    60
cagcccagac tggaggctga                                               80

<210> SEQ ID NO 74
<211> LENGTH: 80
<212> TYPE: DNA
<213> ORGANISM: HOMO SAPIENS

<400> SEQUENCE: 74
tcagcctcca gtctgggctg ctccttgctc acctccttca gctcctcgaa tttcaaaaag   60
aaagcctggt gcgcatgagc                                               80

<210> SEQ ID NO 75
<211> LENGTH: 8
<212> TYPE: PRT
<213> ORGANISM: bacteriophage T7

<400> SEQUENCE: 75

Asp Tyr Lys Asp Asp Asp Asp Lys
1               5

<210> SEQ ID NO 76
<211> LENGTH: 733
<212> TYPE: DNA
```

-continued

```
<213> ORGANISM: homo sapiens

<400> SEQUENCE: 76
gggatccgga gcccaaatct tctgacaaaa ctcacacatg cccaccgtgc ccagcacctg      60
aattcgaggg tgcaccgtca gtcttcctct tccccccaaa acccaaggac accctcatga    120
tctcccggac tcctgaggtc acatgcgtgg tggtggacgt aagccacgaa gaccctgagg    180
tcaagttcaa ctggtacgtg gacggcgtgg aggtgcataa tgccaagaca aagccgcggg    240
aggagcagta caacagcacg taccgtgtgg tcagcgtcct caccgtcctg caccaggact    300
ggctgaatgg caaggagtac aagtgcaagg tctccaacaa agccctccca accccatcg     360 agaaaaccat ctccaaagcc aaagggcagc ccgagaacc acaggtgtac accctgcccc     420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733
```

```
<210> SEQ ID NO 77
<211> LENGTH: 7
<212> TYPE: PRT
<213> ORGANISM: HOMO SAPIENS

<400> SEQUENCE: 77

Asp Tyr Ile Asn Ala Ser Asn
1               5
```

```
<210> SEQ ID NO 78
<211> LENGTH: 6
<212> TYPE: PRT
<213> ORGANISM: HOMO SAPIENS
<220> FEATURE:
<221> NAME/KEY: VARIANT
<222> LOCATION: (2)..(2)
<223> OTHER INFORMATION: wherein 'Xaa' is any amino acid.
<220> FEATURE:
<221> NAME/KEY: VARIANT
<222> LOCATION: (3)..(3)
<223> OTHER INFORMATION: wherein 'Xaa' is any amino acid.

<400> SEQUENCE: 78

Cys Xaa Xaa Tyr Trp Pro
1               5
```

```
<210> SEQ ID NO 79
<211> LENGTH: 9
<212> TYPE: PRT
<213> ORGANISM: HOMO SAPIENS
<220> FEATURE:
<221> NAME/KEY: Variant
<222> LOCATION: (5)..(5)
<223> OTHER INFORMATION: wherein 'Xaa' is any amino acid.
<220> FEATURE:
<221> NAME/KEY: Variant
<222> LOCATION: (6)..(6)
<223> OTHER INFORMATION: wherein 'Xaa' is any amino acid.
<220> FEATURE:
<221> NAME/KEY: Variant
<222> LOCATION: (7)..(7)
<223> OTHER INFORMATION: wherein 'Xaa' is any amino acid.
<220> FEATURE:
<221> NAME/KEY: Variant
```

```
<222> LOCATION: (8)..(8)
<223> OTHER INFORMATION: wherein 'Xaa' is any amino acid.

<400> SEQUENCE: 79

Ile Val Val Met Xaa Xaa Xaa Xaa Glu
1               5

<210> SEQ ID NO 80
<211> LENGTH: 8
<212> TYPE: PRT
<213> ORGANISM: HOMO SAPIENS

<400> SEQUENCE: 80

Asp Asn Tyr Ile Asn Ala Ser Asn
1               5

<210> SEQ ID NO 81
<211> LENGTH: 6
<212> TYPE: PRT
<213> ORGANISM: HOMO SAPIENS
<220> FEATURE:
<221> NAME/KEY: Variant
<222> LOCATION: (2)..(2)
<223> OTHER INFORMATION: wherein 'Xaa' is any amino acid.
<220> FEATURE:
<221> NAME/KEY: Variant
<222> LOCATION: (3)..(3)
<223> OTHER INFORMATION: wherein 'Xaa' is any amino acid.

<400> SEQUENCE: 81

Cys Xaa Xaa Tyr Trp Pro
1               5

<210> SEQ ID NO 82
<211> LENGTH: 9
<212> TYPE: PRT
<213> ORGANISM: HOMO SAPIENS
<220> FEATURE:
<221> NAME/KEY: Variant
<222> LOCATION: (5)..(5)
<223> OTHER INFORMATION: wherein 'Xaa' is any amino acid.
<220> FEATURE:
<221> NAME/KEY: Variant
<222> LOCATION: (6)..(6)
<223> OTHER INFORMATION: wherein 'Xaa' is any amino acid.
<220> FEATURE:
<221> NAME/KEY: Variant
<222> LOCATION: (7)..(7)
<223> OTHER INFORMATION: wherein 'Xaa' is any amino acid.
<220> FEATURE:
<221> NAME/KEY: Variant
<222> LOCATION: (8)..(8)
<223> OTHER INFORMATION: wherein 'Xaa' is any amino acid.

<400> SEQUENCE: 82

Ile Val Val Met Xaa Xaa Xaa Xaa Glu
1               5

<210> SEQ ID NO 83
<211> LENGTH: 511
<212> TYPE: DNA
<213> ORGANISM: homo sapiens

<400> SEQUENCE: 83
atggctagaa tgaacctccc tgcttctgtg gacattgcat acaaaaatgt gagatttctt      60
attacacaca acccaaccaa tacctacttt aatagattct tacaggaact taagcaggat     120
ggagttacca ccatagtaag agtatgaaaa gcaacttaca acattgctct tttagagaag     180
```

```
ggaagcatcc aggttccgga ctggcctttt gatgatggta cagcaccatc cagccagata    240
attgataact ggttaaaact tatgaaaaat aaatttcatg aagatcctgg ttgttgtatt    300
gcaattcact gtgttgtagg ttttgggtga gctccagttg ctagttgccc tagctttaat    360
tgaaggtgga atgaaatatg aaatgtagt acagttcatc agataaaagt gacatggaac     420
ttttaacagc aaacaacttt tgtatttgga gaaatattgt cttaaaatat gcttgcacct    480
cagaaatccc agaataact gtttccttca g                                    511
```

<210> SEQ ID NO 84
<211> LENGTH: 167
<212> TYPE: PRT
<213> ORGANISM: homo sapiens

<400> SEQUENCE: 84

```
Met Ala Arg Met Asn Leu Pro Ala Ser Val Asp Ile Ala Tyr Lys Asn
1               5                   10                  15

Val Arg Phe Leu Ile Thr His Asn Pro Thr Asn Thr Tyr Phe Asn Arg
            20                  25                  30

Phe Leu Gln Glu Leu Lys Gln Asp Gly Val Thr Thr Ile Val Arg Val
        35                  40                  45

Lys Ala Thr Tyr Asn Ile Ala Leu Leu Glu Lys Gly Ser Ile Gln Val
    50                  55                  60

Pro Asp Trp Pro Phe Asp Asp Gly Thr Ala Pro Ser Ser Gln Ile Ile
65                  70                  75                  80

Asp Asn Trp Leu Lys Leu Met Lys Asn Lys Phe His Glu Asp Pro Gly
                85                  90                  95

Cys Cys Ile Ala Ile His Cys Val Val Gly Phe Gly Glu Leu Gln Leu
            100                 105                 110

Leu Val Ala Leu Ala Leu Ile Glu Gly Gly Met Lys Tyr Glu Asn Val
        115                 120                 125

Val Gln Phe Ile Arg Lys His Gly Thr Phe Asn Ser Lys Gln Leu Leu
    130                 135                 140

Tyr Leu Glu Lys Tyr Cys Leu Lys Ile Cys Leu His Leu Arg Asn Pro
145                 150                 155                 160

Arg Asn Asn Cys Phe Leu Gln
                165
```

<210> SEQ ID NO 85
<211> LENGTH: 14
<212> TYPE: PRT
<213> ORGANISM: homo sapiens

<400> SEQUENCE: 85

```
Pro Phe Val Glu Tyr Asn Thr Ser His Ile Leu Glu Ala Ile
1               5                   10
```

<210> SEQ ID NO 86
<211> LENGTH: 14
<212> TYPE: PRT
<213> ORGANISM: homo sapiens

<400> SEQUENCE: 86

```
Glu Ala Ile Asn Ile Asn Cys Ser Lys Leu Met Lys Arg Arg
1               5                   10
```

<210> SEQ ID NO 87
<211> LENGTH: 14
<212> TYPE: PRT

<213> ORGANISM: homo sapiens

<400> SEQUENCE: 87

Ile Gly Tyr Val Leu Asn Ala Ser Asn Thr Cys Pro Lys Pro
1               5                   10

<210> SEQ ID NO 88
<211> LENGTH: 14
<212> TYPE: PRT
<213> ORGANISM: homo sapiens

<400> SEQUENCE: 88

Leu Arg Val Pro Val Asn Asp Ser Phe Cys Glu Lys Ile Leu
1               5                   10

<210> SEQ ID NO 89
<211> LENGTH: 14
<212> TYPE: PRT
<213> ORGANISM: homo sapiens

<400> SEQUENCE: 89

Glu Lys Lys Ile Lys Asn Gln Thr Gly Ala Ser Gly Pro Lys
1               5                   10

<210> SEQ ID NO 90
<211> LENGTH: 14
<212> TYPE: PRT
<213> ORGANISM: homo sapiens

<400> SEQUENCE: 90

Ser Ile Met Ser Glu Asn Arg Ser Arg Glu Glu Leu Gly Lys
1               5                   10

<210> SEQ ID NO 91
<211> LENGTH: 13
<212> TYPE: PRT
<213> ORGANISM: homo sapiens

<400> SEQUENCE: 91

Gly Thr Gln Ile Val Thr Glu Arg Leu Val Ala Leu Leu
1               5                   10

<210> SEQ ID NO 92
<211> LENGTH: 13
<212> TYPE: PRT
<213> ORGANISM: homo sapiens

<400> SEQUENCE: 92

Leu Leu Glu Ser Gly Thr Glu Lys Val Leu Leu Ile Asp
1               5                   10

<210> SEQ ID NO 93
<211> LENGTH: 13
<212> TYPE: PRT
<213> ORGANISM: homo sapiens

<400> SEQUENCE: 93

Glu Leu Ile Gln His Ser Ala Lys His Lys Val Asp Ile
1               5                   10

<210> SEQ ID NO 94
<211> LENGTH: 13
<212> TYPE: PRT
<213> ORGANISM: homo sapiens -continued

```
<400> SEQUENCE: 94

Val Asp Ile Asp Cys Ser Gln Lys Val Val Tyr Asp
1               5                   10

<210> SEQ ID NO 95
<211> LENGTH: 13
<212> TYPE: PRT
<213> ORGANISM: homo sapiens

<400> SEQUENCE: 95

Asp Arg Leu Glu Asp Ser Asn Lys Leu Lys Arg Ser Phe
1               5                   10

<210> SEQ ID NO 96
<211> LENGTH: 13
<212> TYPE: PRT
<213> ORGANISM: homo sapiens

<400> SEQUENCE: 96

Thr Thr Leu Asp Gly Thr Asn Lys Leu Cys Gln Phe Ser
1               5                   10

<210> SEQ ID NO 97
<211> LENGTH: 13
<212> TYPE: PRT
<213> ORGANISM: homo sapiens

<400> SEQUENCE: 97

Pro Lys Lys Leu Gln Thr Ala Arg Pro Ser Asp Ser Gln
1               5                   10

<210> SEQ ID NO 98
<211> LENGTH: 13
<212> TYPE: PRT
<213> ORGANISM: homo sapiens

<400> SEQUENCE: 98

Pro Ser Asp Ser Gln Ser Lys Arg Leu His Ser Val Arg
1               5                   10

<210> SEQ ID NO 99
<211> LENGTH: 13
<212> TYPE: PRT
<213> ORGANISM: homo sapiens

<400> SEQUENCE: 99

Ser Lys Arg Leu His Ser Val Arg Thr Ser Ser Ser Gly
1               5                   10

<210> SEQ ID NO 100
<211> LENGTH: 13
<212> TYPE: PRT
<213> ORGANISM: homo sapiens

<400> SEQUENCE: 100

Gly Asp Gln Val Tyr Ser Val Arg Arg Arg Gln Lys Pro
1               5                   10

<210> SEQ ID NO 101
<211> LENGTH: 13
<212> TYPE: PRT
<213> ORGANISM: homo sapiens

<400> SEQUENCE: 101
```

```
Arg Arg Gln Lys Pro Ser Asp Arg Ala Asp Ser Arg Arg
1               5                  10
```

<210> SEQ ID NO 102
<211> LENGTH: 13
<212> TYPE: PRT
<213> ORGANISM: homo sapiens

<400> SEQUENCE: 102

```
Ser Asp Arg Ala Asp Ser Arg Arg Ser Trp His Glu Glu
1               5                  10
```

<210> SEQ ID NO 103
<211> LENGTH: 23
<212> TYPE: PRT
<213> ORGANISM: homo sapiens

<400> SEQUENCE: 103

```
Asn Gly Cys Val Leu Val His Cys Leu Ala Gly Ile Ser Arg Ser Ala
1               5                  10                 15

Thr Ile Ala Ile Ala Tyr Ile
            20
```

<210> SEQ ID NO 104
<211> LENGTH: 39
<212> TYPE: DNA
<213> ORGANISM: Homo sapiens

<400> SEQUENCE: 104
gcagcagcgg ccgcatcgcc tacatcatga agaggatgg                              39

<210> SEQ ID NO 105
<211> LENGTH: 37
<212> TYPE: DNA
<213> ORGANISM: Homo sapiens

<400> SEQUENCE: 105
gcagcagtcg acggagacct caatgatttc catgctg                                37

<210> SEQ ID NO 106
<211> LENGTH: 39
<212> TYPE: DNA
<213> ORGANISM: Homo sapiens

<400> SEQUENCE: 106
gcagcagcgg ccgcatggcc catgagatga ttggaactc                              39

<210> SEQ ID NO 107
<211> LENGTH: 37
<212> TYPE: DNA
<213> ORGANISM: Homo sapiens

<400> SEQUENCE: 107
gcagcagtcg acctgcacgc tgggcacgct gggcacg                                37

<210> SEQ ID NO 108
<211> LENGTH: 5450
<212> TYPE: DNA
<213> ORGANISM: Homo sapiens
<220> FEATURE:
<221> NAME/KEY: CDS
<222> LOCATION: (538)..(2532)

<400> SEQUENCE: 108

```
gaaaagaaga cgaggaggag agcgacggga cgggacgcga gcgggagcgc agccgccctc    60
tcggctccgc ggcggcgcct cgcaagtccg ggaggcgagg ggggcccgag gggagacgcc   120
gtgacaactt tcgtttccct ctgagggaat tgggaggtcg gcggccccaa aagctttcag   180
tccagtgtaa agctgttgga gcgcgggagc aaaggtaaag aatgatgtaa tgcgctggct   240
gctccaaagc atcttttgtt gtggaatggt tattccagtc atctctttat gaatcaaatg   300
tgagggggctg ctttgtggac ggagtccttt gcaagagcac atcaacggga aagagaaaga   360
gacattcact tggagggctc ttgctgaaaa tgggtttaac tctccttttg ccagtcacca   420
ccagcctgac ctcatacact tttagtacaa tggagtggct gagcctttga gcacaccacc   480
attacatcat cgtggcaaat taaagaagga ggtgggaaaa gaggacttat tgttgtc      537
```

| | | | | | | | | | | | | | | | | |
|---|---|---|---|---|---|---|---|---|---|---|---|---|---|---|---|---|
| atg | gcc | cat | gag | atg | att | gga | act | caa | att | gtt | act | gag | agg | ttg | gtg | 585 |
| Met | Ala | His | Glu | Met | Ile | Gly | Thr | Gln | Ile | Val | Thr | Glu | Arg | Leu | Val | |
| 1 | | | | 5 | | | | | 10 | | | | | 15 | | |

| gct | ctg | ctg | gaa | agt | gga | acg | gaa | aaa | gtg | ctg | cta | att | gat | agc | cgg | 633 |
|---|---|---|---|---|---|---|---|---|---|---|---|---|---|---|---|---|
| Ala | Leu | Leu | Glu | Ser | Gly | Thr | Glu | Lys | Val | Leu | Leu | Ile | Asp | Ser | Arg | |
| | | | | 20 | | | | | 25 | | | | | 30 | | |

| cca | ttt | gtg | gaa | tac | aat | aca | tcc | cac | att | ttg | gaa | gcc | att | aat | atc | 681 |
|---|---|---|---|---|---|---|---|---|---|---|---|---|---|---|---|---|
| Pro | Phe | Val | Glu | Tyr | Asn | Thr | Ser | His | Ile | Leu | Glu | Ala | Ile | Asn | Ile | |
| | | 35 | | | | | 40 | | | | | 45 | | | | |

| aac | tgc | tcc | aag | ctt | atg | aag | cga | agg | ttg | caa | cag | gac | aaa | gtg | tta | 729 |
|---|---|---|---|---|---|---|---|---|---|---|---|---|---|---|---|---|
| Asn | Cys | Ser | Lys | Leu | Met | Lys | Arg | Arg | Leu | Gln | Gln | Asp | Lys | Val | Leu | |
| | 50 | | | | | 55 | | | | | 60 | | | | | |

| att | aca | gag | ctc | atc | cag | cat | tca | gcg | aaa | cat | aag | gtt | gac | att | gat | 777 |
|---|---|---|---|---|---|---|---|---|---|---|---|---|---|---|---|---|
| Ile | Thr | Glu | Leu | Ile | Gln | His | Ser | Ala | Lys | His | Lys | Val | Asp | Ile | Asp | |
| 65 | | | | | 70 | | | | | 75 | | | | | 80 | |

| tgc | agt | cag | aag | gtt | gta | gtt | tac | gat | caa | agc | tcc | caa | gat | gtt | gcc | 825 |
|---|---|---|---|---|---|---|---|---|---|---|---|---|---|---|---|---|
| Cys | Ser | Gln | Lys | Val | Val | Val | Tyr | Asp | Gln | Ser | Ser | Gln | Asp | Val | Ala | |
| | | | | 85 | | | | | 90 | | | | | 95 | | |

| tct | ctc | tct | tca | gac | tgt | ttt | ctc | act | gta | ctt | ctg | ggt | aaa | ctg | gag | 873 |
|---|---|---|---|---|---|---|---|---|---|---|---|---|---|---|---|---|
| Ser | Leu | Ser | Ser | Asp | Cys | Phe | Leu | Thr | Val | Leu | Leu | Gly | Lys | Leu | Glu | |
| | | | 100 | | | | | 105 | | | | | 110 | | | |

| aag | agc | ttc | aac | tct | gtt | cac | ctg | ctt | gca | ggt | ggg | ttt | gct | gag | ttc | 921 |
|---|---|---|---|---|---|---|---|---|---|---|---|---|---|---|---|---|
| Lys | Ser | Phe | Asn | Ser | Val | His | Leu | Leu | Ala | Gly | Gly | Phe | Ala | Glu | Phe | |
| | | 115 | | | | | 120 | | | | | 125 | | | | |

| tct | cgt | tgt | ttc | cct | ggc | ctc | tgt | gaa | gga | aaa | tcc | act | cta | gtc | cct | 969 |
|---|---|---|---|---|---|---|---|---|---|---|---|---|---|---|---|---|
| Ser | Arg | Cys | Phe | Pro | Gly | Leu | Cys | Glu | Gly | Lys | Ser | Thr | Leu | Val | Pro | |
| | 130 | | | | | 135 | | | | | 140 | | | | | |

| acc | tgc | att | tct | cag | cct | tgc | tta | cct | gtt | gcc | aac | att | ggg | cca | acc | 1017 |
|---|---|---|---|---|---|---|---|---|---|---|---|---|---|---|---|---|
| Thr | Cys | Ile | Ser | Gln | Pro | Cys | Leu | Pro | Val | Ala | Asn | Ile | Gly | Pro | Thr | |
| 145 | | | | | 150 | | | | | 155 | | | | | 160 | |

| cga | att | ctt | ccc | aat | ctt | tat | ctt | ggc | tgc | cag | cga | gat | gtc | ctc | aac | 1065 |
|---|---|---|---|---|---|---|---|---|---|---|---|---|---|---|---|---|
| Arg | Ile | Leu | Pro | Asn | Leu | Tyr | Leu | Gly | Cys | Gln | Arg | Asp | Val | Leu | Asn | |
| | | | | 165 | | | | | 170 | | | | | 175 | | |

| aag | gag | ctg | ata | cag | cag | aat | ggg | att | ggt | tat | gtg | tta | aat | gcc | agc | 1113 |
|---|---|---|---|---|---|---|---|---|---|---|---|---|---|---|---|---|
| Lys | Glu | Leu | Ile | Gln | Gln | Asn | Gly | Ile | Gly | Tyr | Val | Leu | Asn | Ala | Ser | |
| | | | 180 | | | | | 185 | | | | | 190 | | | |

| tat | acc | tgt | cca | aag | cct | gac | ttt | atc | ccc | gag | tct | cat | ttc | ctg | cgt | 1161 |
|---|---|---|---|---|---|---|---|---|---|---|---|---|---|---|---|---|
| Tyr | Thr | Cys | Pro | Lys | Pro | Asp | Phe | Ile | Pro | Glu | Ser | His | Phe | Leu | Arg | |
| | | 195 | | | | | 200 | | | | | 205 | | | | |

| gtg | cct | gtg | aat | gac | agc | ttt | tgt | gag | aaa | att | ttg | ccg | tgg | ttg | gac | 1209 |
|---|---|---|---|---|---|---|---|---|---|---|---|---|---|---|---|---|
| Val | Pro | Val | Asn | Asp | Ser | Phe | Cys | Glu | Lys | Ile | Leu | Pro | Trp | Leu | Asp | |
| | 210 | | | | | 215 | | | | | 220 | | | | | |

| aaa | tca | gta | gat | ttc | att | gag | aaa | gca | aaa | gcc | tcc | aat | gga | tgt | gtt | 1257 |
|---|---|---|---|---|---|---|---|---|---|---|---|---|---|---|---|---|
| Lys | Ser | Val | Asp | Phe | Ile | Glu | Lys | Ala | Lys | Ala | Ser | Asn | Gly | Cys | Val | |
| 225 | | | | | 230 | | | | | 235 | | | | | 240 | |

| cta | gtg | cac | tgt | tta | gct | ggg | atc | tcc | cgc | tcc | gcc | acc | atc | gct | atc | 1305 |
|---|---|---|---|---|---|---|---|---|---|---|---|---|---|---|---|---|
| Leu | Val | His | Cys | Leu | Ala | Gly | Ile | Ser | Arg | Ser | Ala | Thr | Ile | Ala | Ile | |
| | | | | 245 | | | | | 250 | | | | | 255 | | |

| gcc | tac | atc | atg | aag | agg | atg | gac | atg | tct | tta | gat | gaa | gct | tac | aga | 1353 |
|---|---|---|---|---|---|---|---|---|---|---|---|---|---|---|---|---|
| Ala | Tyr | Ile | Met | Lys | Arg | Met | Asp | Met | Ser | Leu | Asp | Glu | Ala | Tyr | Arg | |
| | | | 260 | | | | | 265 | | | | | 270 | | | |

```
ttt gtg aaa gaa aaa aga cct act ata tct cca aac ttc aat ttt ctg    1401
Phe Val Lys Glu Lys Arg Pro Thr Ile Ser Pro Asn Phe Asn Phe Leu
        275                 280                 285 ggc caa ctc ctg gac tat gag aag aag att aag aac cag act gga gca    1449
Gly Gln Leu Leu Asp Tyr Glu Lys Lys Ile Lys Asn Gln Thr Gly Ala
290                 295                 300 tca ggg cca aag agc aaa ctc aag ctg ctg cac ctg gag aag cca aat    1497
Ser Gly Pro Lys Ser Lys Leu Lys Leu Leu His Leu Glu Lys Pro Asn
305                 310                 315                 320 gaa cct gtc cct gct gtc tca gag ggt gga cag aaa agc gag acg ccc    1545
Glu Pro Val Pro Ala Val Ser Glu Gly Gly Gln Lys Ser Glu Thr Pro
                325                 330                 335 ctc agt cca ccc tgt gcc gac tct gct acc tca gag gca gca gga caa    1593
Leu Ser Pro Pro Cys Ala Asp Ser Ala Thr Ser Glu Ala Ala Gly Gln
            340                 345                 350 agg ccc gtg cat ccc gcc agc gtg ccc agc gtg ccc agc gtg cag ccg    1641
Arg Pro Val His Pro Ala Ser Val Pro Ser Val Pro Ser Val Gln Pro
        355                 360                 365 tcg ctg tta gag gac agc ccg ctg gta cag gcg ctc agt ggg ctg cac    1689
Ser Leu Leu Glu Asp Ser Pro Leu Val Gln Ala Leu Ser Gly Leu His
370                 375                 380 ctg tcc gca gac agg ctg gaa gac agc aat aag ctc aag cgt tcc ttc    1737
Leu Ser Ala Asp Arg Leu Glu Asp Ser Asn Lys Leu Lys Arg Ser Phe
385                 390                 395                 400 tct ctg gat atc aaa tca gtt tca tat tca gcc agc atg gca gca tcc    1785
Ser Leu Asp Ile Lys Ser Val Ser Tyr Ser Ala Ser Met Ala Ala Ser
                405                 410                 415 tta cat ggc ttc tcc tca tca gaa gat gct ttg gaa tac tac aaa cct    1833
Leu His Gly Phe Ser Ser Ser Glu Asp Ala Leu Glu Tyr Tyr Lys Pro
            420                 425                 430 tcc act act ctg gat ggg acc aac aag cta tgc cag ttc tcc cct gtt    1881
Ser Thr Thr Leu Asp Gly Thr Asn Lys Leu Cys Gln Phe Ser Pro Val
        435                 440                 445 cag gaa cta tcg gag cag act ccc gaa acc agt cct gat aag gag gaa    1929
Gln Glu Leu Ser Glu Gln Thr Pro Glu Thr Ser Pro Asp Lys Glu Glu
450                 455                 460 gcc agc atc ccc aag aag ctg cag acc gcc agg cct tca gac agc cag    1977
Ala Ser Ile Pro Lys Lys Leu Gln Thr Ala Arg Pro Ser Asp Ser Gln
465                 470                 475                 480 agc aag cga ttg cat tcg gtc aga acc agc agc agt ggc acc gcc cag    2025
Ser Lys Arg Leu His Ser Val Arg Thr Ser Ser Ser Gly Thr Ala Gln
                485                 490                 495 agg tcc ctt tta tct cca ctg cat cga agt ggg agc gtg gag gac aat    2073
Arg Ser Leu Leu Ser Pro Leu His Arg Ser Gly Ser Val Glu Asp Asn
            500                 505                 510 tac cac acc agc ttc ctt ttc ggc ctt tcc acc agc cag cag cac ctc    2121
Tyr His Thr Ser Phe Leu Phe Gly Leu Ser Thr Ser Gln Gln His Leu
        515                 520                 525 acg aag tct gct ggc ctg ggc ctt aag ggc tgg cac tcg gat atc ttg    2169
Thr Lys Ser Ala Gly Leu Gly Leu Lys Gly Trp His Ser Asp Ile Leu
530                 535                 540 gcc ccc cag acc tct acc cct tcc ctg acc agc agc tgg tat ttt gcc    2217
Ala Pro Gln Thr Ser Thr Pro Ser Leu Thr Ser Ser Trp Tyr Phe Ala
545                 550                 555                 560 aca gag tcc tca cac ttc tac tct gcc tca gcc atc tac gga ggc agt    2265
Thr Glu Ser Ser His Phe Tyr Ser Ala Ser Ala Ile Tyr Gly Gly Ser
                565                 570                 575 gcc agt tac tct gcc tac agc tgc agc cag ctg ccc act tgc gga gac    2313
Ala Ser Tyr Ser Ala Tyr Ser Cys Ser Gln Leu Pro Thr Cys Gly Asp
            580                 585                 590
```

```
caa gtc tat tct gtg cgc agg cgg cag aag cca agt gac aga gct gac    2361
Gln Val Tyr Ser Val Arg Arg Arg Gln Lys Pro Ser Asp Arg Ala Asp
            595                 600                 605 tcg cgg cgg agc tgg cat gaa gag agc ccc ttt gaa aag cag ttt aaa    2409
Ser Arg Arg Ser Trp His Glu Glu Ser Pro Phe Glu Lys Gln Phe Lys
    610                 615                 620 cgc aga agc tgc caa atg gaa ttt gga gag agc atc atg tca gag aac    2457
Arg Arg Ser Cys Gln Met Glu Phe Gly Glu Ser Ile Met Ser Glu Asn
625                 630                 635                 640 agg tca cgg gaa gag ctg ggg aaa gtg ggc agt cag tct agc ttt tcg    2505
Arg Ser Arg Glu Glu Leu Gly Lys Val Gly Ser Gln Ser Ser Phe Ser
                645                 650                 655 ggc agc atg gaa atc att gag gtc tcc tgagaagaaa gacacttgtg          2552
Gly Ser Met Glu Ile Ile Glu Val Ser
                660             665 acttctatag acaattttt tttcttgtt cacaaaaaaa ttccctgtaa atctgaaata    2612
tatatatgta catacatata tatttttgga aaatggagct atggtgtaaa agcaacaggt    2672
ggatcaaccc agttgttact ctcttaacat ctgcatttga gagatcagct aatacttctc    2732
tcaacaaaaa tggaagggca gatgctagaa tccccctag acgaggaaa accatttat      2792
tcagtgaatt acacatcctc ttgttcttaa aaaagcaagt gtctttggtg ttggaggaca    2852
aaatccccta ccattttcac gttgtgctac taagagatct caaatattag tctttgtccg    2912
gaccccttcca tagtacacct tagcgctgag actgagccag cttgggggtc aggtaggtag    2972
accctgttag ggacagagcc tagtggtaaa tccaagagaa atgatcctat ccaaagctga    3032
ttcacaaacc cacgctcacc tgacagccga gggacacgag catcactctg ctggacggac    3092
cattaggggc cttgccaagg tctaccttag caaacccca gtacctcaga caggaaagtc    3152
ggggctttga ccactaccat atctggtagc ccattttcta ggcattgtga ataggtaggt    3212
agctagtcac acttttcaga ccaattcaaa ctgtctatgc acaaaattcc cgtgggccta    3272
gatggagata attttttttt cttctcagct ttatgaagag aagggaaact gtctaggatt    3332
cagctgaacc accaggaacc tggcaacatc acgatttaag ctaaggttgg gaggctaacg    3392
agtctacctc cctctttgta aatcaaagaa ttgttaaaa tgggattgtc aatcctttaa     3452
ataaagatga acttggtttc aagccaaatg tgaatttatt tgggttggta gcagagcagc    3512
agcaccttca aattctcagc caaagcagat gttttgccc tttctgcttc actgcatgga     3572
tacagttggt aaaatgtaat aatatggcag aattttatag gaaacttcct agggaggtaa    3632
attatgggaa gattaagaaa ggtacaaatt gctgaggaga agcaggaaac ctgtttcctt    3692
agtggctttt atccctcgg catgcgatgg ggctgatgtt tctatgattg cctcagactt     3752
tcacatttac tagtagggct gagagaggct ttagtgagga aggaatattc agaataaaac    3812
ggttgagaaa gctgagaaga ccattgagtt ttgatcagtt gtgaatagag tgcaaagcca    3872
tggccaagct gttttttggaa acgctggccg gcgtgtcttc agtggaaaaa gcaaatcaaa    3932
atggagcgag agcaaagggg cgtcctcagt cctcaaccta caatcactgt atggaatcgg    3992
tcctggcagc tgaacatagg aggtcactgg aacaagtgat agtgcagatt ggctttcaaa    4052
catcctcctg gcttgagttt tatcagctac aatgtgggtc ctctttgaa gccttaattc     4112
acaacagcag cttttttgggg gtggggctgg gcgggtgttg tcattgttct ttcccttcct    4172
gtaagtgtcg ctagttgctg cctcgtatct caggttttttc tctgtttttg agaaatggac    4232
agtttttga ccaggatgtg acttcatgtt tcctatggtg acttctaaaa ccagcacaga     4292
```

```
atgatatgac tcaacacaga ccgacttggt tatggggatg atgagccgca cagacctcac    4352
tagttgtgca caaataatgt gctatgatgg ggtgtaaagt gaaggcagaa gagggtcagc    4412
cgcattgtta tgatactggg aaagtgctgg tcaacgattt gagttagttt ttagatatac    4472
attgaaatct ttaatcagac attctcaagt ttcacacagt agtttttgat gttatgtaca    4532
cacacaccaa atgtgtaaca gttcaccact tccagagtgt ggtcatgccc aaaacatgtt    4592
taagaaagga aagcagtagc tccttgctaa cgatgtttca ggaggtttgg ggcacttggt    4652
tttaatgagc ttctgtcatt tagggcttct cttggccatg gtccccttcc ttctggaact    4712
gtgatgtagt cacatcctac agcctttagt gctggttcac tagtgtcaga taatcagttc    4772
ttggaatcga gactgccgtg gcgaaggggt ggcctcggag gcaggctctg gagctgcttg    4832
gatgtcttta ggtggggtgg tggctggctc tcttcagcat gtaattgggg aaaccctcgc    4892
gtctactagg ggtgatacag atggtgattt taaagagcaa aactagactt ctatgtgaga    4952
agtgctggaa aatgatttag gacatgtgta aagttagatg gaaagactgt aaatgtttaa    5012
tatgaatata gtgttctttt gaagtaaggc cagctgttga acggttaaac tgtgcatttc    5072
tcattttgat gtgtcatgta tgttaatgta tgaaatgatt aaataaaatc aaaactggta    5132
cctgtttata cataaatacg agaaaagacc tatctttgca gccataaact cggtgggaac    5192
accaccactc aagttgccaa aggaggcagt ggtgaaacct gtcctgttct cacttaaatg    5252
aggatttagc tcaaaataaa gtggtggtgt catcaggttt attccgtgtt ctgtcattca    5312
catggaacac cggatgatta gctaacagtt tagtgccagc cttcattctt tactgtgtac    5372
gttaaatgca cactacagtg aaaaagccta agacacttgg taaatatttt ctagctgact    5432
gattccagaa cacacaag                                                  5450
```

<210> SEQ ID NO 109
<211> LENGTH: 665
<212> TYPE: PRT
<213> ORGANISM: Homo sapiens

<400> SEQUENCE: 109

```
Met Ala His Glu Met Ile Gly Thr Gln Ile Val Thr Glu Arg Leu Val
1               5                   10                  15

Ala Leu Leu Glu Ser Gly Thr Glu Lys Val Leu Leu Ile Asp Ser Arg
            20                  25                  30

Pro Phe Val Glu Tyr Asn Thr Ser His Ile Leu Glu Ala Ile Asn Ile
        35                  40                  45

Asn Cys Ser Lys Leu Met Lys Arg Arg Leu Gln Gln Asp Lys Val Leu
    50                  55                  60

Ile Thr Glu Leu Ile Gln His Ser Ala Lys His Lys Val Asp Ile Asp
65                  70                  75                  80

Cys Ser Gln Lys Val Val Tyr Asp Gln Ser Ser Gln Asp Val Ala
                85                  90                  95

Ser Leu Ser Ser Asp Cys Phe Leu Thr Val Leu Gly Lys Leu Glu
            100                 105                 110

Lys Ser Phe Asn Ser Val His Leu Leu Ala Gly Phe Ala Glu Phe
        115                 120                 125

Ser Arg Cys Phe Pro Gly Leu Cys Glu Gly Lys Ser Thr Leu Val Pro
    130                 135                 140

Thr Cys Ile Ser Gln Pro Cys Leu Pro Val Ala Asn Ile Gly Pro Thr
145                 150                 155                 160

Arg Ile Leu Pro Asn Leu Tyr Leu Gly Cys Gln Arg Asp Val Leu Asn
```

-continued

```
                165                 170                 175
Lys Glu Leu Ile Gln Gln Asn Gly Ile Gly Tyr Val Leu Asn Ala Ser
            180                 185                 190
Tyr Thr Cys Pro Lys Pro Asp Phe Ile Pro Glu Ser His Phe Leu Arg
        195                 200                 205
Val Pro Val Asn Asp Ser Phe Cys Glu Lys Ile Leu Pro Trp Leu Asp
    210                 215                 220
Lys Ser Val Asp Phe Ile Glu Lys Ala Lys Ser Asn Gly Cys Val
225                 230                 235                 240
Leu Val His Cys Leu Ala Gly Ile Ser Arg Ser Ala Thr Ile Ala Ile
            245                 250                 255
Ala Tyr Ile Met Lys Arg Met Asp Met Ser Leu Asp Glu Ala Tyr Arg
        260                 265                 270
Phe Val Lys Glu Lys Arg Pro Thr Ile Ser Pro Asn Phe Asn Phe Leu
    275                 280                 285
Gly Gln Leu Leu Asp Tyr Glu Lys Lys Ile Lys Asn Gln Thr Gly Ala
290                 295                 300
Ser Gly Pro Lys Ser Lys Leu Lys Leu Leu His Leu Glu Lys Pro Asn
305                 310                 315                 320
Glu Pro Val Pro Ala Val Ser Glu Gly Gly Gln Lys Ser Glu Thr Pro
            325                 330                 335
Leu Ser Pro Pro Cys Ala Asp Ser Ala Thr Ser Glu Ala Ala Gly Gln
        340                 345                 350
Arg Pro Val His Pro Ala Ser Val Pro Ser Val Pro Ser Val Gln Pro
    355                 360                 365
Ser Leu Leu Glu Asp Ser Pro Leu Val Gln Ala Leu Ser Gly Leu His
370                 375                 380
Leu Ser Ala Asp Arg Leu Glu Asp Ser Asn Lys Leu Lys Arg Ser Phe
385                 390                 395                 400
Ser Leu Asp Ile Lys Ser Val Ser Tyr Ser Ala Ser Met Ala Ala Ser
            405                 410                 415
Leu His Gly Phe Ser Ser Ser Glu Asp Ala Leu Glu Tyr Tyr Lys Pro
        420                 425                 430
Ser Thr Thr Leu Asp Gly Thr Asn Lys Leu Cys Gln Phe Ser Pro Val
    435                 440                 445
Gln Glu Leu Ser Glu Gln Thr Pro Glu Thr Ser Pro Asp Lys Glu Glu
450                 455                 460
Ala Ser Ile Pro Lys Lys Leu Gln Thr Ala Arg Pro Ser Asp Ser Gln
465                 470                 475                 480
Ser Lys Arg Leu His Ser Val Arg Thr Ser Ser Gly Thr Ala Gln
            485                 490                 495
Arg Ser Leu Leu Ser Pro Leu His Arg Ser Gly Ser Val Glu Asp Asn
        500                 505                 510
Tyr His Thr Ser Phe Leu Phe Gly Leu Ser Thr Ser Gln Gln His Leu
    515                 520                 525
Thr Lys Ser Ala Gly Leu Gly Leu Lys Gly Trp His Ser Asp Ile Leu
530                 535                 540
Ala Pro Gln Thr Ser Thr Pro Ser Leu Thr Ser Ser Trp Tyr Phe Ala
545                 550                 555                 560
Thr Glu Ser Ser His Phe Tyr Ser Ala Ser Ala Ile Tyr Gly Gly Ser
            565                 570                 575
Ala Ser Tyr Ser Ala Tyr Ser Cys Ser Gln Leu Pro Thr Cys Gly Asp
        580                 585                 590
```

-continued

```
Gln Val Tyr Ser Val Arg Arg Gln Lys Pro Ser Asp Arg Ala Asp
            595                 600                 605
Ser Arg Arg Ser Trp His Glu Glu Ser Pro Phe Glu Lys Gln Phe Lys
    610                 615                 620
Arg Arg Ser Cys Gln Met Glu Phe Gly Glu Ser Ile Met Ser Glu Asn
625                 630                 635                 640
Arg Ser Arg Glu Glu Leu Gly Lys Val Gly Ser Gln Ser Ser Phe Ser
                645                 650                 655
Gly Ser Met Glu Ile Ile Glu Val Ser
                660                 665

<210> SEQ ID NO 110
<211> LENGTH: 625
<212> TYPE: PRT
<213> ORGANISM: Homo sapiens

<400> SEQUENCE: 110

Met Ala Gly Asp Arg Leu Pro Arg Lys Val Met Asp Ala Lys Lys Leu
1               5                   10                  15
Ala Ser Leu Leu Arg Gly Gly Pro Gly Gly Pro Leu Val Ile Asp Ser
                20                  25                  30
Arg Ser Phe Val Glu Tyr Asn Ser Trp His Val Leu Ser Ser Val Asn
            35                  40                  45
Ile Cys Cys Ser Lys Leu Val Lys Arg Arg Leu Gln Gln Gly Lys Val
        50                  55                  60
Thr Ile Ala Glu Leu Ile Gln Pro Ala Ala Arg Ser Gln Val Glu Ala
65                  70                  75                  80
Thr Glu Pro Gln Asp Val Val Val Tyr Asp Gln Ser Thr Arg Asp Ala
                85                  90                  95
Ser Val Leu Ala Ala Asp Ser Phe Leu Ser Ile Leu Leu Ser Lys Leu
            100                 105                 110
Asp Gly Cys Phe Asp Ser Val Ala Ile Leu Thr Gly Gly Phe Ala Thr
        115                 120                 125
Phe Ser Ser Cys Phe Pro Gly Leu Cys Glu Gly Lys Pro Ala Ala Leu
130                 135                 140
Leu Pro Met Ser Leu Ser Gln Pro Cys Leu Pro Val Pro Ser Val Gly
145                 150                 155                 160
Leu Thr Arg Ile Leu Pro His Leu Tyr Leu Gly Ser Gln Lys Asp Val
                165                 170                 175
Leu Asn Lys Asp Leu Met Thr Gln Asn Gly Ile Ser Tyr Val Leu Asn
            180                 185                 190
Ala Ser Asn Ser Cys Pro Lys Pro Asp Phe Ile Cys Glu Ser Arg Phe
        195                 200                 205
Met Arg Val Pro Ile Asn Asp Asn Tyr Cys Glu Lys Leu Leu Pro Trp
    210                 215                 220
Leu Asp Lys Ser Ile Glu Phe Ile Asp Lys Ala Lys Leu Ser Ser Cys
225                 230                 235                 240
Gln Val Ile Val His Cys Leu Ala Gly Ile Ser Arg Ser Ala Thr Ile
                245                 250                 255
Ala Ile Ala Tyr Ile Met Lys Thr Met Gly Met Ser Ser Asp Asp Ala
            260                 265                 270
Tyr Arg Phe Val Lys Asp Arg Arg Pro Ser Ile Ser Pro Asn Phe Asn
        275                 280                 285
Phe Leu Gly Gln Leu Leu Glu Tyr Glu Arg Thr Leu Lys Leu Leu Ala
```

```
                290                 295                 300
Ala Leu Gln Gly Asp Pro Gly Thr Pro Ser Gly Thr Pro Glu Pro Pro
305                 310                 315                 320

Pro Ser Pro Ala Ala Gly Ala Pro Leu Pro Arg Leu Pro Pro Pro Thr
                325                 330                 335

Ser Glu Ser Ala Ala Thr Gly Asn Ala Ala Arg Glu Gly Gly Leu
            340                 345                 350

Ser Ala Gly Gly Glu Pro Pro Ala Pro Pro Thr Pro Pro Ala Thr Ser
            355                 360                 365

Ala Leu Gln Gln Gly Leu Arg Gly Leu His Leu Ser Ser Asp Arg Leu
370                 375                 380

Gln Asp Thr Asn Arg Leu Lys Arg Ser Phe Ser Leu Asp Ile Lys Ser
385                 390                 395                 400

Ala Tyr Ala Pro Ser Arg Arg Pro Asp Gly Pro Gly Pro Pro Asp Pro
                405                 410                 415

Gly Glu Ala Pro Lys Leu Cys Lys Leu Asp Ser Pro Ser Gly Ala Ala
            420                 425                 430

Leu Gly Leu Ser Ser Pro Ser Pro Asp Ser Pro Asp Ala Ala Pro Glu
            435                 440                 445

Ala Arg Pro Arg Pro Arg Arg Arg Pro Arg Pro Ala Gly Ser Pro
450                 455                 460

Ala Arg Ser Pro Ala His Ser Leu Gly Leu Asn Phe Gly Asp Ala Ala
465                 470                 475                 480

Arg Gln Thr Pro Arg His Gly Leu Ser Ala Leu Ser Ala Pro Gly Leu
                485                 490                 495

Pro Gly Pro Gly Gln Pro Ala Gly Pro Gly Ala Trp Ala Pro Pro Leu
            500                 505                 510

Asp Ser Pro Gly Thr Pro Ser Pro Asp Gly Pro Trp Cys Phe Ser Pro
            515                 520                 525

Glu Gly Ala Gln Gly Ala Gly Gly Val Leu Phe Ala Pro Phe Gly Arg
530                 535                 540

Ala Gly Ala Pro Gly Pro Gly Gly Gly Ser Asp Leu Arg Arg Arg Glu
545                 550                 555                 560

Ala Ala Arg Ala Glu Pro Arg Asp Ala Arg Thr Gly Trp Pro Glu Glu
                565                 570                 575

Pro Ala Pro Glu Thr Gln Phe Lys Arg Arg Ser Cys Gln Met Glu Phe
            580                 585                 590

Glu Glu Gly Met Val Glu Gly Arg Ala Arg Gly Glu Glu Leu Ala Ala
            595                 600                 605

Leu Gly Lys Gln Ala Ser Phe Ser Gly Ser Val Glu Val Ile Glu Val
            610                 615                 620

Ser
625

<210> SEQ ID NO 111
<211> LENGTH: 381
<212> TYPE: PRT
<213> ORGANISM: Homo sapiens

<400> SEQUENCE: 111

Met Ile Asp Thr Leu Arg Pro Val Pro Phe Ala Ser Glu Met Ala Ile
1               5                   10                  15

Ser Lys Thr Val Ala Trp Leu Asn Glu Gln Leu Glu Leu Gly Asn Glu
            20                  25                  30
```

-continued

```
Arg Leu Leu Leu Met Asp Cys Arg Pro Gln Glu Leu Tyr Glu Ser Ser
        35                  40                  45

His Ile Glu Ser Ala Ile Asn Val Ala Ile Pro Gly Ile Met Leu Arg
    50                  55                  60

Arg Leu Gln Lys Gly Asn Leu Pro Val Arg Ala Leu Phe Thr Arg Gly
65                  70                  75                  80

Glu Asp Arg Asp Arg Phe Thr Arg Arg Cys Gly Thr Asp Thr Val Val
                85                  90                  95

Leu Tyr Asp Glu Ser Ser Ser Asp Trp Asn Glu Asn Thr Gly Gly Glu
            100                 105                 110

Ser Leu Gly Leu Leu Lys Leu Lys Asp Glu Gly Cys Arg
        115                 120                 125

Ala Phe Tyr Leu Glu Gly Gly Phe Ser Lys Phe Gln Ala Glu Phe Ser
    130                 135                 140

Leu His Cys Glu Thr Asn Leu Asp Gly Ser Cys Ser Ser Ser Ser Pro
145                 150                 155                 160

Pro Leu Pro Val Leu Gly Leu Gly Leu Arg Ile Ser Ser Asp Ser
                165                 170                 175

Ser Ser Asp Ile Glu Ser Asp Leu Asp Arg Asp Pro Asn Ser Ala Thr
            180                 185                 190

Asp Ser Asp Gly Ser Pro Leu Ser Asn Ser Gln Pro Ser Phe Pro Val
        195                 200                 205

Glu Ile Leu Pro Phe Leu Tyr Leu Gly Cys Ala Lys Asp Ser Thr Asn
210                 215                 220

Leu Asp Val Leu Glu Glu Phe Gly Ile Lys Tyr Ile Leu Asn Val Thr
225                 230                 235                 240

Pro Asn Leu Pro Asn Leu Phe Glu Asn Ala Gly Glu Phe Lys Tyr Lys
                245                 250                 255

Gln Ile Pro Ile Ser Asp His Trp Ser Gln Asn Leu Ser Gln Phe Phe
            260                 265                 270

Pro Glu Ala Ile Ser Phe Ile Asp Glu Ala Arg Gly Lys Asn Cys Gly
        275                 280                 285

Val Leu Val His Cys Leu Ala Gly Ile Ser Arg Ser Val Thr Val Thr
290                 295                 300

Val Ala Tyr Leu Met Gln Lys Leu Asn Leu Ser Met Asn Asp Ala Tyr
305                 310                 315                 320

Asp Ile Val Lys Met Lys Lys Ser Asn Ile Ser Pro Asn Phe Asn Phe
                325                 330                 335

Met Gly Gln Leu Leu Asp Phe Glu Arg Thr Leu Gly Leu Ser Ser Pro
            340                 345                 350

Cys Asp Asn Arg Val Pro Ala Gln Gln Leu Tyr Phe Thr Thr Pro Ser
        355                 360                 365

Asn Gln Asn Val Tyr Gln Val Asp Ser Leu Gln Ser Thr
370                 375                 380

<210> SEQ ID NO 112
<211> LENGTH: 482
<212> TYPE: PRT
<213> ORGANISM: Homo sapiens

<400> SEQUENCE: 112

Met Pro Pro Ser Pro Leu Asp Asp Arg Val Val Ala Leu Ser Arg
1               5                  10                  15

Pro Val Arg Pro Gln Asp Leu Asn Leu Cys Leu Asp Ser Ser Tyr Leu
                20                  25                  30
```

-continued

```
Gly Ser Ala Asn Pro Gly Ser Asn Ser His Pro Pro Val Ile Ala Thr
        35                  40                  45

Thr Val Val Ser Leu Lys Ala Ala Asn Leu Thr Tyr Met Pro Ser Ser
 50                  55                  60

Ser Gly Ser Ala Arg Ser Leu Asn Cys Gly Cys Ser Ser Ala Ser Cys
 65                  70                  75                  80

Cys Thr Val Ala Thr Tyr Asp Lys Asp Asn Gln Ala Gln Thr Gln Ala
                 85                  90                  95

Ile Ala Ala Gly Thr Thr Thr Thr Ala Ile Gly Thr Ser Thr Thr Cys
                100                 105                 110

Pro Ala Asn Gln Met Val Asn Asn Glu Asn Thr Gly Ser Leu Ser
            115                 120                 125

Pro Ser Ser Gly Val Gly Ser Pro Val Ser Gly Thr Pro Lys Gln Leu
130                 135                 140

Ala Ser Ile Lys Ile Ile Tyr Pro Asn Asp Leu Ala Lys Lys Met Thr
145                 150                 155                 160

Lys Cys Ser Lys Ser His Leu Pro Ser Gln Gly Pro Val Ile Ile Asp
                165                 170                 175

Cys Arg Pro Phe Met Glu Tyr Asn Lys Ser His Ile Gln Gly Ala Val
                180                 185                 190

His Ile Asn Cys Ala Asp Lys Ile Ser Arg Arg Leu Gln Gln Gly
            195                 200                 205

Lys Ile Thr Val Leu Asp Leu Ile Ser Cys Arg Glu Gly Lys Asp Ser
210                 215                 220

Phe Lys Arg Ile Phe Ser Lys Glu Ile Ile Val Tyr Asp Glu Asn Thr
225                 230                 235                 240

Asn Glu Pro Ser Arg Val Met Pro Ser Gln Pro Leu His Ile Val Leu
                245                 250                 255

Glu Ser Leu Lys Arg Glu Gly Lys Glu Pro Leu Val Leu Lys Gly Gly
                260                 265                 270

Leu Ser Ser Phe Lys Gln Asn His Glu Asn Leu Cys Asp Asn Ser Leu
275                 280                 285

Gln Leu Gln Glu Cys Arg Glu Val Gly Gly Gly Ala Ser Ala Ala Ser
290                 295                 300

Ser Leu Leu Pro Gln Pro Ile Pro Thr Thr Pro Asp Ile Glu Asn Ala
305                 310                 315                 320

Glu Leu Thr Pro Ile Leu Pro Phe Leu Phe Leu Gly Asn Glu Gln Asp
                325                 330                 335

Ala Gln Asp Leu Asp Thr Met Gln Arg Leu Asn Ile Gly Tyr Val Ile
            340                 345                 350

Asn Val Thr Thr His Leu Pro Leu Tyr His Tyr Glu Lys Gly Leu Phe
            355                 360                 365

Asn Tyr Lys Arg Leu Pro Ala Thr Asp Ser Asn Lys Gln Asn Leu Arg
        370                 375                 380

Gln Tyr Phe Glu Glu Ala Phe Glu Phe Ile Glu Glu Ala His Gln Cys
385                 390                 395                 400

Gly Lys Gly Leu Leu Ile His Cys Gln Ala Gly Val Ser Arg Ser Ala
                405                 410                 415

Thr Ile Val Ile Ala Tyr Leu Met Lys His Thr Arg Met Thr Met Thr
            420                 425                 430

Asp Ala Tyr Lys Phe Val Lys Gly Lys Arg Pro Ile Ile Ser Pro Asn
        435                 440                 445
```

```
Leu Asn Phe Met Gly Gln Leu Leu Glu Phe Glu Glu Asp Leu Asn Asn
    450                 455                 460
Gly Val Thr Pro Arg Ile Leu Thr Pro Lys Leu Met Gly Val Glu Thr
465                 470                 475                 480
Val Val

<210> SEQ ID NO 113
<211> LENGTH: 2756
<212> TYPE: DNA
<213> ORGANISM: Mus musculus
<220> FEATURE:
<221> NAME/KEY: CDS
<222> LOCATION: (369)..(2348)

<400> SEQUENCE: 113
gactgaggtt gtcagcccag tgtaaagctg ttggagtgag ggcagaaagg taaaggatga    60
tgtaatgcct ggctgcccta gagcatcttt tgttgtggga tgggtattcc catcatctct   120
atgaatctag tgtgaggggc tgctttgtgg aaggaatcct ttgcaagagc atatcaacag   180
gaaagagaaa gagacattca gttggagggc tcttgctgaa atggatttaa ctctcctctt   240
gccagtcacc actagcctga cctcatacat ttttagtaca atggagtggc tgagcctttg   300
agcacagcac cattcatcca tcgtggcaaa ttaaagaacg aggtggggaa agaggactta   360 ttgttgtc atg gcc cat gag atg att gga act caa att gtt act gag agc    410
         Met Ala His Glu Met Ile Gly Thr Gln Ile Val Thr Glu Ser
           1               5                  10 ttg gtg gct ctg ctg gaa agt gga acg gaa aaa gtg ctg cta att gat    458
Leu Val Ala Leu Leu Glu Ser Gly Thr Glu Lys Val Leu Leu Ile Asp
 15                  20                  25                  30 agc cga cca ttt gtg gaa tac aat acg tct cac att ttg gaa gcc att    506
Ser Arg Pro Phe Val Glu Tyr Asn Thr Ser His Ile Leu Glu Ala Ile
                 35                  40                  45 aat atc aac tgc tcc aaa ctg atg aag cga agg ttg caa cag gac aaa    554
Asn Ile Asn Cys Ser Lys Leu Met Lys Arg Arg Leu Gln Gln Asp Lys
             50                  55                  60 gta tta att aca gaa cta atc cac caa tct aca aag cat aag gtt gac    602
Val Leu Ile Thr Glu Leu Ile His Gln Ser Thr Lys His Lys Val Asp
         65                  70                  75 att gac tgc aat caa aga gtg gta gtt tat gat cac agt tca caa gat    650
Ile Asp Cys Asn Gln Arg Val Val Val Tyr Asp His Ser Ser Gln Asp
     80                  85                  90 gtt ggt tct ctg tcg tca gac tgc ttt ctc act gta ctt ctg ggt aag    698
Val Gly Ser Leu Ser Ser Asp Cys Phe Leu Thr Val Leu Leu Gly Lys
 95                 100                 105                 110 ctg gag aga agc ttc aac tct gtc cac ctg ctt gca ggt ggc ttt gct    746
Leu Glu Arg Ser Phe Asn Ser Val His Leu Leu Ala Gly Gly Phe Ala
                115                 120                 125 gag ttc tct cgt tgt ttc cct ggc ctc tgt gaa gga aag tcc act cta    794
Glu Phe Ser Arg Cys Phe Pro Gly Leu Cys Glu Gly Lys Ser Thr Leu
            130                 135                 140 gtc cct acc tgc ata tct cag cct tgc tta cct gtt gcg aac att ggg    842
Val Pro Thr Cys Ile Ser Gln Pro Cys Leu Pro Val Ala Asn Ile Gly
        145                 150                 155 cca act cga att ctt ccc aat ctc tat ctt ggc tgc cag cga gat gtc    890
Pro Thr Arg Ile Leu Pro Asn Leu Tyr Leu Gly Cys Gln Arg Asp Val
    160                 165                 170 ctc aac aag gac ctg atg caa cag aat ggg att ggc tat gtg tta aat    938
Leu Asn Lys Asp Leu Met Gln Gln Asn Gly Ile Gly Tyr Val Leu Asn
175                 180                 185                 190
```

```
                                                          -continued gcc agc aat acc tgt cca aag cct gac ttc ata cct gaa tct cac ttc      986
Ala Ser Asn Thr Cys Pro Lys Pro Asp Phe Ile Pro Glu Ser His Phe
            195                 200                 205 ctg cga gtg cct gtg aat gac agc ttt tgt gag aaa atc cta cca tgg     1034
Leu Arg Val Pro Val Asn Asp Ser Phe Cys Glu Lys Ile Leu Pro Trp
        210                 215                 220 ttg gac aag tct gtg gat ttc att gag aaa gca aaa gcc tcc aat ggc     1082
Leu Asp Lys Ser Val Asp Phe Ile Glu Lys Ala Lys Ala Ser Asn Gly
            225                 230                 235 tgt gtg ctt atc cac tgc tta gct ggg atc tct cgc tcc gcc act att     1130
Cys Val Leu Ile His Cys Leu Ala Gly Ile Ser Arg Ser Ala Thr Ile
        240                 245                 250 gct att gcc tac atc atg aag agg atg gac atg tct cta gat gag gct     1178
Ala Ile Ala Tyr Ile Met Lys Arg Met Asp Met Ser Leu Asp Glu Ala
255                 260                 265                 270 tac aga ttt gtg aaa gaa aaa aga cct act ata tct ccg aat ttt aat     1226
Tyr Arg Phe Val Lys Glu Lys Arg Pro Thr Ile Ser Pro Asn Phe Asn
                275                 280                 285 ttt atg ggc caa ctc atg gac tat gag aag acg att aat aac cag act     1274
Phe Met Gly Gln Leu Met Asp Tyr Glu Lys Thr Ile Asn Asn Gln Thr
        290                 295                 300 gga atg tca ggg cca aag agc aaa ctg aag ctg ctg cac cta gac aaa     1322
Gly Met Ser Gly Pro Lys Ser Lys Leu Lys Leu Leu His Leu Asp Lys
            305                 310                 315 ccc agt gag ccc gtg cct gca gcc tca gag ggc gga tgg aag agt gca     1370
Pro Ser Glu Pro Val Pro Ala Ala Ser Glu Gly Gly Trp Lys Ser Ala
320                 325                 330 ctg tct ctc agt cca ccc tgt gcc aac tcg acc tcg gag gca tca ggg     1418
Leu Ser Leu Ser Pro Pro Cys Ala Asn Ser Thr Ser Glu Ala Ser Gly
335                 340                 345                 350 caa agg ctt gtg cat cct gca agt gtg ccc cgc tta cag ccg tca ctc     1466
Gln Arg Leu Val His Pro Ala Ser Val Pro Arg Leu Gln Pro Ser Leu
            355                 360                 365 tta gag gac agt ccg ctg gta cag gcg ctc agt ggg ctc cag ctg tcc     1514
Leu Glu Asp Ser Pro Leu Val Gln Ala Leu Ser Gly Leu Gln Leu Ser
        370                 375                 380 tca gag aag ctg gaa gac agc act aag ctc aag cgt tcc ttc tct ctc     1562
Ser Glu Lys Leu Glu Asp Ser Thr Lys Leu Lys Arg Ser Phe Ser Leu
            385                 390                 395 gat atc aaa tct gtt tca tat tca gcc agt atg gcc gcg tcc cta cac     1610
Asp Ile Lys Ser Val Ser Tyr Ser Ala Ser Met Ala Ala Ser Leu His
        400                 405                 410 ggc ttc tcg tca gag gag gct tta gac tac tgc aaa cct tct gcc aca     1658
Gly Phe Ser Ser Glu Glu Ala Leu Asp Tyr Cys Lys Pro Ser Ala Thr
415                 420                 425                 430 ctg gat ggg acc aac aag ctc tgc cag ttc tcc ccc gtt cag gag gta     1706
Leu Asp Gly Thr Asn Lys Leu Cys Gln Phe Ser Pro Val Gln Glu Val
            435                 440                 445 tca gaa cag agt cca gag acc agc ccg gat aag gag gag gcc cac atc     1754
Ser Glu Gln Ser Pro Glu Thr Ser Pro Asp Lys Glu Glu Ala His Ile
        450                 455                 460 ccc aag cag ccc caa cct ccc agg cct tct gag agc cag gtc aca cgc     1802
Pro Lys Gln Pro Gln Pro Pro Arg Pro Ser Glu Ser Gln Val Thr Arg
            465                 470                 475 ttg cac tca gtg aga acc ggc agt agt ggg tcc acc cag agg ccc ttc     1850
Leu His Ser Val Arg Thr Gly Ser Ser Gly Ser Thr Gln Arg Pro Phe
        480                 485                 490 ttc tcg cca ctg cat cgg agc ggg agt gta gag gac aat tac cat acc     1898
Phe Ser Pro Leu His Arg Ser Gly Ser Val Glu Asp Asn Tyr His Thr
495                 500                 505                 510
```

```
aac ttc ctt ttt ggc ctt tcc acc agc cag caa cac ctc acc aag tct    1946
Asn Phe Leu Phe Gly Leu Ser Thr Ser Gln Gln His Leu Thr Lys Ser
            515                 520                 525 gca ggg ctt ggc ctc aag ggc tgg cac tca gat att ctg gct ccc cag    1994
Ala Gly Leu Gly Leu Lys Gly Trp His Ser Asp Ile Leu Ala Pro Gln
        530                 535                 540 tcc tct gcc ccc tcc ctg acc agc agt tgg tat ttt gct acg gag cct    2042
Ser Ser Ala Pro Ser Leu Thr Ser Ser Trp Tyr Phe Ala Thr Glu Pro
            545                 550                 555 tca cac ttg tac tct gct tca gcc atc tat gga ggc aac agc agt tac    2090
Ser His Leu Tyr Ser Ala Ser Ala Ile Tyr Gly Gly Asn Ser Ser Tyr
        560                 565                 570 tct gcc tac agc tgt ggc cag ctg ccc act tgc agt gac caa atc tat    2138
Ser Ala Tyr Ser Cys Gly Gln Leu Pro Thr Cys Ser Asp Gln Ile Tyr
575                 580                 585                 590 tct gtt cgt agg cgg cag aag cct act gac aga gct gac tcg agg cgg    2186
Ser Val Arg Arg Arg Gln Lys Pro Thr Asp Arg Ala Asp Ser Arg Arg
                595                 600                 605 agc tgg cat gaa gag agc ccc ttt gaa aag cag ttt aaa cgc aga agc    2234
Ser Trp His Glu Glu Ser Pro Phe Glu Lys Gln Phe Lys Arg Arg Ser
            610                 615                 620 tgc caa atg gaa ttt gga gag agc att atg tcg gag aac agg tcc agg    2282
Cys Gln Met Glu Phe Gly Glu Ser Ile Met Ser Glu Asn Arg Ser Arg
        625                 630                 635 gag gag ctg ggc aag gtg ggc agc cag tcc agc ttc tcc ggc agc atg    2330
Glu Glu Leu Gly Lys Val Gly Ser Gln Ser Ser Phe Ser Gly Ser Met
            640                 645                 650 gag atc atc gag gtc tct tgagaagacc tcgtcgcttc tgttgacagt           2378
Glu Ile Ile Glu Val Ser
655                 660 tttgtttcct gttcacaaaa aatagtccct gtaaatctga aatatgtata tgtacataca   2438
tatatatttt tggaatatag agctacggta taaaagcaac agatggatca acacagttgt   2498
tctctcagca cctgcactga gaatagctaa ctctcagaaa agattggaag gtagatgtt    2558 agaattctcc cagccaggag aagagatttg gttcagtgaa ttgcacatct tcttgttcct   2618
acaaaagcaa gggttttgtt tgtttgtatg ttgtttgttt ttaatgttag agggcaaaat   2678
ccctcccatt ttcacgtgca acagaggtct cagaactcat ctctgtccag gcccttccct   2738
agtgcacctt agcgctaa                                                 2756

<210> SEQ ID NO 114
<211> LENGTH: 660
<212> TYPE: PRT
<213> ORGANISM: Mus musculus

<400> SEQUENCE: 114

Met Ala His Glu Met Ile Gly Thr Gln Ile Val Thr Glu Ser Leu Val
1               5                   10                  15

Ala Leu Leu Glu Ser Gly Thr Glu Lys Val Leu Leu Ile Asp Ser Arg
            20                  25                  30

Pro Phe Val Glu Tyr Asn Thr Ser His Ile Leu Glu Ala Ile Asn Ile
        35                  40                  45

Asn Cys Ser Lys Leu Met Lys Arg Arg Leu Gln Gln Asp Lys Val Leu
    50                  55                  60

Ile Thr Glu Leu Ile His Gln Ser Thr Lys His Lys Val Asp Ile Asp
65                  70                  75                  80

Cys Asn Gln Arg Val Val Val Tyr Asp His Ser Ser Gln Asp Val Gly
```

-continued

```
                    85                  90                  95
Ser Leu Ser Ser Asp Cys Phe Leu Thr Val Leu Leu Gly Lys Leu Glu
                100                 105                 110
Arg Ser Phe Asn Ser Val His Leu Leu Ala Gly Gly Phe Ala Glu Phe
            115                 120                 125
Ser Arg Cys Phe Pro Gly Leu Cys Glu Gly Lys Ser Thr Leu Val Pro
        130                 135                 140
Thr Cys Ile Ser Gln Pro Cys Leu Pro Val Ala Asn Ile Gly Pro Thr
145                 150                 155                 160
Arg Ile Leu Pro Asn Leu Tyr Leu Gly Cys Gln Arg Asp Val Leu Asn
                165                 170                 175
Lys Asp Leu Met Gln Gln Asn Gly Ile Gly Tyr Val Leu Asn Ala Ser
                180                 185                 190
Asn Thr Cys Pro Lys Pro Asp Phe Ile Pro Glu Ser His Phe Leu Arg
            195                 200                 205
Val Pro Val Asn Asp Ser Phe Cys Glu Lys Ile Leu Pro Trp Leu Asp
        210                 215                 220
Lys Ser Val Asp Phe Ile Glu Lys Ala Lys Ala Ser Asn Gly Cys Val
225                 230                 235                 240
Leu Ile His Cys Leu Ala Gly Ile Ser Arg Ser Ala Thr Ile Ala Ile
                245                 250                 255
Ala Tyr Ile Met Lys Arg Met Asp Met Ser Leu Asp Glu Ala Tyr Arg
                260                 265                 270
Phe Val Lys Glu Lys Arg Pro Thr Ile Ser Pro Asn Phe Asn Phe Met
            275                 280                 285
Gly Gln Leu Met Asp Tyr Glu Lys Thr Ile Asn Asn Gln Thr Gly Met
        290                 295                 300
Ser Gly Pro Lys Ser Lys Leu Lys Leu Leu His Leu Asp Lys Pro Ser
305                 310                 315                 320
Glu Pro Val Pro Ala Ala Ser Glu Gly Gly Trp Lys Ser Ala Leu Ser
                325                 330                 335
Leu Ser Pro Pro Cys Ala Asn Ser Thr Ser Glu Ala Ser Gly Gln Arg
            340                 345                 350
Leu Val His Pro Ala Ser Val Pro Arg Leu Gln Pro Ser Leu Leu Glu
        355                 360                 365
Asp Ser Pro Leu Val Gln Ala Leu Ser Gly Leu Gln Leu Ser Ser Glu
        370                 375                 380
Lys Leu Glu Asp Ser Thr Lys Leu Lys Arg Ser Phe Ser Leu Asp Ile
385                 390                 395                 400
Lys Ser Val Ser Tyr Ser Ala Ser Met Ala Ala Ser Leu His Gly Phe
                405                 410                 415
Ser Ser Glu Glu Ala Leu Asp Tyr Cys Lys Pro Ser Ala Thr Leu Asp
                420                 425                 430
Gly Thr Asn Lys Leu Cys Gln Phe Ser Pro Val Gln Glu Val Ser Glu
            435                 440                 445
Gln Ser Pro Glu Thr Ser Pro Asp Lys Glu Glu Ala His Ile Pro Lys
        450                 455                 460
Gln Pro Gln Pro Pro Arg Pro Ser Glu Ser Gln Val Thr Arg Leu His
465                 470                 475                 480
Ser Val Arg Thr Gly Ser Ser Gly Ser Thr Gln Arg Pro Phe Phe Ser
                485                 490                 495
Pro Leu His Arg Ser Gly Ser Val Glu Asp Asn Tyr His Thr Asn Phe
                500                 505                 510
```

```
Leu Phe Gly Leu Ser Thr Ser Gln Gln His Leu Thr Lys Ser Ala Gly
            515                 520                 525

Leu Gly Leu Lys Gly Trp His Ser Asp Ile Leu Ala Pro Gln Ser Ser
        530                 535                 540

Ala Pro Ser Leu Thr Ser Ser Trp Tyr Phe Ala Thr Glu Pro Ser His
545                 550                 555                 560

Leu Tyr Ser Ala Ser Ala Ile Tyr Gly Gly Asn Ser Ser Tyr Ser Ala
                565                 570                 575

Tyr Ser Cys Gly Gln Leu Pro Thr Cys Ser Asp Gln Ile Tyr Ser Val
            580                 585                 590

Arg Arg Arg Gln Lys Pro Thr Asp Arg Ala Asp Ser Arg Arg Ser Trp
        595                 600                 605

His Glu Glu Ser Pro Phe Glu Lys Gln Phe Lys Arg Arg Ser Cys Gln
            610                 615                 620

Met Glu Phe Gly Glu Ser Ile Met Ser Glu Asn Arg Ser Arg Glu Glu
625                 630                 635                 640

Leu Gly Lys Val Gly Ser Gln Ser Ser Phe Ser Gly Ser Met Glu Ile
                645                 650                 655

Ile Glu Val Ser
            660

<210> SEQ ID NO 115
<211> LENGTH: 408
<212> TYPE: DNA
<213> ORGANISM: Homo sapiens

<400> SEQUENCE: 115
acaatggagt ggctgagcct ttgagcacac caccattaca tcatcgtggc aaattaaaga      60
aggaggtggg aaaagaggac ttattgttgt catggcccat gagatgattg aactcaaat     120 tgttactgag aggttggtgg ctctgctgga aagtggaacg gaaaaagtgc tgctaattga    180
tagccggcca tttgtggaat acaatacatc ccacattttg gaagccatta atatcaactg    240
ctccaagctt atgaagcgaa ggttgcaaca ggacaaagtg ttaattacag agctcatcca    300
gcattcagcg aaacataagg ttgacattga ttgcagtcag aaggttgtag tttacgatca    360
aagctcccaa gatgttgcct ctctctcttc agactgtttt ctcactgt               408

<210> SEQ ID NO 116
<211> LENGTH: 13
<212> TYPE: PRT
<213> ORGANISM: Homo sapiens

<400> SEQUENCE: 116

Gly Thr Gln Ile Val Thr Glu Arg Leu Val Ala Leu Leu
1               5                   10

<210> SEQ ID NO 117
<211> LENGTH: 13
<212> TYPE: PRT
<213> ORGANISM: Homo sapiens

<400> SEQUENCE: 117

Leu Leu Glu Ser Gly Thr Glu Lys Val Leu Leu Ile Asp
1               5                   10

<210> SEQ ID NO 118
<211> LENGTH: 13
<212> TYPE: PRT
```

<213> ORGANISM: Homo sapiens

<400> SEQUENCE: 118

Glu Leu Ile Gln His Ser Ala Lys His Lys Val Asp Ile
1               5                   10

<210> SEQ ID NO 119
<211> LENGTH: 13
<212> TYPE: PRT
<213> ORGANISM: Homo sapiens

<400> SEQUENCE: 119

Val Asp Ile Asp Cys Ser Gln Lys Val Val Val Tyr Asp
1               5                   10

<210> SEQ ID NO 120
<211> LENGTH: 13
<212> TYPE: PRT
<213> ORGANISM: Homo sapiens

<400> SEQUENCE: 120

Asp Arg Leu Glu Asp Ser Asn Lys Leu Lys Arg Ser Phe
1               5                   10

<210> SEQ ID NO 121
<211> LENGTH: 13
<212> TYPE: PRT
<213> ORGANISM: Homo sapiens

<400> SEQUENCE: 121

Thr Thr Leu Asp Gly Thr Asn Lys Leu Cys Gln Phe Ser
1               5                   10

<210> SEQ ID NO 122
<211> LENGTH: 13
<212> TYPE: PRT
<213> ORGANISM: Homo sapiens

<400> SEQUENCE: 122

Pro Lys Lys Leu Gln Thr Ala Arg Pro Ser Asp Ser Gln
1               5                   10

<210> SEQ ID NO 123
<211> LENGTH: 13
<212> TYPE: PRT
<213> ORGANISM: Homo sapiens

<400> SEQUENCE: 123

Pro Ser Asp Ser Gln Ser Lys Arg Leu His Ser Val Arg
1               5                   10

<210> SEQ ID NO 124
<211> LENGTH: 13
<212> TYPE: PRT
<213> ORGANISM: Homo sapiens

<400> SEQUENCE: 124

Ser Lys Arg Leu His Ser Val Arg Thr Ser Ser Ser Gly
1               5                   10

<210> SEQ ID NO 125
<211> LENGTH: 13
<212> TYPE: PRT
<213> ORGANISM: Homo sapiens -continued

```
<400> SEQUENCE: 125

Gly Asp Gln Val Tyr Ser Val Arg Arg Arg Gln Lys Pro
1               5                   10

<210> SEQ ID NO 126
<211> LENGTH: 13
<212> TYPE: PRT
<213> ORGANISM: Homo sapiens

<400> SEQUENCE: 126

Arg Arg Gln Lys Pro Ser Asp Arg Ala Asp Ser Arg Arg
1               5                   10

<210> SEQ ID NO 127
<211> LENGTH: 13
<212> TYPE: PRT
<213> ORGANISM: Homo sapiens

<400> SEQUENCE: 127

Ser Asp Arg Ala Asp Ser Arg Arg Ser Trp His Glu Glu
1               5                   10

<210> SEQ ID NO 128
<211> LENGTH: 14
<212> TYPE: PRT
<213> ORGANISM: Homo sapiens

<400> SEQUENCE: 128

Pro Phe Val Glu Tyr Asn Thr Ser His Ile Leu Glu Ala Ile
1               5                   10

<210> SEQ ID NO 129
<211> LENGTH: 14
<212> TYPE: PRT
<213> ORGANISM: Homo sapiens

<400> SEQUENCE: 129

Glu Ala Ile Asn Ile Asn Cys Ser Lys Leu Met Lys Arg Arg
1               5                   10

<210> SEQ ID NO 130
<211> LENGTH: 14
<212> TYPE: PRT
<213> ORGANISM: Homo sapiens

<400> SEQUENCE: 130

Ile Gly Tyr Val Leu Asn Ala Ser Tyr Thr Cys Pro Lys Pro
1               5                   10

<210> SEQ ID NO 131
<211> LENGTH: 14
<212> TYPE: PRT
<213> ORGANISM: Homo sapiens

<400> SEQUENCE: 131

Leu Arg Val Pro Val Asn Asp Ser Phe Cys Glu Lys Ile Leu
1               5                   10

<210> SEQ ID NO 132
<211> LENGTH: 14
<212> TYPE: PRT
<213> ORGANISM: Homo sapiens

<400> SEQUENCE: 132
```

```
Glu Lys Lys Ile Lys Asn Gln Thr Gly Ala Ser Gly Pro Lys
1               5                   10
```

<210> SEQ ID NO 133
<211> LENGTH: 14
<212> TYPE: PRT
<213> ORGANISM: Homo sapiens

<400> SEQUENCE: 133

```
Ser Ile Met Ser Glu Asn Arg Ser Arg Glu Leu Gly Lys
1               5                   10
```

<210> SEQ ID NO 134
<211> LENGTH: 140
<212> TYPE: PRT
<213> ORGANISM: Homo sapiens

<400> SEQUENCE: 134

```
Gly Pro Thr Arg Ile Leu Pro Asn Leu Tyr Leu Gly Cys Gln Arg Asp
1               5                   10                  15

Val Leu Asn Lys Glu Leu Ile Gln Gln Asn Gly Ile Gly Tyr Val Leu
                20                  25                  30

Asn Ala Ser Tyr Thr Cys Pro Lys Pro Asp Phe Ile Pro Glu Ser His
                35                  40                  45

Phe Leu Arg Val Pro Val Asn Asp Ser Phe Cys Glu Lys Ile Leu Pro
        50                  55                  60

Trp Leu Asp Lys Ser Val Asp Phe Ile Glu Lys Ala Lys Ala Ser Asn
65                  70                  75                  80

Gly Cys Val Leu Val His Cys Leu Ala Gly Ile Ser Arg Ser Ala Thr
                85                  90                  95

Ile Ala Ile Ala Tyr Ile Met Lys Arg Met Asp Met Ser Leu Asp Glu
                100                 105                 110

Ala Tyr Arg Phe Val Lys Glu Lys Arg Pro Thr Ile Ser Pro Asn Phe
            115                 120                 125

Asn Phe Leu Gly Gln Leu Leu Asp Tyr Glu Lys Lys
            130                 135                 140
```

<210> SEQ ID NO 135
<211> LENGTH: 140
<212> TYPE: PRT
<213> ORGANISM: Mus musculus

<400> SEQUENCE: 135

```
Gly Pro Thr Arg Ile Leu Pro Asn Leu Tyr Leu Gly Cys Gln Arg Asp
1               5                   10                  15

Val Leu Asn Lys Asp Leu Met Gln Gln Asn Gly Ile Gly Tyr Val Leu
                20                  25                  30

Asn Ala Ser Asn Thr Cys Pro Lys Pro Asp Phe Ile Pro Glu Ser His
                35                  40                  45

Phe Leu Arg Val Pro Val Asn Asp Ser Phe Cys Glu Lys Ile Leu Pro
        50                  55                  60

Trp Leu Asp Lys Ser Val Asp Phe Ile Glu Lys Ala Lys Ala Ser Asn
65                  70                  75                  80

Gly Cys Val Leu Ile His Cys Leu Ala Gly Ile Ser Arg Ser Ala Thr
                85                  90                  95

Ile Ala Ile Ala Tyr Ile Met Lys Arg Met Asp Met Ser Leu Asp Glu
                100                 105                 110

Ala Tyr Arg Phe Val Lys Glu Lys Arg Pro Thr Ile Ser Pro Asn Phe
```

```
            115                 120                 125
Asn Phe Met Gly Gln Leu Met Asp Tyr Glu Lys Thr
        130                 135                 140
```

<210> SEQ ID NO 136
<211> LENGTH: 38
<212> TYPE: DNA
<213> ORGANISM: Homo sapiens

<400> SEQUENCE: 136
gcagcagcgg ccgcattggg ccaacccgaa ttcttccc           38

<210> SEQ ID NO 137
<211> LENGTH: 37
<212> TYPE: DNA
<213> ORGANISM: Homo sapiens

<400> SEQUENCE: 137
gcagcagtcg acggagacct caatgatttc catgctg            37

<210> SEQ ID NO 138
<211> LENGTH: 39
<212> TYPE: DNA
<213> ORGANISM: Homo sapiens

<400> SEQUENCE: 138
gcagcagcgg ccgcatggcc catgagatga ttggaactc          39

<210> SEQ ID NO 139
<211> LENGTH: 37
<212> TYPE: DNA
<213> ORGANISM: Homo sapiens

<400> SEQUENCE: 139
gcagcagtcg accttcttct catagtccag gagttgg            37

<210> SEQ ID NO 140
<211> LENGTH: 38
<212> TYPE: DNA
<213> ORGANISM: Homo sapiens

<400> SEQUENCE: 140
gcagcagcgg ccgcattggg ccaactcgaa ttcttccc           38

<210> SEQ ID NO 141
<211> LENGTH: 37
<212> TYPE: DNA
<213> ORGANISM: Homo sapiens

<400> SEQUENCE: 141
gcagcagtcg acagagacct cgatgatctc catgctg            37

<210> SEQ ID NO 142
<211> LENGTH: 39
<212> TYPE: DNA
<213> ORGANISM: Homo sapiens

<400> SEQUENCE: 142
gcagcagcgg ccgcatggcc catgagatga ttggaactc          39

<210> SEQ ID NO 143
<211> LENGTH: 37
<212> TYPE: DNA

<210> SEQ ID NO 143
<211> LENGTH: 37
<212> TYPE: DNA
<213> ORGANISM: Homo sapiens

<400> SEQUENCE: 143
gcagcagtcg accgtcttct catagtccat gagttgg    37

<210> SEQ ID NO 144
<211> LENGTH: 23
<212> TYPE: PRT
<213> ORGANISM: Homo sapiens

<400> SEQUENCE: 144

Asn Gly Cys Val Leu Val His Cys Leu Ala Gly Ile Ser Arg Ser Ala
1               5                   10                  15

Thr Ile Ala Ile Ala Tyr Ile
            20

<210> SEQ ID NO 145
<211> LENGTH: 25
<212> TYPE: DNA
<213> ORGANISM: Homo sapiens

<400> SEQUENCE: 145
cacaccacca ttacatcatc gtggc    25

<210> SEQ ID NO 146
<211> LENGTH: 20
<212> TYPE: DNA
<213> ORGANISM: Homo sapiens

<400> SEQUENCE: 146
tgctgctctg ctaccaaccc    20

<210> SEQ ID NO 147
<211> LENGTH: 5450
<212> TYPE: DNA
<213> ORGANISM: Homo sapiens
<220> FEATURE:
<221> NAME/KEY: CDS
<222> LOCATION: (538)..(2532)

<400> SEQUENCE: 147 gaaagaaga cgaggaggag agcgacggga cgggacgcga gcgggagcgc agccgccctc    60
tcggctccgc ggcggcgcct cgcaagtccg ggaggcgagg ggggcccgag gggagacgcc   120
gtgacaactt tcgtttccct ctgagggaat tgggaggtcg cgcggcccaa aagctttcag   180
tccagtgtaa agctgttgga gcgcgggagc aaaggtaaag aatgatgtaa tgcgctggct   240
gctccaaagc atcttttgtt gtggaatggt tattccagtc atctctttat gaatcaaatg   300 tgagggctg ctttgtggac ggagtccttt gcaagagcac atcaacggga aagagaaaga   360
gacattcact tggagggctc ttgctgaaaa tgggtttaac tctccttttg ccagtcacca   420
ccagcctgac ctcatacact tttagtacaa tggagtggct gagcctttga gcacaccacc   480
attacatcat cgtggcaaat taagaagga gtgggaaaa gaggacttat tgttgtc      537 atg gcc cat gag atg att gga act caa att gtt act gag agg ttg gtg    585
Met Ala His Glu Met Ile Gly Thr Gln Ile Val Thr Glu Arg Leu Val
1               5                   10                  15 gct ctg ctg gaa agt gga acg gaa aaa gtg ctg cta att gat agc cgg    633
Ala Leu Leu Glu Ser Gly Thr Glu Lys Val Leu Leu Ile Asp Ser Arg
            20                  25                  30 cca ttt gtg gaa tac aat aca tcc cac att ttg gaa gcc att aat atc    681
Pro Phe Val Glu Tyr Asn Thr Ser His Ile Leu Glu Ala Ile Asn Ile

|  |  |
|---|---|
| aac tgc tcc aag ctt atg aag cga agg ttg caa cag gac aaa gtg tta<br>Asn Cys Ser Lys Leu Met Lys Arg Arg Leu Gln Gln Asp Lys Val Leu<br>50                       55                      60 | 729 |
| att aca gag ctc atc cag cat tca gcg aaa cat aag gtt gac att gat<br>Ile Thr Glu Leu Ile Gln His Ser Ala Lys His Lys Val Asp Ile Asp<br>65                      70                    75                      80 | 777 |
| tgc agt cag aag gtt gta gtt tac gat caa agc tcc caa gat gtt gcc<br>Cys Ser Gln Lys Val Val Val Tyr Asp Gln Ser Ser Gln Asp Val Ala<br>                       85                    90                      95 | 825 |
| tct ctc tct tca gac tgt ttt ctc act gta ctt ctg ggt aaa ctg gag<br>Ser Leu Ser Ser Asp Cys Phe Leu Thr Val Leu Leu Gly Lys Leu Glu<br>              100                    105                  110 | 873 |
| aag agc ttc aac tct gtt cac ctg ctt gca ggt ggg ttt gct gag ttc<br>Lys Ser Phe Asn Ser Val His Leu Leu Ala Gly Gly Phe Ala Glu Phe<br>        115                    120                    125 | 921 |
| tct cgt tgt ttc cct ggc ctc tgt gaa gga aaa tcc act cta gtc cct<br>Ser Arg Cys Phe Pro Gly Leu Cys Glu Gly Lys Ser Thr Leu Val Pro<br>130                      135                    140 | 969 |
| acc tgc att tct cag cct tgc tta cct gtt gcc aac att ggg cca acc<br>Thr Cys Ile Ser Gln Pro Cys Leu Pro Val Ala Asn Ile Gly Pro Thr<br>145                      150                    155                  160 | 1017 |
| cga att ctt ccc aat ctt tat ctt ggc tgc cag cga gat gtc ctc aac<br>Arg Ile Leu Pro Asn Leu Tyr Leu Gly Cys Gln Arg Asp Val Leu Asn<br>                165                    170                  175 | 1065 |
| aag gag ctg ata cag cag aat ggg att ggt tat gtg tta aat gcc agc<br>Lys Glu Leu Ile Gln Gln Asn Gly Ile Gly Tyr Val Leu Asn Ala Ser<br>            180                    185                    190 | 1113 |
| tat acc tgt cca aag cct gac ttt atc ccc gag tct cat ttc ctg cgt<br>Tyr Thr Cys Pro Lys Pro Asp Phe Ile Pro Glu Ser His Phe Leu Arg<br>        195                    200                    205 | 1161 |
| gtg cct gtg aat gac agc ttt tgt gag aaa att ttg ccg tgg ttg gac<br>Val Pro Val Asn Asp Ser Phe Cys Glu Lys Ile Leu Pro Trp Leu Asp<br>210                      215                    220 | 1209 |
| aaa tca gta gat ttc att gag aaa gca aaa gcc tcc aat gga tgt gtt<br>Lys Ser Val Asp Phe Ile Glu Lys Ala Lys Ala Ser Asn Gly Cys Val<br>225                      230                    235                  240 | 1257 |
| cta gtg cac tgt tta gct ggg atc tcc cgc tcc gcc acc atc gct atc<br>Leu Val His Cys Leu Ala Gly Ile Ser Arg Ser Ala Thr Ile Ala Ile<br>                245                    250                  255 | 1305 |
| gcc tac atc atg aag agg atg gac atg tct tta gat gaa gct tac aga<br>Ala Tyr Ile Met Lys Arg Met Asp Met Ser Leu Asp Glu Ala Tyr Arg<br>            260                    265                  270 | 1353 |
| ttt gtg aaa gaa aaa aga cct act ata tct cca aac ttc aat ttt ctg<br>Phe Val Lys Glu Lys Arg Pro Thr Ile Ser Pro Asn Phe Asn Phe Leu<br>275                      280                    285 | 1401 |
| ggc caa ctc ctg gac tat gag aag aag att aag aac cag act gga gca<br>Gly Gln Leu Leu Asp Tyr Glu Lys Lys Ile Lys Asn Gln Thr Gly Ala<br>        290                    295                    300 | 1449 |
| tca ggg cca aag agc aaa ctc aag ctg ctg cac ctg gag aag cca aat<br>Ser Gly Pro Lys Ser Lys Leu Lys Leu Leu His Leu Glu Lys Pro Asn<br>305                      310                    315                  320 | 1497 |
| gaa cct gtc cct gct gtc tca gag ggt gga cag aaa agc gag acg ccc<br>Glu Pro Val Pro Ala Val Ser Glu Gly Gly Gln Lys Ser Glu Thr Pro<br>                       325                    330                  335 | 1545 |
| ctc agt cca ccc tgt gcc gac tct gct acc tca gag gca gca gga caa<br>Leu Ser Pro Pro Cys Ala Asp Ser Ala Thr Ser Glu Ala Ala Gly Gln<br>                340                    345                  350 | 1593 |
| agg ccc gtg cat ccc gcc agc gtg ccc agc gtg ccc agc gtg cag ccg | 1641 |

-continued

```
Arg Pro Val His Pro Ala Ser Val Pro Ser Val Pro Ser Val Gln Pro
        355                 360                 365 tcg ctg tta gag gac agc ccg ctg gta cag gcg ctc agt ggg ctg cac    1689
Ser Leu Leu Glu Asp Ser Pro Leu Val Gln Ala Leu Ser Gly Leu His
370                 375                 380 ctg tcc gca gac agg ctg gaa gac agc aat aag ctc aag cgt tcc ttc    1737
Leu Ser Ala Asp Arg Leu Glu Asp Ser Asn Lys Leu Lys Arg Ser Phe
385                 390                 395                 400 tct ctg gat atc aaa tca gtt tca tat tca gcc agc atg gca gca tcc    1785
Ser Leu Asp Ile Lys Ser Val Ser Tyr Ser Ala Ser Met Ala Ala Ser
                405                 410                 415 tta cat ggc ttc tcc tca tca gaa gat gct ttg gaa tac tac aaa cct    1833
Leu His Gly Phe Ser Ser Ser Glu Asp Ala Leu Glu Tyr Tyr Lys Pro
            420                 425                 430 tcc act act ctg gat ggg acc aac aag cta tgc cag ttc tcc cct gtt    1881
Ser Thr Thr Leu Asp Gly Thr Asn Lys Leu Cys Gln Phe Ser Pro Val
                435                 440                 445 cag gaa cta tcg gag cag act ccc gaa acc agt cct gat aag gag gaa    1929
Gln Glu Leu Ser Glu Gln Thr Pro Glu Thr Ser Pro Asp Lys Glu Glu
        450                 455                 460 gcc agc atc ccc aag aag ctg cag acc gcc agg cct tca gac agc cag    1977
Ala Ser Ile Pro Lys Lys Leu Gln Thr Ala Arg Pro Ser Asp Ser Gln
465                 470                 475                 480 agc aag cga ttg cat tcg gtc aga acc agc agc agt ggc acc gcc cag    2025
Ser Lys Arg Leu His Ser Val Arg Thr Ser Ser Ser Gly Thr Ala Gln
                485                 490                 495 agg tcc ctt tta tct cca ctg cat cga agt ggg agc gtg gag gac aat    2073
Arg Ser Leu Leu Ser Pro Leu His Arg Ser Gly Ser Val Glu Asp Asn
            500                 505                 510 tac cac acc agc ttc ctt ttc ggc ctt tcc acc agc cag cag cac ctc    2121
Tyr His Thr Ser Phe Leu Phe Gly Leu Ser Thr Ser Gln Gln His Leu
                515                 520                 525 acg aag tct gct ggc ctg ggc ctt aag ggc tgg cac tcg gat atc ttg    2169
Thr Lys Ser Ala Gly Leu Gly Leu Lys Gly Trp His Ser Asp Ile Leu
        530                 535                 540 gcc ccc cag acc tct acc cct tcc ctg acc agc agc tgg tat ttt gcc    2217
Ala Pro Gln Thr Ser Thr Pro Ser Leu Thr Ser Ser Trp Tyr Phe Ala
545                 550                 555                 560 aca gag tcc tca cac ttc tac tct gcc tca gcc atc tac gga ggc agt    2265
Thr Glu Ser Ser His Phe Tyr Ser Ala Ser Ala Ile Tyr Gly Gly Ser
                565                 570                 575 gcc agt tac tct gcc tac agc tgc agc cag ctg ccc act tgc gga gac    2313
Ala Ser Tyr Ser Ala Tyr Ser Cys Ser Gln Leu Pro Thr Cys Gly Asp
            580                 585                 590 caa gtc tat tct gtg cgc agg cgg cag aag cca agt gac aga gct gac    2361
Gln Val Tyr Ser Val Arg Arg Arg Gln Lys Pro Ser Asp Arg Ala Asp
        595                 600                 605 tcg cgg cgg agc tgg cat gaa gag agc ccc ttt gaa aag cag ttt aaa    2409
Ser Arg Arg Ser Trp His Glu Glu Ser Pro Phe Glu Lys Gln Phe Lys
610                 615                 620 cgc aga agc tgc caa atg gaa ttt gga gag agc atc atg tca gag aac    2457
Arg Arg Ser Cys Gln Met Glu Phe Gly Glu Ser Ile Met Ser Glu Asn
625                 630                 635                 640 agg tca cgg gaa gag ctg ggg aaa gtg ggc agt cag tct agc ttt tcg    2505
Arg Ser Arg Glu Glu Leu Gly Lys Val Gly Ser Gln Ser Ser Phe Ser
                645                 650                 655 ggc agc atg gaa atc att gag gtc tcc tgagaagaaa gacacttgtg          2552
Gly Ser Met Glu Ile Ile Glu Val Ser
                660                 665
```

```
acttctatag acaattttt ttttcttgtt cacaaaaaaa ttccctgtaa atctgaaata    2612
tatatatgta catacatata tatttttgga aaatggagct atggtgtaaa agcaacaggt    2672
ggatcaaccc agttgttact ctcttaacat ctgcatttga gagatcagct aatacttctc    2732
tcaacaaaaa tggaagggca gatgctagaa tcccccctag acggaggaaa accattttat    2792
tcagtgaatt acacatcctc ttgttcttaa aaaagcaagt gtctttggtg ttggaggaca    2852 aaatcccta ccattttcac gttgtgctac taagagatct caaatattag tctttgtccg    2912
gacccttcca tagtacacct tagcgctgag actgagccag cttgggggtc aggtaggtag    2972
accctgttag ggacagagcc tagtggtaaa tccaagagaa atgatcctat ccaaagctga    3032
ttcacaaacc cacgctcacc tgacagccga gggacacgag catcactctg ctggacggac    3092 cattagggc cttgccaagg tctaccttag agcaaaccca gtacctcaga caggaaagtc    3152
ggggctttga ccactaccat atctggtagc ccattttcta ggcattgtga ataggtaggt    3212
agctagtcac acttttcaga ccaattcaaa ctgtctatgc acaaaattcc cgtgggccta    3272
gatggagata attttttttt cttctcagct ttatgaagag aagggaaact gtctaggatt    3332
cagctgaacc accaggaacc tggcaacatc acgatttaag ctaaggttgg gaggctaacg    3392
agtctacctc cctctttgta aatcaaagaa ttgtttaaaa tgggattgtc aatcctttaa    3452
ataaagatga acttggtttc aagccaaatg tgaatttatt tgggttggta gcagagcagc    3512
agcaccttca aattctcagc caaagcagat gttttgccc tttctgcttc actgcatgga    3572
tacagttggt aaaatgtaat aatatggcag aattttatag gaaacttcct agggaggtaa    3632
attatgggaa gattaagaaa ggtacaaatt gctgaggaga agcaggaaac ctgtttcctt    3692 agtggcttt atccctcgg catgcgatgg ggctgatgtt tctatgattg cctcagactt    3752
tcacatttac tagtagggct gagagaggct ttagtgagga aggaatattc agaataaaac    3812
ggttgagaaa gctgagaaga ccattgagtt ttgatcagtt gtgaatagag tgcaaagcca    3872
tggccaagct gttttggaa acgctggccg gcgtgtcttc agtggaaaaa gcaaatcaaa    3932
atggagcgag agcaaagggg cgtcctcagt cctcaaccta caatcactgt atggaatcgg    3992
tcctggcagc tgaacatagg aggtcactgg aacaagtgat agtgcagatt ggctttcaaa    4052
catcctcctg gcttgagttt tatcagctac aatgtgggtc ctcttttgaa gccttaattc    4112
acaacagcag cttttgggg gtggggctgg gcgggtgttg tcattgttct ttcccttcct    4172
gtaagtgtcg ctagttgctg cctcgtatct caggtttttc tctgttttg agaaatggac    4232 agttttttga ccaggatgtg acttcatgtt tcctatggtg acttctaaaa ccagcacaga    4292
atgatatgac tcaacacaga ccgacttggt tatgggatg atgagccgca cagacctcac    4352
tagttgtgca caaataatgt gctatgatgg ggtgtaaagt gaaggcagaa gagggtcagc    4412
cgcattgtta tgatactggg aaagtgctgg tcaacgattt gagttagttt ttagatatac    4472
attgaaatct ttaatcagac attctcaagt ttcacacagt agtttttgat gttatgtaca    4532
cacacaccaa atgtgtaaca gttcaccact tccagagtgt ggtcatgccc aaaacatgtt    4592
taagaaagga aagcagtagc tccttgctaa cgatgtttca ggaggtttgg ggcacttggt    4652
tttaatgagc ttctgtcatt tagggcttct cttggccatg gtccccttcc ttctggaact    4712
gtgatgtagt cacatcctac agcctttagt gctggttcac tagtgtcaga taatcagttc    4772
ttggaatcga gactgccgtg gcgaaggggt ggcctcggag gcaggctctg gagctgcttg    4832
gatgtcttta ggtggggtgg tggctggctc tcttcagcat gtaattgggg aaaccctcgc    4892
gtctactagg ggtgatacag atggtgattt taaagagcaa aactagactt ctatgtgaga    4952
```

-continued

```
agtgctggaa aatgatttag acatgtgta  aagttagatg gaaagactgt aaatgtttaa    5012
tatgaatata gtgttctttt gaagtaaggc cagctgttga acggttaaac tgtgcatttc    5072
tcattttgat gtgtcatgta tgttaatgta tgaaatgatt aaataaaatc aaaactggta    5132
cctgtttata cataaatacg agaaaagacc tatctttgca gccataaact cggtgggaac    5192
accaccactc aagttgccaa aggaggcagt ggtgaaacct gtcctgttct cacttaaatg    5252
aggatttagc tcaaaataaa gtggtggtgt catcaggttt attccgtgtt ctgtcattca    5312 catgaacac  cggatgatta gctaacagtt tagtgccagc cttcattctt tactgtgtac    5372
gttaaatgca cactacagtg aaaaagccta agacacttgg taaatatttt ctagctgact    5432
gattccagaa cacacaag                                                   5450
```

<210> SEQ ID NO 148
<211> LENGTH: 665
<212> TYPE: PRT
<213> ORGANISM: Homo sapiens

<400> SEQUENCE: 148

```
Met Ala His Glu Met Ile Gly Thr Gln Ile Val Thr Glu Arg Leu Val
1               5                   10                  15

Ala Leu Leu Glu Ser Gly Thr Glu Lys Val Leu Leu Ile Asp Ser Arg
            20                  25                  30

Pro Phe Val Glu Tyr Asn Thr Ser His Ile Leu Glu Ala Ile Asn Ile
        35                  40                  45

Asn Cys Ser Lys Leu Met Lys Arg Arg Leu Gln Gln Asp Lys Val Leu
    50                  55                  60

Ile Thr Glu Leu Ile Gln His Ser Ala Lys His Lys Val Asp Ile Asp
65                  70                  75                  80

Cys Ser Gln Lys Val Val Tyr Asp Gln Ser Ser Gln Asp Val Ala
                85                  90                  95

Ser Leu Ser Ser Asp Cys Phe Leu Thr Val Leu Leu Gly Lys Leu Glu
            100                 105                 110

Lys Ser Phe Asn Ser Val His Leu Leu Ala Gly Gly Phe Ala Glu Phe
        115                 120                 125

Ser Arg Cys Phe Pro Gly Leu Cys Glu Gly Lys Ser Thr Leu Val Pro
    130                 135                 140

Thr Cys Ile Ser Gln Pro Cys Leu Pro Val Ala Asn Ile Gly Pro Thr
145                 150                 155                 160

Arg Ile Leu Pro Asn Leu Tyr Leu Gly Cys Gln Arg Asp Val Leu Asn
                165                 170                 175

Lys Glu Leu Ile Gln Gln Asn Gly Ile Gly Tyr Val Leu Asn Ala Ser
            180                 185                 190

Tyr Thr Cys Pro Lys Pro Asp Phe Ile Pro Glu Ser His Phe Leu Arg
        195                 200                 205

Val Pro Val Asn Asp Ser Phe Cys Glu Lys Ile Leu Pro Trp Leu Asp
    210                 215                 220

Lys Ser Val Asp Phe Ile Glu Lys Ala Lys Ser Asn Gly Cys Val
225                 230                 235                 240

Leu Val His Cys Leu Ala Gly Ile Ser Arg Ser Ala Thr Ile Ala Ile
                245                 250                 255

Ala Tyr Ile Met Lys Arg Met Asp Met Ser Leu Asp Glu Ala Tyr Arg
            260                 265                 270

Phe Val Lys Glu Lys Arg Pro Thr Ile Ser Pro Asn Phe Asn Phe Leu
```

```
                275                 280                 285
Gly Gln Leu Leu Asp Tyr Glu Lys Lys Ile Lys Asn Gln Thr Gly Ala
            290                 295                 300

Ser Gly Pro Lys Ser Lys Leu Lys Leu Leu His Leu Glu Lys Pro Asn
305                 310                 315                 320

Glu Pro Val Pro Ala Val Ser Glu Gly Gln Lys Ser Glu Thr Pro
                325                 330                 335

Leu Ser Pro Pro Cys Ala Asp Ser Ala Thr Ser Glu Ala Ala Gly Gln
                340                 345                 350

Arg Pro Val His Pro Ala Ser Val Pro Ser Val Pro Ser Val Gln Pro
                355                 360                 365

Ser Leu Leu Glu Asp Ser Pro Leu Val Gln Ala Leu Ser Gly Leu His
    370                 375                 380

Leu Ser Ala Asp Arg Leu Glu Asp Ser Asn Lys Leu Lys Arg Ser Phe
385                 390                 395                 400

Ser Leu Asp Ile Lys Ser Val Ser Tyr Ser Ala Ser Met Ala Ala Ser
                405                 410                 415

Leu His Gly Phe Ser Ser Glu Asp Ala Leu Glu Tyr Tyr Lys Pro
                420                 425                 430

Ser Thr Thr Leu Asp Gly Thr Asn Lys Leu Cys Gln Phe Ser Pro Val
    435                 440                 445

Gln Glu Leu Ser Glu Gln Thr Pro Glu Thr Ser Pro Asp Lys Glu Glu
    450                 455                 460

Ala Ser Ile Pro Lys Lys Leu Gln Thr Ala Arg Pro Ser Asp Ser Gln
465                 470                 475                 480

Ser Lys Arg Leu His Ser Val Arg Thr Ser Ser Gly Thr Ala Gln
                485                 490                 495

Arg Ser Leu Leu Ser Pro Leu His Arg Ser Gly Ser Val Glu Asp Asn
                500                 505                 510

Tyr His Thr Ser Phe Leu Phe Gly Leu Ser Thr Ser Gln Gln His Leu
    515                 520                 525

Thr Lys Ser Ala Gly Leu Gly Leu Lys Gly Trp His Ser Asp Ile Leu
    530                 535                 540

Ala Pro Gln Thr Ser Thr Pro Ser Leu Thr Ser Ser Trp Tyr Phe Ala
545                 550                 555                 560

Thr Glu Ser Ser His Phe Tyr Ser Ala Ser Ile Tyr Gly Gly Ser
                565                 570                 575

Ala Ser Tyr Ser Ala Tyr Ser Cys Ser Gln Leu Pro Thr Cys Gly Asp
            580                 585                 590

Gln Val Tyr Ser Val Arg Arg Arg Gln Lys Pro Ser Asp Arg Ala Asp
            595                 600                 605

Ser Arg Arg Ser Trp His Glu Glu Ser Pro Phe Glu Lys Gln Phe Lys
    610                 615                 620

Arg Arg Ser Cys Gln Met Glu Phe Gly Glu Ser Ile Met Ser Glu Asn
625                 630                 635                 640

Arg Ser Arg Glu Glu Leu Gly Lys Val Gly Ser Gln Ser Ser Phe Ser
                645                 650                 655

Gly Ser Met Glu Ile Ile Glu Val Ser
                660                 665

<210> SEQ ID NO 149
<211> LENGTH: 4393
<212> TYPE: DNA
<213> ORGANISM: Homo sapiens
```

-continued

```
<220> FEATURE:
<221> NAME/KEY: CDS
<222> LOCATION: (628)..(2448)

<400> SEQUENCE: 149
ccacgcgtcc ggctcttgcc tcccagtgcc atgcaggtgc aggatgcaac caggcggccc    60
tcagccgtgc gcttcctcag ctcctttctc cagggccgcc ggcactccac ctcagaccca   120
gtactgcggc tgcagcaggc ccggcggggc tctggcttgg gctccggctc tgccacgaag   180
ctgctgtcct cgtcctctct ccaggtgatg gtggctgttt cctcagtcag ccatgcagag   240
ggaaacccaa ctttccccga agaaaaaga aatttagaac gtccaacacc aaagtacaca   300
aaagtagggg agcgtttacg gcatgtcatt cctggacaca tggcatgttc catggcgtgt   360
ggcggtagag cttgcaagta tgagaaccca gcccgctgga gtgagcagga gcaagccatt   420
aagggggttt actcatcctg ggtcactgat aatatactgg ccatggcccg cccatcctct   480
gagctcctgg agaagtacca catcattgat cagttcctca gccatggcat aaaaacaata   540
atcaacctcc agcgccctgg tgagcatgct agctgtggga accctctgga caagaaagt    600
ggcttcacat accttcctga ggctttc atg gag gct ggc att tac ttc tac aat   654
                                Met Glu Ala Gly Ile Tyr Phe Tyr Asn
                                  1               5 ttc gga tgg aag gat tat ggt gta gcg tct ctt act act atc cta gat    702
Phe Gly Trp Lys Asp Tyr Gly Val Ala Ser Leu Thr Thr Ile Leu Asp
 10                  15                  20                  25 atg gtg aag gtg atg aca ttt gcc tta cag gaa gga aaa gta gct atc    750
Met Val Lys Val Met Thr Phe Ala Leu Gln Glu Gly Lys Val Ala Ile
                 30                  35                  40 cat tgt cat gca ggg ctt ggt cga aca ggt gtt tta ata gcc tgt tac    798
His Cys His Ala Gly Leu Gly Arg Thr Gly Val Leu Ile Ala Cys Tyr
             45                  50                  55 tta gtt ttt gca acg aga atg act gct gac caa gca att ata ttt gtg    846
Leu Val Phe Ala Thr Arg Met Thr Ala Asp Gln Ala Ile Ile Phe Val
         60                  65                  70 cgg gca aag cga ccc aat tcc ata caa acc aga gga cag ctc ctc tgt    894
Arg Ala Lys Arg Pro Asn Ser Ile Gln Thr Arg Gly Gln Leu Leu Cys
 75                  80                  85 gta agg gaa ttt act cag ttt cta act cct ctc cgc aat ata ttc tct    942
Val Arg Glu Phe Thr Gln Phe Leu Thr Pro Leu Arg Asn Ile Phe Ser
 90                  95                 100                 105 tgc tgt gat ccc aaa gca cat gct gtc acc tta cct caa tat cta att    990
Cys Cys Asp Pro Lys Ala His Ala Val Thr Leu Pro Gln Tyr Leu Ile
                110                 115                 120 cgc cag cgt cat ctg ctt cat ggt tat gag gca cga ctt ctg aaa cac   1038
Arg Gln Arg His Leu Leu His Gly Tyr Glu Ala Arg Leu Leu Lys His
            125                 130                 135 gtg cca aaa att atc cac cta gtt tgc aaa ttg ctg ctg gac tta gcg   1086
Val Pro Lys Ile Ile His Leu Val Cys Lys Leu Leu Leu Asp Leu Ala
        140                 145                 150 gag aac agg cca gtg atg atg aag gat gtg tcc gaa gga cct ggt ctc   1134
Glu Asn Arg Pro Val Met Met Lys Asp Val Ser Glu Gly Pro Gly Leu
155                 160                 165 tct gct gaa ata gaa aag aca atg tct gag atg gtc acc atg cag ctg   1182
Ser Ala Glu Ile Glu Lys Thr Met Ser Glu Met Val Thr Met Gln Leu
170                 175                 180                 185 gat aaa gag tta ctg agg cat gac agt gat gtg tcc aac ccg cct aac   1230
Asp Lys Glu Leu Leu Arg His Asp Ser Asp Val Ser Asn Pro Pro Asn
                190                 195                 200 ccc act gca gtg gca gca gat ttt gac aat cga ggc atg att ttc tcc   1278
Pro Thr Ala Val Ala Ala Asp Phe Asp Asn Arg Gly Met Ile Phe Ser
```

-continued

```
                        205                 210                 215
aat gag caa cag ttt gac cct ctt tgg aaa agg cgg aat gtt gag tgc      1326
Asn Glu Gln Gln Phe Asp Pro Leu Trp Lys Arg Arg Asn Val Glu Cys
            220                 225                 230 ctt caa ccc ctg act cat ctg aaa agg cgg ctc agc tac agt gac tca      1374
Leu Gln Pro Leu Thr His Leu Lys Arg Arg Leu Ser Tyr Ser Asp Ser
235                 240                 245 gat tta aag agg gcc gag aac ctc ctg gag caa ggg gag act cca cag      1422
Asp Leu Lys Arg Ala Glu Asn Leu Leu Glu Gln Gly Glu Thr Pro Gln
250                 255                 260                 265 aca gtg cct gcc cag atc ttg gtt ggc cac aag ccc agg cag cag aag      1470
Thr Val Pro Ala Gln Ile Leu Val Gly His Lys Pro Arg Gln Gln Lys
                270                 275                 280 ctc ata agc cat tgt tac atc cca cag tct cca gaa cca gac tta cac      1518
Leu Ile Ser His Cys Tyr Ile Pro Gln Ser Pro Glu Pro Asp Leu His
            285                 290                 295 aag gaa gcc ttg gtt cgc agc aca ctt tct ttc tgg agt cag tca aag      1566
Lys Glu Ala Leu Val Arg Ser Thr Leu Ser Phe Trp Ser Gln Ser Lys
            300                 305                 310 ttt gga ggc ctg gaa gga ctc aaa gat aat ggg tca cca att ttc cat      1614
Phe Gly Gly Leu Glu Gly Leu Lys Asp Asn Gly Ser Pro Ile Phe His
315                 320                 325 gga agg atc att cca aag gaa gca cag cag agt gga gct ttc tct gca      1662
Gly Arg Ile Ile Pro Lys Glu Ala Gln Gln Ser Gly Ala Phe Ser Ala
330                 335                 340                 345 gat gtt tca ggc tca cac agc cct ggg gag cca gtt tca ccc agc ttt      1710
Asp Val Ser Gly Ser His Ser Pro Gly Glu Pro Val Ser Pro Ser Phe
                350                 355                 360 gca aat gtc cat aag gat cca aac cct gct cac cag caa gtg tct cac      1758
Ala Asn Val His Lys Asp Pro Asn Pro Ala His Gln Gln Val Ser His
            365                 370                 375 tgt cag tgt aaa act cat ggt gtt ggg agc cct ggc tct gtc agg cag      1806
Cys Gln Cys Lys Thr His Gly Val Gly Ser Pro Gly Ser Val Arg Gln
            380                 385                 390 aac agc agg aca ccc cga agc cct ctg gac tgt ggc tcc agt ccc aaa      1854
Asn Ser Arg Thr Pro Arg Ser Pro Leu Asp Cys Gly Ser Ser Pro Lys
395                 400                 405 gca cag ttc ttg gtt gaa cat gaa acc cag gac agt aaa gat ctg tct      1902
Ala Gln Phe Leu Val Glu His Glu Thr Gln Asp Ser Lys Asp Leu Ser
410                 415                 420                 425 gaa gca gct tca cac tct gca tta cag tct gaa ttg agt gct gag gca      1950
Glu Ala Ala Ser His Ser Ala Leu Gln Ser Glu Leu Ser Ala Glu Ala
                430                 435                 440 aga aga ata ctg gcg gcc aaa gcc cta gca aat tta aat gaa tct gta      1998
Arg Arg Ile Leu Ala Ala Lys Ala Leu Ala Asn Leu Asn Glu Ser Val
            445                 450                 455 gaa aag gag gaa cta aaa agg aag gta gaa atg tgg cag aaa gag ctt      2046
Glu Lys Glu Glu Leu Lys Arg Lys Val Glu Met Trp Gln Lys Glu Leu
            460                 465                 470 aat tcc cga gat gga gct tgg gaa aga ata tgt ggc gag agg gac cct      2094
Asn Ser Arg Asp Gly Ala Trp Glu Arg Ile Cys Gly Glu Arg Asp Pro
475                 480                 485 ttc atc cta tgc agc ttg atg tgg tct tgg gtg gag caa ctg aag gag      2142
Phe Ile Leu Cys Ser Leu Met Trp Ser Trp Val Glu Gln Leu Lys Glu
490                 495                 500                 505 cct gta atc acc aaa gag gat gtg gac atg ttg gtt gac agg cga gca      2190
Pro Val Ile Thr Lys Glu Asp Val Asp Met Leu Val Asp Arg Arg Ala
                510                 515                 520 gat gcc gca gaa gca ctt ttt tta tta gag aag gga cag cac cag act      2238
```

-continued

```
Asp Ala Ala Glu Ala Leu Phe Leu Leu Glu Lys Gly Gln His Gln Thr
            525                 530                 535 att ctc tgc gtg ttg cac tgc ata gtg aac ctg cag aca att ccc gtg      2286
Ile Leu Cys Val Leu His Cys Ile Val Asn Leu Gln Thr Ile Pro Val
            540                 545                 550 gat gtg gag gaa gct ttc ctt gcc cat gcc att aag gca ttc act aag      2334
Asp Val Glu Glu Ala Phe Leu Ala His Ala Ile Lys Ala Phe Thr Lys
            555                 560                 565 gtt aat ttt gat tct gaa aat gga cca aca gtt tac aac acc ctg aag      2382
Val Asn Phe Asp Ser Glu Asn Gly Pro Thr Val Tyr Asn Thr Leu Lys
570                 575                 580                 585 aaa ata ttt aag cac acg ctg gaa gaa aaa aga aaa atg aca aaa gat      2430
Lys Ile Phe Lys His Thr Leu Glu Glu Lys Arg Lys Met Thr Lys Asp
                590                 595                 600 ggc cct aag cct ggc ctc tagctttcac tcatggtgaa tatttcagac             2478
Gly Pro Lys Pro Gly Leu
            605
```

| | |
|---|---|
| ctaaagatcc agatagtatc tctgttcata tgtgaataag ttgaagattg tggggctact | 2538 |
| ttttctcata gcactttatt ttgaatgttg ttagtttgtg ctgagaatgg tcgtccgtat | 2598 |
| ttgaaccaat tatttatttt aaaatatatt taagctacat ttttgttttg aaaaattgcc | 2658 |
| ataaatttgg tgccactttc ttttatttat ttgactgagt taatattatt gtattaacat | 2718 |
| tttaagtata tggtgtttac attcttattt cttttgacat tttggaaata atcataactt | 2778 |
| gtctttccaa aataaccatt ttcttgatgg aactcttcct agagttttta ccaaatagct | 2838 |
| aactttagta gtaaaacctc attgtgtatc cattccccca cagatgaact aagaaagtca | 2898 |
| ccaagtgtct taagctgttt tatatttgtt acgaagaagg ctattgctac aatatttta | 2958 |
| aaggtttctt ttttaacttt gaaattttt gttttccttt tctttttat aaatgtaaca | 3018 |
| gagggtttca aagcatatta ttttcagag atttagtt ttactttaat ggagtgactg | 3078 |
| tgaagtggtt gggattttt gcttgtagaa agtagacttg ctctttgtca gatttccaaa | 3138 |
| caaccttgcc agccttggct gtcaaaagga ggcaggagca gttctcaaca caccaagcct | 3198 |
| tattcccact cccttgggtt gctgctgagc caaatagcat cttttacagag gaagtgggat | 3258 |
| cagaggcagg aagtgtggaa agttgctaag aagcagggct tgcctctgtc ctcccgggga | 3318 |
| ctccacaggg atattcgtgc agggcagggg ctctgtgcca gccctgctct tcagatgcc | 3378 |
| acagccactc tgcagaggtg actcttggag ctggaggaag tcaaaactgg gccactgttt | 3438 |
| gtactgatgg tgtattagca tgagcagcgt ggccctggcc ccacactccc aaatctgcca | 3498 |
| ctccatagac ccacttgcct caaggcttta tatttggctg ctttcttaca atgagaatta | 3558 |
| agatttttaa actgaagttg accatacagg ttgcattagc cctaactggc ttcatgtaag | 3618 |
| aagggtgact gcctaaacta gttccttgta agctgaacca tcaattatca gttgaagcca | 3678 |
| tacttttatt taaattaata tacgtagata ccagaggcca agccacagag aggataaatag | 3738 |
| ttcttcccaa taaaggtgat attaatcaga ctaatttcga actaaagaag ttactgctta | 3798 |
| aagacggaat tcaggggaa gcaagactca tttagaacaa atgaaatttc tccagtccta | 3858 |
| catttctgaa ttgacttcta gcacatcaaa aatatttcag tcattatcag tctcattaac | 3918 |
| tgaaatgcca aatgctaaat gcagtgttct ttcacactgt tttaattttc ttgggaaatt | 3978 |
| gagtccagtg gatgttaatg gagtgggttg cccatccctg aaatgtctta ttttcaagtg | 4038 |
| cctggcctgg gaagaaggg gaagaaacaa ttgcattata tccaaagata cactataaaa | 4098 |
| atagagtttt taccaaaaaa agatgtttgt tctcatctca gtaggcctca tttgggcaag | 4158 |

```
tgacccacag gtcttttggc gagtttgcta tttgcctgtt gaaatacttg tttcaactta      4218
gagaacagtt atgatgtgac catagcatgg cacaactaaa aatctaagcc tgaaacctga      4278
aaaaagagat atgacaaggg aaattaatca ggctatacat aagtattgta tttatttgaa      4338
taaaaataaa aagagcaacc cataaaaaaa aaaaaaaaaa aaaaaaaaaa aaaag           4393
```

<210> SEQ ID NO 150
<211> LENGTH: 607
<212> TYPE: PRT
<213> ORGANISM: Homo sapiens

<400> SEQUENCE: 150

```
Met Glu Ala Gly Ile Tyr Phe Tyr Asn Phe Gly Trp Lys Asp Tyr Gly
1               5                   10                  15

Val Ala Ser Leu Thr Thr Ile Leu Asp Met Val Lys Val Met Thr Phe
            20                  25                  30

Ala Leu Gln Glu Gly Lys Val Ala Ile His Cys His Ala Gly Leu Gly
        35                  40                  45

Arg Thr Gly Val Leu Ile Ala Cys Tyr Leu Val Phe Ala Thr Arg Met
    50                  55                  60

Thr Ala Asp Gln Ala Ile Ile Phe Val Arg Ala Lys Arg Pro Asn Ser
65                  70                  75                  80

Ile Gln Thr Arg Gly Gln Leu Leu Cys Val Arg Glu Phe Thr Gln Phe
                85                  90                  95

Leu Thr Pro Leu Arg Asn Ile Phe Ser Cys Cys Asp Pro Lys Ala His
            100                 105                 110

Ala Val Thr Leu Pro Gln Tyr Leu Ile Arg Gln Arg His Leu Leu His
        115                 120                 125

Gly Tyr Glu Ala Arg Leu Leu Lys His Val Pro Lys Ile Ile His Leu
    130                 135                 140

Val Cys Lys Leu Leu Asp Leu Ala Glu Asn Arg Pro Val Met Met
145                 150                 155                 160

Lys Asp Val Ser Glu Gly Pro Gly Leu Ser Ala Glu Ile Glu Lys Thr
                165                 170                 175

Met Ser Glu Met Val Thr Met Gln Leu Asp Lys Glu Leu Leu Arg His
            180                 185                 190

Asp Ser Asp Val Ser Asn Pro Pro Asn Pro Thr Ala Val Ala Ala Asp
        195                 200                 205

Phe Asp Asn Arg Gly Met Ile Phe Ser Asn Glu Gln Gln Phe Asp Pro
    210                 215                 220

Leu Trp Lys Arg Arg Asn Val Glu Cys Leu Gln Pro Leu Thr His Leu
225                 230                 235                 240

Lys Arg Arg Leu Ser Tyr Ser Asp Ser Asp Leu Lys Arg Ala Glu Asn
                245                 250                 255

Leu Leu Glu Gln Gly Glu Thr Pro Gln Thr Val Pro Ala Gln Ile Leu
            260                 265                 270

Val Gly His Lys Pro Arg Gln Gln Lys Leu Ile Ser His Cys Tyr Ile
        275                 280                 285

Pro Gln Ser Pro Glu Pro Asp Leu His Lys Glu Ala Leu Val Arg Ser
    290                 295                 300

Thr Leu Ser Phe Trp Ser Gln Ser Lys Phe Gly Gly Leu Glu Gly Leu
305                 310                 315                 320

Lys Asp Asn Gly Ser Pro Ile Phe His Gly Arg Ile Ile Pro Lys Glu
                325                 330                 335
```

-continued

```
Ala Gln Gln Ser Gly Ala Phe Ser Ala Asp Val Ser Gly Ser His Ser
            340                 345                 350

Pro Gly Glu Pro Val Ser Pro Ser Phe Ala Asn Val His Lys Asp Pro
        355                 360                 365

Asn Pro Ala His Gln Gln Val Ser His Cys Gln Cys Lys Thr His Gly
    370                 375                 380

Val Gly Ser Pro Gly Ser Val Arg Gln Asn Ser Arg Thr Pro Arg Ser
385                 390                 395                 400

Pro Leu Asp Cys Gly Ser Ser Pro Lys Ala Gln Phe Leu Val Glu His
            405                 410                 415

Glu Thr Gln Asp Ser Lys Asp Leu Ser Glu Ala Ala Ser His Ser Ala
        420                 425                 430

Leu Gln Ser Glu Leu Ser Ala Glu Ala Arg Arg Ile Leu Ala Ala Lys
    435                 440                 445

Ala Leu Ala Asn Leu Asn Glu Ser Val Glu Lys Glu Glu Leu Lys Arg
450                 455                 460

Lys Val Glu Met Trp Gln Lys Glu Leu Asn Ser Arg Asp Gly Ala Trp
465                 470                 475                 480

Glu Arg Ile Cys Gly Glu Arg Asp Pro Phe Ile Leu Cys Ser Leu Met
            485                 490                 495

Trp Ser Trp Val Glu Gln Leu Lys Glu Pro Val Ile Thr Lys Glu Asp
        500                 505                 510

Val Asp Met Leu Val Asp Arg Ala Asp Ala Glu Ala Leu Phe
    515                 520                 525

Leu Leu Glu Lys Gly Gln His Gln Thr Ile Leu Cys Val Leu His Cys
    530                 535                 540

Ile Val Asn Leu Gln Thr Ile Pro Val Asp Val Glu Glu Ala Phe Leu
545                 550                 555                 560

Ala His Ala Ile Lys Ala Phe Thr Lys Val Asn Phe Asp Ser Glu Asn
            565                 570                 575

Gly Pro Thr Val Tyr Asn Thr Leu Lys Lys Ile Phe Lys His Thr Leu
        580                 585                 590

Glu Glu Lys Arg Lys Met Thr Lys Asp Gly Pro Lys Pro Gly Leu
    595                 600                 605

<210> SEQ ID NO 151
<211> LENGTH: 878
<212> TYPE: DNA
<213> ORGANISM: Homo sapiens
<220> FEATURE:
<221> NAME/KEY: CDS
<222> LOCATION: (89)..(538)

<400> SEQUENCE: 151
ccacgcgtcc ggcgagggga cgcgtgggcg gagcggggct ggccagcctc ggcccccatg      60
acccgctgtc ctgtgccctt tcccagcg atg ggc gtg cag ccc ccc aac ttc       112
                              Met Gly Val Gln Pro Pro Asn Phe
                                1               5 tcc tgg gtg ctt ccg ggc cgg ctg gcg gga ctg gcg ctg ccg cgg ctc       160
Ser Trp Val Leu Pro Gly Arg Leu Ala Gly Leu Ala Leu Pro Arg Leu
     10                  15                  20 ccc gcc cac tac cag ttc ctg ttg gac ctg ggc gtg cgg cac ctg gtg       208
Pro Ala His Tyr Gln Phe Leu Leu Asp Leu Gly Val Arg His Leu Val
 25                  30                  35                  40 tcc ctg acg gag cgc ggg ccc cct cac agc gac agc tgc ccc ggc ctc       256
Ser Leu Thr Glu Arg Gly Pro Pro His Ser Asp Ser Cys Pro Gly Leu
             45                  50                  55
```

-continued

```
acc ctg cac cgc ctg cgc atc ccc gac ttc tgc ccg ccg gcc ccc gac       304
Thr Leu His Arg Leu Arg Ile Pro Asp Phe Cys Pro Pro Ala Pro Asp
         60                   65                  70 cag atc gac cgc ttc gtg cag atc gtg gac gag gcc aac gca cgg gga       352
Gln Ile Asp Arg Phe Val Gln Ile Val Asp Glu Ala Asn Ala Arg Gly
             75                  80                  85 gag gct gtg gga gtg cac tgt gct ctg ggc ttt ggc cgc act ggc acc       400
Glu Ala Val Gly Val His Cys Ala Leu Gly Phe Gly Arg Thr Gly Thr
     90                  95                 100 atg ctg gcc tgt tac ctg gtg aag gag cgg ggc ttg gct gca gga gat       448
Met Leu Ala Cys Tyr Leu Val Lys Glu Arg Gly Leu Ala Ala Gly Asp
105                 110                 115                 120 gcc att gct gaa atc cga cga cta cga ccc ggc tcc atc gag acc tat       496
Ala Ile Ala Glu Ile Arg Arg Leu Arg Pro Gly Ser Ile Glu Thr Tyr
                125                 130                 135 gag cag gag aaa gca gtc ttc cag ttc tac cag cga acg aaa               538
Glu Gln Glu Lys Ala Val Phe Gln Phe Tyr Gln Arg Thr Lys
            140                 145                 150 taagggcct  tagtacccttc taccaggcc ctcactcccc ttccccatgt tgtcgatggg      598
gccagagatg aagggaagtg gactaaagta ttaaaccctc tagctcccat ggctgaaga      658 cactgaagta gcccacccct gcaggcaggt cctgattgaa ggggaggctt gtactgcttt     718
gttgaataaa tgagttttac gaaccaggaa aaaaaaaaa aaaaaaaaa aaaaaaaaa        778 aaaaaaaaa aaaaaaaaa aaaaaaaaa aaaaaaaaa aaaaaaaaa aaaaaaaaa           838 aaaaaaaaa aaaaaaaaa aaaaaaaaa aaaaagggc                                878
```

<210> SEQ ID NO 152
<211> LENGTH: 150
<212> TYPE: PRT
<213> ORGANISM: Homo sapiens

<400> SEQUENCE: 152

```
Met Gly Val Gln Pro Pro Asn Phe Ser Trp Val Leu Pro Gly Arg Leu
1               5                   10                  15

Ala Gly Leu Ala Leu Pro Arg Leu Pro Ala His Tyr Gln Phe Leu Leu
            20                  25                  30

Asp Leu Gly Val Arg His Leu Val Ser Leu Thr Glu Arg Gly Pro Pro
        35                  40                  45

His Ser Asp Ser Cys Pro Gly Leu Thr Leu His Arg Leu Arg Ile Pro
    50                  55                  60

Asp Phe Cys Pro Pro Ala Pro Asp Gln Ile Asp Arg Phe Val Gln Ile
65                  70                  75                  80

Val Asp Glu Ala Asn Ala Arg Gly Glu Ala Val Gly Val His Cys Ala
                85                  90                  95

Leu Gly Phe Gly Arg Thr Gly Thr Met Leu Ala Cys Tyr Leu Val Lys
            100                 105                 110

Glu Arg Gly Leu Ala Ala Gly Asp Ala Ile Ala Glu Ile Arg Arg Leu
        115                 120                 125

Arg Pro Gly Ser Ile Glu Thr Tyr Glu Gln Glu Lys Ala Val Phe Gln
    130                 135                 140

Phe Tyr Gln Arg Thr Lys
145                 150
```

<210> SEQ ID NO 153
<211> LENGTH: 470

<212> TYPE: PRT
<213> ORGANISM: Homo sapiens

<400> SEQUENCE: 153

```
Met Glu Ala Gly Ile Tyr Phe Asn Phe Gly Trp Lys Asp Tyr Gly Val
1               5                   10                  15

Ala Ser Leu Thr Thr Ile Asp Met Val Lys Val Met Thr Phe Ala Leu
            20                  25                  30

Gln Glu Gly Lys Val Ile His Cys His Ala Gly Leu Gly Arg Thr Gly
        35                  40                  45

Val Leu Ile Ala Tyr Leu Val Phe Ala Thr Arg Met Thr Ala Asp Gln
50                  55                  60

Ala Ile Ile Val Arg Ala Lys Arg Pro Asn Ser Ile Gln Thr Arg Gly
65                  70                  75                  80

Gln Leu Cys Val Arg Glu Phe Thr Gln Phe Leu Thr Pro Leu Arg Asn
                85                  90                  95

Ile Ser Cys Cys Asp Pro Lys Ala His Ala Val Thr Leu Pro Gln Tyr
            100                 105                 110

Ile Arg Gln Arg His Leu Leu His Gly Tyr Glu Ala Arg Leu Leu His
        115                 120                 125

Val Pro Lys Ile Ile His Leu Val Cys Lys Leu Leu Leu Asp Ala Glu
130                 135                 140

Asn Arg Pro Val Met Met Lys Asp Val Ser Glu Gly Pro Leu Ser Ala
145                 150                 155                 160

Glu Ile Glu Lys Thr Met Ser Glu Met Val Thr Met Leu Asp Lys Glu
                165                 170                 175

Leu Leu Arg His Asp Ser Asp Val Ser Asn Pro Asn Pro Thr Ala Val
            180                 185                 190

Ala Ala Asp Phe Asp Asn Arg Gly Met Ile Ser Asn Glu Gln Gln Phe
        195                 200                 205

Asp Pro Leu Trp Lys Arg Arg Asn Val Cys Leu Gln Pro Leu Thr His
210                 215                 220

Leu Lys Arg Arg Leu Ser Tyr Ser Ser Asp Leu Lys Arg Ala Glu Asn
225                 230                 235                 240

Leu Leu Glu Gln Gly Glu Thr Gln Thr Val Pro Ala Gln Ile Leu Val
                245                 250                 255

Gly His Lys Pro Arg Gln Lys Leu Ile Ser His Cys Tyr Ile Pro Gln
            260                 265                 270

Ser Pro Glu Pro Asp His Lys Glu Ala Leu Val Arg Ser Thr Leu Ser
        275                 280                 285

Phe Trp Ser Gln Lys Phe Gly Gly Leu Glu Gly Leu Lys Asp Asn Gly
290                 295                 300

Ser Pro Ile His Gly Arg Ile Ile Pro Lys Glu Ala Gln Gln Ser Gly
305                 310                 315                 320

Ala Phe Ala Asp Val Ser Gly Ser His Ser Pro Gly Glu Pro Val Ser
                325                 330                 335

Pro Phe Ala Asn Val His Lys Asp Pro Asn Pro Ala His Gln Gln Val
            340                 345                 350

His Cys Gln Cys Lys Thr His Gly Val Gly Ser Pro Gly Ser Val Gln
        355                 360                 365

Asn Ser Arg Thr Pro Arg Ser Pro Leu Asp Cys Gly Ser Ser Lys Ala
370                 375                 380

Gln Phe Leu Val Glu His Glu Thr Gln Asp Ser Lys Asp Ser Glu Ala
385                 390                 395                 400
```

```
Ala Ser His Ser Ala Leu Gln Ser Glu Leu Ser Ala Ala Arg Arg Ile
            405                 410                 415

Leu Ala Ala Lys Ala Leu Ala Asn Leu Asn Glu Val Glu Lys Glu Glu
            420                 425                 430

Leu Lys Arg Lys Val Glu Met Trp Gln Lys Leu Asn Ser Arg Asp Gly
            435                 440                 445

Ala Trp Glu Arg Ile Cys Gly Glu Arg Pro Phe Ile Leu Cys Ser Leu
        450                 455                 460

Met Trp Ser Trp Val Glu
465             470

<210> SEQ ID NO 154
<211> LENGTH: 24
<212> TYPE: DNA
<213> ORGANISM: Homo sapiens

<400> SEQUENCE: 154
tacaatttcg gatggaagga ttat                                              24

<210> SEQ ID NO 155
<211> LENGTH: 23
<212> TYPE: DNA
<213> ORGANISM: Homo sapiens

<400> SEQUENCE: 155
gcatgacaat ggatagctac ttt                                               23

<210> SEQ ID NO 156
<211> LENGTH: 24
<212> TYPE: DNA
<213> ORGANISM: Homo sapiens

<400> SEQUENCE: 156
gagaaagcag tcttccagtt ctac                                              24

<210> SEQ ID NO 157
<211> LENGTH: 24
<212> TYPE: DNA
<213> ORGANISM: Homo sapiens

<400> SEQUENCE: 157
atgggagcta gagggtttaa tact                                              24

<210> SEQ ID NO 158
<211> LENGTH: 14
<212> TYPE: PRT
<213> ORGANISM: Homo sapiens

<400> SEQUENCE: 158

Leu Thr Pro Leu Arg Asn Ile Ser Cys Cys Asp Pro Lys Ala
1               5                   10

<210> SEQ ID NO 159
<211> LENGTH: 13
<212> TYPE: PRT
<213> ORGANISM: Homo sapiens

<400> SEQUENCE: 159

Thr Leu Ser Phe Trp Ser Gln Lys Phe Gly Gly Leu Glu
1               5                   10
```

```
<210> SEQ ID NO 160
<211> LENGTH: 13
<212> TYPE: PRT
<213> ORGANISM: Homo sapiens

<400> SEQUENCE: 160

Val Gln Asn Ser Arg Thr Pro Arg Ser Pro Leu Asp Cys
1               5                   10

<210> SEQ ID NO 161
<211> LENGTH: 13
<212> TYPE: PRT
<213> ORGANISM: Homo sapiens

<400> SEQUENCE: 161

Pro Leu Asp Cys Gly Ser Ser Lys Ala Gln Phe Leu Val
1               5                   10

<210> SEQ ID NO 162
<211> LENGTH: 13
<212> TYPE: PRT
<213> ORGANISM: Homo sapiens

<400> SEQUENCE: 162

Pro Thr Val Tyr Asn Thr Lys Lys Ile Phe Lys His Thr
1               5                   10

<210> SEQ ID NO 163
<211> LENGTH: 23
<212> TYPE: PRT
<213> ORGANISM: Homo sapiens

<400> SEQUENCE: 163

Gln Glu Gly Lys Val Ile His Cys His Ala Gly Leu Gly Arg Thr Gly
1               5                   10                  15

Val Leu Ile Ala Tyr Leu Val
            20

<210> SEQ ID NO 164
<211> LENGTH: 14
<212> TYPE: PRT
<213> ORGANISM: Homo sapiens

<400> SEQUENCE: 164

Gly Val Gln Pro Pro Asn Phe Ser Trp Val Leu Pro Gly Arg
1               5                   10

<210> SEQ ID NO 165
<211> LENGTH: 13
<212> TYPE: PRT
<213> ORGANISM: Homo sapiens

<400> SEQUENCE: 165

His Leu Val Ser Leu Thr Glu Arg Gly Pro Pro His Ser
1               5                   10

<210> SEQ ID NO 166
<211> LENGTH: 23
<212> TYPE: PRT
<213> ORGANISM: Homo sapiens

<400> SEQUENCE: 166

Gly Glu Ala Val Gly Val His Cys Ala Leu Gly Phe Gly Arg Thr Gly
1               5                   10                  15
```

Thr Met Leu Ala Cys Tyr Leu
            20

<210> SEQ ID NO 167
<211> LENGTH: 39
<212> TYPE: DNA
<213> ORGANISM: Homo sapiens

<400> SEQUENCE: 167
gcagcagcgg ccgcaatttc ggatggaagg attatggtg                              39

<210> SEQ ID NO 168
<211> LENGTH: 33
<212> TYPE: DNA
<213> ORGANISM: Homo sapiens

<400> SEQUENCE: 168
gcagcagtcg acgaggccag gcttagggcc atc                                    33

<210> SEQ ID NO 169
<211> LENGTH: 38
<212> TYPE: DNA
<213> ORGANISM: Homo sapiens

<400> SEQUENCE: 169
gcagcagcgg ccgcatggag gctggcattt acttctac                               38

<210> SEQ ID NO 170
<211> LENGTH: 35
<212> TYPE: DNA
<213> ORGANISM: Homo sapiens

<400> SEQUENCE: 170
gcagcagtcg accacccaag accacatcaa gctgc                                  35

<210> SEQ ID NO 171
<211> LENGTH: 39
<212> TYPE: DNA
<213> ORGANISM: Homo sapiens

<400> SEQUENCE: 171
gcagcagcgg ccgcctgttg gacctgggcg tgcggcacc                              39

<210> SEQ ID NO 172
<211> LENGTH: 37
<212> TYPE: DNA
<213> ORGANISM: Homo sapiens

<400> SEQUENCE: 172
gcagcagtcg actttcgttc gctggtagaa ctggaag                                37

<210> SEQ ID NO 173
<211> LENGTH: 38
<212> TYPE: DNA
<213> ORGANISM: Homo sapiens

<400> SEQUENCE: 173
gcagcagcgg ccgcatgggc gtgcagcccc ccaacttc                               38

<210> SEQ ID NO 174
<211> LENGTH: 37
<212> TYPE: DNA
<213> ORGANISM: Homo sapiens -continued

<400> SEQUENCE: 174
gcagcagtcg accaccaggt aacaggccag catggtg                                   37

<210> SEQ ID NO 175
<211> LENGTH: 806
<212> TYPE: PRT
<213> ORGANISM: Homo sapiens

<400> SEQUENCE: 175

Met Gln Val Gln Asp Ala Thr Arg Arg Pro Ser Ala Val Arg Phe Leu
1               5                   10                  15

Ser Ser Phe Leu Gln Gly Arg Arg His Ser Thr Ser Asp Pro Val Leu
            20                  25                  30

Arg Leu Gln Gln Ala Arg Arg Gly Ser Gly Leu Gly Ser Gly Ser Ala
        35                  40                  45

Thr Lys Leu Leu Ser Ser Ser Leu Gln Val Met Val Ala Val Ser
    50                  55                  60

Ser Val Ser His Ala Glu Gly Asn Pro Thr Phe Pro Glu Arg Lys Arg
65                  70                  75                  80

Asn Leu Glu Arg Pro Thr Pro Lys Tyr Thr Lys Val Gly Glu Arg Leu
                85                  90                  95

Arg His Val Ile Pro Gly His Met Ala Cys Ser Met Ala Cys Gly Gly
            100                 105                 110

Arg Ala Cys Lys Tyr Glu Asn Pro Ala Arg Trp Ser Glu Gln Glu Gln
        115                 120                 125

Ala Ile Lys Gly Val Tyr Ser Ser Trp Val Thr Asp Asn Ile Leu Ala
    130                 135                 140

Met Ala Arg Pro Ser Ser Glu Leu Leu Glu Lys Tyr His Ile Ile Asp
145                 150                 155                 160

Gln Phe Leu Ser His Gly Ile Lys Thr Ile Ile Asn Leu Gln Arg Pro
                165                 170                 175

Gly Glu His Ala Ser Cys Gly Asn Pro Leu Glu Gln Glu Ser Gly Phe
            180                 185                 190

Thr Tyr Leu Pro Glu Ala Phe Met Glu Ala Gly Ile Tyr Phe Tyr Asn
        195                 200                 205

Phe Gly Trp Lys Asp Tyr Gly Val Ala Ser Leu Thr Thr Ile Leu Asp
    210                 215                 220

Met Val Lys Val Met Thr Phe Ala Leu Gln Glu Gly Lys Val Ala Ile
225                 230                 235                 240

His Cys His Ala Gly Leu Gly Arg Thr Gly Val Leu Ile Ala Cys Tyr
                245                 250                 255

Leu Val Phe Ala Thr Arg Met Thr Ala Asp Gln Ala Ile Ile Phe Val
            260                 265                 270

Arg Ala Lys Arg Pro Asn Ser Ile Gln Thr Arg Gly Gln Leu Leu Cys
        275                 280                 285

Val Arg Glu Phe Thr Gln Phe Leu Thr Pro Leu Arg Asn Ile Phe Ser
    290                 295                 300

Cys Cys Asp Pro Lys Ala His Ala Val Thr Leu Pro Gln Tyr Leu Ile
305                 310                 315                 320

Arg Gln Arg His Leu Leu His Gly Tyr Glu Ala Arg Leu Leu Lys His
                325                 330                 335

Val Pro Lys Ile Ile His Leu Val Cys Lys Leu Leu Leu Asp Leu Ala
            340                 345                 350

Glu Asn Arg Pro Val Met Met Lys Asp Val Ser Glu Gly Pro Gly Leu

-continued

```
            355                 360                 365
Ser Ala Glu Ile Glu Lys Thr Met Ser Glu Met Val Thr Met Gln Leu
    370                 375                 380
Asp Lys Glu Leu Leu Arg His Asp Ser Asp Val Ser Asn Pro Pro Asn
385                 390                 395                 400
Pro Thr Ala Val Ala Ala Asp Phe Asp Asn Arg Gly Met Ile Phe Ser
                405                 410                 415
Asn Glu Gln Gln Phe Asp Pro Leu Trp Lys Arg Asn Val Glu Cys
                420                 425                 430
Leu Gln Pro Leu Thr His Leu Lys Arg Arg Leu Ser Tyr Ser Asp Ser
                435                 440                 445
Asp Leu Lys Arg Ala Glu Asn Leu Leu Glu Gln Gly Glu Thr Pro Gln
450                 455                 460
Thr Val Pro Ala Gln Ile Leu Val Gly His Lys Pro Arg Gln Gln Lys
465                 470                 475                 480
Leu Ile Ser His Cys Tyr Ile Pro Gln Ser Pro Glu Pro Asp Leu His
                485                 490                 495
Lys Glu Ala Leu Val Arg Ser Thr Leu Ser Phe Trp Ser Gln Ser Lys
                500                 505                 510
Phe Gly Gly Leu Glu Gly Leu Lys Asp Asn Gly Ser Pro Ile Phe His
                515                 520                 525
Gly Arg Ile Ile Pro Lys Glu Ala Gln Gln Ser Gly Ala Phe Ser Ala
                530                 535                 540
Asp Val Ser Gly Ser His Ser Pro Gly Glu Pro Val Ser Pro Ser Phe
545                 550                 555                 560
Ala Asn Val His Lys Asp Pro Asn Pro Ala His Gln Gln Val Ser His
                565                 570                 575
Cys Gln Cys Lys Thr His Gly Val Gly Ser Pro Gly Ser Val Arg Gln
                580                 585                 590
Asn Ser Arg Thr Pro Arg Ser Pro Leu Asp Cys Gly Ser Ser Pro Lys
                595                 600                 605
Ala Gln Phe Leu Val Glu His Glu Thr Gln Asp Ser Lys Asp Leu Ser
610                 615                 620
Glu Ala Ala Ser His Ser Ala Leu Gln Ser Glu Leu Ser Ala Glu Ala
625                 630                 635                 640
Arg Arg Ile Leu Ala Ala Lys Ala Leu Ala Asn Leu Asn Glu Ser Val
                645                 650                 655
Glu Lys Glu Glu Leu Lys Arg Lys Val Glu Met Trp Gln Lys Glu Leu
                660                 665                 670
Asn Ser Arg Asp Gly Ala Trp Glu Arg Ile Cys Gly Glu Arg Asp Pro
                675                 680                 685
Phe Ile Leu Cys Ser Leu Met Trp Ser Trp Val Glu Gln Leu Lys Glu
690                 695                 700
Pro Val Ile Thr Lys Glu Asp Val Asp Met Leu Val Asp Arg Arg Ala
705                 710                 715                 720
Asp Ala Ala Glu Ala Leu Phe Leu Leu Glu Lys Gly Gln His Gln Thr
                725                 730                 735
Ile Leu Cys Val Leu His Cys Ile Val Asn Leu Gln Thr Ile Pro Val
                740                 745                 750
Asp Val Glu Glu Ala Phe Leu Ala His Ala Ile Lys Ala Phe Thr Lys
                755                 760                 765
Val Asn Phe Asp Ser Glu Asn Gly Pro Thr Val Tyr Asn Thr Leu Lys
770                 775                 780
```

-continued

```
Lys Ile Phe Lys His Thr Leu Glu Glu Lys Arg Lys Met Thr Lys Asp
785                 790                 795                 800

Gly Pro Lys Pro Gly Leu
                805
```

<210> SEQ ID NO 176
<211> LENGTH: 747
<212> TYPE: PRT
<213> ORGANISM: Homo sapiens

<400> SEQUENCE: 176

```
Met Val Ala Val Ser Ser Val Ser His Ala Glu Gly Asn Pro Thr Phe
1               5                   10                  15

Pro Glu Arg Lys Arg Asn Leu Glu Arg Pro Thr Pro Lys Tyr Thr Lys
                20                  25                  30

Val Gly Glu Arg Leu Arg His Val Ile Pro Gly His Met Ala Cys Ser
            35                  40                  45

Met Ala Cys Gly Gly Arg Ala Cys Lys Tyr Glu Asn Pro Ala Arg Trp
    50                  55                  60

Ser Glu Gln Glu Gln Ala Ile Lys Gly Val Tyr Ser Ser Trp Val Thr
65                  70                  75                  80

Asp Asn Ile Leu Ala Met Ala Arg Pro Ser Ser Glu Leu Leu Glu Lys
                85                  90                  95

Tyr His Ile Ile Asp Gln Phe Leu Ser His Gly Ile Lys Thr Ile Ile
            100                 105                 110

Asn Leu Gln Arg Pro Gly Glu His Ala Ser Cys Gly Asn Pro Leu Glu
        115                 120                 125

Gln Glu Ser Gly Phe Thr Tyr Leu Pro Glu Ala Phe Met Glu Ala Gly
    130                 135                 140

Ile Tyr Phe Tyr Asn Phe Gly Trp Lys Asp Tyr Gly Val Ala Ser Leu
145                 150                 155                 160

Thr Thr Ile Leu Asp Met Val Lys Val Met Thr Phe Ala Leu Gln Glu
                165                 170                 175

Gly Lys Val Ala Ile His Cys His Ala Gly Leu Gly Arg Thr Gly Val
            180                 185                 190

Leu Ile Ala Cys Tyr Leu Val Phe Ala Thr Arg Met Thr Ala Asp Gln
        195                 200                 205

Ala Ile Ile Phe Val Arg Ala Lys Arg Pro Asn Ser Ile Gln Thr Arg
    210                 215                 220

Gly Gln Leu Leu Cys Val Arg Glu Phe Thr Gln Phe Leu Thr Pro Leu
225                 230                 235                 240

Arg Asn Ile Phe Ser Cys Cys Asp Pro Lys Ala His Ala Val Thr Leu
                245                 250                 255

Pro Gln Tyr Leu Ile Arg Gln Arg His Leu Leu His Gly Tyr Glu Ala
            260                 265                 270

Arg Leu Leu Lys His Val Pro Lys Ile Ile His Leu Val Cys Lys Leu
        275                 280                 285

Leu Leu Asp Leu Ala Glu Asn Arg Pro Val Met Met Lys Asp Val Ser
    290                 295                 300

Glu Gly Pro Gly Leu Ser Ala Glu Ile Glu Lys Thr Met Ser Glu Met
305                 310                 315                 320

Val Thr Met Gln Leu Asp Lys Glu Leu Leu Arg His Asp Ser Asp Val
                325                 330                 335

Ser Asn Pro Pro Asn Pro Thr Ala Val Ala Ala Asp Phe Asp Asn Arg
```

-continued

```
              340                 345                 350
Gly Met Ile Phe Ser Asn Glu Gln Gln Phe Asp Pro Leu Trp Lys Arg
                355                 360                 365
Arg Asn Val Glu Cys Leu Gln Pro Leu Thr His Leu Lys Arg Arg Leu
        370                 375                 380
Ser Tyr Ser Asp Ser Asp Leu Lys Arg Ala Glu Asn Leu Leu Glu Gln
385                 390                 395                 400
Gly Glu Thr Pro Gln Thr Val Pro Ala Gln Ile Leu Val Gly His Lys
                    405                 410                 415
Pro Arg Gln Gln Lys Leu Ile Ser His Cys Tyr Ile Pro Gln Ser Pro
            420                 425                 430
Glu Pro Asp Leu His Lys Glu Ala Leu Val Arg Ser Thr Leu Ser Phe
                435                 440                 445
Trp Ser Gln Ser Lys Phe Gly Gly Leu Glu Gly Leu Lys Asp Asn Gly
            450                 455                 460
Ser Pro Ile Phe His Gly Arg Ile Ile Pro Lys Glu Ala Gln Gln Ser
465                 470                 475                 480
Gly Ala Phe Ser Ala Asp Val Ser Gly Ser His Ser Pro Gly Glu Pro
                    485                 490                 495
Val Ser Pro Ser Phe Ala Asn Val His Lys Asp Pro Asn Pro Ala His
                500                 505                 510
Gln Gln Val Ser His Cys Gln Cys Lys Thr His Gly Val Gly Ser Pro
            515                 520                 525
Gly Ser Val Arg Gln Asn Ser Arg Thr Pro Arg Ser Pro Leu Asp Cys
530                 535                 540
Gly Ser Ser Pro Lys Ala Gln Phe Leu Val Glu His Glu Thr Gln Asp
545                 550                 555                 560
Ser Lys Asp Leu Ser Glu Ala Ala Ser His Ser Ala Leu Gln Ser Glu
                565                 570                 575
Leu Ser Ala Glu Ala Arg Arg Ile Leu Ala Ala Lys Ala Leu Ala Asn
            580                 585                 590
Leu Asn Glu Ser Val Glu Lys Glu Leu Lys Arg Lys Val Glu Met
            595                 600                 605
Trp Gln Lys Glu Leu Asn Ser Arg Asp Gly Ala Trp Glu Arg Ile Cys
        610                 615                 620
Gly Glu Arg Asp Pro Phe Ile Leu Cys Ser Leu Met Trp Ser Trp Val
625                 630                 635                 640
Glu Gln Leu Lys Glu Pro Val Ile Thr Lys Glu Asp Val Asp Met Leu
                    645                 650                 655
Val Asp Arg Arg Ala Asp Ala Ala Glu Ala Leu Phe Leu Leu Glu Lys
                660                 665                 670
Gly Gln His Gln Thr Ile Leu Cys Val Leu His Cys Ile Val Asn Leu
            675                 680                 685
Gln Thr Ile Pro Val Asp Val Glu Glu Ala Phe Leu Ala His Ala Ile
        690                 695                 700
Lys Ala Phe Thr Lys Val Asn Phe Asp Ser Glu Asn Gly Pro Thr Val
705                 710                 715                 720
Tyr Asn Thr Leu Lys Lys Ile Phe Lys His Thr Leu Glu Glu Lys Arg
                725                 730                 735
Lys Met Thr Lys Asp Gly Pro Lys Pro Gly Leu
                740                 745
```

<210> SEQ ID NO 177

-continued

```
<211> LENGTH: 699
<212> TYPE: PRT
<213> ORGANISM: Homo sapiens

<400> SEQUENCE: 177

Met Ala Cys Gly Gly Arg Ala Cys Lys Tyr Glu Asn Pro Ala Arg Trp
1               5                   10                  15

Ser Glu Gln Glu Gln Ala Ile Lys Gly Val Tyr Ser Ser Trp Val Thr
                20                  25                  30

Asp Asn Ile Leu Ala Met Ala Arg Pro Ser Ser Glu Leu Leu Glu Lys
            35                  40                  45

Tyr His Ile Ile Asp Gln Phe Leu Ser His Gly Ile Lys Thr Ile Ile
    50                  55                  60

Asn Leu Gln Arg Pro Gly Glu His Ala Ser Cys Gly Asn Pro Leu Glu
65                  70                  75                  80

Gln Glu Ser Gly Phe Thr Tyr Leu Pro Glu Ala Phe Met Glu Ala Gly
                85                  90                  95

Ile Tyr Phe Tyr Asn Phe Gly Trp Lys Asp Tyr Gly Val Ala Ser Leu
            100                 105                 110

Thr Thr Ile Leu Asp Met Val Lys Val Met Thr Phe Ala Leu Gln Glu
        115                 120                 125

Gly Lys Val Ala Ile His Cys His Ala Gly Leu Gly Arg Thr Gly Val
130                 135                 140

Leu Ile Ala Cys Tyr Leu Val Phe Ala Thr Arg Met Thr Ala Asp Gln
145                 150                 155                 160

Ala Ile Ile Phe Val Arg Ala Lys Arg Pro Asn Ser Ile Gln Thr Arg
                165                 170                 175

Gly Gln Leu Leu Cys Val Arg Glu Phe Thr Gln Phe Leu Thr Pro Leu
            180                 185                 190

Arg Asn Ile Phe Ser Cys Cys Asp Pro Lys Ala His Ala Val Thr Leu
        195                 200                 205

Pro Gln Tyr Leu Ile Arg Gln Arg His Leu Leu His Gly Tyr Glu Ala
    210                 215                 220

Arg Leu Leu Lys His Val Pro Lys Ile Ile His Leu Val Cys Lys Leu
225                 230                 235                 240

Leu Leu Asp Leu Ala Glu Asn Arg Pro Val Met Met Lys Asp Val Ser
                245                 250                 255

Glu Gly Pro Gly Leu Ser Ala Glu Ile Glu Lys Thr Met Ser Glu Met
            260                 265                 270

Val Thr Met Gln Leu Asp Lys Glu Leu Leu Arg His Asp Ser Asp Val
        275                 280                 285

Ser Asn Pro Pro Asn Pro Thr Ala Val Ala Ala Asp Phe Asp Asn Arg
    290                 295                 300

Gly Met Ile Phe Ser Asn Glu Gln Gln Phe Asp Pro Leu Trp Lys Arg
305                 310                 315                 320

Arg Asn Val Glu Cys Leu Gln Pro Leu Thr His Leu Lys Arg Arg Leu
                325                 330                 335

Ser Tyr Ser Asp Ser Asp Leu Lys Arg Ala Glu Asn Leu Leu Glu Gln
            340                 345                 350

Gly Glu Thr Pro Gln Thr Val Pro Ala Gln Ile Leu Val Gly His Lys
        355                 360                 365

Pro Arg Gln Gln Lys Leu Ile Ser His Cys Tyr Ile Pro Gln Ser Pro
    370                 375                 380

Glu Pro Asp Leu His Lys Glu Ala Leu Val Arg Ser Thr Leu Ser Phe
```

```
                385                 390                 395                 400
Trp Ser Gln Ser Lys Phe Gly Gly Leu Glu Gly Leu Lys Asp Asn Gly
                405                 410                 415

Ser Pro Ile Phe His Gly Arg Ile Ile Pro Lys Glu Ala Gln Gln Ser
            420                 425                 430

Gly Ala Phe Ser Ala Asp Val Ser Gly Ser His Ser Pro Gly Glu Pro
            435                 440                 445

Val Ser Pro Ser Phe Ala Asn Val His Lys Asp Pro Asn Pro Ala His
    450                 455                 460

Gln Gln Val Ser His Cys Gln Cys Lys Thr His Gly Val Gly Ser Pro
465                 470                 475                 480

Gly Ser Val Arg Gln Asn Ser Arg Thr Pro Arg Ser Pro Leu Asp Cys
                485                 490                 495

Gly Ser Ser Pro Lys Ala Gln Phe Leu Val Glu His Glu Thr Gln Asp
                500                 505                 510

Ser Lys Asp Leu Ser Glu Ala Ala Ser His Ser Ala Leu Gln Ser Glu
            515                 520                 525

Leu Ser Ala Glu Ala Arg Arg Ile Leu Ala Ala Lys Ala Leu Ala Asn
530                 535                 540

Leu Asn Glu Ser Val Glu Lys Glu Leu Lys Arg Lys Val Glu Met
545                 550                 555                 560

Trp Gln Lys Glu Leu Asn Ser Arg Asp Gly Ala Trp Glu Arg Ile Cys
                565                 570                 575

Gly Glu Arg Asp Pro Phe Ile Leu Cys Ser Leu Met Trp Ser Trp Val
            580                 585                 590

Glu Gln Leu Lys Glu Pro Val Ile Thr Lys Glu Asp Val Asp Met Leu
            595                 600                 605

Val Asp Arg Arg Ala Asp Ala Ala Glu Ala Leu Phe Leu Leu Glu Lys
    610                 615                 620

Gly Gln His Gln Thr Ile Leu Cys Val Leu His Cys Ile Val Asn Leu
625                 630                 635                 640

Gln Thr Ile Pro Val Asp Val Glu Glu Ala Phe Leu Ala His Ala Ile
                645                 650                 655

Lys Ala Phe Thr Lys Val Asn Phe Asp Ser Glu Asn Gly Pro Thr Val
            660                 665                 670

Tyr Asn Thr Leu Lys Lys Ile Phe Lys His Thr Leu Glu Glu Lys Arg
            675                 680                 685

Lys Met Thr Lys Asp Gly Pro Lys Pro Gly Leu
            690                 695

<210> SEQ ID NO 178
<211> LENGTH: 662
<212> TYPE: PRT
<213> ORGANISM: Homo sapiens

<400> SEQUENCE: 178

Met Ala Arg Pro Ser Ser Glu Leu Leu Glu Lys Tyr His Ile Ile Asp
1               5                   10                  15

Gln Phe Leu Ser His Gly Ile Lys Thr Ile Ile Asn Leu Gln Arg Pro
            20                  25                  30

Gly Glu His Ala Ser Cys Gly Asn Pro Leu Glu Gln Gly Ser Gly Phe
        35                  40                  45

Thr Tyr Leu Pro Glu Ala Phe Met Glu Ala Gly Ile Tyr Phe Tyr Asn
    50                  55                  60
```

-continued

Phe Gly Trp Lys Asp Tyr Gly Val Ala Ser Leu Thr Thr Ile Leu Asp
65                  70                  75                  80

Met Val Lys Val Met Thr Phe Ala Leu Gln Glu Gly Lys Val Ala Ile
                85                  90                  95

His Cys His Ala Gly Leu Gly Arg Thr Gly Val Leu Ile Ala Cys Tyr
            100                 105                 110

Leu Val Phe Ala Thr Arg Met Thr Ala Asp Gln Ala Ile Ile Phe Val
        115                 120                 125

Arg Ala Lys Arg Pro Asn Ser Ile Gln Thr Arg Gly Gln Leu Leu Cys
    130                 135                 140

Val Arg Glu Phe Thr Gln Phe Leu Thr Pro Leu Arg Asn Ile Phe Ser
145                 150                 155                 160

Cys Cys Asp Pro Lys Ala His Ala Val Thr Leu Pro Gln Tyr Leu Ile
                165                 170                 175

Arg Gln Arg His Leu Leu His Gly Tyr Glu Ala Arg Leu Leu Lys His
            180                 185                 190

Val Pro Lys Ile Ile His Leu Val Cys Lys Leu Leu Leu Asp Leu Ala
        195                 200                 205

Glu Asn Arg Pro Val Met Met Lys Asp Val Ser Glu Gly Pro Gly Leu
    210                 215                 220

Ser Ala Glu Ile Glu Lys Thr Met Ser Glu Met Val Thr Met Gln Leu
225                 230                 235                 240

Asp Lys Glu Leu Leu Arg His Asp Ser Asp Val Ser Asn Pro Pro Asn
                245                 250                 255

Pro Thr Ala Val Ala Ala Asp Phe Asp Asn Arg Gly Met Ile Phe Ser
            260                 265                 270

Asn Glu Gln Gln Phe Asp Pro Leu Trp Lys Arg Asn Val Glu Cys
        275                 280                 285

Leu Gln Pro Leu Thr His Leu Lys Arg Arg Leu Ser Tyr Ser Asp Ser
    290                 295                 300

Asp Leu Lys Arg Ala Glu Asn Leu Leu Glu Gln Gly Glu Thr Pro Gln
305                 310                 315                 320

Thr Val Pro Ala Gln Ile Leu Val Gly His Lys Pro Arg Gln Gln Lys
                325                 330                 335

Leu Ile Ser His Cys Tyr Ile Pro Gln Ser Pro Glu Pro Asp Leu His
            340                 345                 350

Lys Glu Ala Leu Val Arg Ser Thr Leu Ser Phe Trp Ser Gln Ser Lys
        355                 360                 365

Phe Gly Gly Leu Glu Gly Leu Lys Asp Asn Gly Ser Pro Ile Phe His
    370                 375                 380

Gly Arg Ile Ile Pro Lys Glu Ala Gln Gln Ser Gly Ala Phe Ser Ala
385                 390                 395                 400

Asp Val Ser Gly Ser His Ser Pro Gly Glu Pro Val Ser Pro Ser Phe
                405                 410                 415

Ala Asn Val His Lys Asp Pro Asn Pro Ala His Gln Val Ser His
            420                 425                 430

Cys Gln Cys Lys Thr His Gly Val Gly Ser Pro Gly Ser Val Arg Gln
        435                 440                 445

Asn Ser Arg Thr Pro Arg Ser Pro Leu Asp Cys Gly Ser Ser Pro Lys
    450                 455                 460

Ala Gln Phe Leu Val Glu His Glu Thr Gln Asp Ser Lys Asp Leu Ser
465                 470                 475                 480

Glu Ala Ala Ser His Ser Ala Leu Gln Ser Glu Leu Ser Ala Glu Ala

-continued

```
                485                 490                 495
Arg Arg Ile Leu Ala Ala Lys Ala Leu Ala Asn Leu Asn Glu Ser Val
            500                 505                 510
Glu Lys Glu Glu Leu Lys Arg Lys Val Glu Met Trp Gln Lys Glu Leu
            515                 520                 525
Asn Ser Arg Asp Gly Ala Trp Glu Arg Ile Cys Gly Glu Arg Asp Pro
            530                 535                 540
Phe Ile Leu Cys Ser Leu Met Trp Ser Trp Val Glu Gln Leu Lys Glu
545                 550                 555                 560
Pro Val Ile Thr Lys Glu Asp Val Asp Met Leu Val Asp Arg Arg Ala
            565                 570                 575
Asp Ala Ala Glu Ala Leu Phe Leu Leu Glu Lys Gly Gln His Gln Thr
            580                 585                 590
Ile Leu Cys Val Leu His Cys Ile Val Asn Leu Gln Thr Ile Pro Val
            595                 600                 605
Asp Val Glu Glu Ala Phe Leu Ala His Ala Ile Lys Ala Phe Thr Lys
            610                 615                 620
Val Asn Phe Asp Ser Glu Asn Gly Pro Thr Val Tyr Asn Thr Leu Lys
625                 630                 635                 640
Lys Ile Phe Lys His Thr Leu Glu Glu Lys Arg Lys Met Thr Lys Asp
                    645                 650                 655
Gly Pro Lys Pro Gly Leu
            660

<210> SEQ ID NO 179
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 179
ggauaucacu acugcauugc cugga                                            25

<210> SEQ ID NO 180
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 180
uacagcagau cugugcaggc caggu                                            25

<210> SEQ ID NO 181
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 181
ugaucacaca guagcggaag augcu                                            25

<210> SEQ ID NO 182
<211> LENGTH: 25
<212> TYPE: DNA
<213> ORGANISM: Artificial Sequence
<220> FEATURE:
<223> OTHER INFORMATION: Synthesized Oligonucleotide.
```

-continued

```
<400> SEQUENCE: 182
aggaguagca gaaugguuag ccuuc                                              25

<210> SEQ ID NO 183
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 183
ugaaagcagg cgagauucga uccga                                              25

<210> SEQ ID NO 184
<211> LENGTH: 20
<212> TYPE: DNA
<213> ORGANISM: Homo sapiens

<400> SEQUENCE: 184
actaccgcct cacacgcttc                                                    20

<210> SEQ ID NO 185
<211> LENGTH: 20
<212> TYPE: DNA
<213> ORGANISM: Homo sapiens

<400> SEQUENCE: 185
cttgactcca gcagggcttc                                                    20

<210> SEQ ID NO 186
<211> LENGTH: 26
<212> TYPE: DNA
<213> ORGANISM: Homo sapiens

<400> SEQUENCE: 186
atcaagtgtg acccagactg cctccg                                             26

<210> SEQ ID NO 187
<211> LENGTH: 28
<212> TYPE: DNA
<213> ORGANISM: Homo sapiens

<400> SEQUENCE: 187
catatgggat ccatggccca tgagattg                                           28

<210> SEQ ID NO 188
<211> LENGTH: 30
<212> TYPE: DNA
<213> ORGANISM: Homo sapiens

<400> SEQUENCE: 188
ggtaccctcg agtcaggaga cctcaatgat                                         30

<210> SEQ ID NO 189
<211> LENGTH: 30
<212> TYPE: DNA
<213> ORGANISM: Homo sapiens

<400> SEQUENCE: 189
ggtaccctcg agtcaagtct ggttcttaat                                         30

<210> SEQ ID NO 190
<211> LENGTH: 664
```

<212> TYPE: PRT
<213> ORGANISM: Homo sapiens

<400> SEQUENCE: 190

```
Met Ala His Glu Ile Gly Thr Gln Ile Val Thr Glu Arg Leu Val Ala
1               5                   10                  15

Leu Leu Glu Ser Gly Thr Glu Lys Val Leu Leu Ile Asp Ser Arg Pro
            20                  25                  30

Phe Val Glu Tyr Asn Thr Ser His Ile Leu Glu Ala Ile Asn Ile Asn
        35                  40                  45

Cys Ser Lys Leu Met Lys Arg Arg Leu Gln Gln Asp Lys Val Leu Ile
50                  55                  60

Thr Glu Leu Ile Gln His Ser Ala Lys His Lys Val Asp Ile Asp Cys
65                  70                  75                  80

Ser Gln Lys Val Val Val Tyr Asp Gln Ser Ser Gln Asp Val Ala Ser
                85                  90                  95

Leu Ser Ser Asp Cys Phe Leu Thr Val Leu Leu Gly Lys Leu Glu Lys
            100                 105                 110

Ser Phe Asn Ser Val His Leu Leu Ala Gly Gly Phe Ala Glu Phe Ser
        115                 120                 125

Arg Cys Phe Pro Gly Leu Cys Glu Gly Lys Ser Thr Leu Val Pro Thr
130                 135                 140

Cys Ile Ser Gln Pro Cys Leu Pro Val Ala Asn Ile Gly Pro Thr Arg
145                 150                 155                 160

Ile Leu Pro Asn Leu Tyr Leu Gly Cys Gln Arg Asp Val Leu Asn Lys
                165                 170                 175

Glu Leu Met Gln Gln Asn Gly Ile Gly Tyr Val Leu Asn Ala Ser Asn
            180                 185                 190

Thr Cys Pro Lys Pro Asp Phe Ile Pro Glu Ser His Phe Leu Arg Val
        195                 200                 205

Pro Val Asn Asp Ser Phe Cys Glu Lys Ile Leu Pro Trp Leu Asp Lys
        210                 215                 220

Ser Val Asp Phe Ile Glu Lys Ala Lys Ala Ser Asn Gly Cys Val Leu
225                 230                 235                 240

Val His Cys Leu Ala Gly Ile Ser Arg Ser Ala Thr Ile Ala Ile Ala
                245                 250                 255

Tyr Ile Met Lys Arg Met Asp Met Ser Leu Asp Glu Ala Tyr Arg Phe
            260                 265                 270

Val Lys Glu Lys Arg Pro Thr Ile Ser Pro Ser Phe Asn Phe Leu Gly
        275                 280                 285

Gln Leu Leu Asp Tyr Glu Lys Lys Ile Lys Asn Gln Ala Gly Ala Ser
    290                 295                 300

Gly Pro Lys Ser Lys Leu Lys Leu His Leu Glu Lys Pro Asn Glu
305                 310                 315                 320

Pro Val Pro Ala Val Ser Glu Gly Gly Gln Lys Ser Glu Thr Pro Leu
                325                 330                 335

Ser Pro Pro Cys Ala Asp Ser Ala Thr Ser Glu Ala Ala Gly Gln Arg
            340                 345                 350

Pro Val His Pro Ala Ser Val Pro Ser Val Pro Ser Val Gln Pro Ser
        355                 360                 365

Leu Leu Glu Asp Ser Pro Leu Val Gln Ala Leu Ser Gly Leu His Leu
    370                 375                 380

Ser Ala Asp Arg Leu Glu Asp Ser Asn Lys Leu Lys Arg Ser Phe Ser
385                 390                 395                 400
```

-continued

```
Leu Asp Ile Lys Ser Val Ser Tyr Ser Ala Ser Met Ala Ala Ser Leu
                405                 410                 415

His Gly Phe Ser Ser Ser Glu Asp Ala Leu Glu Tyr Tyr Lys Pro Ser
            420                 425                 430

Thr Thr Leu Asp Gly Thr Asn Lys Leu Cys Gln Phe Ser Pro Val Gln
        435                 440                 445

Glu Leu Ser Glu Gln Thr Pro Glu Thr Ser Pro Asp Lys Glu Glu Ala
    450                 455                 460

Ser Ile Pro Lys Lys Leu Gln Thr Ala Arg Pro Ser Asp Ser Gln Ser
465                 470                 475                 480

Lys Arg Leu His Ser Val Arg Thr Ser Ser Gly Thr Ala Gln Arg
                485                 490                 495

Ser Leu Leu Ser Pro Leu His Arg Ser Gly Ser Val Glu Asp Asn Tyr
            500                 505                 510

His Thr Ser Phe Leu Phe Gly Leu Ser Thr Ser Gln Gln His Leu Thr
        515                 520                 525

Lys Ser Ala Gly Leu Gly Leu Lys Gly Trp His Ser Asp Ile Leu Ala
    530                 535                 540

Pro Gln Thr Ser Thr Pro Ser Leu Thr Ser Ser Trp Tyr Phe Ala Thr
545                 550                 555                 560

Glu Ser Ser His Phe Tyr Ser Ala Ser Ala Ile Tyr Gly Gly Ser Ala
                565                 570                 575

Ser Tyr Ser Ala Tyr Ser Arg Ser Gln Leu Pro Thr Cys Gly Asp Gln
            580                 585                 590

Val Tyr Ser Val Arg Arg Gln Lys Pro Ser Asp Arg Ala Asp Ser
        595                 600                 605

Arg Arg Ser Trp His Glu Glu Ser Pro Phe Glu Lys Gln Phe Lys Arg
    610                 615                 620

Arg Ser Cys Gln Met Glu Phe Gly Glu Ser Ile Met Ser Glu Asn Arg
625                 630                 635                 640

Ser Arg Glu Glu Leu Gly Lys Val Gly Ser Gln Ser Ser Phe Ser Gly
                645                 650                 655

Ser Met Glu Ile Ile Glu Val Ser
            660

<210> SEQ ID NO 191
<211> LENGTH: 302
<212> TYPE: PRT
<213> ORGANISM: Homo sapiens

<400> SEQUENCE: 191

Met Ala His Glu Ile Val Gly Thr Gln Ile Val Thr Glu Arg Leu Val
1               5                   10                  15

Ala Leu Leu Glu Ser Gly Thr Glu Lys Val Leu Leu Ile Asp Ser Arg
            20                  25                  30

Pro Phe Val Glu Tyr Asn Thr Ser His Ile Leu Glu Ala Ile Asn Ile
        35                  40                  45

Asn Cys Ser Lys Leu Met Lys Arg Arg Leu Gln Gln Asp Lys Val Leu
    50                  55                  60

Ile Thr Glu Leu Ile Gln His Ser Ala Lys His Lys Val Asp Ile Asp
65                  70                  75                  80

Cys Ser Gln Lys Val Val Tyr Asp Gln Ser Ser Gln Asp Val Ala
                85                  90                  95

Ser Leu Ser Ser Asp Cys Phe Leu Thr Val Leu Leu Gly Lys Leu Glu
```

```
                100                 105                 110
Lys Ser Phe Asn Ser Val His Leu Leu Ala Gly Gly Phe Ala Glu Phe
            115                 120                 125

Ser Arg Cys Phe Pro Gly Leu Cys Glu Gly Lys Ser Thr Leu Val Pro
        130                 135                 140

Thr Cys Ile Ser Gln Pro Cys Leu Pro Val Ala Asn Ile Gly Pro Thr
145                 150                 155                 160

Arg Ile Leu Pro Asn Leu Tyr Leu Gly Cys Gln Arg Asp Val Leu Asn
                165                 170                 175

Lys Glu Leu Met Gln Gln Asn Gly Ile Gly Tyr Val Leu Asn Ala Ser
            180                 185                 190

Asn Thr Cys Pro Lys Pro Asp Phe Ile Pro Glu Ser His Phe Leu Arg
        195                 200                 205

Val Pro Val Asn Asp Ser Phe Cys Glu Lys Ile Leu Pro Trp Leu Asp
    210                 215                 220

Lys Ser Val Asp Phe Ile Glu Lys Ala Lys Ser Asn Gly Cys Val
225                 230                 235                 240

Leu Val His Cys Leu Ala Gly Ile Ser Arg Ser Ala Thr Ile Ala Ile
                245                 250                 255

Ala Tyr Ile Met Lys Arg Met Asp Met Ser Leu Asp Glu Ala Tyr Arg
            260                 265                 270

Phe Val Lys Glu Lys Arg Pro Thr Ile Ser Pro Ser Phe Asn Phe Leu
        275                 280                 285

Gly Gln Leu Leu Asp Tyr Glu Lys Lys Ile Lys Asn Gln Thr
    290                 295                 300

<210> SEQ ID NO 192
<211> LENGTH: 20
<212> TYPE: PRT
<213> ORGANISM: Artificial Sequence
<220> FEATURE:
<223> OTHER INFORMATION: Synthesized Peptide.

<400> SEQUENCE: 192

Lys Asn Gln Thr Gly Ala Ser Gly Pro Lys Ser Lys Lys Leu Lys Leu
1               5                   10                  15

Leu His Leu Glu
            20

<210> SEQ ID NO 193
<211> LENGTH: 19
<212> TYPE: PRT
<213> ORGANISM: Artificial Sequence
<220> FEATURE:
<223> OTHER INFORMATION: Synthesized Peptide.

<400> SEQUENCE: 193

Cys Lys Lys Leu Gln Thr Ala Arg Pro Ser Asp Ser Gln Ser Lys Arg
1               5                   10                  15

Leu His Ser

<210> SEQ ID NO 194
<211> LENGTH: 21
<212> TYPE: DNA
<213> ORGANISM: Homo sapiens

<400> SEQUENCE: 194
ctgcgtgttg cactgcatag t                                        21
```

```
<210> SEQ ID NO 195
<211> LENGTH: 19
<212> TYPE: DNA
<213> ORGANISM: Homo sapiens

<400> SEQUENCE: 195
tgggcaagga aagcttcct                                                    19

<210> SEQ ID NO 196
<211> LENGTH: 26
<212> TYPE: DNA
<213> ORGANISM: Homo sapiens

<400> SEQUENCE: 196
aacctgcaga caattcccgt ggatgt                                            26

<210> SEQ ID NO 197
<211> LENGTH: 21
<212> TYPE: DNA
<213> ORGANISM: Homo sapiens

<400> SEQUENCE: 197
gagatgccat tgctgaaatc c                                                 21

<210> SEQ ID NO 198
<211> LENGTH: 23
<212> TYPE: DNA
<213> ORGANISM: Homo sapiens

<400> SEQUENCE: 198
gactgctttc tcctgctcat agg                                               23

<210> SEQ ID NO 199
<211> LENGTH: 23
<212> TYPE: DNA
<213> ORGANISM: Homo sapiens

<400> SEQUENCE: 199
cgactacgac ccggctccat cga                                               23

<210> SEQ ID NO 200
<211> LENGTH: 23
<212> TYPE: DNA
<213> ORGANISM: Homo sapiens

<400> SEQUENCE: 200
aggagcagat ggtagacgtg ttc                                               23

<210> SEQ ID NO 201
<211> LENGTH: 20
<212> TYPE: DNA
<213> ORGANISM: Homo sapiens

<400> SEQUENCE: 201
ggctcagggt ctggatcatg                                                   20

<210> SEQ ID NO 202
<211> LENGTH: 25
<212> TYPE: DNA
<213> ORGANISM: Homo sapiens

<400> SEQUENCE: 202
tgctgtgtat gcactccgga tgcac                                             25
```

<210> SEQ ID NO 203
<211> LENGTH: 25
<212> TYPE: DNA
<213> ORGANISM: Homo sapiens

<400> SEQUENCE: 203
cacacaccaa atgtgtaaca gttca                                    25

<210> SEQ ID NO 204
<211> LENGTH: 27
<212> TYPE: DNA
<213> ORGANISM: Homo sapiens

<400> SEQUENCE: 204
gctactgctt tcctttctta aacatgt                                  27

<210> SEQ ID NO 205
<211> LENGTH: 25
<212> TYPE: DNA
<213> ORGANISM: Homo sapiens

<400> SEQUENCE: 205
cacttccaga gtgtggtcat gccca                                    25

<210> SEQ ID NO 206
<211> LENGTH: 321
<212> TYPE: PRT
<213> ORGANISM: Homo sapiens

<400> SEQUENCE: 206

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val Val His Ser Ser Ala Gly Ile Gly Arg Ser Gly Thr

-continued

```
            210                 215                 220
Phe Cys Leu Ala Asp Thr Cys Leu Leu Met Asp Lys Arg Lys Asp
225                 230                 235                 240

Pro Ser Ser Val Asp Ile Lys Lys Val Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
            275                 280                 285

Asp Gln Trp Lys Glu Leu Ser His Glu Asp Leu Glu Pro Pro Pro Gly
            290                 295                 300

His Ile Pro Pro Pro Arg Pro Pro Lys Arg Ile Leu Glu Pro His
305                 310                 315                 320

Asn

<210> SEQ ID NO 207
<211> LENGTH: 184
<212> TYPE: PRT
<213> ORGANISM: Homo sapiens

<400> SEQUENCE: 207

Ser Gly Ser Phe Glu Leu Ser Val Gln Asp Leu Asn Asp Leu Leu Ser
1               5                   10                  15

Asp Gly Ser Gly Cys Tyr Ser Leu Pro Ser Gln Pro Cys Asn Glu Val
                20                  25                  30

Thr Pro Arg Ile Tyr Val Gly Asn Ala Ser Val Ala Gln Asp Ile Pro
            35                  40                  45

Lys Leu Gln Lys Leu Gly Ile Thr His Val Leu Asn Ala Ala Glu Gly
        50                  55                  60

Arg Ser Phe Met His Val Asn Thr Asn Ala Asn Phe Tyr Lys Asp Ser
65                  70                  75                  80

Gly Ile Thr Tyr Leu Gly Ile Lys Ala Asn Asp Thr Gln Glu Phe Asn
                85                  90                  95

Leu Ser Ala Tyr Phe Glu Arg Ala Ala Asp Phe Ile Asp Gln Ala Leu
            100                 105                 110

Ala Gln Lys Asn Gly Arg Val Leu Val His Cys Arg Glu Gly Tyr Ser
        115                 120                 125

Arg Ser Pro Thr Leu Val Ile Ala Tyr Leu Met Met Arg Gln Lys Met
130                 135                 140

Asp Val Lys Ser Ala Leu Ser Ile Val Arg Gln Asn Arg Glu Ile Gly
145                 150                 155                 160

Pro Asn Asp Gly Phe Leu Ala Gln Leu Cys Gln Leu Asn Asp Arg Leu
                165                 170                 175

Ala Lys Glu Gly Lys Leu Lys Pro
            180

<210> SEQ ID NO 208
<211> LENGTH: 144
<212> TYPE: PRT
<213> ORGANISM: Homo sapiens

<400> SEQUENCE: 208

Ala Ser Phe Pro Val Glu Ile Leu Pro Phe Leu Tyr Leu Gly Cys Ala
1               5                   10                  15

Lys Asp Ser Thr Asn Leu Asp Val Leu Glu Glu Phe Gly Ile Lys Tyr
                20                  25                  30
```

```
                            -continued

Ile Leu Asn Val Thr Pro Asn Leu Pro Asn Leu Phe Glu Asn Ala Gly
        35                  40                  45

Glu Phe Lys Tyr Lys Gln Ile Pro Ile Ser Asp His Trp Ser Gln Asn
        50                  55                  60

Leu Ser Gln Phe Phe Pro Glu Ala Ile Ser Phe Ile Asp Glu Ala Arg
65                  70                  75                  80

Gly Lys Asn Cys Gly Val Leu Val His Ser Leu Ala Gly Ile Ser Arg
                85                  90                  95

Ser Val Thr Val Thr Val Ala Tyr Leu Met Gln Lys Leu Asn Leu Ser
            100                 105                 110

Met Asn Asp Ala Tyr Asp Ile Val Lys Met Lys Lys Ser Asn Ile Ser
        115                 120                 125

Pro Asn Phe Asn Phe Met Gly Gln Leu Leu Asp Phe Glu Arg Thr Leu
        130                 135                 140
```